(12) United States Patent
Levy et al.

(10) Patent No.: US 10,791,909 B2
(45) Date of Patent: *Oct. 6, 2020

(54) IMAGE CAPTURE ASSEMBLY FOR USE IN A MULTI-VIEWING ELEMENTS ENDOSCOPE

(71) Applicant: EndoChoice, Inc., Alpharetta, GA (US)

(72) Inventors: Avi Levy, Herzliya (IL); Moshiko Levi, Ganey Tikva (IL); Golan Salman, Atlit (IL); Amram Aizenfeld, Ramot Menashe (IL); Stephan Wieth, Klein Nordende (DE); Jeruham Avron, Haifa (IL); Robby Dascalo, Zichron Yaaqov (IL); Mark Gilreath, Alpharetta, GA (US); Leonid Krivopisk, Nesher (IL); Yaniv Kirma, Karcur (IL); Victor Levin, Haifa (IL)

(73) Assignee: Endochoice, Inc., Alpharetta, GA (US)

( * ) Notice: Subject to any disclaimer, the term of this patent is extended or adjusted under 35 U.S.C. 154(b) by 494 days.

This patent is subject to a terminal disclaimer.

(21) Appl. No.: 15/608,356

(22) Filed: May 30, 2017

(65) Prior Publication Data

US 2017/0325663 A1    Nov. 16, 2017

Related U.S. Application Data

(63) Continuation of application No. 14/271,270, filed on May 6, 2014, now Pat. No. 9,713,417, which is a
(Continued)

(51) Int. Cl.
*A61B 1/04*     (2006.01)
*A61B 1/00*     (2006.01)
(Continued)

(52) U.S. Cl.
CPC ........ *A61B 1/00096* (2013.01); *A61B 1/0011* (2013.01); *A61B 1/00101* (2013.01);
(Continued)

(58) Field of Classification Search
CPC . A61B 1/00096; A61B 1/00101; A61B 1/053; A61B 1/0676; A61B 1/0615; A61B 1/000091; A61B 1/018; A61B 1/00137
(Continued)

(56) References Cited

U.S. PATENT DOCUMENTS 3,639,714 A    2/1972  Fujimoto
3,955,064 A    5/1976  Demetrio
(Continued)

FOREIGN PATENT DOCUMENTS

CN    1376443      10/2002
CN    2829646 Y    10/2006
(Continued)

OTHER PUBLICATIONS

Office Action dated Aug. 27, 2015 for U.S. Appl. No. 13/655,120.
(Continued)

*Primary Examiner* — Matthew J Kasztejna
(74) *Attorney, Agent, or Firm* — Bookoff McAndrews, PLLC

(57) ABSTRACT

An image capturing assembly for use in an endoscope includes a manifold with a base and a casing extending outward from the base, a partially enclosed housing adapted to physically attach to the manifold, a foldable LED carrier substrate capable of carrying a plurality of LEDs, a flexible optical carrier substrate capable of carrying a plurality of camera sensors, and a tip cover adapted to cover the manifold, housing, LED carrier substrate, and optical carrier substrate. The manifold includes at least one continuous channel extending throughout its length. The foldable LED
(Continued)

carrier substrate includes a central, forward facing portion, adapted to carry at least one illuminator for a front viewing element, and a pair of arms extending proximally from the central portion. Each arm includes at least one foldable protrusion adapted to carry an illuminator for a side viewing element.

20 Claims, 201 Drawing Sheets

Related U.S. Application Data continuation-in-part of application No. 13/984,028, filed as application No. PCT/IL2012/050037 on Feb. 6, 2012, now Pat. No. 9,101,266, said application No. 14/271,270 is a continuation-in-part of application No. 13/992,021, filed as application No. PCT/IL2011/050050 on Dec. 8, 2011, now Pat. No. 9,320,419, said application No. 14/271,270 is a continuation-in-part of application No. 13/992,014, filed as application No. PCT/IL2011/050049 on Dec. 8, 2011, now Pat. No. 9,814,374, said application No. 14/271,270 is a continuation-in-part of application No. 13/882,004, filed as application No. PCT/IL2011/000832 on Oct. 27, 2011, now abandoned, said application No. 14/271,270 is a continuation-in-part of application No. 13/822,908, filed as application No. PCT/IL2011/000745 on Sep. 20, 2011, now Pat. No. 10,080,486, said application No. 14/271,270 is a continuation-in-part of application No. 13/713,449, filed on Dec. 13, 2012, now Pat. No. 9,655,502, said application No. 14/271,270 is a continuation-in-part of application No. 13/655,120, filed on Oct. 18, 2012, now Pat. No. 9,872,609, which is a continuation-in-part of application No. 13/119,032, filed as application No. PCT/IL2010/000476 on Jun. 16, 2010, now Pat. No. 9,554,692, said application No. 14/271,270 is a continuation-in-part of application No. 13/212,627, filed on Aug. 18, 2011, now Pat. No. 9,492,063, which is a continuation-in-part of application No. 13/119,032, filed on Jul. 15, 2011, now Pat. No. 9,554,692, said application No. 14/271,270 is a continuation-in-part of application No. 13/190,968, filed on Jul. 26, 2011, now Pat. No. 9,101,268, which is a continuation-in-part of application No. 13/119,032, filed on Jul. 15, 2011, now Pat. No. 9,554,692, said application No. 14/271,270 is a continuation-in-part of application No. 13/413,252, filed on Mar. 6, 2012, now Pat. No. 9,101,287, said application No. 14/271,270 is a continuation of application No. 13/413,141, filed on Mar. 6, 2012, now Pat. No. 8,926,502, said application No. 14/271,270 is a continuation-in-part of application No. 13/413,059, filed on Mar. 6, 2012, now Pat. No. 9,402,533, said application No. 14/271,270 is a continuation-in-part of application No. 13/412,974, filed on Mar. 6, 2012, now abandoned.

(60) Provisional application No. 61/968,436, filed on Mar. 21, 2014, provisional application No. 61/950,696, filed on Mar. 10, 2014, provisional application No. 61/948,009, filed on Mar. 4, 2014, provisional application No. 61/936,562, filed on Feb. 6, 2014, provisional application No. 61/935,647, filed on Feb. 4, 2014, provisional application No. 61/926,732, filed on Jan. 13, 2014, provisional application No. 61/925,080, filed on Jan. 8, 2014, provisional application No. 61/910,863, filed on Dec. 2, 2013, provisional application No. 61/899,455, filed on Nov. 4, 2013, provisional application No. 61/897,896, filed on Oct. 31, 2013, provisional application No. 61/881,661, filed on Sep. 24, 2013, provisional application No. 61/841,863, filed on Jul. 1, 2013, provisional application No. 61/840,706, filed on Jun. 28, 2013, provisional application No. 61/840,691, filed on Jun. 28, 2013, provisional application No. 61/828,039, filed on May 28, 2013, provisional application No. 61/824,863, filed on May 17, 2013, provisional application No. 61/824,653, filed on May 17, 2013, provisional application No. 61/824,236, filed on May 16, 2013, provisional application No. 61/822,563, filed on May 13, 2013, provisional application No. 61/821,579, filed on May 9, 2013, provisional application No. 61/820,100, filed on May 6, 2013, provisional application No. 61/439,948, filed on Feb. 7, 2011, provisional application No. 61/421,240, filed on Dec. 9, 2010, provisional application No. 61/421,238, filed on Dec. 9, 2010, provisional application No. 61/407,495, filed on Oct. 28, 2010, provisional application No. 61/384,354, filed on Sep. 20, 2010, provisional application No. 61/569,796, filed on Dec. 13, 2011, provisional application No. 61/218,085, filed on Jun. 18, 2009, provisional application No. 61/449,746, filed on Mar. 7, 2011, provisional application No. 61/449,743, filed on Mar. 7, 2011, provisional application No. 61/449,741, filed on Mar. 7, 2011, provisional application No. 61/449,739, filed on Mar. 7, 2011, provisional application No. 61/987,984, filed on May 2, 2014.

(51) Int. Cl.
*A61B 1/06* (2006.01)
*G02B 23/24* (2006.01)
*A61B 1/05* (2006.01)

(52) U.S. Cl.
CPC ...... *A61B 1/00105* (2013.01); *A61B 1/00124* (2013.01); *A61B 1/051* (2013.01); *A61B 1/053* (2013.01); *A61B 1/0615* (2013.01); *A61B 1/0676* (2013.01); *A61B 1/0684* (2013.01); *G02B 23/2484* (2013.01)

(58) Field of Classification Search
USPC ........ 600/109, 113, 129–130, 156–157, 165, 600/170–171
See application file for complete search history.

(56) References Cited

U.S. PATENT DOCUMENTS

| | | |
|---|---|---|
| 4,037,588 A | 7/1977 | Heckele |
| 4,084,401 A | 4/1978 | Belardi |
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |

(56) References Cited

U.S. PATENT DOCUMENTS

| | | |
|---|---|---|
| 4,641,635 A | 2/1987 | Yabe |
| 4,699,463 A | 10/1987 | D'Amelio |
| 4,708,126 A | 11/1987 | Toda |
| 4,727,859 A | 3/1988 | Lia |
| 4,736,732 A | 4/1988 | Shimonaka |
| 4,753,222 A | 6/1988 | Morishita |
| 4,764,001 A | 8/1988 | Yokota |
| 4,801,792 A | 1/1989 | Yamasita |
| 4,836,189 A | 6/1989 | Allred, III |
| 4,841,952 A | 6/1989 | Sato |
| 4,846,154 A | 7/1989 | MacAnally |
| 4,868,644 A | 9/1989 | Yabe |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,475,420 A | 12/1995 | Buchin |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uchara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,662,588 A | 9/1997 | Iida |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yate |
| 5,707,344 A | 1/1998 | Nakazawa |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,836,894 A | 11/1998 | Sarvazyan |
| 5,852,511 A | 12/1998 | Tateyama |
| 5,860,913 A | 1/1999 | Yamaya |
| 5,870,234 A | 2/1999 | EbbesmeierneeSchitthof |
| 5,871,439 A | 2/1999 | Takahashi |
| 5,871,440 A | 2/1999 | Okada |
| 5,876,326 A | 3/1999 | Takamura |
| 5,879,284 A | 3/1999 | Tsujita |
| 5,894,322 A | 4/1999 | Haman |
| 5,912,764 A | 6/1999 | Togino |
| 5,913,817 A | 6/1999 | Lee |
| 5,914,610 A | 6/1999 | Watts |
| 5,916,148 A | 6/1999 | Tsuyuki |
| 5,936,773 A | 6/1999 | Togino |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tornioka |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,117,068 A | 9/2000 | Gourley |
| 6,124,989 A | 9/2000 | Ode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,196,967 B1 | 3/2001 | Lim |
| 6,201,646 B1 | 3/2001 | Togino |
| 6,201,648 B1 | 3/2001 | Togino |
| 6,210,322 B1 | 4/2001 | Byrne |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |

(56) References Cited

U.S. PATENT DOCUMENTS

| | | |
|---|---|---|
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,953 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,930,705 B2 | 6/2005 | Tanaka |
| 6,918,693 B2 | 7/2005 | Ota |
| 6,921,362 B2 | 7/2005 | Ouchi |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |

(56) References Cited

U.S. PATENT DOCUMENTS

| | | |
|---|---|---|
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Yashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,995,093 B2 | 6/2011 | Takeuchi |
| 7,976,462 B2 | 7/2011 | Wright |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 * | 5/2013 | Aizenfeld .......... A61B 1/00096 600/160 |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,585,584 B2 | 11/2013 | Ratnakar |
| 8,715,168 B2 | 5/2014 | Ratnakar |

(56) References Cited

U.S. PATENT DOCUMENTS

| | | |
|---|---|---|
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0004257 A1 | 1/2006 | Gilad |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Havol |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0185384 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0246506 A1 | 10/2007 | Hamazaki |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0221388 A1 | 7/2008 | Courtney |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |

(56) References Cited

U.S. PATENT DOCUMENTS

| | | |
|---|---|---|
| 2008/0275298 A1 | 11/2008 | Ratnakar |
| 2008/0312497 A1 | 12/2008 | Elmouelhi |
| 2009/0005643 A1 | 1/2009 | Smith |
| 2009/0023998 A1 | 1/2009 | Ratnakar |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2010/0326703 A1* | 12/2010 | Gilad .............. A61B 1/041 174/254 |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0232345 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172676 A1 | 7/2013 | Levy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0267778 A1 | 10/2013 | Rehe |
| 2013/0271588 A1 | 10/2013 | Kirma |
| 2013/0274551 A1 | 10/2013 | Kirma |
| 2013/0296649 A1 | 11/2013 | Kirma |
| 2013/0314521 A1 | 11/2013 | Satake |
| 2013/0317295 A1 | 11/2013 | Morse |
| 2014/0107418 A1 | 4/2014 | Ratnakar |
| 2014/0213850 A1 | 7/2014 | Levy |
| 2014/0364691 A1 | 12/2014 | Krivopisk |
| 2015/0164308 A1 | 6/2015 | Ratnakar |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |

(56) References Cited

FOREIGN PATENT DOCUMENTS

| | | |
|---|---|---|
| CN | 201108422 Y | 9/2008 |
| CN | 101385633 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 2010279539 | 12/1920 |
| JP | S5551270 | 5/1980 |
| JP | 55078932 | 6/1980 |
| JP | 61055657 | 11/1986 |
| JP | S6296616 | 6/1987 |
| JP | 6359332 | 11/1988 |
| JP | H0253701 | 4/1990 |
| JP | H02188709 A | 7/1990 |
| JP | H03116801 | 12/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 8122000657 | 5/1996 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325306 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049756 | 2/2004 |
| JP | 2009049754 | 2/2004 |
| JP | 2004129834 | 4/2004 |
| JP | 2004205779 A | 7/2004 |
| JP | 2004354888 A | 12/2004 |
| JP | 2005013557 A | 1/2005 |
| JP | 2005058547 | 3/2005 |
| JP | 2005253543 | 9/2005 |
| JP | 2005323874 A | 11/2005 |
| JP | 2006003549 A | 1/2006 |
| JP | 3765500 | 2/2006 |
| JP | 2006068109 | 3/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008/139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066788 | 6/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2013131578 | 3/2012 |
| WO | 2012056453 A2 | 5/2012 |
| WO | 2012077116 | 6/2012 |
| WO | 2012077117 A1 | 6/2012 |
| WO | 2012088201 A2 | 6/2012 |
| WO | 2012103266 | 8/2012 |
| WO | 2012120507 A1 | 9/2012 |
| WO | 2012153324 | 11/2012 |
| WO | 2013014673 | 1/2013 |

(56) References Cited

FOREIGN PATENT DOCUMENTS

| WO | 2013024476 | 2/2013 |
|---|---|---|
| WO | 2013043704 | 3/2013 |
| WO | 2013128136 | 9/2013 |
| WO | 2013144944 | 10/2013 |
| WO | 2014061023 | 4/2014 |
| WO | 2014160983 | 10/2014 |
| WO | 2014182728 | 11/2014 |

OTHER PUBLICATIONS

Office Action dated Jun. 3, 2015 for U.S. Appl. No. 13/992,014.
Office Action dated Feb. 17, 2015 for U.S. Appl. No. 13/882,004.
Office Action dated Mar. 6, 2015 for U.S. Appl. No. 13/413,059.
Office Action dated Mar. 12, 2005 for U.S. Appl. No. 13/822,908.
Office Action dated Jan. 15, 2015 for U.S. Appl. No. 13/190,968.
Office Action dated Feb. 13, 2015 for U.S. Appl. No. 13/713,449.
Office Action dated Nov. 26, 2014 for U.S. Appl. No. 13/713,466.
First Office Action for CN 2012800171292, dated Feb. 28, 2015.
Office Action dated May 1, 2015 for U.S. Appl. No. 13/992,021.
First offfice action for CN2011800627366, dated Feb. 25, 2015.
Office Action dated Aug. 4, 2015 for U.S. Appl. No. 13/557,114.
First Office Action for CN 2012800368972, dated Jun. 1, 2015.
Office Action dated Aug. 6, 2015 for U.S. Appl. No. 13/119,032.
Office Action dated Aug. 5, 2015 for U.S. Appl. No. 13/212,627.
Office Action dated Aug. 19, 2015 for U.S. Appl. No. 13/713,449.
Office Action dated Aug. 19, 2015 for U.S. Appl. No. 13/713,466.
Office Action for Chinese Patent Application No. 201180067259.2, dated May 29, 2015.
Office Action dated Jul. 21, 2015 for U.S. Appl. No. 13/992,021.
International Search Report for PCT/US2014/037010, dated Apr. 6, 2015.
Extended European Search Report for EP14186113.8, dated Apr. 1, 2015.
Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
International Search Report for PCT/EP2009/066726, dated Aug. 16, 2010.
International Search Report for PCT/IL20111/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL10/00476, dated Sep. 27, 2010, 2 pages.
International Search Report of PCT/IL2011/000745, dated May 8, 2012.
Notice of Allowance dated Jun. 8, 2015 for U.S. Appl. No. 13/413,252.
Notice of Allowance dated Jun. 8, 2015 for U.S. Appl. No. 13/984,028.
Prosecution File History for U.S. Appl. No. 13/190,968, dated Jul. 26, 2011 through Jun. 17, 2015.
Notice of Allowance dated Jun. 17, 2015 for U.S. Appl. No. 13/190,968.
Supplementary European Search Report for European Application No. EP12823972, dated May 13, 2015.
Corrected European Search Opinion for EP14186113.8, dated Apr. 29, 2015.
Office Action dated Oct. 7, 2015 for U.S. Appl. No. 13/882,004.
Extended European Search Report for EP11846069.0, dated Apr. 24, 2014.
Office Action dated Nov. 3. 2015 for U.S. Appl. No. 13/992,014.
Office Action dated Nov. 16, 2015 for U.S. Appl. No. 13/557,114.
Office Action dated Nov. 24, 2015 for U.S. Appl. No. 13/413,059.
Office Action dated Dec. 4, 2015 for U.S. Appl. No. 13/822,908.
Notice of Allowance dated Dec. 15, 2014 for U.S. Appl. No. 13/713,466.
Notice of Allowance dated Dec. 15, 2015 for U.S. Appl. No. 13/713,466.
Notice of Allowance dated Dec. 23, 2015 for U.S. Appl. No. 13/992,021.
International Search Report for PCT/US2014/032265, dated Oct. 7, 2014.
Second office action for Chinese Patent Application No. 201180062736.6, dated Oct. 12, 2015.
Office Action for Japanese Patent Application No. 2013-535586, dated Sep. 24, 2015.
Office Action for Japanese Patent Application No. 2013-542668, dated Oct. 1, 2015.
Extended European Search Report for EP12817452.1, dated Mar. 9, 2015.
Office Action dated Jan. 12, 2016 for U.S. Appl. No. 13/713,466.
Office Action for Chinese Patent Application No. 201280038808.8, dated May 20, 2015.
Extended European Search Report for EP11847191.1, dated Jan. 15, 2016.
Supplementary European Search Report for EP118471911, dated Jan. 16, 2015.
Examination Report for Canadian Patent Application No. CA2765559, dated Jan. 18, 2016.
Office Action dated Oct. 5, 2016 for U.S. Appl. No. 14/271,270.
Office Action dated Feb. 14, 2017 for U.S. Appl. No. 14/271,270.
Notice of Allowance dated May 15, 2017 for U.S. Appl. No. 14/271,270.
Examination Search Report for Canadian Patent Application No. CA2765559, dated Jan. 18, 2016.
Second Office Action for Chinese Patent Applicatio No. CN201280038808.8, dated Feb. 25, 2016.
First Office Action for Chinese Patent Application No. CN201380053351.2, dated Mar. 2, 2016.
Office Action for Japanese Patent Application No. JP2014-522214, dated Apr. 26, 2016.
Office Action for Japanese Patent Application No. JP2014-525562, dated Apr. 26, 2016.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Office Action dated Mar. 24, 2016 for U.S. Appl. No. 13/212,627.
Office Action dated Mar. 28, 2016 for U.S. Appl. No. 13/119,032.
Office Action dated Mar. 23, 2016 for U.S. Appl. No. 13/713,449.
Office Action dated Jun. 30, 2016 for U.S. Appl. No. 13/655,120.
Extended European Search Report for application No. EP12755186, completed on May 23, 2016.
Second Office Action for Chinese Patent Application No. 201180067259.2, dated Mar. 30, 2016.
Supplementary European Search Report for EP13847670, completed on May 19, 2016.
Office Action dated Apr. 28, 2016 for U.S. Appl. No. 13/992,014.
Notice of Allowance dated Aug. 26, 2016 for U.S. Appl. No. 13/212,627.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Notice of Allowance dated Nov. 9, 2016 for U.S. Appl. No. 13/557,114.
Third Office Action for Chinese Patent Application No. 201180067259.2, dated Oct. 21, 2016.
First Office Action for Chinese Patent Application No. 201480036105.0, dated Nov. 30, 2016.

(56) References Cited

OTHER PUBLICATIONS

Office Action for Chinese Patent Application No. 201180062736.6, dated Dec. 23, 2016.
Office Action for Japanese Patent Application No. 2016-105009, dated Jan. 16, 2017.
Office Action for Chinese Patent Application No. 201380053351.2, dated Dec. 13, 2016.
Extended European Search Report for EP14795278.2, dated Jan. 30, 2017.
First Office Action for EP11847191.1, dated Feb. 21, 2017.
Office Action dated Mar. 21, 2017 for U.S. Appl. No. 13/992,014.
Notice of Allowance dated Apr. 18, 2017 for U.S. Appl. No. 13/713,449.
Examination Report for EP11846069.0, dated Feb. 21, 2017.
Extended European Search Report for EP11826512.3, dated Apr. 6, 2017.
Office Action dated May 23, 2017 for U.S. Appl. No. 13/655,120.

\* cited by examiner

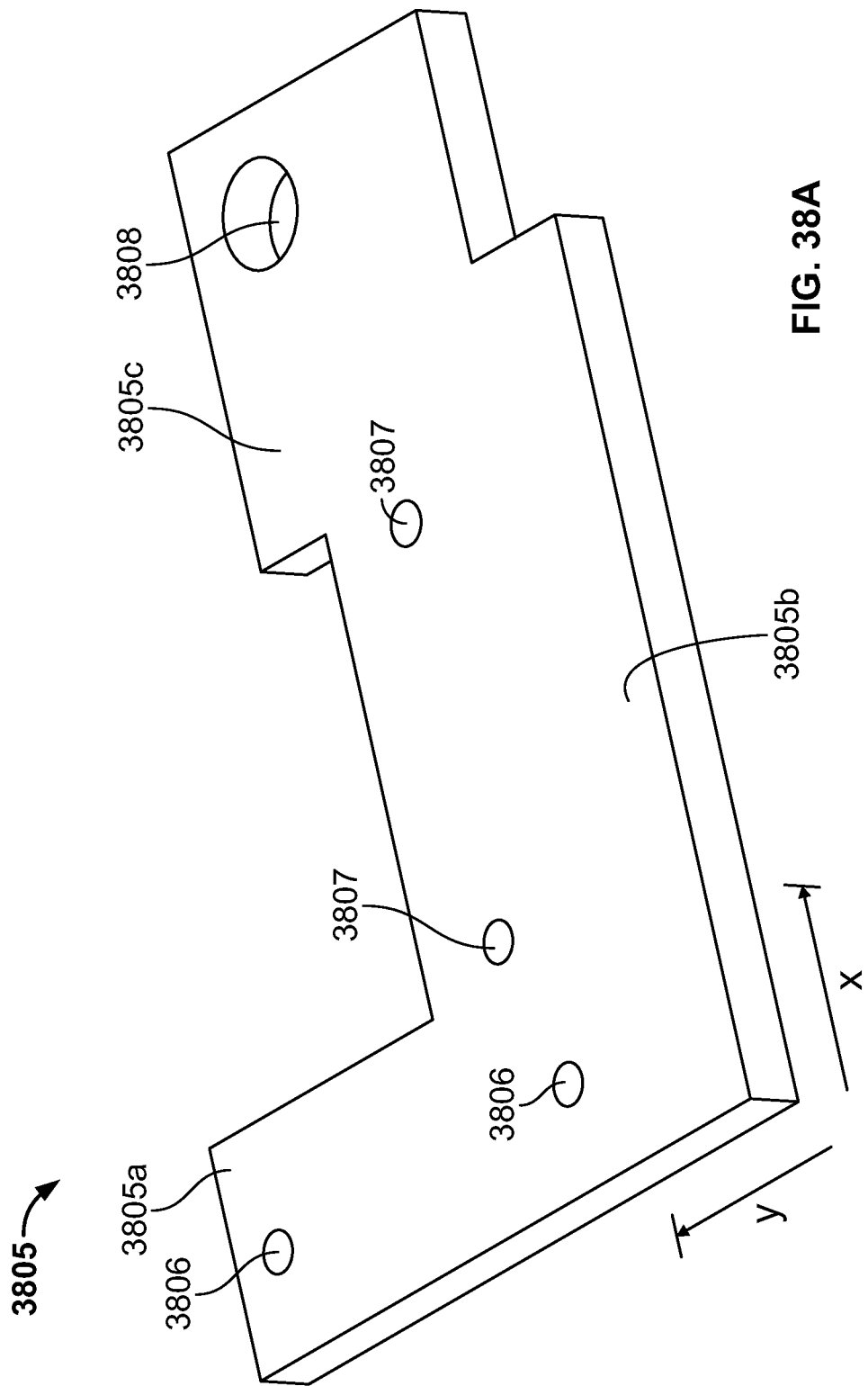

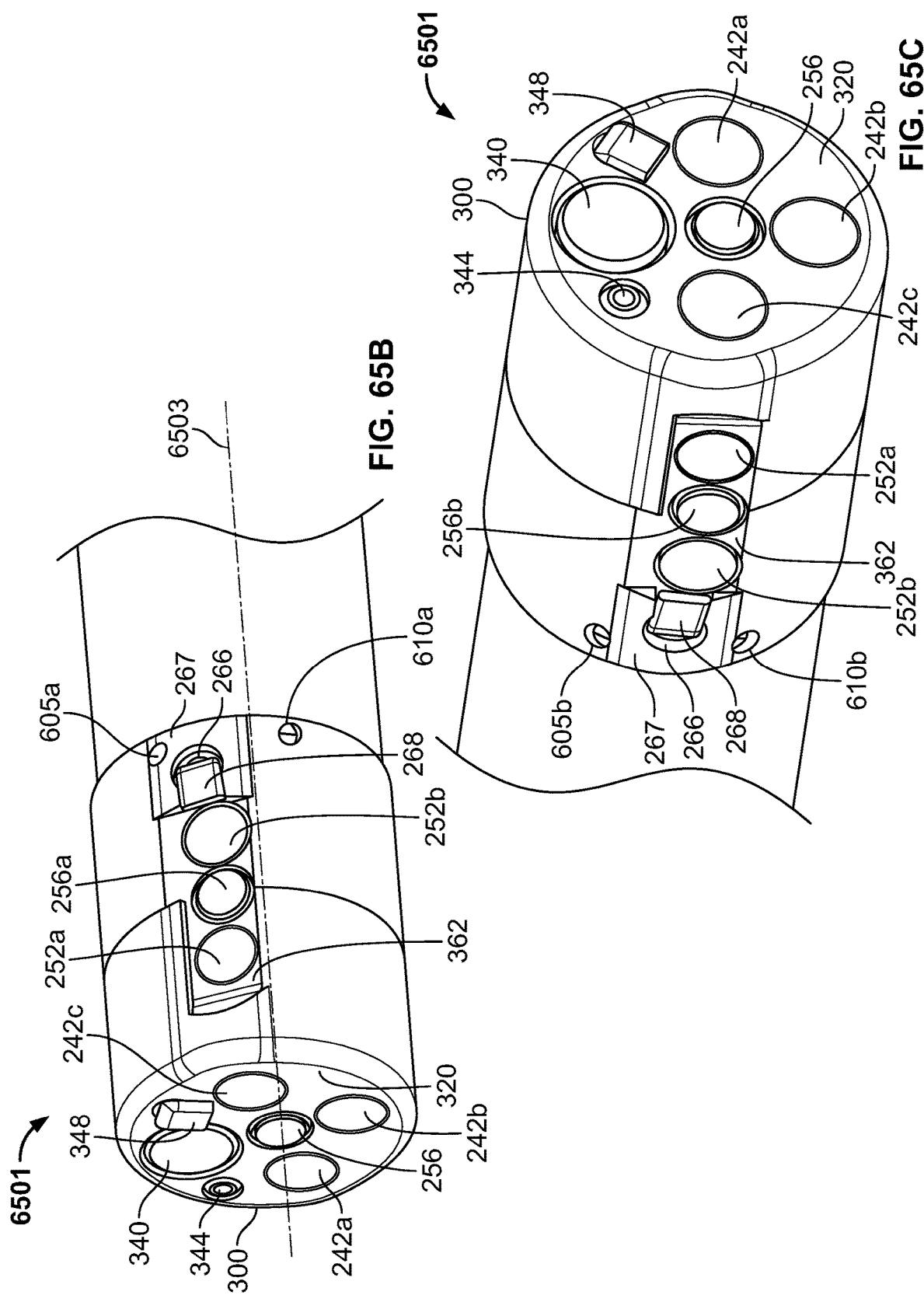

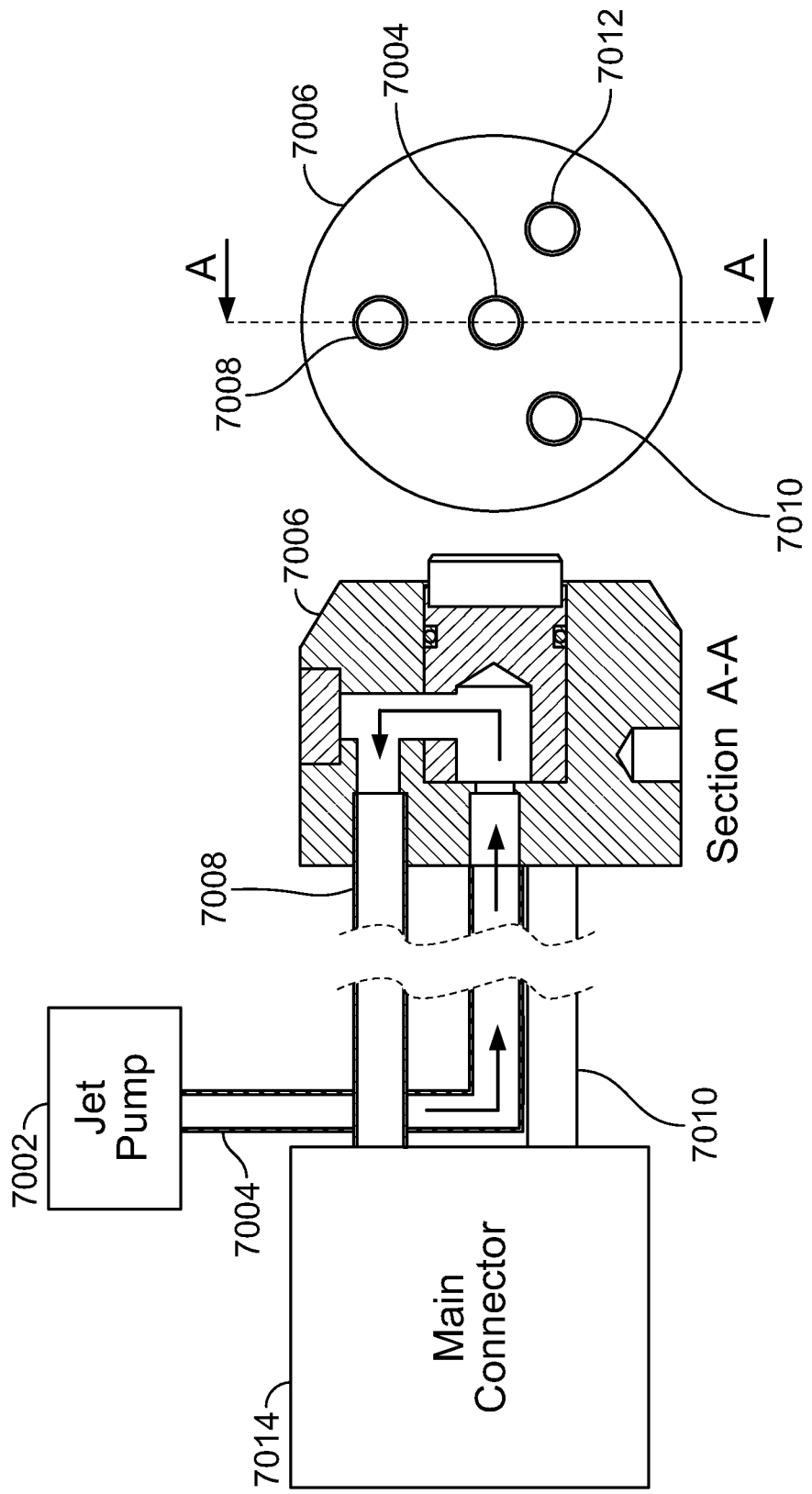

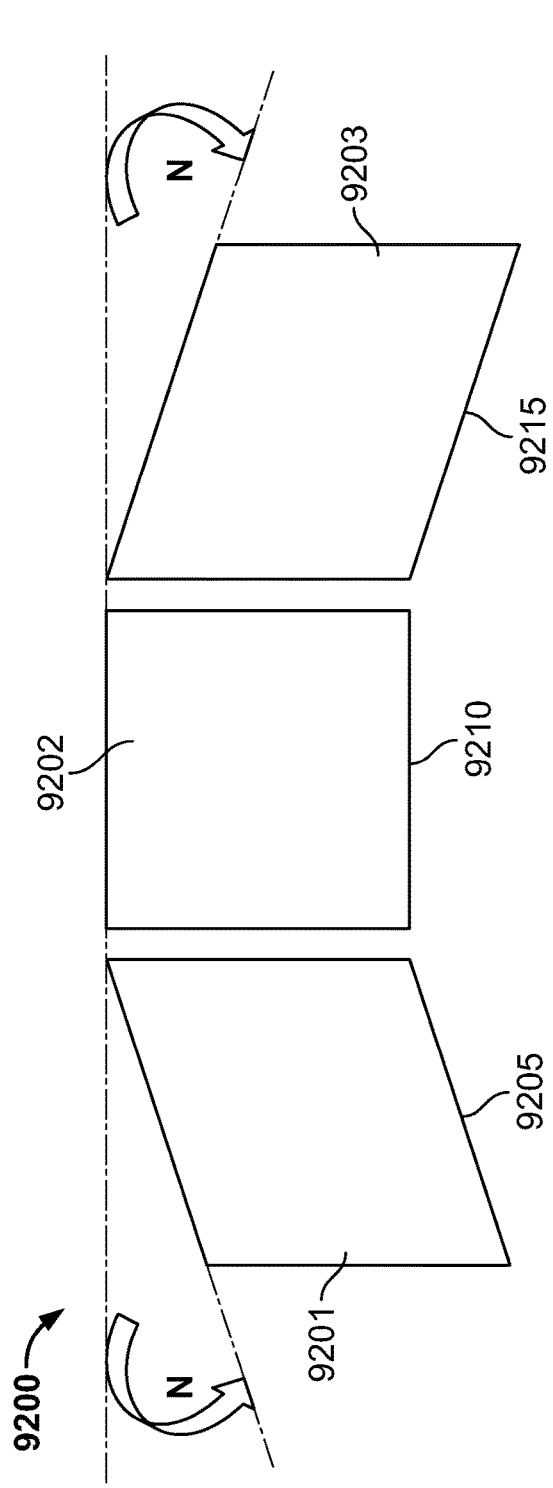
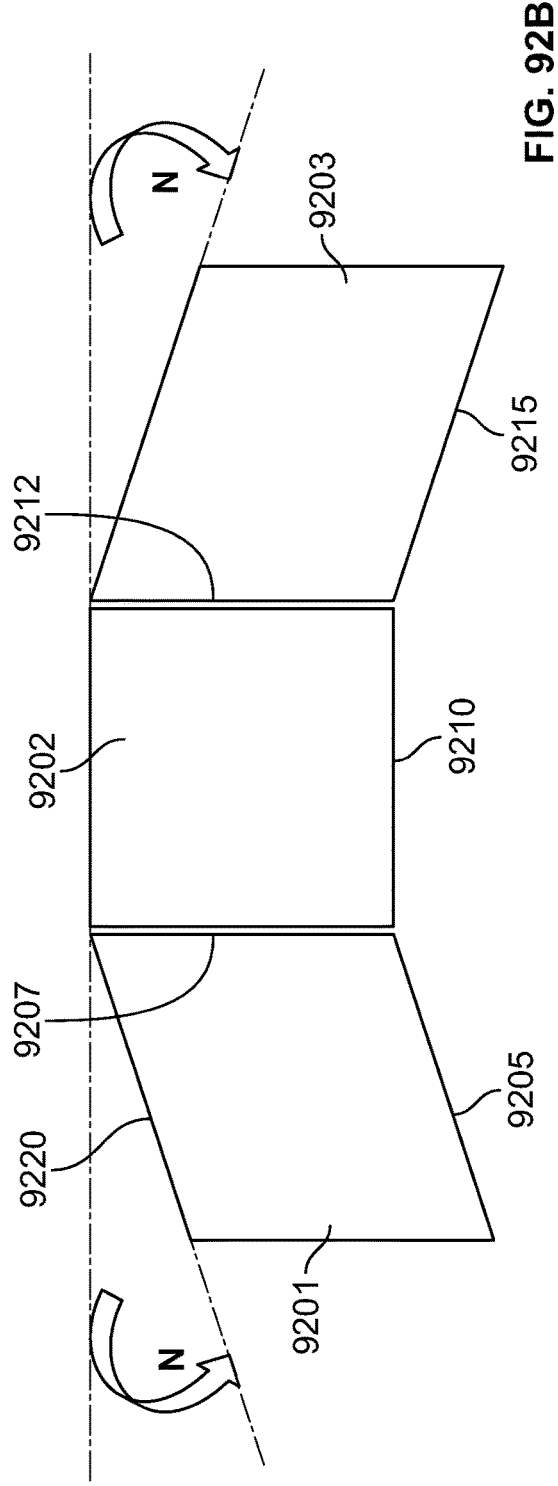

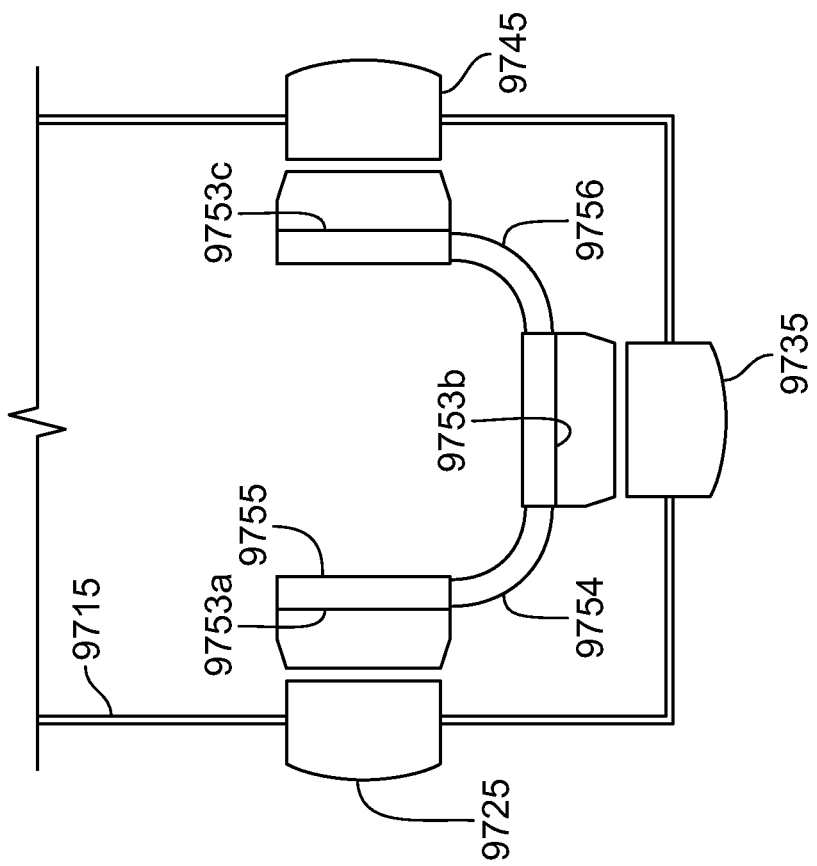
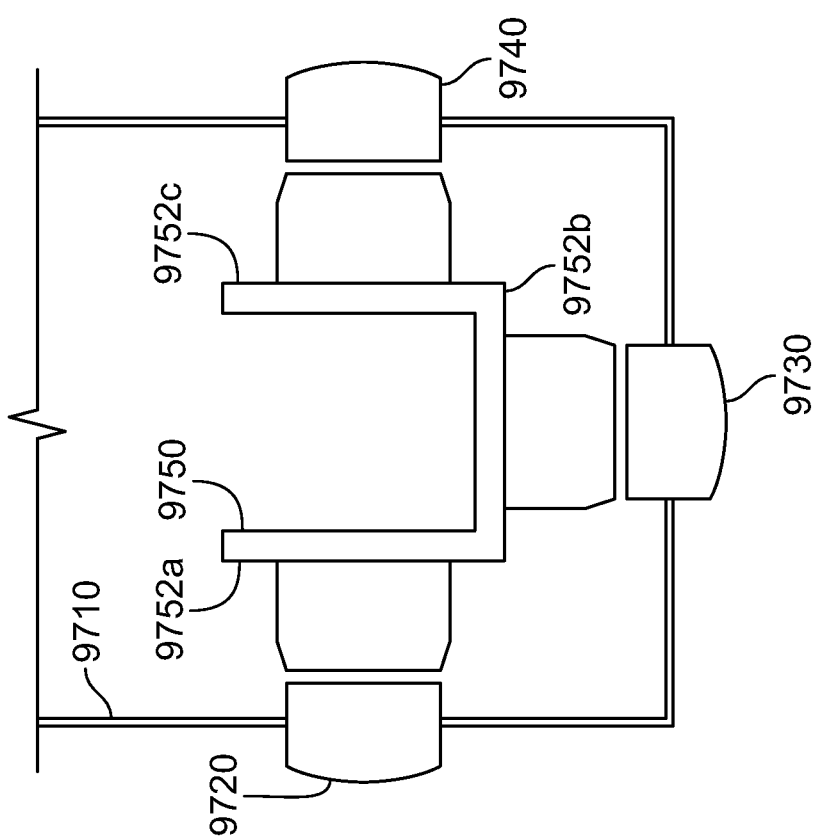
FIG. 97B
FIG. 97A

| Signal | Camera | Connector Type (in Main Connector) | Note |
|---|---|---|---|
| Pre-Video Channel A | Front | Coax Only | 1 |
| Pre-Video Channel B | Side 1 | Coax Only | 2 |
| Pre-Video Channel C | Side 2 | Coax Only | 3 |
| H1 (Horizontal HF Sync) | Jointed for All Cameras | Coax Only | 4 |
| H2 (Horizontal HF Sync) | Jointed for All Cameras | Coax Only | 5 |
| RG (Horizontal HF Sync) | Jointed for All Cameras | Coax Only | 6 |
| V01 (Vertical LF Sync) | Jointed for All Cameras | Single Pin | 7 |
| V02 (Vertical LF Sync) | Jointed for All Cameras | Single Pin | 8 |
| V03 (Vertical LF Sync) | Jointed for All Cameras | Single Pin | 9 |
| V04 (Vertical LF Sync) | Jointed for All Cameras | Single Pin | 10 |
| Vsub1 | Front | Single Pin or Coax-TBD | 11 |
| Vsub2 | Side 1 | Single Pin or Coax-TBD | 12 |
| Vsub3 | Side 2 | Single Pin or Coax-TBD | 13 |
| Vdd | Jointed for All Cameras | Single Pin | 14 |
| VL | Jointed for All Cameras | Single Pin | 15 |
| LED 1 | Front | Single Pin | 16 |
| LED 2 | Side 1 | Single Pin | 17 |
| LED 3 | Side 2 | Single Pin | 18 |
| +3.3V Secondary Insulated | Scope Control Power | Single Pin | 19 |
| SCL_1 | I2C | Single Pin | 20 |
| SDA_1 | I2C | Single Pin | 21 |
| Functional GND | All Scope | Single Pins + Connector Body | 22 |

FIG. 100

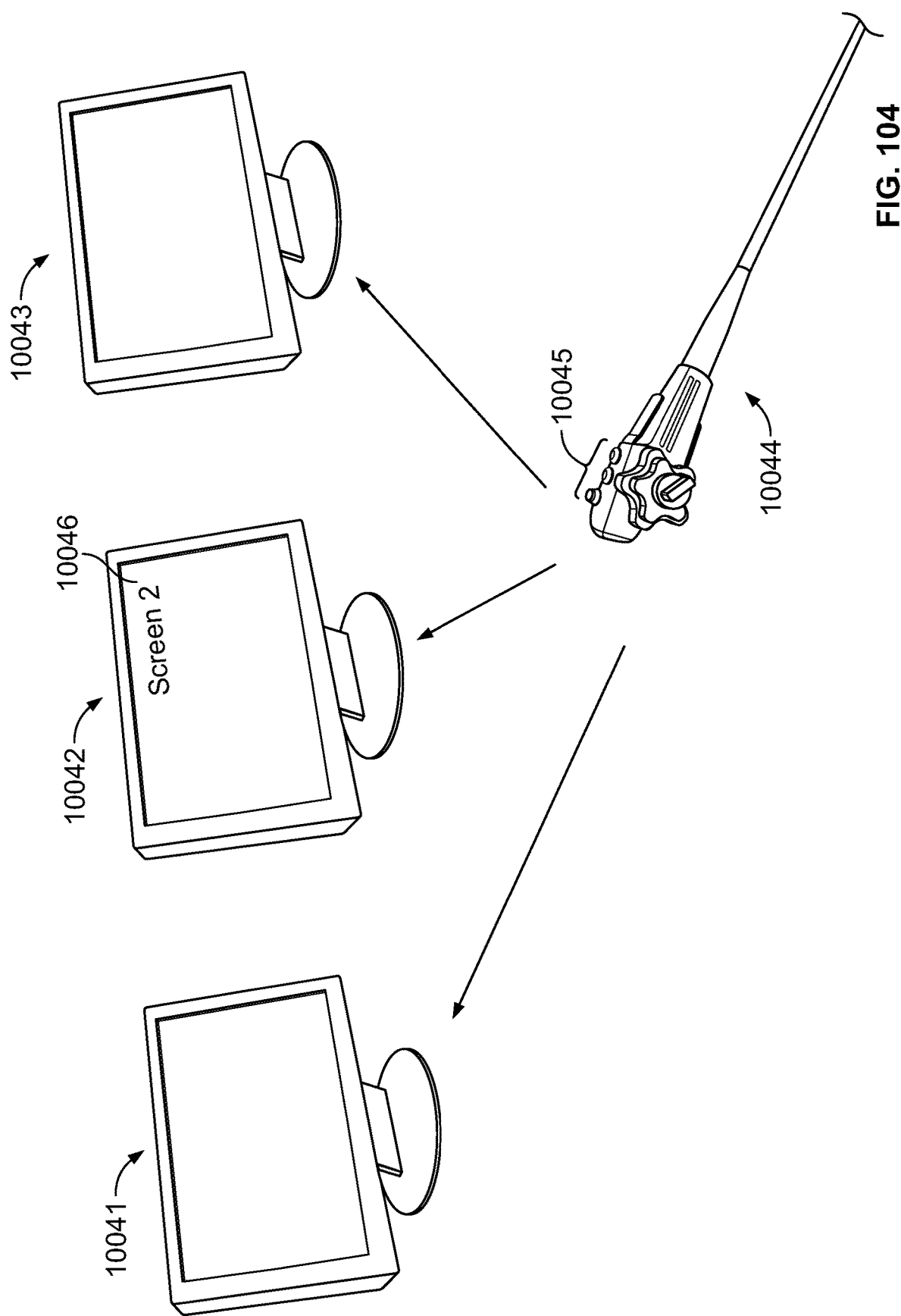

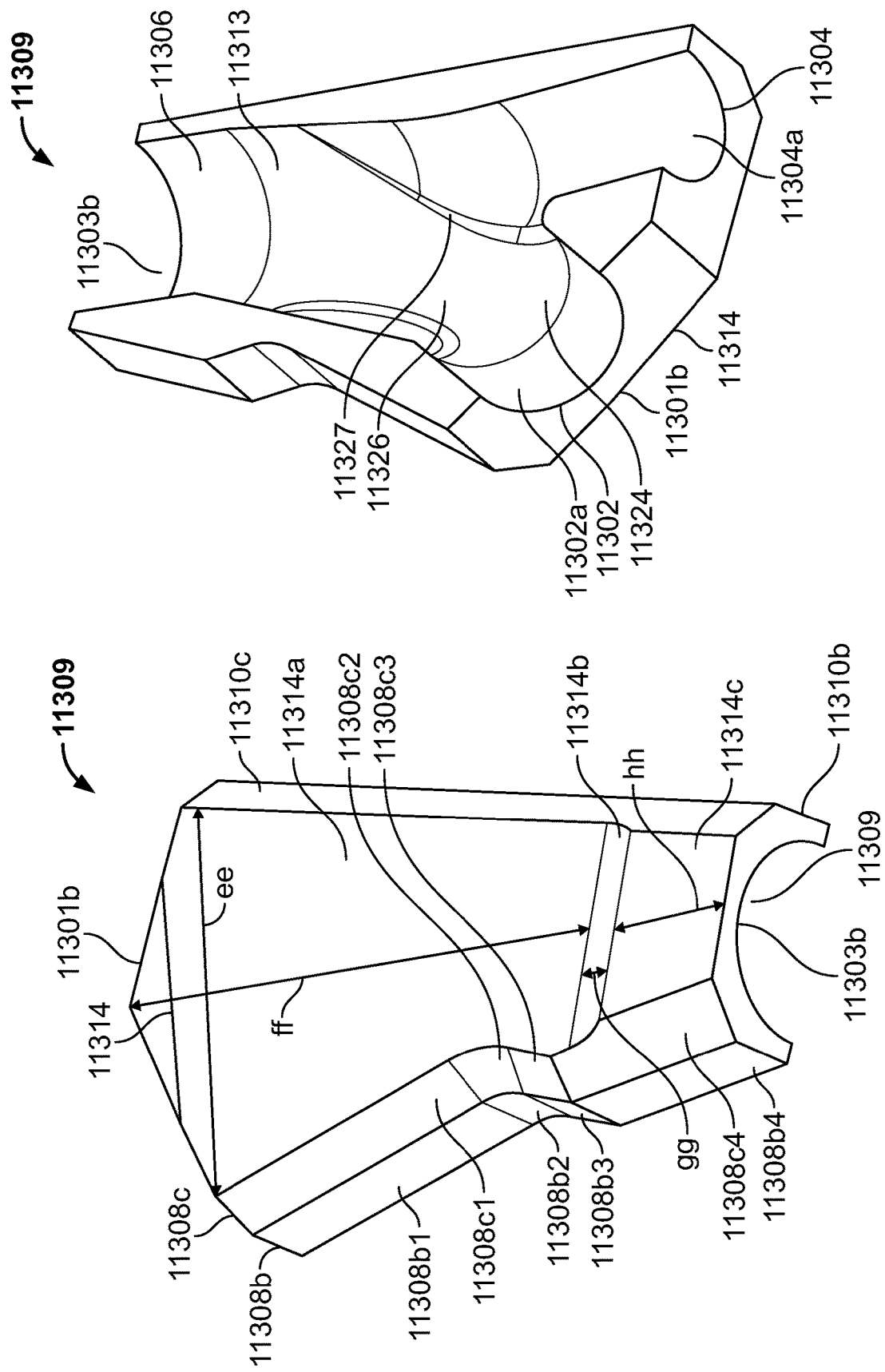

IMAGE CAPTURE ASSEMBLY FOR USE IN A MULTI-VIEWING ELEMENTS ENDOSCOPE

CROSS-REFERENCE TO RELATED APPLICATIONS

The present application is a continuation application of U.S. patent application Ser. No. 14/271,270, entitled "Image Capture Assembly for Use in a Multi-Viewing Elements Endoscope" and filed on May 6, 2014, which relies on, for priority, the following United States Provisional Patent Applications, which are also herein incorporated by reference in their entirety:

U.S. Provisional Patent Application No. 61/820,100, entitled "Image Capture Assembly for Use with Endoscope" and filed on May 6, 2013;

U.S. Provisional Patent Application No. 61/821,579, entitled "Operational Interface in a Multi-Viewing Element Endoscope" and filed on May 9, 2013;

U.S. Provisional Patent Application No. 61/822,563, entitled "Systems and Methods of Displaying a Plurality of Contiguous Images with Minimal Distortion", and filed on May 13, 2013.

U.S. Provisional Patent Application No. 61/824,236, entitled "Multi-Viewing Endoscope" and filed on May 16, 2013;

U.S. Provisional Patent Application No. 61/824,653, entitled "Interface Unit for Endoscopic System" and filed on May 17, 2013;

U.S. Provisional Patent Application No. 61/824,863, entitled "Multi-Viewing Element Endoscope Having Two Front Service Channels" and filed on May 17, 2013;

U.S. Provisional Patent Application No. 61/828,039, entitled "Multi-Viewing Element Endoscope Having Two Front Service Channels" and filed on May 28, 2013;

U.S. Provisional Patent Application No. 61/840,691, entitled "Multi-Viewing Element Endoscope With Modular Imaging Units" and filed on Jun. 28, 2013;

U.S. Provisional Patent Application No. 61/840,706, entitled "Multi-Jet Distributor For An Endoscope" and filed on Jun. 28, 2013;

U.S. Provisional Patent Application No. 61/841,863, entitled "Circuit Board Assembly of a Multi Viewing Elements Endoscope" and filed on Jul. 1, 2013;

U.S. Provisional Patent Application No. 61/881,661, entitled "Circuit Board Assembly of An Endoscope" and filed on Sep. 24, 2013;

U.S. Provisional Patent Application No. 61/897,896, entitled "Circuit Board Assembly of a Multi Viewing Elements Endoscope" and filed on Oct. 31, 2013;

U.S. Provisional Patent Application No. 61/899,465, entitled "Illuminator Circuit Board Assembly of An Endoscope" and filed on Nov. 4, 2013;

U.S. Provisional Patent Application No. 61/910,863, entitled "Multi-Jet Endoscope" and filed on Dec. 2, 2013;

U.S. Provisional Patent Application No. 61/925,080, entitled "Circuit Board Assembly of a Multi Viewing Elements Endoscope" and filed on Jan. 8, 2014;

U.S. Provisional Patent Application No. 61/926,732, entitled "Multi-Jet Endoscope" and filed on Jan. 13, 2014;

U.S. Provisional Patent Application No. 61/935,647, entitled "Circuit Board Assembly of An Endoscope" and filed on Feb. 4, 2014;

U.S. Provisional Patent Application No. 61/936,562, entitled "Method and System for Video Processing In A Multi-Viewing Element Endoscope" and filed on Feb. 6, 2014;

U.S. Provisional Patent Application No. 61/948,009, entitled "Manifold for Multi-Viewing Element Endoscope" and filed on Mar. 4, 2014;

U.S. Provisional Patent Application No. 61/950,696, entitled "Service Channel Connector of An Endoscope" and filed on Mar. 10, 2014;

U.S. Provisional Patent Application No. 61/968,436, entitled "System for Connecting and Disconnecting A Main Connector and A Main Control Unit of An Endoscope" and filed on Mar. 21, 2014; and U.S. Provisional Patent Application No. 61/987,984, entitled "Circuit Board Assembly of An Endoscope" and filed on May 2, 2014.

The present specification is also a continuation-in-part application of U.S. patent application Ser. No. 13/984,028, entitled "Multi-Element Cover for a Multi-Camera Endoscope" and filed on Aug. 22, 2013, which is a 371 National Stage Entry of PCT Application Number PCT/IL2012/050037, of the same title and filed on Feb. 6, 2012, which, in turn, relies upon U.S. Provisional Patent Application No. 61/439,948, filed on Feb. 7, 2011, for priority, and is herein incorporated by reference.

The present specification is also a continuation-in-part application of U.S. patent application Ser. No. 13/992,021, entitled "Fluid Channeling Component of a Multi-Camera Endoscope" and filed on Jun. 6, 2013, which is a 371 National Stage Entry of PCT Application Number PCT/IL2011/050050, entitled "Flexible Electronic Circuit Board Multi-Camera Endoscope" and filed on Dec. 8, 2011, which, in turn, relies upon U.S. Provisional Patent Application No. 61/421,240, filed on Dec. 9, 2010, for priority, and is herein incorporated by reference.

The present specification is also a continuation-in-part application of U.S. patent application Ser. No. 13/992,014, entitled "Flexible Electronic Circuit Board for a Multi-Camera Endoscope" and filed on Jun. 6, 2013, which is a 371 National Stage Entry of PCT Application Number PCT/IL2011/050049, of the same title and filed on Dec. 8, 2011, which, in turn, relies upon U.S. Provisional Patent Application No. 61/421,238, filed on Dec. 9, 2010, for priority, and is herein incorporated by reference.

The present specification is also a continuation-in-part application of U.S. patent application Ser. No. 13/882,004, entitled "Optical Systems for Multi-Sensor Endoscopes" and filed on May 23, 2013, which is a 371 National Stage Entry of PCT Application Number PCT/IL2011/000832, of the same title and filed on Oct. 27, 2011, which, in turn, relies upon U.S. Provisional Patent Application No. 61/407,495, filed on Oct. 28, 2010, for priority, and is herein incorporated by reference.

The present specification is also a continuation-in-part application of U.S. patent application Ser. No. 13/822,908, entitled "Multi-Camera Endoscope Having Fluid Channels" and filed on Mar. 13, 2013, which is a 371 National Stage Entry of PCT Application Number PCT/IL2011/000745, of the same title and filed on Sep. 20, 2011, which, in turn, relies upon U.S. Provisional Patent Application No. 61/384,354, filed on Sep. 20, 2010, for priority, and is herein incorporated by reference.

The present specification is also a continuation-in-part application of U.S. patent application Ser. No. 13/713,449, entitled "Removable Tip Endoscope" and filed on Dec. 13, 2012, which, in turn, relies upon U.S. Provisional Patent Application No. 61/569,796, of the same title and filed on Dec. 13, 2011, for priority, and is herein incorporated by reference.

The present application is also a continuation-in-part application of the following United States Patent Applications, which are herein incorporated by reference in their entirety:

U.S. patent application Ser. No. 13/655,120, entitled "Multi-Camera Endoscope" and filed on Oct. 18, 2012;

U.S. patent application Ser. No. 13/212,627, entitled "Multi-Viewing Element Endoscope" and filed on Aug. 18, 2011; and U.S. patent application Ser. No. 13/190,968, entitled "Multi-Camera Endoscope" and filed on Jul. 26, 2011, all of which are continuation-in-part applications of U.S. patent application Ser. No. 13/119,032, entitled "Multi-Camera Endoscope" and filed on Jul. 15, 2011, which is a 371 National Stage Entry of PCT Application Number PCT/IL2010/000476, of the same title and filed on Jun. 16, 2010, which, in turn, relies upon U.S. Provisional Patent Application No. 61/218,085, for priority.

The present specification is also a continuation-in-part application of U.S. patent application Ser. No. 13/413,252, entitled "Multi Camera Endoscope Assembly Having Multiple Working Channels" and filed on Mar. 6, 2012, which, in turn, relies upon U.S. Provisional Patent Application No. 61/449,746, of the same title and filed on Mar. 7, 2011, for priority, and is herein incorporated by reference.

The present specification is also a continuation-in-part application of U.S. patent application Ser. No. 13/413,141, entitled "Multi Camera Endoscope Having a Side Service Channel" and filed on Mar. 6, 2012, which, in turn, relies upon U.S. Provisional Patent Application No. 61/449,743, of the same title and filed on Mar. 7, 2011, for priority, and is herein incorporated by reference.

The present specification is also a continuation-in-part application of U.S. patent application Ser. No. 13/413,059, entitled "Endoscope Circuit Board Assembly" and filed on Mar. 6, 2012, which, in turn, relies upon U.S. Provisional Patent Application No. 61/449,741, of the same title and filed on Mar. 7, 2011, for priority, and is herein incorporated by reference.

The present specification is also a continuation-in-part application of U.S. patent application Ser. No. 13/412,974, entitled "Camera Assembly for Medical Probes" and filed on Mar. 6, 2012, which, in turn, relies upon U.S. Provisional Patent Application No. 61/449,739, of the same title and filed on Mar. 7, 2011, for priority, and is herein incorporated by reference.

The present specification is also related to the following United States Provisional Patent Applications:

U.S. Provisional Patent Application No. 61/806,065, entitled "Multi Camera, Multi Jet Endoscope Having Two Side Service Channels" and filed on Mar. 28, 2013;

U.S. Provisional Patent Application No. 61/812,709, entitled "Multi Camera, Multi Jet Endoscope Having Two Side Service Channels" and filed on Apr. 16, 2013; and U.S. Provisional Patent Application No. 61/817,237, entitled "Method and System for Video Processing in a Multi-Viewing Element Endoscope" and filed on Apr. 29, 2013.

All of the above-mentioned applications are herein incorporated by reference in their entirety.

FIELD

The present specification relates generally to a multi-viewing element endoscope assembly comprising a tip section with a modular or component-based structure thus enabling the tip section to be compactly packed in accordance with various embodiments.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used typically have a front camera for viewing the internal organ, such as the colon, an illuminator, a fluid injector for cleaning the camera lens and sometimes also the illuminator, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes are their limited field of view and their limited options for operating medical and surgical tools.

There is thus a need in the art for endoscopes, such as colonoscopes, that provide a broader field of view and allow extended access of surgical tools and also enable efficient packing of all necessary elements in the tip section, while maintaining their functionality.

SUMMARY

The following embodiments and aspects thereof are described and illustrated in conjunction with systems, tools and methods, which are meant to be exemplary and illustrative, not limiting in scope. The present application discloses numerous embodiments.

The present specification discloses an image capturing assembly adapted to be used in an endoscope, the assembly comprising: a manifold having a proximal base with a first length and a first width and a casing extending outward from said proximal base, wherein said casing has a second length and second width and wherein said first length is less than the second length and the first width is greater than the second width; a partially enclosed housing wherein said partially enclosed housing is adapted to physically attach to the manifold; a LED carrier substrate, wherein said LED carrier substrate is adapted to be foldable and to carry a plurality of LEDs; a flexible optical carrier substrate, wherein said flexible optical carrier substrate is adapted to be foldable and to carry a plurality of camera sensors; and a tip cover adapted to cover said manifold, said partially enclosed housing, said LED carrier substrate, and said flexible optical carrier substrate.

In one embodiment, the manifold is a unitary part. In one embodiment, the proximal base is substantially cylindrical.

In one embodiment, the casing comprises at least one continuous channel that extends from the proximal base throughout the second length. Further, in one embodiment, the proximal base comprises a plurality of channels extending through the entire first length wherein at least one of said channels together with said continuous channel in the casing, creates a fluidically isolated channel extending through the proximal base and casing.

In one embodiment, the manifold combined with the partially enclosed housing creates a substantially cylindrical housing.

Optionally, in one embodiment, the partially enclosed housing comprises a protrusion. Further, in one embodiment, the proximal base comprises a groove wherein said groove is adapted to receive said protrusion.

In one embodiment, the manifold combined with the partially enclosed housing create a substantially cylindrical housing having openings and an internal volume, wherein the flexible optical carrier substrate is adapted to be folded to fit within said internal volume, and wherein said openings are positioned to receive said camera sensors. In one embodiment, the substantially cylindrical housing is adapted to receive a folded LED carrier substrate. Further, in one embodiment, the substantially cylindrical housing in combination with the folded LED carrier and folded flexible optical carrier creates an assembled image capture assembly having a front facing camera together with at least one LED and a side facing camera together with at least one LED.

In one embodiment, the tip cover comprises a first portion that covers a first half of said assembled image capturing assembly and a second portion that covers a second half of said assembled image capturing assembly.

The present specification also discloses an image capturing assembly adapted to be used in an endoscope, the assembly comprising a manifold having a continuous fluidically isolated channel extending through its length; a curved member wherein said curved member is adapted to physically attach to the manifold; a discrete illuminator carrier substrate, wherein said discrete illuminator carrier substrate is foldable and comprises at least two discrete illuminators; an optical assembly positioned on a flexible substrate comprising at least two viewing elements; and a tip cover adapted to cover said manifold, said curved member, said discrete illuminator carrier substrate, and said flexible optical carrier substrate, wherein the at least two discrete illuminators, the at least two viewing elements, and the optical assembly are configured to fit within a maximum volume in a range of 2.75 cm$^3$ to 3.5 cm$^3$, where each of the at least two viewing elements is configured to generate a field of view ranging from 120 to 180 degrees, a depth of field ranging from 3 to 100 mm, and a peripheral distortion of less than 80%, without reliance on any aspherical components, and wherein the optical assembly has a maximum focal length in a range of 1 mm go 1.4 mm.

In one embodiment, each viewing element has a field of view having a depth of field ranging from 3 mm to 100 mm wherein the first and second viewing elements are positioned such that the field of view of the first viewing element intersects with the field of view of the second viewing element. In one embodiment, the field of view of the first viewing element intersects with the field of view of the second viewing element within 15 mm from the first viewing element or the second viewing element.

In one embodiment, the maximum focal length is 1.2 mm.

The present specification also discloses an endoscopic tip having a distal face and side edges extending from said distal face, wherein the distal face and side edges together define an internal volume of said tip, said tip comprising: a flexible substrate positioned within the internal volume comprising a central carrier portion and two parallel strips, wherein the two strips extend from the central carrier portion at a second end; a first arm extending from the central carrier portion and connecting said second end of said central carrier portion with a first of said parallel strips, wherein said first arm is flexible and is configured to have a first discrete front illuminator mounted thereon; a second arm extending from the central carrier portion and connecting said second end of said central carrier portion with a second of said parallel strips, wherein said second arm is flexible and is configured to have a second discrete front illuminator mounted thereon; and a flexible substrate positioned within the internal volume and comprising a front viewing element, wherein the front viewing element is positioned facing outward from the distal face and wherein at least one of the first and second arms is configured such that the front viewing element is positioned adjacent at least one of the first and second discrete front illuminators within a plane defined by the distal face.

In one embodiment, the first and second arms are configured such that the front viewing element is positioned between the first and second discrete front illuminators within a plane defined by the distal face.

In one embodiment, the endoscopic tip further comprises a third discrete front illuminator positioned on said central carrier portion and between and below said first and second arms.

In one embodiment, the endoscopic tip further comprises a first protrusion extending from the first of said two parallel strips, wherein the first protrusion is flexible and has a first discrete side illuminator mounted thereon, and a first side viewing element, wherein the first side viewing element is positioned facing outward from a first of the side edges.

In one embodiment, the first protrusion is configured such that the first side viewing element is positioned adjacent the first discrete side illuminator within a plane defined by the first of the side edges.

In one embodiment, the endoscopic tip further comprises a second protrusion extending from the first of said two parallel strips, wherein the second protrusion is flexible and has a second discrete side illuminator mounted thereon.

In one embodiment, the second protrusion is configured such that the first side viewing element is positioned between the first and second discrete side illuminators within a plane defined by the first of the side edges.

In one embodiment, the endoscopic tip further comprises a third protrusion extending from the second of said two parallel strips, wherein the third protrusion is flexible and has a third discrete side illuminator mounted thereon, and a second side viewing element, wherein the second side viewing element is positioned facing outward from a second of the side edges.

In one embodiment, the third protrusion is configured such that the second side viewing element is positioned adjacent the third discrete side illuminator within a plane defined by the second of the side edges.

In one embodiment, the endoscopic tip further comprises a fourth protrusion extending from the second of said two parallel strips, wherein the fourth protrusion is flexible and has a fourth discrete side illuminator mounted thereon.

In one embodiment, the fourth protrusion is configured such that the second side viewing element is positioned between the third and fourth discrete side illuminators within a plane defined by the second of the side edges.

The present specification also discloses an endoscope configured to provide quasi-simultaneously N views, N being greater than 1, said endoscope comprising N optical systems configured to collect light from directions associated with said N views, and further comprising M image capturing devices, where M is smaller than N, and said image capturing devices are configured to capture light collected by said N optical systems, thereby providing N views quasi-simultaneously.

Optionally, in one embodiment, at least one of said M image capturing devices comprises a CCD. In one embodiment, M=1.

In one embodiment, the image capturing device comprises a single planar light sensitive surface. In one embodiment, each of said optical systems is configured to transfer collected light onto an associated portion of said planar light-sensitive surface.

In one embodiment, N=3.

In one embodiment, a first optical system collects light from a first direction substantially facing said light sensitive surface, and a second optical system and a third optical system, respectively, collect light from directions substantially perpendicular to said first direction.

In one embodiment, at least two of said optical systems are configured to transfer collected light onto a same portion of said planar light-sensitive surface. In one embodiment, the endoscope further comprises a step-wise rotating optical element configured to be controllably positioned in at least two positions corresponding to said at least two optical systems, respectively, wherein in each such position said step-wise rotating optical element allows transfer of collected light from said respective optical system to said portion of said planar light-sensitive surface.

Optionally, in one embodiment, said step-wise rotating optical element comprises a mirror. In one embodiment, said mirror comprises a semi transparent portion.

Optionally, in another embodiment, said step-wise rotating optical element comprises a lens.

Optionally, in one embodiment, the endoscope further comprises at least one shutter operable to be shut and opened synchronously with said step-wise rotating optical element.

In one embodiment, said image capturing device comprises N planar light sensitive surfaces, and each of said optical systems is configured to transfer light to one of said N planar light sensitive surfaces, respectively.

In one embodiment, said image capturing device is substantially rigid and said N planar light sensitive surfaces are tilted at a fixed angle relative to one another.

In one embodiment, said image capturing device comprises a substantially flexible portion allowing to controllably tilt at an angle one of said N planar light sensitive surfaces relative to another one of said N planar light sensitive surfaces.

In one embodiment, said image capturing device comprises two planar light sensitive surfaces, aligned back to back thereby facing substantially opposite directions.

In one embodiment, M is greater than one and N is greater than two and at least two of said optical systems transfer light onto a light sensitive planar element of one of said image capturing devices. In one embodiment, M is equal to two and N is equal to three.

The present specification also discloses an endoscopic tip comprising: a first lens positioned on a front face of said tip; a second lens positioned on a lateral side of said tip; a third lens positioned on a lateral side of said tip and substantially opposite said second lens; an imager having a plurality of light sensitive surfaces; a first light guide for directing light from said first lens to one of said plurality of light sensitive surfaces; a second light guide for directing light from said second lens to a second of said plurality of light sensitive surfaces; and, a third light guide for directing light from said third lens to a third one of said plurality of light sensitive surfaces; wherein light waves passing through each of said first, second, and third light guides are isolated from each other.

The present specification also discloses an endoscopic tip comprising: a first lens positioned on a front face of said tip; a second lens positioned on a lateral side of said tip; a third lens positioned on a lateral side of said tip and substantially opposite said second lens; a first imager having a first light sensitive surface; a second imager having a plurality of light sensitive surfaces; a first light guide for directing light from said first lens to said first light sensitive surface of said first imager; a second light guide for directing light from said second lens to a first one of said plurality of light sensitive surfaces of said second imager; and, a third light guide for directing light from said third lens to a second one of said plurality of light sensitive surfaces of said second imager; wherein light waves passing through each of said first, second, and third light guides are isolated from each other.

The present specification also discloses an endoscopic tip comprising: a first lens positioned on a front face of said tip; a second lens positioned on a lateral side of said tip; a third lens positioned on a lateral side of said tip and substantially opposite said second lens; a double-sided imager having a first side and a second side wherein said first side is substantially opposite said second side, further wherein said first side comprises a first light sensitive surface and said second side comprises a plurality of light sensitive surfaces; a first light guide for directing light from said first lens to said first light sensitive surface of said first side of said double-sided imager; a second light guide for directing light from said second lens to a first one of said plurality of light sensitive surfaces of said second side of said double-side imager; and, a third light guide for directing light from said third lens to a second one of said plurality of light sensitive surfaces of said second side of said double-sided imager; wherein light waves passing through each of said first, second, and third light guides are isolated from each other.

One embodiment of the present specification is directed toward a manifold for use in an endoscope, comprising: 1) a manifold housing having a partially cylindrical shape with a curved top surface, a partially curved first side and a partially curved second side wherein the manifold housing comprises a base portion with a first width, a first length, and a proximal surface and an elongated portion, which is attached to the base portion, with a second width, a second length, and a distal surface, wherein the first width is greater than the second width and the first length is less than the second length; 2) a first channel extending from the base portion through the elongated portion, wherein the first channel has an entrance port positioned on said proximal surface of the base portion and an exit port positioned on a distal surface of the elongated portion; 3) a second channel extending from the base portion through the elongated portion, wherein the second channel has an entrance port positioned on said proximal surface of the base portion and an exit port positioned on a distal surface of the elongated portion; 4) a Y-shaped fluid conduit comprising a central stem portion, a first prong portion, and a second prong portion, wherein the central stem portion extends from an entrance port on the proximal surface of the base portion through the base portion, wherein the first prong portion extends from an end of the central portion through the base portion to an exit port on the partially curved first side; and wherein the second prong portion extends from an end of the central portion through the base portion to an exit port the partially curved second side; 5) a third channel extending from an entrance port on the proximal surface of the base portion through to an exit port on the partially curved first side; and 6) a fourth channel extending from an entrance port on the proximal surface of the base portion through to an exit port on the partially curved second side, wherein each of the first, second, third, and fourth channels are fluidically isolated and separated from each other.

Optionally, the manifold further comprises a fifth channel extending from the base portion through the elongated portion, wherein the third channel has an entrance port positioned on said proximal surface of the base portion and an exit port positioned on a distal surface of the elongated portion and wherein the first, second, third, fourth, and fifth channels are fluidically isolated and separated from each other. The manifold housing is formed from a unitary block of material. The exit port on the partially curved first side of the first prong portion is positioned in a depression in the partially curved first side. The exit port on the partially curved second side of the second prong portion is positioned in a depression in the partially curved second side. A portion of the third channel proximate to the exit port positioned on the partially curved first side bends at an angle relative a portion of the third channel proximate to the entrance port. The angle of bending ranges from 45 degrees to 135 degrees relative to the longitudinal axis of the endoscope. A portion of the fourth channel proximate to the exit port positioned on the partially curved first side bends at an angle relative a portion of the fourth channel proximate to the entrance port.

Optionally, the angle of bending ranges from 45 degrees to 135 degrees relative to the longitudinal axis of the endoscope. The third and fourth channels have diameters ranging from approximately 2.8 to 3.2 millimeters. The first channel manifold has a substantially constant diameter within a range from 2.8 millimeters to 4.8 millimeters. The manifold is configured to be a heat sink for transferring heat generated by a plurality of illuminators. The manifold further comprises a groove located on a side of the base portion for receiving a utility cable.

In another embodiment, the present application discloses an image capture section having a length and adapted to be attached to an end of a shaft of an endoscope, wherein the shaft has a length defining a longitudinal axis, the image capture section comprising: 1) a housing that defines a partially enclosed interior volume and that is substantially cylindrical with a substantially flat front face, a first curved side face, a second curved side face, 2) a manifold comprising: a manifold housing having a partially cylindrical shape with a curved top surface, a partially curved first side and a partially curved second side wherein the manifold housing comprises a base portion with a first width, a first length, and a proximal surface and an elongated portion, which is attached to the base portion, with a second width, a second length, and a distal surface, wherein the first width is greater than the second width and the first length is less than the second length; a first channel extending from the base portion through the elongated portion, wherein the first channel has an entrance port positioned on said proximal surface of the base portion and exit port positioned on a distal surface of the elongated portion; a second channel extending from the base portion through the elongated portion, wherein the second channel has an entrance port positioned on said proximal surface of the base portion and an exit port positioned on a distal surface of the elongated portion; a Y-shaped fluid conduit comprising a central stem portion, a first prong portion, and a second prong portion, wherein the central stem portion extends from an entrance port on the proximal surface of the base portion through the base portion, wherein the first prong portion extends from an end of the central portion through the base portion to an exit port on the partially curved first side; and wherein the second prong portion extends from an end of the central portion through the base portion to an exit port the partially curved second side; a third channel extending from an entrance port on the proximal surface of the base portion through to an exit port on the partially curved first side; and a fourth channel extending from an entrance port on the proximal surface of the base portion through to an exit port on the partially curved second side, wherein each of the first, second, third, and fourth channels are fluidically isolated and separated from each other, wherein the elongated portion of the manifold is configured to occupy a first portion of the interior volume; 3) a front image sensor, defined by a first optical axis, having a lens and an electrical assembly, wherein the lens is positioned on a surface of said substantially flat front face; 4) a first side image sensor, defined by a second optical axis, having a lens and an electrical assembly, wherein the lens is positioned in the first curved side face; and 5) a first integrated circuit assembly comprising a print circuit board having mounted thereon the electrical assembly of the front image sensor and the electrical assembly of the first side image sensor, wherein the first integrated circuit assembly is configured to occupy a second portion of the interior volume.

Optionally, the exit port of third channel is positioned 9.5 to 10.5 millimeters from the first side image sensor. The image capture section further comprises a second side image sensor, defined by a third optical axis, having a lens and an electrical assembly, wherein the lens is positioned in the second curved side face. The first integrated circuit assembly further comprises the electrical assembly of the second side image sensor. Each of the front image sensor, first side image sensor, and second side image sensor generates and receives at least 12 signals each. Each of the front image sensor, first side image sensor, and second side image sensor generates and receives at least 12 signals each. The first integrated circuit assembly is connected to a video processing system via a utility cable and wherein less than 36 signals are transmitted between the first integrated assembly and video processing system. The image capture section further comprises a plurality of discrete illuminators. The manifold is configured to be a heat sink for transferring heat generated by the plurality of discrete illuminators.

Optionally, a maximum volume of the partially enclosed interior volume ranges from 2.75 $cm^3$ to 3.5 $cm^3$ and wherein each of the front image sensor and first side image sensor is configured to generate a field of view ranging from 120 to 180 degrees, a depth of field ranging from 3 to 100 mm, have a peripheral distortion of less than 80% without reliance on any aspherical components, and have a maximum focal length in a range of 1 to 1.4 mm.

In one embodiment, the application discloses an image capture section having a length and adapted to be attached to an end of a shaft of a colonscope, wherein the shaft has a length defining a longitudinal axis, the image capture section comprising: 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a manifold comprising an elongated housing extending the length of the image capture section and having a first end and a second end, wherein the manifold has at least three separate and fluidically isolated conduits extending through said elongated housing from the first end through the second end and wherein the manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; and 8) a fluid injector channel comprising an exit port and a conduit, wherein the exit port is positioned in the top right quadrant and wherein the conduit is defined by one of said three separate and fluidically isolated conduits extending through the elongated housing of the fluid manifold.

The embodiment further comprising a jet channel comprising an exit port and a conduit, wherein the exit port is positioned in the top left quadrant and wherein the conduit is defined by one of said three separate and fluidically isolated conduits extending through the elongated housing of the fluid manifold; a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume; at least two first side illuminators, each comprising a first side transparent cover and a first side electrical assembly, wherein the first side transparent covers are positioned on either side of the lens of the first side image sensor within the depression in the first curved surface and the first side electrical assemblies are positioned within the interior volume; a first side fluid injector having an exit port positioned within the depression in the first curved side face and configured to eject fluid on the lens of the first side image sensor; a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume; at least two second side illuminators, each comprising a second side transparent cover and a second side electrical assembly, wherein the second side transparent covers are positioned on either side of the lens of the second side image sensor within the depression in the second curved surface and the second side electrical assemblies are positioned within the interior volume; a second side fluid injector having an exit port positioned within the depression in the second curved side face and configured to eject fluid on the lens of the second side image sensor; and a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume.

Optionally, the manifold further comprises at least one side service channel comprising at least one exit port and at least one conduit, wherein the at least one exit port is positioned within the depression in at least one of the curved side faces and wherein at least one proximal section of the at least one conduit extends through the elongated housing from the first end of said fluid manifold and at least one distal section of the at least one conduit bends towards at least one of the curved side faces.

Optionally, the at least one exit port of said at least one side service channel is positioned 9.5 to 10.5 millimeters and preferably 10.2 millimeters from the second and/or third optical axes of said first and/or second side image sensors.

Optionally, the at least one conduit of said at least one side service channel has a diameter ranging from approximately 2.8 to 3.2 millimeters.

Optionally, the at least one distal section of the at least one conduit bends at acute angles relative to the longitudinal axis of the colonoscope. The at least one distal section of the at least one conduit bends at an angle ranging from 45 to 60 degrees relative to the longitudinal axis of the colonoscope. The at least one distal section of the at least one conduit bends at an angle of 90 degrees relative to the longitudinal axis of the colonoscope. The at least one distal section of the at least one conduit bends at obtuse angles relative to the longitudinal axis of the colonoscope. The at least one distal section of the at least one conduit bends at an angle ranging from 120 to 135 degrees relative to the longitudinal axis of the colonoscope. The at least one exit port has an angle of exit ranging from 5 to 90 degrees. The at least one exit port has an angle of exit of 45 degrees.

Optionally, the housing is a cover for the image capture section that is configured to cover and fluidly seal said first integrated circuit assembly and said fluid manifold, said substantially flat front face of the housing comprising a first opening corresponding to the exit port of the front working channel, a second opening corresponding to the exit port of the fluid injection channel, a third opening corresponding to the exit port of the jet channel, a fourth opening corresponding to the lens of the front image sensor, a fifth opening corresponding to the first front illuminator, a sixth opening corresponding to the second front illuminator, a seventh opening corresponding to the third front illuminator.

Optionally, the housing is a cover for the image capture section that is configured to cover and fluidly seal said first integrated circuit assembly and said manifold, said first curved side of the housing comprising a first opening corresponding to the lens of the first side image sensor, a second opening corresponding to the exit port of the first side fluid injection channel, and a third and fourth opening corresponding to the two first side illuminators.

Optionally, the housing is a cover for the image capture section that is configured to cover and fluidly seal said first integrated circuit assembly and said manifold, said second curved side of the housing comprising a first opening corresponding to the lens of the second side image sensor, a second opening corresponding to the exit port of the second side fluid injection channel, and a third and fourth opening corresponding to the two second side illuminators. Optionally, the manifold functions as a heat sink for transferring heat generated by the front and side illuminators.

Optionally, the image capture section has a diameter ranging from approximately 10 to 15 millimeters or approximately 9 to 17 millimeters or approximately 5 to 18 millimeters or approximately 7 to 12 millimeters or approximately 11.7 millimeters or approximately 11.9 millimeters. Optionally, the lens of said front image sensor has a focal length of about 3 to 100 millimeters, 100 millimeters or 110 millimeters. Optionally, the lens of said first and/or second side image sensor has a focal length of about 3 to 100 millimeters or 2 to 33 millimeters or 2 to 100 millimeters.

Optionally, the second and third optical axes of the first and second side image sensors are approximately 8 to 10 millimeters from the flat front face, approximately 7 to 11 millimeters from the flat front face, 9 or 9.1 millimeters from the flat front face, approximately 6 to 9 millimeters from the flat front face, or 7.8 or 7.9 millimeters from the flat front face Optionally, the respective centers of the at least two first side illuminators are separated by a distance ranging from 5.5 to 6.5 millimeters. Optionally, the respective centers of the at least two second side illuminators are separated by a distance ranging from 5.5 to 6.5 millimeters.

Optionally, the conduit of said front working channel is substantially constant extending through the shaft and the image capture section and wherein said conduit has a diameter ranging from approximately 2.8 to 4.8 millimeters, ranging from approximately 3.2 to 4.8 millimeters or ranging from approximately 4.2 to 4.8 millimeters. Optionally, the diameter is 3.2 millimeters, 3.8 millimeters, or 4.8 millimeters Optionally, the lens of each of the front image sensor, first side image sensor, and second side image sensor is configured to generate peripheral distortion of less than 80%. Optionally, the lens of each of the front image sensor, first side image sensor, and second side image sensor is configured to have an optical length of up to 5 millimeters. Optionally, the lens of each of the front image sensor, first side image sensor, and second side image sensor is configured to have a field of view of at least 90 degrees and up to essentially 180 degrees. Optionally, the exit ports of the corresponding first and second side fluid injectors are respectively positioned at a distance ranging from 5.8 to 7.5 millimeters and preferably 6.7 millimeters from the second and third optical axes.

In another embodiment, the present application discloses an image capture section having a length and adapted to be attached to an end of a shaft of a colonscope, wherein the shaft has a length defining a longitudinal axis, the image capture section comprising: 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold, having a first end and a second end, comprising a base portion with a first width and a first length attached to an elongated housing, having a second width and a second length, wherein the second width is less than the first width and wherein the second length is longer than the first length and extends the length of the image capture section, wherein the fluid manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a service channel conduit extending through a center of the base portion, wherein the proximal section of the service channel conduit splits into a first distal section of the service channel conduit that bends towards the first curved side face leading to an exit port and a second distal section of the service channel conduit that bends towards the second curved side face leading to an exit port, and wherein the exit port of the first distal section is located in the depression in the first curved surface and the exit port of the second distal section is located in the depression in the second curved surface; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; 8) a fluid injector channel comprising an exit port and a conduit, wherein the exit port is positioned in the top right quadrant and wherein the conduit is defined by one of said three separate and fluidically isolated conduits extending through the elongated housing of the fluid manifold.

Optionally, the embodiment comprises a jet channel comprising an exit port and a conduit, wherein the exit port is positioned in the top left quadrant and wherein the conduit is defined by one of said three separate and fluidically isolated conduits extending through the elongated housing of the fluid manifold. Optionally, the embodiment comprises a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume. Optionally, the embodiment comprises at least two first side illuminators, each comprising a first side transparent cover and a first side electrical assembly, wherein the first side transparent covers are positioned on either side of the lens of the first side image sensor within the depression in the first curved surface and the first side electrical assemblies are positioned within the interior volume. Optionally, the embodiment comprises a first side fluid injector having an exit port positioned within the depression in the first curved side face and configured to eject fluid on the lens of the first side image sensor. Optionally, the embodiment comprises a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume.

Optionally, the embodiment comprises at least two second side illuminators, each comprising a second side transparent cover and a second side electrical assembly, wherein the second side transparent covers are positioned on either side of the lens of the second side image sensor within the depression in the second curved surface and the second side electrical assemblies are positioned within the interior volume. Optionally, the embodiment comprises a second side fluid injector having an exit port positioned within the depression in the second curved side face and configured to eject fluid on the lens of the second side image sensor. Optionally, the embodiment comprises a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume.

In another embodiment, the present application discloses a manifold for use in an image capture section in an endoscope, the manifold having a first end and a second end and comprising a base portion with a first width and a first length attached to an elongated housing, having a second width and a second length, wherein the second width is less than the first width and wherein the second length is longer than the first length and extends the length of the image capture section, wherein the manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a service channel conduit extending through a center of the base portion, wherein the proximal section of the service channel conduit splits into a first distal section of the service channel conduit that bends towards a first curved side face leading to an exit port and a second distal section of the service channel conduit that bends towards a second curved side face leading to an exit port, and wherein the exit port of the first distal section is located in a depression in the first curved surface and the exit port of the second distal section is located in a depression in the second curved surface.

In another embodiment, the present application discloses an image capture section having a length and adapted to be attached to an end of a shaft of a colonoscope, wherein the shaft has a length defining a longitudinal axis, the image capture section comprising: 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold, having a first end and a second end, comprising a base portion with a first width and a first length attached to an elongated housing, having a second width and a second length, wherein the second width is less than the first width and wherein the second length is longer than the first length and extends the length of the image capture section, wherein the fluid manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a service channel conduit extending through a center of the base portion and a distal section of the service channel conduit bends towards the first curved side face leading to an exit port, and wherein the exit port is located in the depression in the first curved surface; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume.

Optionally, the present embodiment discloses a second front illuminator comprising a second transparent cover and a second electrical assembly, wherein the second transparent cover is positioned at least partially within said bottom left quadrant of the substantially flat front face and the second electrical assembly is positioned within the interior volume. Optionally, the present embodiment discloses a third front illuminator comprising a third transparent cover and a third electrical assembly, wherein the third transparent cover is positioned at least partially within said bottom right quadrant of the substantially flat front face and the third electrical assembly is positioned within the interior volume. Optionally, the present embodiment discloses a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold. Optionally, the present embodiment discloses a fluid injector channel comprising an exit port and a conduit, wherein the exit port is positioned in the top right quadrant and wherein the conduit is defined by one of said three separate and fluidically isolated conduits extending through the elongated housing of the fluid manifold. Optionally, the present embodiment discloses a jet channel comprising an exit port and a conduit, wherein the exit port is positioned in the top left quadrant and wherein the conduit is defined by one of said three separate and fluidically isolated conduits extending through the elongated housing of the fluid manifold. Optionally, the present embodiment discloses a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume.

Optionally, the present embodiment discloses at least two first side illuminators, each comprising a first side transparent cover and a first side electrical assembly, wherein the first side transparent covers are positioned on either side of the lens of the first side image sensor within the depression in the first curved surface and the first side electrical assemblies are positioned within the interior volume. Optionally, the present embodiment discloses a first side fluid injector having an exit port positioned within the depression in the first curved side face and configured to eject fluid on the lens of the first side image sensor. Optionally, the present embodiment discloses a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume. Optionally, the present embodiment discloses at least two second side illuminators, each comprising a second side transparent cover and a second side electrical assembly, wherein the second side transparent covers are positioned on either side of the lens of the second side image sensor within the depression in the second curved surface and the second side electrical assemblies are positioned within the interior volume.

Optionally, the present embodiment discloses a second side fluid injector having an exit port positioned within the depression in the second curved side face and configured to eject fluid on the lens of the second side image sensor. Optionally, the present embodiment discloses a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume.

In another embodiment, the present application discloses a fluid manifold for use in an image capture section in an endoscope, the fluid manifold having a first end and a second end and comprising a base portion with a first width and a first length attached to an elongated housing, having a second width and a second length, wherein the second width is less than the first width and wherein the second length is longer than the first length and extends the length of the image capture section, wherein the fluid manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a service channel conduit extending through a center of the base portion and a distal section of the service channel conduit that bends towards the first curved side face leading to an exit port, and wherein the exit port is located in a depression in the first curved surface.

In another embodiment, the present application discloses an image capture section having a length and adapted to be attached to an end of a shaft of a colonoscope, wherein the shaft has a length defining a longitudinal axis, the image capture section comprising 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a manifold, having a first end and a second end, comprising a base portion with a first width and a first length attached to an elongated housing, having a second width and a second length, wherein the second width is less than the first width and wherein the second length is longer than the first length and extends the length of the image capture section, wherein the manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a first service channel conduit extending through the base portion and a distal section of the first service channel conduit that bends towards the first curved side face leading to an exit port, and wherein the exit port is located in the depression in the first curved surface; and a proximal section of a second service channel conduit also extending through the base portion and a distal section of the second service channel conduit that bends towards the second curved side face leading to an exit port, and wherein the exit port is located in the depression in the second curved surface; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; and 5) a second front illuminator comprising a second transparent cover and a second electrical assembly, wherein the second transparent cover is positioned at least partially within said bottom left quadrant of the substantially flat front face and the second electrical assembly is positioned within the interior volume.

Optionally, the present application discloses a third front illuminator comprising a third transparent cover and a third electrical assembly, wherein the third transparent cover is positioned at least partially within said bottom right quadrant of the substantially flat front face and the third electrical assembly is positioned within the interior volume. Optionally, the present application discloses a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold. Optionally, the present application discloses a fluid injector channel comprising an exit port and a conduit, wherein the exit port is positioned in the top right quadrant and wherein the conduit is defined by one of said three separate and fluidically isolated conduits extending through the elongated housing of the fluid manifold. Optionally, the present application discloses a jet channel comprising an exit port and a conduit, wherein the exit port is positioned in the top left quadrant and wherein the conduit is defined by one of said three separate and fluidically isolated conduits extending through the elongated housing of the fluid manifold. Optionally, the present application discloses a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume. Optionally, the present application discloses at least two first side illuminators, each comprising a first side transparent cover and a first side electrical assembly, wherein the first side transparent covers are positioned on either side of the lens of the first side image sensor within the depression in the first curved surface and the first side electrical assemblies are positioned within the interior volume.

Optionally, the present application discloses a first side fluid injector having an exit port positioned within the depression in the first curved side face and configured to eject fluid on the lens of the first side image sensor. Optionally, the present application discloses a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume. Optionally, the present application discloses at least two second side illuminators, each comprising a second side transparent cover and a second side electrical assembly, wherein the second side transparent covers are positioned on either side of the lens of the second side image sensor within the depression in the second curved surface and the second side electrical assemblies are positioned within the interior volume. Optionally, the present application discloses a second side fluid injector having an exit port positioned within the depression in the second curved side face and configured to eject fluid on the lens of the second side image sensor. Optionally, the present application discloses a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume.

In another embodiment, the present application discloses a manifold for use in an image capture section in an endoscope, the fluid manifold having a first end and a second end and comprising a base portion with a first width and a first length attached to an elongated housing, having a second width and a second length, wherein the second width is less than the first width and wherein the second length is longer than the first length and extends the length of the image capture section, wherein the fluid manifold has at least three separate and fluidically isolated conduits extending through said elongated housing and said base portion from the first end through the second end, wherein the manifold is configured to occupy a first portion of the interior volume, wherein a bottom surface of the base portion comprises a proximal section of a first service channel conduit extending through the base portion and a distal section of the first service channel conduit that bends towards a first curved side face leading to an exit port, and wherein the exit port is located in a depression in the first curved surface; and a proximal section of a second service channel conduit also extending through the base portion and a distal section of the second service channel conduit that bends towards a second curved side face leading to an exit port, and wherein the exit port is located in the depression in the second curved surface.

In another embodiment, the present application discloses an image capture section having a length and adapted to be attached to an end of a shaft of a colonscope, wherein the shaft has a length defining a longitudinal axis, the image capture section comprising 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least three separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; 8) a fluid injector channel comprising an exit port and a conduit, wherein the exit port is positioned in the top right quadrant and wherein the conduit is defined by one of said three separate and fluidically isolated conduits extending through the elongated housing of the fluid manifold; 9) a jet channel comprising an exit port and a conduit, wherein the exit port is positioned in the top left quadrant and wherein the conduit is defined by one of said three separate and fluidically isolated conduits extending through the elongated housing of the fluid manifold; 10) a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume; 11) at least two first side illuminators, each comprising a first side transparent cover and a first side electrical assembly, wherein the first side transparent covers are positioned on either side of the lens of the first side image sensor within the depression in the first curved surface and the first side electrical assemblies are positioned within the interior volume; 12) a first side fluid injector having an exit port positioned within the depression in the first curved side face and configured to eject fluid on the lens of the first side image sensor; 13) a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume; 14) at least two second side illuminators, each comprising a second side transparent cover and a second side electrical assembly, wherein the second side transparent covers are positioned on either side of the lens of the second side image sensor within the depression in the second curved surface and the second side electrical assemblies are positioned within the interior volume; 15) a second side fluid injector having an exit port positioned within the depression in the second curved side face and configured to eject fluid on the lens of the second side image sensor; 16) at least one side jet channel comprising at least two exit ports and at least one conduit, wherein the at least two exit ports are positioned around a periphery of said housing and wherein the at least one conduit has at least one corresponding entry port at the first end of said fluid manifold; 17) a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume Optionally, the present application discloses at least one of said at least two exit ports of the at least one side jet channel is partially positioned within the depression. Optionally, one or both of the side fluid injectors are positioned between the at least two exit ports of said at least one side jet channel. Optionally, the at least two exit ports of the at least one side jet channel comprise 2, 4, 6 or 8 exit ports. Optionally, the at least one conduit of the at least one side jet channel has a diameter of approximately 1.4 to 1.7 millimeters. Optionally, the at least one exit port of the at least one side jet channel has an acute angle of exit. Optionally, the at least one exit port of the at least one side jet channel has an obtuse angle of exit. Optionally, the at least one exit port of the at least one side jet channel has an angle of exit ranging from 45 to 60 degrees. Optionally, the at least one exit port of the at least one side jet channel has an angle of exit ranging from 120 to 135 degrees. Optionally, the at least one exit port of the at least one side jet channel operates at a predefined algorithm. Optionally, the at least one exit port of the at least one side jet channel operates at a different predefined algorithm.

In another embodiment, the present application discloses an image capture section having a length and adapted to be attached to an end of a shaft of a gastroscope, wherein the shaft has a length defining a longitudinal axis, the image capture section comprising 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least three separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the gastroscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; 8) a fluid injector channel comprising an exit port and a conduit, wherein the exit port is positioned in the top right quadrant and wherein the conduit is defined by one of said three separate and fluidically isolated conduits extending through the elongated housing of the fluid manifold; 9) a jet channel comprising an exit port and a conduit, wherein the exit port is positioned in the top left quadrant and wherein the conduit is defined by one of said three separate and fluidically isolated conduits extending through the elongated housing of the fluid manifold; 10) a side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the gastroscope, and wherein the electrical assembly is positioned in the interior volume; 11) at least two side illuminators, each comprising a side transparent cover and a side electrical assembly, wherein the side transparent covers are positioned on either side of the lens of the side image sensor within the depression in the first curved surface and the side electrical assemblies are positioned within the interior volume; 12) a side fluid injector having an exit port positioned within the depression in the first curved side face and configured to eject fluid on the lens of the side image sensor; and 13) a first integrated circuit assembly comprising a print circuit board having mounted thereon the electrical assembly of the front image sensor, and the electrical assembly of the side image sensor, wherein the first integrated circuit assembly is configured to occupy a second portion of the interior volume.

In another embodiment, the present application discloses an image capture section having a length and adapted to be attached to an end of a shaft of a gastroscope, wherein the shaft has a length defining a longitudinal axis, the image capture section comprising: 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least three separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the gastroscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; 8) a fluid injector channel comprising an exit port and a conduit, wherein the exit port is positioned in the top right quadrant and wherein the conduit is defined by one of said three separate and fluidically isolated conduits extending through the elongated housing of the fluid manifold; 9) a jet channel comprising an exit port and a conduit, wherein the exit port is positioned in the top left quadrant and wherein the conduit is defined by one of said three separate and fluidically isolated conduits extending through the elongated housing of the fluid manifold; 10) a side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the gastroscope, and wherein the electrical assembly is positioned in the interior volume; 11) at least two side illuminators, each comprising a side transparent cover and a side electrical assembly, wherein the side transparent covers are positioned on either side of the lens of the side image sensor within the depression in the first curved surface and the side electrical assemblies are positioned within the interior volume; 12) a side fluid injector having an exit port positioned within the depression in the first curved side face and configured to eject fluid on the lens of the side image sensor; 13) a side service channel comprising an exit port and a conduit, wherein the exit port is positioned within the depression in the first curved side face and wherein a proximal section of the conduit extends through said elongated housing from the first end of said fluid manifold and a distal section of the conduit bends towards the first curved side face; 14) a first integrated circuit assembly comprising a print circuit board having mounted thereon the electrical assembly of the front image sensor, and the electrical assembly of the side image sensor, wherein the first integrated circuit assembly is configured to occupy a second portion of the interior volume.

In another embodiment, the present application discloses an image capture section having a length and adapted to be attached to an end of a shaft of a gastroscope, wherein the shaft has a length defining a longitudinal axis, the image capture section comprising: 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least three separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the gastroscope, and wherein the electrical assembly is positioned in the interior volume; 4) a first front illuminator comprising a first transparent cover and a first electrical assembly, wherein the first transparent cover is positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is positioned at least partially within said bottom left quadrant of the substantially flat front face and the second electrical assembly is positioned within the interior volume; 6) a third front illuminator comprising a third transparent cover and a third electrical assembly, wherein the third transparent cover is positioned at least partially within said bottom right quadrant of the substantially flat front face and the third electrical assembly is positioned within the interior volume; 7) a front working channel comprising an exit port and a conduit, wherein the exit port is positioned along the vertical axis of the substantially flat front face and is at least partially in the top left quadrant and the top right quadrant and wherein the conduit is defined by one of said three separate and fluidically isolated conduits extending through the elongated housing of the fluid manifold; 8) a fluid injector channel comprising an exit port and a conduit, wherein the exit port is positioned in the top right quadrant and wherein the conduit is defined by one of said three separate and fluidically isolated conduits extending through the elongated housing of the fluid manifold; 9) a jet channel comprising an exit port and a conduit, wherein the exit port is positioned in the top left quadrant and wherein the conduit is defined by one of said three separate and fluidically isolated conduits extending through the elongated housing of the fluid manifold; 10) a side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the gastroscope, and wherein the electrical assembly is positioned in the interior volume; 11) at least two side illuminators, each comprising a side transparent cover and a side electrical assembly, wherein the side transparent covers are positioned on either side of the lens of the side image sensor within the depression in the first curved surface and the side electrical assemblies are positioned within the interior volume; 12) a side fluid injector having an exit port positioned within the depression in the first curved side face and configured to eject fluid on the lens of the side image sensor; 13) at least one side jet channel comprising at least one exit port and at least one conduit, wherein the at least one exit port is positioned around a periphery of said housing and wherein the at least one conduit has at least one corresponding entry port at the first end of said fluid manifold; and 14) a first integrated circuit assembly comprising a print circuit board having mounted thereon the electrical assembly of the front image sensor, and the electrical assembly of the side image sensor, wherein the first integrated circuit assembly is configured to occupy a second portion of the interior volume.

Optionally, the present application discloses at least one exit port of the at least one side jet channel is partially positioned within the depression. The at least one exit port of the at least one side jet channel comprises 2, 4, 6 or 8 exit ports. The at least one exit port of the at least one side jet channel is positioned at a distance ranging from 8.5 to 9.5 millimeters from the optical axis of the corresponding side image sensor. The fluid exiting the at least one exit port of the at least one side jet channel forms an angle ranging from 50 to 60 degrees relative to a lateral plane containing the lens of the corresponding side image sensor and side illuminators. The at least one conduit of the at least one side jet channel has a diameter of approximately 1.4 to 1.7 millimeters. The at least one exit port of the at least one side jet channel has an acute angle of exit. The at least one exit port of the at least one side jet channel has an obtuse angle of exit. The at least one exit port of the at least one side jet channel has an angle of exit ranging from 45 to 60 degrees. The at least one exit port of the at least one side jet channel has an angle of exit ranging from 120 to 135 degrees. The at least one exit port of the at least one side jet channel operates at a predefined algorithm. The at least one exit port of the at least one side jet channel operates at a different predefined algorithm.

In another embodiment, the present application discloses an image capture section having a length and adapted to be attached to an end of a shaft of a colonscope, wherein the shaft has a length defining a longitudinal axis, the image capture section comprising 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least four separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the colonoscope, and wherein the electrical assembly is positioned in the interior volume; 4) a first front illuminator comprising a first transparent cover and a first electrical assembly, wherein the first transparent cover is oval and positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is oval and positioned at least partially within said bottom left quadrant of the substantially flat front face and the second electrical assembly is positioned within the interior volume; 6) a third front illuminator comprising a third transparent cover and a third electrical assembly, wherein the third transparent cover is oval and positioned at least partially within said bottom right quadrant of the substantially flat front face and the third electrical assembly is positioned within the interior volume; 7) a first front working channel comprising an exit port and a conduit, wherein a substantial portion of the exit port is positioned in the top right quadrant of the substantially flat front face and wherein the conduit is defined by one of said four separate and fluidically isolated conduits extending through the elongated housing of the fluid manifold; 8) a second front working channel comprising an exit port and a conduit, wherein a substantial portion of the exit port is positioned in the top left quadrant of the substantially flat front face and wherein the conduit is defined by one of said four separate and fluidically isolated conduits extending through the elongated housing of the fluid manifold; 9) a fluid injector channel comprising an exit port and a conduit, wherein the exit port is positioned at least partially within said top right quadrant and bottom right quadrant and wherein the conduit is defined by one of said four separate and fluidically isolated conduits extending through the elongated housing of the fluid manifold; 10) a jet channel comprising an exit port and a conduit, wherein the exit port is positioned at least partially within said top left quadrant and top right quadrant and wherein the conduit is defined by one of said four separate and fluidically isolated conduits extending through the elongated housing of the fluid manifold; 11) a first side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the colonoscope, and wherein the electrical assembly is positioned in the interior volume; 12) at least two first side illuminators, each comprising a first side transparent cover and a first side electrical assembly, wherein the first side transparent covers are oval and positioned on either side of the lens of the first side image sensor within the depression in the first curved surface and the first side electrical assemblies are positioned within the interior volume; 13) a first side fluid injector having an exit port positioned within the depression in the first curved side face and configured to eject fluid on the lens of the first side image sensor; 14) a second side image sensor, defined by a third optical axis, having a lens and an electrical assembly, wherein the lens is positioned within the depression in the second curved side face and configured to capture images within a range of 0 to 80 degrees from the third optical axis, wherein the third optical axis is positioned in a center of the lens and perpendicular to said longitudinal axis of the colonoscope, and wherein the electrical assembly is positioned in the interior volume; 15) at least two second side illuminators, each comprising a second side transparent cover and a second side electrical assembly, wherein the second side transparent covers are oval and positioned on either side of the lens of the second side image sensor within the depression in the second curved surface and the second side electrical assemblies are positioned within the interior volume; 16) a second side fluid injector having an exit port positioned within the depression in the second curved side face and configured to eject fluid on the lens of the second side image sensor; and 17) a first integrated circuit assembly comprising a print circuit board having mounted thereon the electrical assembly of the front image sensor, the electrical assembly of the first side image sensor, and the electrical assembly of the second side image sensor, wherein the first integrated circuit assembly is configured to occupy a second portion of the interior volume.

Optionally, said first and second front working channels are both adapted for insertion of a medical tool. The first and second front working channels are both adapted for applying suction. One of said first and second front working channel is adapted for insertion of a medical tool and another of said first and second front working channel is adapted for applying suction. The distance between the exit ports of said first and second working channels is in a range of 0.40 to 0.45 millimeters. The conduit of said first working channel has a diameter in a range of 3.6 to 4.0 millimeters and the conduit of said second working channel has a diameter in a range of 2.6 to 3.0 millimeters. The conduit of said first working channel has a diameter of 3.8 millimeters and the conduit of said second working channel has a diameter of 2.8 millimeters.

In another embodiment, the present application discloses an image capture section having a length and adapted to be attached to an end of a shaft of a gastroscope, wherein the shaft has a length defining a longitudinal axis, the image capture section comprising 1) a housing that defines a partially enclosed interior volume and that is substantially cylindrical with a substantially flat front face, a first curved side face, a second curved side face, wherein the substantially flat front face comprises four quadrants defined by a vertical axis passing through a center of said substantially flat front face and a horizontal axis passing through said center, said four quadrants including a top left quadrant, a top right quadrant, a bottom left quadrant and a bottom right quadrant and wherein each of said first curved surface and second curved surface comprises a substantially flat depression; 2) a fluid manifold comprising an elongated housing extending the length of the image capture section and having a first end and a second end, wherein the fluid manifold has at least four separate and fluidically isolated conduits extending through said elongated housing from the first end through the second end and wherein the fluid manifold is configured to occupy a first portion of the interior volume; 3) a front image sensor, defined by a first optical axis, having a lens and an electrical assembly, wherein the lens is positioned on a surface of said substantially flat front face and configured to capture images within at least a range of 0 to 80 degrees from the first optical axis, wherein the first optical axis is positioned in a center of the lens and in parallel to said longitudinal axis of the gastroscope, and wherein the electrical assembly is positioned in the interior volume; 4) a first front illuminator comprising a first transparent cover and a first electrical assembly, wherein the first transparent cover is oval and positioned at least partially within said bottom right quadrant and bottom left quadrant of the substantially flat front face and the first electrical assembly is positioned within the interior volume; 5) a second front illuminator comprising a second transparent cover and a second electrical assembly, wherein the second transparent cover is oval and positioned at least partially within said bottom left quadrant of the substantially flat front face and the second electrical assembly is positioned within the interior volume; 6) a third front illuminator comprising a third transparent cover and a third electrical assembly, wherein the third transparent cover is oval and positioned at least partially within said bottom right quadrant of the substantially flat front face and the third electrical assembly is positioned within the interior volume; 7) a first front working channel comprising an exit port and a conduit, wherein a substantial portion of the exit port is positioned in the top right quadrant of the substantially flat front face and wherein the conduit is defined by one of said four separate and fluidically isolated conduits extending through the elongated housing of the fluid manifold; 8) a second front working channel comprising an exit port and a conduit, wherein a substantial portion of the exit port is positioned in the top left quadrant of the substantially flat front face and wherein the conduit is defined by one of said four separate and fluidically isolated conduits extending through the elongated housing of the fluid manifold; 9) a fluid injector channel comprising an exit port and a conduit, wherein the exit port is positioned at least partially within said top right quadrant and bottom right quadrant and wherein the conduit is defined by one of said four separate and fluidically isolated conduits extending through the elongated housing of the fluid manifold; 10) a jet channel comprising an exit port and a conduit, wherein the exit port is positioned at least partially within said top left quadrant and top right quadrant and wherein the conduit is defined by one of said four separate and fluidically isolated conduits extending through the elongated housing of the fluid manifold; 11) a side image sensor, defined by a second optical axis, having a lens and an electrical assembly, wherein the lens is positioned within the depression in the first curved side face and configured to capture images within a range of 0 to 80 degrees from the second optical axis, wherein the second optical axis is positioned in a center of the lens and perpendicular to said longitudinal axis of the gastroscope, and wherein the electrical assembly is positioned in the interior volume; 12) at least two side illuminators, each comprising a side transparent cover and a side electrical assembly, wherein the side transparent covers are oval and positioned on either side of the lens of the side image sensor within the depression in the first curved surface and the side electrical assemblies are positioned within the interior volume; 13) a side fluid injector having an exit port positioned within the depression in the first curved side face and configured to eject fluid on the lens of the first side image sensor; and 14) a first integrated circuit assembly comprising a print circuit board having mounted thereon the electrical assembly of the front image sensor, and the electrical assembly of the side image sensor, wherein the first integrated circuit assembly is configured to occupy a second portion of the interior volume.

Optionally, the first and second front working channels are both adapted for insertion of a medical tool. The first and second front working channels are both adapted for applying suction. One of said first and second front working channel is adapted for insertion of a medical tool and another of said first and second front working channel is adapted for applying suction. The distance between the exit ports of said first and second working channels is in a range of 0.40 to 0.45 millimeters. The conduit of said first working channel has a diameter in a range of 3.6 to 4.0 millimeters and the conduit of said second working channel has a diameter in a range of 2.6 to 3.0 millimeters. The conduit of said first working channel has a diameter of 3.8 millimeters and the conduit of said second working channel has a diameter of 2.8 millimeters.

Optionally, the optical axis of said at least one side-looking viewing element forms an obtuse angle with an optical axis of said at least one front-pointing viewing element. The optical axis of said at least one side-looking viewing element forms an acute angle with an optical axis of said at least one front-pointing viewing element. The openings are positioned to allow at least one said side-looking camera to view a medical tool protruding from the openings.

In conjunction with any of the above embodiments, the at least one side jet channel circulates a fluid through a groove connected to the at least one side jet channel, wherein said housing further comprises a plurality of holes drilled above the groove, and wherein the plurality of holes allow the fluid circulating through the groove to exit. The one or more side jet channels comprise two side jet channels positioned on opposing sides of the tip section of the endoscope assembly. The plurality of holes bend at acute angles relative to a long dimension of the endoscope assembly. The plurality of holes bend at 90 degrees relative to a long dimension of the endoscope assembly. The plurality of holes bend at obtuse angles relative to a long dimension of the endoscope assembly. The plurality of holes bend at angles that are a combination of acute, right and obtuse angles, relative to a long dimension of the endoscope assembly. The plurality of holes are placed linearly, above the groove. Each hole of the plurality of holes is at a distance of at least 0.2 millimeters from each adjacent hole. Each hole of the plurality of holes has a diameter of 5 millimeters.

Optionally, the at least one side jet channel circulates a fluid through a removable ring assembly placed on said housing, the removable ring assembly comprising a peripheral groove placed on an internal periphery of the ring assembly, wherein the at least two exit ports of the at least one side jet channel are aligned with the peripheral groove; and a plurality of holes drilled along the peripheral groove, wherein the plurality of holes allow exit of the fluid circulating through the removable ring assembly.

Optionally, the first diameter of the tip cover is less than a second diameter of the peripheral grove. The one or more side jet channels comprise two side jet channels positioned on opposing sides of the tip section of the endoscope assembly. The plurality of holes bend at acute angles relative to a long dimension of the endoscope assembly. The plurality of holes bend at 90 degrees relative to a long dimension of the endoscope assembly. The plurality of holes bend at obtuse angles relative to a long dimension of the endoscope assembly. The plurality of holes bend at angles that are a combination of acute, right and obtuse angles, relative to a long dimension of the endoscope assembly. The plurality of holes are placed linearly, above the peripheral groove. Each hole of the plurality of holes is at a distance of at least 0.2 millimeters from each adjacent hole. Each of the plurality of holes has a diameter of 5 millimeters.

In conjunction with any of the above embodiments, the present application discloses a sprinkler assembly in a tip section. The tip section of a multi-viewing elements endoscope assembly, comprises: 1) one or more jet channels circulating a fluid; 2) a tip cover associated with the tip section and comprising one or more jet channel openings aligned with the one or more jet channels; and 3) a removable sprinkler assembly comprising a patch placed above each of the one or more jet channel openings and a plurality of holes drilled along the patch, wherein the plurality of holes allow exit of the fluid circulated through the one or more jet channels.

Optionally, the one or more jet channels comprise two side jet channels positioned on opposing sides of the tip section of the endoscope assembly. The one or more jet channels comprise a front jet channel positioned on a front panel of the tip section of the endoscope assembly. The plurality of holes bend at acute angles relative to a long dimension of the endoscope assembly. The plurality of holes bend at 90 degrees relative to a long dimension of the endoscope assembly. The plurality of holes bend at angles that are a combination of acute, right and obtuse angles, relative to a long dimension of the endoscope assembly. The plurality of holes bend at different angles relative to a long dimension of the endoscope assembly. The plurality of holes are placed linearly on the patch, along a circumference of the tip cover. The one or more jet channel openings operate at a predefined algorithm. Each of the one or more jet channel openings operate at a different predefined algorithm.

Optionally, the tip section further comprises a front injector; at least one side injector; at least one front-pointing viewing element and at least one front illuminator associated therewith; at least one side-looking viewing element and at least one side illuminator associated therewith; and a front working channel configured for insertion of a medical tool.

In conjunction with any of the above embodiments, the present application discloses a multi jet distributor for supplying fluid to a plurality of jet openings in a tip section of a multi-viewing elements endoscope, the multi jet distributor comprising a distributor housing; a distributor motor located within the distributor housing; a motor shaft coupled to the distributor motor and located within the distributor housing; and a distributor disc located within the distributor housing and coupled with the motor shaft, wherein the distributor disc comprises an entering fluid pipeline for supplying said fluid to the multi jet distributor; and at least one exiting fluid pipeline for providing said fluid supplied by the entering fluid pipeline to the plurality of jet openings.

Optionally, the plurality of jet openings comprise a front jet opening and at least one side jet opening. The plurality of jet openings comprise a front jet opening; a first side jet opening and a second side jet opening. The distributor housing further comprises a locking element for fixedly positioning the distributor disc within the distributor housing. The distributor disc further comprises a plug for connecting the distributor disc with the motor shaft. The distributor disc further comprises a groove on an outer surface of said distributor disc for receiving the locking element. The pump supplies said fluid to the entering fluid pipeline. The multi jet distributor is connected to the endoscope via a main connector. The main connector has a multi jet controller comprising a shaft leading to a valve placed in a housing that operatively connects the valve to the main connector through a jet connector, wherein the valve has screws formed thereon, and wherein a first position of the shaft rotates the screws causing the fluid to exit only the front jet opening and a second position of the shaft rotates the screws causing the fluid to exit through both the front jet opening and the at least one side jet opening.

Optionally, the distributor disc has a distributor rate ranging between 30 rounds per minute to 100 rounds per minute. The distributor disc has a distributor rate ranging between 50 and 65 rounds per minute. The at least one exiting fluid pipeline comprises three fluid pipelines for providing said fluid supplied by the entering fluid pipeline to the plurality of jet openings. The plurality of jet openings comprise a front jet opening and at least one side jet opening. The plurality of jet openings comprise a front jet opening; a first side jet opening and a second side jet opening. The at least one exiting fluid pipeline comprises two exiting fluid pipelines for providing said fluid supplied by the entering fluid pipeline to the plurality of jet openings. The plurality of jet openings comprise a front jet opening and at least one side jet opening. The plurality of jet openings comprise a front jet opening; a first side jet opening and a second side jet opening. The main connector has a multi-jet controller comprising a shaft leading to a valve placed in a housing that operatively connects the valve to the main connector through a jet connector, wherein the valve has screws formed thereon, and wherein a first position of the shaft rotates the screws causing the fluid to exit only the front jet opening and a second position of the shaft rotates the screws causing the fluid to exit through both the front jet opening and the at least one side jet opening.

In conjunction with any of the above embodiments, the present application discloses a housing with a front portion and a rear portion, and wherein said image capture section further comprises a front sealed modular unit comprising said front image sensor, lens and an associated front printed circuit board; a first side sealed modular unit comprising said first side image sensor, lens and an associated first side printed circuit board; a second side sealed module unit comprising said second side image sensor, lens and an associated second side printed circuit board, wherein the front, first side and second side printed circuit boards are coupled to each other; and a holder to encapsulate the front and side modular units from each other, the said holder having a front concave area to carry the front sealed modular unit, a first side compartment to carry the first side sealed modular unit, a second side compartment to carry the second side sealed modular, and a rectangular strip to carry an electrical cable connected to the coupled printed circuit boards of the front and side modular units, wherein the compartments have slots configured to carry the lens of the side modular units and wherein the holder is configured to occupy a third portion of the interior volume.

Optionally, the housing comprises a front portion and a rear portion, and wherein said image capture section further comprises: a front sealed modular unit comprising said front image sensor, lens and an associated front printed circuit board; a first side sealed modular unit comprising said first side image sensor, lens and an associated first side printed circuit board; a second side sealed module unit comprising said second side image sensor, lens and an associated second side printed circuit board, wherein the front, first side and second side printed circuit boards are coupled to each other; a holder comprising a front surface, a first side surface, a second side surface and a rear portion, wherein each of the front and side surfaces have a plurality of recesses configured to receive a plurality of connectors of the front and side modular units and wherein the rear portion is configured to carry an electrical cable to supply power to and transmit data from the front and side modular units; and a frame to support the holder, said frame comprising a front concave area to accommodate the front modular unit, a first side with a slot configured to carry the lens of the first side modular unit and a second side with a slot configured to carry the lens of the second side modular unit, wherein the holder and the frame are configured to occupy a third portion of the interior volume.

In conjunction with any of the above embodiments, the present application discloses an electronic circuit board of a tip section of a multi-viewing elements endoscope, the electronic circuit board comprising one or more optical assemblies, wherein each of said one or more optical assemblies comprise 1) at least one lens assembly and 2) an image sensor, wherein each of said one or more optical assemblies supports said at least one lens assembly and the image sensor, wherein the image sensor is placed in a folded position with a first surface facing a tip section end of the endoscope and an opposing second surface facing away from the tip section end of the endoscope, and wherein the first surface is a front surface and the second surface is a back surface, the first surface receiving an associated lens assembly of said at least one lens assembly; one or more illuminators associated with said at least one lens assembly; an upper base board and a lower base board adapted to support said one or more optical assemblies; and a plurality of grooves on said upper and lower base boards for supporting said one or more illuminators.

Optionally, the first surface is a glass surface. The second surface comprises an electronic chip. The second surface comprises a printed circuit board. Each of said one or more optical assemblies is a metal frame functioning as a heat sink for heat generated by one or more illuminators.

In conjunction with any of the above embodiments, the present application discloses an electronic circuit board of a tip section of a multi-viewing elements endoscope, the electronic circuit board comprising a plurality of viewing element holders, each viewing element holder supporting an optical lens assembly and an associated image sensor, and one or more illuminators associated with the optical lens assembly, and wherein each viewing element holder comprises one or more grooves for supporting the one or more illuminators.

Optionally, the image sensor is placed in a folded position with a first front surface facing a tip section end of the endoscope, and an opposing second back surface facing away from the tip section end of the endoscope, the first front surface receiving the associated optical lens assembly. The first front surface is a glass surface. The second back surface comprises an electronic chip. The second back surface comprises a printed circuit board. The electronic circuit board comprises an upper base board and a lower base board. The viewing element holder is a metal frame functioning as a heat sink for heat generated by said one or more illuminators. The metal component is placed between said plurality of viewing element holders to act as a heat sink for said one or more illuminators and support the viewing element holders fixedly between an upper and a lower base boards.

Optionally, the electronic circuit board comprises one or more viewing element holders of a tip section of a multi-viewing elements endoscope, wherein each of said one or more viewing element holder comprises at least one optical lens assembly, an image sensor, one or more illuminators, and one or more grooves for supporting the one or more illuminators.

Optionally, the tip section further comprises a front injector; at least one side injector; a front jet; at least one side jet; and a front working channel configured for insertion of a medical tool. The front jet and said front injector are positioned adjacent to each other and on a side of said front working channel. The front jet and said front injector are positioned on either side of said front working channel.

In conjunction with any of the above embodiments, the present application discloses an illuminator electronic circuit board assembly for a tip section of a multi-viewing elements endoscope, the illuminator electronic circuit board assembly comprising: a front illuminator electronic circuit board supporting one or more front illuminators associated with a front optical assembly, wherein said front optical assembly comprises a front lens assembly and a front image sensor; at least one side illuminator electronic circuit board supporting one or more side illuminators associated with one or more side optical assemblies wherein each of said one or more side optical assemblies comprise a side lens assembly and a side image sensor; and an upper base board and a lower base board adapted to hold therebetween said front and at least one side illuminator electronic circuit boards.

Optionally, the illuminator electronic circuit board assembly comprises a metal frame having front and rear portions supporting said front illuminator electronic circuit board and said at least one side illuminator electronic circuit board. The metal frame functions as a heat sink for said one or more front and side illuminators. The metal frame approximates an H shape with four side support walls extending outwardly at 90 degrees from each leg of said H shape and two front support walls are positioned at an end of and perpendicular to two of said four side support walls. The front illuminator electronic circuit board and said at least one side illuminator electronic circuit board are U shaped. The front illuminator electronic circuit board supports three illuminators. Two of said three illuminators are positioned between said upper and lower base boards and one of said three illuminators is placed above said upper base board. The at least one side illuminator electronic circuit board supports two illuminators. The at least one side illuminator electronic circuit board comprises two side illuminator electronic circuit boards, one on either side of said tip section. The tip section further comprises: a front injector; at least one side injector; a front jet; at least one side jet; and a front working channel configured for insertion of a medical tool. The front jet and said front injector are positioned adjacent to each other and on a side of said front working channel. The front jet and said front injector are positioned on either side of said front working channel.

In conjunction with any of the above embodiments, the present application discloses an electronic circuit board assembly for a tip section of a multi-viewing elements endoscope, the electronic circuit board assembly comprising: a base board configured to carry a first metal frame to support a front looking viewing element and a second metal frame to support a side looking viewing element; a front illumination circuit board comprising a front panel configured to carry three sets of front illuminators for illuminating a field of view of the front looking viewing element, and a side illumination circuit board comprising a side panel configured to carry at least one set of side illuminators for illuminating a field of view of the side looking viewing element.

Optionally, each of said three sets of front illuminators comprise 2, 3 or 4 illuminator elements. Each of said at least one side illuminators comprise 2, 3 or 4 illuminator elements. The front illumination circuit board and said side illumination circuit board approximate a U shape. The base board is roughly L shaped comprising: a first member extending in a y direction and in an x direction and a second member extending in a y direction and in an x direction, wherein the first member is integrally formed with the second member, wherein said first member and said second member lie in a same horizontal plane and wherein said second member extends from said first member at an angle of substantially 90 degrees. The front looking viewing element comprises a front looking image sensor and a corresponding lens assembly with an associated printed circuit board. The side looking viewing element comprises a side looking image sensor and a corresponding lens assembly with an associated printed circuit board. The axes of said first and second metal frames make an angle within a range of 70 to 135 degrees with each other. The axes of said first and second metal frames make an angle of 90 degrees with each other.

In conjunction with any of the above embodiments, the present application discloses a tip section of a multi-viewing elements endoscope, the tip section comprising: a front looking viewing element and three sets of front illuminators associated therewith; a side looking viewing element and two sets of side illuminators associated therewith; and an electronic circuit board assembly, comprising: a base board configured to carry a first metal frame to support the front looking viewing element and a second metal frame to support the side looking viewing element; and an illumination circuit board comprising a front foldable panel configured to carry the three sets of front illuminators for illuminating a field of view of the front looking viewing element, and a side panel configured to carry a set of side illuminators for illuminating a field of view of the side looking viewing element.

Optionally, the front looking viewing element comprises a front looking image sensor and a corresponding lens assembly with an associated printed circuit board. The side looking viewing element comprises a side looking image sensor and a corresponding lens assembly with an associated printed circuit board. The axes of said first and second metal frames make an angle within a range of 70 to 135 degrees with each other. The axes of said first and second metal frames make an angle of 90 degrees with each other. The tip section further comprises a tip cover and a fluid channeling component. The diameter of said tip section is less than 11 millimeters. The diameter of said tip section is 10.5 millimeters. The fluid channeling component comprises a front working channel adapted for insertion of a medical tool; a front jet channel adapted to clean a body cavity into which said endoscope is inserted; and an injector opening having a nozzle aimed at the front looking viewing element and associated illuminators.

Optionally, the fluid channeling component further comprises a side injector opening having a nozzle aimed at the side looking viewing element and associated illuminators. The fluid channeling component further comprises at least one side jet channel opening. The front working channel is adapted to apply suction. The front working channel has a diameter ranging from 2.8 to 4.8 millimeters. The front working channel has a diameter ranging from 3.2 to 3.5 millimeters. The front working channel has a diameter ranging from 3.8 to 4.2 millimeters.

In conjunction with any of the above embodiments, the present application discloses an interface unit configured to functionally associate with an endoscope system which comprises at least two simultaneously operating imaging channels associated with at least two displays, respectively, wherein the interface unit comprises: an image processor functionally associated with said at least two imaging channels and configured to generate images comprising image data received simultaneously from said at least two imaging channels, and an interface unit display, functionally associated with said image processor, wherein images generated by said image processor and comprising image data from said at least two imaging channels are displayable on said interface unit display.

Optionally, each imaging channel is associated with an image capturing device, respectively. The interface unit display is substantially portable. The interface unit display is functionally associated with said image processor wirelessly. The image capturing devices capture video images, and said image data in each of said at least two imaging channels comprise an incoming video stream corresponding to video images, and said image processor is configured to generate a single video stream displayable on said interface unit display, so that reduced-size images corresponding to each incoming video stream are simultaneously displayed on said interface unit display. The image processor is configured to generate a single video stream from the at least two incoming video streams substantially in real time.

Optionally, the interface unit further comprises an interface unit computer operating a files managing system and comprising a files storage module, wherein said interface unit computer is configured to generate and store in said files storage module files of images generated by said image processor. The interface unit further comprises a user interface module allowing a user to command said computer.

Optionally, the user interface module comprises a touch screen. The interface unit further comprises a communication channel configured to allow communication between said interface unit computer and a computer network at least for transferring files between said interface unit computer and said computer network. The computer network is a local computer network. The local computer network is a hospital network. The computer network is the Internet. The communication channel comprises a LAN communication interface port, and operates an Internet Protocol. The communication channel comprises a WiFi communication interface port. The communication channel comprises a video/audio communication interface port, configured for outputting a video stream. The communication interface port comprises an S-video or a composite port. The communication interface port comprises an HDMI port. The interface unit is configured to communicate through said communication interface port to a network computer, substantially in real time, a video stream generated by said image processor. The image processor is configured, when commanded, to capture a substantially single video frame in each of said imaging channels at the moment of said command and to communicate through said communication interface port to a network computer, a video stream comprising sequentially, still images of said single video frames wherein each such still image is included in the video stream for a pre-determined time period.

Optionally, the interface unit further comprises a synchronization module functionally associated with at least two of said image capturing devices, and configured for generating a synchronization signal for synchronizing incoming video streams in the imaging channels corresponding to said at least two image capturing devices.

In conjunction with any of the above embodiments, the present application discloses a method for capturing images using an interface unit in an endoscope system, said endoscope system comprising a plurality of simultaneously operating imaging channels, said interface unit having an interface unit display and capable of receiving and individually capturing an image from each one of said plurality of imaging channels, said method comprising the steps of: triggering an image capture event; displaying a first image from a first imaging channel of said plurality of imaging channels on said interface unit display; sending a first trigger pulse from said interface unit to an image capture computer to notify said image capture computer to save a digital copy of said first image on a non-volatile medium; displaying a second image from a second imaging channel of said plurality of imaging channels on said interface unit display; and sending a second trigger pulse from said interface unit to an image capture computer to notify said image capture computer to save a digital copy of said second image on a non-volatile medium, wherein, said first and second images are captured and saved sequentially and the original aspect ratio of said first and second images is preserved.

Optionally, said triggering an image capture event is accomplished by pressing a button on the endoscope of said endoscope system. The triggering an image capture event is accomplished by pressing a button on said interface unit. The interface unit display includes a touchscreen and said triggering an image capture event is accomplished by pressing a portion of said touchscreen. The interface unit and said capture computer are connected via a serial connection.

In conjunction with any of the above embodiments, the present application discloses a system of displaying videos generated in a native aspect ratio corresponding to a left-side looking, a front-looking and a right-side looking viewing element of an endoscopic tip, the system comprising: a left-side wide-screen monitor for displaying a first video from the left-side looking viewing element; a center square monitor for displaying a second video from the front-looking viewing element; a right-side wide-screen monitor for displaying a third video from the right-side looking viewing element; and a main control unit for aligning and modulating a native aspect ratio of the first and third videos, wherein said first video is right-aligned and said third video is left-aligned, and wherein said left-side, center and right-side monitors are placed contiguously so that the respective bottom edges of each of said first, second, and third videos are at a substantially same level.

Optionally, the native aspect ratio is 4:3 or 5:4. The main control unit modulates the native aspect ratio of said first and third videos by no more than 30%. The main control unit modulates the native aspect ratio of said first and third videos by 5%, 10%, 15%, 20%, 25% or 30%. The main control unit modulates the native aspect ratio of said first and third videos by 0%. The left-side and right-side monitors have respective longer edges horizontal. The left-side, center and right-side monitors are placed linearly. The first portion to the left of said right-aligned first video and a second portion to the right of said left-aligned third video, comprise a plurality of patient related information.

In conjunction with any of the above embodiments, the present application discloses a method of displaying videos generated in a native aspect ratio corresponding to a left-side looking, a front-looking and a right-side looking viewing element of an endoscopic tip, the method comprising: displaying a first video from the left-side looking viewing element onto a left-side wide-screen monitor; displaying a second video from the front-looking viewing element onto a center square monitor; displaying a third video from the right-side looking viewing element onto a right-side wide-screen monitor; and aligning and modulating the native aspect ratio of the first and third videos, wherein said first video is right-aligned and said third video is left-aligned, and wherein said first video, second video, and third video are positioned contiguously so that respective top edges of said videos are at a substantially same level.

Optionally, the native aspect ratio is 4:3 or 5:4. The native aspect ratio of said first and third videos is modulated by no more than 30%. The native aspect ratio of said first and third videos is modulated by 5%, 10%, 15%, 20%, 25% or 30%. The native aspect ratio of said first and third videos is modulated by 0%. The left-side and right-side monitors have respective longer edges horizontal. The left-side, center and right-side monitors are placed linearly. The first portion to the left of said right-aligned first and a second portion to the right of said left-aligned third video, comprise a plurality of patient related information.

In conjunction with any of the above embodiments, the present application discloses a system of displaying videos generated in a native aspect ratio corresponding to a left-side looking, a front-looking and a right-side looking viewing element of an endoscopic tip, the system comprising: a left-side wide-screen monitor for displaying a first video from the left-side looking viewing element; a center wide-screen monitor for displaying a second video from the front-looking viewing element; a right-side wide-screen monitor for displaying a third video from the right-side looking viewing element; and a main control unit for aligning, rotating and modulating the native aspect ratio of at least one of said first, second or third videos, wherein said left-side, center and right-side monitors are placed contiguously. The left-side, center and right-side monitors are integrated within a unitary frame encasement. Optionally, the left-side and right-side monitors are placed at an angle 'N' with reference to said center monitor. The angle 'N' may range from 10 to 30 degrees.

Optionally, the native aspect ratio is 4:3 or 5:4. The native aspect ratio of said first and third videos is modulated by no more than 30%. The native aspect ratio of said first and third videos is modulated by 5%, 10%, 15%, 20%, 25% or 30%. The left-side and right-side monitors have respective longer edges horizontal. The left-side, center and right-side monitors are placed linearly. The first portion to the left of said right-aligned first and a second portion to the right of said left-aligned third video, comprise a plurality of patient related information. The main control unit modulates the native aspect ratio of said first, second and third videos by 0%. The left-side and right-side widescreen monitors have respective longer edges horizontal and said center widescreen monitor has a shorter edge horizontal. The bottom edges of said left-side, center and right-side widescreen monitors are at a substantially same level. The first, second and third videos are respectively right, bottom and left-aligned. The second video is also rotated for display on said center widescreen monitor. A first portion on the left of said right-aligned first video, a second portion on the top of said bottom-aligned second video and a third portion on the right of said left-aligned third video, comprise plurality of patient related information. The top edges of said left-side, center and right-side widescreen monitors are at a substantially same level. The first, second and third videos are respectively right, top and left-aligned. The second video is also rotated for display on said center widescreen monitor. The first, second and third videos are respectively right, vertically-center and left aligned. The left-side, center and right-side widescreen monitors have respective shorter edges horizontal. The respective centroids of said left-side, center and right-side monitors are at a substantially same level. The first, second and third videos are all bottom-aligned. The first, second and third videos are all rotated for display on said respective left-side, center and right-side widescreen monitors. The first, second and third portions to the top of said bottom aligned first, second and third videos, comprise a plurality of patient related information. The first, second and third videos are all top-aligned. The left-side, center and right-side monitors are integrated within a unitary frame encasement. Optionally, the left-side and right-side monitors are placed at an angle 'N' with reference to said center monitor. The angle 'N' may range from 10 to 30 degrees.

In conjunction with any of the above embodiments, the present application discloses a method of displaying videos generated in a native aspect ratio corresponding to a left-side looking, a front-looking and a right-side looking viewing element of an endoscopic tip, the method comprising: displaying a first video from the left-side looking viewing element onto a left-side wide-screen monitor; displaying a second video from the front-looking viewing element onto a center wide-screen monitor; displaying a third video from the right-side looking viewing element onto a right-side wide-screen monitor; and aligning, rotating and modulating the native aspect ratio of at least one of said first, second or third videos, wherein a top edge and a bottom edge of each of said first, second, and third videos are linearly contiguous.

In conjunction with any of the above embodiments, the present application discloses a system of displaying first, second and third videos generated in a native aspect ratio corresponding to a left-side looking, a front-looking and a right-side looking viewing element of an endoscopic tip, the system comprising: a monitor; and a main control unit for combining the first, second and third videos into a resultant single video frame, wherein said resultant single video frame represents an integrated field of view of said left-side looking, front-looking and right-side looking viewing elements, wherein said main control unit slices said resultant single video frame to generate modulated left, center and right video frames for contiguous display on said monitor, and wherein said modulated left and right video frames are displayed as skewed with respect to said modulated center video frame.

Optionally, the center video frame comprises a sum of X degrees of views on either side of a center of the integrated field of view of the resultant single video frame and wherein the left and right video frames comprise respective remaining left and right portions of the resultant single video frame. X is approximately 15 degrees. X ranges from 15 degrees up to 30 degrees. The left, center and right video frames are separated by black image stripes. The black image stripes are no more than 6 inches wide. The native aspect ratio is 4:3 or 5:4. The main control unit modulates the left, center and right video frames by no more than 30%.

In conjunction with any of the above embodiments, the present application discloses a method of displaying first, second and third videos generated in a native aspect ratio corresponding to a left-side looking, a front-looking and a right-side looking viewing element of an endoscopic tip, the method comprising: combining the first, second and third videos into a resultant single video frame, wherein said resultant single video frame represents an integrated field of view of said left-side looking, front-looking and right-side looking viewing elements; and slicing said resultant single video frame to generate modulated left, center and right video frames for contiguous display on a monitor, wherein said modulated left and right video frames are displayed as skewed with respect to said modulated center video frame.

Optionally, the center video frame comprises a sum of X degrees of views on either side of a center of the integrated field of view of the resultant single video frame and wherein the left and right video frames comprise respective remaining left and right portions of the resultant single video frame. X is approximately 15 degrees. X ranges from 15 degrees up to 30 degrees. The left, center and right video frames are separated by black image stripes. The black image stripes are no more than 6 inches wide.

In conjunction with any of the above embodiments, the present application discloses a system of displaying one of first, second and third videos generated in a native aspect ratio corresponding to a left-side looking, a front-looking and a right-side looking viewing element of an endoscopic tip, the system comprising: a monitor; and a main control unit for slicing selected one of said first, second and third videos to generate modulated left, center and right video frames for contiguous display on said monitor, wherein said modulated left and right video frames are displayed as skewed with respect to said modulated center video frame.

In conjunction with any of the above embodiments, the present application discloses a method of displaying one of first, second and third videos generated in a native aspect ratio corresponding to a left-side looking, a front-looking and a right-side looking viewing element of an endoscopic tip, the method comprising: selecting one of said first, second and third videos for display on a monitor; and slicing said selected one of said first, second and third videos to generate modulated left, center and right video frames for contiguous display on said monitor, wherein said modulated left and right video frames are displayed as skewed with respect to said modulated center video frame.

In conjunction with any of the above embodiments, the present application discloses an endoscope configured to provide quasi-simultaneous N views, N being greater than 1, said endoscope comprising N optical systems configured to collect light from directions associated with said N views, and further comprising M image capturing devices, where M is smaller than N, and said image capturing devices are configured to capture light collected by said N optical systems, thereby providing N views quasi-simultaneously. Optionally, at least one of said M image capturing devices comprises a CCD. M is approximately 1. The image capturing device comprises a single planar light sensitive surface. Each of the optical systems is configured to transfer collected light onto an associated portion of said planar light-sensitive surface. N is approximately 3. The first optical system collects light from a first direction substantially facing said light sensitive surface, and a second optical system and a third optical system, respectively, collect light from directions substantially perpendicular to said first direction. At least two of said optical systems are configured to transfer collected light onto a same portion of said planar light-sensitive surface.

Optionally, the endoscope further comprises a step-wise rotating optical element configured to be controllably positioned in at least two positions corresponding to said at least two optical systems, respectively, wherein in each such position said step-wise rotating optical element allows transfer of collected light from said respective optical system to said portion of said planar light-sensitive surface. The step-wise rotating optical element comprises a mirror. The mirror comprises a semi transparent portion. The step-wise rotating optical element comprises a lens. The endoscope further comprises at least one shutter operable to be shut and opened synchronously with said step-wise rotating optical element. The image capturing device comprises N planar light sensitive surfaces, and each of said optical systems is configured to transfer light to one of said N planar light sensitive surfaces, respectively. The image capturing device is substantially rigid and said N planar light sensitive surfaces are tilted at a fixed angle relative to one another. The image capturing device comprises a substantially flexible portion allowing to controllably tilt at an angle one of said N planar light sensitive surfaces relative to another one of said N planar light sensitive surfaces. The image capturing device comprises two planar light sensitive surfaces, aligned back to back thereby facing substantially opposite directions. M is greater than one and N is greater than two and at least two of said optical systems transfer light onto a light sensitive planar element of one of said image capturing devices. M is equal to two and N is equal to three.

In conjunction with any of the above embodiments, the present application discloses an endoscopic tip comprising: a first lens positioned on a front face of said tip; a second lens positioned on a lateral side of said tip; a third lens positioned on a lateral side of said tip and substantially opposite said second lens; an imager having a plurality of light sensitive surfaces; a first light guide for directing light from said first lens to one of said plurality of light sensitive surfaces; a second light guide for directing light from said second lens to a second of said plurality of light sensitive surfaces; and, a third light guide for directing light from said third lens to a third one of said plurality of light sensitive surfaces, wherein light waves passing through each of said first, second, and third light guides are isolated from each other.

In conjunction with any of the above embodiments, the present application discloses an endoscopic tip comprising: a first lens positioned on a front face of said tip; a second lens positioned on a lateral side of said tip; a third lens positioned on a lateral side of said tip and substantially opposite said second lens; a first imager having a first light sensitive surface; a second imager having a plurality of light sensitive surfaces; a first light guide for directing light from said first lens to said first light sensitive surface of said first imager; a second light guide for directing light from said second lens to a first one of said plurality of light sensitive surfaces of said second imager; and, a third light guide for directing light from said third lens to a second one of said plurality of light sensitive surfaces of said second imager, wherein light waves passing through each of said first, second, and third light guides are isolated from each other.

In conjunction with any of the above embodiments, the present application discloses an endoscopic tip comprising: a first lens positioned on a front face of said tip; a second lens positioned on a lateral side of said tip; a third lens positioned on a lateral side of said tip and substantially opposite said second lens; a double-sided imager having a first side and a second side wherein said first side is substantially opposite said second side, further wherein said first side comprises a first light sensitive surface and said second side comprises a plurality of light sensitive surfaces; a first light guide for directing light from said first lens to said first light sensitive surface of said first side of said double-sided imager; a second light guide for directing light from said second lens to a first one of said plurality of light sensitive surfaces of said second side of said double-side imager; and a third light guide for directing light from said third lens to a second one of said plurality of light sensitive surfaces of said second side of said double-sided imager, wherein light waves passing through each of said first, second, and third light guides are isolated from each other.

In conjunction with any of the above embodiments, the present application discloses a main control unit connected to an image capture section of an endoscope using a utility tube, wherein the image capture section comprises a front viewing element along with associated at least one front illuminator, a first side viewing element along with associated at least one first side illuminators and a second side viewing element along with associated at least one second side illuminators, the main control unit comprising: a video processing system comprising a camera circuit board, a power supply, an electronic memory and a plurality of interfaces and additional processing elements; an electrical cable that runs through the utility tube to connect the front and side viewing elements and associated illuminators with the camera circuit board, wherein a set of N signals are configured to be transmitted between the camera circuit board and the image capture section, wherein M signals out of the N signals are shared so that N<36 and wherein the camera board processes the M signals to generate signals specific to each of the viewing elements.

Optionally, the M signals comprise synchronization signals for the viewing elements. The M signals comprise clock signals for the viewing elements. The M signals comprise supply voltage of the viewing elements. The electrical cable has a diameter ranging from 2 to 2.5 millimeters.

In conjunction with any of the above embodiments, the present application discloses an image capture section or tip where a maximum volume of the image capture section ranges from 2.75 $cm^3$ to 3.5 $cm^3$, where each of the viewing elements is configured to generate a field of view ranging from 120 to 180 degrees, a depth of field ranging from 3 to 100 mm and a peripheral distortion of less than 80% without reliance on any aspherical components, and a maximum focal length in a range of 1 to 1.4 mm. Optionally, the depth of field ranges from 3.5 to 50 mm. The maximum volume of the image capture section is 3.12 $cm^3$ and maximum focal length of said viewing elements is approximately 1.2 mm. The field of views of the front and at least one of side viewing element intersects over a depth of field ranging from 3 to 100 mm. The field of views of the front and at least one side viewing element intersects within a distance of 15 mm from the side viewing element.

In conjunction with any of the above embodiments, the present application discloses a method for operating an endoscope with multiple viewing elements, the method comprising: generating a front view using a front-pointing viewing element located on a front panel of a tip section of the endoscope; generating one or more side views using one or more side-pointing viewing elements located at or in proximity to a distal end of said tip section, wherein fields of view of said front and one or more side viewing elements overlap; displaying said front and side views in real-time on at least one display; generating data indicative of which display should be selected based upon an interaction with an interface on a handle of the endoscope; and switching between said front and side views on the at least one display based upon the generated data.

Optionally, the handle comprises a plurality of buttons, wherein manipulation of said buttons causes said display to zoom in and out, record, capture or freeze images in at least one of said front and side views. The front and side views are displayed on a single screen. The front and side views are displayed on different screens. The handle comprises a plurality of buttons and wherein manipulation of said buttons causes said at least one display to record, capture or freeze images in all of said front and side views concurrently.

In conjunction with any of the above embodiments, the present application discloses a method for operating an endoscope with multiple viewing elements, the method comprising: generating a front view using a front-pointing viewing element located in a tip section of the endoscope; generating at least one side view using at least one side-pointing viewing element located at or in proximity to a distal end of said tip section; displaying said front and side views concurrently and in real-time on at least one display; generating data indicative of which display should be selected based upon a manipulation of at least one button on a endoscope handle; and performing at least one action selected from recording, zooming or freezing, said at least one selected action being performed on the front view, the at least one side view, or both, based upon the generated data, wherein at least one icon or indicator is also displayed related to said at least one selected action.

Optionally, the method further comprises the step of displaying a timer that visually shows a progression of the endoscope through an anatomical region based on time. The timer counts down from a pre-set amount of time, as the endoscope progresses.

In conjunction with any of the above embodiments, the present application discloses an endoscope with multiple viewing elements, comprising: a front-pointing viewing element located in a tip section of the endoscope for generating a front view; at least one side-pointing viewing element located at or in proximity to a distal end of said tip section for generating at least one side view; one or more displays for displaying said front and side views concurrently and in real-time; at least one button on an endoscope handle that can be manipulated to generate data indicative of which display should be selected; and processing means for performing at least one action selected from recording, zooming or freezing, the at least one selected action being performed on the front view, the at least one side view, or both, based upon the generated data, wherein at least one icon or indicator is also displayed related to said at least one selected action.

Optionally, the processing means comprises an FPGA processor and an MPEG digital signal processor.

In conjunction with any of the above embodiments, the present application discloses a method of visualizing navigation path way of an endoscope assembly, wherein said endoscope assembly comprises a tip section having a front-pointing viewing element and two side-pointing viewing elements, the method comprising: inserting the endoscope assembly into a lumen of a body cavity; navigating the endoscope assembly through the lumen, wherein said lumen defines a navigation pathway and wherein said navigation pathway comprises a plurality of junctures in which the pathway changes substantially; operating the endoscope assembly to display a video output from each of the front and side-pointing viewing elements on to at least one monitor, said video output representative of the navigation pathway within the body cavity; and maneuvering the endoscope assembly through the lumen when obstructed by said plurality of junctures, wherein said maneuvering is guided by at least one visual highlight on said at least one monitor.

In conjunction with any of the above embodiments, the present application discloses a service channel connector comprising: at least one service channel opening positioned at a proximal end of the connector; a working channel opening positioned at a distal end of the connector, wherein said service channel opening and working channel opening are in communication via an intermediate channel for inserting medical instruments therethrough, the working channel opening being coupled with an insertion tube of an endoscope; a front wall comprising a first portion, a second portion, and a third portion; a back wall, comprising a first portion, a second portion, and a third portion, each portion having a substantially flat surface; and two side walls.

Optionally, the service channel connector of claim 1 wherein said first, second and third portions of said front wall further comprise four portions each, connected at an angle to one another, and wherein said first, second and third portions of said back wall are substantially straight, rectangular and without any surface indentations. The two side walls approximate a "Y" shape. The service channel connector further comprises a suction channel. The intermediate channel is a service channel. The intermediate channel is a combined channel formed from a service channel and a suction channel. The service channel connector comprises a first section and a second section, wherein said first and second sections are fixedly connected to each other forming the service channel connector. The first section and the second section are joined together by using a laser welding process. The second section is a mirror image of the first section. The first section and the second section are joined together by aligning one or more edges of the two sections leaving no gap between the two sections along a joint line. The first section and the second section are fabricated using a milling process. The first section and the second section comprise smooth internal surfaces. When measured from said proximal end to said distal end and along the back wall, the connector has a length in a range of approximately 15 to 21 millimeters. The working channel opening has an internal diameter in a range of approximately 2.5-8 millimeters.

In conjunction with any of the above embodiments, the present application discloses an endoscope assembly comprising a handle for connecting the endoscope to a control unit, the handle comprising a Y-shaped service channel connector comprising: a first section and a second section, each section comprising at least a service channel opening coupled with a working channel opening via an intermediate channel for inserting medical instruments therethrough, wherein said first and second section are fixedly connected to each other forming the service channel connector, the first section being a mirror image of the second section. Each section further comprises a suction channel. The intermediate channel is a service channel. The intermediate channel is a combined channel formed from a service channel and a suction channel. The first section and the second section are fixably connected to each by using a laser welding process.

Optionally, the first section and the second section are fixably connected to each other leaving at least one service channel opening at a top proximal end of the service channel connector and at least one working channel opening at a bottom distal end of the service channel connector, the at least one service channel opening being used for inserting one or more medical instruments into an insertion tube of an endoscope via the working channel opening. The first section and the second section are fixably connected to each other by aligning one or more edges of the two portions leaving no gap between the two portions along a line of joining. The first section and the second section are fabricated using a milling process. The internal surfaces of the first section and the second section are smooth.

The presently disclosed embodiments enable a plurality of innovative medical procedures. In one embodiment, the present application discloses an improved endoscopic mucosal resection procedure comprising inserting an endoscope into a body cavity and positioned a tip of said endoscope next to a target tissue; inserting an injection needle through a front working channel in said endoscope and positioning said injection needle proximate said target tissue; injecting fluid into the target tissue using said injection needle; inserting a grasping forceps device through a first side service channel of the endoscope; inserting a dissection device through a second side service channel of the endoscope; dissecting the target tissue from the submucosa of the body cavity; withdrawing the dissection tool from the second side service channel; inserting a retrieval net through the second side service channel; and using the grasping forceps to place the dissected target tissue into the retrieval net. Optionally the dissection device is a snare, needle, knife, or other cutting tool.

In another embodiment, the present application discloses another improved endoscopic mucosal resection procedure comprising inserting an endoscope into a body cavity and positioned a tip of said endoscope next to a target tissue; inserting an injection needle through a first channel in said endoscope and positioning said injection needle proximate said target tissue; injecting fluid into the target tissue using said injection needle; inserting a grasping forceps device through a second channel of the endoscope; inserting a dissection device through a third channel of the endoscope; dissecting the target tissue from the submucosa of the body cavity; withdrawing the dissection tool from the third channel; inserting a retrieval net through the third channel; and using the grasping forceps to place the dissected target tissue into the retrieval net. Optionally the dissection device is a snare, needle, knife, or other cutting tool.

In another embodiment, the present application discloses another improved endoscopic retrograde cholangiopancreatography procedure comprising inserting an endoscope into a body cavity and positioning it proximate a target papilla; inserting a guidewire through a first channel, such as the front working channel, inserting a grasper through a second channel, such as one of two side service channels; using the grasper to position the papilla in a position to facilitate the cannulation of the papilla with the guidewire; inserting a sphinctertome through a third channel, such as the second of two side service channels; using the sphinctertome to cut the papilla; withdrawing the sphinctertome; inserting a balloon over the guidewire; positioning the balloon in the papilla and inflating it to widen the sphincter; insert other devices through the third channel to perform a task. Optionally, the other devices can be stone baskets, stents, injection needles, ablation devices, biopsy forceps, and/or cytology brushes.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 38A illustrates a base board of an electronic circuit board assembly in accordance with an embodiment of the present specification;

FIG. 38Hb illustrates one embodiment of a side illumination circuit board;

Figure 2A:
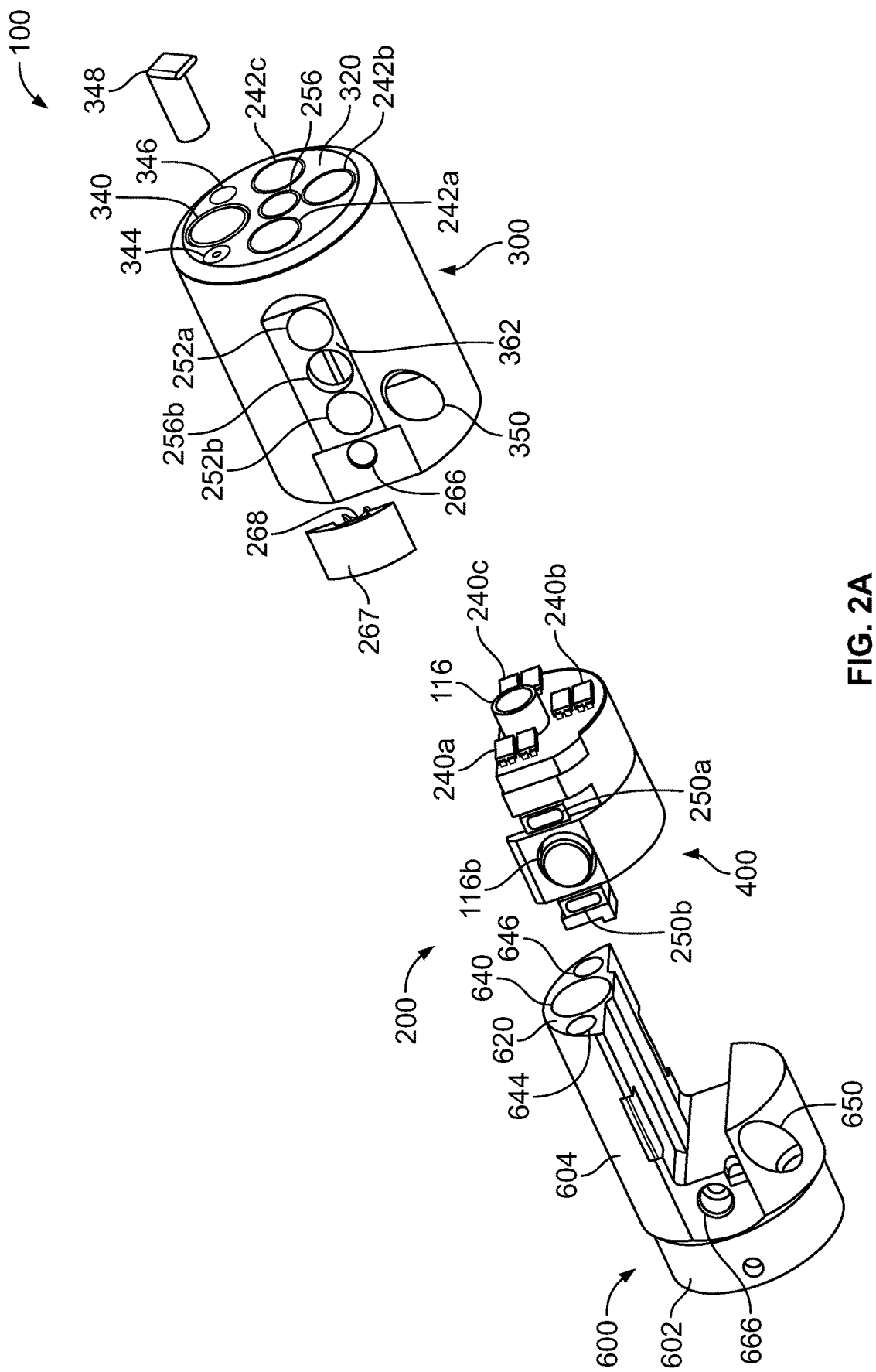
FIG. 2A shows an exploded perspective view of a tip section of an endoscope assembly according to an embodiment.
Figure 53A:
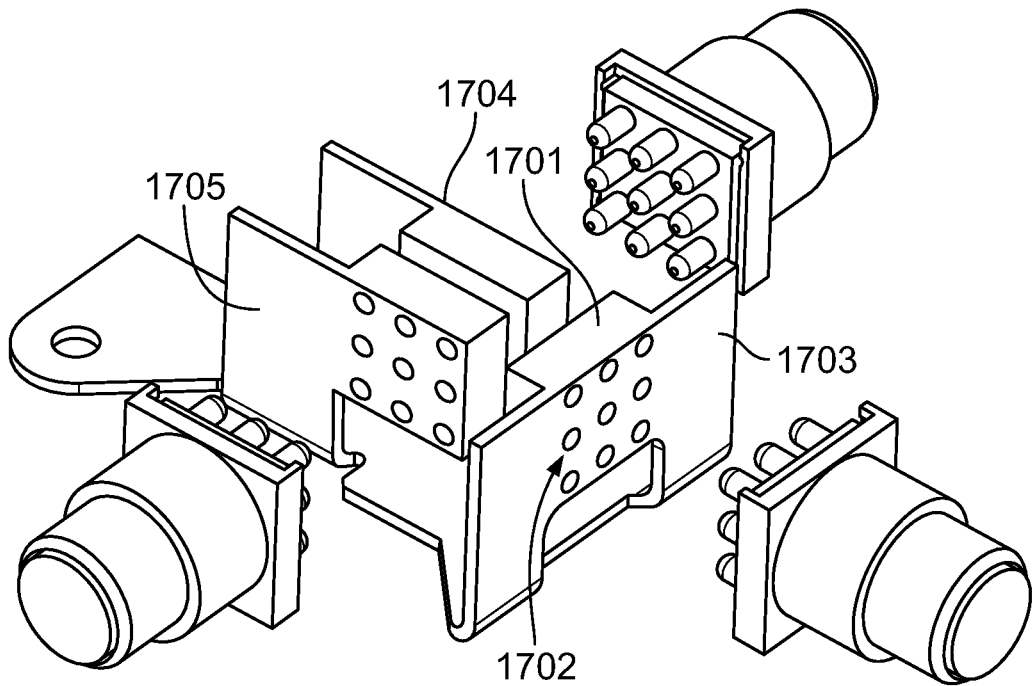
Figure 53B:
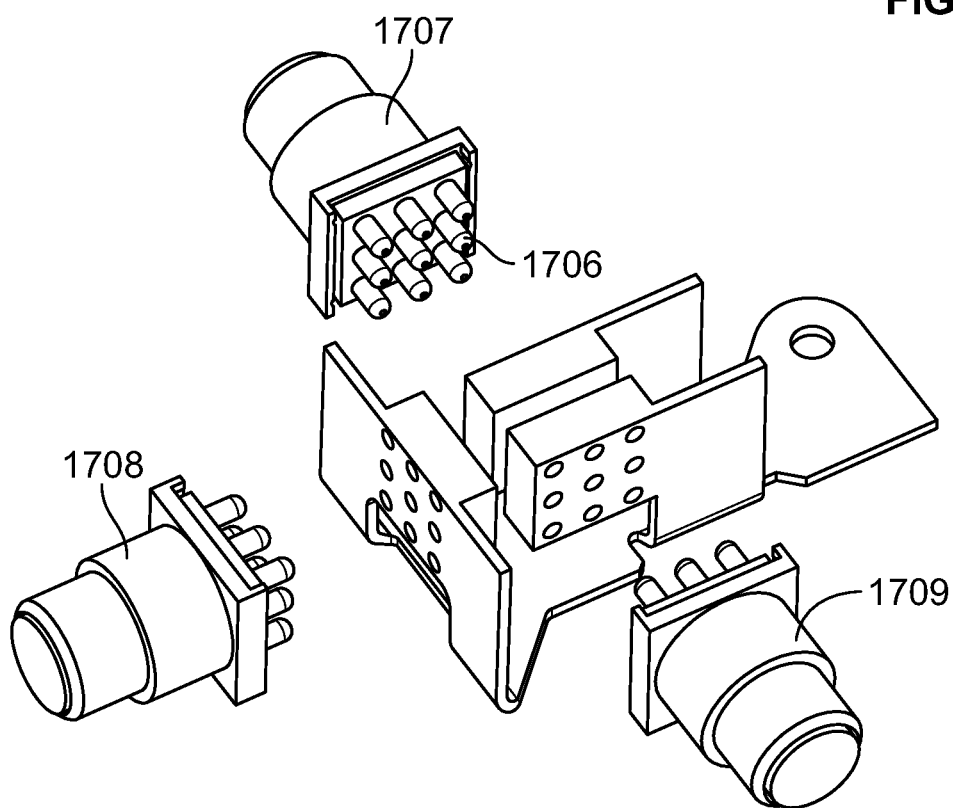
Figure 54:
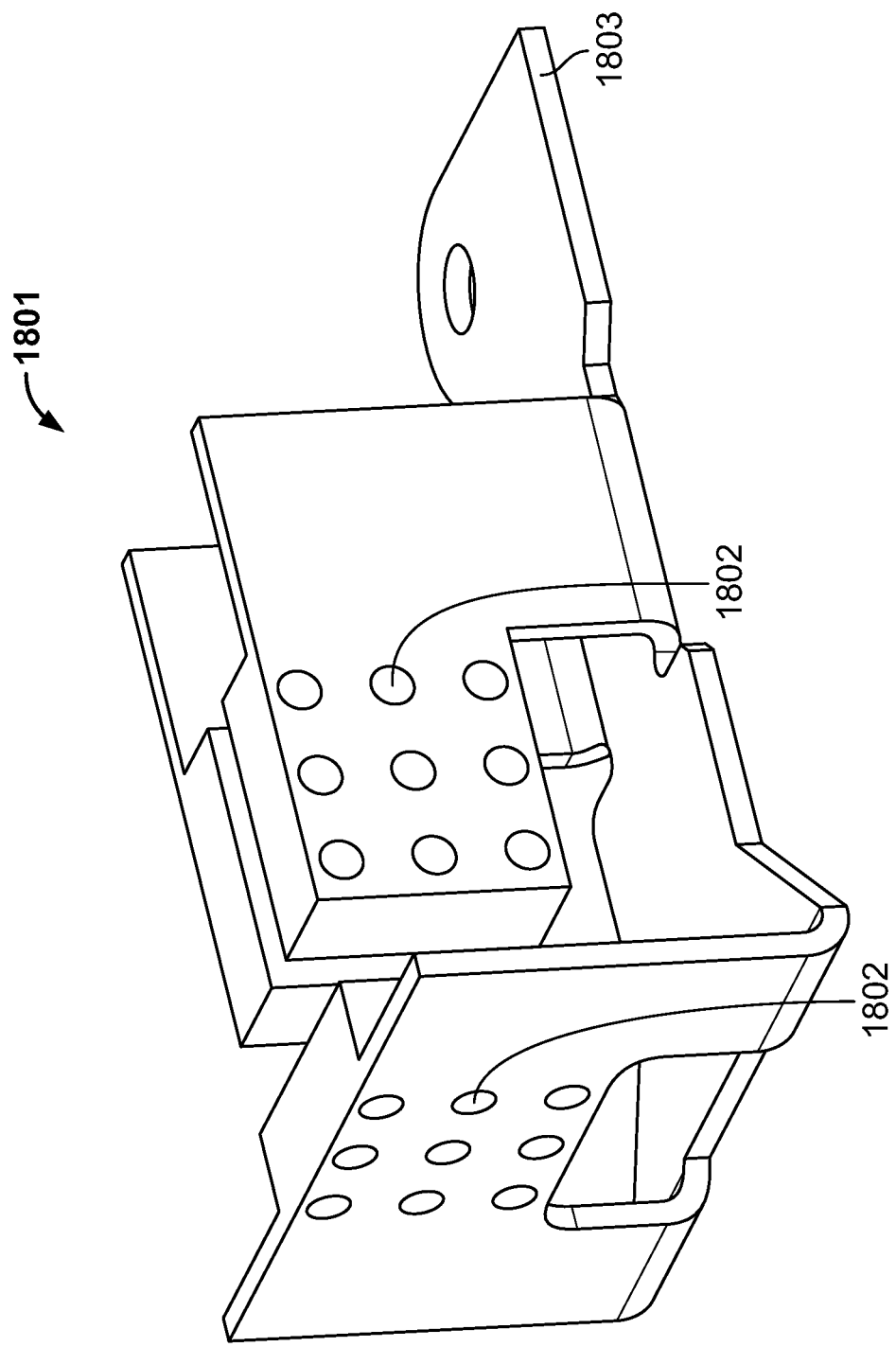
Figure 55A:
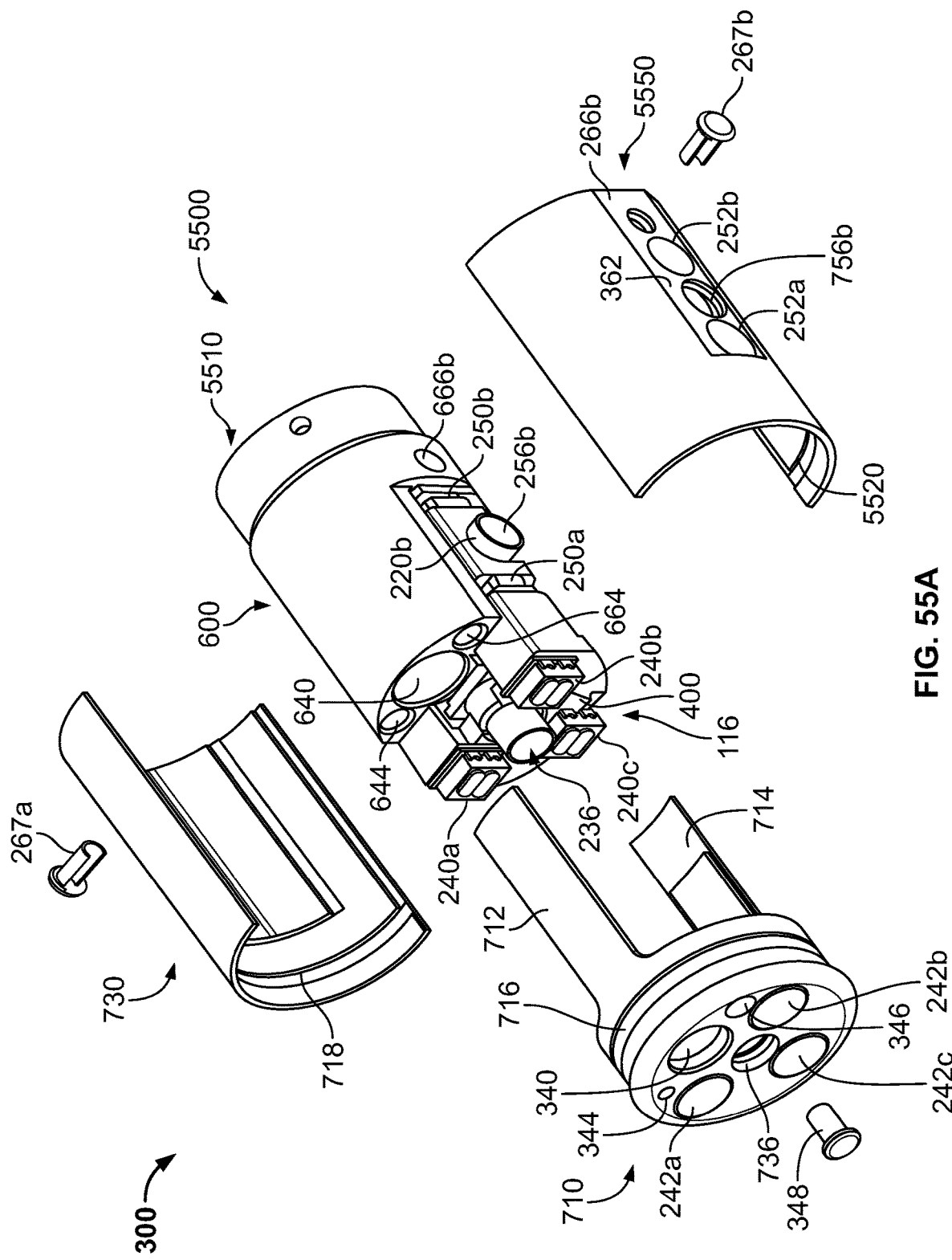
Figure 55B:
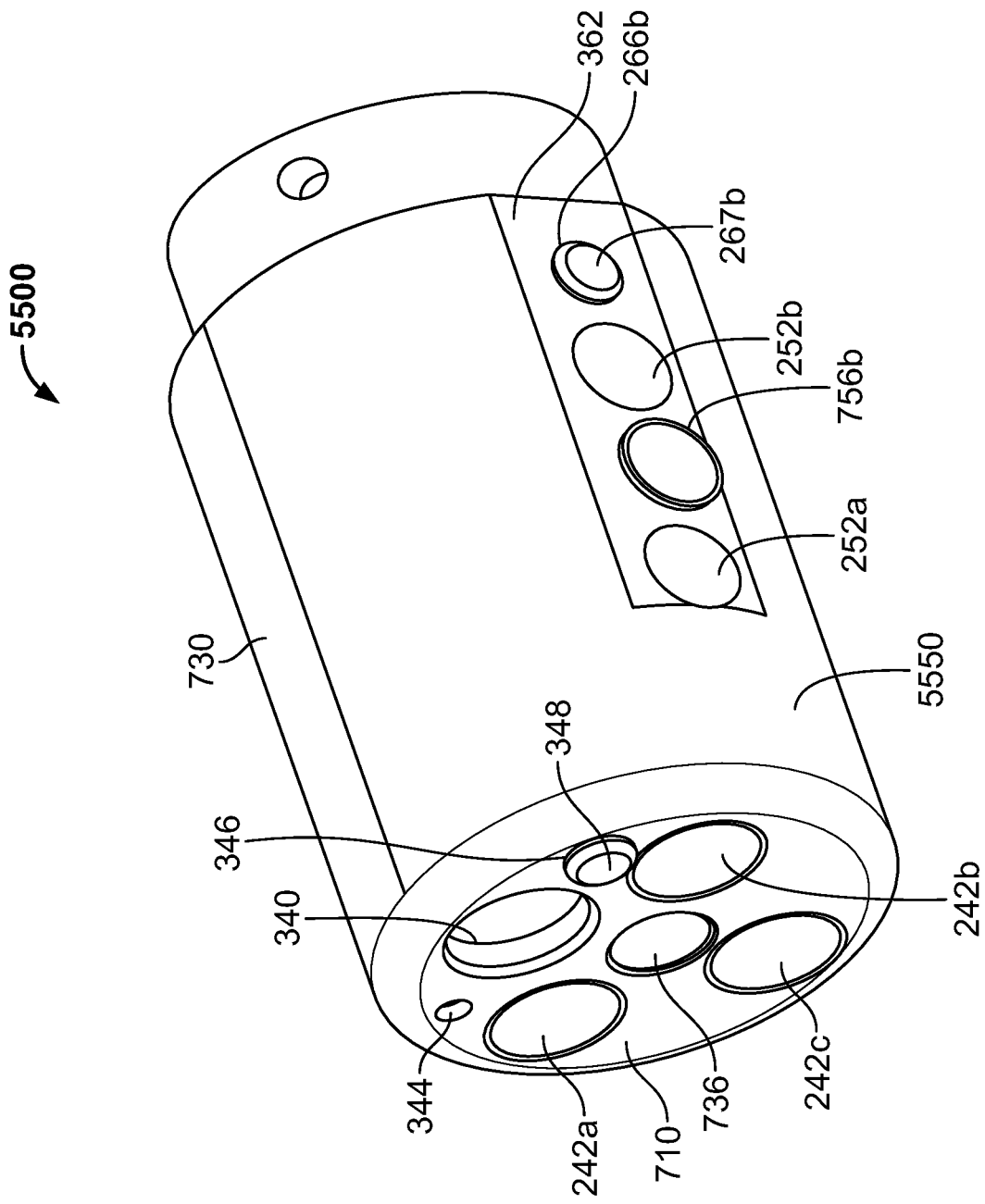
Figure 56:
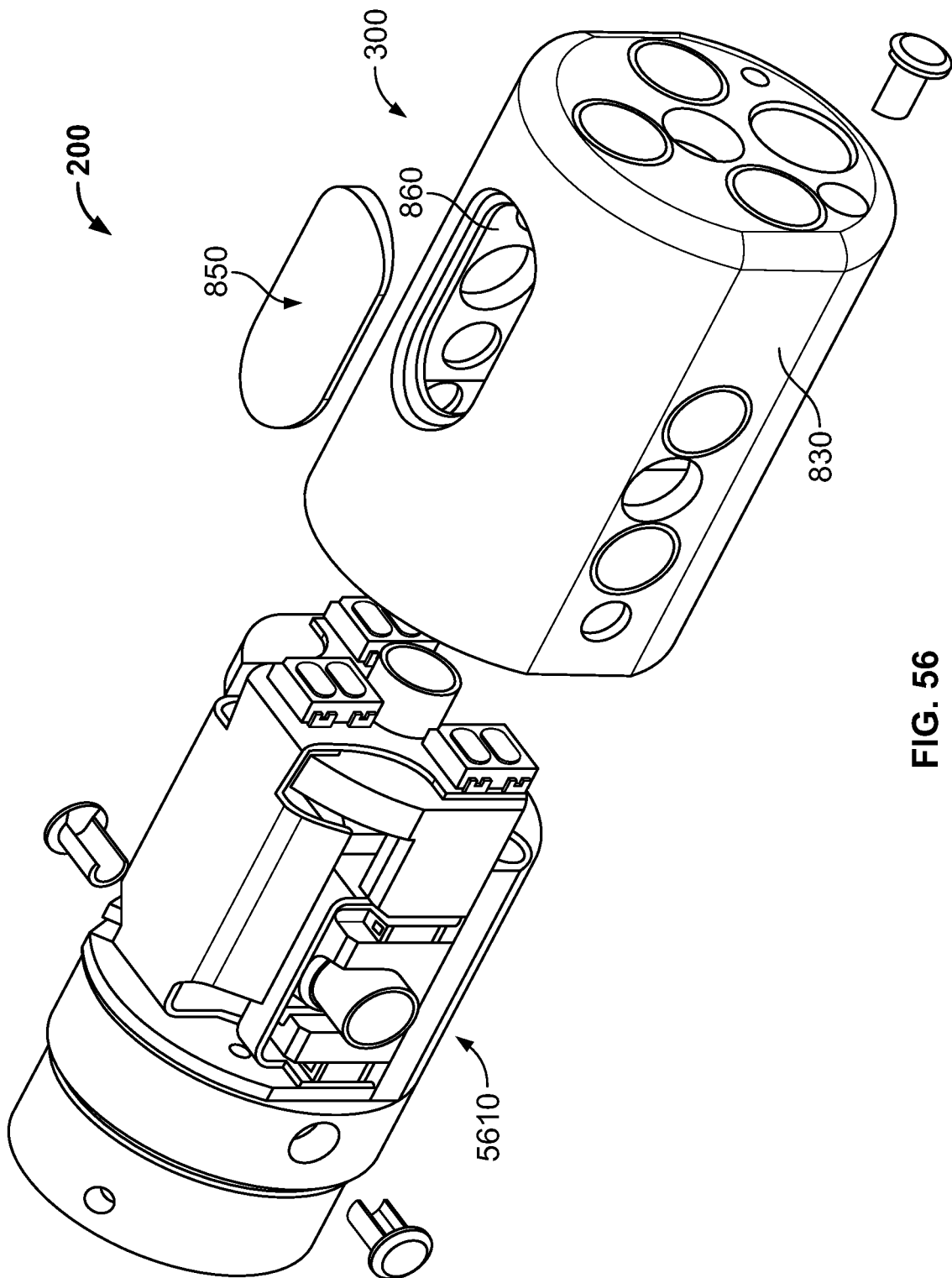
Figure 57:
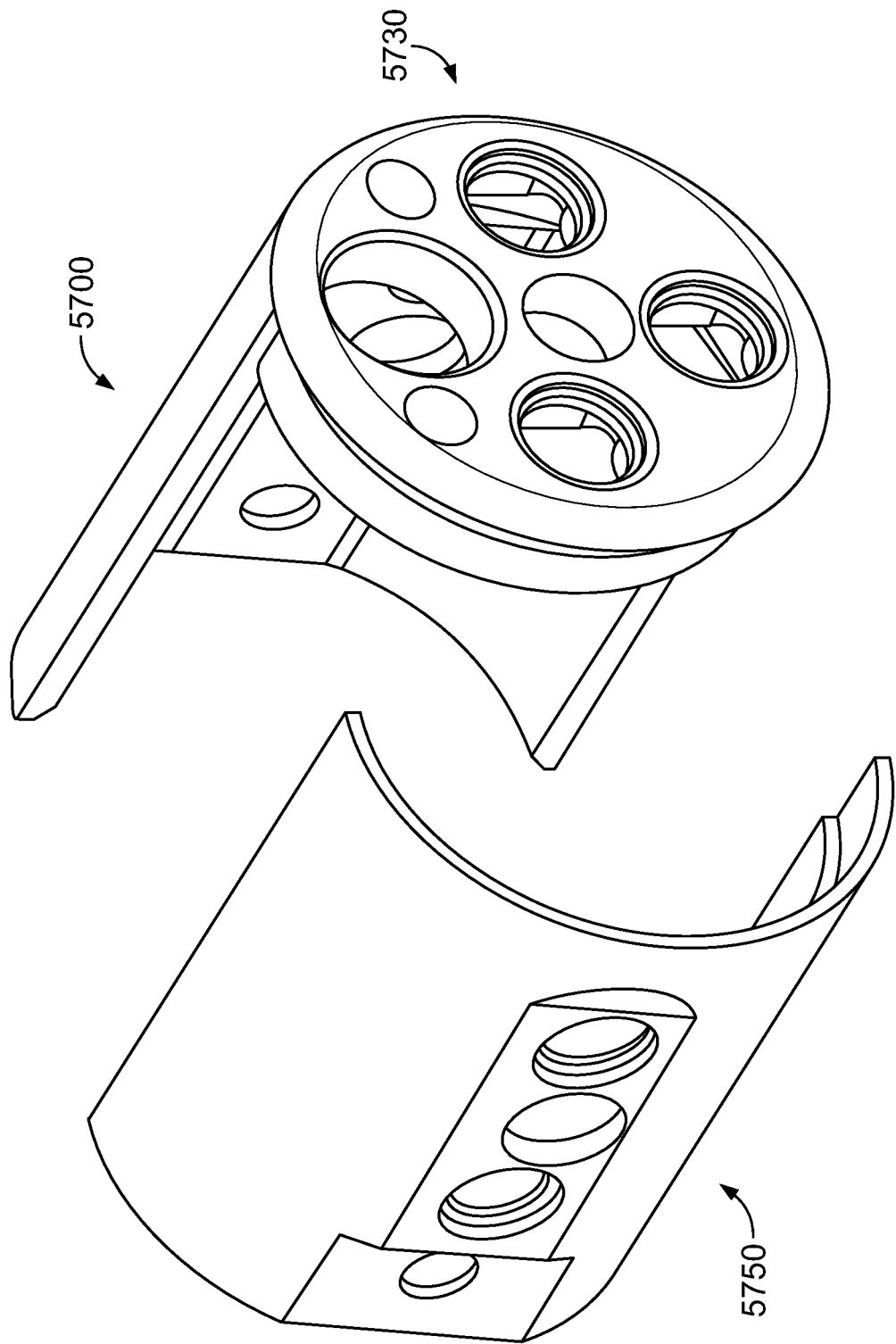
Figure 58A:
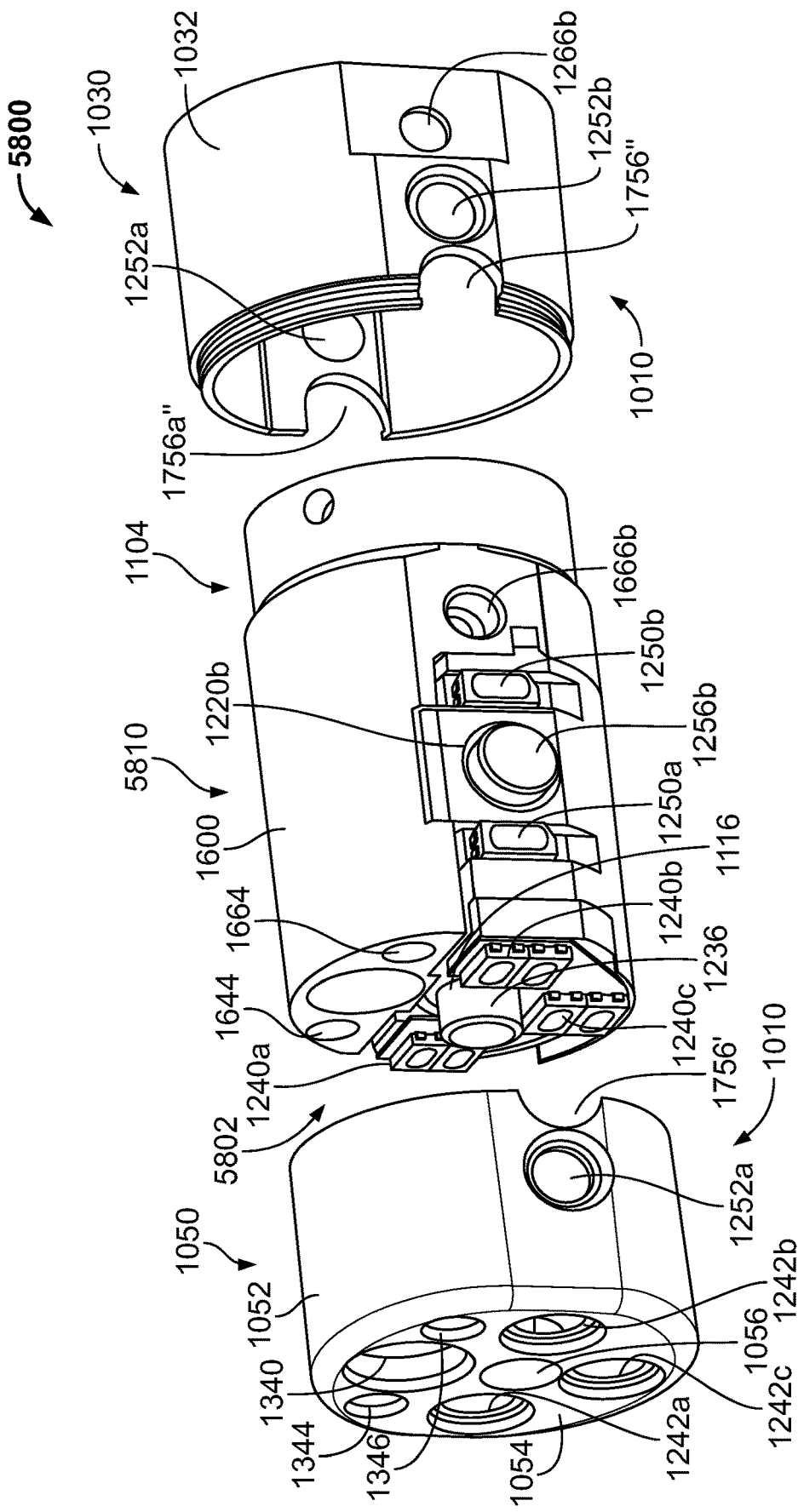
Figure 58B:
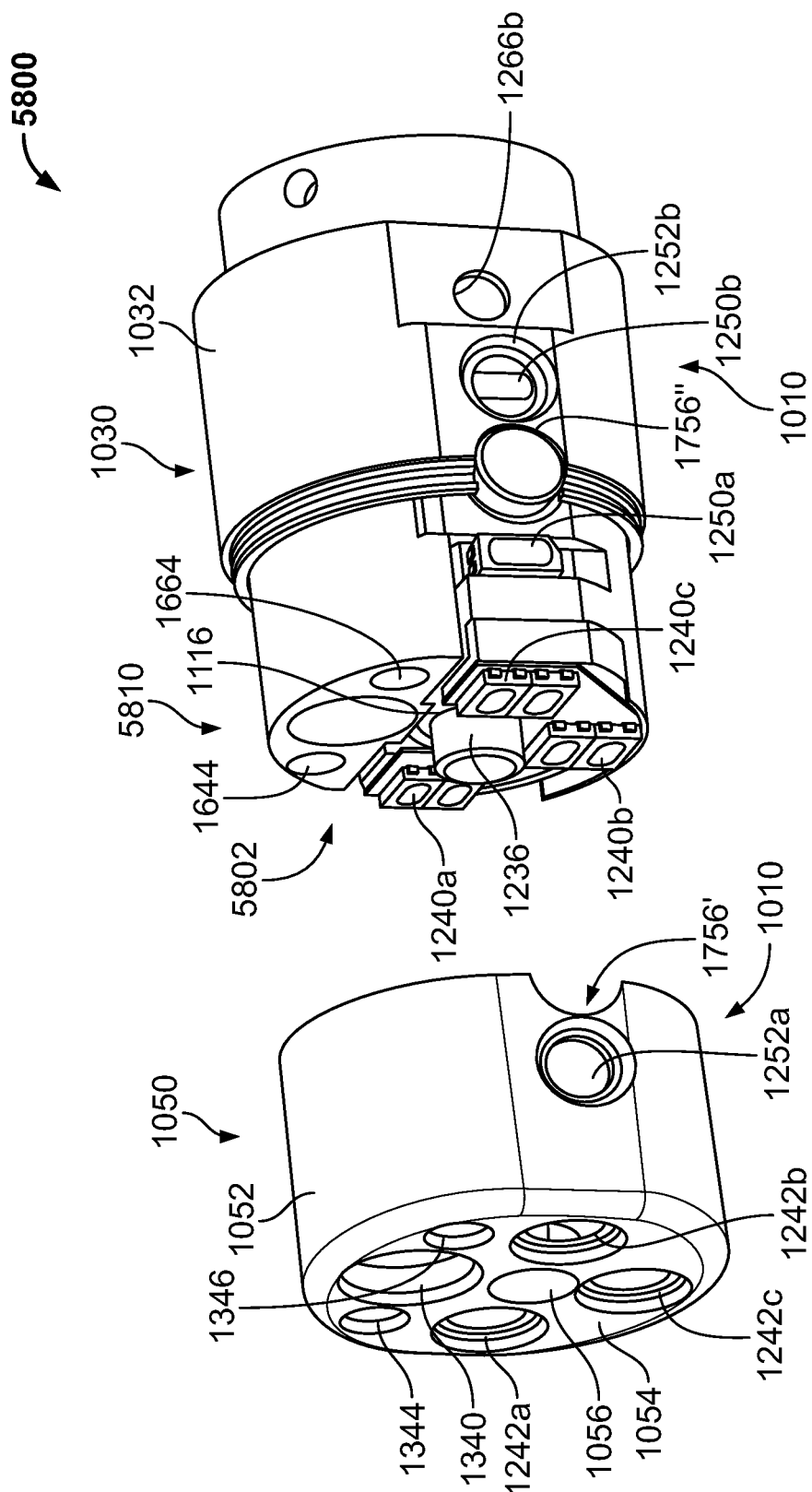
Figure 58C:
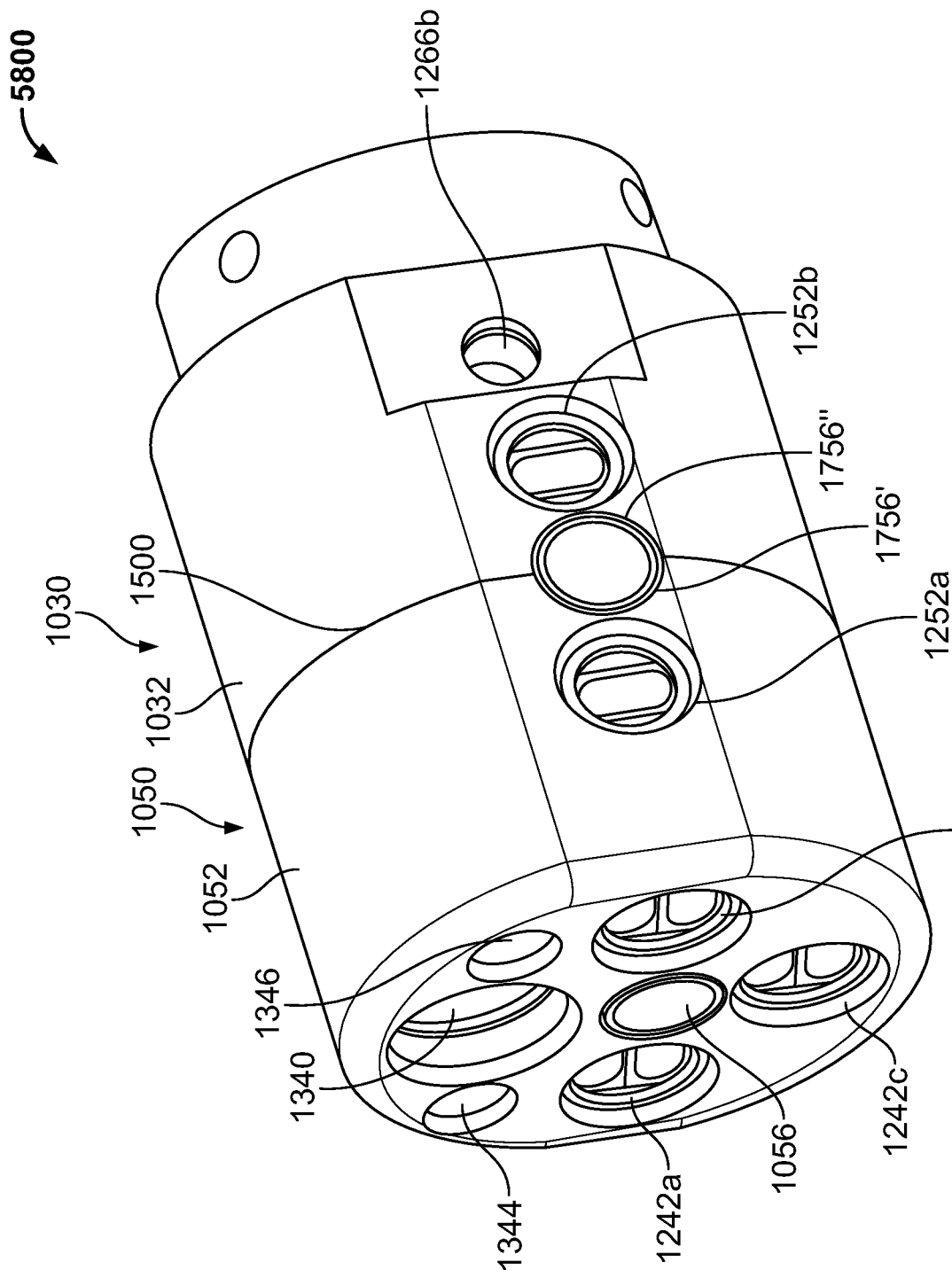
Figure 59A:
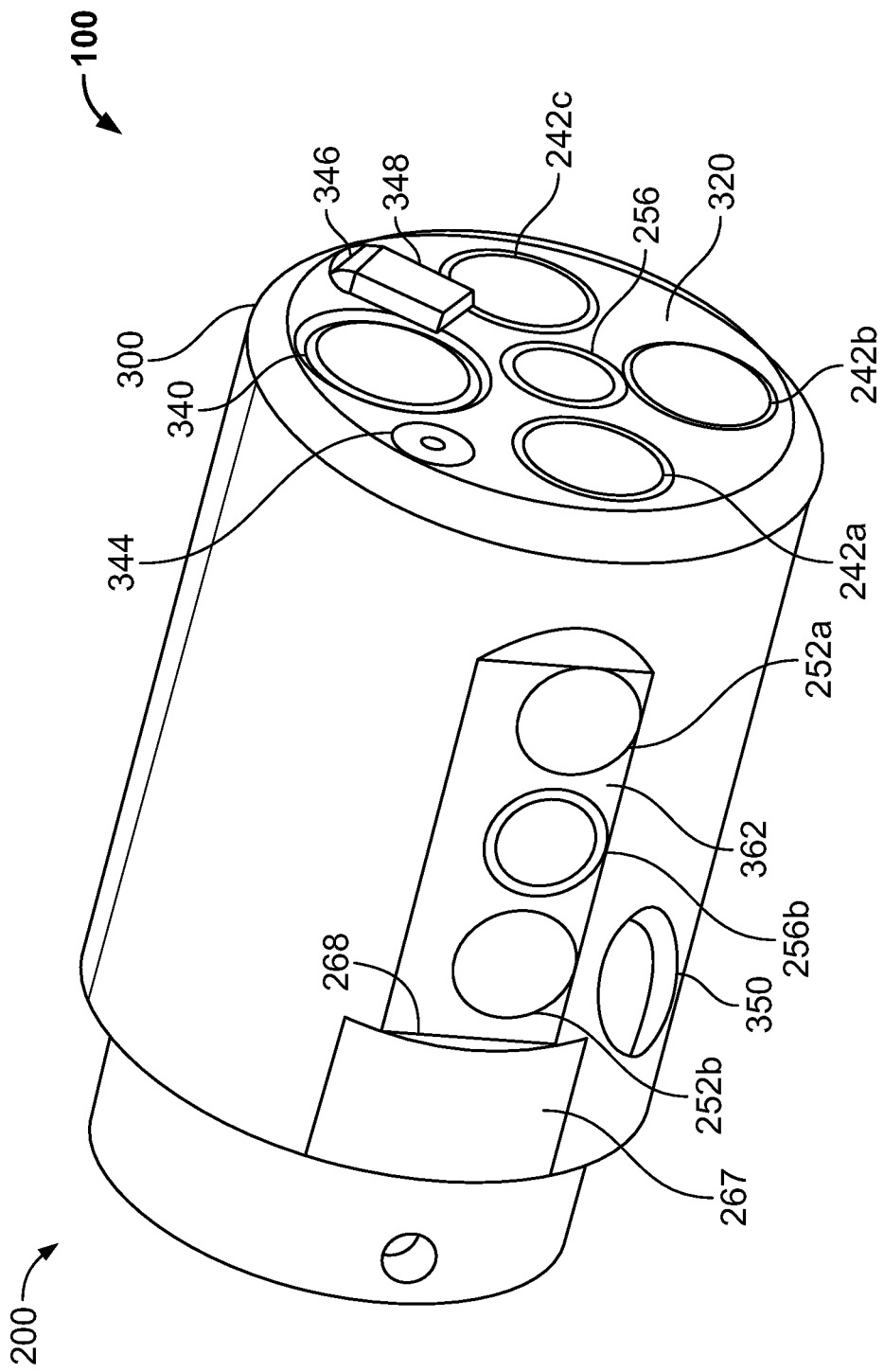
Figure 59B:
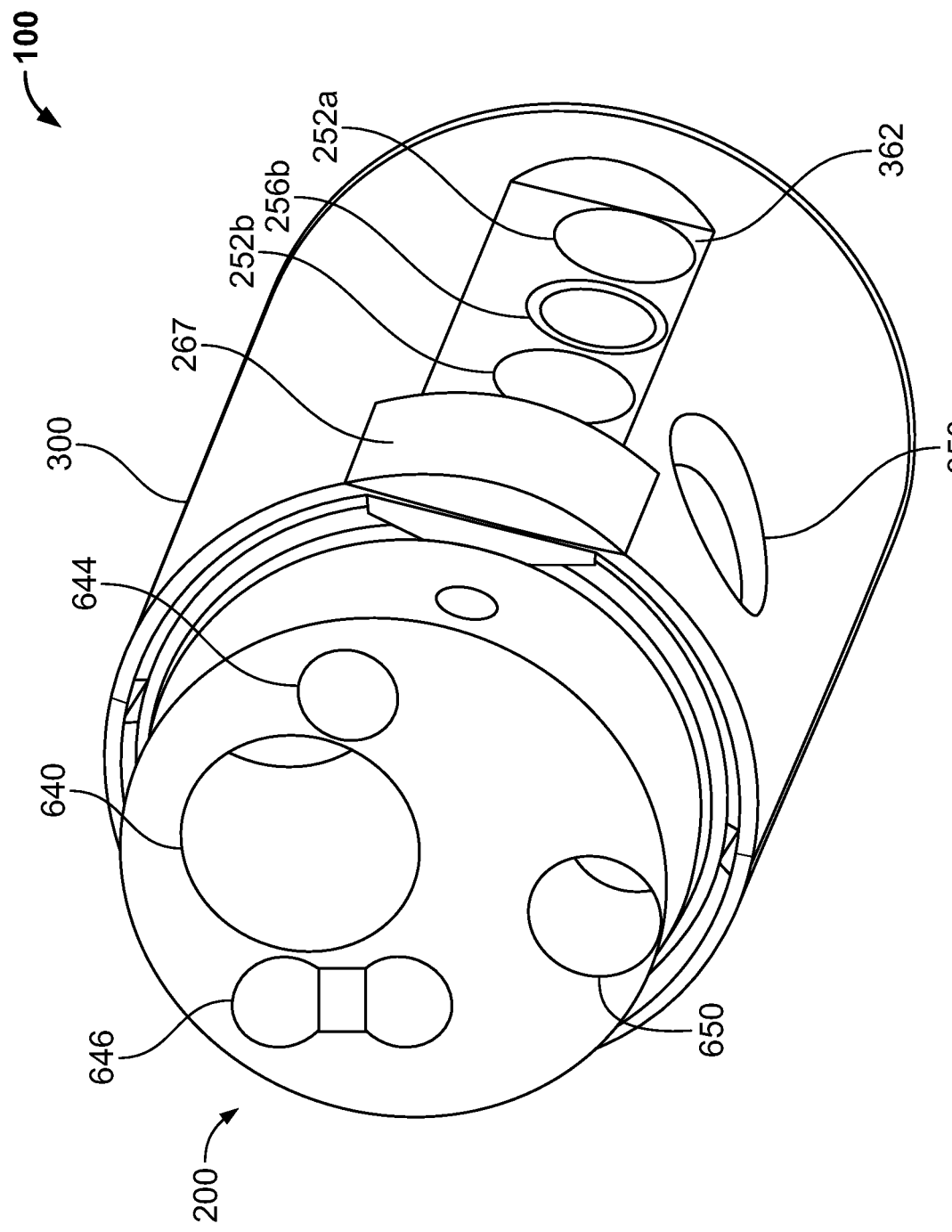
Figure 59C:
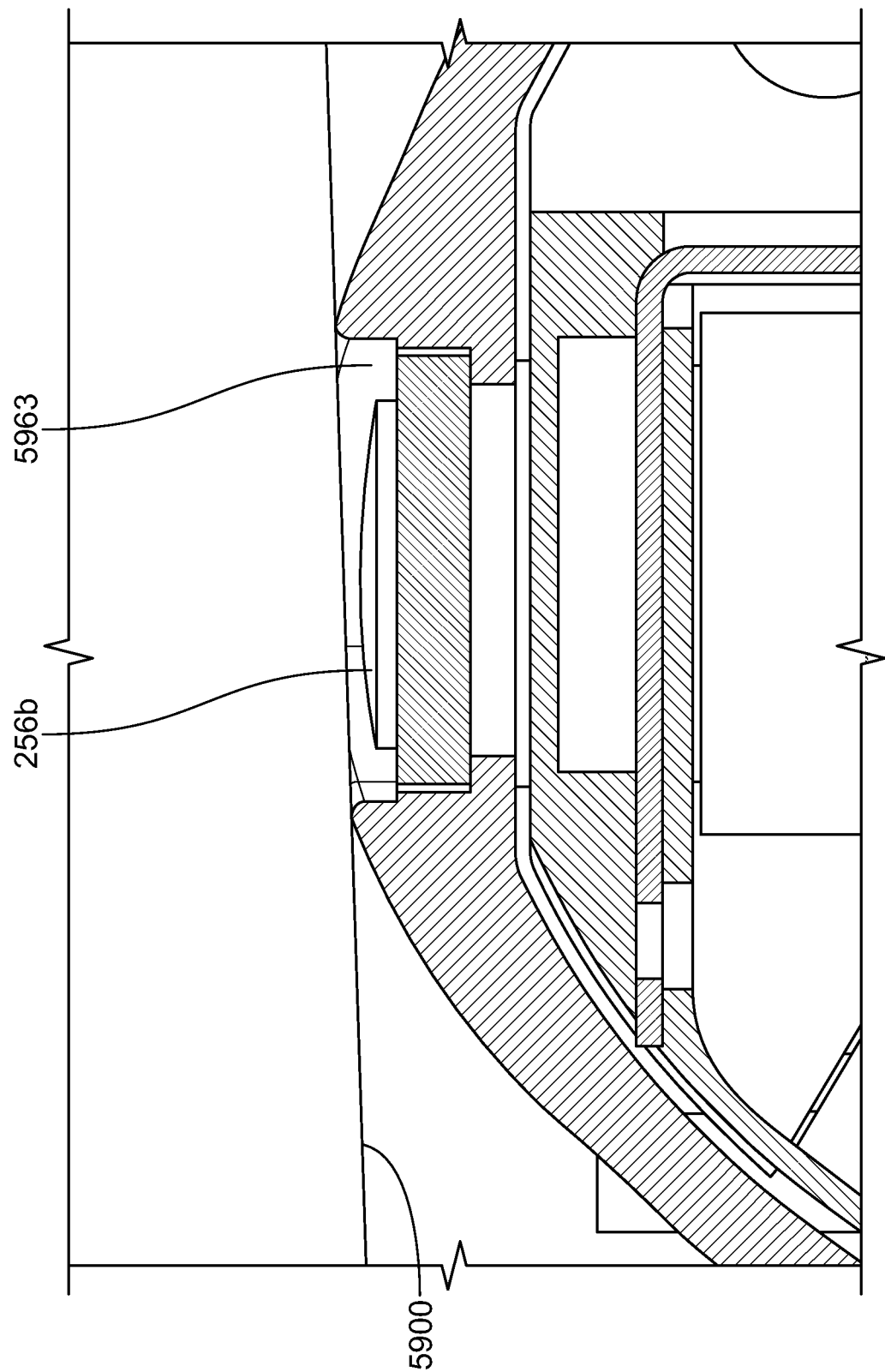
Figure 60A:
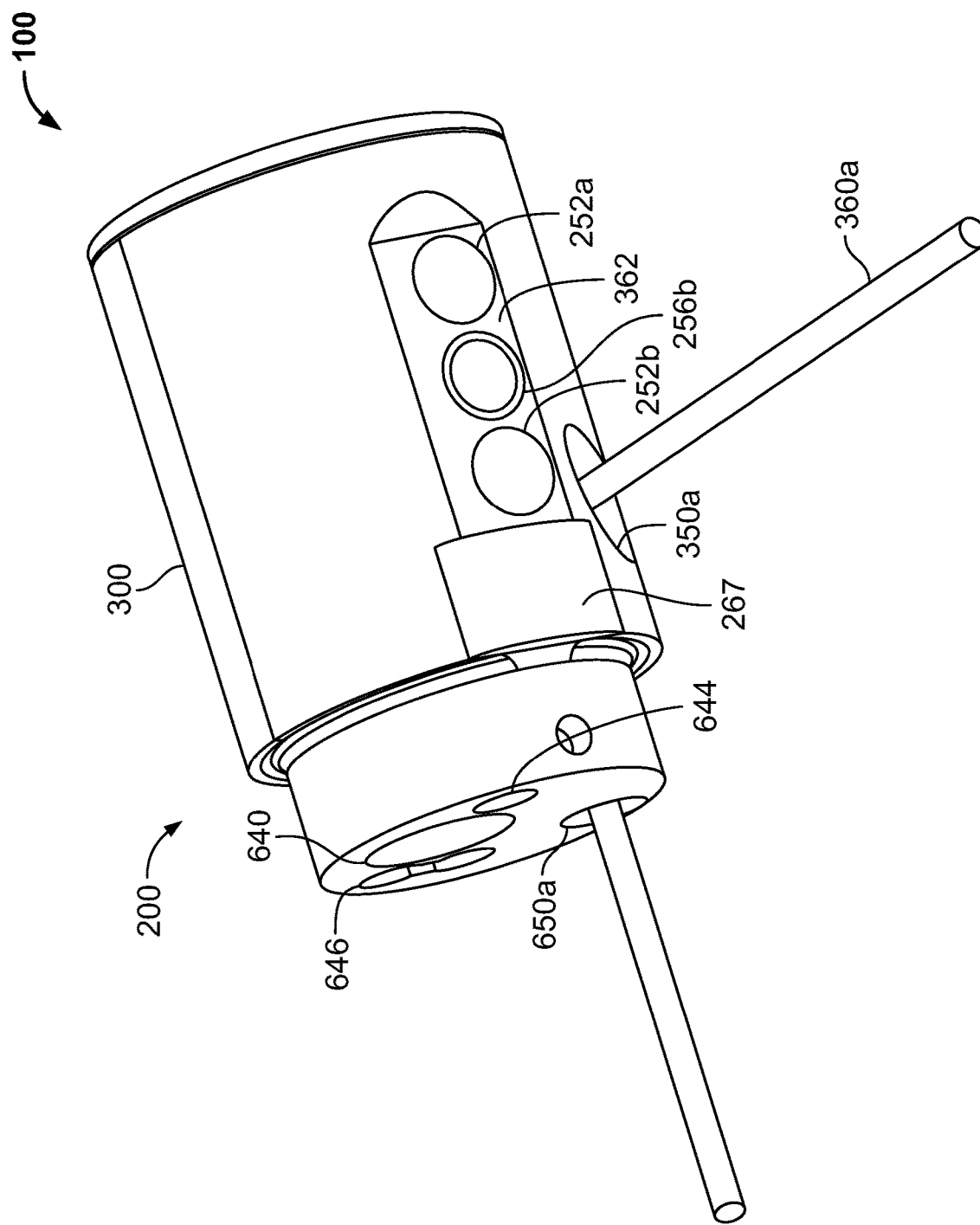
Figure 60B:
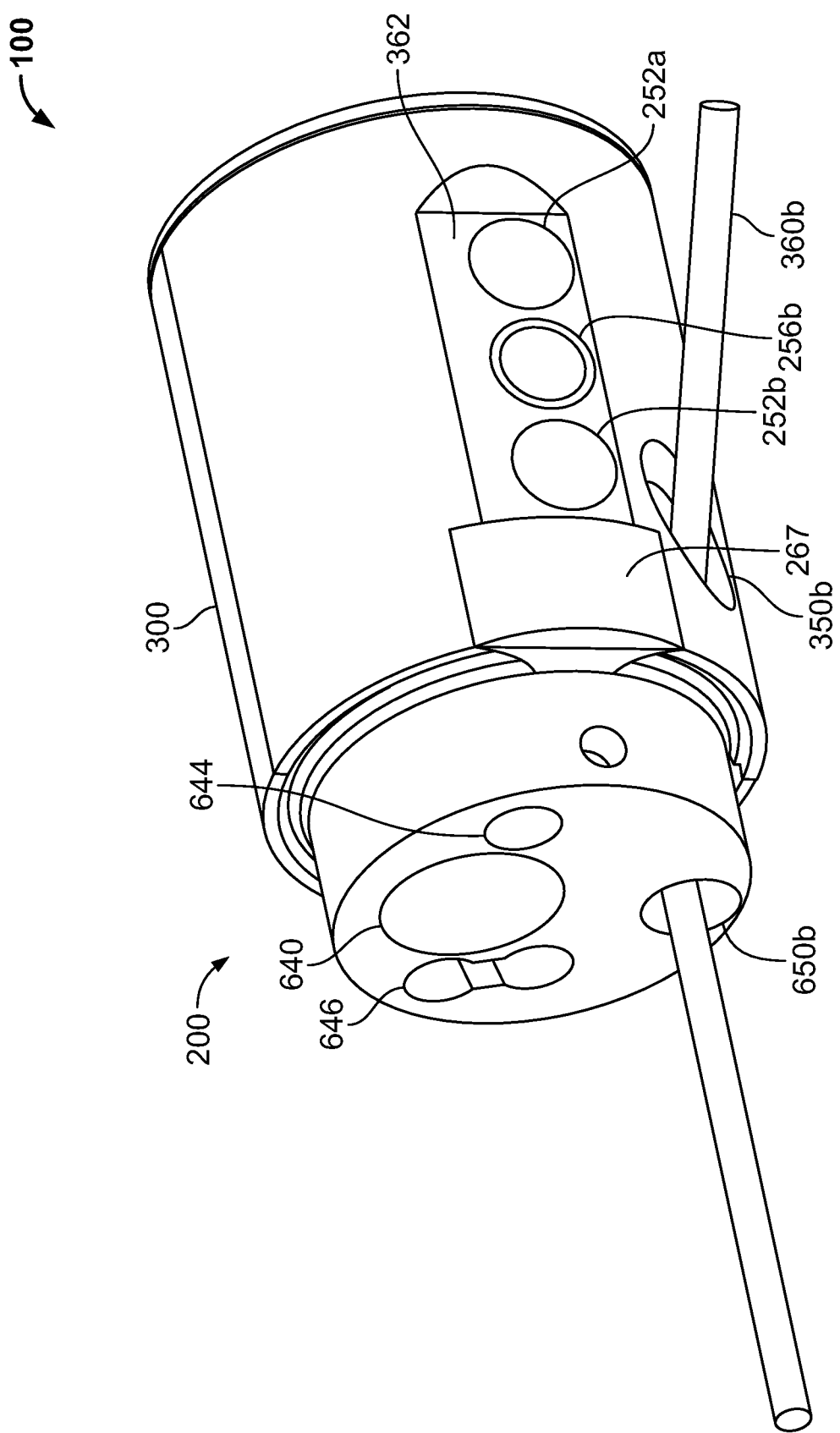
Figure 61A:
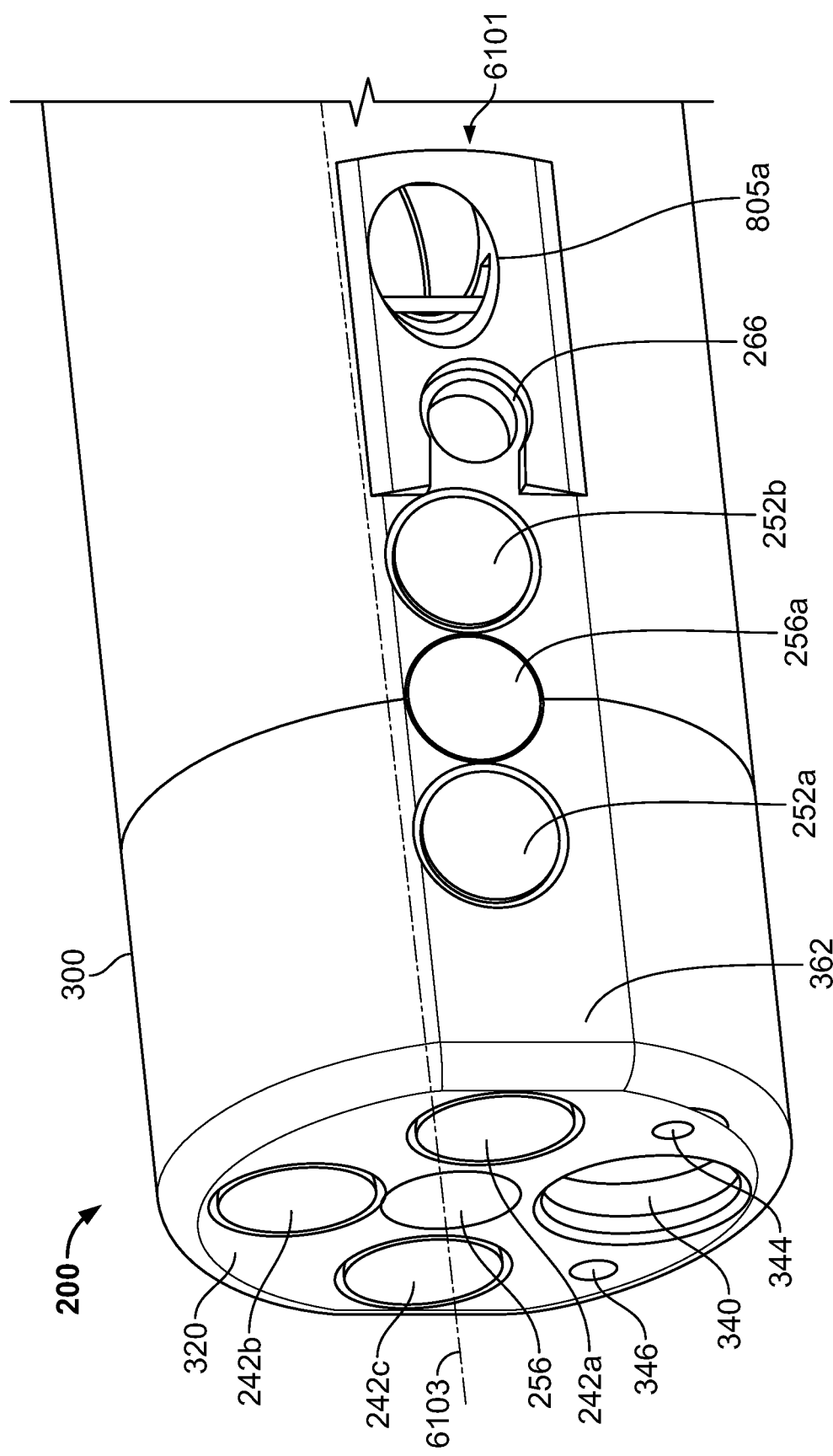
Figure 61B:
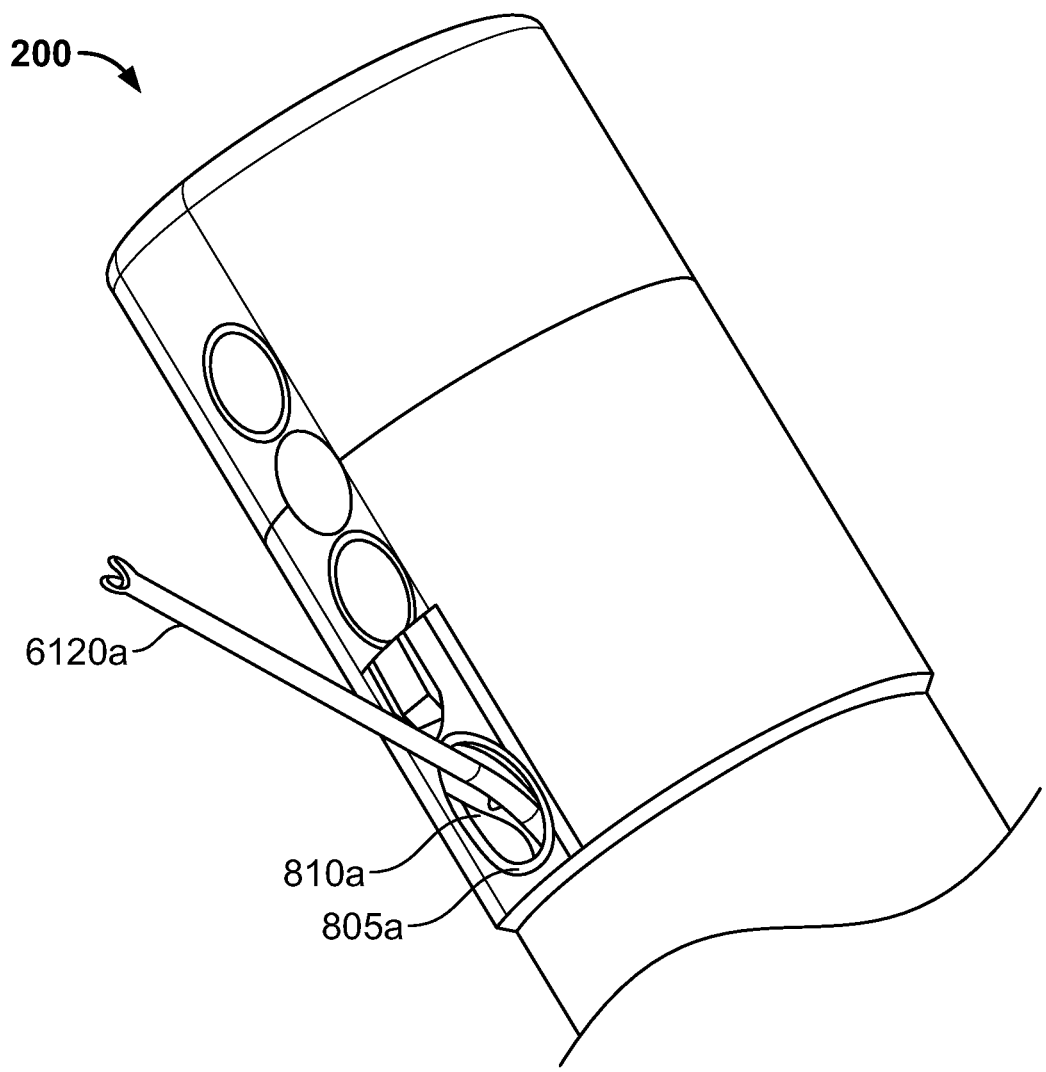
Figure 61C:
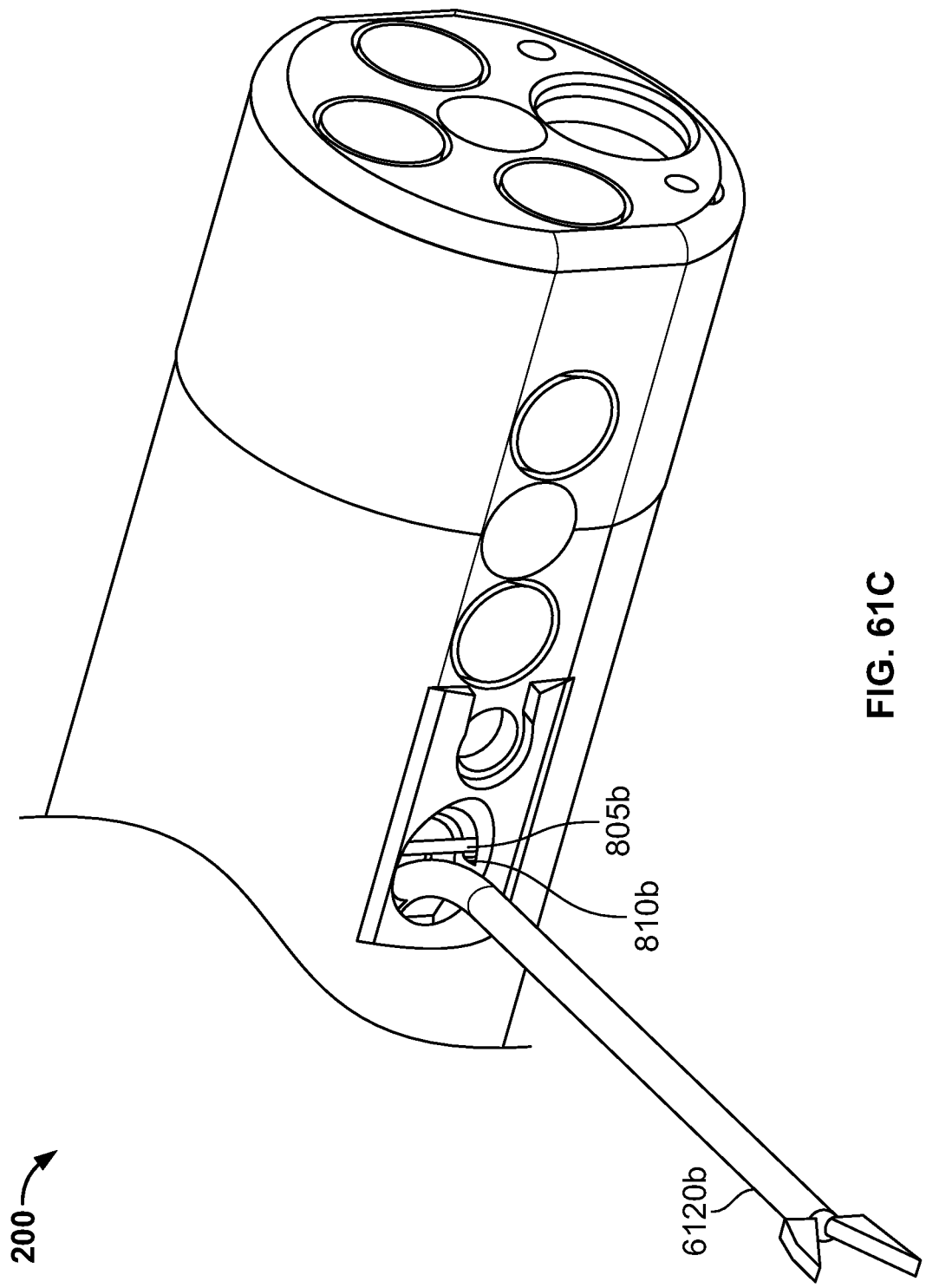
Figure 62:
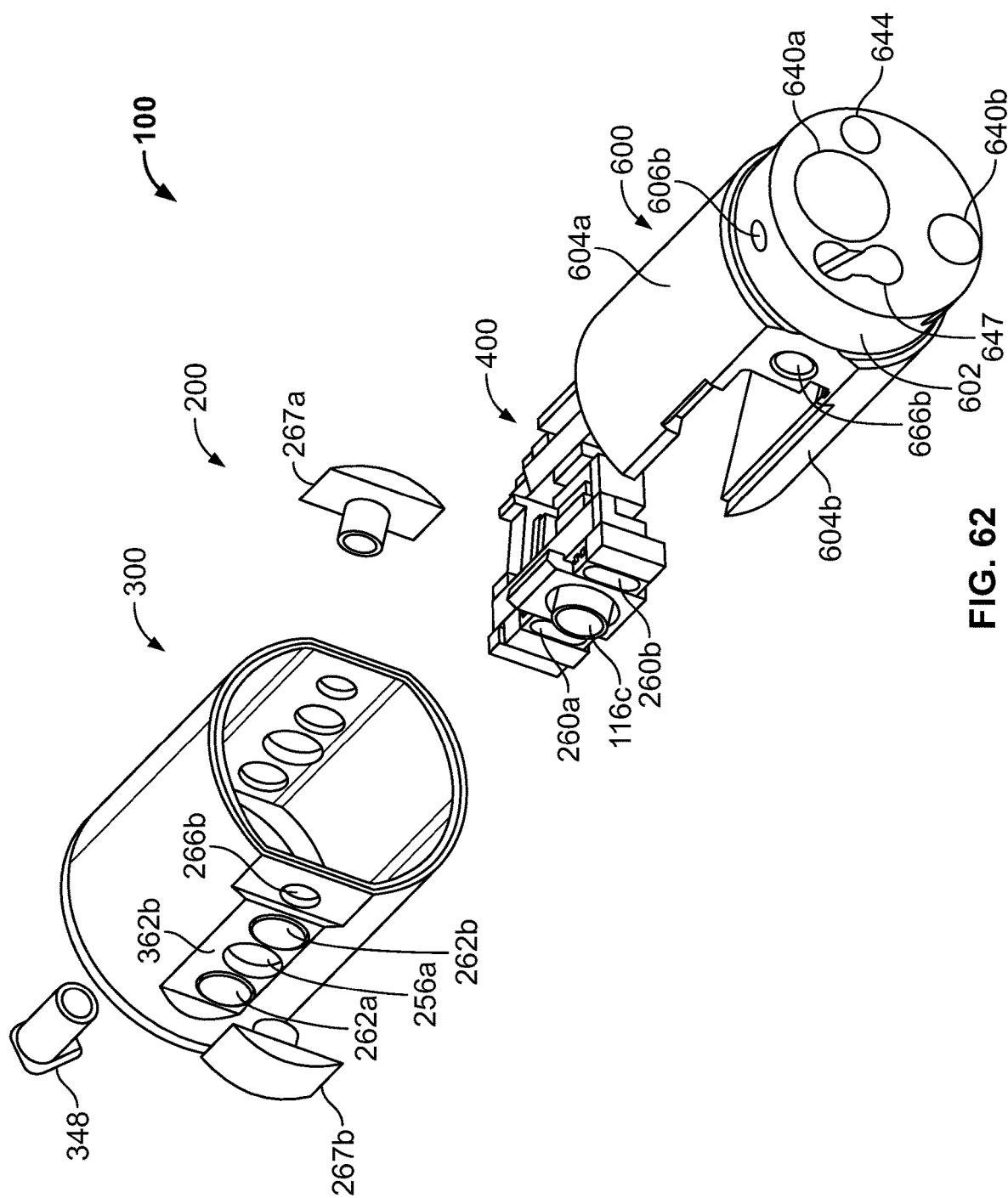
Figure 63:
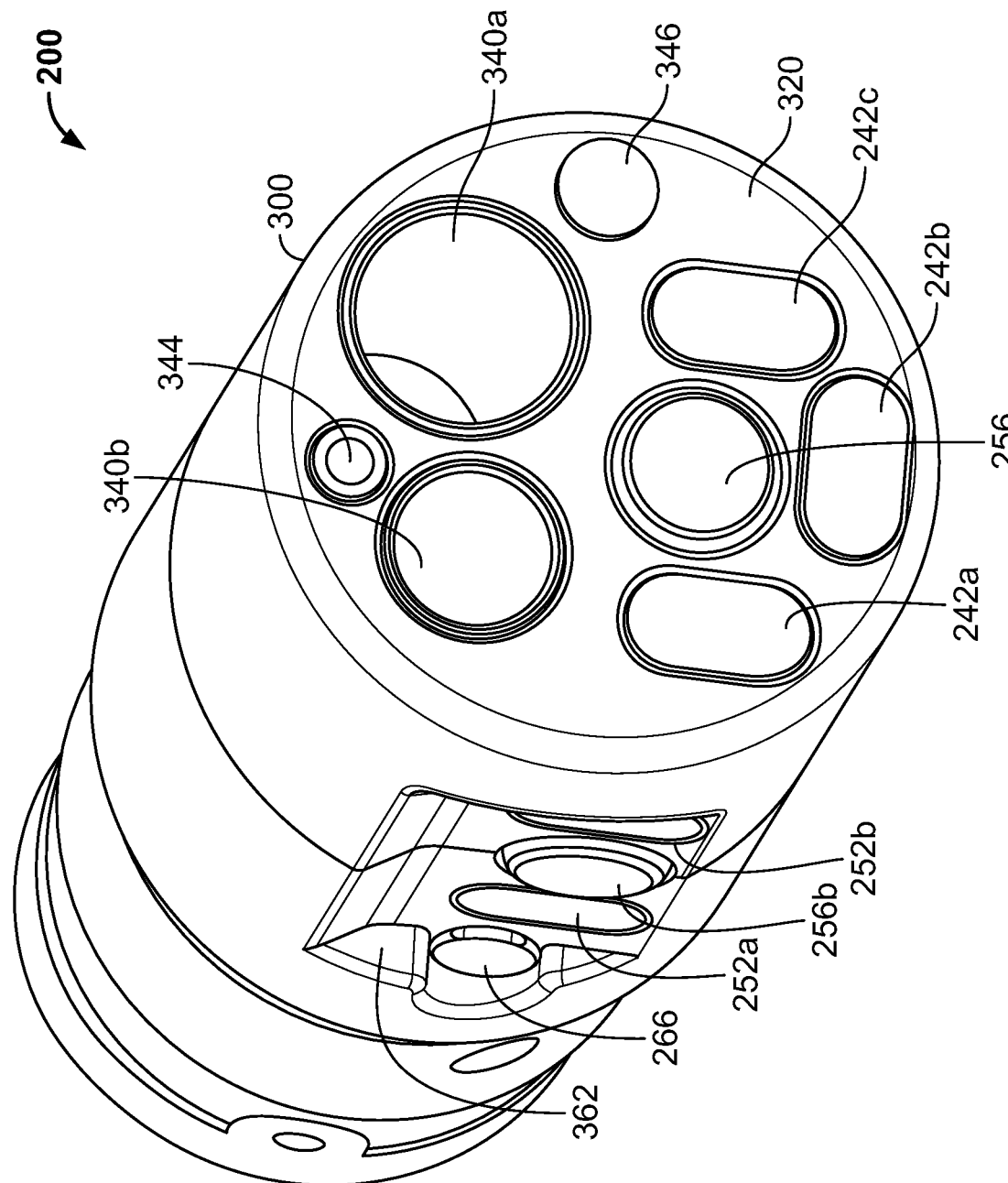
Figure 64:
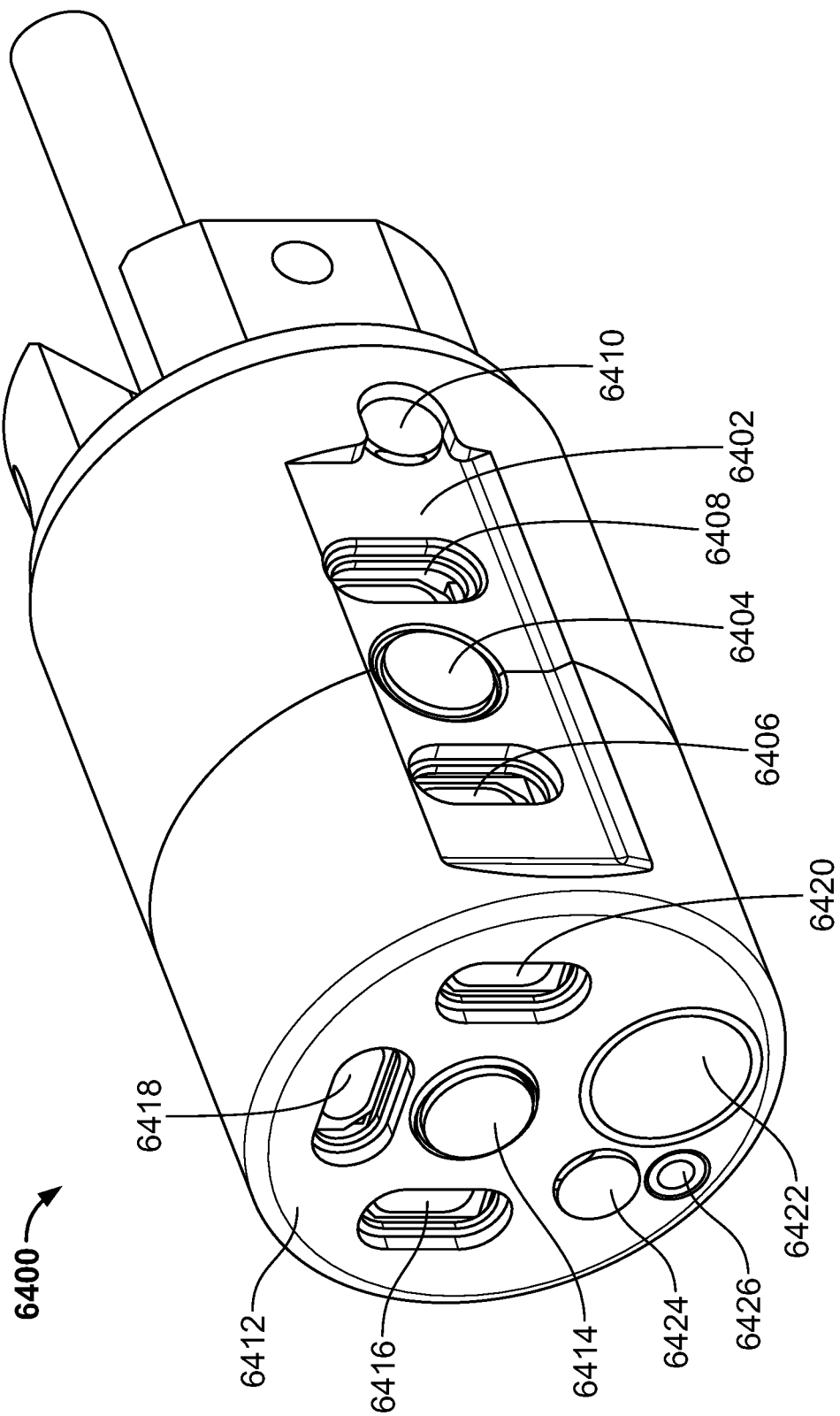
Figure 65A:
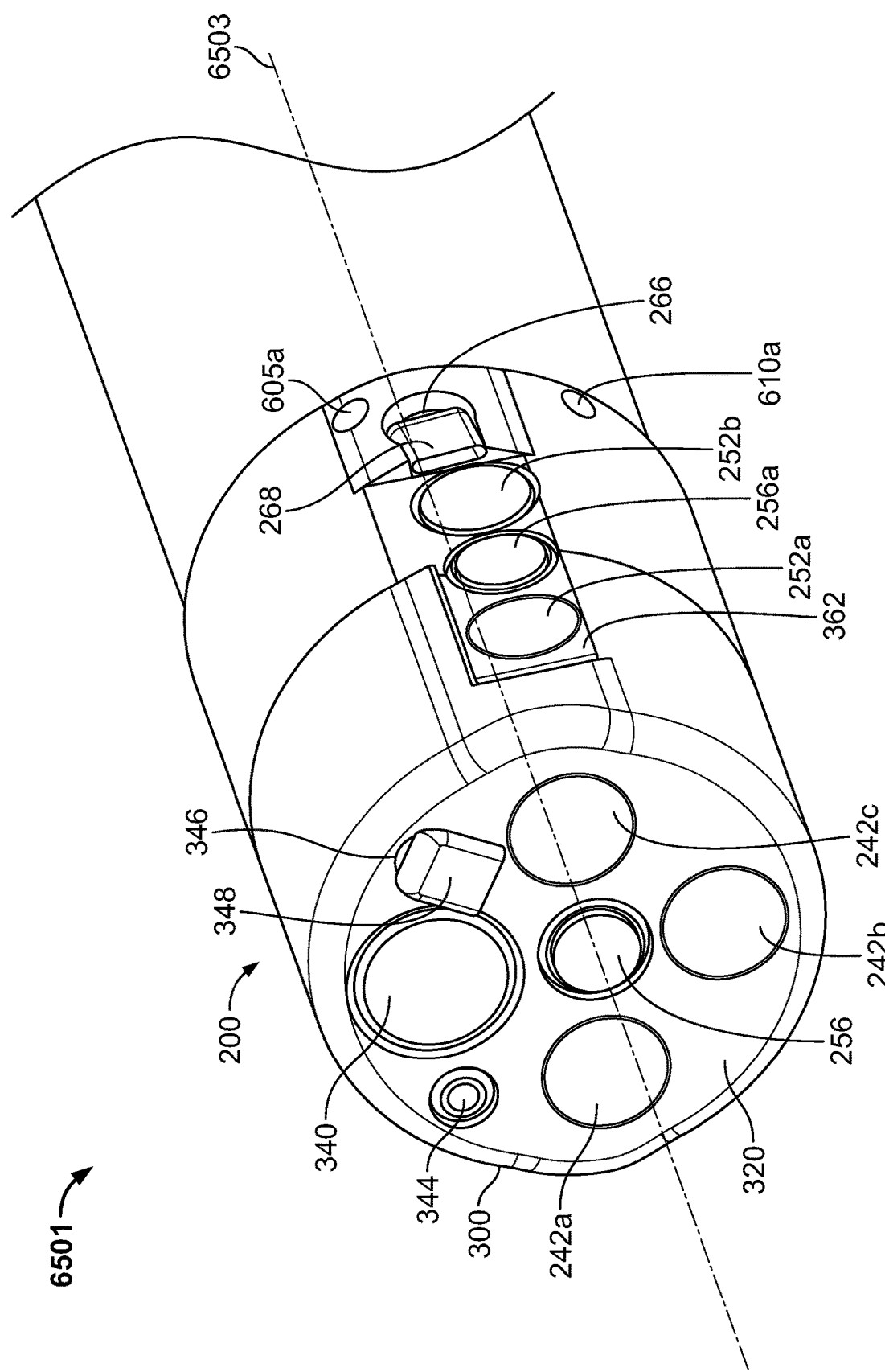
Figure 65D:
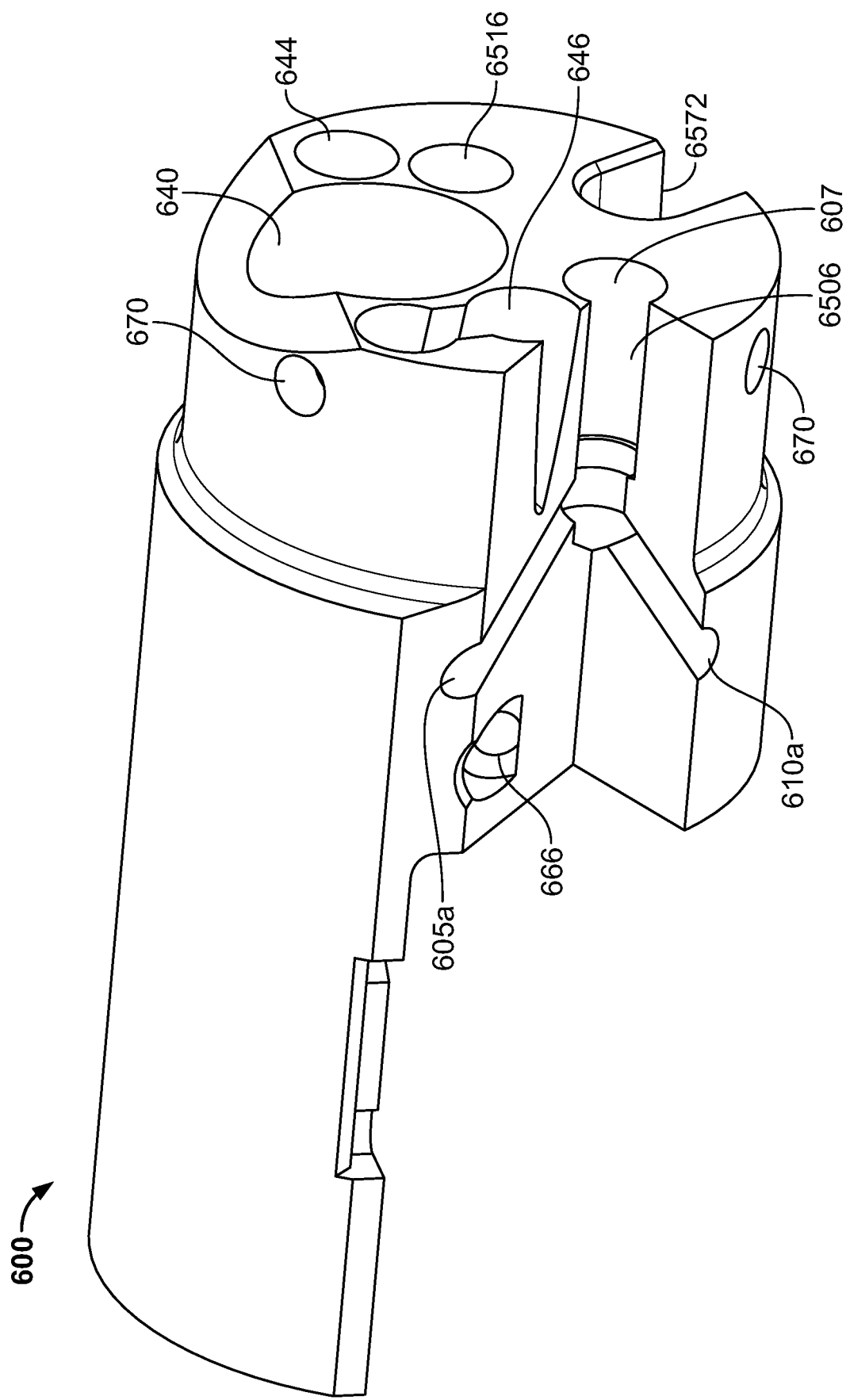
Figure 65E:
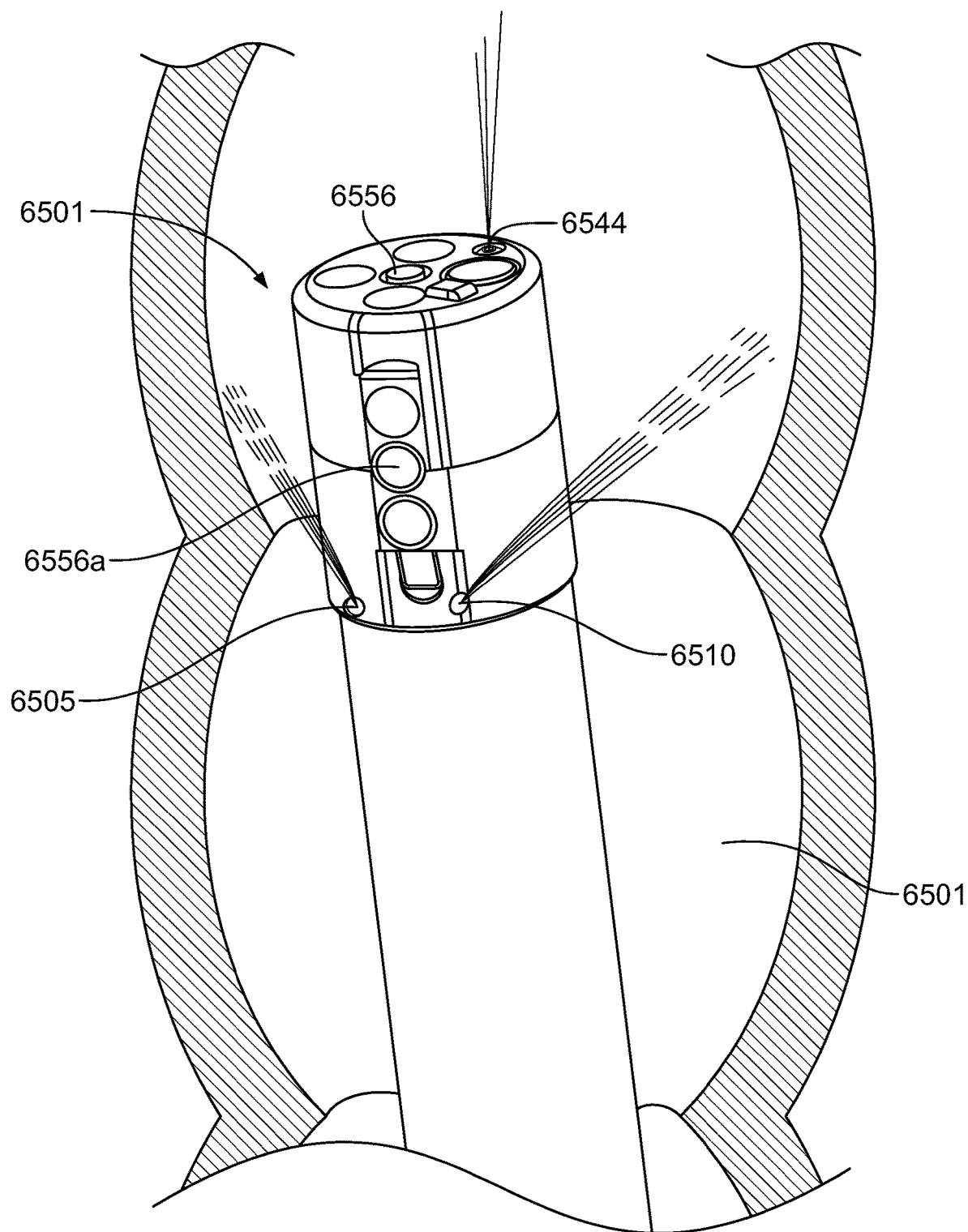
Figure 66:
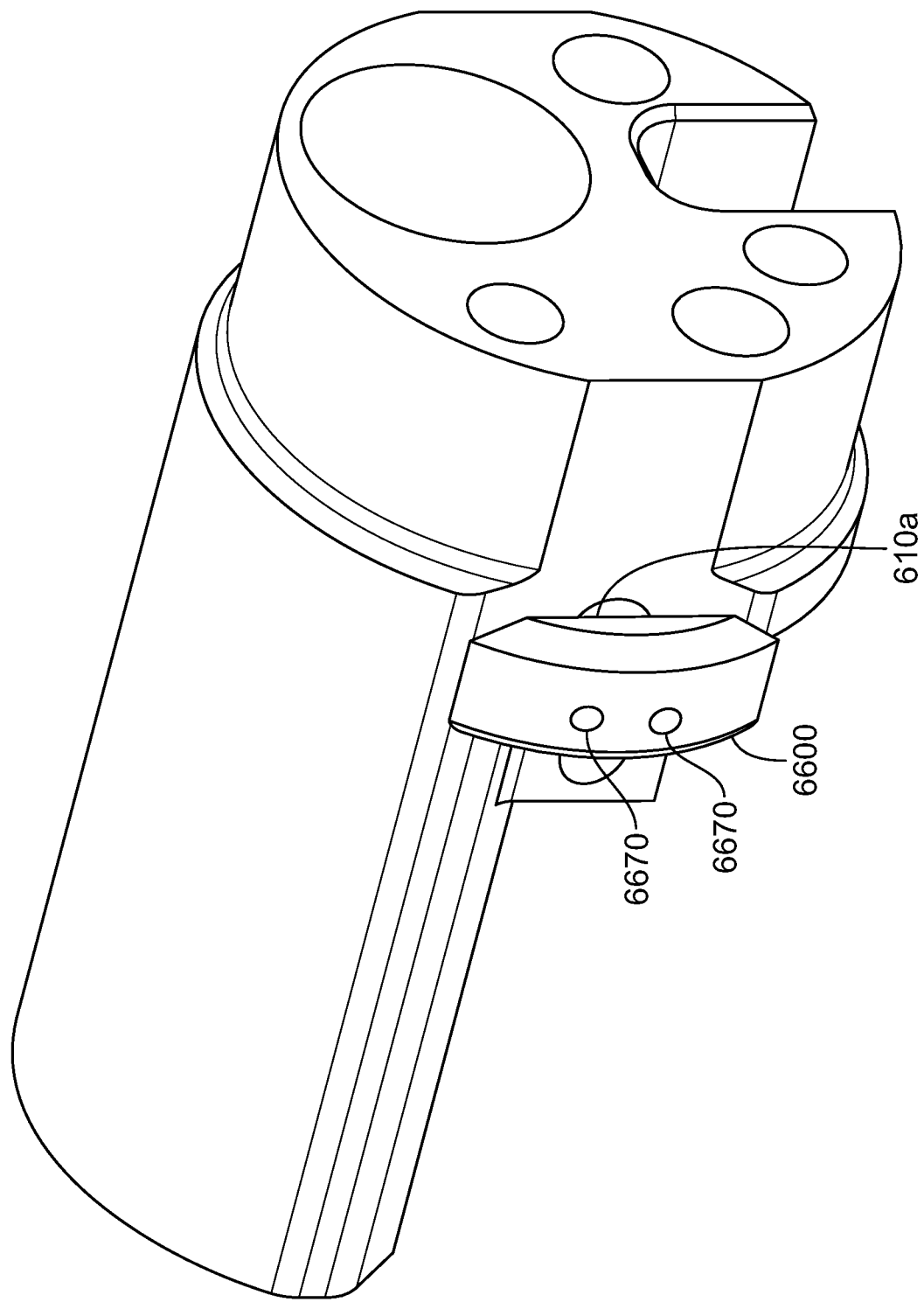
Figure 67A:
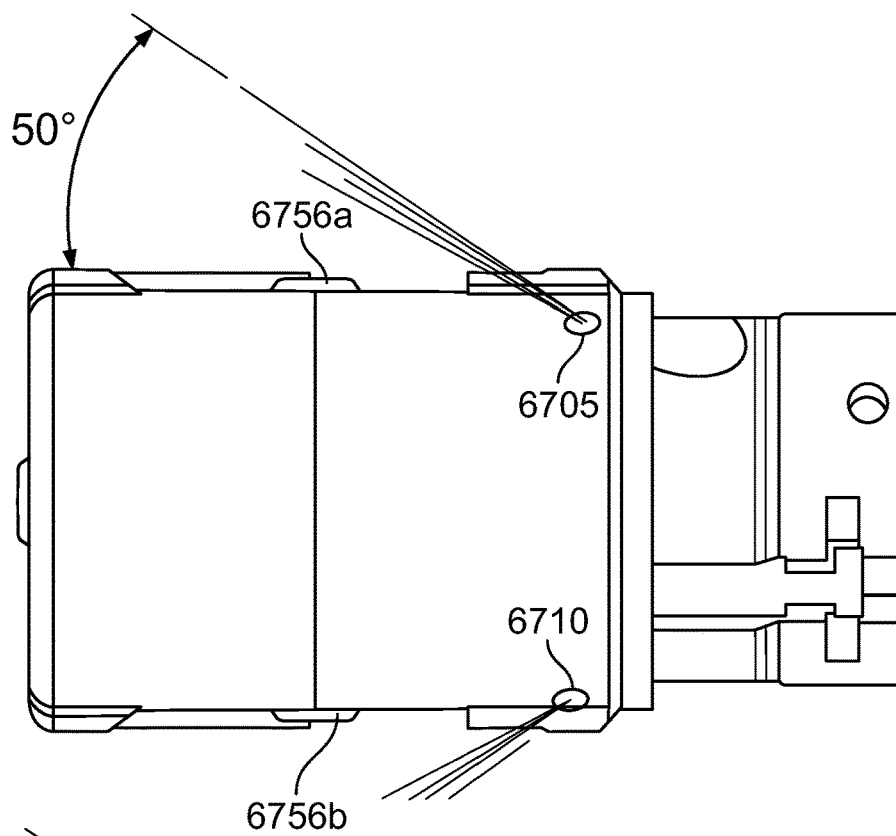
Figure 67B:
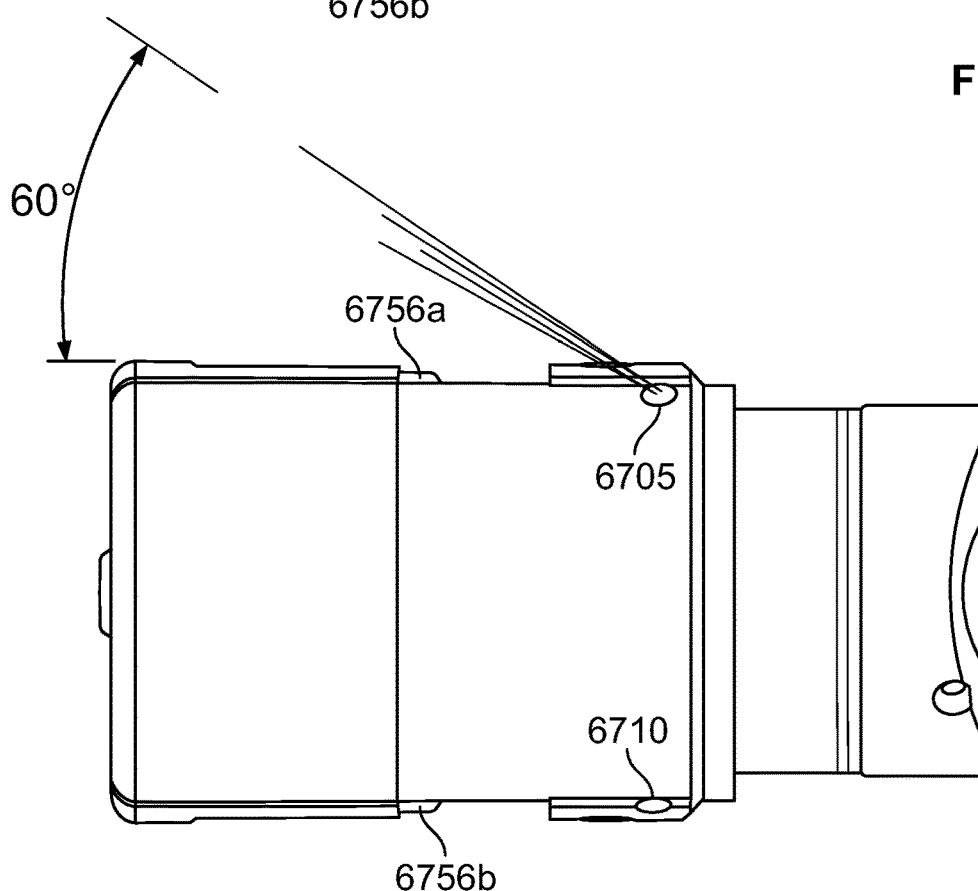
Figure 68A:
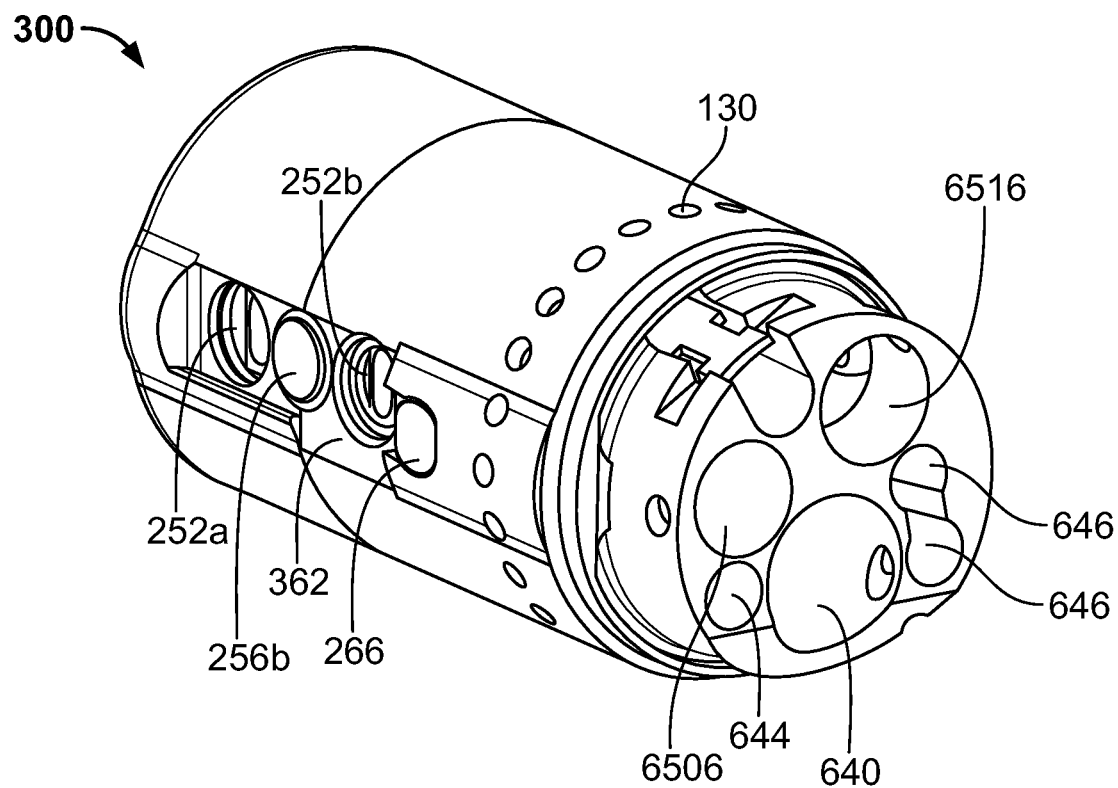
Figure 68B:
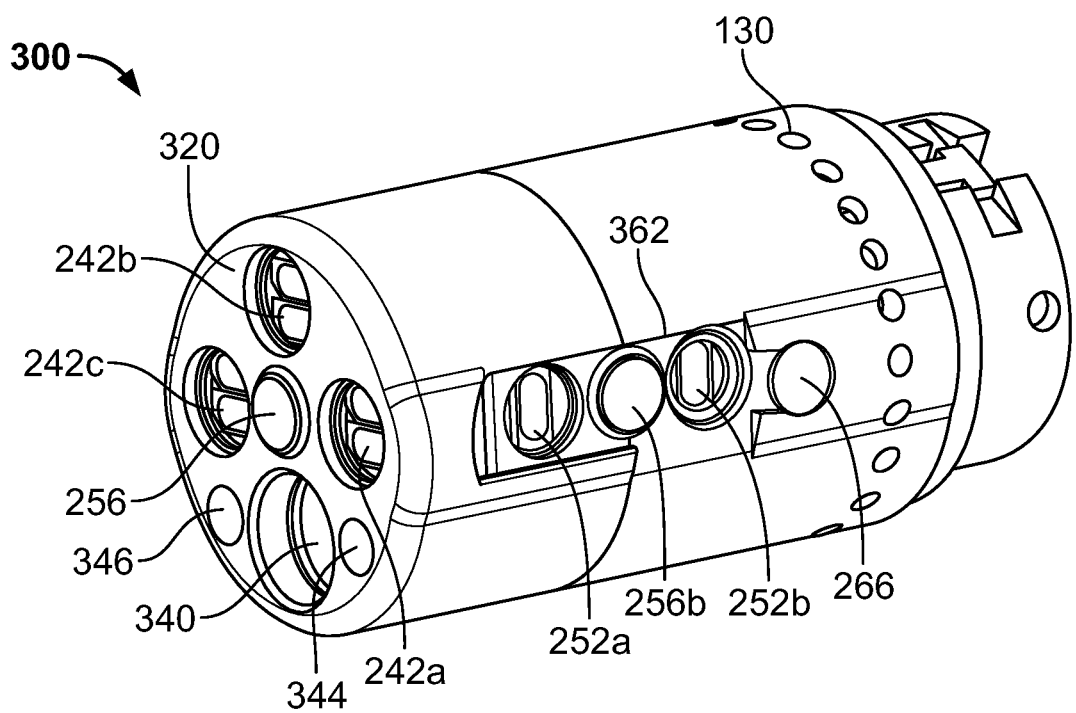
Figure 69A:
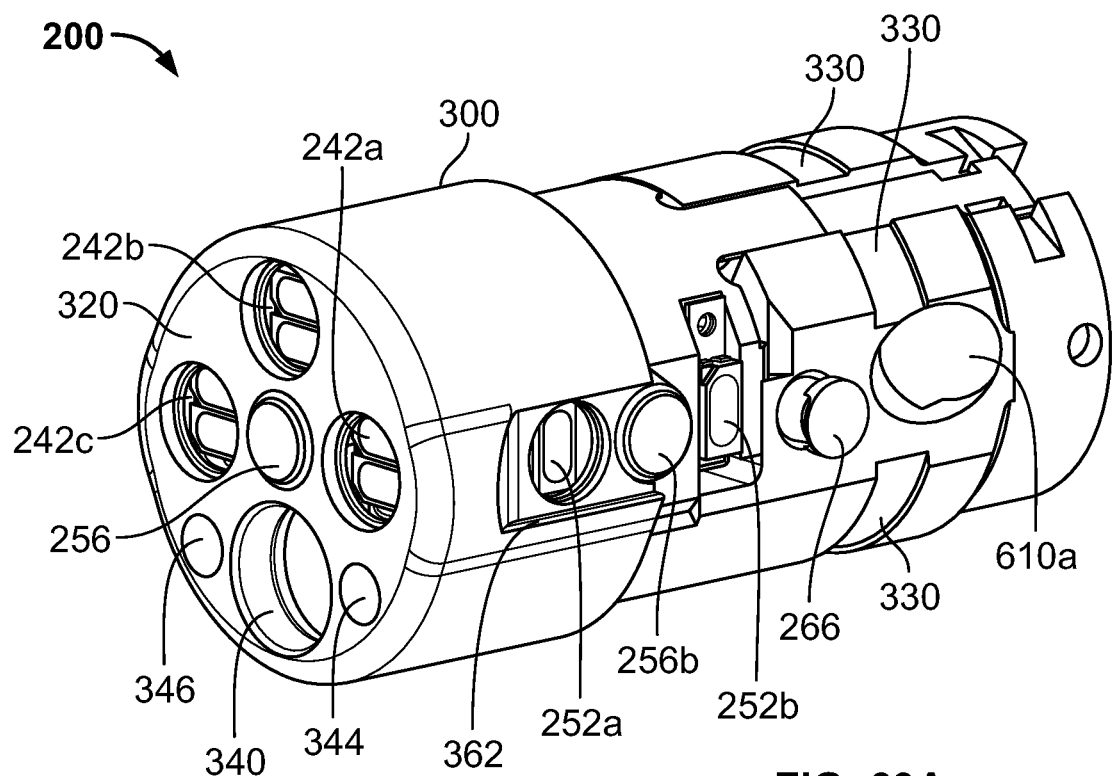
Figure 69B:
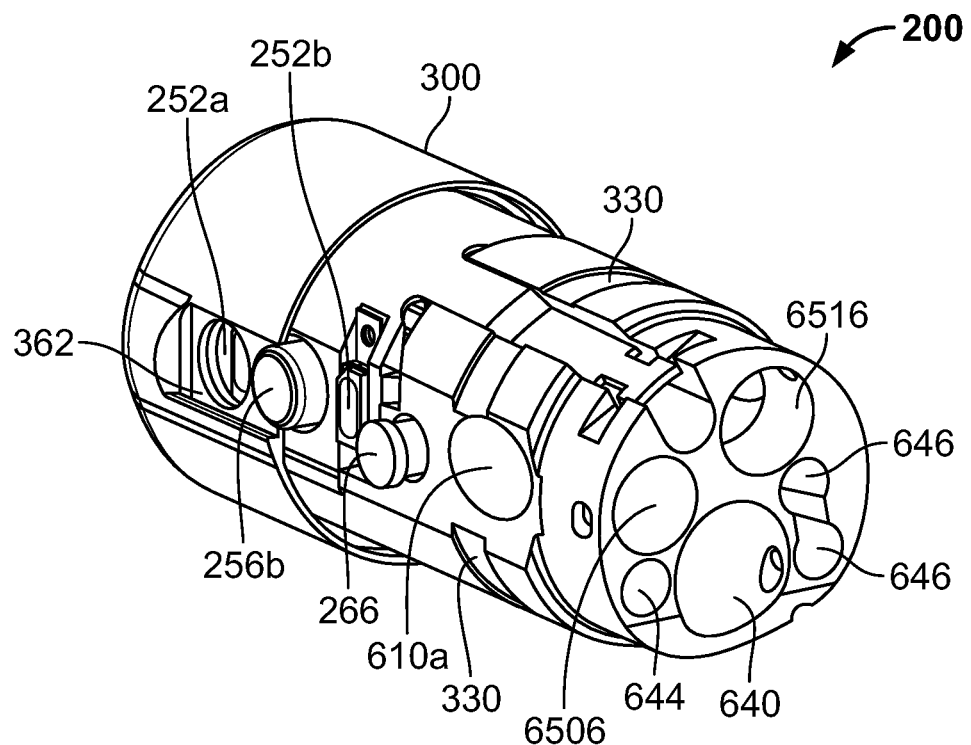
Figure 70:
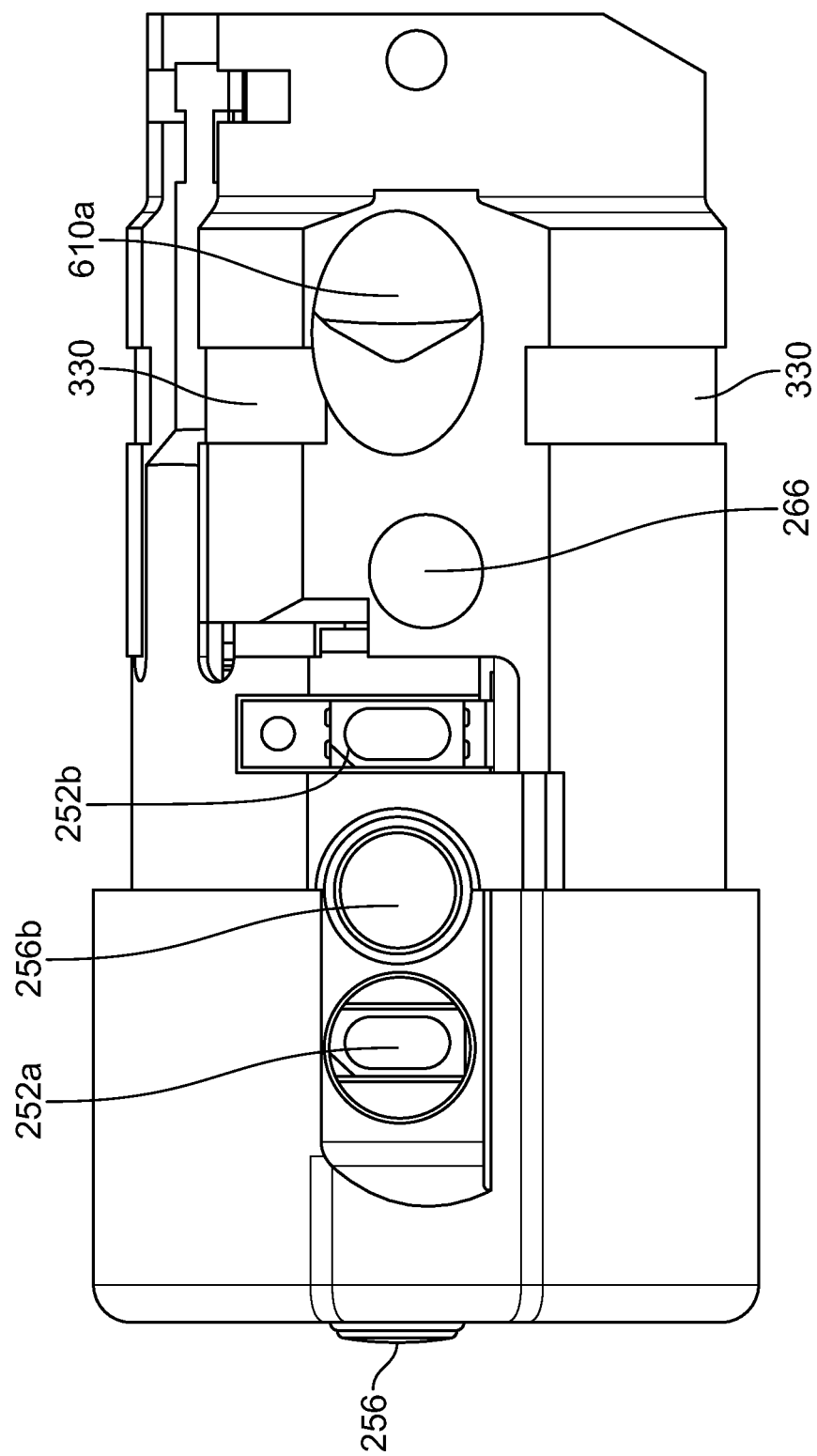
Figure 71:
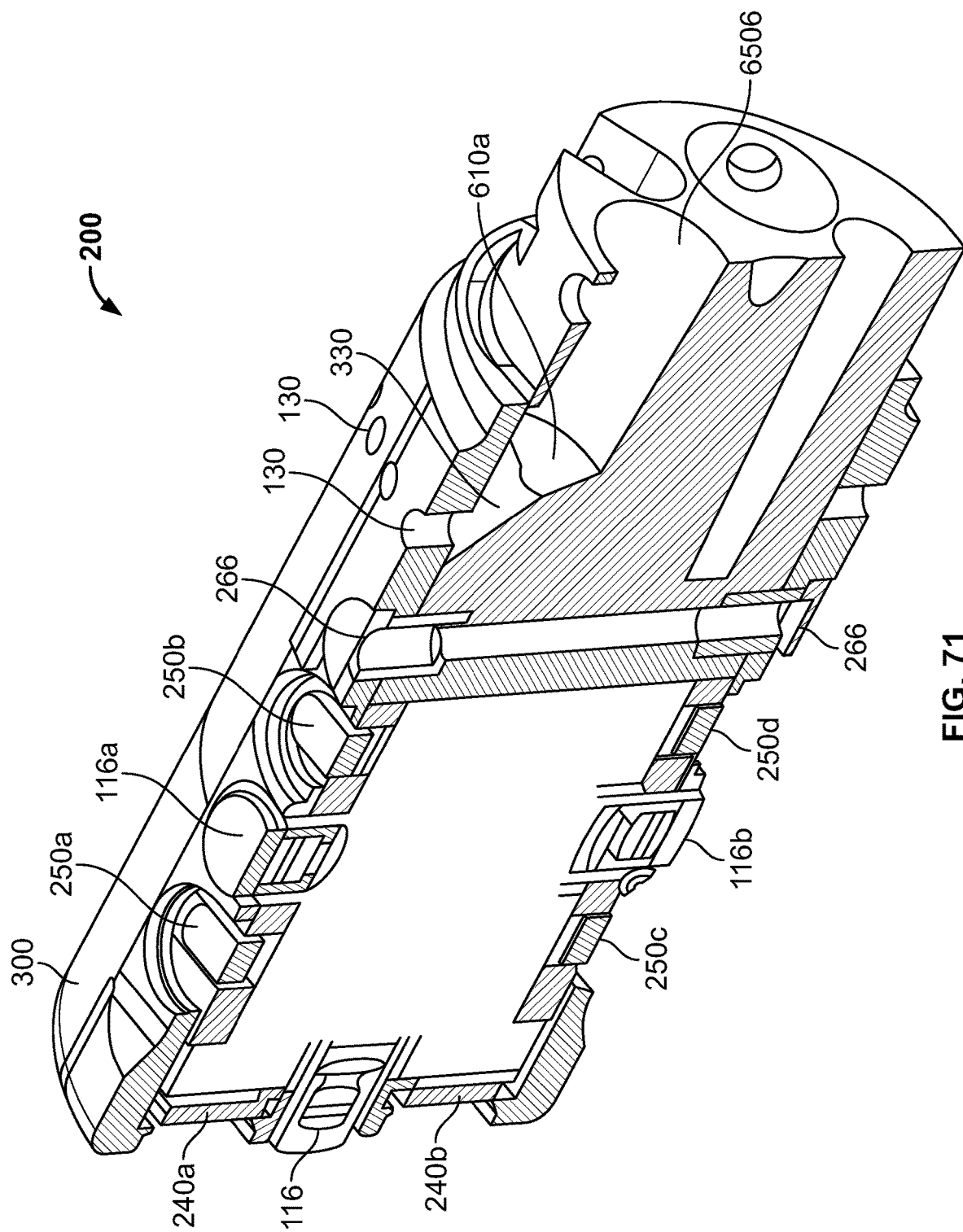
Figure 72:
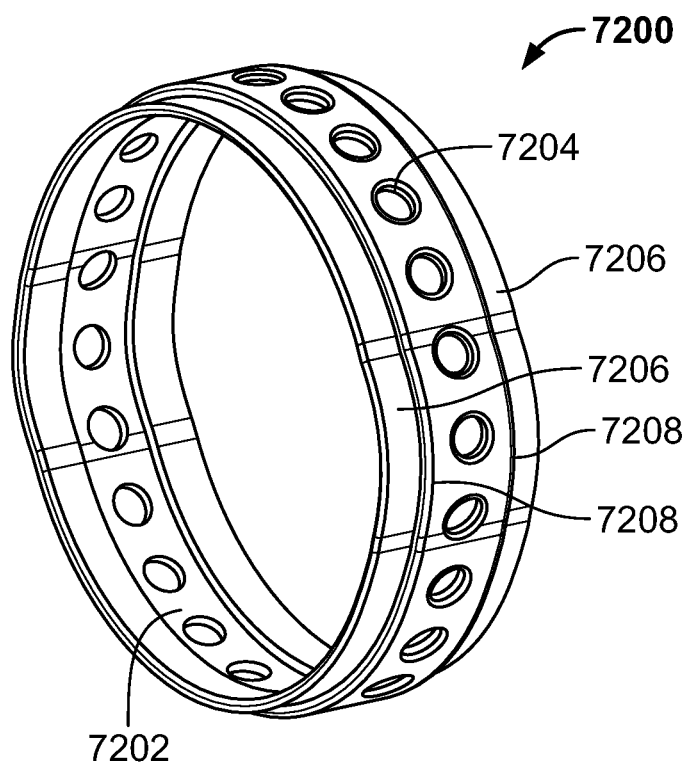
Figure 73:
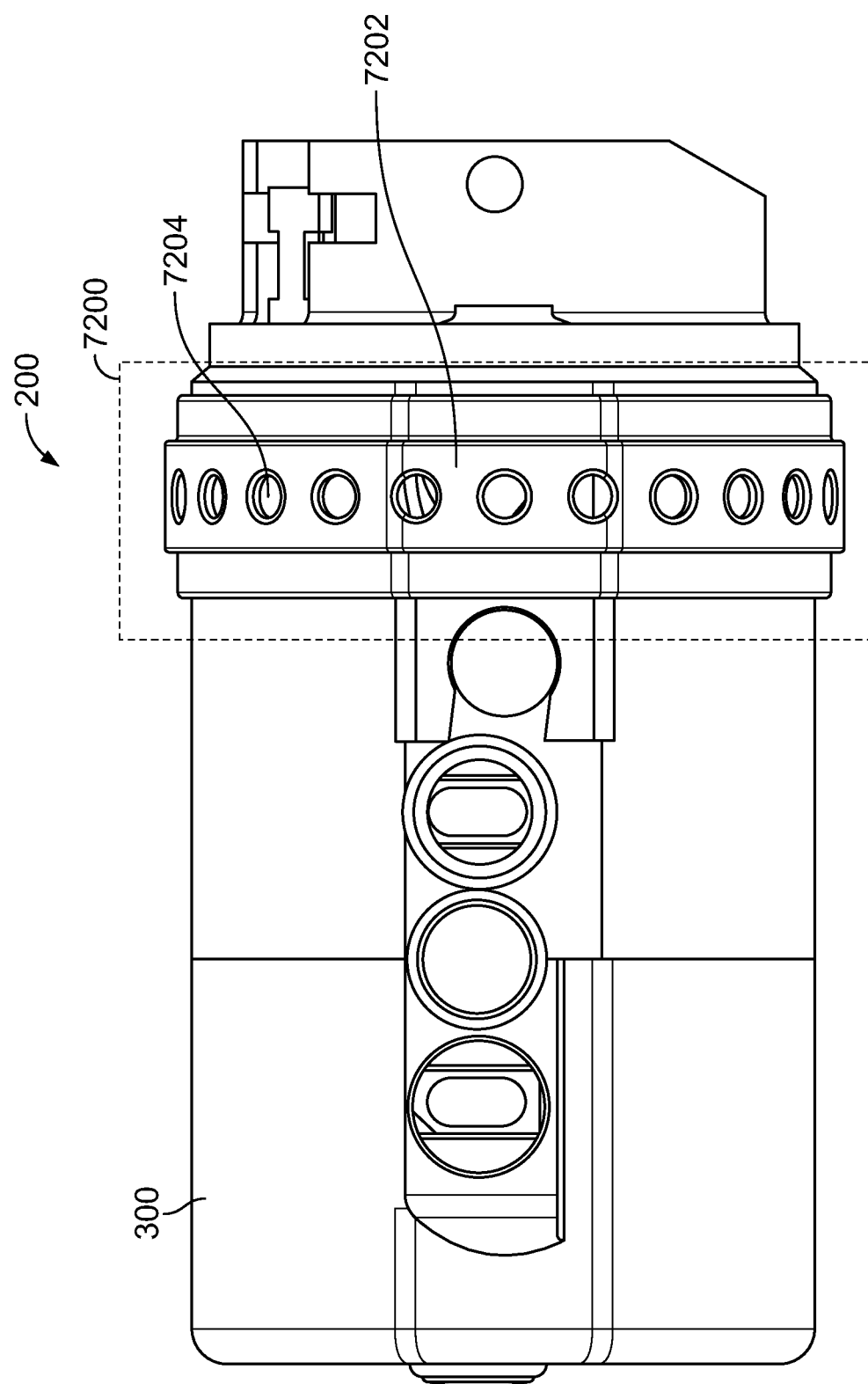
Figure 74A:
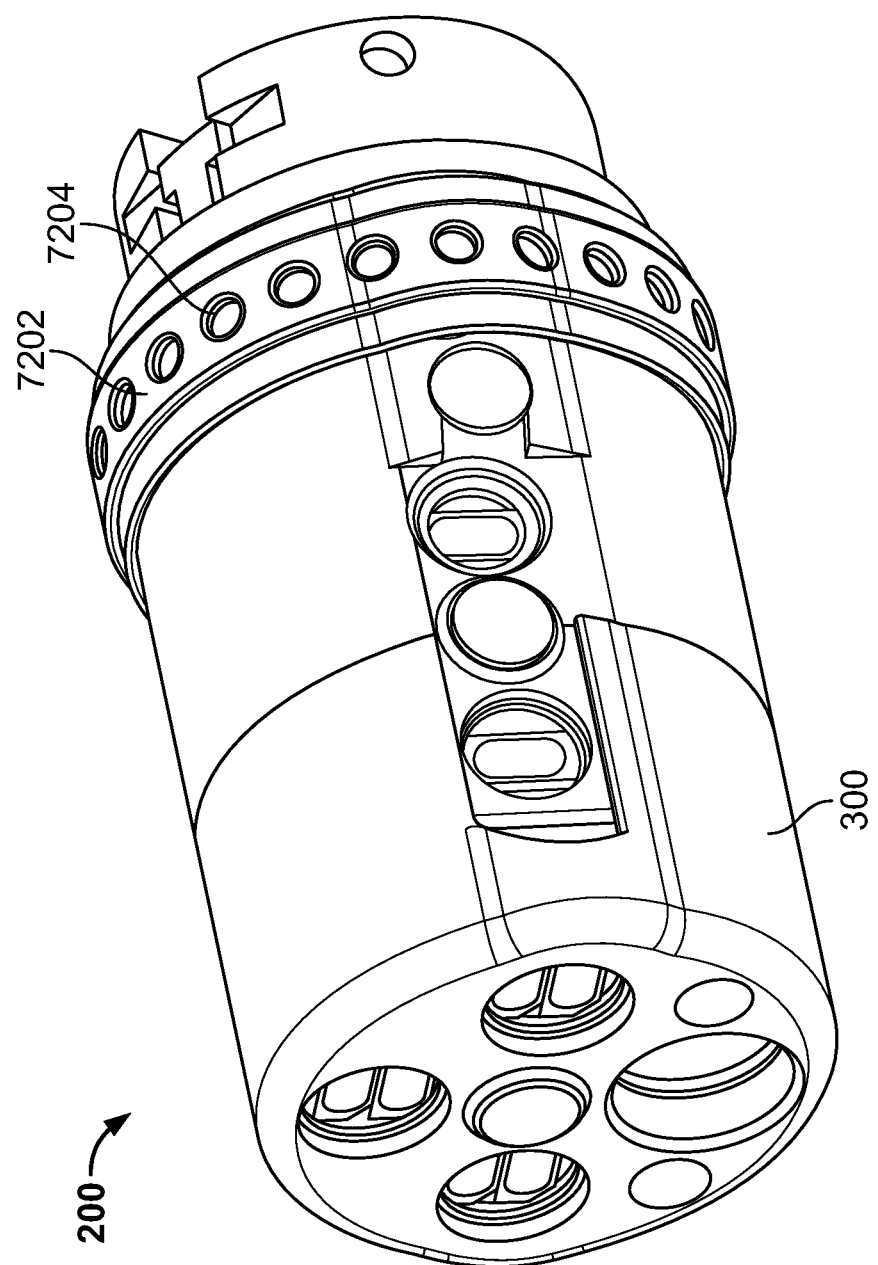
Figure 74B:
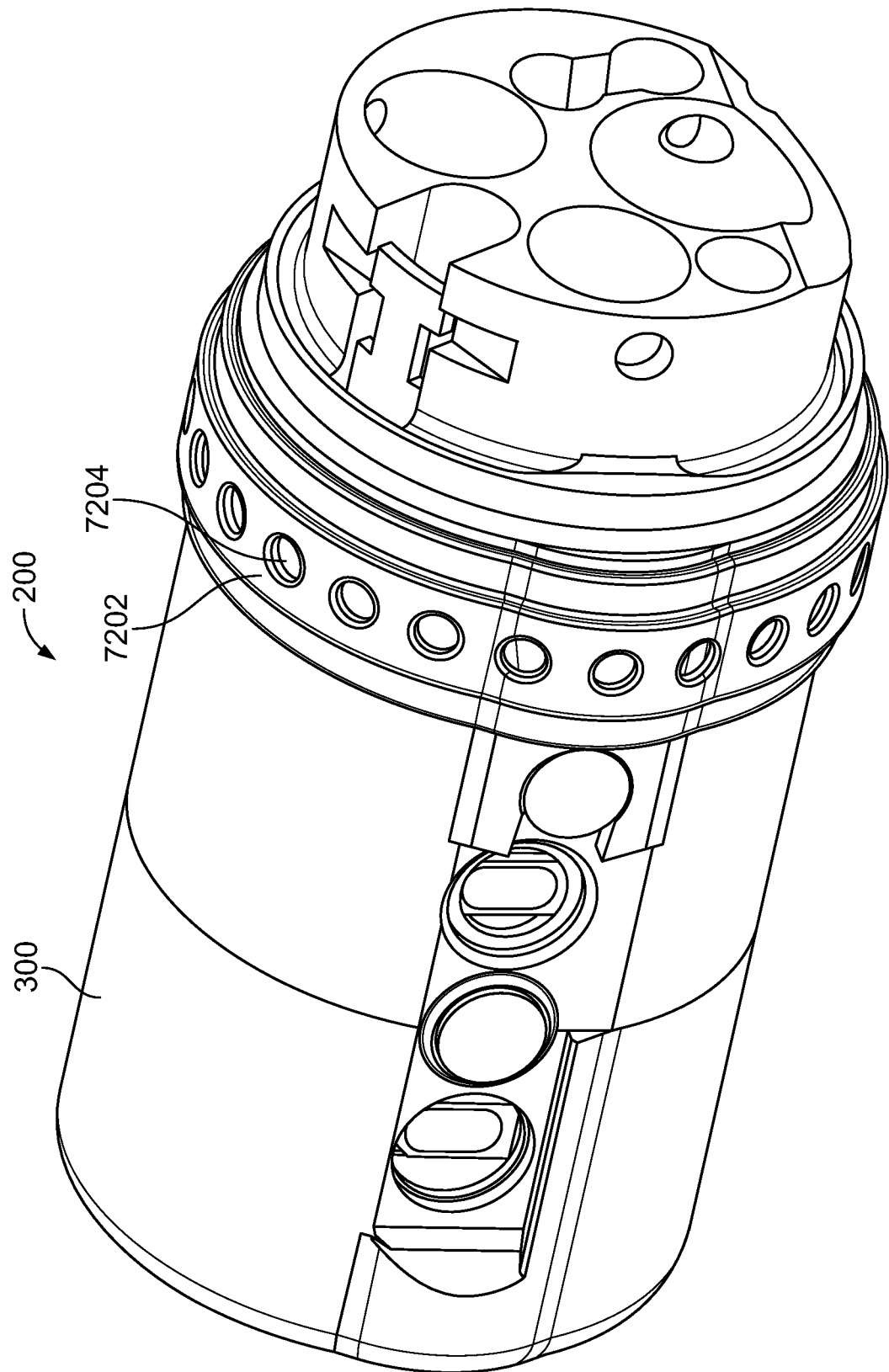
Figure 75A:
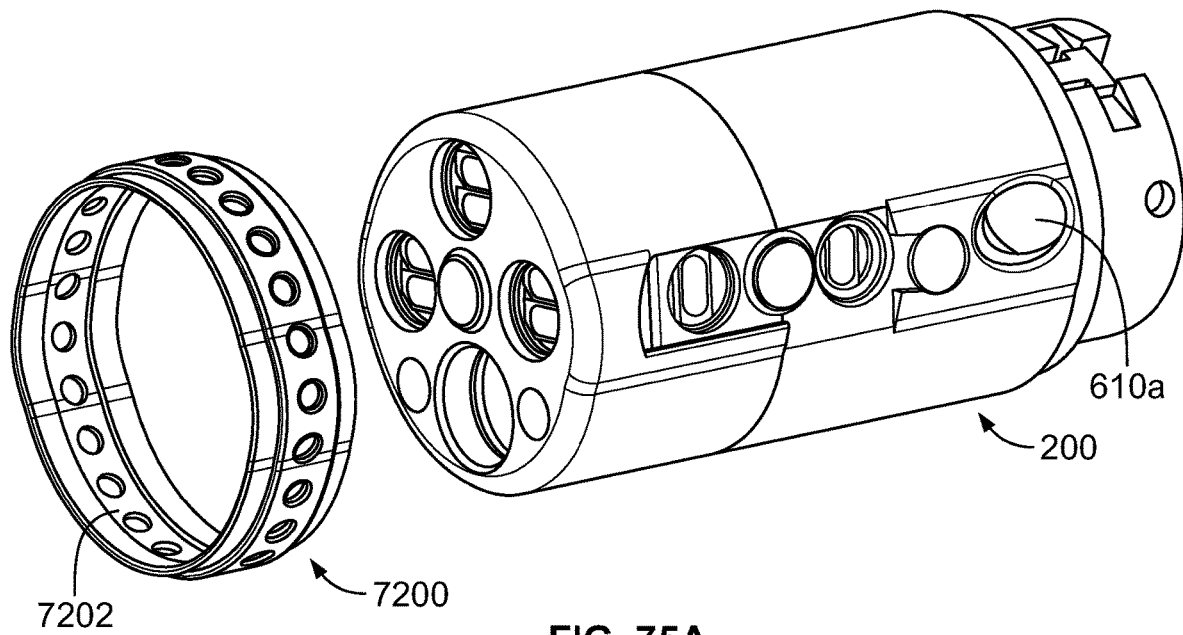
Figure 75B:
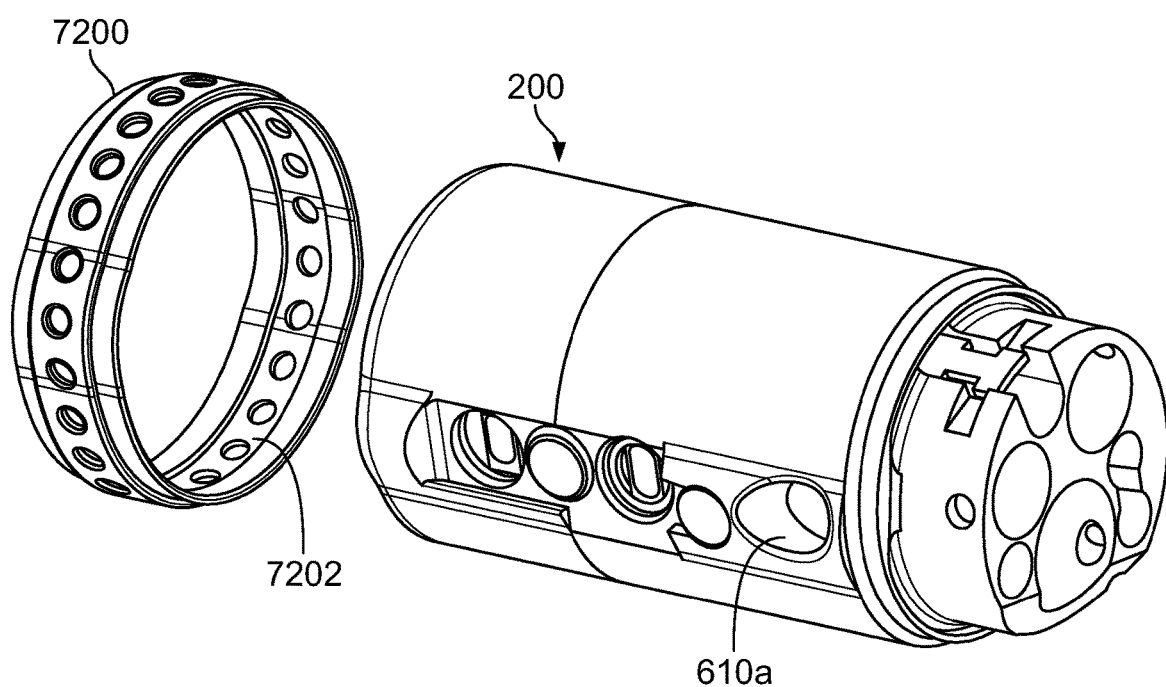
Figure 76A:
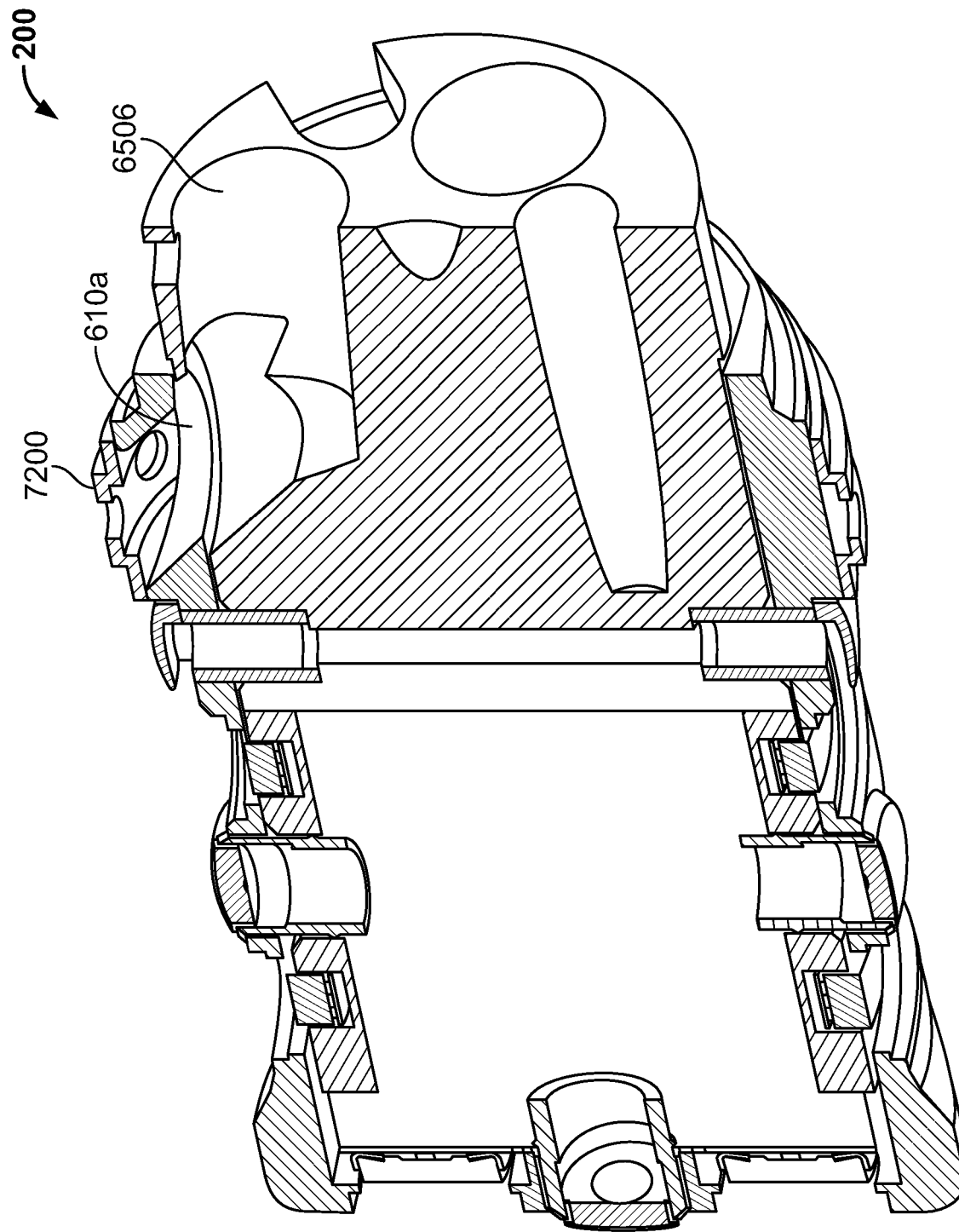
Figure 76B:
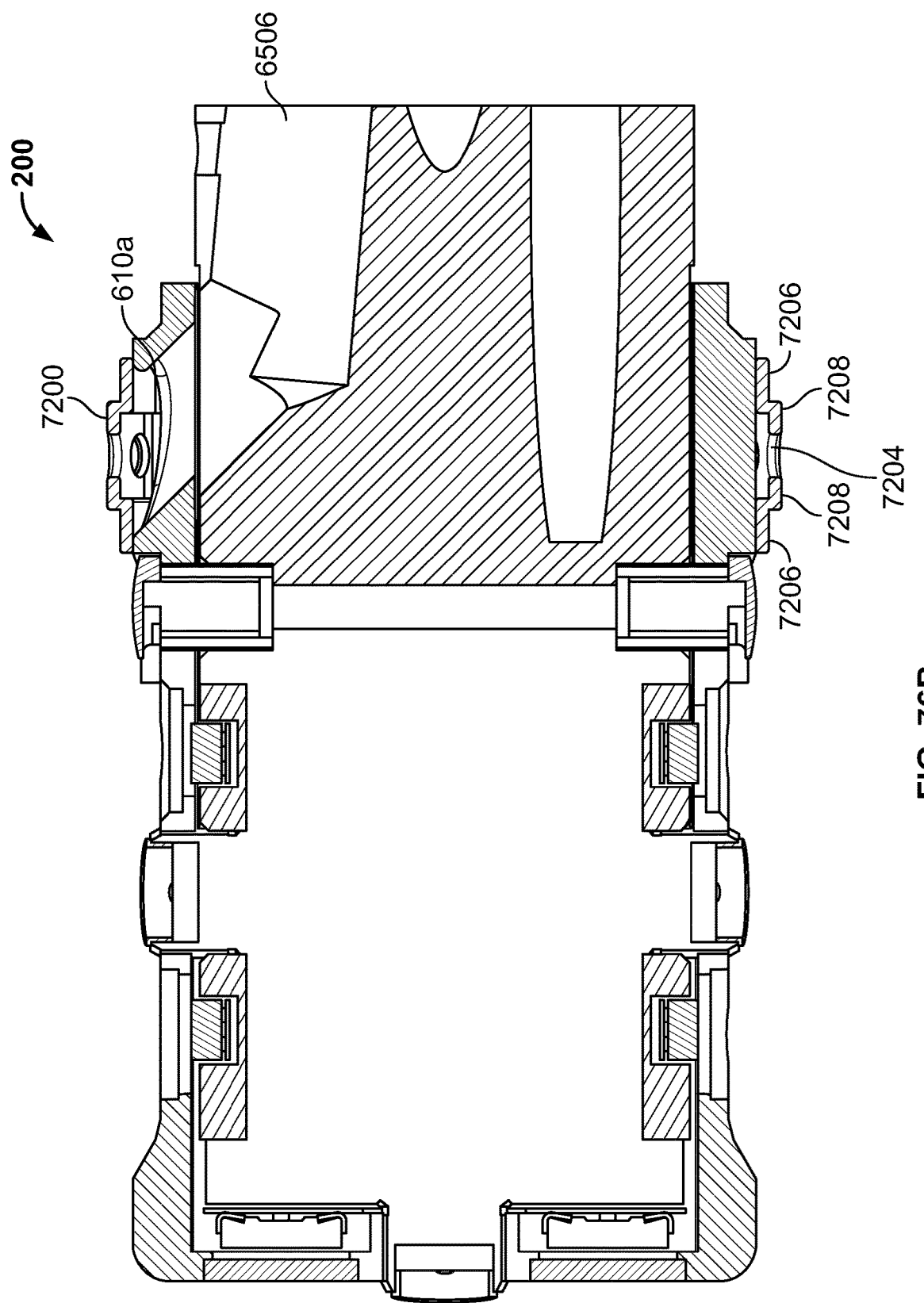
Figure 77A:
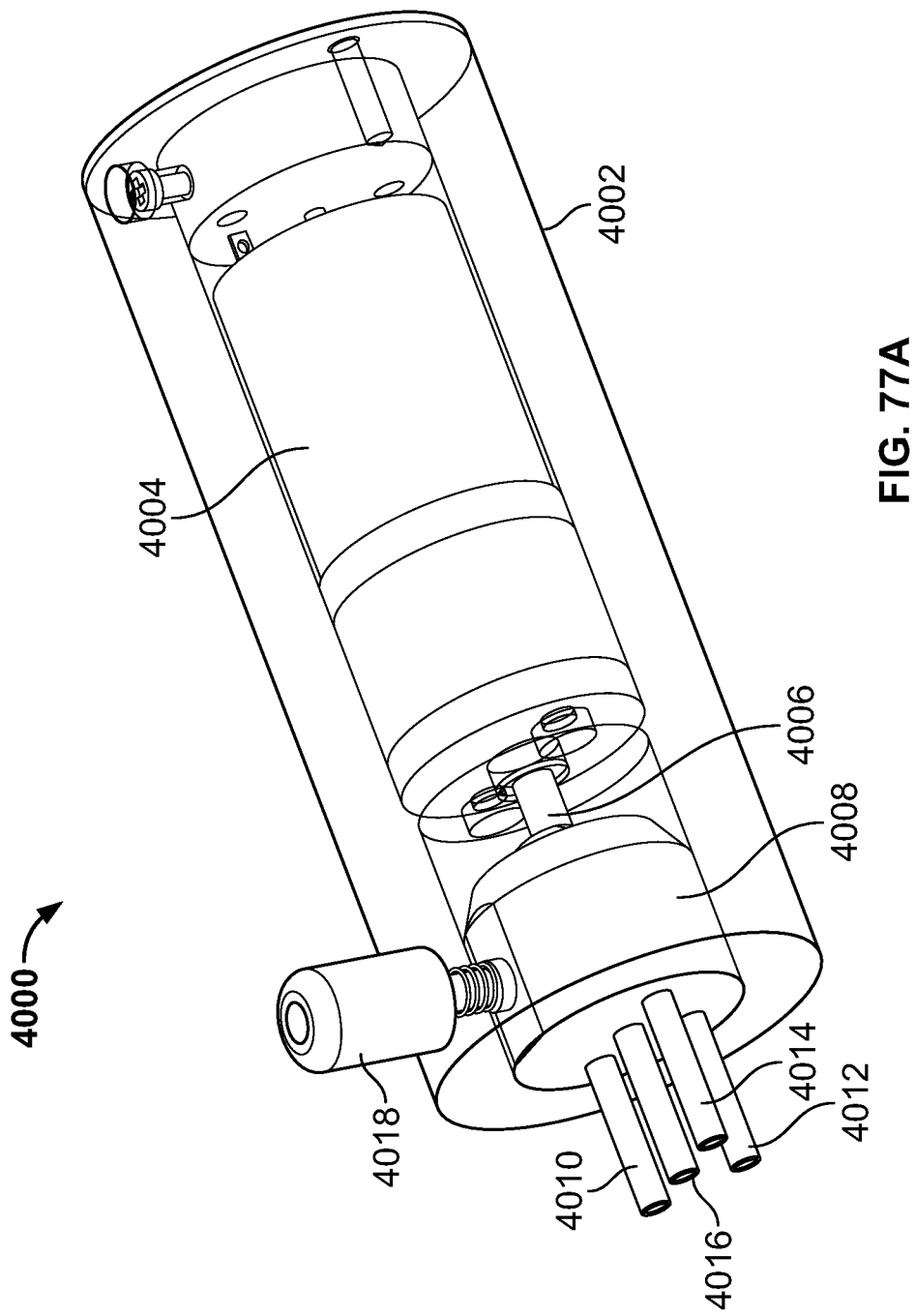
Figure 77B:
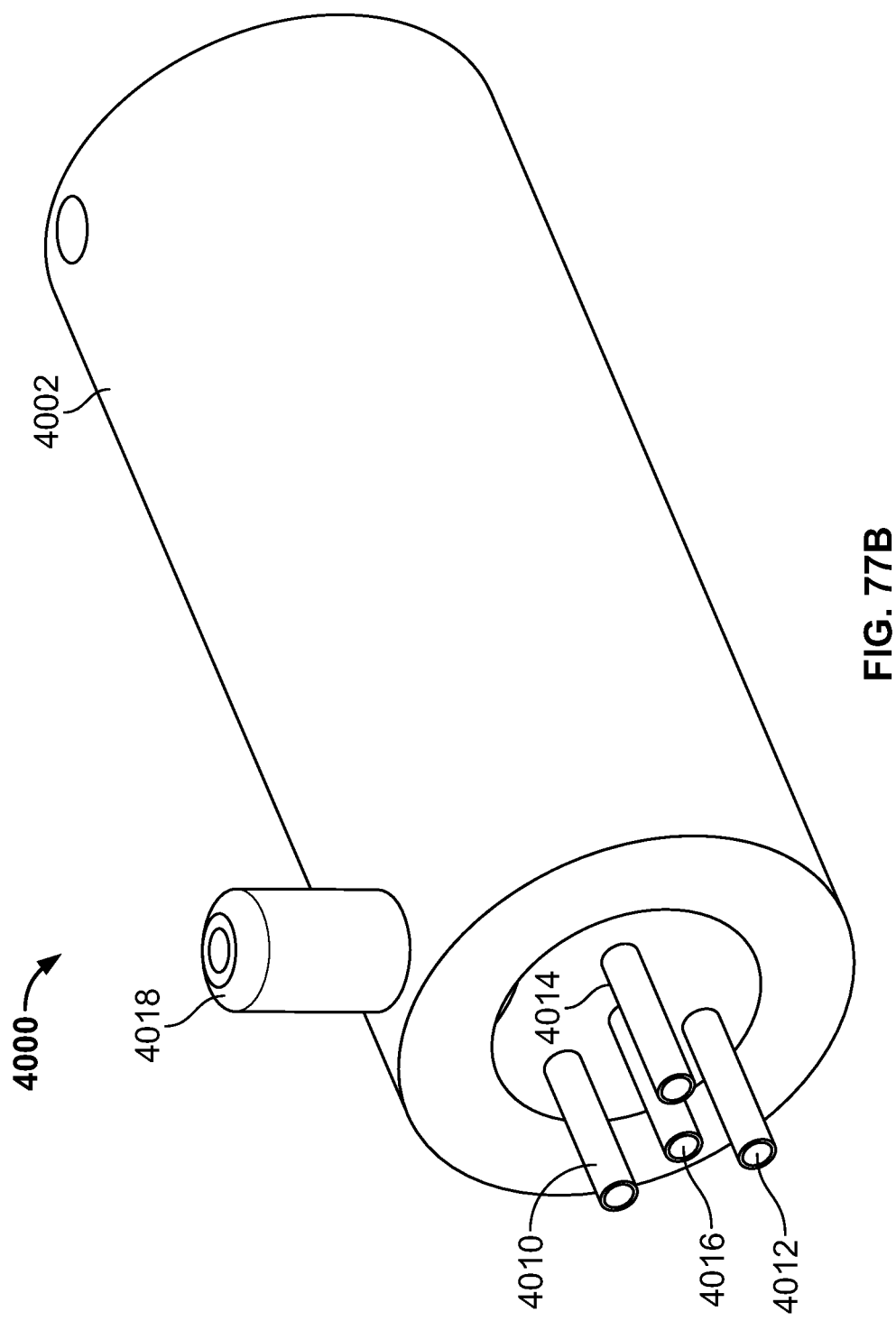
Figure 77C:
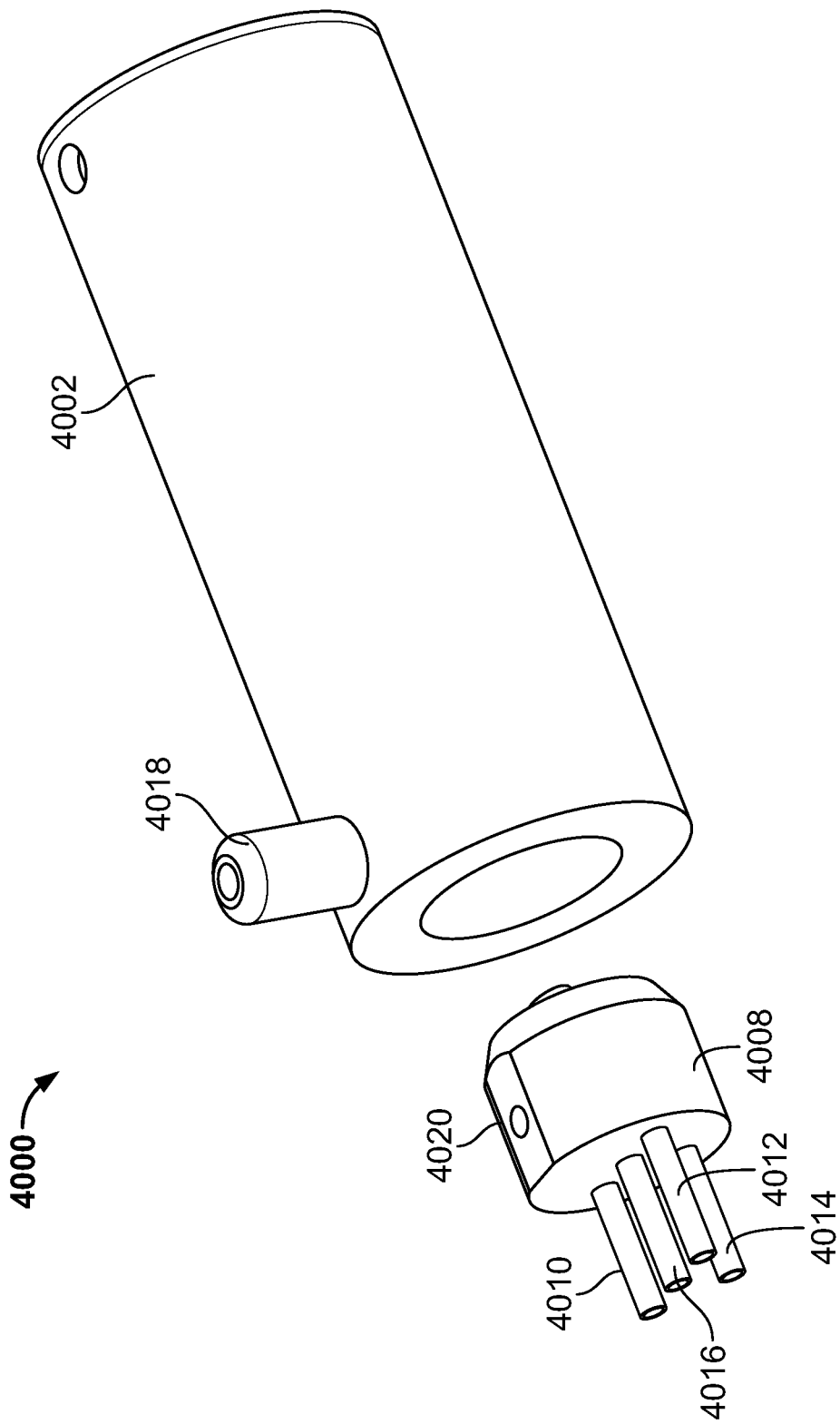
Figure 78A:
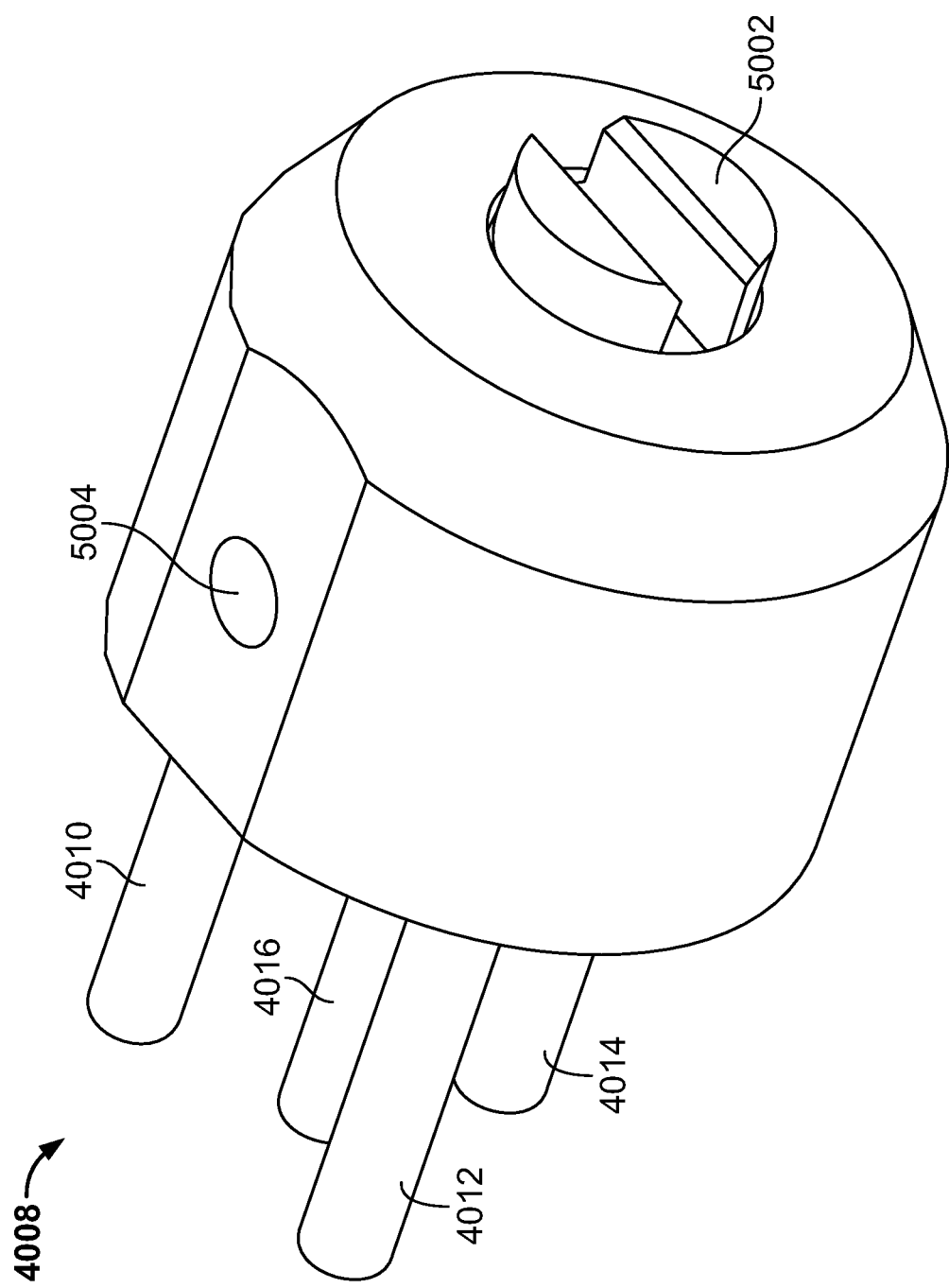
Figure 78B:
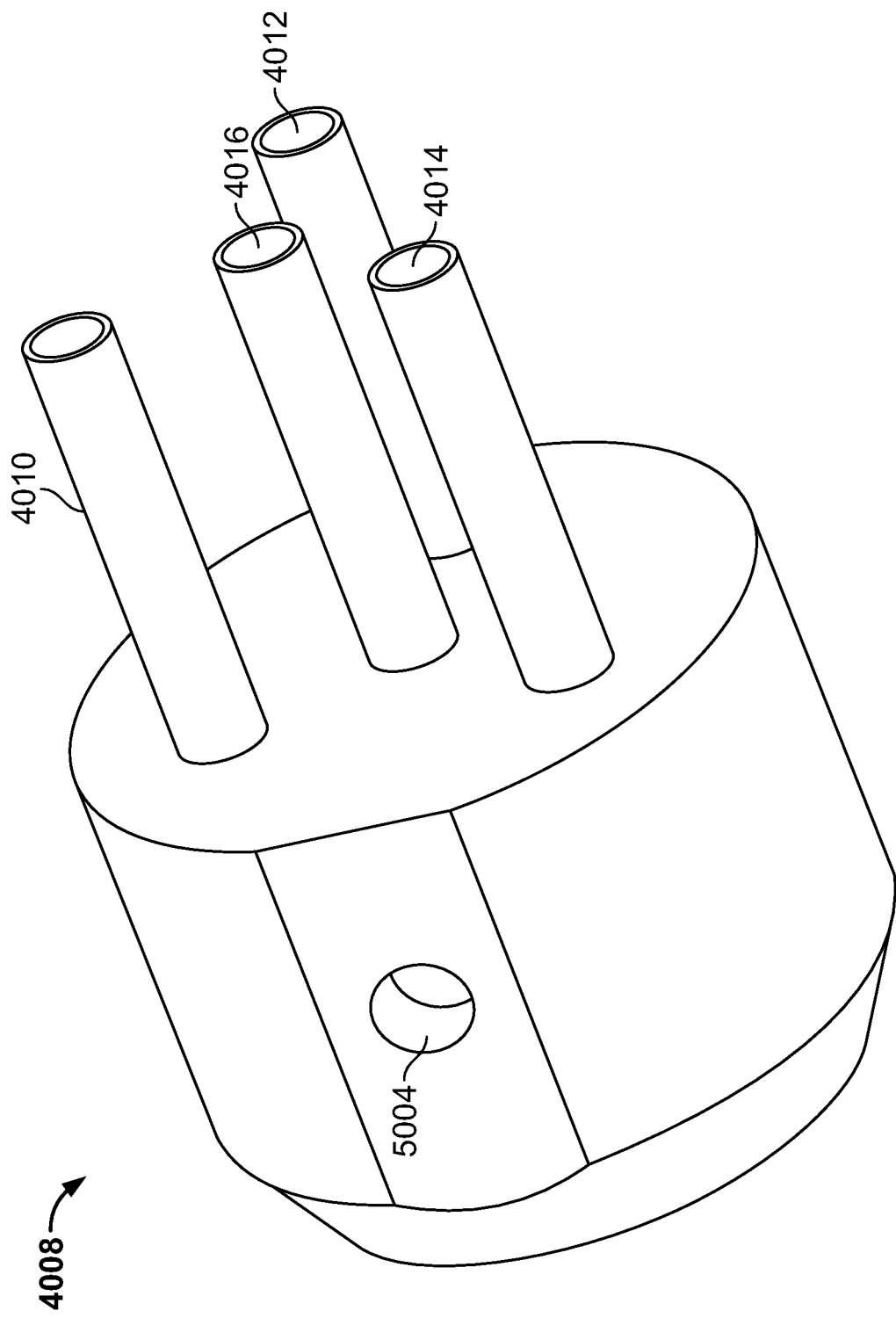
Figure 79A:
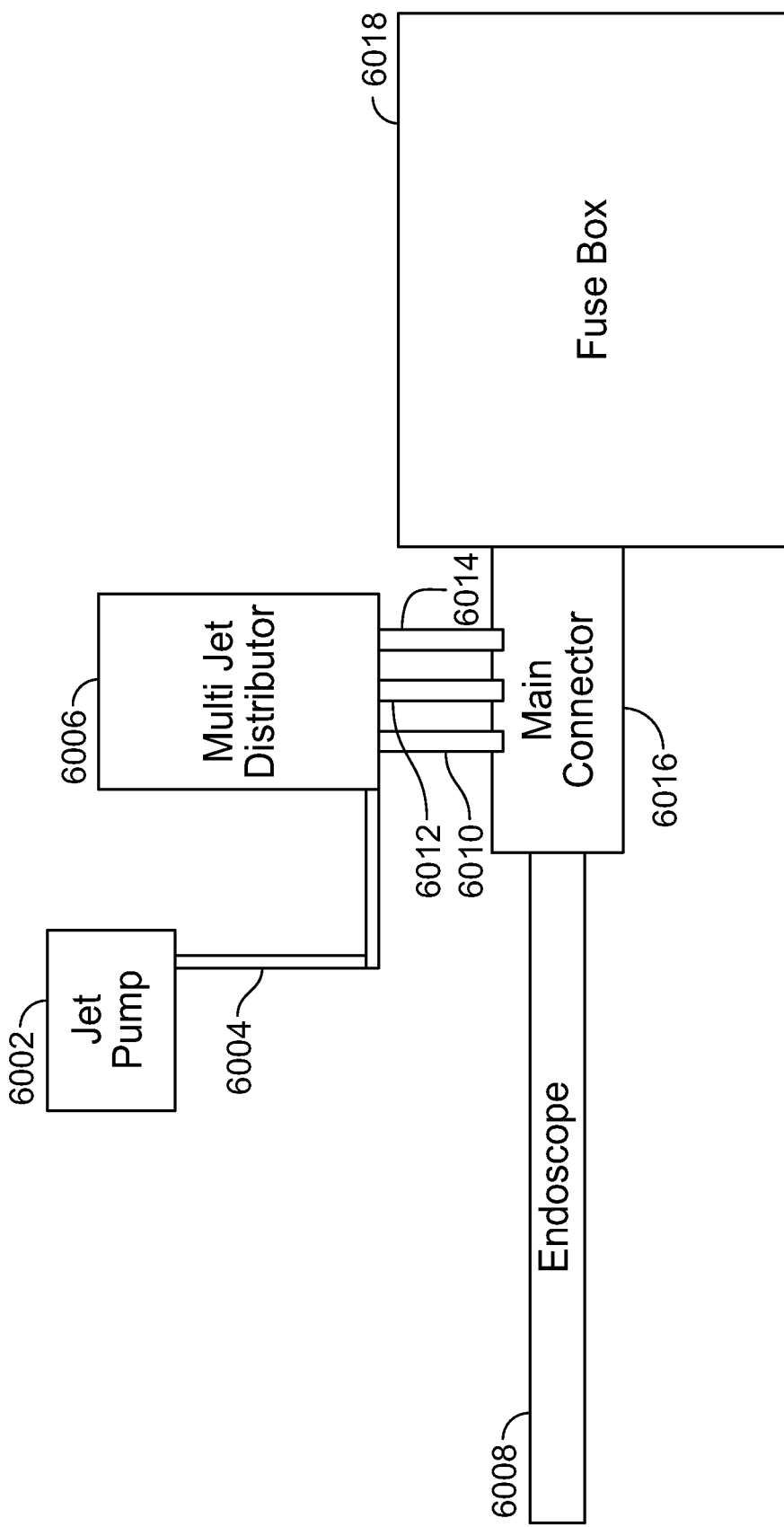
Figure 79B:
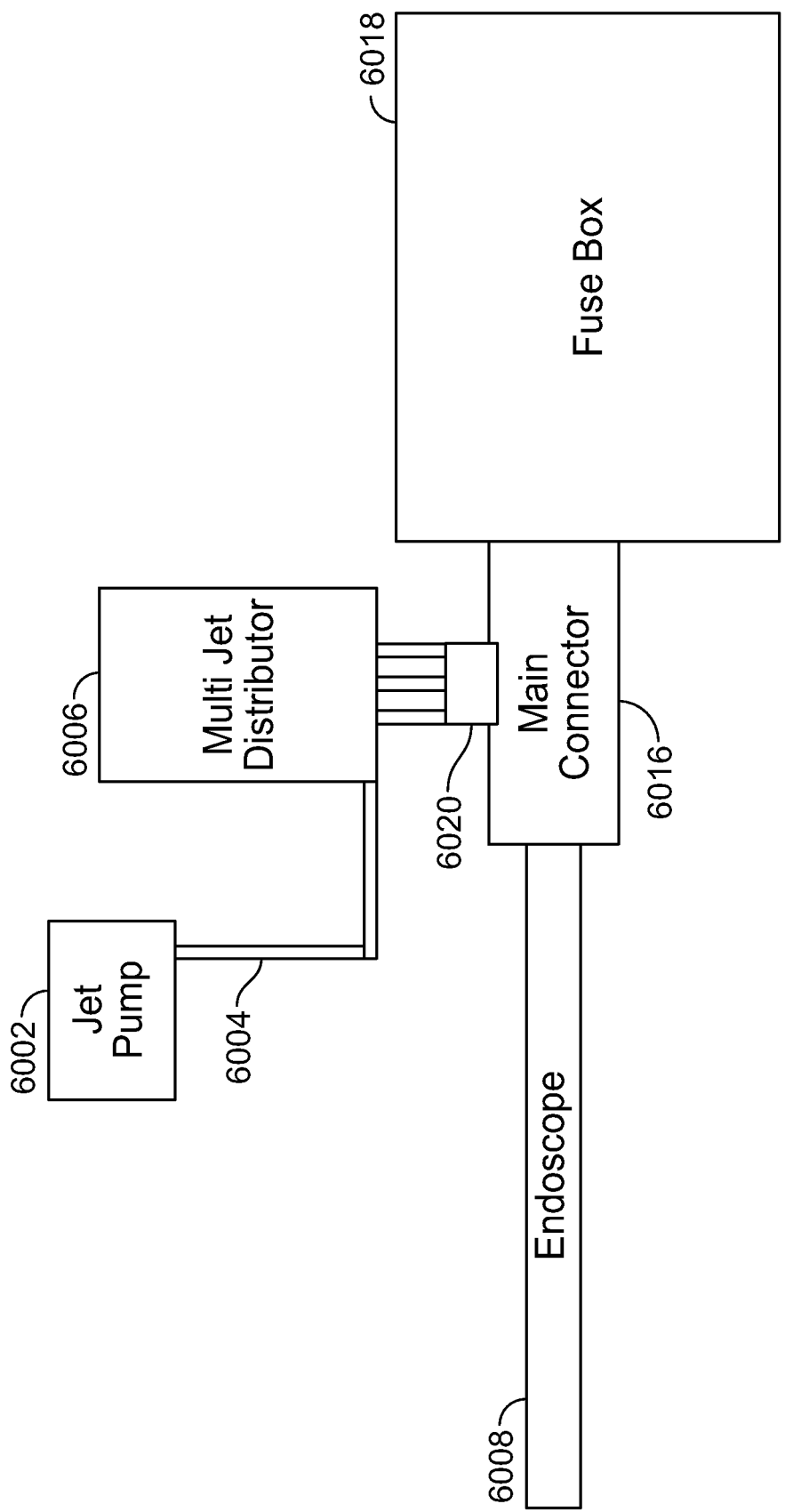
Figure 81A:
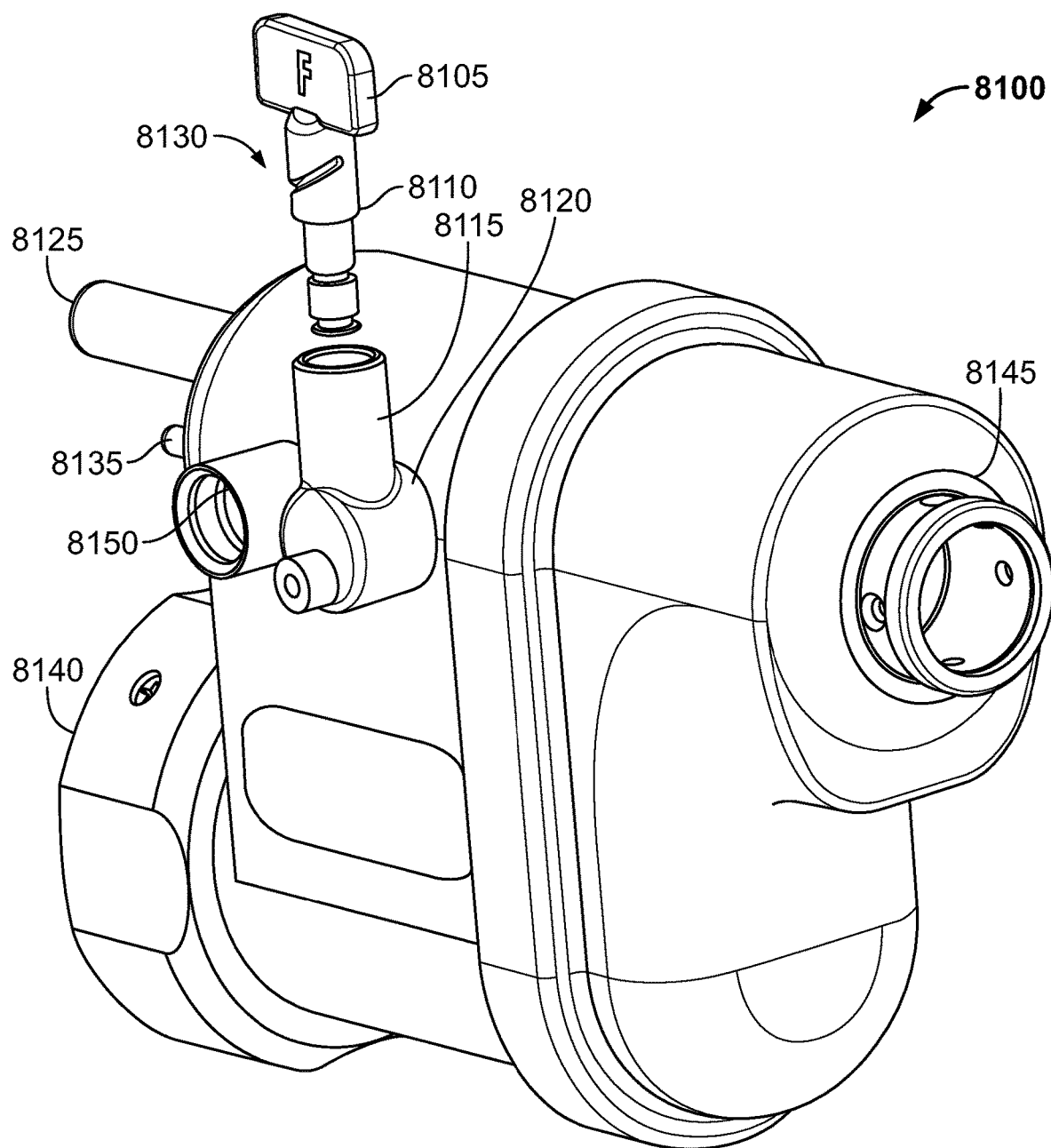
Figure 81B:
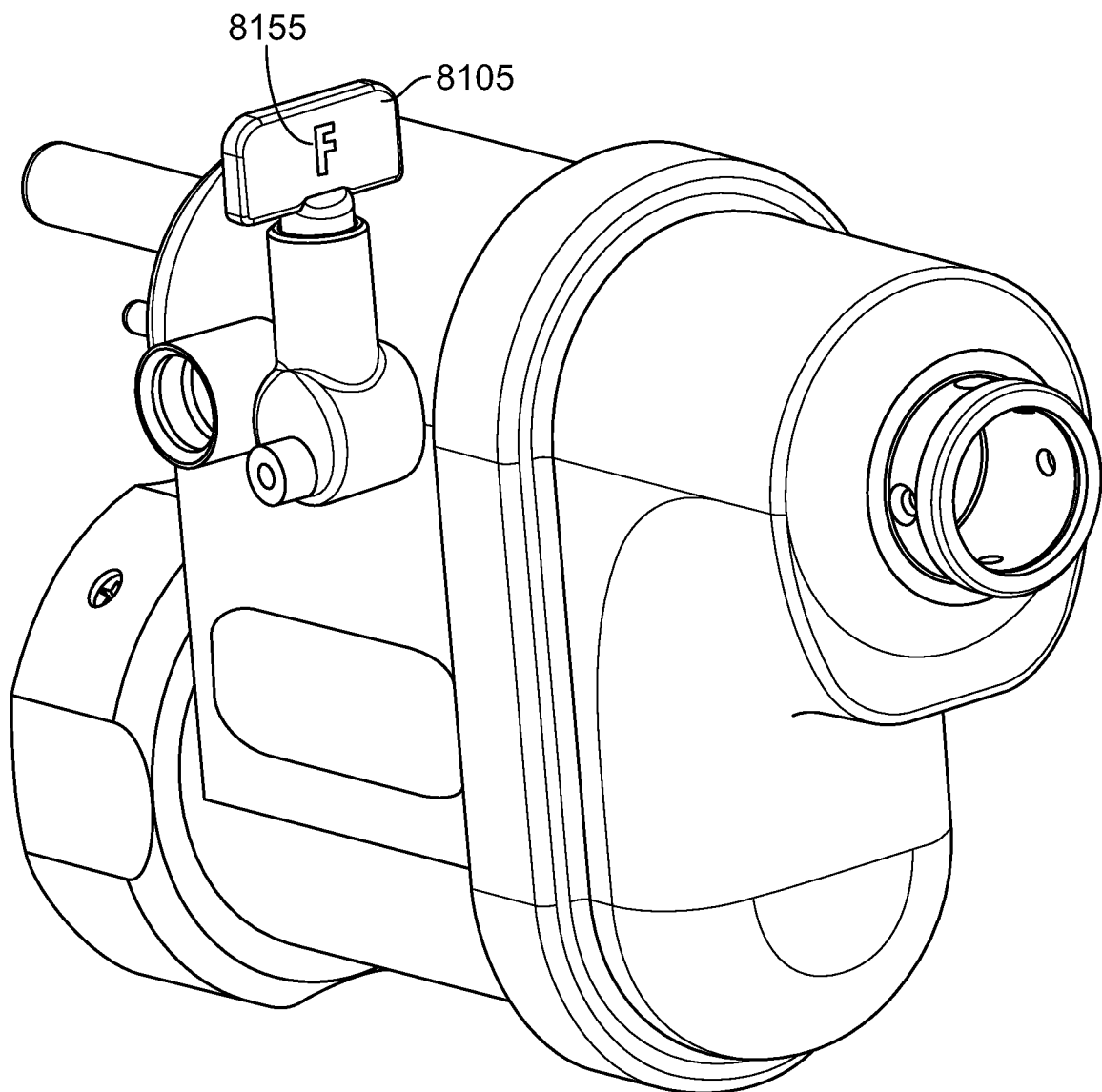
Figure 81C:
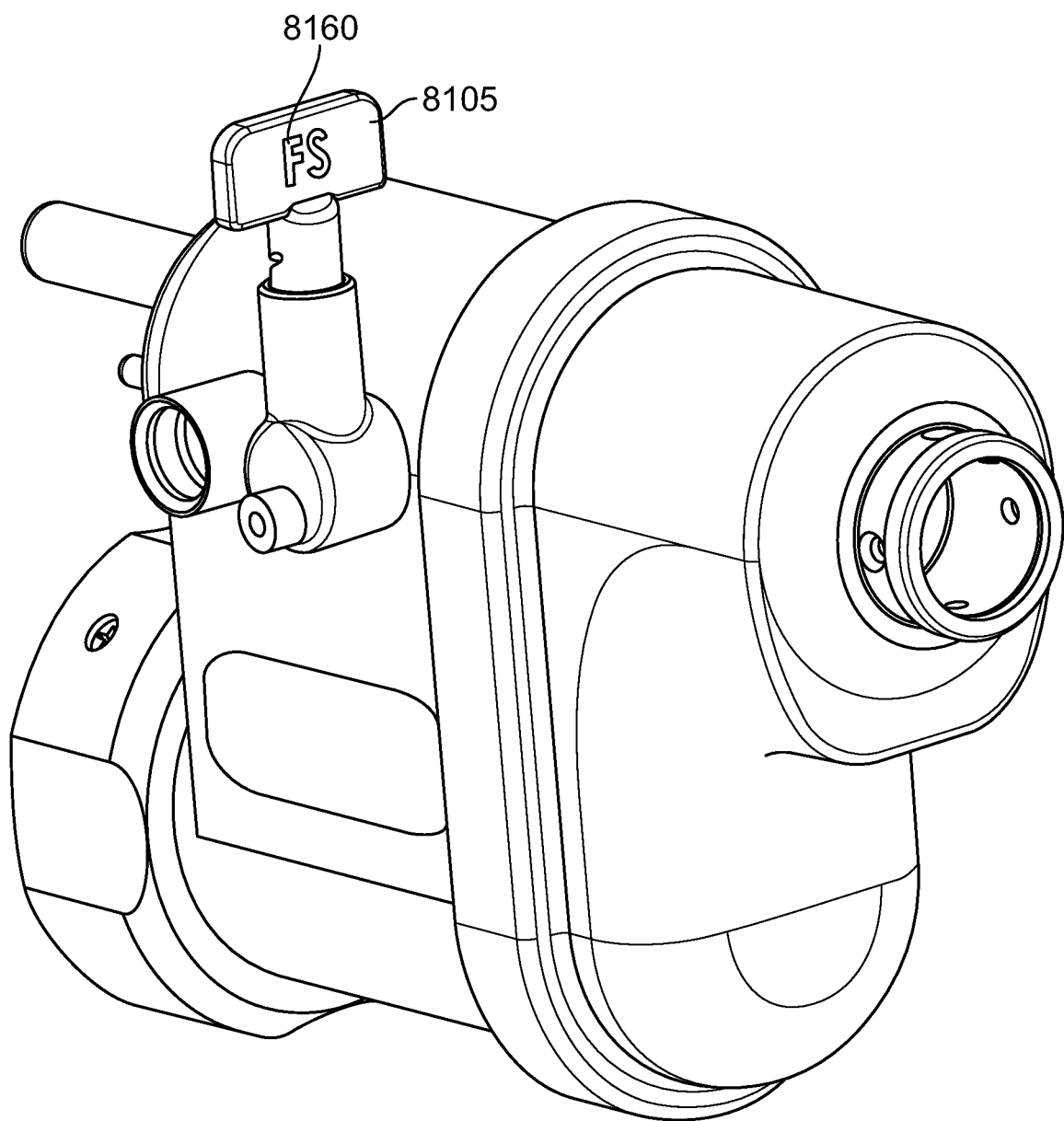
Figure 82:
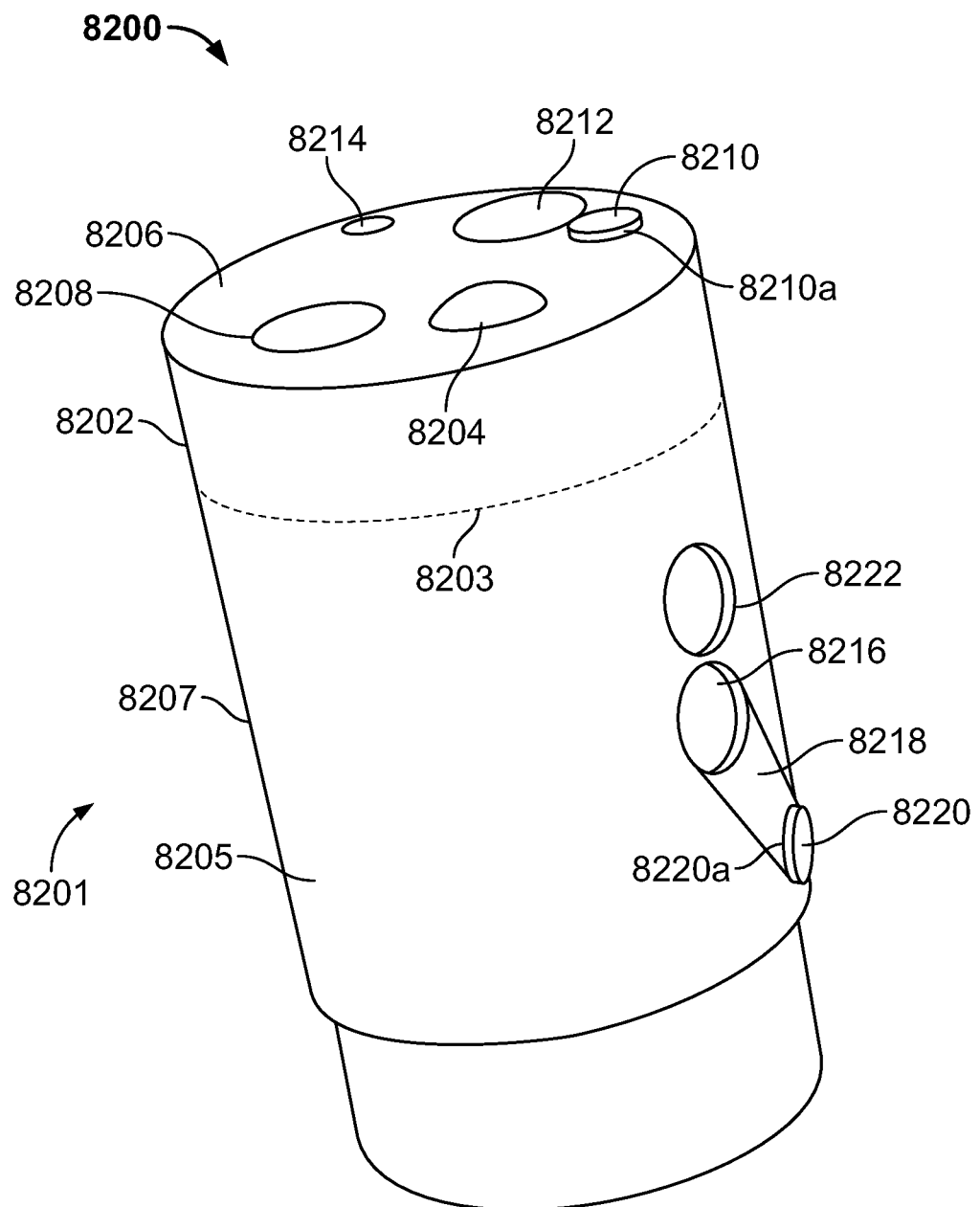
Figure 83:
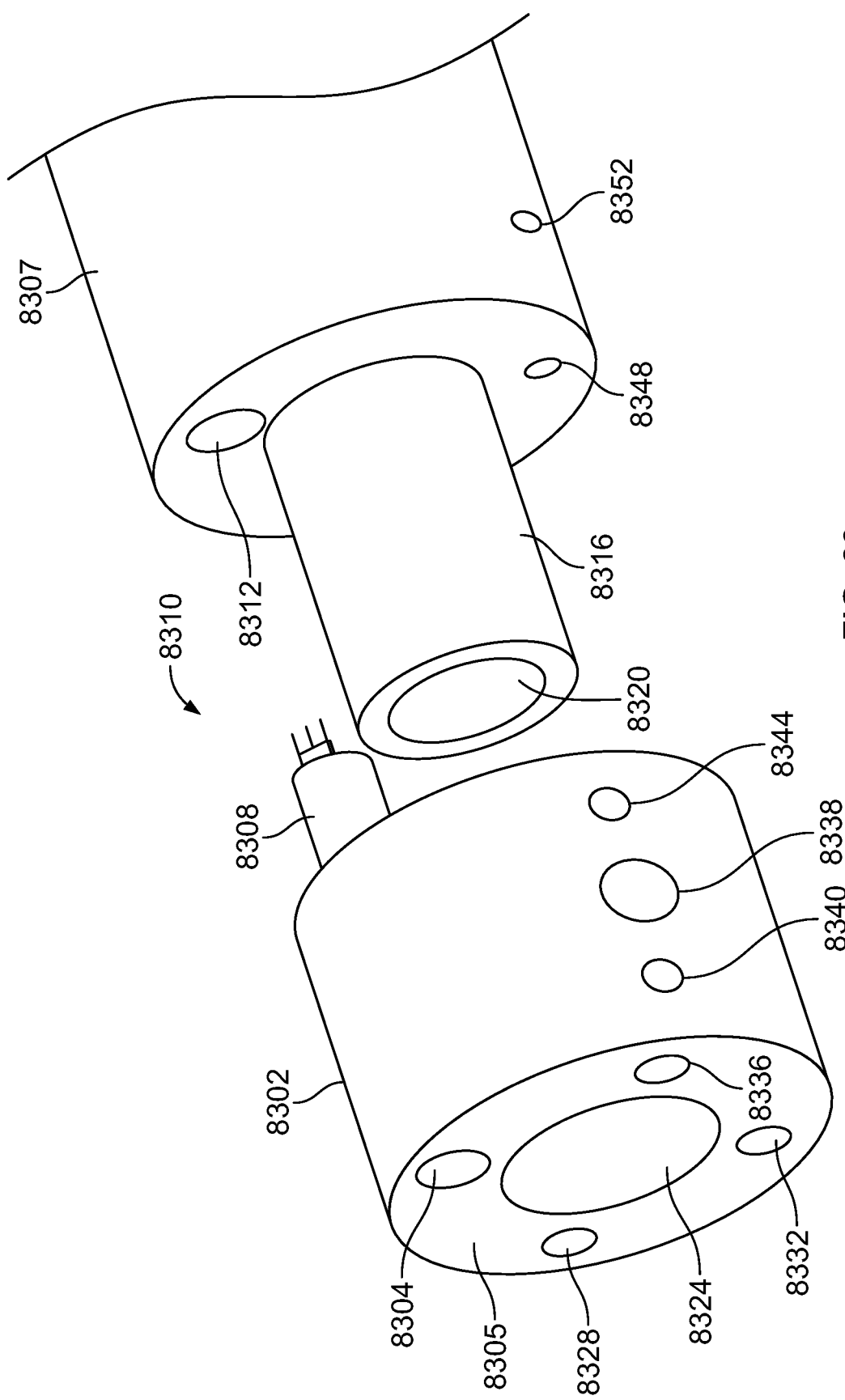
Figure 84:
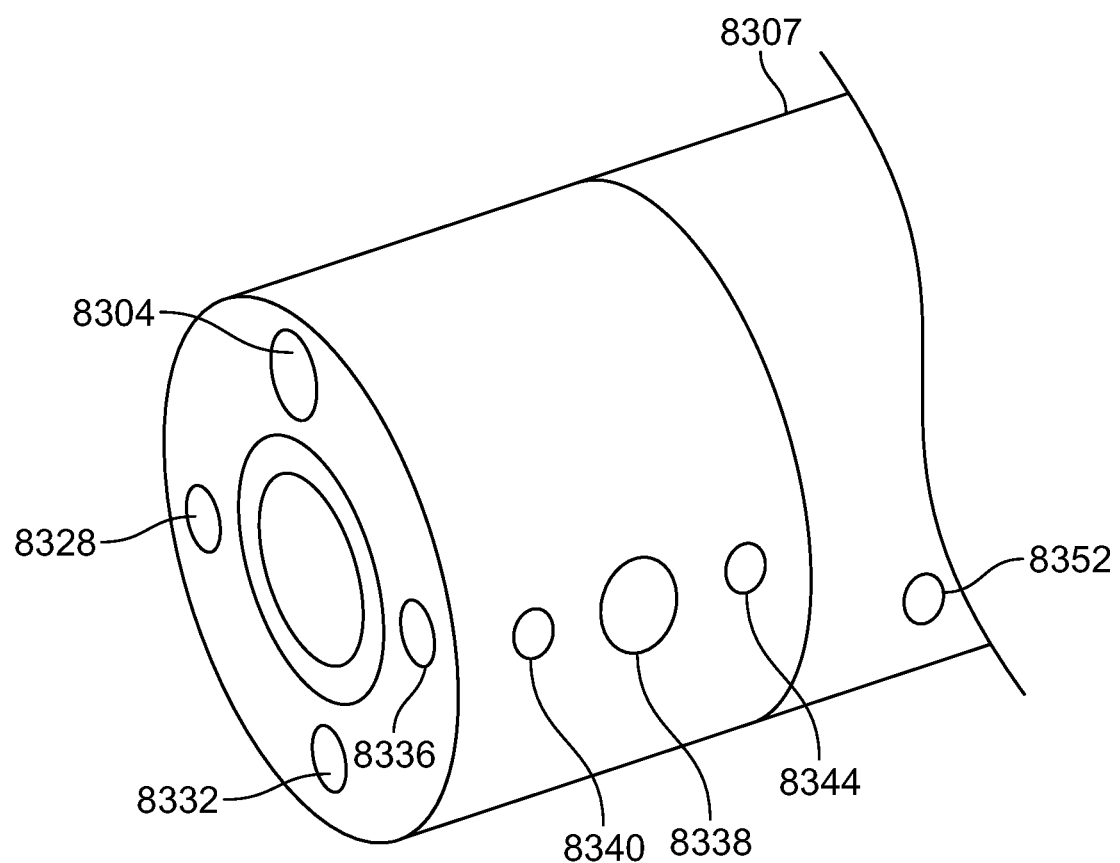
Figure 85:
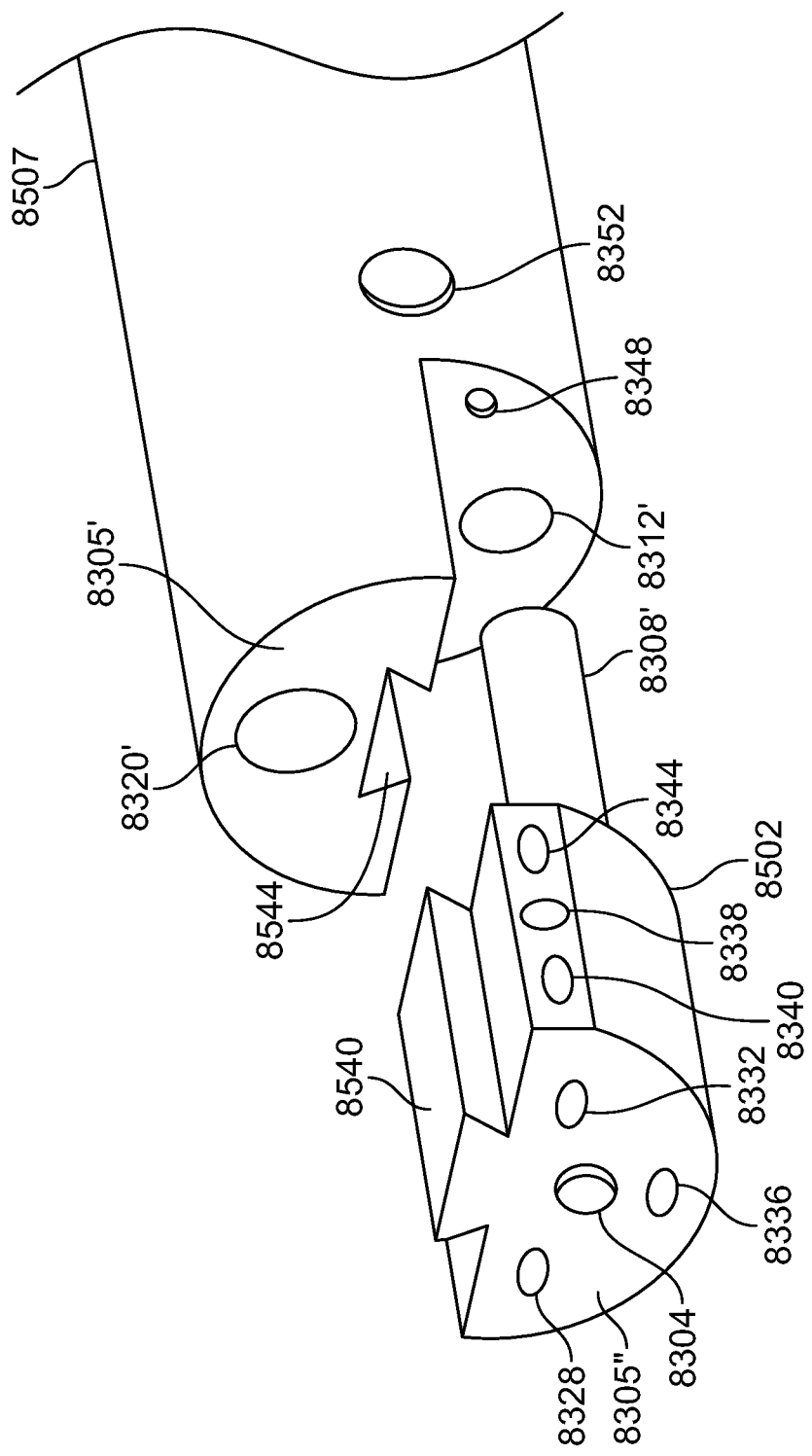
Figure 86:
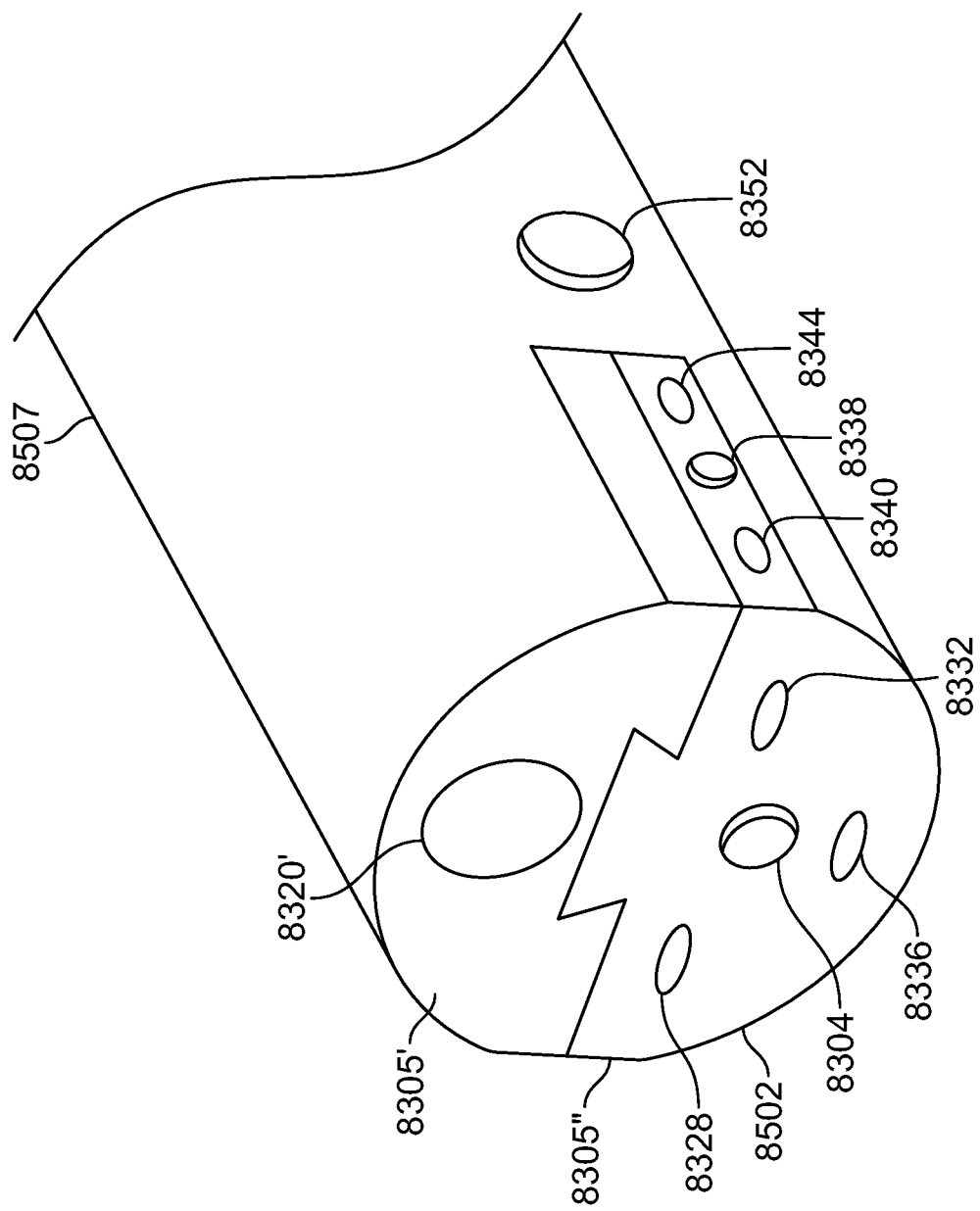
Figure 87B:
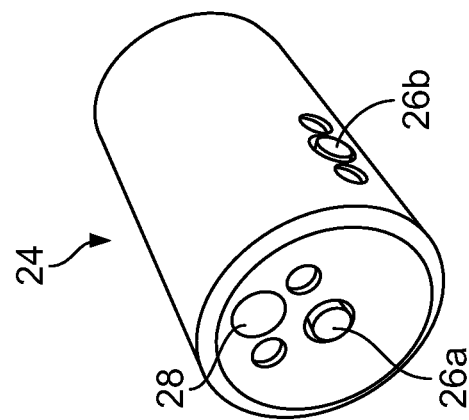
Figure 87A:
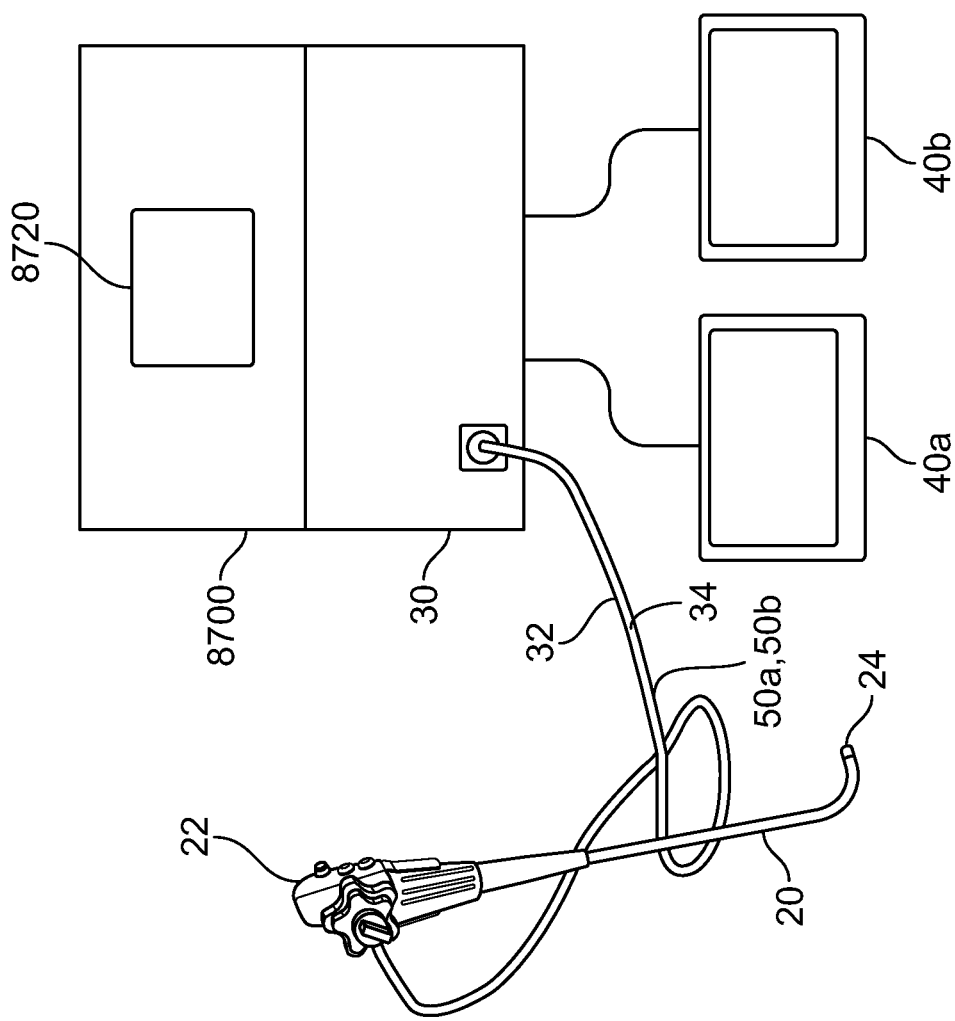
Figure 88:
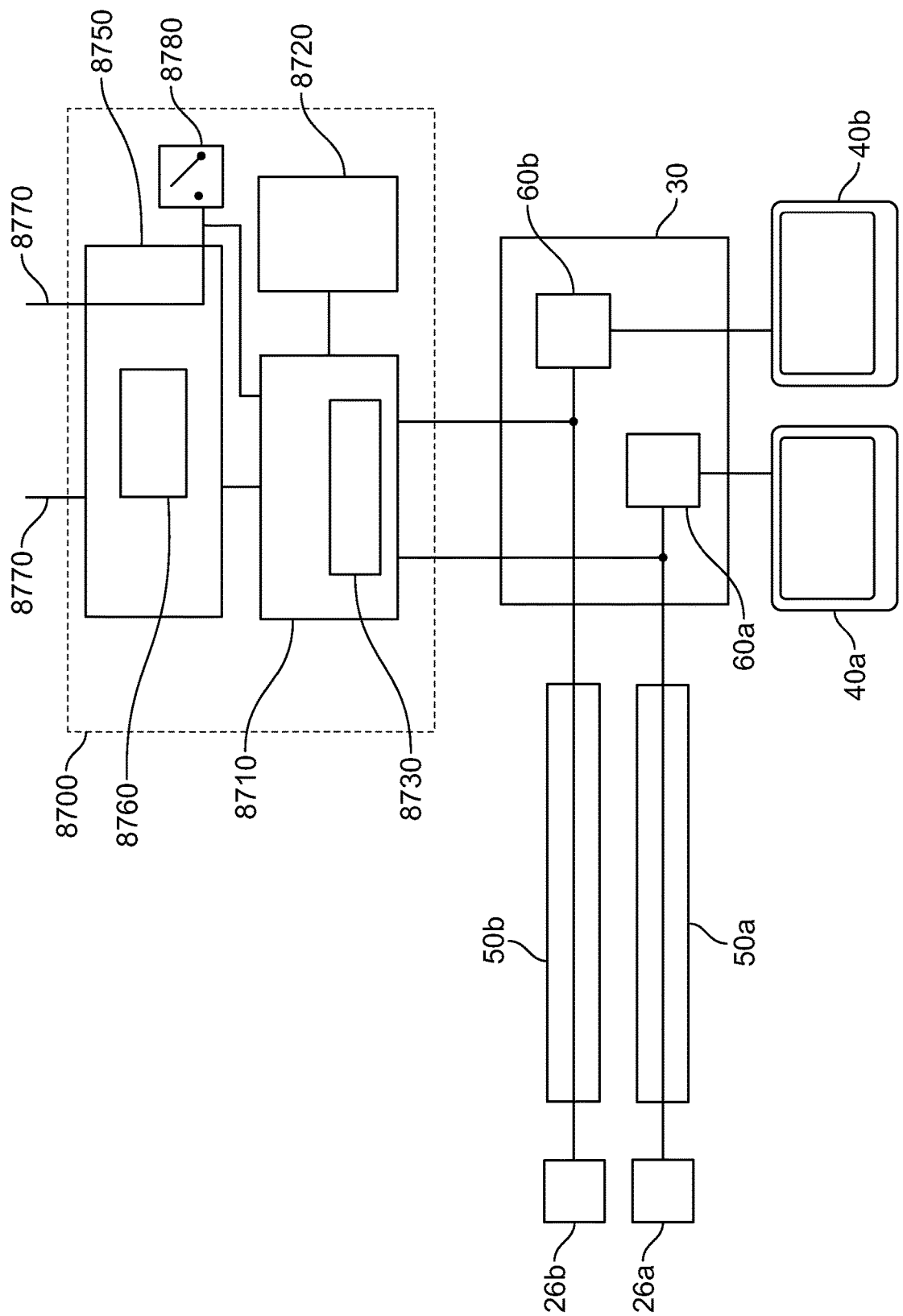
Figure 89:
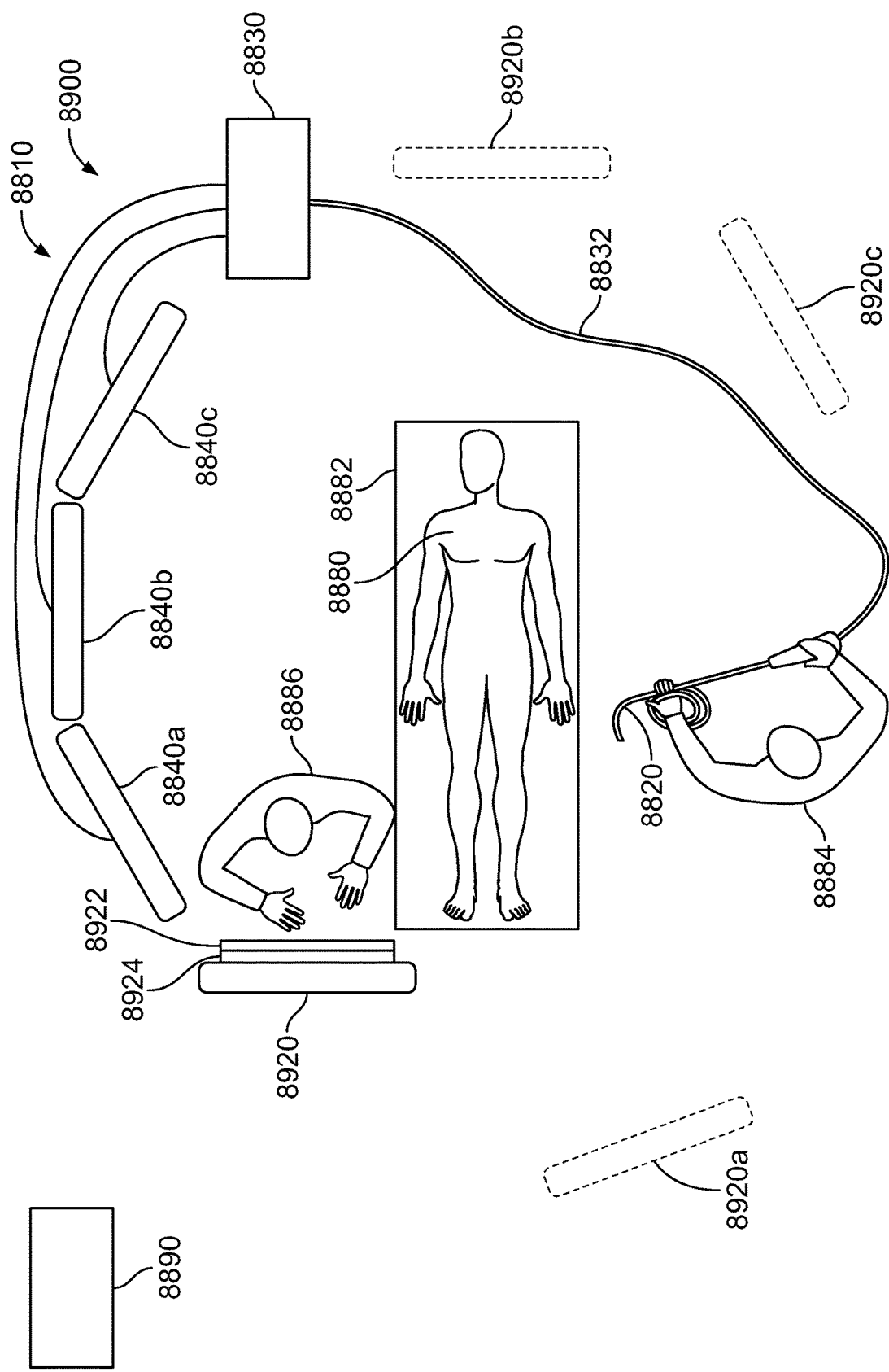
Figure 90:
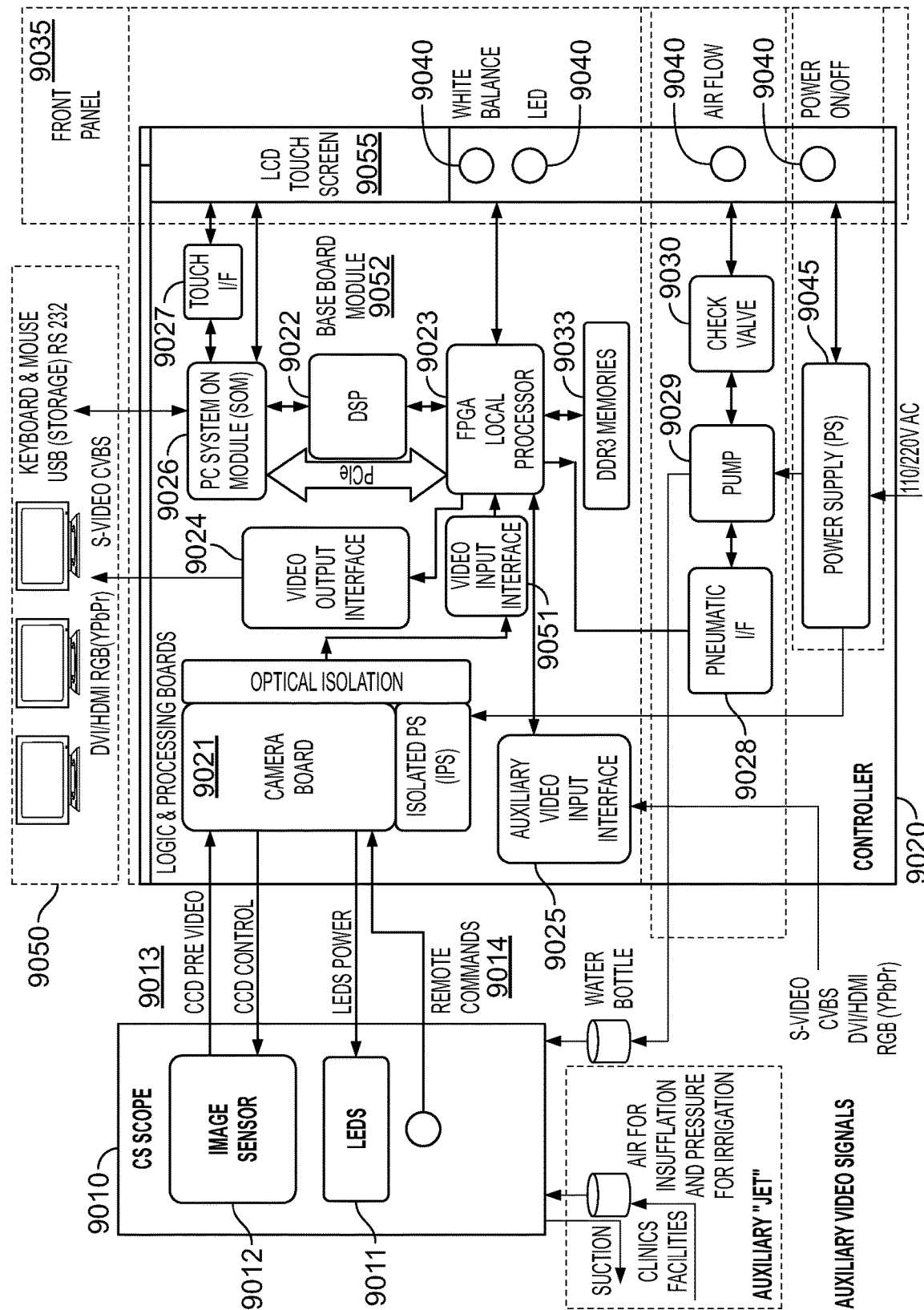
Figure 91A:
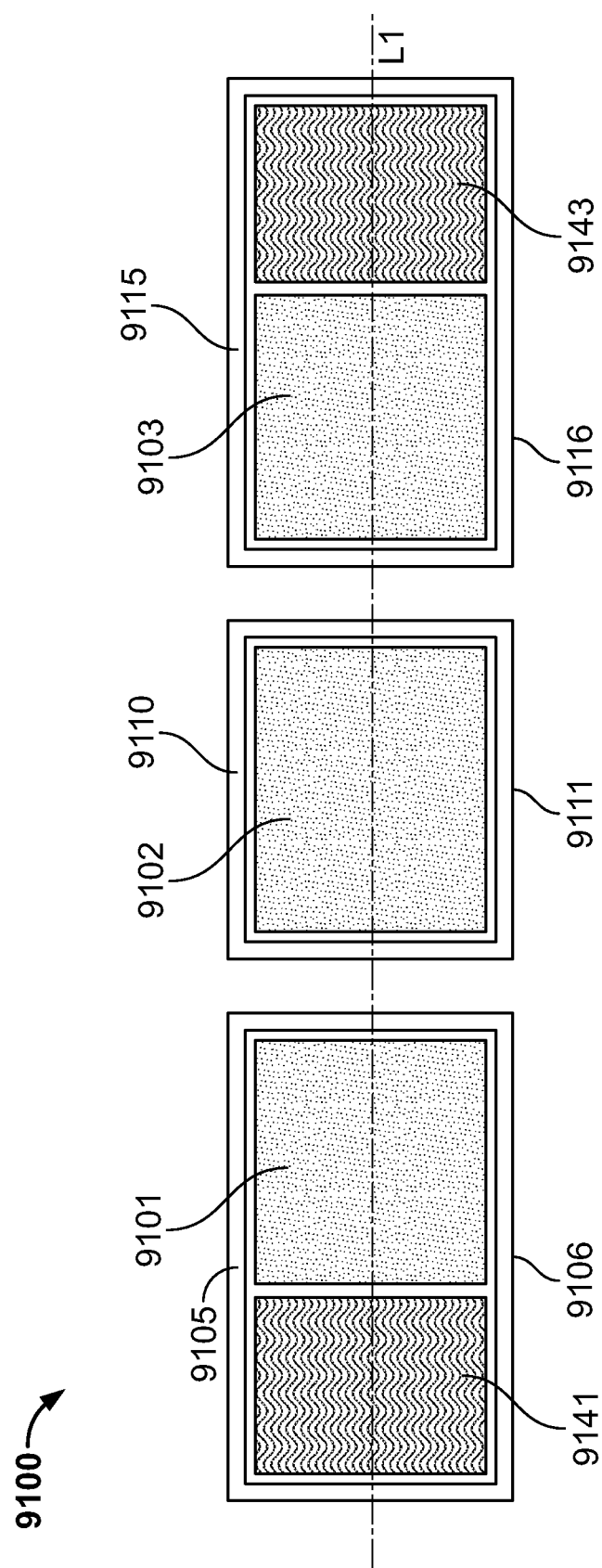
Figure 91B:
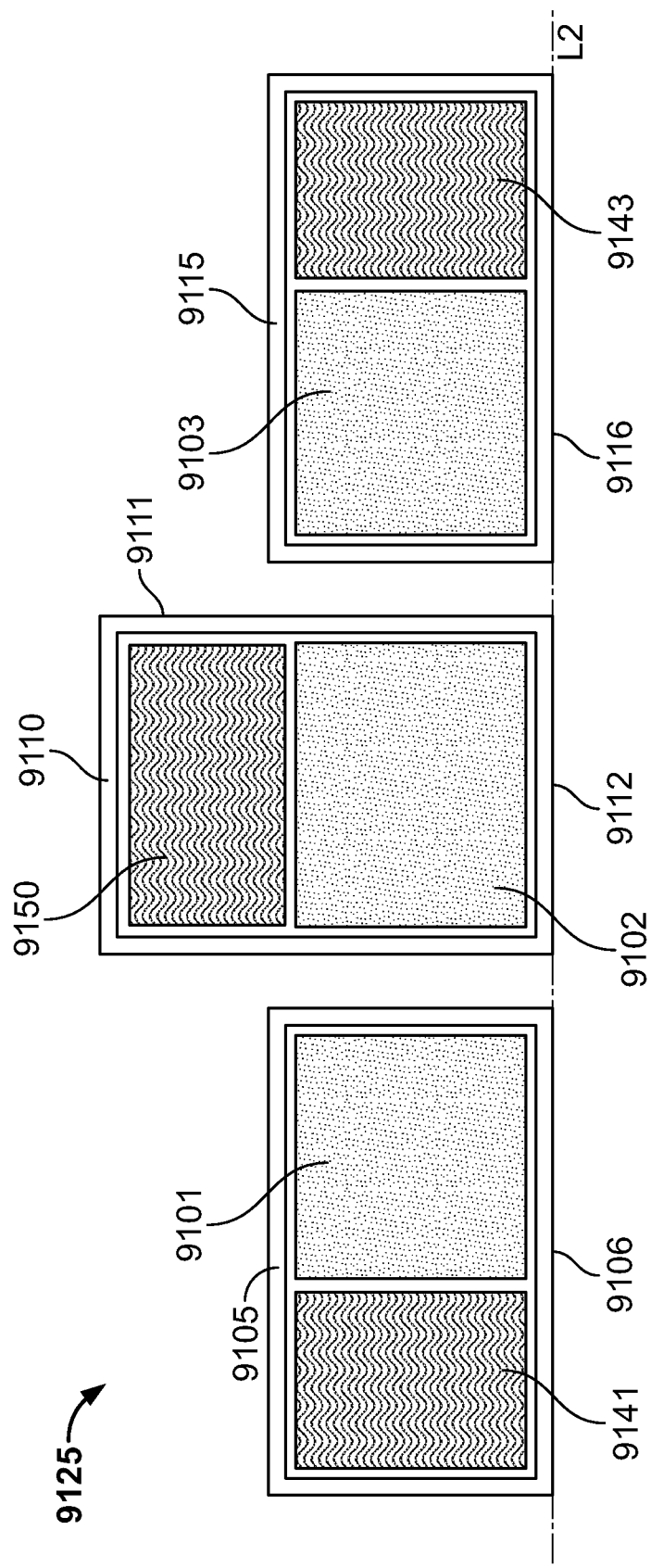
Figure 91C:
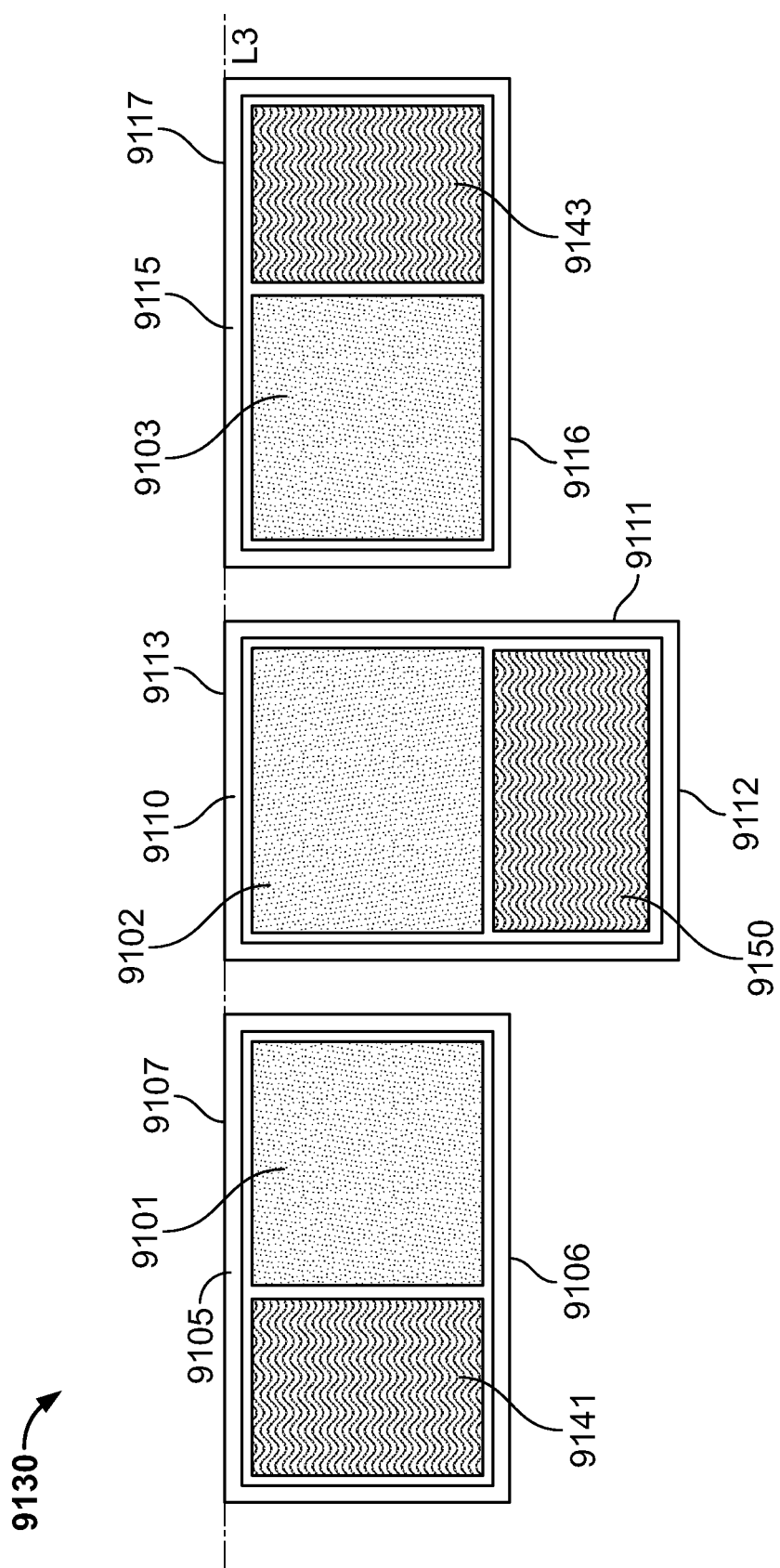
Figure 91D:
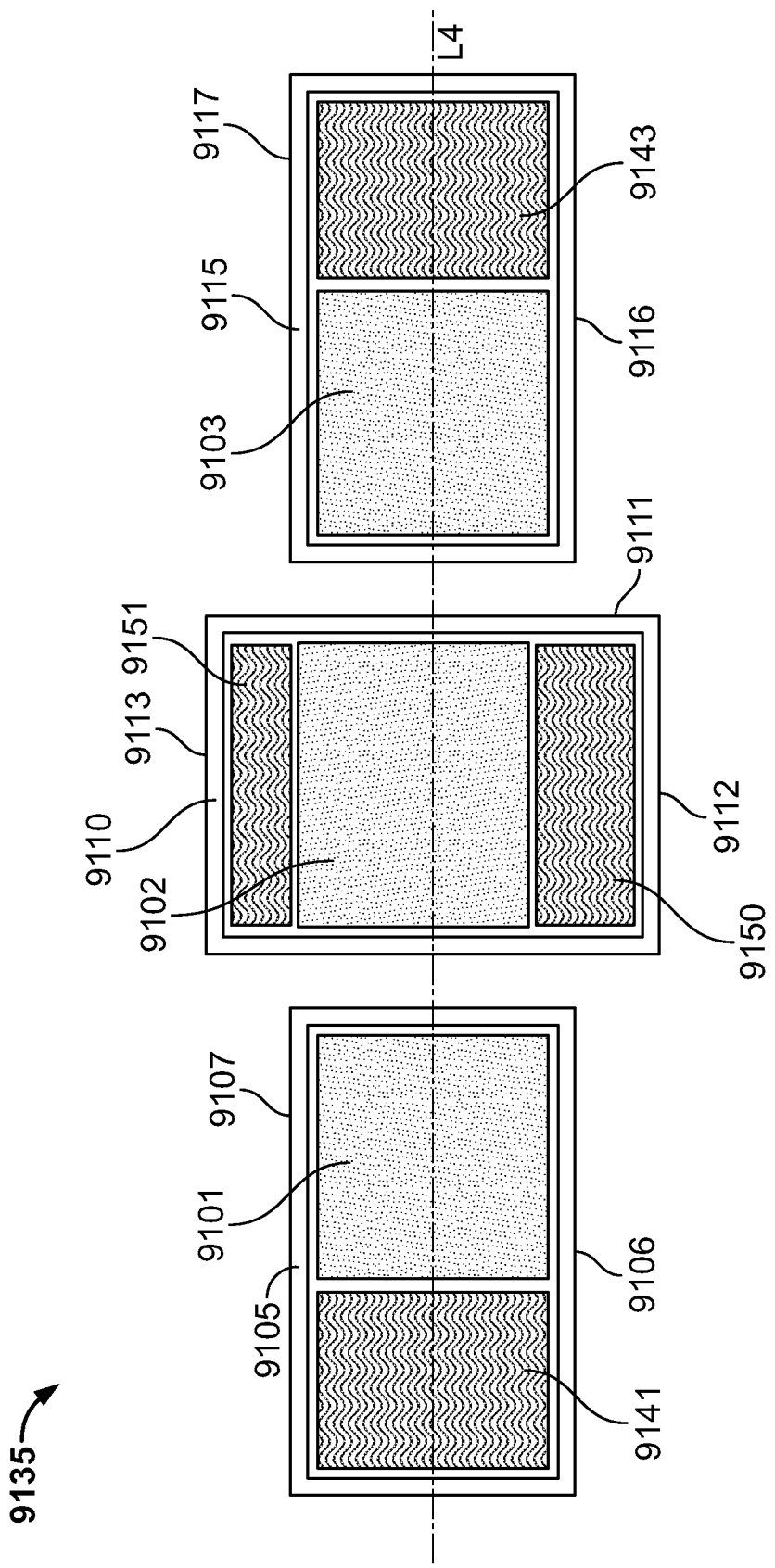
Figure 91E:
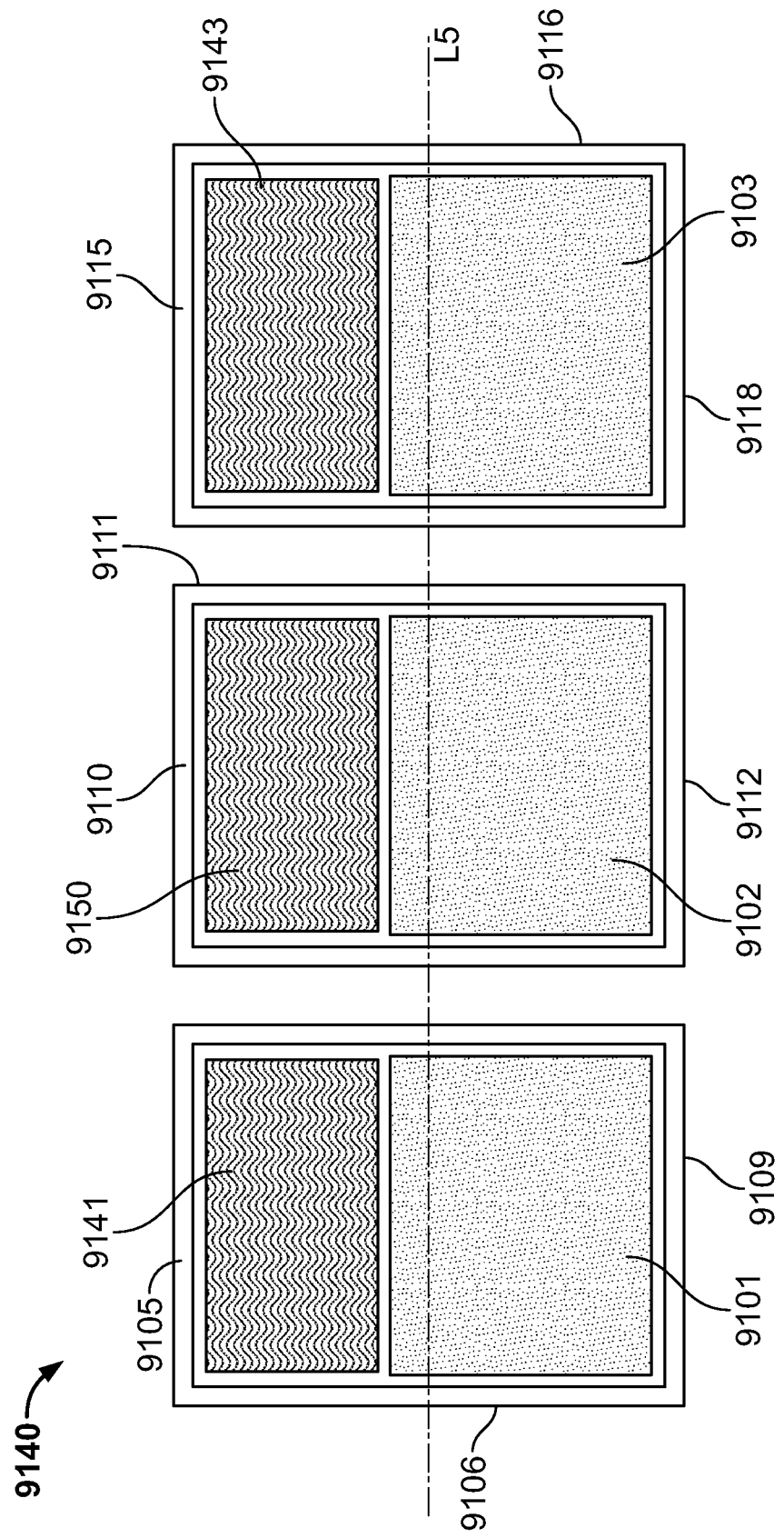
Figure 93A:
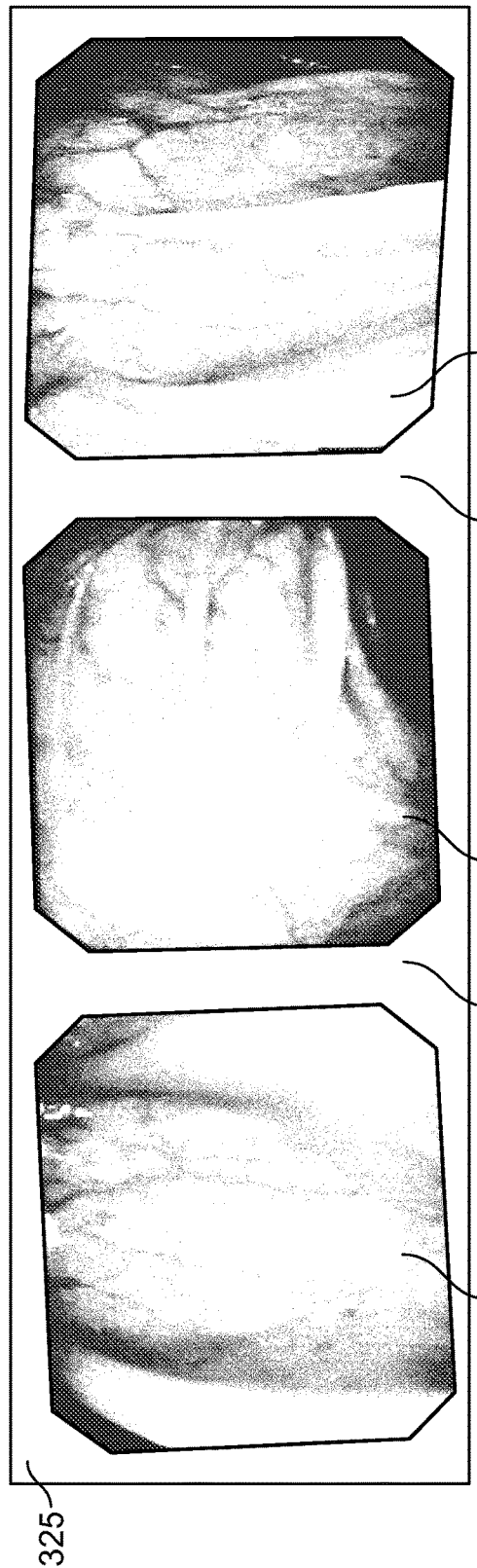
Figure 93B:
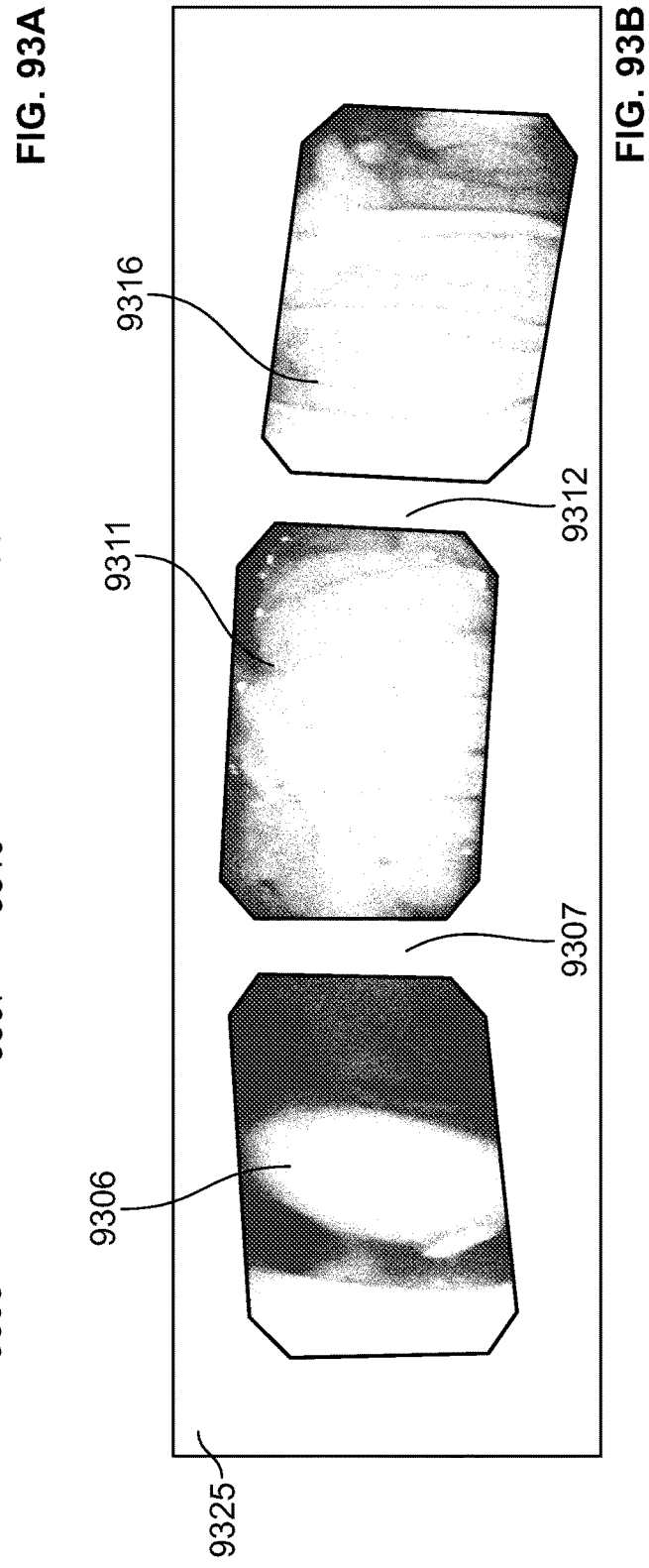
Figure 94:
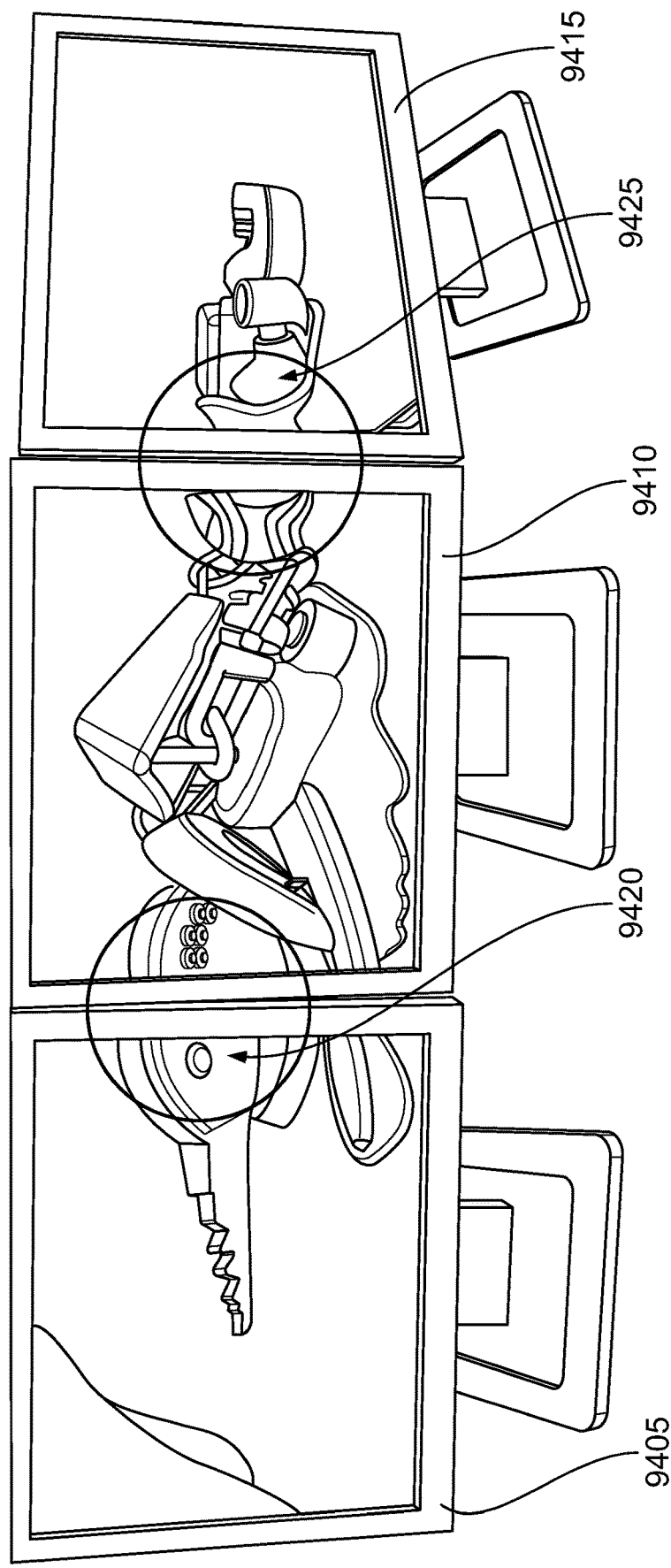
Figure 95A:
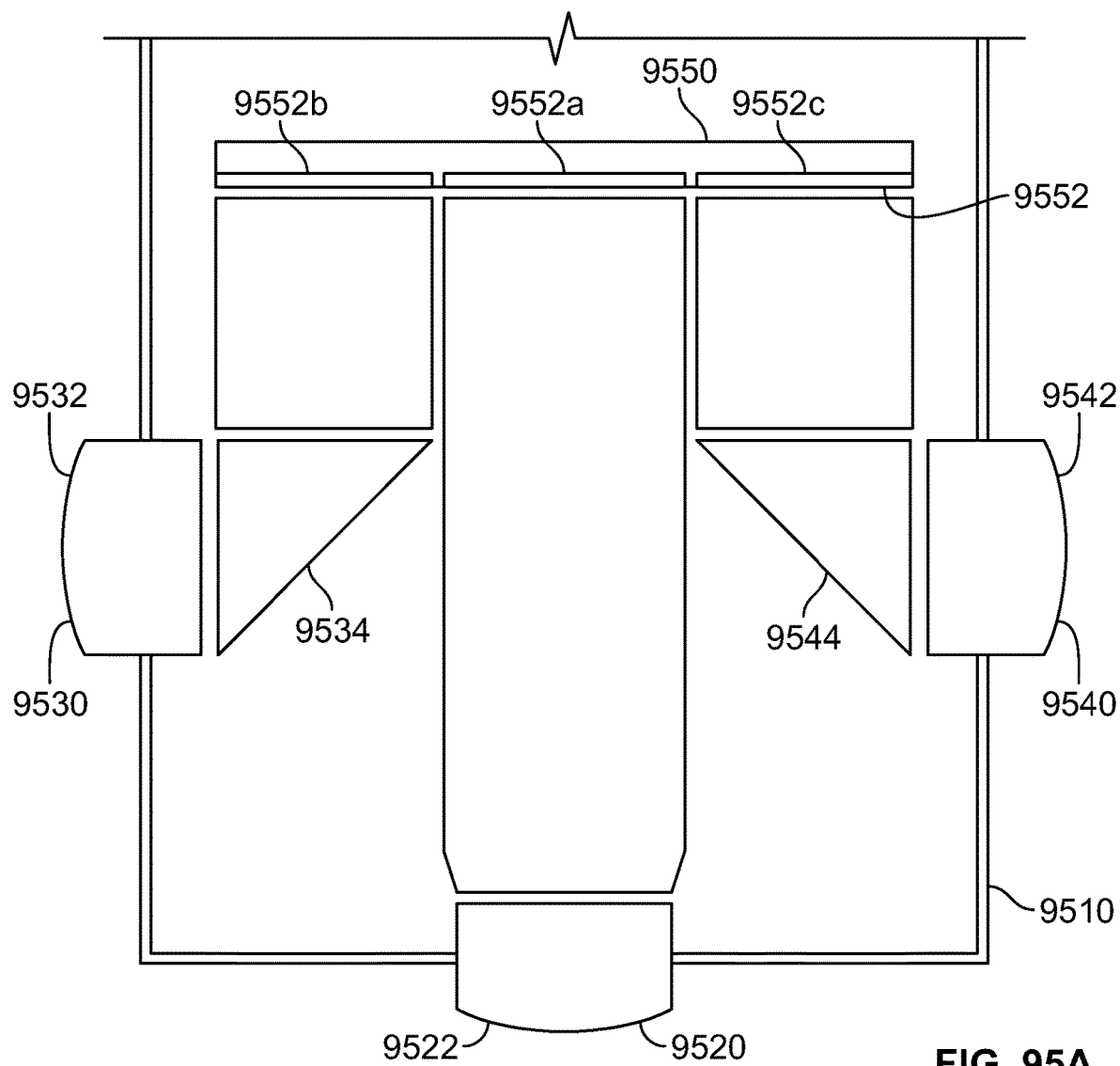
Figure 95B:
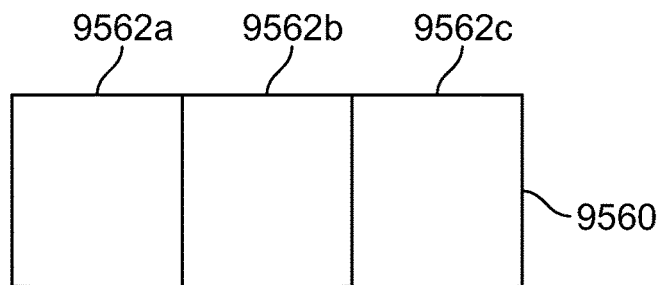
Figure 96:
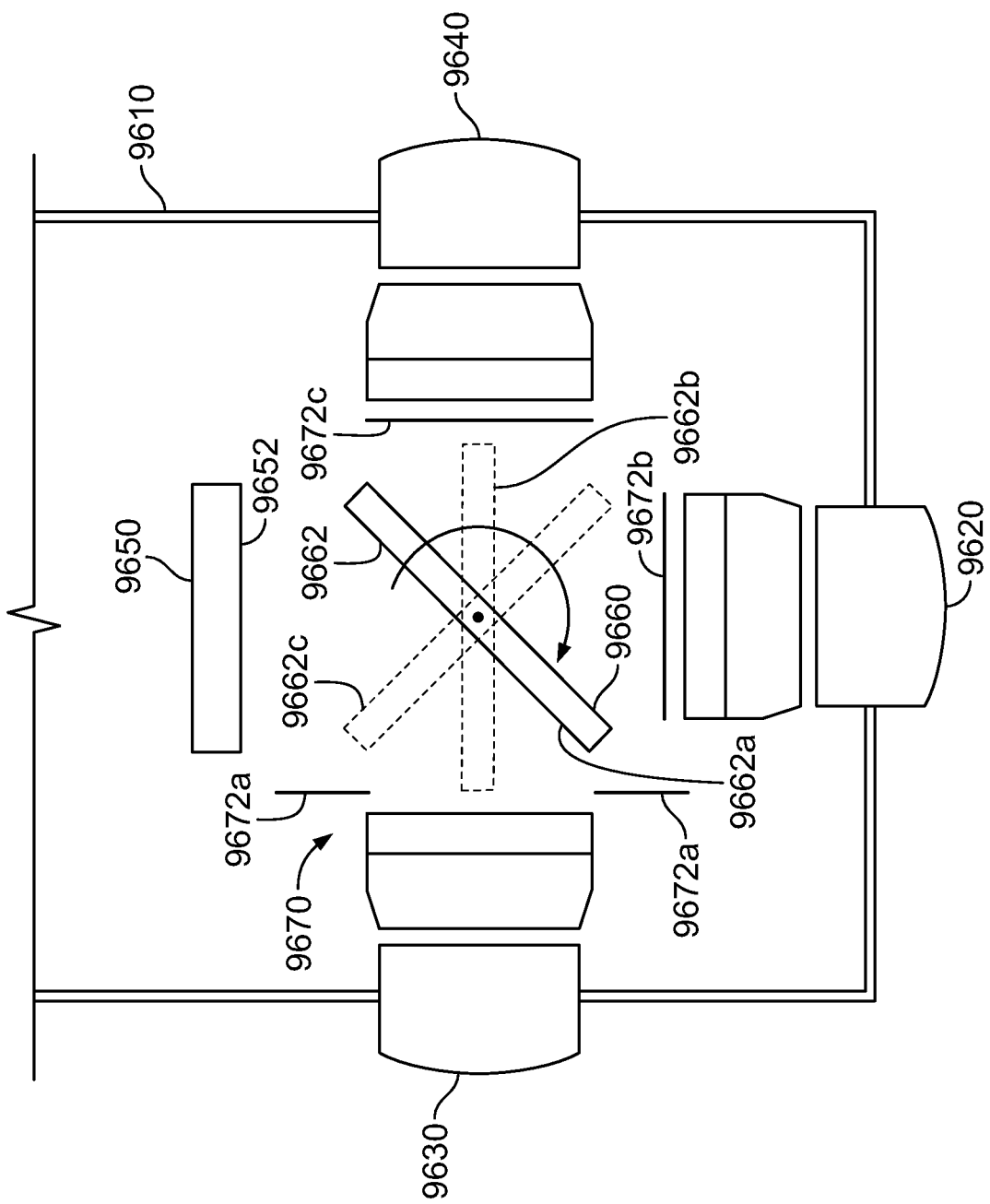
Figure 98:
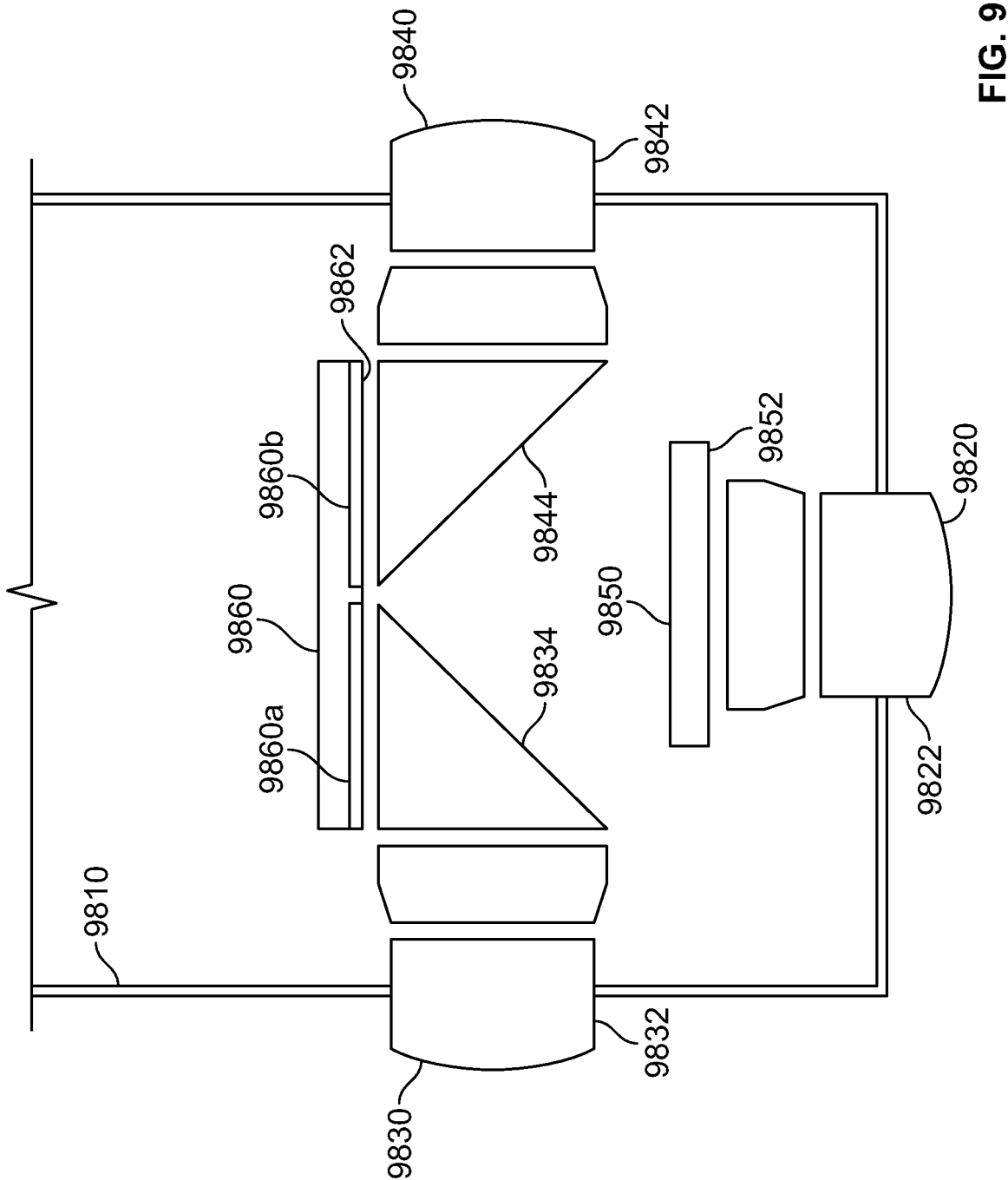
Figure 99:
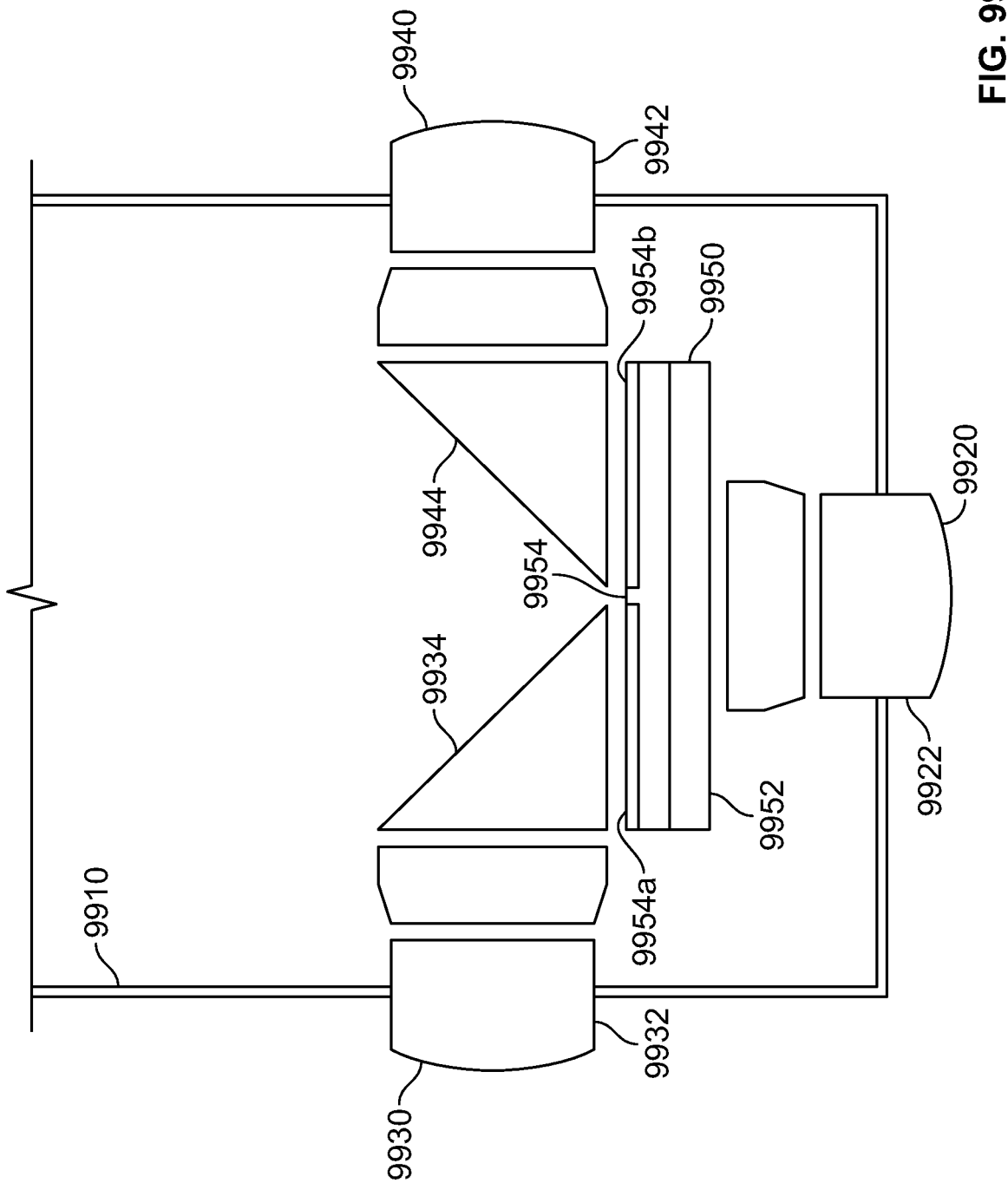
Figure 101:
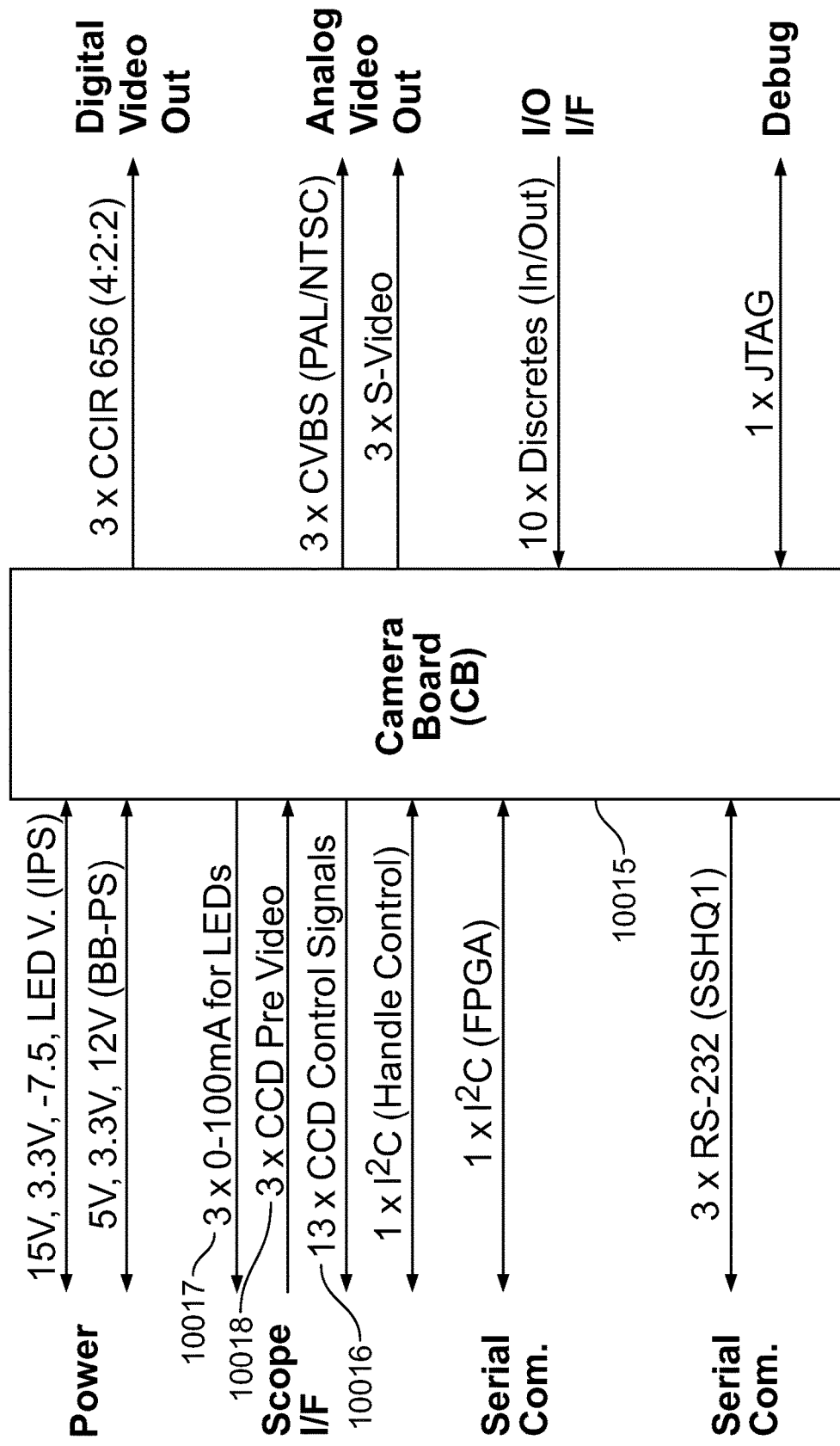
Figure 102A:
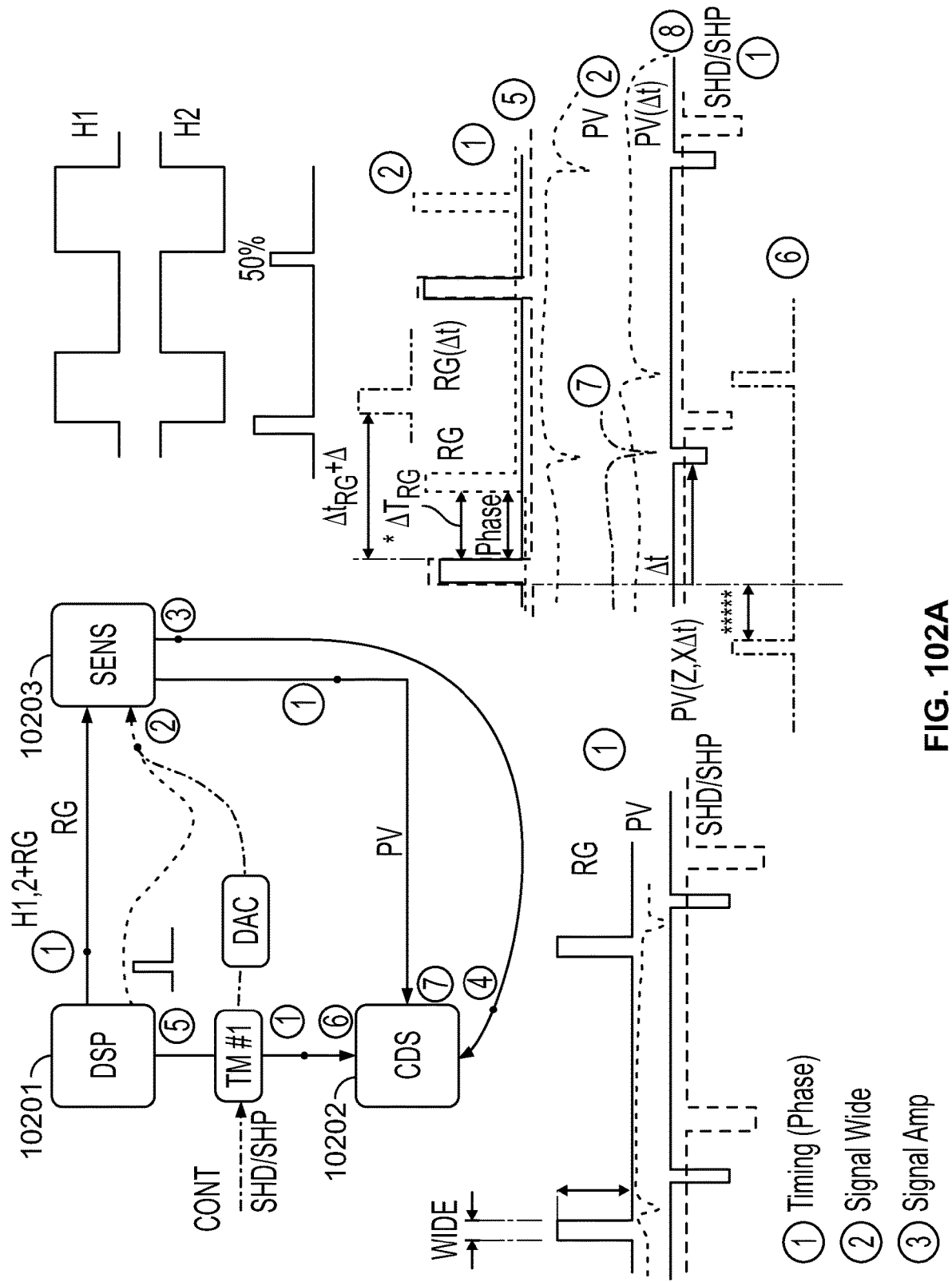
Figure 102B:
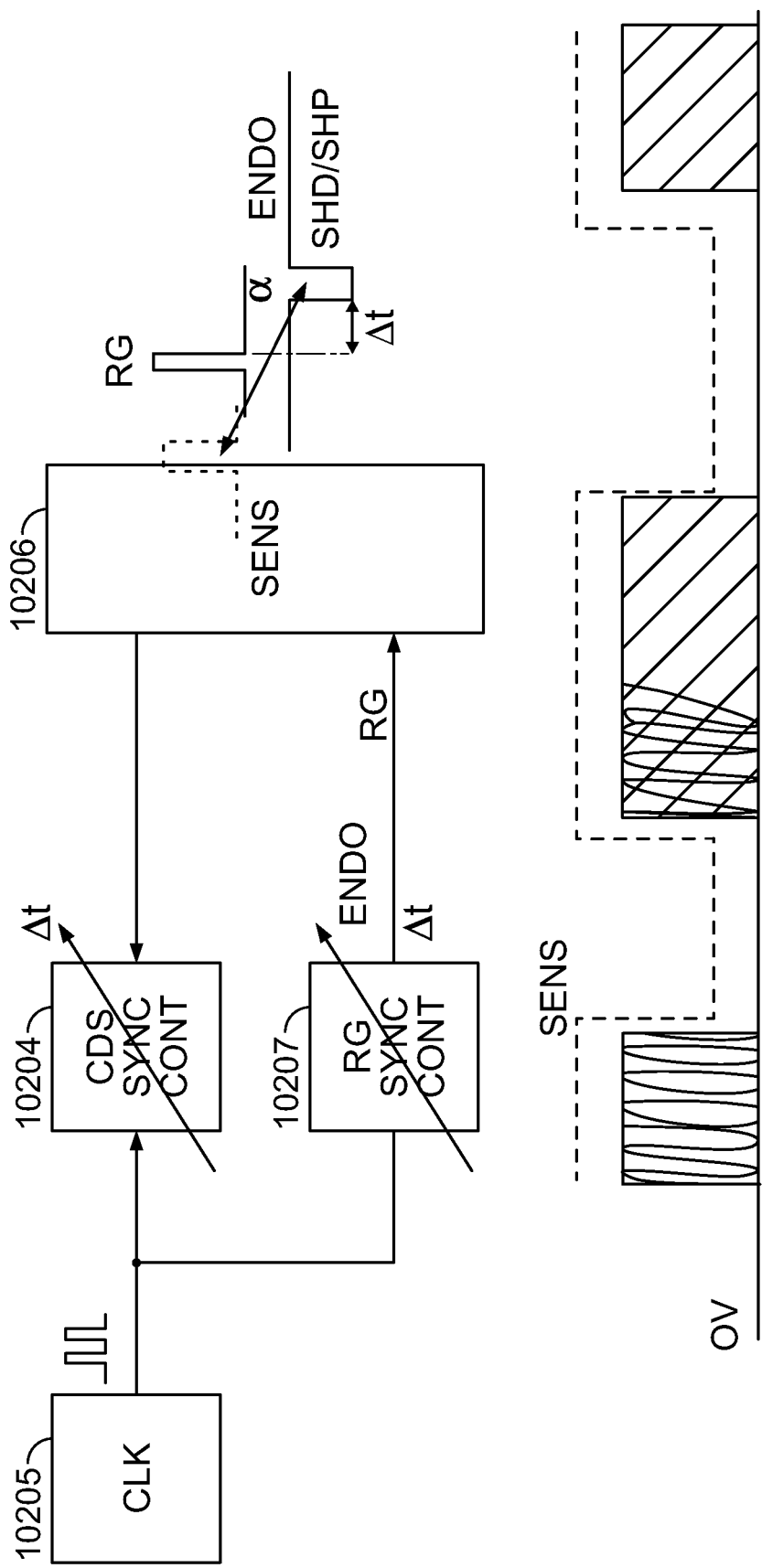
Figure 103A:
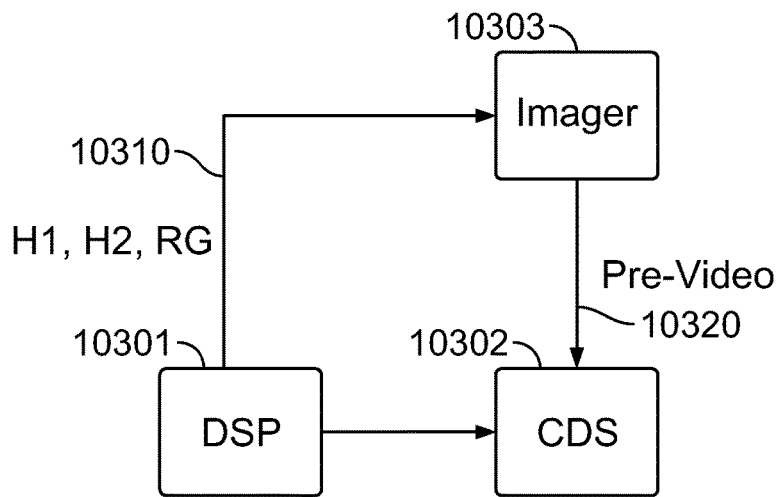
Figure 103B:
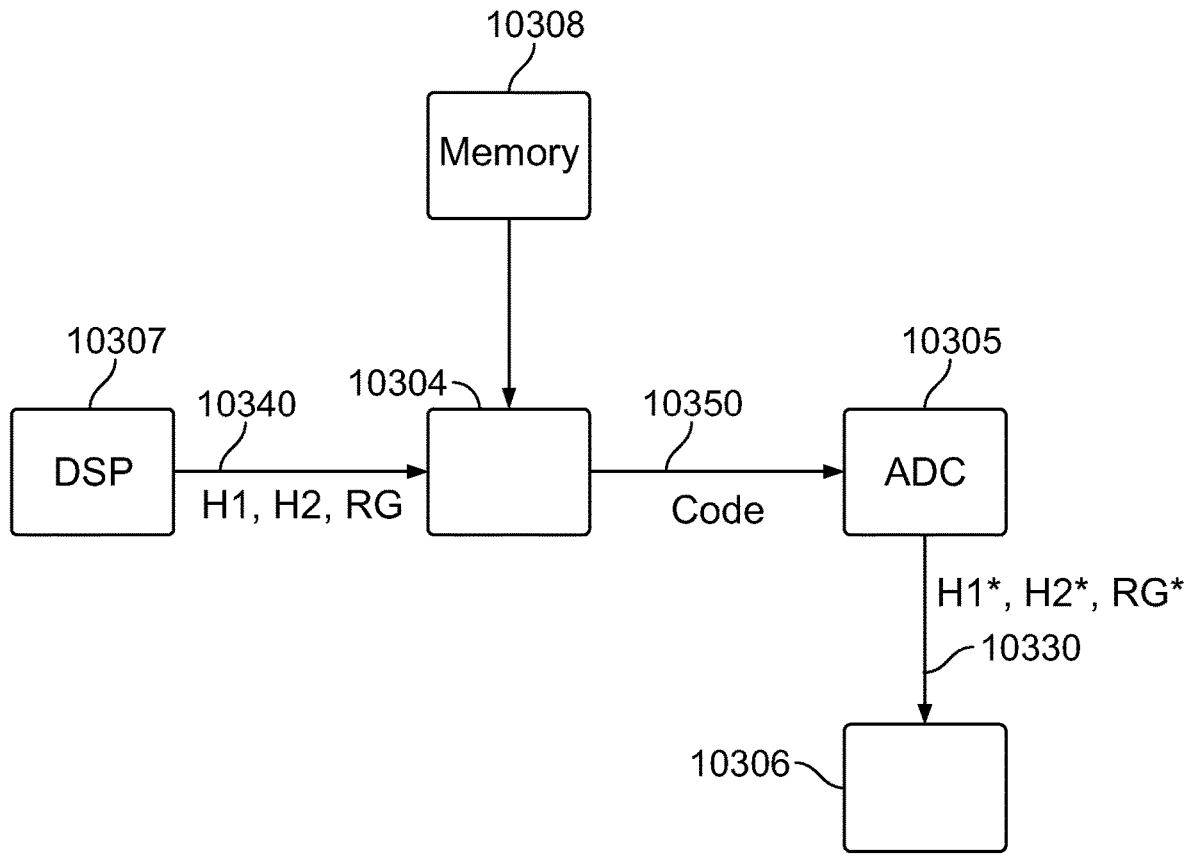
Figure 105A:
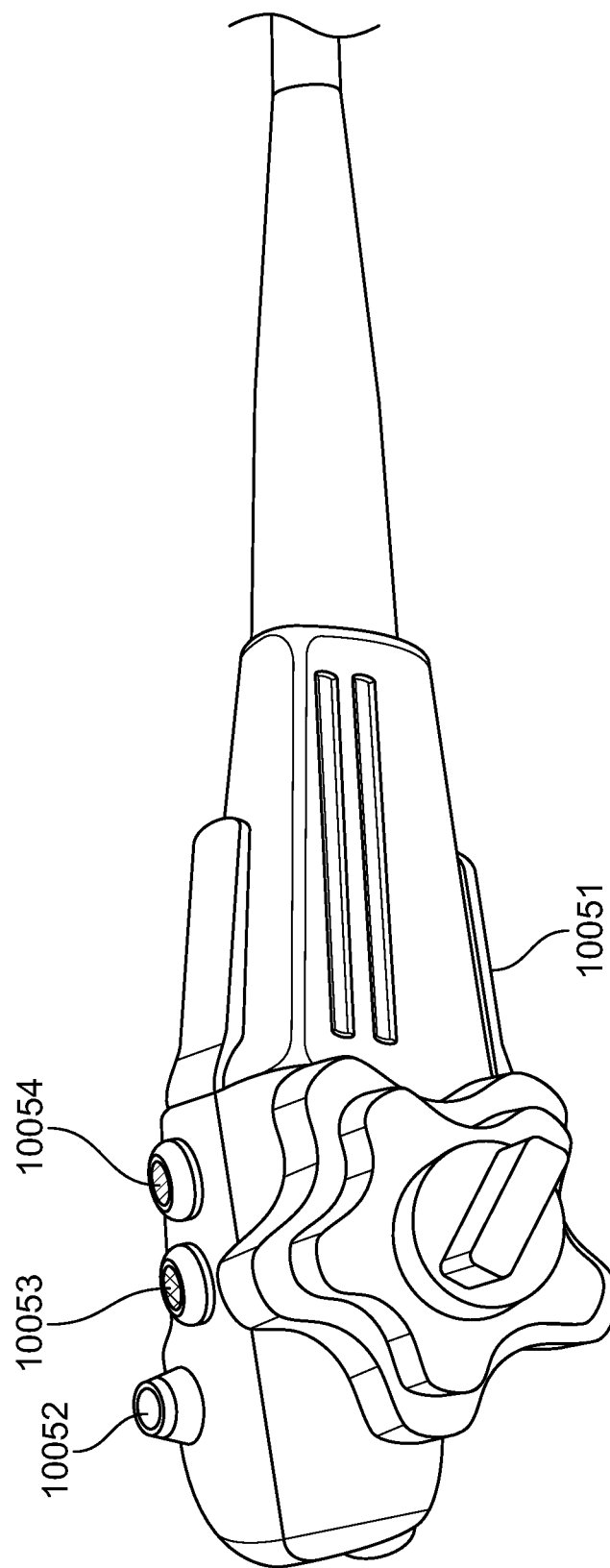
Figure 105B:
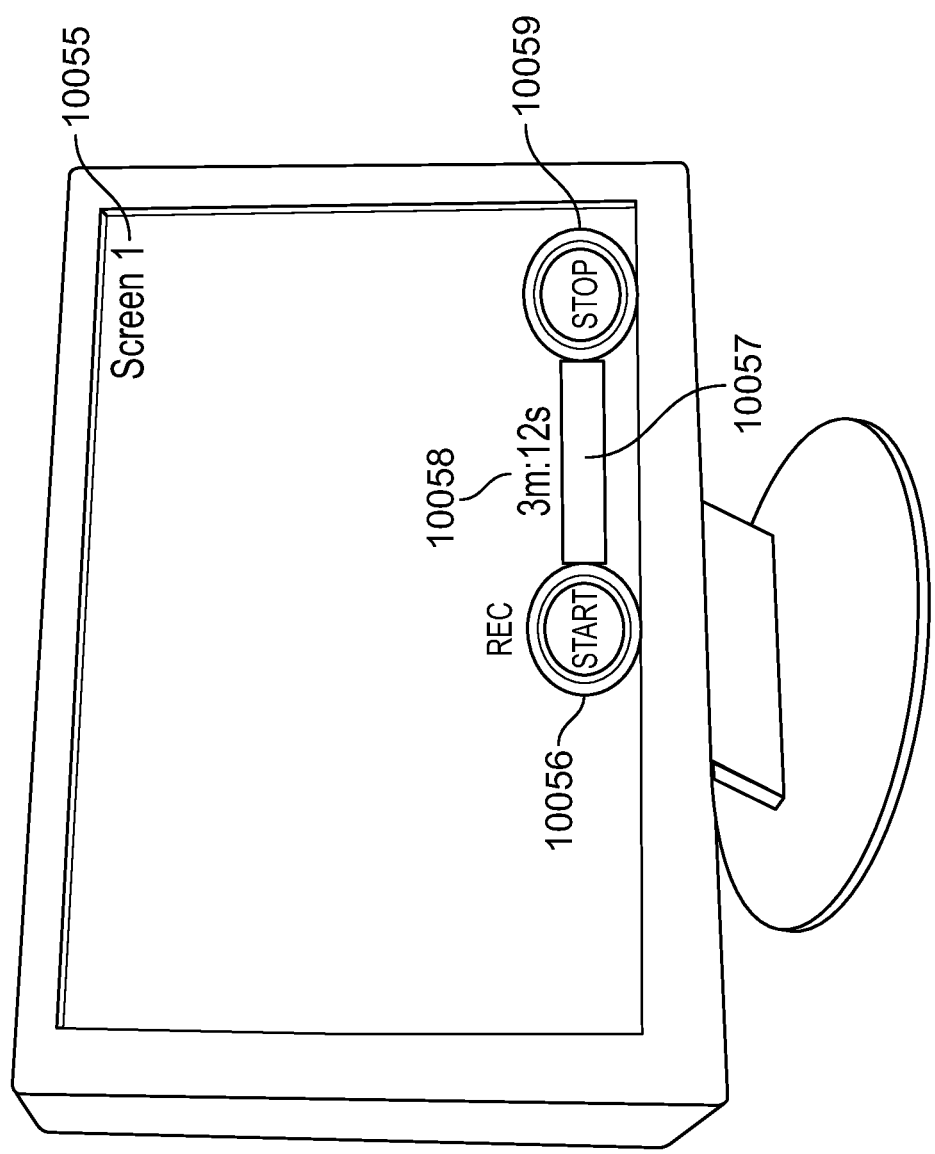
Figure 106A:
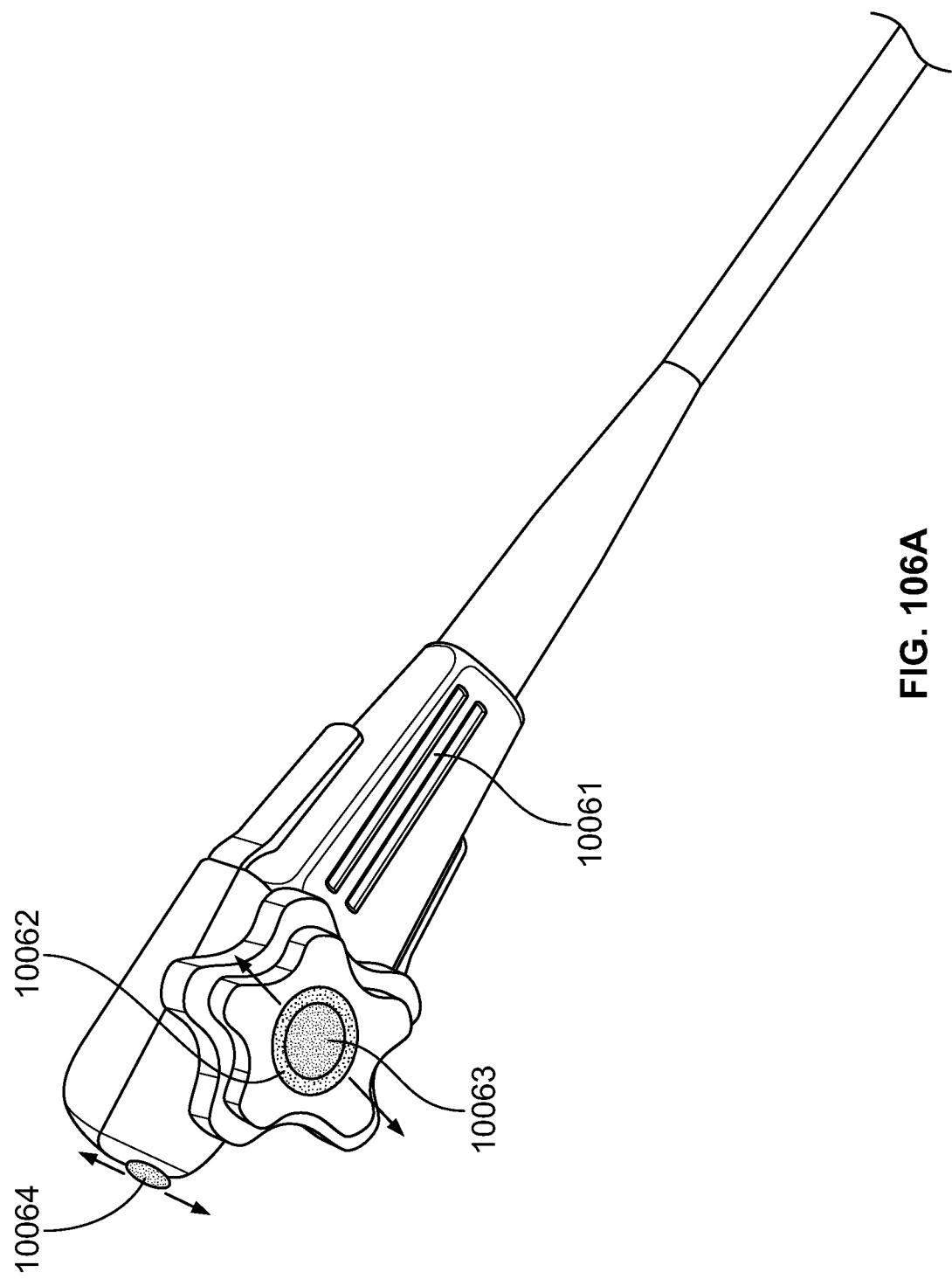
Figure 106B:
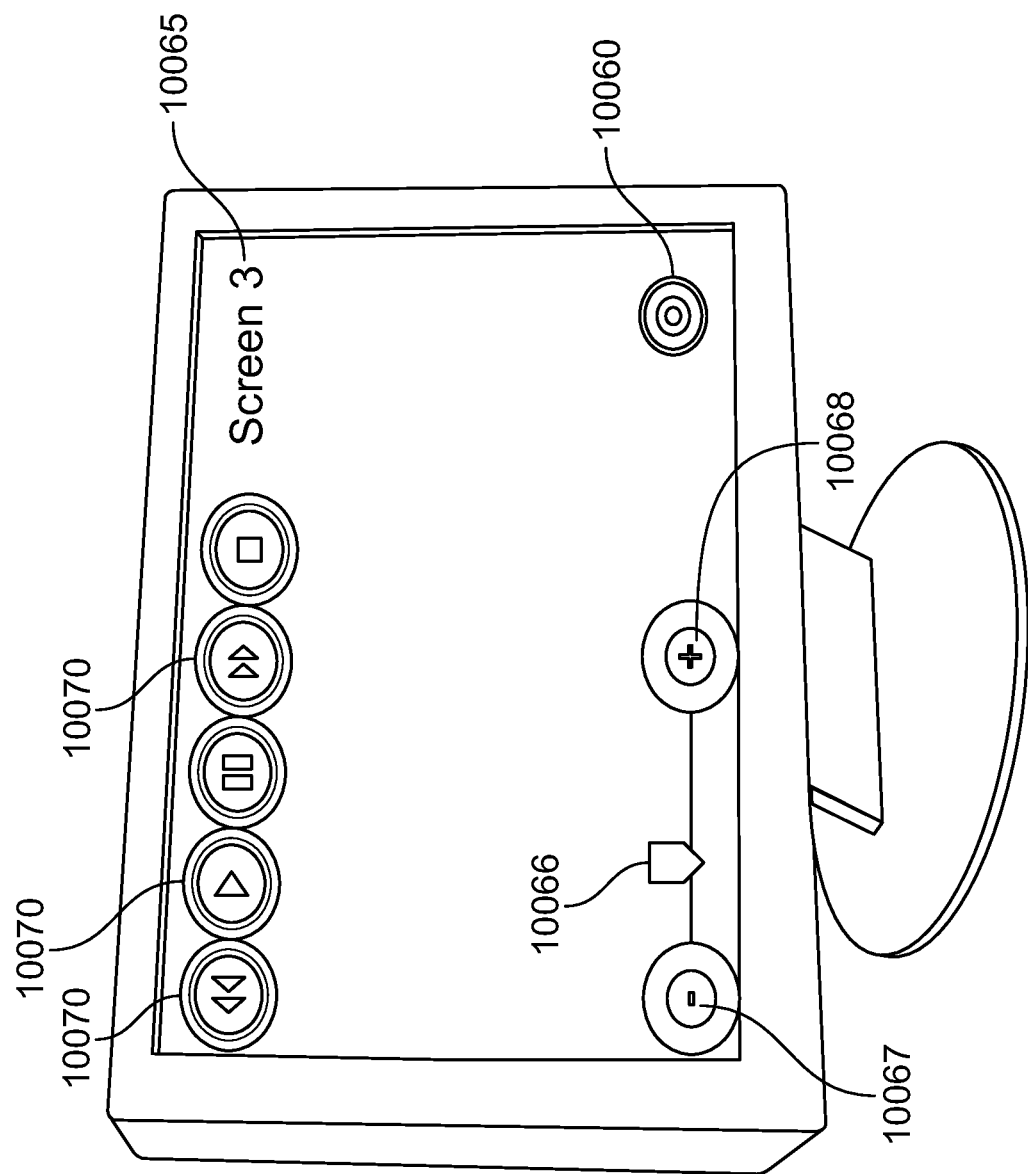
Figure 107:
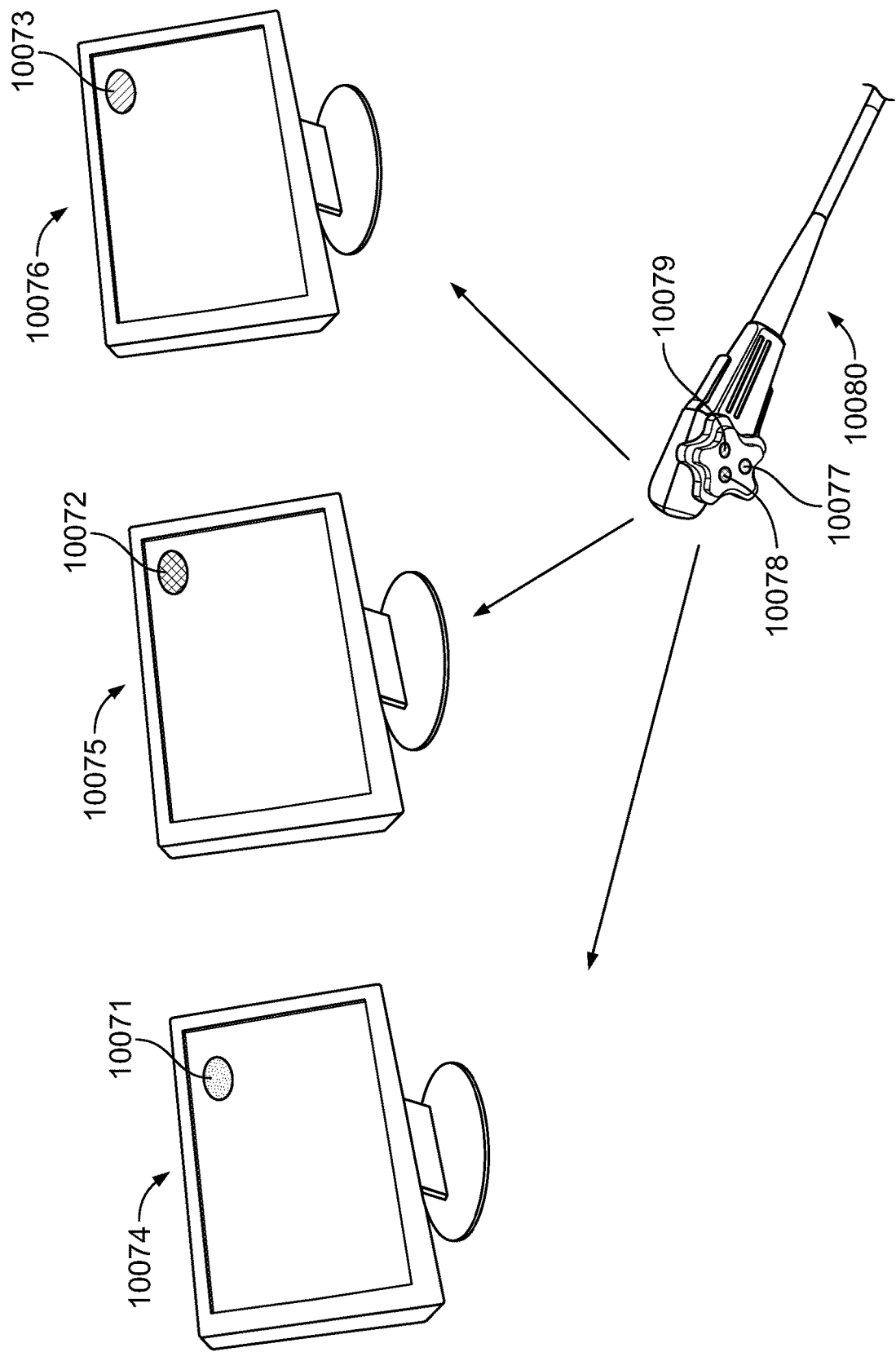
Figure 108:
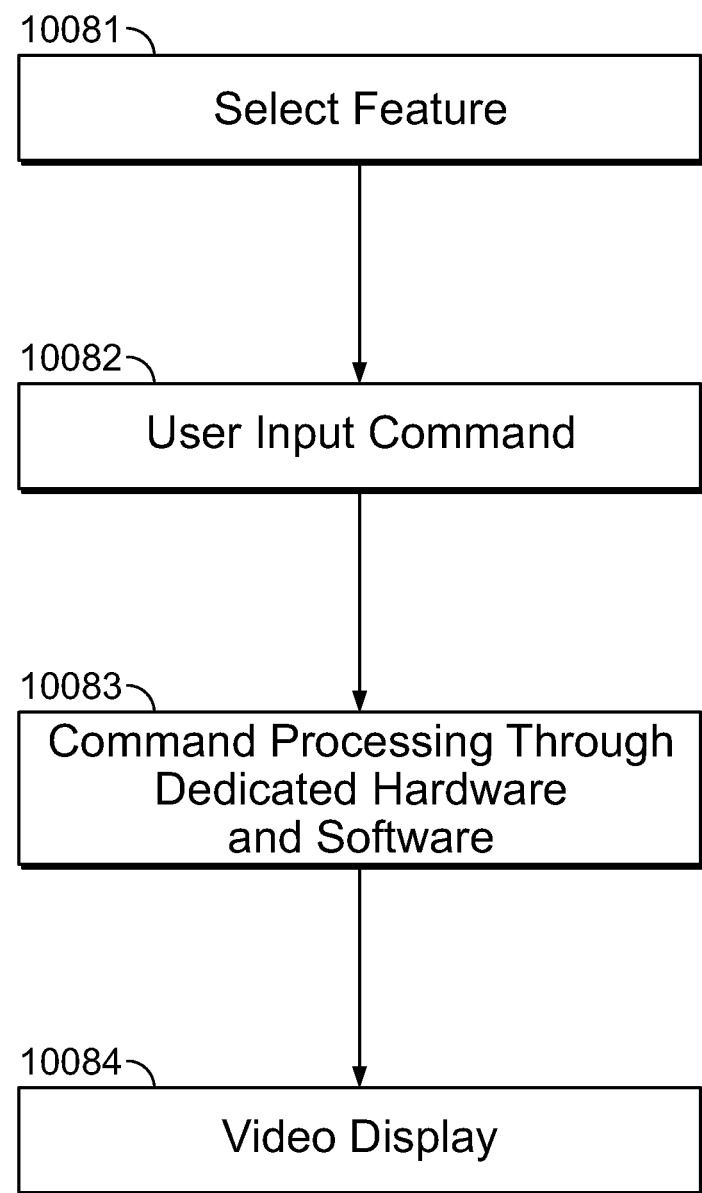
Figure 109:
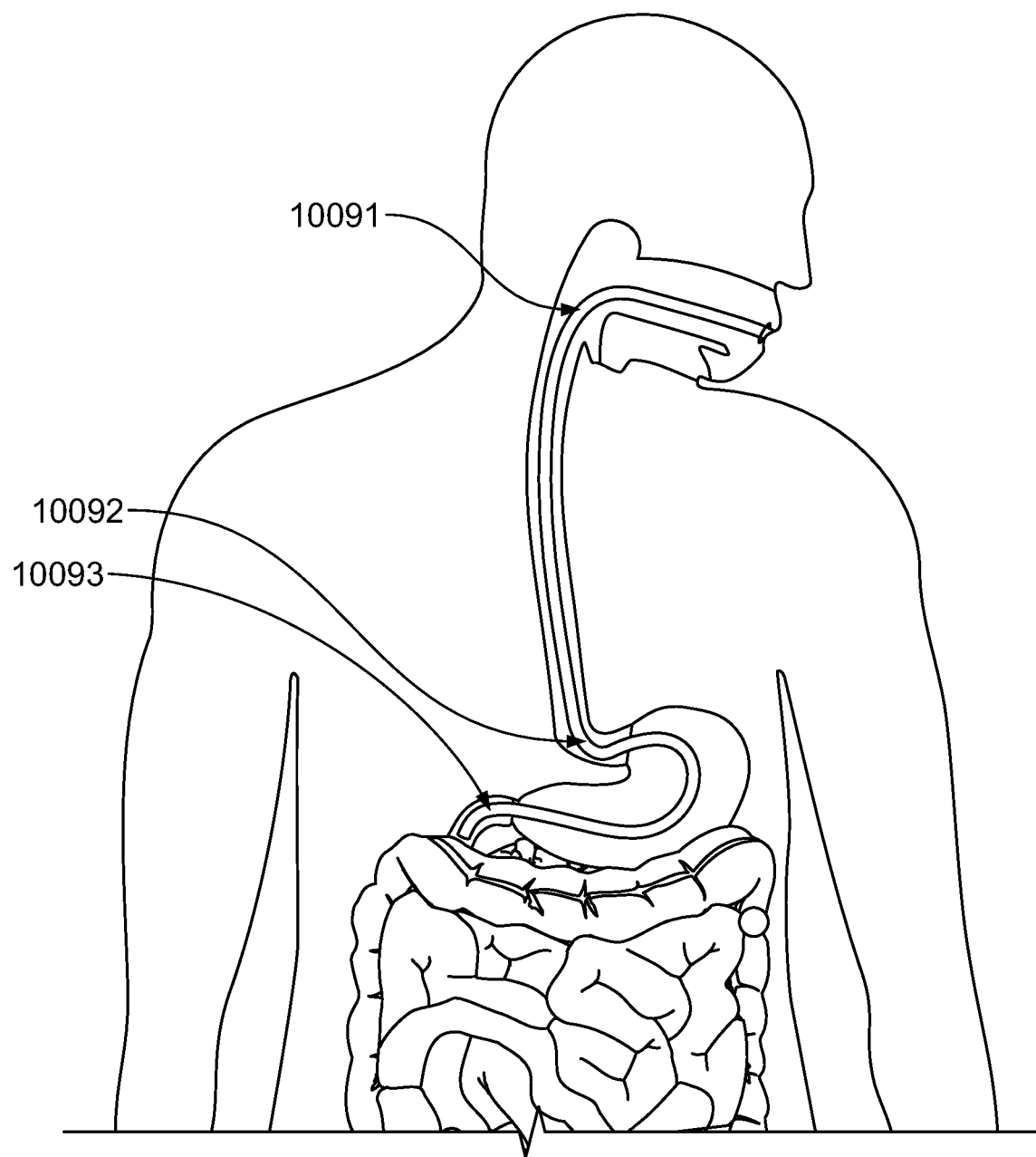
Figure 110A:
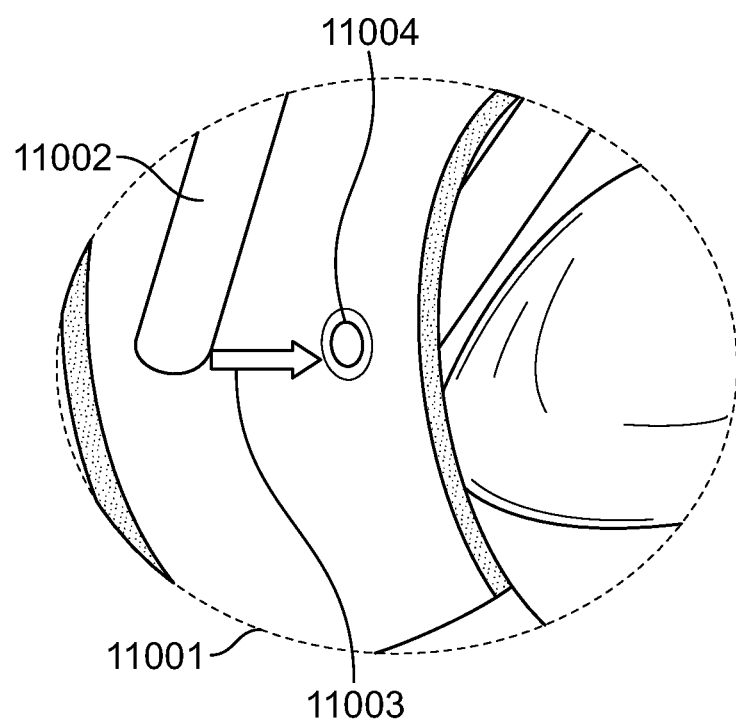
Figure 110B:
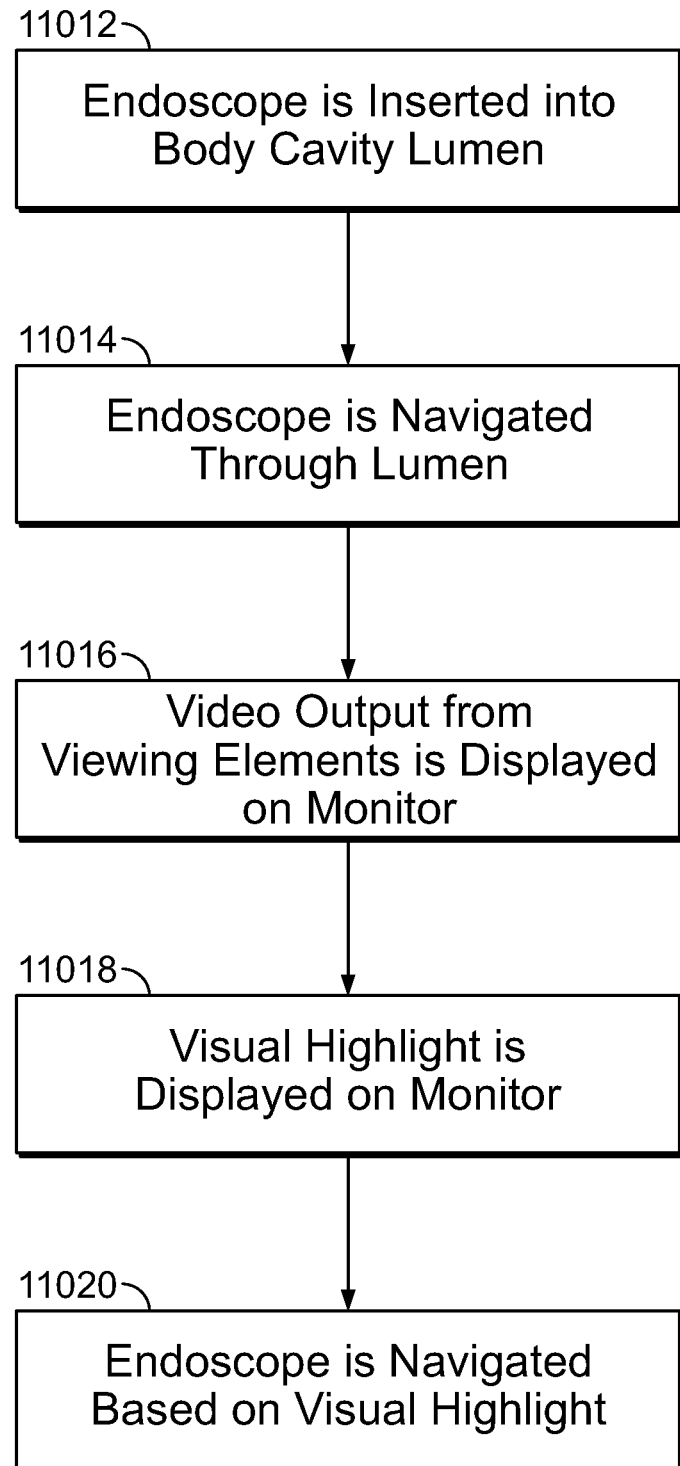
Figures 111A, 111B:
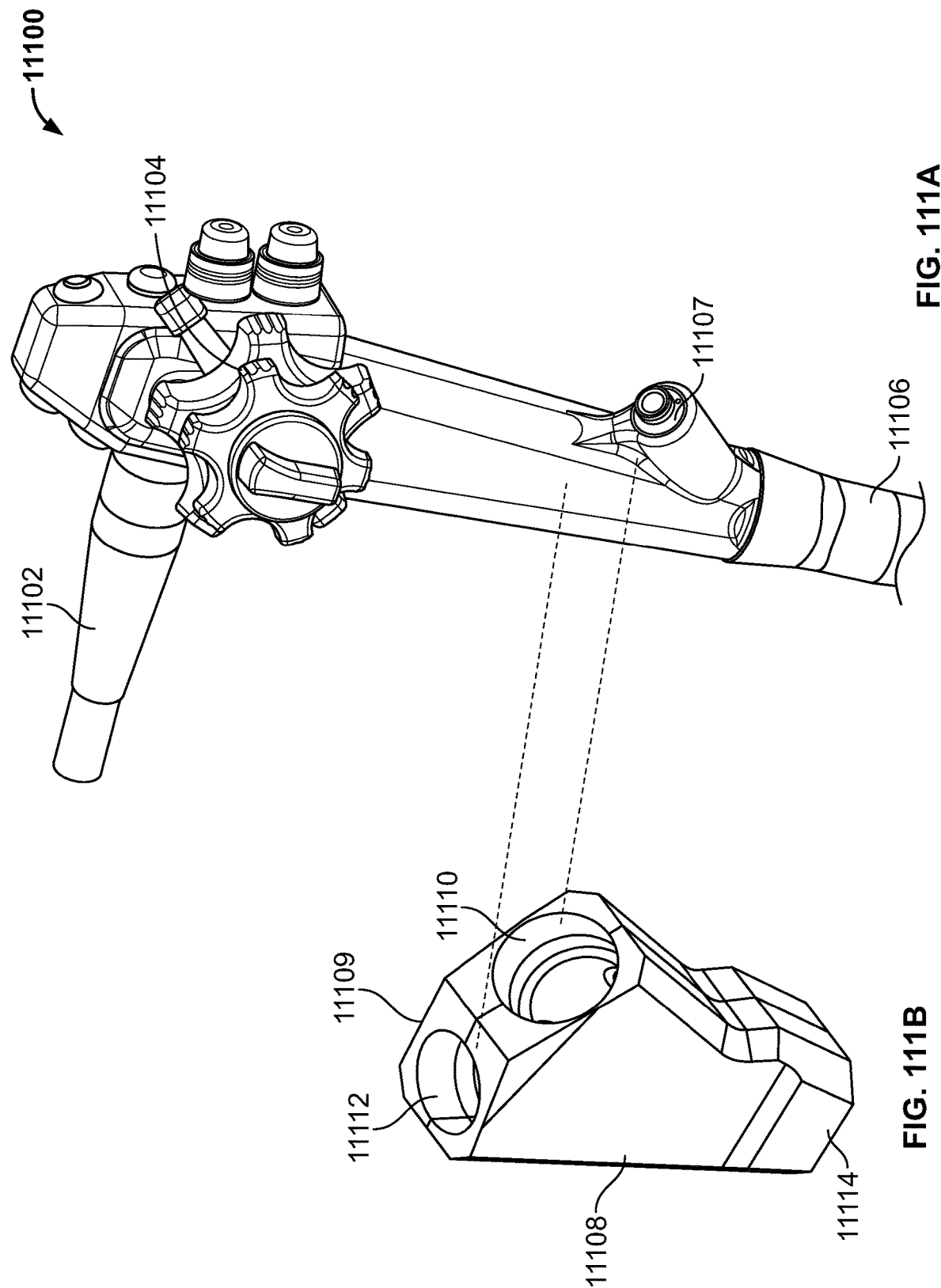
Figure 112:
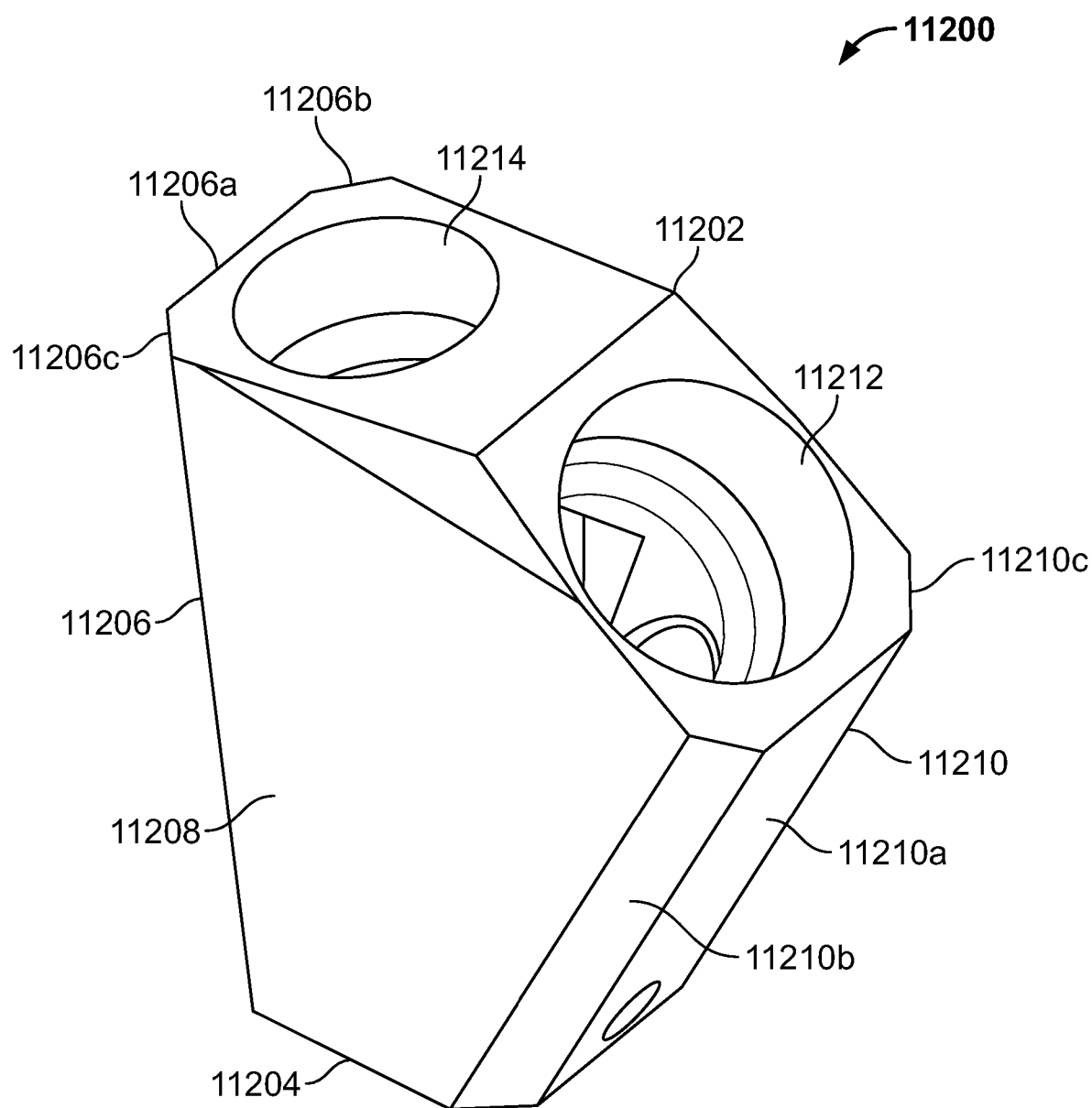
Figure 113A:
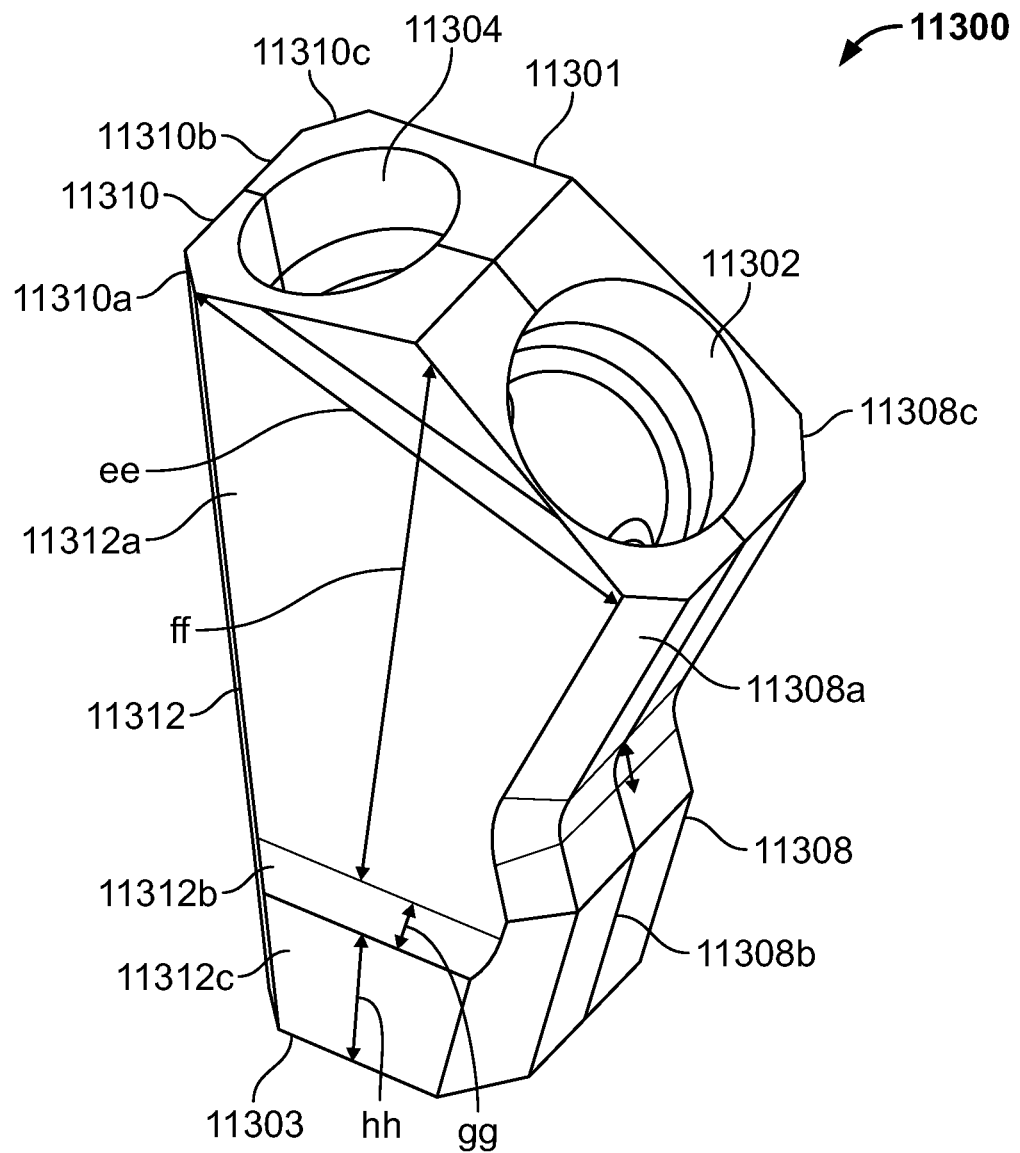
Figure 113C:
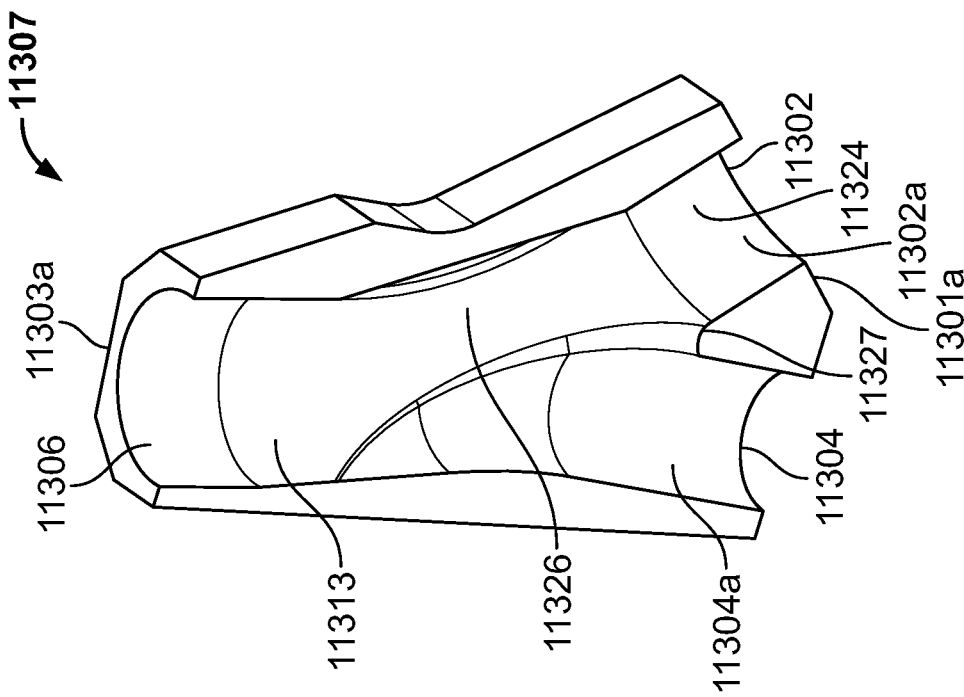
Figure 113B:
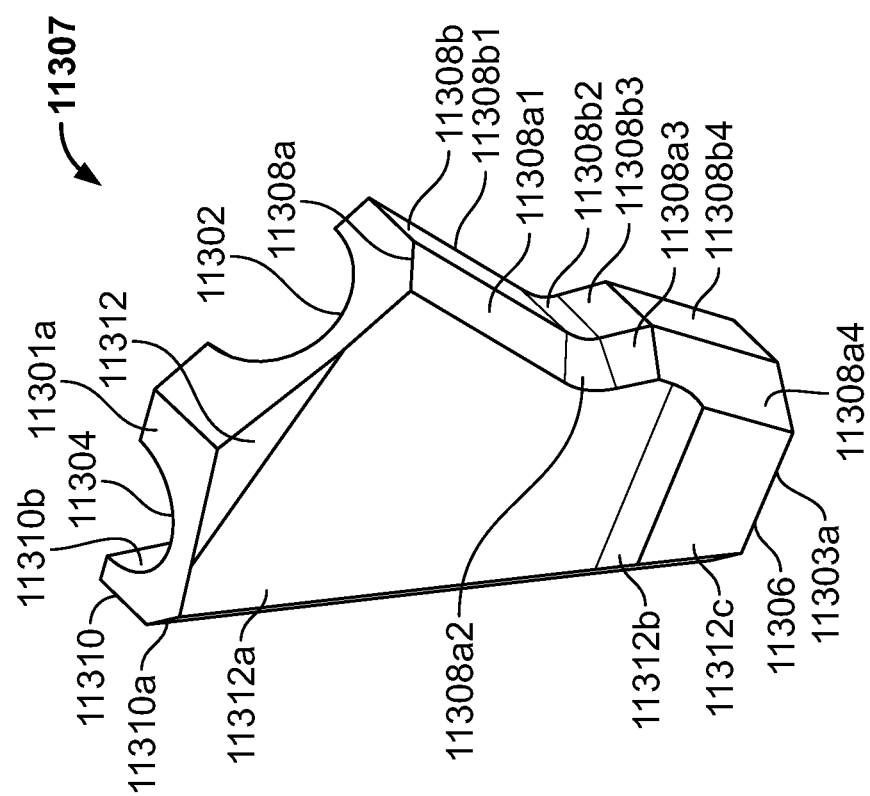
Figures 113F, 113G:
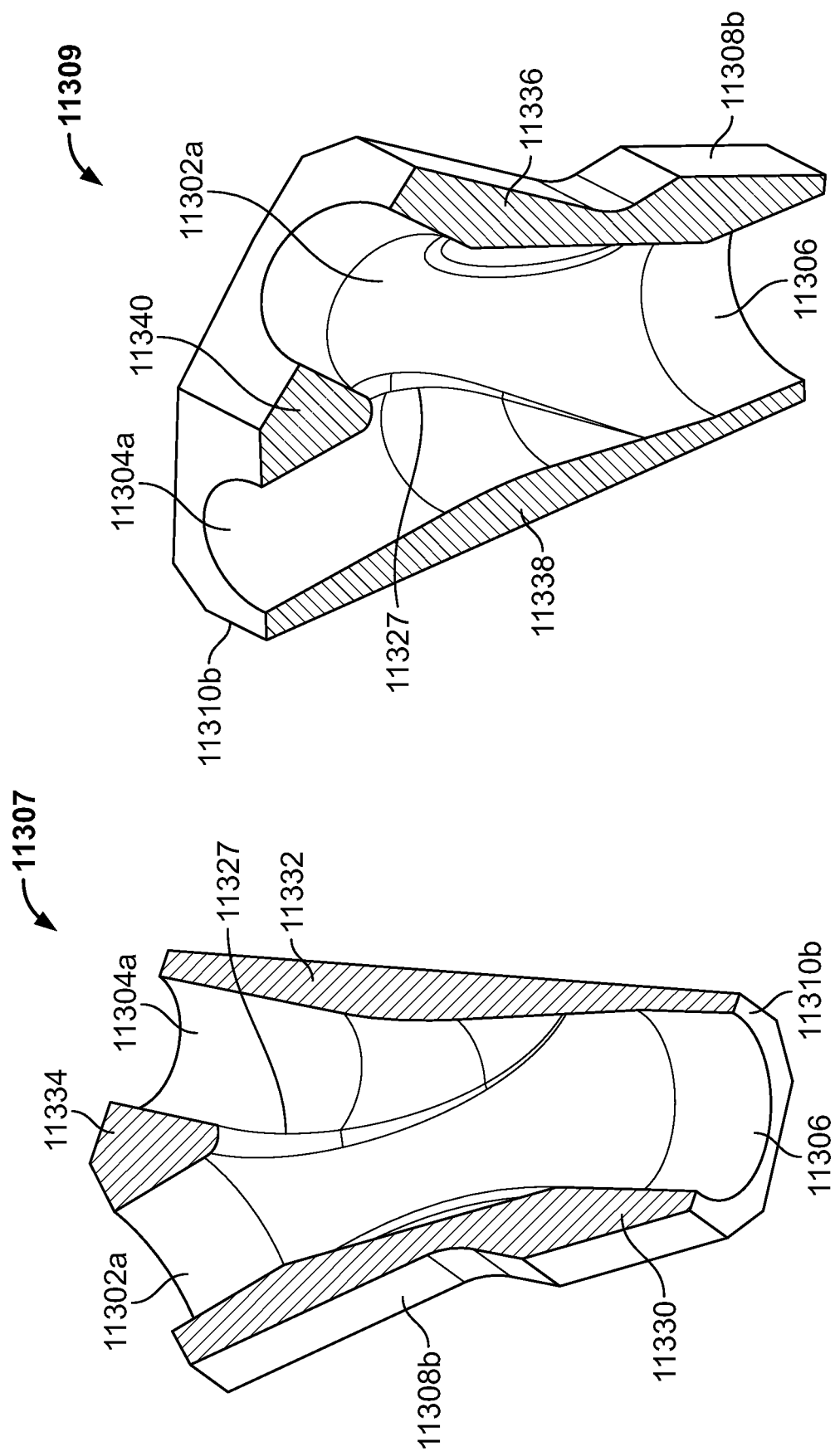

FIG. 53A provides a first perspective view of the connecting mechanism between the imaging modules, according to an embodiment;

FIG. 53B provides a second perspective view of the connecting mechanism between the imaging modules, according to an embodiment;

FIG. 54 illustrates a detailed view of the modular holder, according to one embodiment of the present specification;

FIG. 55A schematically depicts an isometric view of a tip section of an endoscope (including an electronic circuit board carrying cameras and illumination sources, and fluid channeling component), having a multi component tip cover (shown in an exploded view), according to an exemplary embodiment of the current specification;

FIG. 55B schematically depicts an isometric view of the tip section of FIG. 55A, having an assembled multi component tip cover, according to some exemplary embodiment of the current specification;

FIG. 56 schematically depicts an isometric view of a tip section of an endoscope (including an electronic circuit board carrying cameras and illumination sources, and a fluid channeling component), having a multi component tip cover (shown in an exploded view), according to an exemplary embodiment of the current specification;

FIG. 57 schematically depicts an exploded view of a multi component tip cover, according to an exemplary embodiment of the current specification;

FIG. 58A schematically depicts an isometric view of a tip section of an endoscope (including an electronic circuit board carrying cameras and illumination sources, and a fluid channeling component), having a multi component tip cover (shown in an exploded view), according to an exemplary embodiment of the current specification;

FIG. 58B schematically depicts an isometric view of the tip section of FIG. 58A, having a multi component tip cover (partially in an exploded view), according to an exemplary embodiment of the current specification;

FIG. 58C schematically depicts an isometric view of the tip section of FIGS. 58A and 58B having an assembled multi component tip cover, according to an exemplary embodiment of the current specification;

FIG. 59A shows a perspective side view of a tip section of an endoscope assembly according to some embodiments;

FIG. 59B shows a perspective rear view of a tip section of an endoscope assembly according to some embodiments;

FIG. 59C shows a well-defined or deep notch/depression of a side wall of a tip section of an endoscope assembly according to some embodiments;

FIG. 60A shows a first perspective view of a tip section of an endoscope assembly with a medical tool inserted through a side service channel thereof, according to some embodiments;

FIG. 60B shows a second perspective view of a tip section of an endoscope assembly with a medical tool inserted through a side service channel thereof, according to some embodiments;

FIG. 61A shows a perspective view of a tip section of an endoscope assembly comprising two independent side service channel openings in accordance with an embodiment of the present specification;

FIG. 61B shows a first perspective view of the tip section of the endoscope assembly of FIG. 61A with a medical tool inserted through a side service channel thereof, according to an embodiment;

FIG. 61C shows a second perspective view of the tip section of the endoscope assembly of FIG. 61A with a medical tool inserted through a side service channel thereof, according to another embodiment;

FIG. 62 shows an exploded view of the tip section of the endoscope assembly of FIG. 2A;

FIG. 63 illustrates a perspective front view of a tip section of an endoscope assembly comprising two front working/service channels in close proximity, in accordance with an embodiment of the present specification;

FIG. 64 illustrates a tip of an endoscope, comprising front jet and nozzle openings adjacent to each other, in accordance with an embodiment of the present specification;

FIG. 65A shows a perspective view of a tip section of a multi jet endoscope assembly according to an embodiment of the present specification;

FIG. 65B shows a perspective first side view of the tip section of the multi jet endoscope assembly of FIG. 65A;

FIG. 65C shows a perspective second side view of the tip section of the multi jet endoscope assembly of FIG. 65A;

FIG. 65D shows a perspective view of a fluid channeling component of the multi-jet endoscope assembly of FIG. 65A;

FIG. 65E shows the multi jet endoscope assembly of FIG. 65A being moved inside a body cavity;

FIG. 66 shows a side jet sprinkler attachment, in accordance with some embodiments of the specification;

FIG. 67A shows the position of side jet openings relative to side optical assemblies, in accordance with one embodiment;

FIG. 67B shows the position of side jet openings relative to side optical assemblies, in accordance with another embodiment;

FIG. 68A shows a perspective view of the tip cover of an endoscope assembly according to some embodiments;

FIG. 68B shows another perspective view of the tip cover of an endoscope assembly according to some embodiments;

FIG. 69A shows a perspective view of a tip section of an endoscope assembly according to some embodiments, without the tip cover;

FIG. 69B shows another perspective view of the tip section of an endoscope assembly according to some embodiments, without the tip cover;

FIG. 70 shows a side view of the tip section of an endoscope assembly according to some embodiments, without the tip cover;

FIG. 71 shows a cross-section view of the tip section of an endoscope assembly according to some embodiments, with the tip cover;

FIG. 72 shows a multi-jet ring assembly of an endoscope assembly according to an embodiment;

FIG. 73 shows a side view of the multi-jet ring assembly placed on a tip cover of an endoscope assembly, according to another embodiment;

FIG. 74A shows a perspective view of the multi jet ring assembly placed on the tip cover of an endoscope assembly, according to some embodiments;

FIG. 74B shows another perspective view of the multi-jet ring assembly placed on the tip cover of an endoscope assembly, according to some embodiments;

FIG. 75A shows a perspective view of the multi jet ring assembly detached from the tip cover of the endoscope assembly of FIGS. 74A and 74B;

FIG. 75B shows another perspective view of the multi-jet ring assembly detached from the tip cover of the endoscope assembly of FIGS. 74A and 74B;

FIG. 76A is a cross-sectional view of a tip section of an endoscope assembly, with the tip cover and the multi-jet ring assembly, according to some embodiments;

FIG. 76B is another cross-sectional view of a tip section of an endoscope assembly, with the tip cover and the multi-jet ring assembly, according to some embodiments;

FIG. 77A illustrates a multi jet distributer pump, in accordance with an embodiment of the present specification;

FIG. 77B illustrates another view of the multi jet distributer pump of FIG. 77A, in accordance with an embodiment of the present specification;

FIG. 77C illustrates yet another view of the multi jet distributer pump of FIG. 77A, in accordance with an embodiment of the present specification;

FIG. 78A illustrates a distributer disc of a multi jet distributer, in accordance with an embodiment of the present specification;

FIG. 78B illustrates another view of the distributer disc of a multi jet distributer, in accordance with an embodiment of the present specification;

FIG. 79A is a block diagram illustrating the connection between a multi jet distributor and an endoscope, in accordance with an embodiment of the present specification;

FIG. 79B is a block diagram illustrating another connection between a multi jet distributor and an endoscope, in accordance with an embodiment of the present specification;

FIG. 80A illustrates a sectional view of a distributor disc of a multi jet distributor, in accordance with an embodiment of the present specification;

FIG. 80B illustrates another sectional view of a distributor disc of a multi jet distributor, in accordance with an embodiment of the present specification;

FIG. 81A shows a perspective view of a main connector employing a multi jet controller in accordance with an embodiment of the present specification;

FIG. 81B shows a first position of a multi jet controller shaft corresponding to a first control option of the multi jet controller, according to one embodiment of the present specification;

FIG. 81C shows a second position of the multi jet controller shaft corresponding to the second control option of the multi jet controller, according to one embodiment of the present specification;

FIG. 82 shows a perspective view of a multi-camera endoscope according to one embodiment of the present specification;

FIG. 83 shows a perspective view of a full cross section removable tip section removed from the permanent section, in accordance with some exemplary embodiments of the specification;

FIG. 84 shows a perspective view of a full cross section removable tip section attached to the permanent section, in accordance with some exemplary embodiments of the specification;

FIG. 85 shows a perspective view of a partial cross section removable tip section removed from the permanent section, in accordance with some exemplary embodiments of the specification;

FIG. 86 shows a perspective view of a partial cross section removable tip section attached to the permanent section, in accordance with some exemplary embodiments of the specification;

FIG. 87A schematically depicts an endoscope system and an interface unit associated with the endoscope system according to an aspect of some embodiments;

FIG. 87B schematically depicts an embodiment of a tip of the endoscope of FIG. 87A;

FIG. 88 schematically depicts a functional block diagram of the interface unit of FIG. 87A;

FIG. 89 schematically depicts an exemplary layout of an endoscope system and an interface unit deployed in an operating room, according to one embodiment of the present specification;

FIG. 90 is a block diagram illustrating an exemplary video processing architecture, according to one embodiment of the present specification;

FIG. 91A is a first linear configuration of monitors for displaying a plurality of contiguous videos in accordance with an embodiment of the present specification;

FIG. 91B is a second linear configuration of monitors for displaying a plurality of contiguous videos in accordance with an embodiment of the present specification;

FIG. 91C is a third linear configuration of monitors for displaying a plurality of contiguous videos in accordance with an embodiment of the present specification;

FIG. 91D is a fourth linear configuration of monitors for displaying a plurality of contiguous videos in accordance with an embodiment of the present specification;

FIG. 91E is a fifth linear configuration of monitors for displaying a plurality of contiguous videos in accordance with an embodiment of the present specification;

FIG. 92A is a first embodiment of a non-linear configuration of monitors for displaying a plurality of contiguous videos;

FIG. 92B is a second embodiment of a non-linear configuration of monitors for displaying a plurality of contiguous videos;

FIG. 93A shows a first contiguous video feed group displayed on a single monitor in accordance with an embodiment of the present specification;

FIG. 93B shows a second contiguous video feed group displayed on a single monitor in accordance with an embodiment of the present specification;

FIG. 94 shows a panoramic view of video feeds generated by viewing elements of an endoscopic tip and displayed on three square monitors, according to one embodiment of the present specification;

FIG. 95A schematically depicts an embodiment of a tip of an endoscope configured to provide multiple views and having a single image capturing device;

FIG. 95B schematically depicts an embodiment of an image split to three fields as obtained from the image capturing device of FIG. 95A;

FIG. 96 schematically depicts an embodiment of a tip of an endoscope configured to provide multiple views and having a single image capturing device and a rotatable optical element;

FIG. 97A schematically depicts one embodiment of a tip of an endoscope configured to provide multiple views and having a single image capturing device having several light sensitive elements;

FIG. 97B schematically depicts another embodiment of a tip of an endoscope configured to provide multiple views and having a single image capturing device having several light sensitive elements;

FIG. 98 schematically depicts an embodiment of a tip of an endoscope configured to provide three views and having two image capturing devices;

FIG. 99 schematically depicts an embodiment of a tip of an endoscope configured to provide three views and having a single double-sided image capturing device;

FIG. 100 is a table detailing an exemplary set of shared and unshared signals for each camera, according to one embodiment of the present specification;

FIG. 101 illustrates a camera circuit board with a plurality of inputs and outputs, according to one embodiment of the present specification;

FIG. 102A is a block diagram illustrating synchronization of video signals, according to one embodiment;

FIG. 102B is another block diagram illustrating synchronization of video signals, according to one embodiment of the present specification;

FIG. 103A is a block diagram illustrating compensation of time lag for synchronization signals and pre-video signals in accordance with one embodiment of the present specification;

FIG. 103B is a block diagram illustrating compensation of time lag for synchronization signals and pre-video signals in accordance with another embodiment of the present specification;

FIG. 104 illustrates one embodiment with multiple displays operated with a single endoscope;

FIG. 105A shows one exemplary configuration of the endoscope handle, according to one embodiment of the present specification;

FIG. 105B illustrates an indication of video recording on display, according to one embodiment;

FIG. 106A shows another exemplary configuration of the endoscope handle, according to another embodiment of the present specification;

FIG. 106B illustrates indications of various image management features, according to one embodiment;

FIG. 107 illustrates another embodiment of multiple displays being operated with a single endoscope;

FIG. 108 is a flow chart detailing the process of implementing an image manipulation feature, according to one embodiment of the present specification;

FIG. 109 illustrates exemplary critical navigation junctures during an endoscopic procedure;

FIG. 110A illustrates highlighting the areas of interest in the display image, according to one embodiment of the present specification;

FIG. 110B is a flowchart illustrating the steps involved in a method of visualizing a navigation pathway of an endoscope comprising a tip section having a front-pointing viewing element and two side-pointing viewing elements by using a highlighting feature;

FIG. 111A illustrates an endoscope handle comprising a service channel port, in accordance with an embodiment of the present specification;

FIG. 111B illustrates an exploded view of a service channel connector shown in FIG. 111A, in accordance with an embodiment of the present specification;

FIG. 112 is an illustration of a conventional service channel connector;

FIG. 113A illustrates a service channel connector, having an approximate Y-shape, in accordance with an embodiment of the present specification;

FIG. 113B is an external, cross-sectional view of a first section of a service channel connector having an approximate Y-shape, in accordance with an embodiment of the present specification;

FIG. 113C is an internal, cross-sectional view of a first section of a service channel having an approximate Y-shape, in accordance with an embodiment of the present specification;

FIG. 113D is an external, cross-sectional view of a second section of a service channel connector having an approximate Y-shape, in accordance with an embodiment of the present specification;

FIG. 113E is an internal, cross-sectional view of a second section of a service channel connector having an approximate Y-shape, in accordance with an embodiment of the present specification;

FIG. 113F illustrates another internal, cross-sectional view of a first section of a service channel connector showing edges that are welded, in accordance with an embodiment of the present specification; and FIG. 113G illustrates another internal, cross-sectional view of a second section of a service channel connector showing edges that are welded, in accordance with an embodiment of the present specification.

DETAILED DESCRIPTION

An aspect of some embodiments relates to an endoscope having a tip section equipped with two or more viewing elements. According to one embodiment, one of the viewing elements is positioned at a distal end of the tip section and points forward, and the remaining viewing elements(s) is positioned further back in the tip section, and points sideways.

According to another embodiment, one of the viewing elements is positioned at a distal (front) end surface of the tip section and points forward, and the remaining viewing elements(s) is positioned further back in the tip section, and points sideways.

According to another embodiment, two or more viewing elements (for example, three, four or more) are positioned in proximity to or at the distal end of the tip section and point sideways such that the field of view provided by the viewing elements covers a front and side views. Even though in such configuration, according to some embodiments, no viewing element is positioned at the distal (front) end surface of the tip section (or in other words, no viewing element is pointing directly forward), still the field of view of the side cameras allows view of the front direction of the tip and accordingly of the endoscope.

This configuration, advantageously, may allow for a higher rate of detection, compared to conventional configurations, of pathological objects that exist in the body cavity in which the endoscope operates.

Another aspect of some embodiments relates to an endoscope having a tip section equipped with one or more front working/service channels. According to still further aspects of some embodiments, an endoscope tip section comprises one or more side working/service channels. Endoscopic tip configurations having more than one front and/or side working/service channels may significantly improve the performance of the endoscope and allow the endoscope operator to perform more complex medical procedures using multiple medical tools simultaneously. Such configurations may also provide the endoscope operator better access to the object of interest and greater flexibility with operating the medical tools, while at the same time viewing the procedure by a plurality of front and side pointing viewing elements.

Still further aspects of some embodiments relate to an endoscope having a tip section equipped with a plurality of advantageous configurations of an electronic circuit board assembly. These configurations consume less space and leave more volume for additional necessary features.

Yet another aspect of some embodiments relates to an endoscope having a tip section comprising a plurality of side jets, in addition to a front jet, to enable improved flushing performance of the endoscope.

The viewing elements and optionally other elements that exist in the tip section (such as a plurality of illuminators or light sources, one or more front and/or side working/service channels, one or more front and side jet channels, a side fluid injector, an electronic circuit board assembly and/or the like) are uniquely scaled, configured and packaged so that they fit within the minimalistic space available inside the tip section, while still providing valuable results.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

Embodiments of methods and/or devices of the specification may involve performing or completing selected tasks manually, automatically, or a combination thereof. Some embodiments of the specification are implemented with the use of components that comprise hardware, software, firmware or combinations thereof. In some embodiments, some components are general-purpose components such as general purpose computers or oscilloscopes. In some embodiments, some components are dedicated or custom components such as circuits, integrated circuits or software.

For example, in some embodiments, some of an embodiment is implemented as a plurality of software instructions executed by a data processor, for example, which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more input devices (e.g., allowing input of commands and/or parameters) and output devices (e.g., allowing reporting parameters of operation and results).

It is appreciated that certain features of the specification, which are, for clarity, described in the context of separate embodiments, may also be provided in combination in a single embodiment. Conversely, various features of the specification, which are, for brevity, described in the context of a single embodiment, may also be provided separately or in any suitable subcombination or as suitable in any other described embodiment of the specification. Certain features described in the context of various embodiments are not to be considered essential features of those embodiments, unless the embodiment is inoperative without those elements.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

It should also be noted that a plurality of terms, as follows, appearing in this specification are used interchangeably to apply or refer to similar components:

Utility tube/cable is also umbilical tube/cable
Main control unit is also controller unit, main controller or fuse box.
Viewing element is also image capturing device, viewing components, camera, TV camera or video camera.
Working channel is also service channel.
Illuminator is also LED, illumination source.
Flexible shaft is also bending section or vertebra mechanism.

Endoscopes that are currently being used typically have a front and side viewing elements for viewing the internal organs, illuminators, a fluid injector for cleaning the lens of the viewing elements, and sometimes also illuminators and a working channel for insertion of surgical tools. The illuminators commonly used are fiber optics that transmit light, generated remotely, to the endoscope tip section. The use of light-emitting diodes (LEDs) for illumination is also known.

A tip section of the endoscope assembly may be inserted into a patient's body through a natural body orifice, such as the mouth, nose, urethra, vagina, or anus.

In accordance with an embodiment of the present specification, a tip cover may house the tip section. The tip section, with the tip cover, may be turned or maneuvered by way of a flexible shaft, which may also be referred to as a bending section, for example, a vertebra mechanism. Tip cover may be configured to fit over the inner parts of the tip section, including an electronic circuit board assembly and a fluid channeling component, and to provide protection to the internal components in the inner parts, such as a body cavity. The endoscope can then perform diagnostic or surgical procedures inside the body cavity. The tip section carries one or more viewing elements, such as cameras, to view areas inside body cavities that are the target of these procedures.

Tip cover may include panels having optical assemblies of viewing elements. The panels and viewing elements may be located at the front and sides of the tip section. Optical assemblies may include a plurality of lenses, static or movable, providing different fields of view.

An electronic circuit board assembly may be configured to carry the viewing elements, which may view through openings on the panels. Viewing elements may include an image sensor, such as but not limited to a Charge Coupled Device (CCD) or a Complementary Metal Oxide Semiconductor (CMOS) image sensor.

The electronic circuit board assembly may be configured to carry illuminators that are able to provide illumination through illuminator optical windows. The illuminators may be associated with viewing elements, and may be positioned to illuminate the viewing elements' fields of view.

One or more illuminators may illuminate the viewing fields of the viewing elements. In an embodiment, the illuminators may be fiber optic illuminators that carry light from remote sources. The optical fibers are light carriers that carry light from a remotely located light source to the illuminators. The optical fibers extend along an insertion tube between the tip section at a distal end of the endoscope, and a handle at a proximal end. An umbilical/utility tube connects the handle to a main control unit. The main control unit enables control of several functions of the endoscope assembly, including power delivered and communication of signals between the endoscope and its display, among others.

Figure 1A:
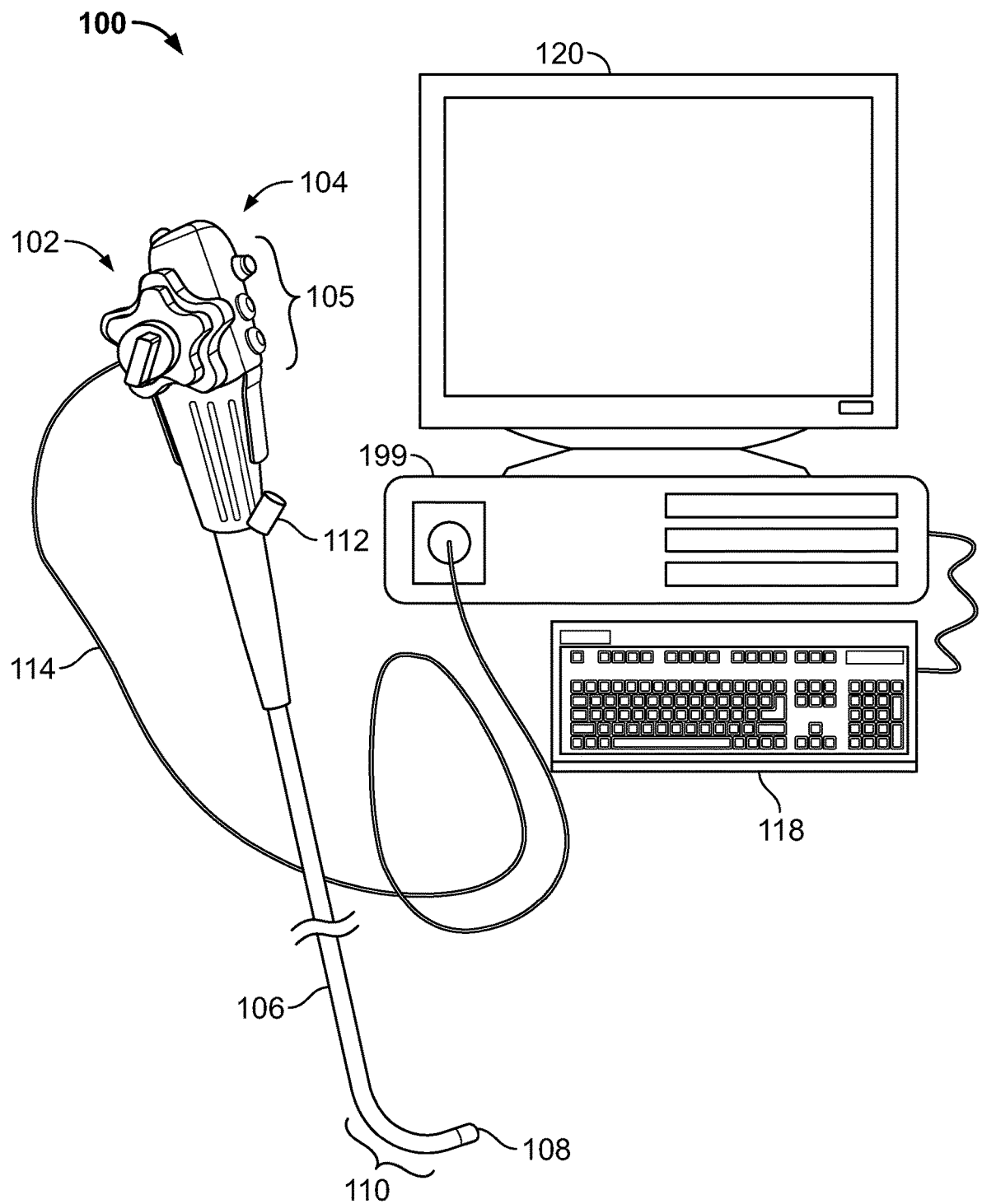
FIG. 1A shows a semi-pictorial view of a multi-camera endoscopy system, according to some embodiments.

Reference is now made to FIG. 1A, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1A, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 116 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. Provisional Patent Application No. 61/817,237, entitled "Method and System for Video Processing in a Multi-Viewing Element Endoscope" and filed on Apr. 29, 2013, which is herein incorporated by reference in its entirety.

Figure 1B:
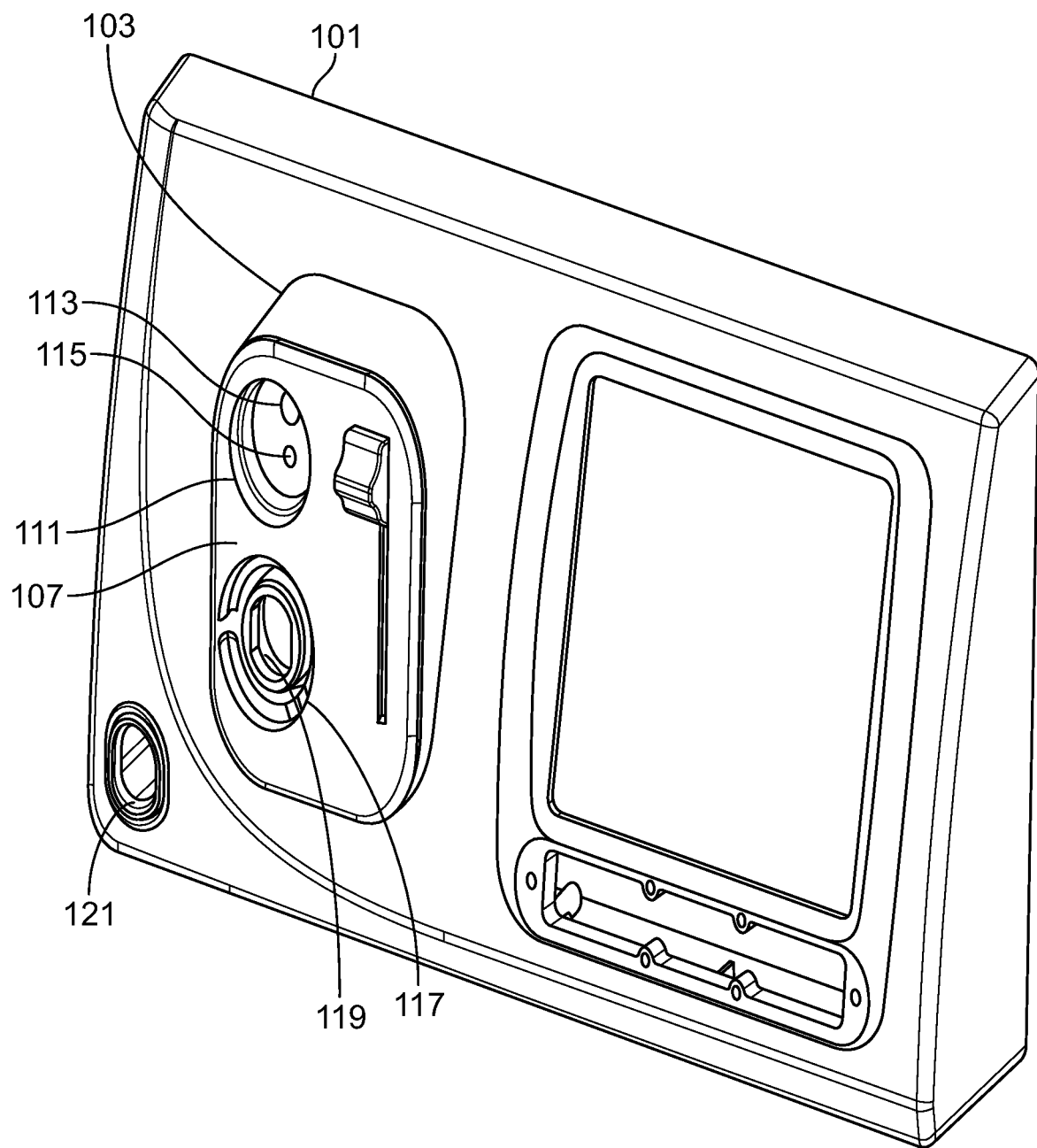
FIG. 1B shows a perspective view of one embodiment of a control panel of a main control unit of a multi-camera endoscopy system.
Figure 1C:
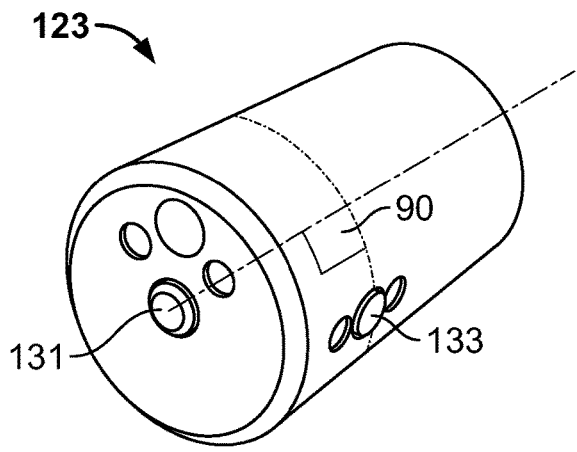
FIG. 1C shows a perspective view of a first multiple viewing element tip section configuration, according to some embodiments.
Figure 1D:
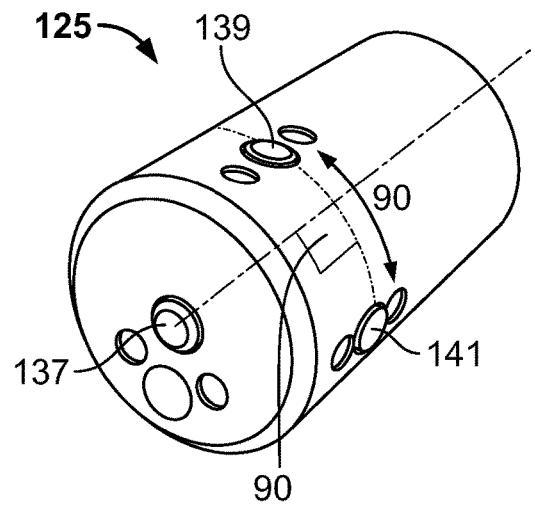
FIG. 1D shows a perspective view of a second multiple viewing element tip section configuration, according to some embodiments.
Figure 1E:
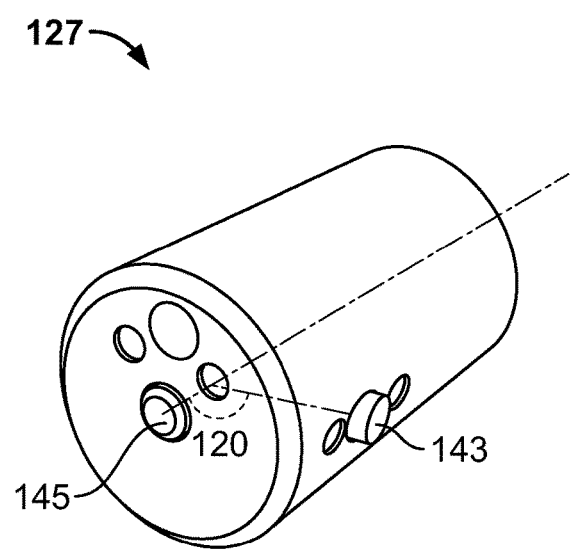
FIG. 1E shows a perspective view of a third multiple viewing element tip section configuration, according to some embodiments.
Figure 1F:
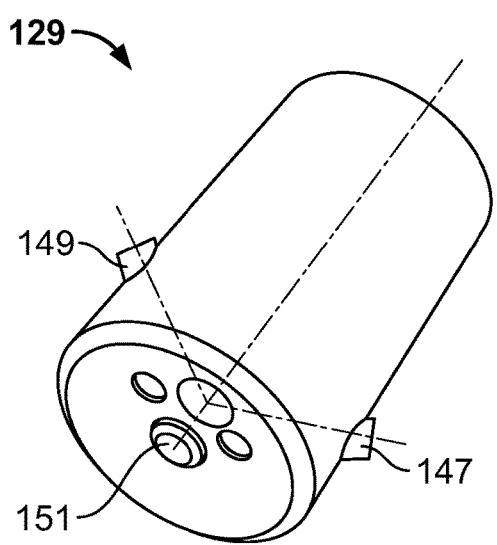
FIG. 1F shows a perspective view of a fourth multiple viewing element tip section configuration, according to some embodiments.

FIG. 1B shows a perspective view of one embodiment of a control panel of a main control unit of a multi-camera endoscopy system. As shown in FIG. 1B, the control panel 101 contains a main connector housing 103 having a front panel 107. The main connector housing front panel 107 comprises a first section 111, containing a light guide opening 113 and a gas channel opening 115, and a second section 117, comprising a utility cable opening 119. The light guide opening 113 and gas channel opening 115 are configured to receive and connect with a light guide and a gas channel respectively, on a main connector and the utility cable opening 119 is configured to receive and connect with an electric connector of a scope. A switch 121 is used to switch on and switch off the main control unit.

FIGS. 1C through 1F show multiple exemplary configurations 123, 125, 127 and 129 of the tip section 108.

In configuration 123, a front-pointing camera 131 and a side-pointing camera 133 are essentially perpendicular to one another, and have, correspondingly, perpendicular fields of view.

In configuration 125, a front-pointing camera 137 is essentially perpendicular to a first side-pointing camera 139 and a second side-pointing camera 141. First and second side-pointing cameras 139, 141 are pointing perpendicularly to one another, and are positioned essentially 90 degrees apart in the cylindrical surface of the tip section. In another configuration (not shown), first and second side-pointing cameras may be positioned more than 90 degrees apart in the cylindrical surface of the tip section, such as 120-150 degrees apart or 150-180 degrees apart. For example, the first and second side-pointing cameras may be positioned 180 degrees apart, in opposite sides of the cylindrical surface of the tip section, so that they point in opposite directions. In yet further configurations (not shown), three or more side-pointing cameras may be positioned in the cylindrical surface of the tip section, for example, three cameras having 120 degrees in between them.

In configuration 127, a side-pointing camera 143 is pointing slightly backwards, so that it forms an angle larger than 90 degrees relative to a front-pointing camera 145. As an example, an angle of 120 degrees is shown. In another configuration (not shown), the angle ranges from 100-145 degrees.

In configuration 129, two opposing side cameras, 147 and 149, are shown, which are pointing slightly backwards, so that they each form an angle larger than 90 degrees relative to a front-pointing camera 151. As an example, an angle of 120 degrees is shown. In another configuration (not shown), the angle is 100-145 degrees.

Similarly, in other configurations (not shown), three or more side-pointing cameras may be positioned in the cylindrical surface of the tip section, each pointing slightly backwards and having a certain angle in between; in the case of three cameras, they may have an angle of 120 degrees in between them.

Figure 1G:
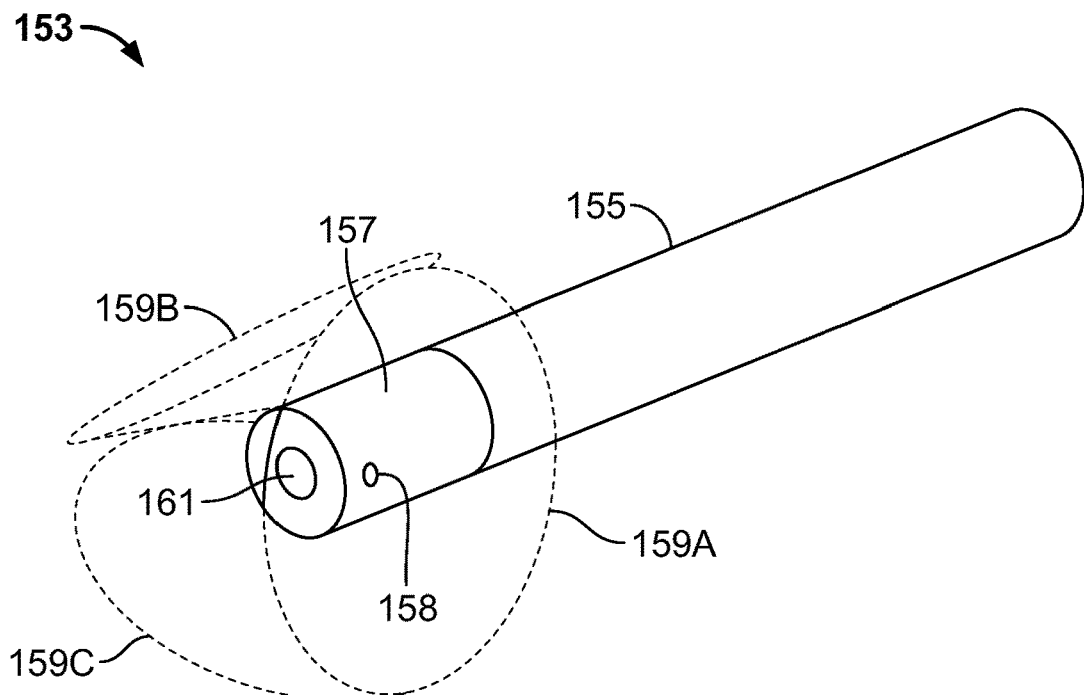
FIG. 1G shows a perspective view of a multi-camera endoscope, according to some embodiments.

Reference is now made to FIG. 1G, which shows a perspective view of a multi-camera endoscope 153, according to some embodiments. Endoscope 153 includes an elongated shaft 155 which typically includes a bending section (not shown) and a tip section 157 which terminates the endoscope. Tip section 157 includes three side-pointing cameras: a first side-pointing camera 158A, a second side-pointing camera, and a third side-pointing camera. The first side-pointing camera 158A has an associated first field of view 159A, while the second side-pointing camera has an associated second field of view 159B, and the third side-pointing camera has an associated third field of view 159C. Discrete side illuminators (for example LEDs), may be associated with the side-pointing cameras for illuminating their respective fields of view 159A, 159B, and 159C. Tip section 157 further includes a working channel 161 which may be a hollow opening configured for insertion of a surgical tool to operate on various tissues. For example, miniature forceps may be inserted through working channel 161 in order to remove a polyp or sample of which for biopsy.

Tip 157 may further include other elements/components, (for example, as described herein according to various embodiments) such as fluid injector(s) for cleaning the cameras and/or their illuminators and pathway fluid injector(s) for inflating and/or cleaning the body cavity into which endoscope 153 is inserted.

Figure 1H:
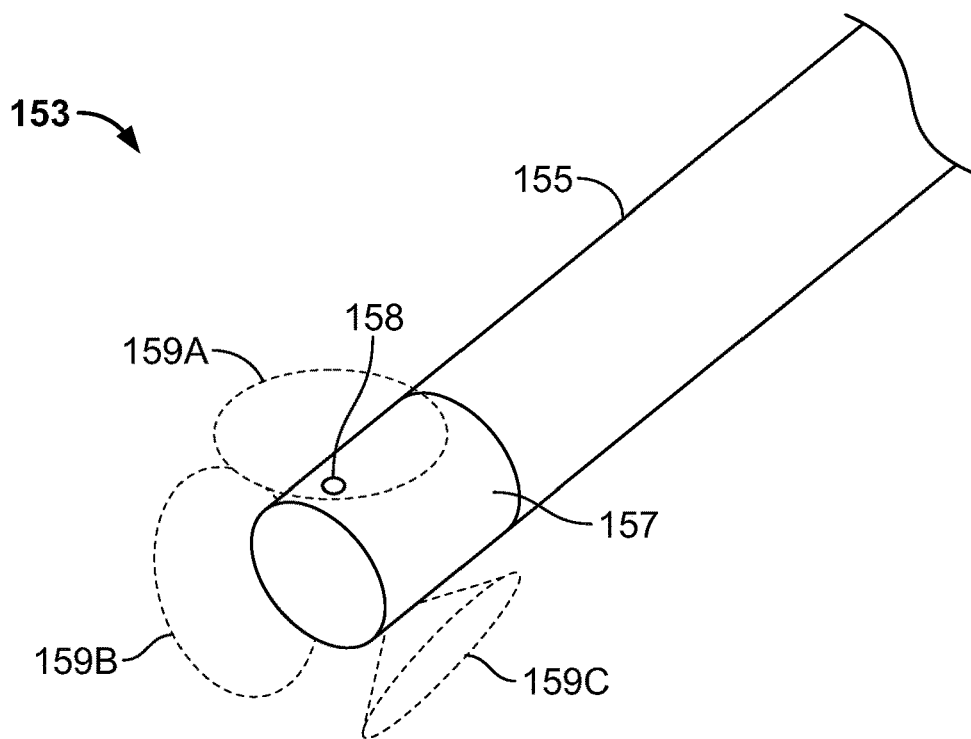
FIG. 1H shows a perspective view of a multi-camera endoscope, according to other embodiments.

Reference is now made to FIG. 1H, which shows a perspective view of a multi-camera endoscope 153, according to other embodiments. The endoscope shown in FIG. 1H, is similar to that shown in FIG. 1G, however, it does not include a working channel. Elongated shaft 155, tip section 157, first side-pointing camera 158A, second side-pointing camera and third side-pointing camera, and their respective fields of view 159A, 159B, and 159C are similar to those described above with reference to FIG. 1G.

Figure 1I:
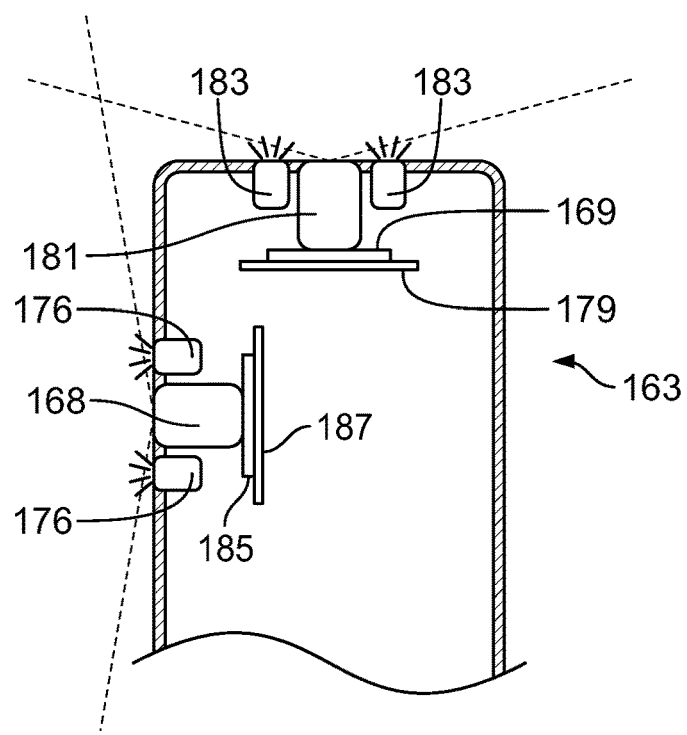
FIG. 1I shows a first cross-sectional view of a tip section of a multi-camera endoscope, according to some embodiments.

Reference is now made to FIG. 1I, which shows a cross-sectional view of a tip section 163 of a multi-camera endoscope, according to an embodiment. Tip section 163 may include a front-pointing image sensor 169, such as a Charge Coupled Device (CCD) or a Complementary Metal Oxide Semiconductor (CMOS) image sensor. Front-pointing image sensor 169 may be mounted on an integrated circuit board 179, which may be rigid or flexible. Integrated circuit board 179 may supply front-pointing image sensor 169 with necessary electrical power and may derive still images and/or video feeds captured by the image sensor. Integrated circuit board 179 may be connected to a set of electrical cables (not shown) which may be threaded through an electrical channel running through the elongated shaft of the endoscope. Front-pointing image sensor 169 may have a lens assembly 181 mounted on top of it and providing the necessary optics for receiving images. Lens assembly 181 may include a plurality of lenses, static or movable, which may provide a field of view of at least 90 degrees and up to essentially 180 degrees. Lens assembly 181 may provide a focal length of about 3 to 100 millimeters. Front-pointing image sensor 169 and lens assembly 181, with or without integrated circuit board 179, may be jointly referred to as a "front pointing camera".

One or more discrete front illuminators 183 may be placed next to lens assembly 181, for illuminating its field of view. Optionally, discrete front illuminators 183 may be attached to the same integrated circuit board 179 on which front-pointing image sensor 169 is mounted (this configuration is not shown).

Tip section 163 may include a side-pointing image sensor 185, such as a Charge Coupled Device (CCD) or a Complementary Metal Oxide Semiconductor (CMOS) image sensor. Side-pointing image sensor 185 may be mounted on an integrated circuit board 187, which may be rigid or flexible. Integrated circuit board 187 may supply side-pointing image sensor 185 with necessary electrical power and may derive still images and/or video feeds captured by the image sensor. Integrated circuit board 187 may be connected to a set of electrical cables (not shown) which may be threaded through an electrical channel running through the elongated shaft of the endoscope.

Side-pointing image sensor 185 may have a lens assembly 168 mounted on top of it and providing the necessary optics for receiving images. Lens assembly 168 may include a plurality of lenses, static or movable, which may provide a field of view of at least 90 degrees and up to essentially 180 degrees. Lens assembly 168 may provide a focal length of about 2 to 33 millimeters. Side-pointing image sensor 185 and lens assembly 168, with or without integrated circuit board 187, may be jointly referred to as a "side pointing camera".

One or more discrete side illuminators 176 may be placed next to lens assembly 168, for illuminating its field of view. Optionally, discrete side illuminators 176 may be attached to the same integrated circuit board 187 on which side-pointing image sensor 185 is mounted (this configuration is not shown).

In another configuration (not shown), integrated circuit boards 179 and 187 may be a single integrated circuit board on which both front and side-pointing image sensors 169 and 185, respectively, are mounted. For this purpose, the integrated circuit board may be essentially L-shaped.

Front and side-pointing image sensors 169 and 185 may be similar or identical in terms of, for example, field of view, resolution, light sensitivity, pixel size, focal length, focal distance and/or the like.

Optionally, side-pointing image sensor 185 and lens assembly 168 are advantageously positioned relatively close to the distal end surface of tip section 163. For example, a center of the side-pointing camera (which is the center axis of side-pointing image sensor 185 and lens assembly 168) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

Figure 1J:
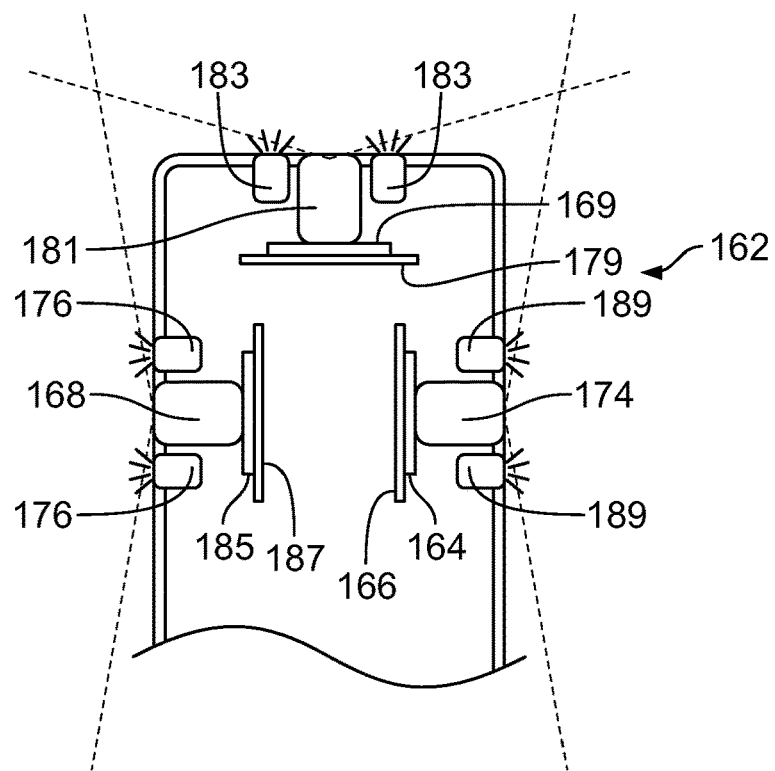
FIG. 1J shows a second cross-sectional view of a tip section of a multi-camera endoscope, according to some embodiments.

Reference is now made to FIG. 1J, which shows a cross-sectional view of a tip section 162 of a multi-camera endoscope, according to another embodiment of the specification. Tip section 162, similar to tip section 163 of FIG. 1I, may include a front-pointing image sensor 169, such as a Charge Coupled Device (CCD) or a Complementary Metal Oxide Semiconductor (CMOS) image sensor. Front-pointing image sensor 169 may be mounted on an integrated circuit board 179, which may be rigid or flexible. Integrated circuit board 179 may supply front-pointing image sensor 169 with necessary electrical power and may derive still images and/or video feeds captured by the image sensor. Integrated circuit board 179 may be connected to a set of electrical cables (not shown) which may be threaded through an electrical channel running through the elongated shaft of the endoscope. Front-pointing image sensor 169 may have a lens assembly 181 mounted on top of it and providing the necessary optics for receiving images. Lens assembly 181 may include a plurality of lenses, static or movable, which may provide a field of view of at least 90 degrees and up to essentially 180 degrees. Lens assembly 181 may provide a focal length of about 3 to 100 millimeters. Front-pointing image sensor 169 and lens assembly 181, with or without integrated circuit board 179, may be jointly referred to as a "front pointing camera". One or more discrete front illuminators 183 may be placed next to lens assembly 181, for illuminating its field of view. Optionally, discrete front illuminators 183 may be attached to the same integrated circuit board 179 on which front-pointing image sensor 169 is mounted (this configuration is not shown).

Tip section 162 may include, in addition to side-pointing image sensor 185, another side-pointing image sensor 164. Side-pointing image sensors 185 and 164 may include a Charge Coupled Device (CCD) or a Complementary Metal Oxide Semiconductor (CMOS) image sensor. Side-pointing image sensors 185 and 164 may be mounted on integrated circuit boards 187 and 166, respectively, which may be rigid or flexible. Integrated circuit boards 187 and 166 may supply side-pointing image sensors 185 and 164 with necessary electrical power and may derive still images and/or video feeds captured by the image sensor. Integrated circuit boards 187 and 166 may be connected to a set of electrical cables (not shown) which may be threaded through an electrical channel running through the elongated shaft of the endoscope.

Side-pointing image sensors 185 and 164 may have lens assemblies 168 and 174, respectively, mounted on top of them and providing the necessary optics for receiving images. Lens assemblies 168 and 174 may include a plurality of lenses, static or movable, which may provide a field of view of at least 90 degrees and up to essentially 180 degrees. Lens assemblies 168 and 174 may provide a focal length of about 2 to 33 millimeters. Side-pointing image sensors 185 and 164 and lens assemblies 168 and 174, with or without integrated circuit boards 187 and 166, respectively, may be jointly referred to as a "side pointing cameras".

Discrete side illuminators 176 and 189 may be placed next to lens assemblies 168 and 174, respectively, for illuminating its field of view. Optionally, discrete side illuminators 176 and 189 may be attached to the same integrated circuit boards 187 and 166 on which side-pointing image sensors 185 and 164 are mounted (this configuration is not shown).

In another configuration (not shown), integrated circuit boards 179, 187, and 166 may be a single integrated circuit board on which front and side-pointing image sensors 169, 185, and 164, respectively, are mounted.

Front and side-pointing image sensors 169, 185, and 164 may be similar, identical or distinct in terms of, for example, field of view, resolution, light sensitivity, pixel size, focal length, focal distance and/or the like.

Optionally, side-pointing image sensors 185 and 164 and lens assemblies 168 and 174 are advantageously positioned relatively close to the distal end surface of tip section 162. For example, a center of the side-pointing cameras (which is the center axis of side-pointing image sensors 185 and 164 and lens assemblies 168 and 174) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

According to some embodiments, the front and side-pointing cameras are all positioned on the same (imaginary) plain which "divides" tip section 162 into two equal parts along its length. According to some embodiments, each of the side-pointing cameras is perpendicular to the front pointing camera.

In accordance with an aspect of the present specification, the fields of view of the front and side-pointing viewing elements overlap. These fields of view are configured to maximize the area of overlap (and minimize a dead space which may be defined as an area that is not covered by the overlap) and bring the point of intersection of the fields of view as close as possible to the endoscope tip.

In one embodiment, the area of overlap, or intersecting field of view, occurs over a depth of field range of between 3 mm and 100 mm for the forward looking viewing element and over a depth of field range of between 3 mm and 100 mm for the first side viewing element. In another embodiment, the area of overlap, or intersecting field of view, occurs over a depth of field range of between the minimum and maximum depth of field for the forward looking viewing element and over a depth of field range of between the minimum and maximum depth of field for the first side viewing element.

In another embodiment, the area of overlap, or intersecting field of view, occurs over a depth of field range of between 3 mm and 100 mm for the forward looking viewing element and over a depth of field range of between 3 mm and 100 mm for each of the two side viewing elements. In another embodiment, the area of overlap, or intersecting field of view, occurs over a depth of field range of between the minimum and maximum depth of field for the forward looking viewing element and over a depth of field range of between the minimum and maximum depth of field for each of the side viewing elements.

In an embodiment, each of the forward looking and side looking viewing elements generates a view ranging from 120 to 180 degrees, as measured from the planar surface defined by the forward looking viewing element surface and the planar surface defined by the side viewing element surface, respectively. In an embodiment, these angle ranges of the forward looking and side viewing elements overlap.

In an embodiment, the field of view of the first viewing element intersects with the field of view of the second and/or third viewing elements within a distance of 15 mm from the endoscope tip, first viewing element, second viewing element, or third viewing element. Preferably the distance is less than 15 mm, such as, 14, 13, 12, 11, 10, 9, 8, 7, 6, 5, 4, 3, or 2 mm.

Figure 2B:
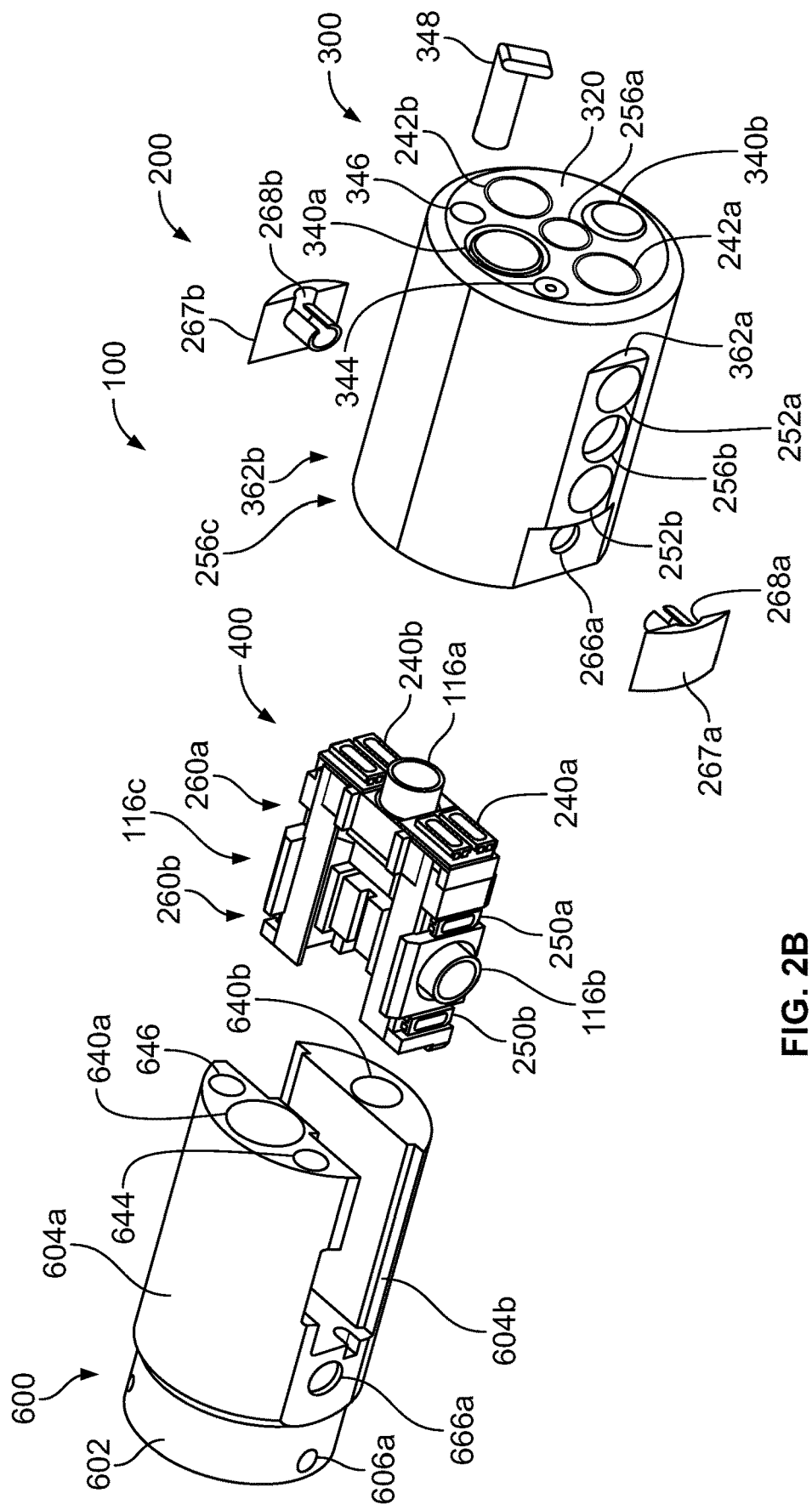
FIG. 2B shows an exploded perspective view of a tip section of an endoscope assembly according to another embodiment.

FIGS. 2A and 2B show exploded views of a tip section 200 of a multi-viewing element endoscope assembly 100 comprising one and two front working/service channels, respectively, according to various embodiments. An aspect of some embodiments also relates to endoscope assembly 100 having the tip section 200 equipped with one or more side working/service channels.

Persons of ordinary skill in the art would appreciate that available space in the tip section may impose a constraint on the total number and/or the relative orientations of image capturing devices that may be packaged within the tip section. Further, each viewing element, and related supporting electronic circuitry, dissipates some power in the form of heat. Thus, an acceptable working temperature of the tip section and an allowed heat dissipation rate from the tip section to the patient's body impose yet another restriction on the total number of operative viewing elements therein. Further yet, each viewing element outputs image data through an imaging channel, generally employed by a dedicated video cable. Moreover, each viewing element may require, for proper operation, dedicated control signals also delivered by wires along the endoscope. Thus, the number of viewing elements may also be limited by the amount of wiring that can be included within the endoscope. Further yet, electronic interference between wires and cables may generally increase with the number of such wires along the endoscope, adversely affecting the quality and integrity of the signals.

The aforementioned constraints or limitations, among others, are addressed in various embodiments of the tip section of the endoscope assembly of the present specification. Accordingly, in an embodiment, tip section 200 of the endoscope 100 of FIGS. 2A and 2B may include a tip cover 300, an electronic circuit board assembly 400 and a fluid channeling component 600.

According to some embodiments, fluid channeling component 600 may be configured as a separate component from electronic circuit board assembly 400. This configuration may be adapted to separate the fluid channels, at least one side service channel, such as side service channel 650, and at least one front working/service channel, such as working/service channel 640, which are located in fluid channeling component 600, from the sensitive electronic and optical parts which may be located in the area of electronic circuit board assembly 400. Thus, the component structure of the tip section 200 enables effective insulation of the plurality of electronic elements from the plurality of fluid channels.

According to some embodiments, the use of metal for the construction of a flexible electronic circuit board holder is important for electric conductivity and heat transfer purposes. The flexible electronic circuit board holder, according to embodiments of the specification (such as flexible electronic circuit board holder 500 of FIG. 19), can be used as a heat sink for some or all of the electronic components located at the tip section, particularly illuminators (such as side or front LEDs) and reduce overall temperature of the endoscope tip. This may solve or at least mitigate a major problem of raised temperatures of the endoscope tip and/or any of its components, particularly when using LED illuminators.

According to some embodiments, the viewing elements and optionally other elements that exist in the tip section (such as a plurality of illuminators or light sources, one or more front and/or side working/service channels, one or more front and side jet channels, a side fluid injector, an electronic circuit board assembly and/or the like) are uniquely modularized into a three part component structure comprising the tip cover 300, electronic circuit board assembly 400 and fluid channeling component 600 and packaged so that they fit within the minimalistic space available inside the tip section, while still providing valuable results.

Referring to FIG. 2A, according to some embodiments, the tip section 200 includes a front panel 320 which comprises four quadrants defined by a vertical axis passing through a center of the front panel 320 and a horizontal axis passing through the center, wherein the four quadrants include a top left quadrant, a top right quadrant, a bottom left quadrant and a bottom right quadrant.

In various embodiments, a front optical assembly 256 is positioned on the front panel 320. In various embodiments, a first front optical window 242b, for a first front illuminator 240b, is positioned on the front panel 320, at least partially within the bottom right quadrant and at least partially within the bottom left quadrant. In various embodiments, a second front optical window 242a, for a second front illuminator 240a, is positioned on the front panel 320, at least partially within the bottom left quadrant. In various embodiments, a third front optical window 242c, for a third front illuminator 240c, is positioned on the front panel 320, at least partially within the bottom right quadrant.

In various embodiments, a front working channel opening 340, for working channel 640, is positioned on the front panel 320, along the vertical axis and at least partially within the top left quadrant and partially within the top right quadrant. In various embodiments, a fluid injector opening 346, for a fluid injector channel 646, is positioned on the front panel 320, at least partially within the top right quadrant. In various embodiments, a jet channel opening 344, for a jet channel 644, is positioned on the front panel 320, at least partially within the top left quadrant.

Figure 3A:
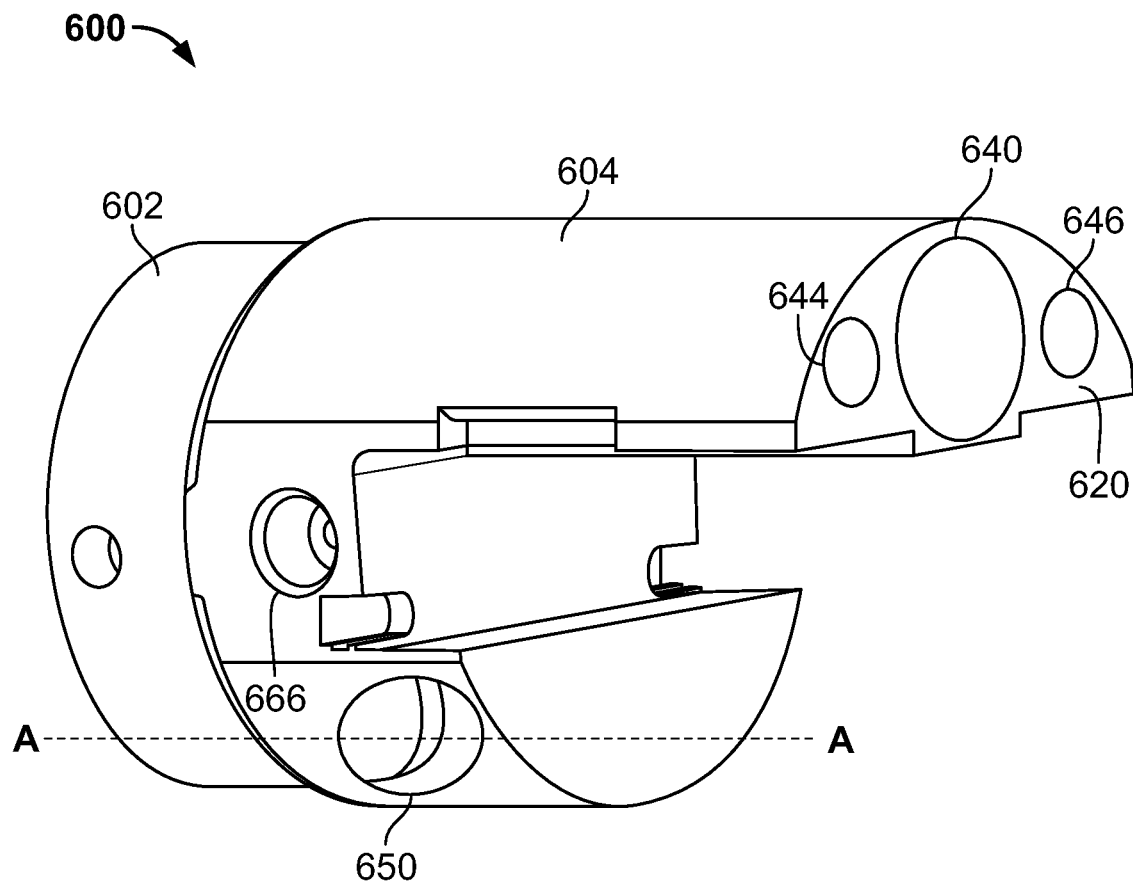
FIG. 3A shows a perspective view of a fluid channeling component of an endoscope assembly according to a first embodiment.
Figure 3B:
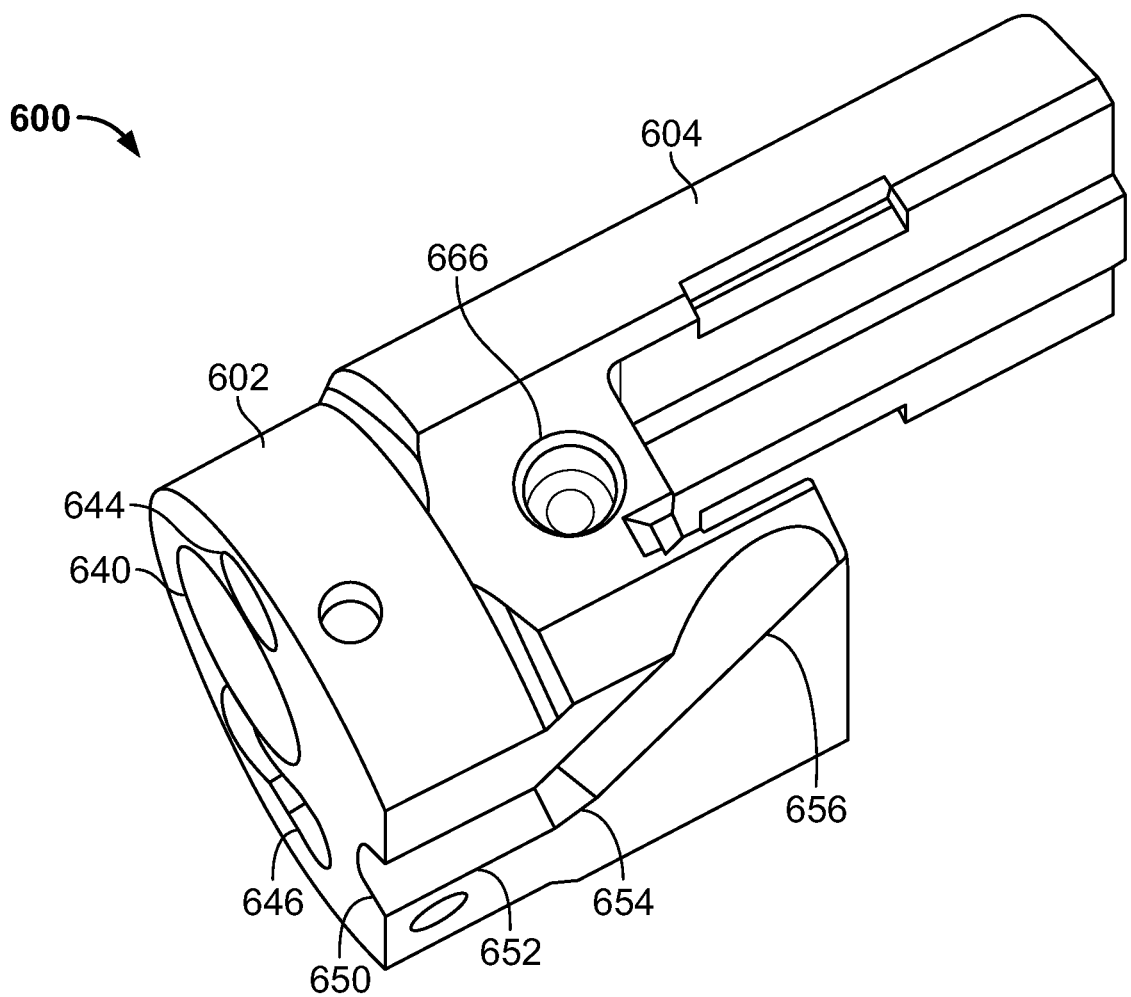
FIG. 3B shows a perspective view of a fluid channeling component of an endoscope assembly according to a second embodiment.

Reference is now made to FIG. 2A along with FIGS. 3A and 3B, which show a perspective view of a fluid channeling component 600 of an endoscope assembly according to an embodiment. According to some embodiments, fluid channeling component 600 may include a proximal fluid channeling section 602 (or base) which may have an essentially cylindrical shape and a unitary distal channeling section 604 (or elongated housing). Distal fluid channeling section 604 may partially continue the cylindrical shape of proximal fluid channeling section 602 and may have a shape of a partial cylinder (optionally elongated partial cylinder). Distal fluid channeling section 604 may have only a fraction of the cylinder (along the height or length axis of the cylinder), wherein another fraction of the cylinder (along the height or length axis of the cylinder) is missing. In other words, in various embodiments, proximal fluid channeling section 602 has a greater width than distal fluid channeling section 604. Distal fluid channeling section 604 may be integrally formed as a unitary block with proximal fluid channeling section 602. The height or length of distal fluid channeling section 604 may by higher or longer than the height or length of proximal fluid channeling section 602. In the embodiment comprising distal fluid channeling section 604, the shape of the partial cylinder (for example, partial cylinder having only a fraction of a cylinder shape along one side of the height axis) may provide a space to accommodate electronic circuit board assembly 400 (FIG. 2A).

Distal fluid channeling section 604 may include a working channel 640, which may be configured for insertion of a surgical tool, for example, to remove, treat and/or extract a sample of the object of interest found in the colon or its entirety for biopsy.

Distal fluid channeling section 604 may further include a jet fluid channel 644 which may be configured for providing a high pressure jet of fluid, such as water or saline, for cleaning the walls of the body cavity (such as the colon) and optionally for suction. Distal fluid channeling section 604 may further include injector channel 646, which may be used for injecting fluid (liquid and/or gas) to wash contaminants such as blood, feces and other debris from front optical assembly 256 (FIG. 2A) of forward-looking viewing element 116 (FIG. 2A). Proximal fluid channeling section 602 of fluid channeling component 600 may include a side injector channel 666 which may be connected to side injector opening 266 (FIG. 2A).

In one embodiment, fluid channeling component 600 comprises a fluid manifold and may include a side service channel 650 having a side service channel opening 350 (FIG. 2A). Side service channel 650 includes a proximal section 652, a curve 654 and a distal section 656 and is located within fluid channeling component 600.

Proximal section 652 of side service channel 650 is essentially directed along the long dimension of the endoscope.

Curve 654 of side service channel 650 is configured to connect proximal section 652 and distal section 656 and curve (at essentially a right angle or in an obtuse angle) distal section 656 towards the side of fluid channeling component 600.

It is noted that according to some embodiments, a curve, such as curve 654 may be configured to create an acute angle between proximal section 652 and distal section 656.

Side service channel 650 may be configured to allow the endoscope operator to insert a surgical tool (not shown) and remove, treat and/or extract a sample of the object of interest or its entirety for biopsy.

Advantageously, side service channel 650 may allow greater flexibility to the endoscope operator and allow the insertion of extra surgical tools in addition to the surgical tools which may be inserted through working channel 640.

Figure 4A:
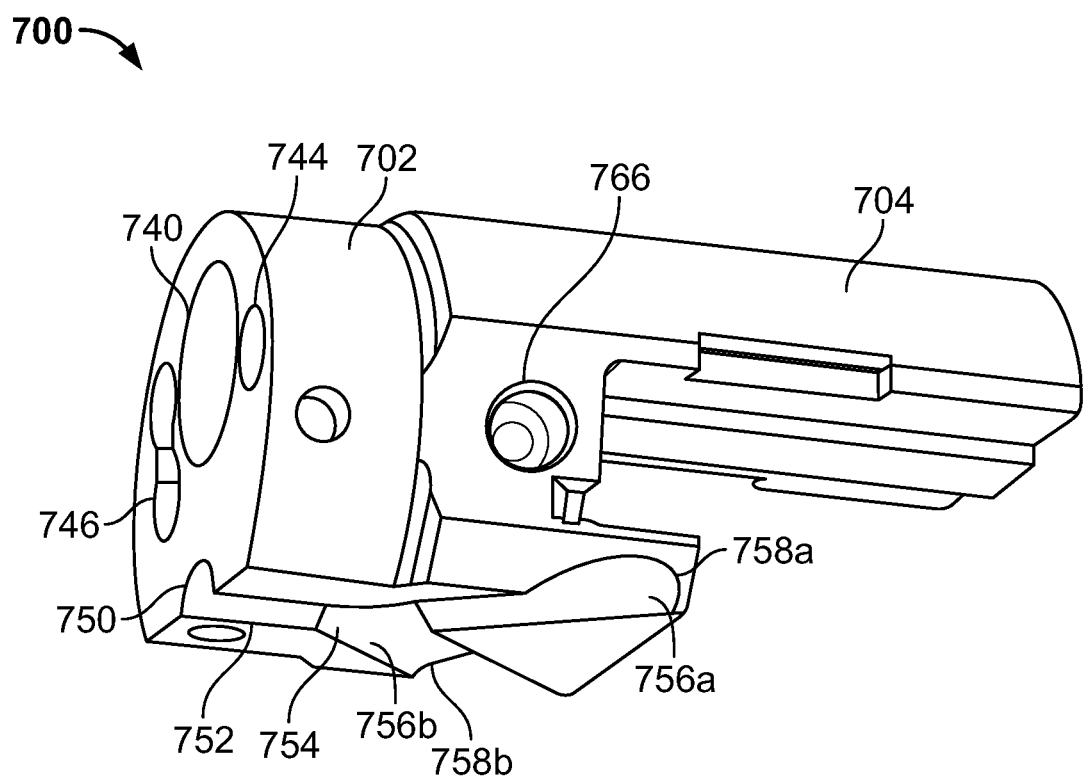
FIG. 4A shows a perspective view of a fluid channeling component of an endoscope assembly according to a third embodiment.
Figure 4B:
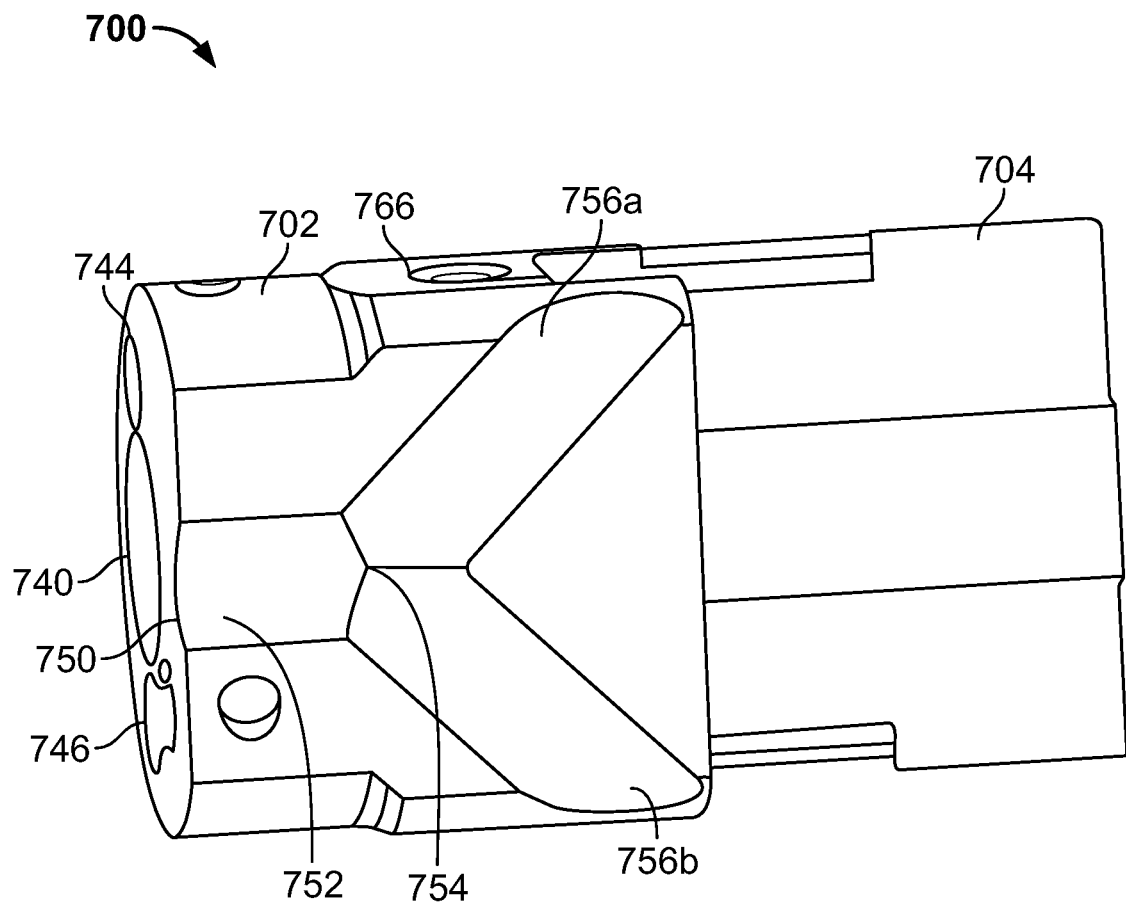
FIG. 4B shows a perspective view of a fluid channeling component of an endoscope assembly according to a fourth embodiment.
Figure 4C:
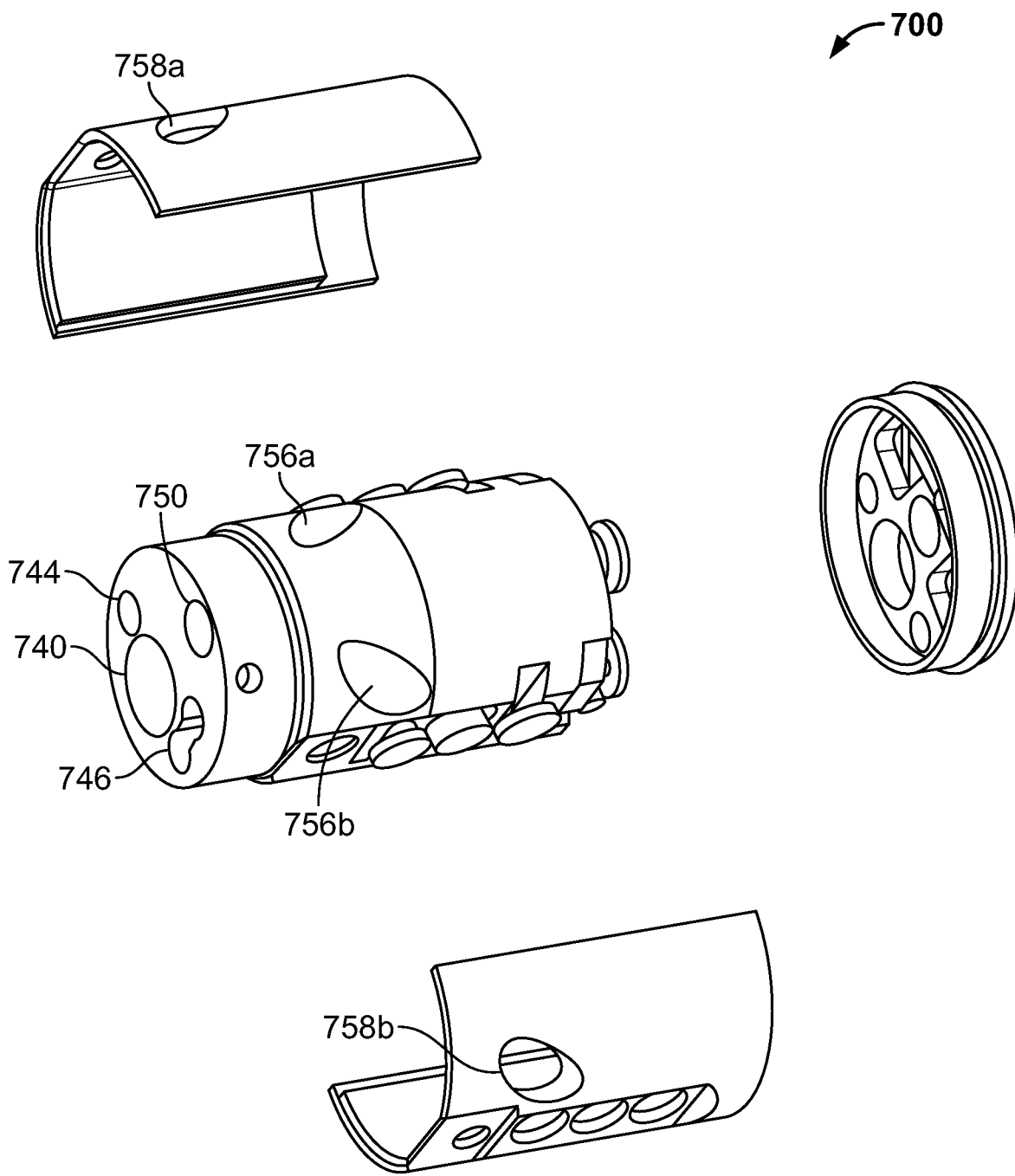
FIG. 4C shows a perspective view of a fluid channeling component along with an exploded view of a corresponding tip cover of an endoscope assembly, according to some embodiments.

Reference is now made to FIG. 2A along with FIGS. 4A, 4B, and 4C, which show a perspective view of a fluid channeling component 700 of an endoscope assembly according to another embodiment. The fluid channeling component 700 comprises a jet fluid channel 744 which may be configured for providing a high pressure jet of fluid such as water or saline for cleaning the walls of the body cavity (such as the colon) and optionally for suction. Component 700 may further include injector channel 746, which may be used for injecting fluid (liquid and/or gas) to wash contaminants such as blood, feces and other debris from front optical assembly 256 (FIG. 2A) of forward-looking viewing element 116 (FIG. 2A).

According to some embodiments, fluid channeling component 700 may include a proximal fluid channeling section 702 (or base) which may have an essentially cylindrical shape and a unitary distal channeling section 704 (or elongated housing). Distal fluid channeling section 704 may partially continue the cylindrical shape of proximal fluid channeling section 702 and may have a shape of a partial cylinder (optionally elongated partial cylinder). Distal fluid channeling section 704 may have only a fraction of the cylinder (along the height or length axis of the cylinder), wherein another fraction of the cylinder (along the height or length axis of the cylinder) is missing. In other words, in various embodiments, proximal fluid channeling section 702 has a greater width than distal fluid channeling section 704. Distal fluid channeling section 704 may be integrally formed as a unitary block with proximal fluid channeling section 702. The height or length of distal fluid channeling section 704 may by higher or longer than the height or length of proximal fluid channeling section 702. In the embodiment comprising distal fluid channeling section 704, the shape of the partial cylinder (for example, partial cylinder having only a fraction of a cylinder shape along one side of the height axis) may provide a space to accommodate electronic circuit board assembly 400 (FIG. 2A).

According to some embodiments, fluid channeling component 700 comprises a fluid manifold and may include a side service channel 750 having two side service channel openings 758a and 758b. In various embodiments, side service channel openings 758a and 758b have an angle of exit ranging from 5 to 90 degrees relative to the longitudinal axis of the endoscope. In one embodiment, side service channel openings 758a and 758b have an angle of exit of 45 degrees relative to the longitudinal axis of the endoscope.

Side service channel 750 may be located within fluid channeling component 700 and may include a proximal section 752, a split 754 and two distal sections 756a and 756b.

Proximal section 752 of side service channel 750 may be essentially directed along the long dimension of the endoscope and may be positioned at the bottom and center of the proximal fluid channeling section 702.

Split 754 of side service channel 750 may be configured to split proximal section 752 into two distal sections 756a and 756b and divert distal sections 756a and 756b towards two essentially opposite sides of fluid channeling component 700.

In various embodiments, the distal sections 756a and 756b bend at different angles relative to the long dimension of the endoscope. In one embodiment, the distal sections 756a and 756b bend at an acute angle relative to the long dimension of the endoscope. In another embodiment, the distal sections 756a and 756b bend at an angle having a range between 45 to 60 degrees relative to the long dimension of the endoscope. In another embodiment, the distal sections 756a and 756b bend at an angle of 90 degrees relative to the long dimension of the endoscope. In another embodiment, the distal sections 756a and 756b bend at an obtuse angle relative to the long dimension of the endoscope. In yet another embodiment, the distal sections 756a and 756b bend at an angle having a range of 120 to 135 degrees relative to the long dimension of the endoscope.

Side service channel 750 may be configured to allow the endoscope operator to insert a surgical tool (not shown) and remove, treat and/or extract a sample of the object of interest or its entirety for biopsy.

Advantageously, side service channel 750 may allow greater flexibility to the endoscope operator and allow the insertion of extra surgical tools in addition to the surgical tools, which may be inserted through working channel 740.

While some objects of interest may be visible and/or accessible via the endoscope front panel 320 (FIG. 2A), some objects of interest may be more visible via side looking viewing element 116b (FIG. 2A) and/or accessible via endoscope side service channel 750. Therefore, side service channel 750 may reduce the need to turn the tip section 200 towards the object of interest. Furthermore, side service channel 750 may allow the endoscope operator to access objects of interest, and perform surgical operations while the object of interest is still visible by one of side looking viewing elements 116b or 116c (on the opposite side of viewing element 116b of FIG. 2B).

Referring to FIGS. 3A, 3B, 4A, 4B and 4C in various embodiments, a surgical tool inserted into the side service channel 650 or 750 will exit the endoscope at different angles relative to the long dimension of the endoscope, dependent upon the degree of the bend of the distal sections of said service channel 650 or 750. In one embodiment, the surgical tool exits the endoscope at an acute angle relative to the long dimension of the endoscope. In another embodiment, the surgical tool exits the endoscope at an angle having a range between 45 to 60 degrees relative to the long dimension of the endoscope. In another embodiment, the surgical tool exits the endoscope at an angle of 90 degrees relative to the long dimension of the endoscope. In another embodiment, the surgical tool exits the endoscope at an obtuse angle relative to the long dimension of the endoscope. In yet another embodiment, the surgical tool exits the endoscope at an angle having a range of 120 to 135 degrees relative to the long dimension of the endoscope.

Figure 5A:
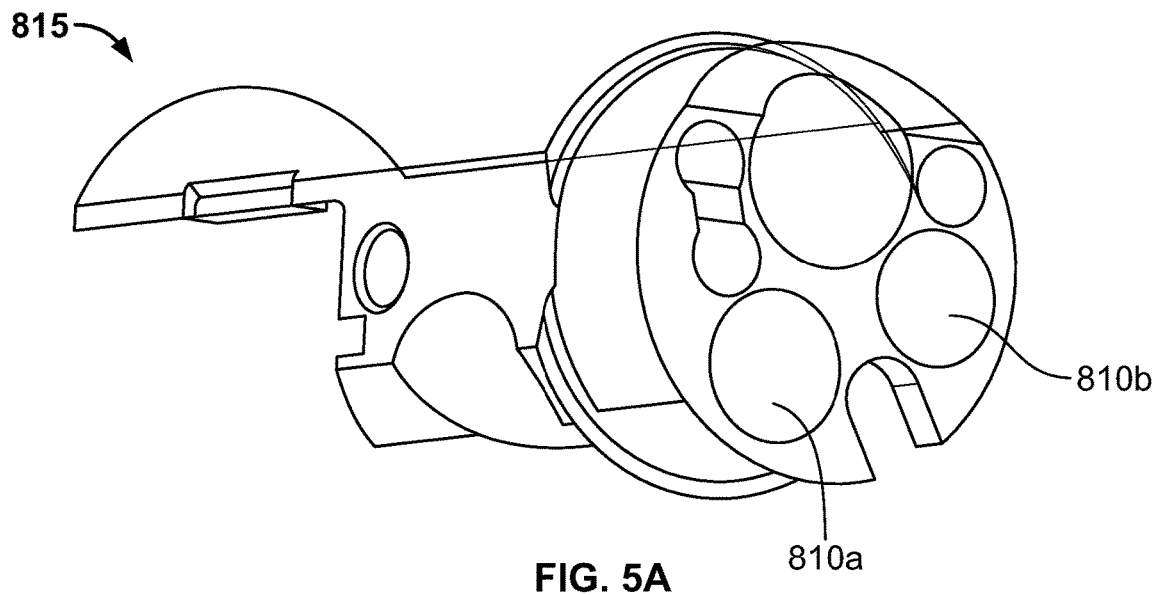
FIG. 5A shows a first perspective view of a fluid channeling component of the tip section of FIG. 61A.
Figure 5B:
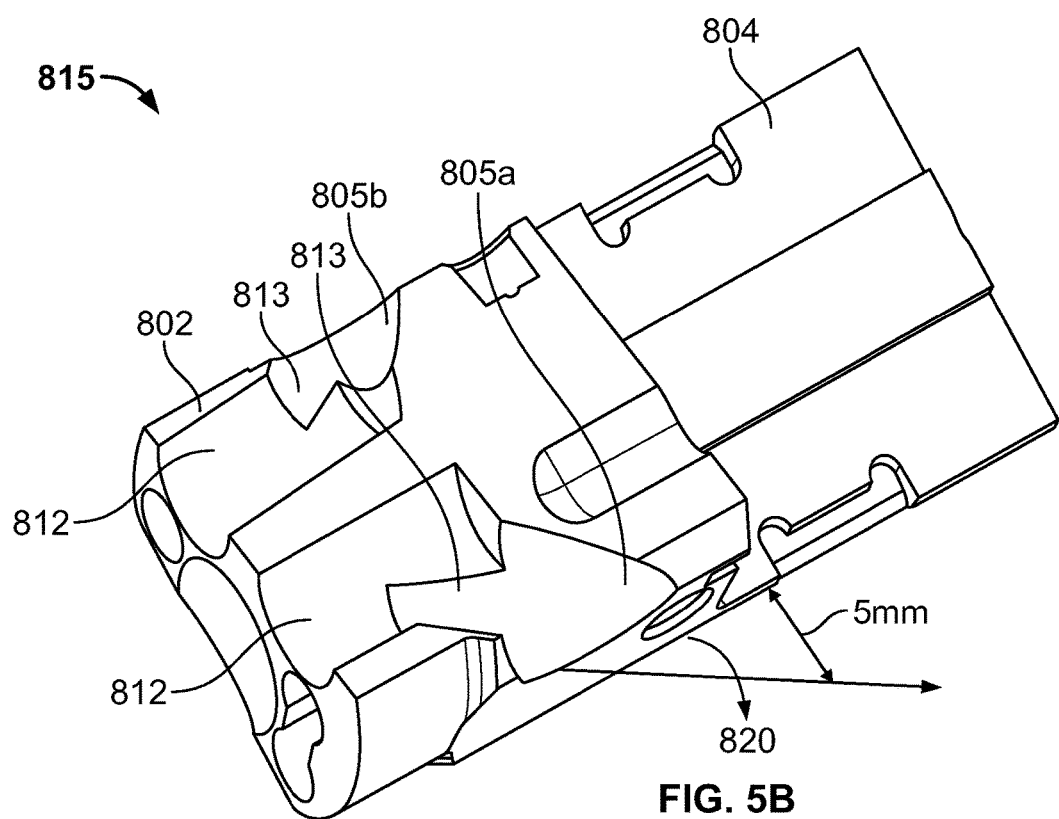
FIG. 5B shows a second perspective view of the fluid channeling component of the tip section of FIG. 61A.

Reference is now made to FIGS. 5A and 5B, which show a perspective view of a fluid channeling component 815 of an endoscope assembly according to another embodiment.

According to some embodiments, fluid channeling component 815 may include a proximal fluid channeling section 802 (or base) which may have an essentially cylindrical shape and a unitary distal channeling section 804 (or elongated housing). Distal fluid channeling section 804 may partially continue the cylindrical shape of proximal fluid channeling section 802 and may have a shape of a partial cylinder (optionally elongated partial cylinder). Distal fluid channeling section 804 may have only a fraction of the cylinder (along the height or length axis of the cylinder), wherein another fraction of the cylinder (along the height or length axis of the cylinder) is missing. In other words, in various embodiments, proximal fluid channeling section 802 has a greater width than distal fluid channeling section 804. Distal fluid channeling section 804 may be integrally formed as a unitary block with proximal fluid channeling section 802. The height or length of distal fluid channeling section 804 may by higher or longer than the height or length of proximal fluid channeling section 802. In the embodiment comprising distal fluid channeling section 804, the shape of the partial cylinder (for example, partial cylinder having only a fraction of a cylinder shape along one side of the height axis) may provide a space to accommodate electronic circuit board assembly 400 (FIG. 2A).

The fluid channeling component 815 comprises two side service channels 810a, 810b leading to corresponding two side service channel openings 805a, 805b on either side of a tip section of an endoscope, such as the tip section 200 of FIG. 61A. Thus, two independent and distinct side service channels 810a, 810b, one for each side, are located within the fluid channeling component 815. The side service channels 810a, 810b comprise proximal sections 812 directed along the long dimension of the endoscope and distal sections 813 that bend towards the respective sides of the fluid channeling component 815. In various embodiments, the proximal sections 812 of the two side service channels 810a, 810b extend through a bottom portion of the proximal fluid channeling section 802. In one embodiment, the distal sections 813 bend at acute angles with reference to the long dimension of the endoscope. In an embodiment, the distal sections 813 bend at a range of 5 degrees to 90 degrees and any increment therein, but preferably 45 degrees relative to the long dimension of the endoscope.

According to some embodiments of this specification, there is provided herein an endoscope (such as a colonoscope) that includes (in a tip section thereof), in addition to a front viewing element and one or more side viewing elements, and in addition to a front working/service channel, a second front working/service channel that is configured for insertion of a medical (such as a surgical) tool, optionally in addition to a medical tool inserted from the front working/service channel.

Figure 6A:
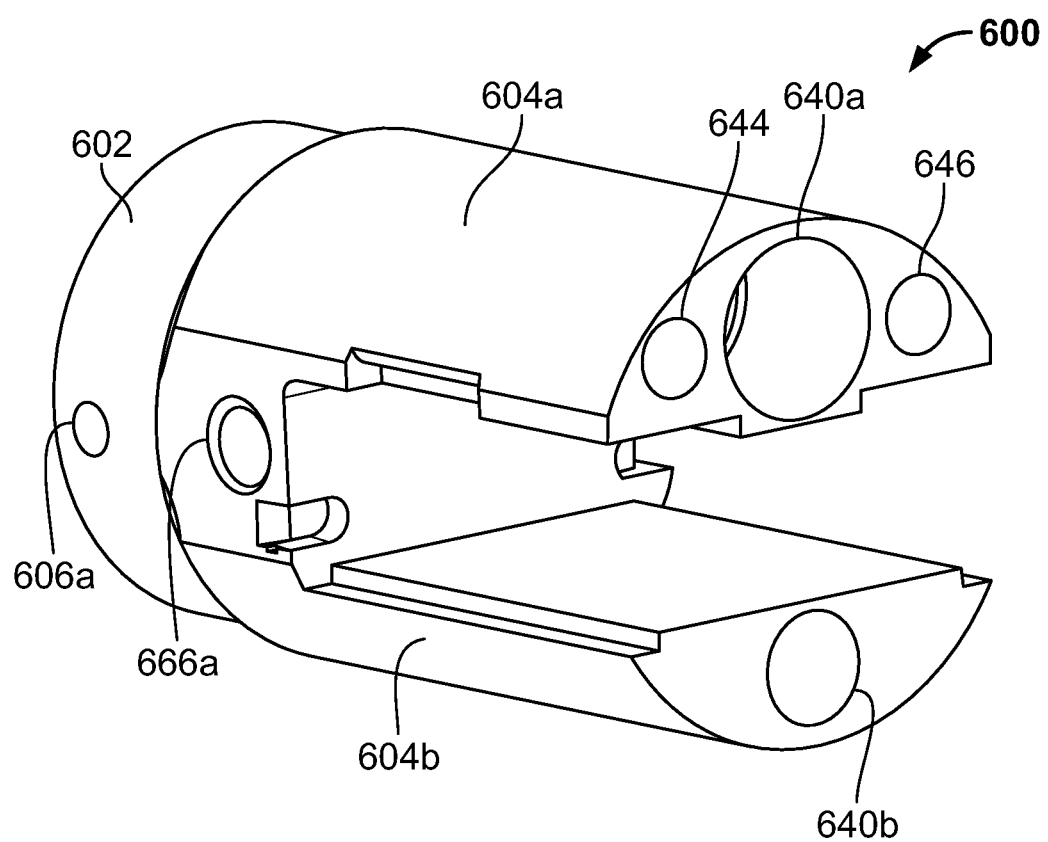
FIG. 6A shows a perspective view of a fluid channeling component of an endoscope assembly according to some embodiments.
Figure 6B:
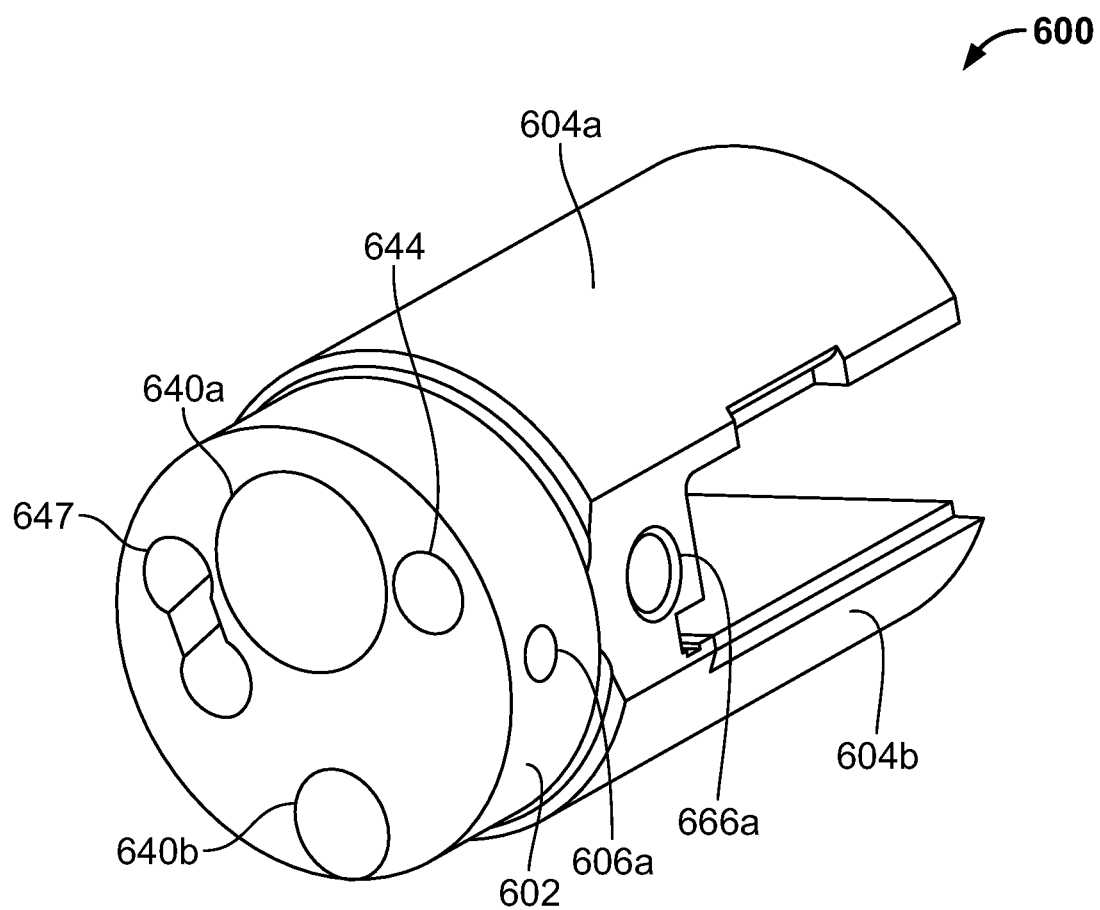
FIG. 6B shows a perspective view of a fluid channeling component of an endoscope assembly according to some embodiments.
Figure 6C:
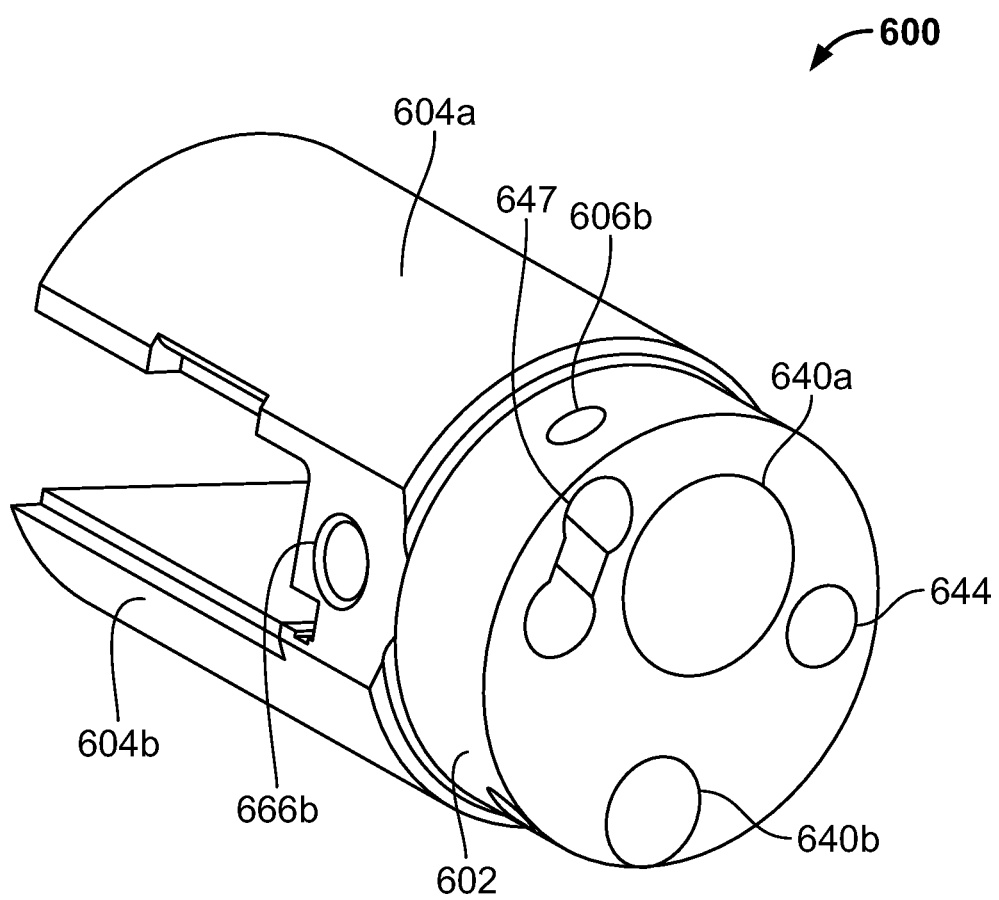
FIG. 6C shows a perspective view of a fluid channeling component of an endoscope assembly according to some embodiments.

Reference is now made to FIG. 2B along with FIGS. 6A, 6B and 6C which show perspective views of a fluid channeling component 600 of an endoscope assembly 100 according to another embodiment.

According to some embodiments, fluid channeling component 600 may be configured as a separate component from electronic circuit board assembly 400 (FIG. 2B). This configuration may be adapted to separate the fluid channels 640b and working channels 640a, which are located in fluid channeling component 600, from the sensitive electronic and optical parts which may be located in the area of electronic circuit board assembly 400 (FIG. 2B).

According to some embodiments, fluid channeling component 600 may include a proximal fluid channeling section 602 which may have an essentially cylindrical shape, a primary distal channeling section 604a and a secondary distal channeling section 604b. Primary distal fluid channeling section 604a and secondary distal channeling section 604b may partially continue the cylindrical shape of proximal fluid channeling section 602 and may have a shape of a partial cylinder (optionally elongated partial cylinder). Primary distal fluid channeling section 604a and secondary distal channeling section 604b may form solely two parallel fractions of the cylinder (along the height axis of the cylinder), wherein the third fraction of the cylinder (along the height axis of the cylinder) is missing. Primary distal fluid channeling section 604a and secondary distal channeling section 604b may be integrally formed as a unitary block with proximal fluid channeling section 602. The height of primary distal fluid channeling section 604a and secondary distal channeling section 604b may by higher than that of proximal fluid channeling section 602. The primary distal fluid channeling section 604a and secondary distal channeling section 604b may have the shape of the partial cylinder (for example, partial cylinder having only a fraction of a cylinder shape along one side of the height axis) and provide a space to accommodate electronic circuit board assembly 400 (FIG. 2B).

Proximal fluid channeling section 602 may include integrated screw nuts 606a and 606b, which may be configured for securing tip section 200 (FIG. 2B) to the endoscope shaft (not shown).

Primary distal fluid channeling section 604a may include working channel 640a having a working channel opening 340a, which may be configured for insertion of a medical (such as a surgical) tool, for example, to remove, treat and/or extract a sample of the object of interest found in the colon or its entirety for biopsy.

Working channel 640a may be formed as an essentially cylindrical channel located within primary distal channeling section 604a along the long dimension of the endoscope and placed in parallel to primary distal fluid channeling section 604a.

Once an object of interest has been detected, the endoscope operator may desire to insert one or more medical tools and remove, treat and/or extract a sample of the polyp or its entirety for biopsy. Therefore, it may be beneficial for the endoscope's operator to be able to use more than one medical tool.

Advantageously, secondary distal channeling section 604b may include a second working channels 640b having a working channel opening 340b which may be similar to working channel 640a and may be configured for insertion of a medical tool, for example but not necessarily, in addition to the medical tool which may be inserted through working channel 640a. The operator may also choose from which working channel he or she would like to insert the medical tool, for example, according to the position of the polyp.

Second working channel 640b may be formed as an essentially cylindrical channel located within secondary distal channeling section 604b along the long dimension of the endoscope and placed in parallel to secondary distal channeling section 604b. Other configurations may also be possible. First and second working channels may be the same or different in shape and size.

Second working channel 640b may be configured to improve the performance of the endoscope (particularly, the colonoscope). Current colonoscopes typically have one working channel, which opens at the front distal section of the colonoscope. Such front working channel is adapted for insertion of a surgical tool. The physician is required to perform all necessary medical procedures, such as biopsy, polyp removal and other procedures, via this one channel.

A second working channel, such as second working channel 640b, allows greater flexibility to the endoscope operator and allows the insertion of medical tools in addition to (or instead of) the medical tools which may be inserted through working channel 640a.

This may significantly improve the performance of the endoscope and allow the endoscope operator to perform more complex medical procedures using two medical tools. Second working channel 640b provides the endoscope operator better access to the object of interest and greater flexibility with operating the medical tools while at the same time viewing the procedure by the front pointing viewing element 116a (FIG. 2B). This substantially increases the performance of the endoscope. Moreover, the two front working channels may be used simultaneously for medical procedures. An example of such a procedure may include surgery that requires stitching which can more easily be performed using two tools from two channels.

Another example of simultaneous usage of two working channels may include cleaning of the colon. A common problem exists when physicians find out that the patient's colon is not sufficiently clean. In such cases, the physician can try to clean the colon part using the "jet" exiting from the front part of the tip and in bad cases the physician is forced to send the patient home and reschedule his/her appointment. According to embodiments of the specification, the two channels can be used simultaneously for cleaning. For example, a cleaning fluid (such as water or water with air) may be inserted through one working channel and suctioned out from a second working channel. This may allow a better cleaning procedure that may solve or mitigate the problem of less efficient colonoscopies due to a non-cleaned colon.

In addition, a colonoscopy performed using a colonoscope according to embodiments of the specification may save the need of a cleaning procedure, currently performed by the patient him/herself, prior to colonoscopy.

Distal fluid channeling section 604a may further include a jet fluid channel 644 which may be configured for providing high pressure jet of fluid such as water or saline for cleaning the walls of the body cavity (such as the colon) and optionally for suction. Distal fluid channeling section 604a may further include an injector channel pathway 647 of fluid injector channel 646, which may be used for blending two fluids (like air and water) and convey the fluid blend into injector channel 646 which may be configured to inject the fluid blend and wash contaminants such as blood, feces and other debris from front optical assembly 256a (FIG. 2B) of front-pointing viewing element 116a (FIG. 2B).

Proximal fluid channeling section 602 of fluid channeling component 600 may include side injector channels 666a and 666b, which may be connected to a first side injector opening 266a and a second side injector opening (not visible, but present on the opposite side of opening 266a of FIG. 2B) respectively.

In accordance with another embodiment, the present specification provides an endoscope with a second front working/service channel in close proximity to a first front working/service channel. In an embodiment, the distance between the two front working/service channels provided ranges from 0.40 mm to 0.45 mm. In an embodiment, the two front working/service channels may be configured for insertion of medical tools allowing simultaneous operation for a specific treatment, such as, treating a tumor or polyp. In another embodiment, one or both of the front working/service channels may be adapted to allow for suction during a procedure.

Figure 7:
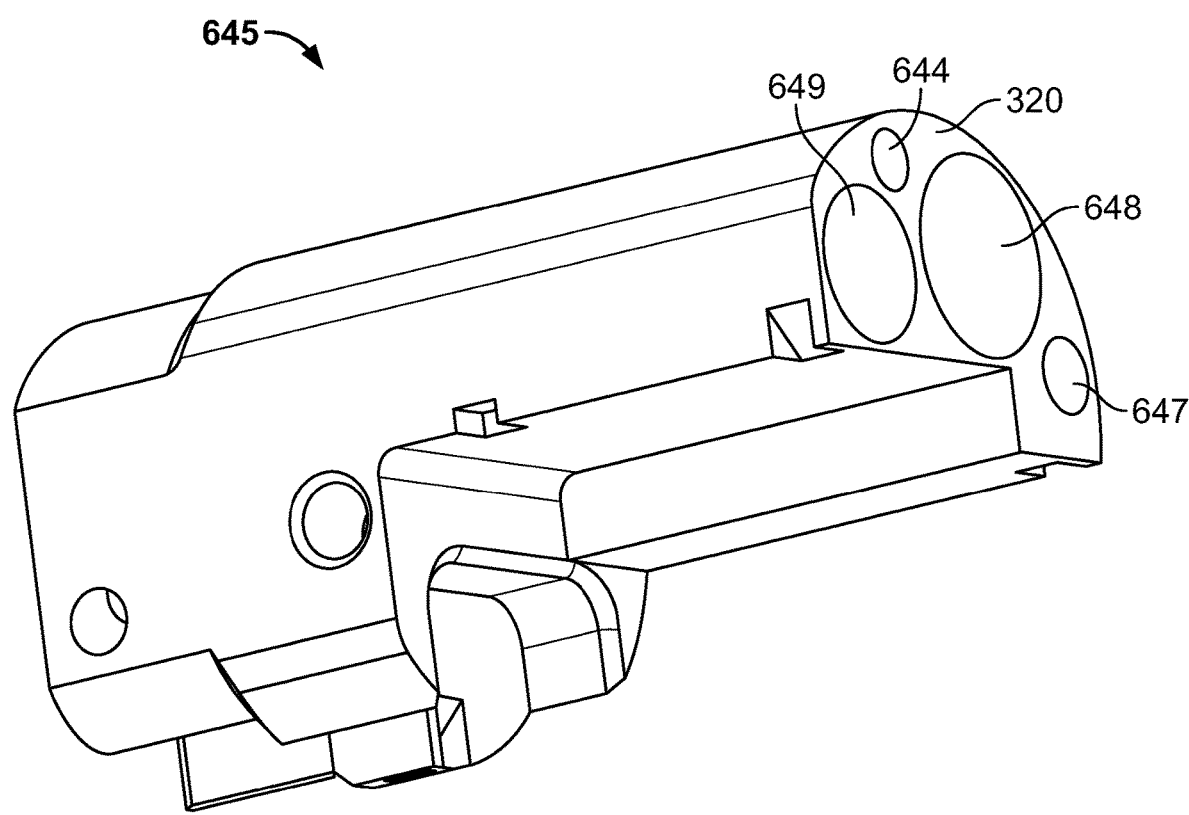
FIG. 7 illustrates a perspective view of a tip section of an endoscope assembly showing a fluid channeling component, in accordance with an embodiment of the present specification.

FIG. 7 illustrates a perspective view of a tip section of an endoscope assembly showing a fluid channeling component 645, in accordance with an embodiment of the present specification. As illustrated, the fluid channeling component 645 comprises a front panel 320 having a jet fluid channel

644, an injector channel pathway 647, a first front working/service channel 648 and a second front working/service channel 649. In one embodiment, the diameter of the first front working/service channel 648 is in a range of 3.6 mm to 4.0 mm and the diameter of the second front working/service channel 649 is in a range of 2.6 mm to 3.0 mm. In an embodiment, the diameters of the first and the second front working/service channels 648, 649 are 3.8 mm and 2.8 mm respectively.

Similar to FIG. 2A, according to some embodiments, the front panel 320 of the fluid channeling component 645 depicted in FIG. 7 comprises four quadrants defined by a vertical axis passing through a center of the front panel 320 and a horizontal axis passing through the center, wherein the four quadrants include a top left quadrant, a top right quadrant, a bottom left quadrant and a bottom right quadrant. In various embodiments, the first front working/service channel 648 includes an exit port positioned substantially within the top right quadrant of the front panel 320 and the second working/service channel 649 includes an exit port positioned substantially within the top left quadrant of the front panel 320.

Provision of the two front working/service channels may significantly improve the performance of the endoscope and allow the endoscope operator to perform more complex medical procedures using two medical tools. The second working/service channel provides the endoscope operator better access to an object of interest and greater flexibility with operating the medical tools while simultaneously viewing the procedure via the front-pointing viewing element. This substantially increases the performance of the endoscope. Moreover, the two front working/service channels may be used simultaneously for medical procedures. An example of such a procedure includes a surgery that requires stitching which can more easily be performed using two tools from two channels.

Another example employing simultaneous usage of two front working/service channels include cleaning of the colon. A common problem exists when physicians find out that the patient's colon is not sufficiently clean. In such cases, the physician can try to clean the colon part using the "jet" exiting from the front part of the tip. However, for cases in which the colon cannot be cleaned by the front jet, the physician is forced to send the patient home and reschedule his/her appointment. According to embodiments of the present specification, the two channels can be used simultaneously for cleaning. For example, a cleaning fluid (such as water or water with air) may be inserted through one service channel and suctioned out from a second service channel. This may allow a better cleaning procedure that may solve or mitigate the problem of less efficient colonoscopies due to a non-cleaned colon.

In addition, a colonoscopy performed using a colonoscope according to embodiments of the present specification may eliminate the need of a cleaning procedure, currently performed by the patient him/herself, prior to colonoscopy.

In addition, a gastroscopy performed using a gastroscope according to embodiments of the present specification may eliminate the need of a cleaning procedure, currently performed by the patient him/herself, prior to gastroscopy.

In an embodiment, the two front working/service channels are provided in a colonoscope with a front optical assembly and two side optical assemblies. In another embodiment, the two front working/service channels are provided in a gastroscope with a front optical assembly and one side optical assembly.

In accordance with some embodiments of the specification, there is provided a tip section of a multi-viewing element endoscope, the tip section comprising: a unitary fluid channeling component adapted to channel fluid for insufflation and/or irrigation (hereinafter abbreviated to 'I/I'), the unitary fluid channeling component comprising: a proximal opening adapted to receive a fluid tube, the proximal opening being in fluid flow connection with a front fluid channel and a side fluid channel, in accordance with an embodiment.

Figure 8:
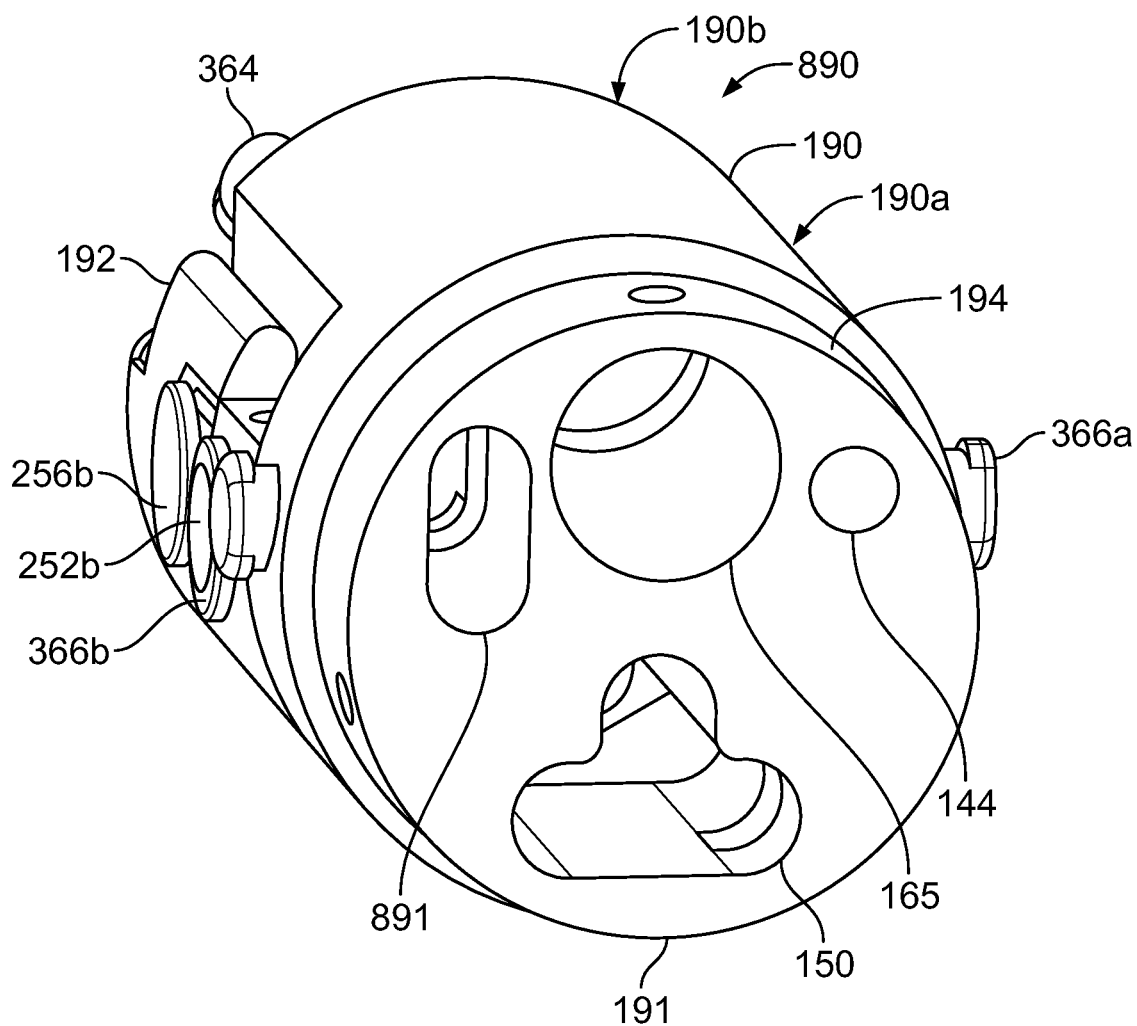
FIG. 8 schematically depicts an isometric proximal view of an inner part of an endoscope tip section according to an embodiment of the current specification.

FIG. 8 schematically depicts an isometric proximal view of an inner part of a tip section of an endoscope according to an exemplary embodiment of the current specification, showing the entrances of various channels in the inner part of a tip section.

Inner part 890 of a tip section is located within the tip section and may be used for holding in place the components of the endoscope's tip section such as injectors 364, 366a and 366b, viewing elements, lenses and other elements. A cover (not seen in this figure) is placed over inner part 890. Some elements, for example injectors 364, 366a, and 366b (and optionally side viewing element 256b) may be assembled after the cover is placed.

Inner part 890 of a tip section may comprise of several parts. In the depicted embodiment, inner part 890 of the tip section comprises: unitary fluid channeling component 190, central section 192 and front section 194 (also seen in FIGS. 9A, 9B below). Unitary fluid channeling component 190 may be made of a metal or any other material, such as a polymer, a composite material or any other appropriate material or combination of materials. Unitary fluid channeling component 190, according to some embodiments, may generally include two parts: a proximal fluid channeling component section 190a and a distal fluid channeling component section 190b. Proximal fluid channeling component section 190a may have an essentially cylindrical shape. Distal unitary channeling component section 190b may partially continue the cylindrical shape of proximal fluid channeling component section 190a and may have a shape of a partial cylinder (optionally elongated partial cylinder), having only a fraction of the cylinder (along the height axis of the cylinder), wherein another fraction of the cylinder (along the height axis of the cylinder) is missing.

Distal fluid channeling component section 190b may be integrally formed as a unitary block with proximal fluid channeling component section 190a. The height of distal fluid channeling component section 190b may be higher than that of proximal fluid channeling component section 190a. In the embodiment comprising distal fluid channeling component section 190b, the shape of the partial cylinder (for example, partial cylinder having only a fraction of a cylinder shape along one side of the height axis) may provide a space to accommodate central section 192. Central section 192 may include electronics and optical components, such as light means (LEDs for example), viewing elements (CCD or CMOS, for example), lenses, and other elements. This configuration of inner part 890 of the tip section may thus be adapted to separate the fluid channels and working channels, which are located in fluid channeling component 190 from the sensitive electronic and optical parts which are located in central section 192.

On the proximal surface 191 of unitary fluid channeling component 190 is proximal opening 144 of the jet fluid channel leading to a distal opening of the jet channel. Fluid tube (not shown in this figure for simplification purposes) may be inserted into, and affixed to the distal opening of the jet fluid channel. The jet fluid tube is threaded through a flexible shaft and is used for delivering fluid to the body cavity.

On the proximal surface 191 of unitary fluid channeling component 190 is proximal opening 165 of a working channel leading to distal opening 340 (FIG. 9B) of the working channel. Working channel tube/tools may be inserted into, and optionally affixed to proximal opening 165 of the working channel. The working channel is threaded through the flexible shaft and is used for delivering surgical tools to the body cavity. The working channel may also be used for suction of fluid from the body cavity.

On the proximal surface 191 of unitary fluid channeling component 190 is the electric cable opening 150 for an electrical cable. The electrical cable is connected at its distal end to the electronic components such as cameras and light sources in the endoscope's tip section. The electrical cable is threaded through the flexible shaft and is used for delivering electrical power and command signals to the tip section and transmitting video signal from the cameras to be displayed to the user.

Figure 9A:
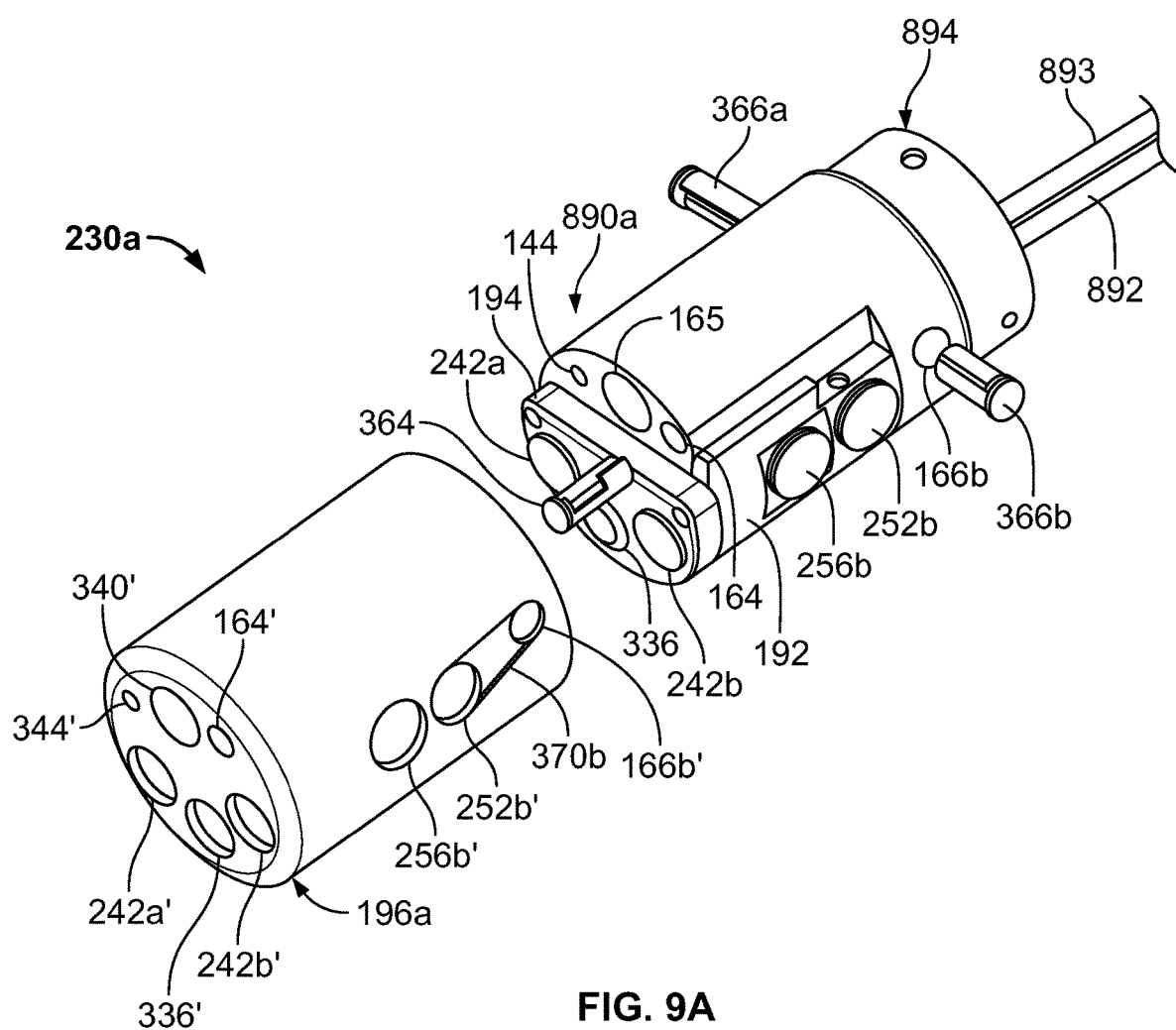
FIG. 9A schematically depicts a partially disassembled tip section of an endoscope having a insufflation and/or irrigation (I/I) channels manifold internal to a unitary fluid channeling component, according to a first embodiment of the current specification.

On the proximal surface 191 of unitary fluid channeling component 190 is the I/I tubes proximal opening 891 for gas tube 892 and liquid tube 893 (seen in FIG. 9A). Gas and fluid tubes may be inserted into, and affixed to proximal opening 110 of I/I channels manifold which delivers cleaning fluids to I/I injectors 364, 366a, and 366b. The gas and liquid tubes (such as gas tube 892 and liquid tube 893) may be threaded through the flexible shaft and are used for delivering fluid (gas and/or liquid) to I/I injectors 364, 366a, and 366b for cleaning the optical surfaces on the endoscope's tip section and for inflating a body cavity. The gas and liquid tubes (such as gas tube 892 and liquid tube 893) may also be combined into one tube and connected to the tip section as one tube.

It should be realized that it is important to keep the dimensions of the tip section of the endoscope small. Within the tight confines of the endoscope's tip section are the sensors, lenses, electric cables, at least one working channel, and a plurality of fluid channels. In contrast to endoscopes of the art, wherein each of the fluid tubes was directed to its destination, embodiments of the current specification provide I/I channels manifold to supply cleaning liquid and gas to the plurality of I/I injectors.

While FIG. 8 generically depicts the unitary fluid channeling component 190, and shows its proximal surface 191, the following figures depict some specific exemplary embodiments of the I/I channels manifolds and main bodies (such as cylinders), according to embodiments within the general scope of the current specification.

FIG. 9A schematically depicts a partially disassembled tip section 230a of an endoscope having I/I channels manifold internal to unitary fluid channeling component 894 according to a first exemplary embodiment of the current specification.

Cover 196a is designed to fit over inner part (of the tip section) 890a, and to provide protection to the internal components in the inner part. Holes 164', 340', 344', 242a', 336', 242b', 256b', 252b' and 166b' in cover 196a are aligned with the corresponding components and channel openings 164, 165, 144, 242a, 336, 242b, 256b, 252b and 366b in inner part 890a respectively. Optional groove 370b' in cover 196a enables cleaning fluid from injector 366b to arrive, and clean the front surface 252b of side looking viewing element. Not seen in this view are grooves and holes in cover 196a which are aligned with the corresponding components and channel openings on the other side of inner part 100a respectively.

After fitting and attaching cover 196a over inner part 890a, injectors 364, 366b and 366a may be inserted into the corresponding front opening 164, first side opening 166b and opposite side opening respectively, in unitary fluid channeling component 894 through the corresponding front hole 164', first side hole 166b' and opposite side hole respectively, in cover 196a. Preferably, injectors 364, 366a and 366b may be removed from their corresponding openings for cleaning the endoscope after use. Optionally, injectors 364, 366a and 366b may be replaceable or disposable. Optionally, nozzles, such as nozzle 348 (seen in FIGS. 2A and 2B) or any other nozzle, may be inserted into the unitary fluid channeling component, such as unitary fluid channeling component 894, within an isolating (e.g., plastic) part into the opening to allow better electric isolation, particularly when the unitary fluid channeling component and the nozzles are made of metal.

In the first exemplary embodiment of the current specification, front opening 164, first side opening 166b and the opening on the opposite side are connected to proximal opening 891 for gas tube 892 and liquid tube 893 via I/I manifold channels which are within unitary fluid channeling component 894. Distal opening 344' is the opening of a jet fluid channel which may be used for providing a high pressure jet of fluid, such as water or saline, for cleaning the walls of the body cavity (such as the colon) and optionally for suction.

Figure 9B:
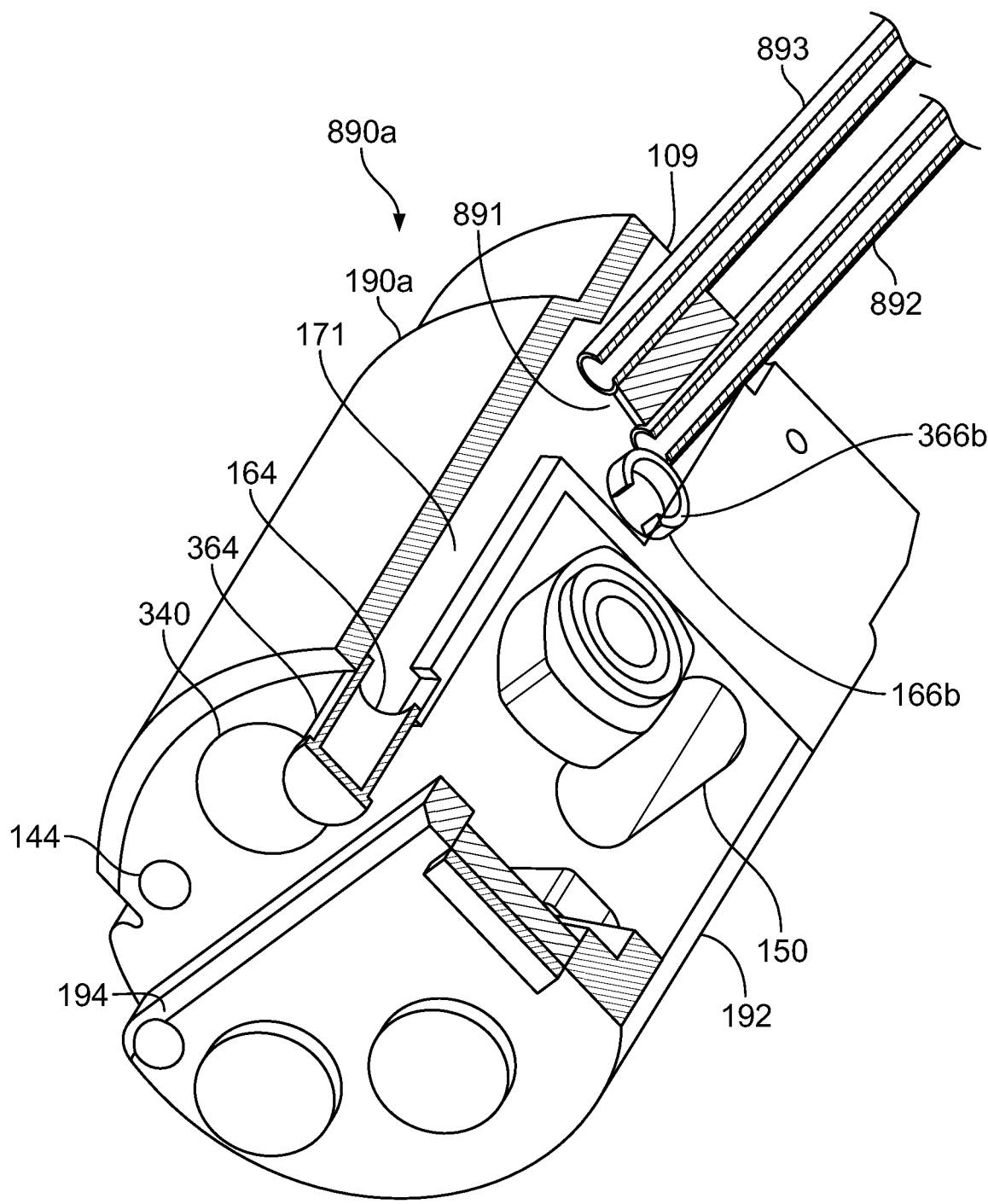
FIG. 9B schematically depicts an isometric cross section of an inner part of a tip section, having a I/I channels manifold internal to a unitary fluid channeling component, according to a first embodiment of the current specification.

FIG. 9B schematically depicts an isometric cross section of inner part 890a having I/I channels manifold internal to unitary fluid channeling component 894 according to a first exemplary embodiment of the current specification.

In the depicted embodiment, gas tube 892 and liquid tube 893 are terminated in a plug 109 adapted to fit into proximal opening 891. It should be noted that although gas tube 892 appears above liquid tube 893, their order may be reversed, they may be positioned side by side, or replaced with a single tube or the tubes may be joined to one tube before entering inner part 890a. Alternatively, each of gas tube 892 and liquid tube 893 is separately connected to unitary fluid channeling component 894, and their lumens open to a common conduit.

Proximal opening 891 for gas tube 892 and liquid tube 893 is opened to I/I channel manifold. This cross section shows proximal opening 891 opened to front channel 171 leading to front opening 164 into which front injector 364 is inserted. According to some embodiments, front channel 171 (may also be referred to as front fluid channel) may be drilled in unitary fluid channeling component 894. It should be noted that unitary fluid channeling component 894 and other parts of inner part 890a may be machined or be made by casting, sintering, injection or other manufacturing techniques.

Figure 9C:
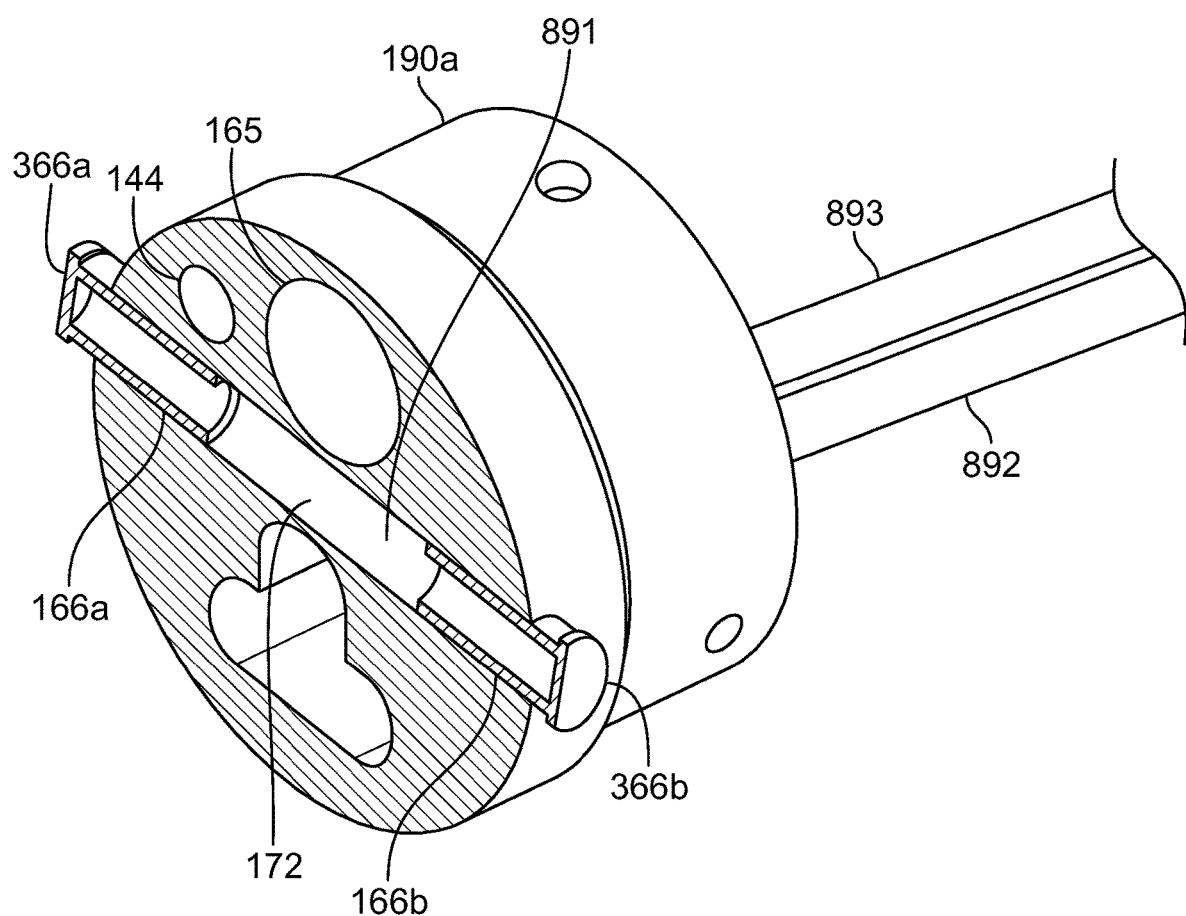
FIG. 9C schematically depicts an isometric cross section of a unitary fluid channeling component of an inner part of a tip section having a I/I channels manifold internal to the unitary fluid channeling component, according to a first embodiment of the current specification.
Figure 9D:
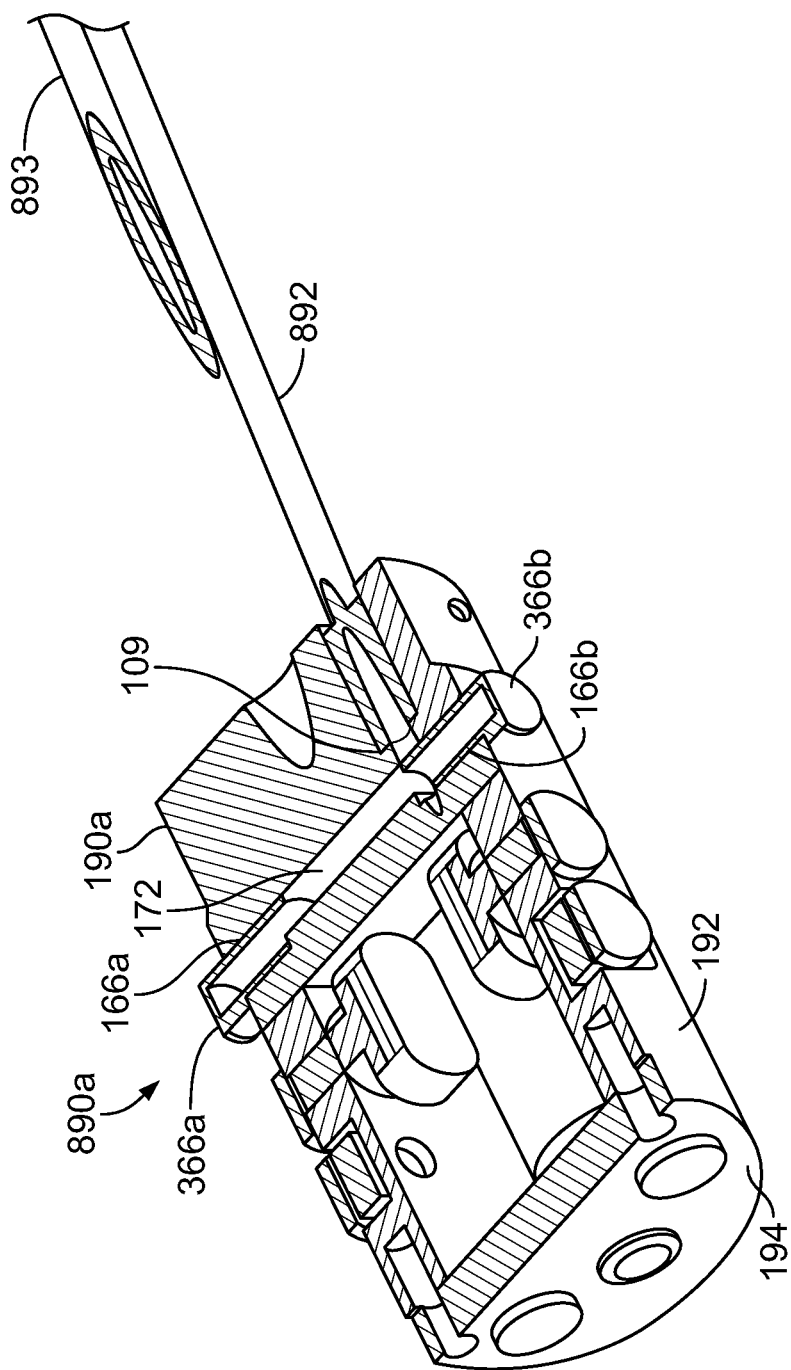
FIG. 9D schematically depicts another isometric cross section of an inner part of a tip section, showing the unitary fluid channeling component having a I/I channels manifold internal to it, according to a first embodiment of the current specification.

Reference is now made to FIG. 9C, which schematically depicts an isometric cross section of unitary fluid channeling component 894 having I/I channels manifold internal to it according to a first exemplary embodiment of the current specification and to FIG. 9D, which schematically depicts another isometric cross section of inner part 890a, showing unitary fluid channeling component 894 having I/I channels manifold internal to it according to a first exemplary embodiment of the current specification.

Proximal opening 891 for gas tube 892 and liquid tube 893 is seen in this figure opened to I/I channel manifold. This cross section shows proximal opening 891 opened to cross channel 172 (may also be referred to as side fluid channel or side channel) leading to left opening 166a into which left injector 366a is inserted and to right opening 166b into which right injector 366b is inserted.

According to some embodiments, cross channel 172 may be drilled in unitary fluid channeling component 894.

According to the first exemplary embodiment of the current specification, proximal opening 891 for gas tube 892 and liquid tube 893 is directly opened to I/I channel manifold, within unitary fluid channeling component 894 which comprises:

a) a right opening 166b, connected to proximal opening 891, and into which right injector 366b is inserted;
b) a front channel 171 connected to proximal opening 891, and leading to front opening 164 into which front injector 364 is inserted (as seen in FIG. 9B); and
c) a cross channel 172, connected to the proximal opening 891, and which is opened to left opening 166a into which left injector 366a is inserted.

Figure 10A:
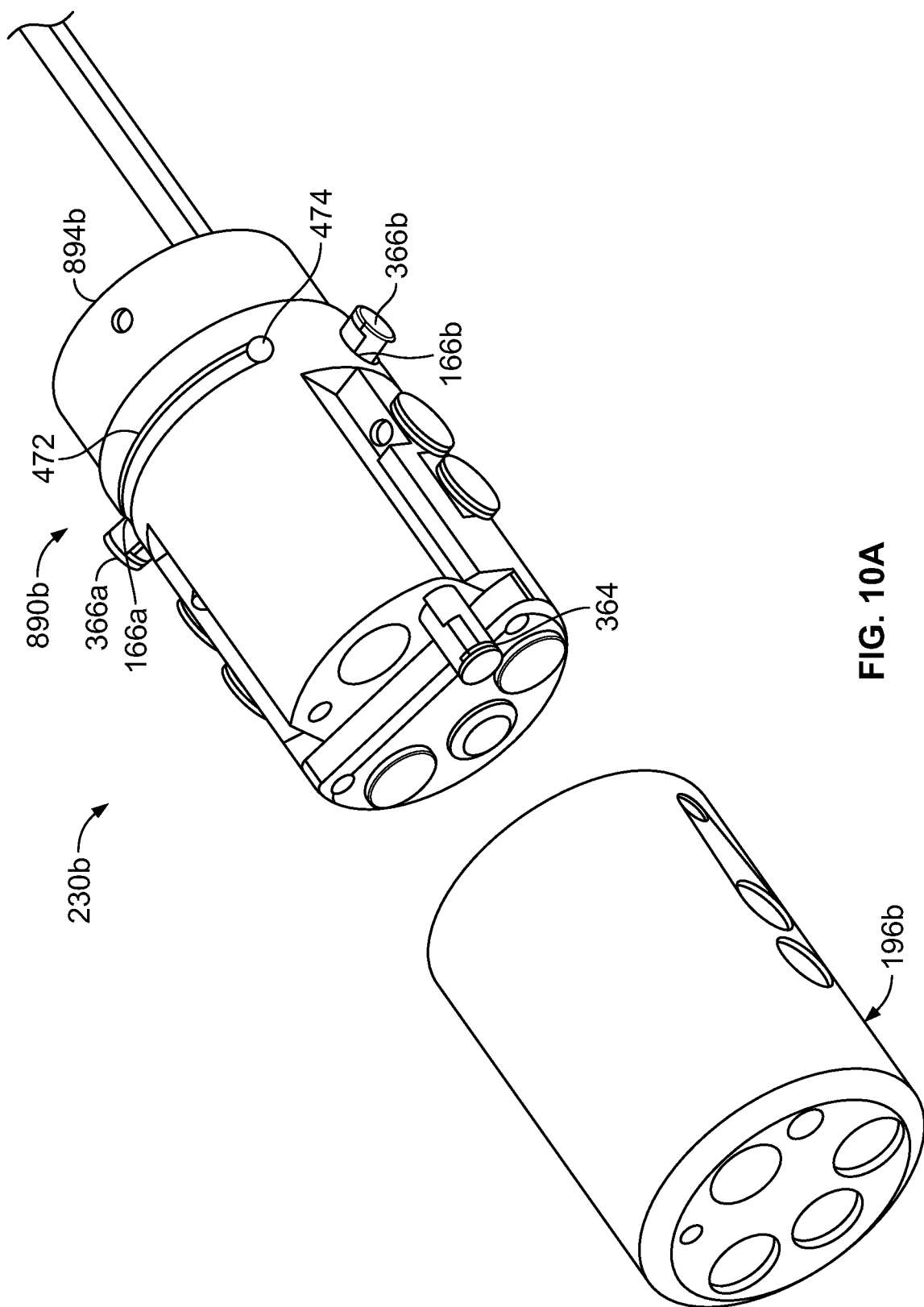
FIG. 10A schematically depicts an isometric view of a partially disassembled tip section of an endoscope having a I/I channels manifold partially internal and partially external to the unitary fluid channeling component of the tip section, according to a second embodiment of the current specification.

FIG. 10A schematically depicts an isometric view of a partially disassembled tip section 230b of an endoscope having I/I channels manifold partially internal and partially external to unitary fluid channeling component 894b according to a second exemplary embodiment of the current specification.

Figure 10B:
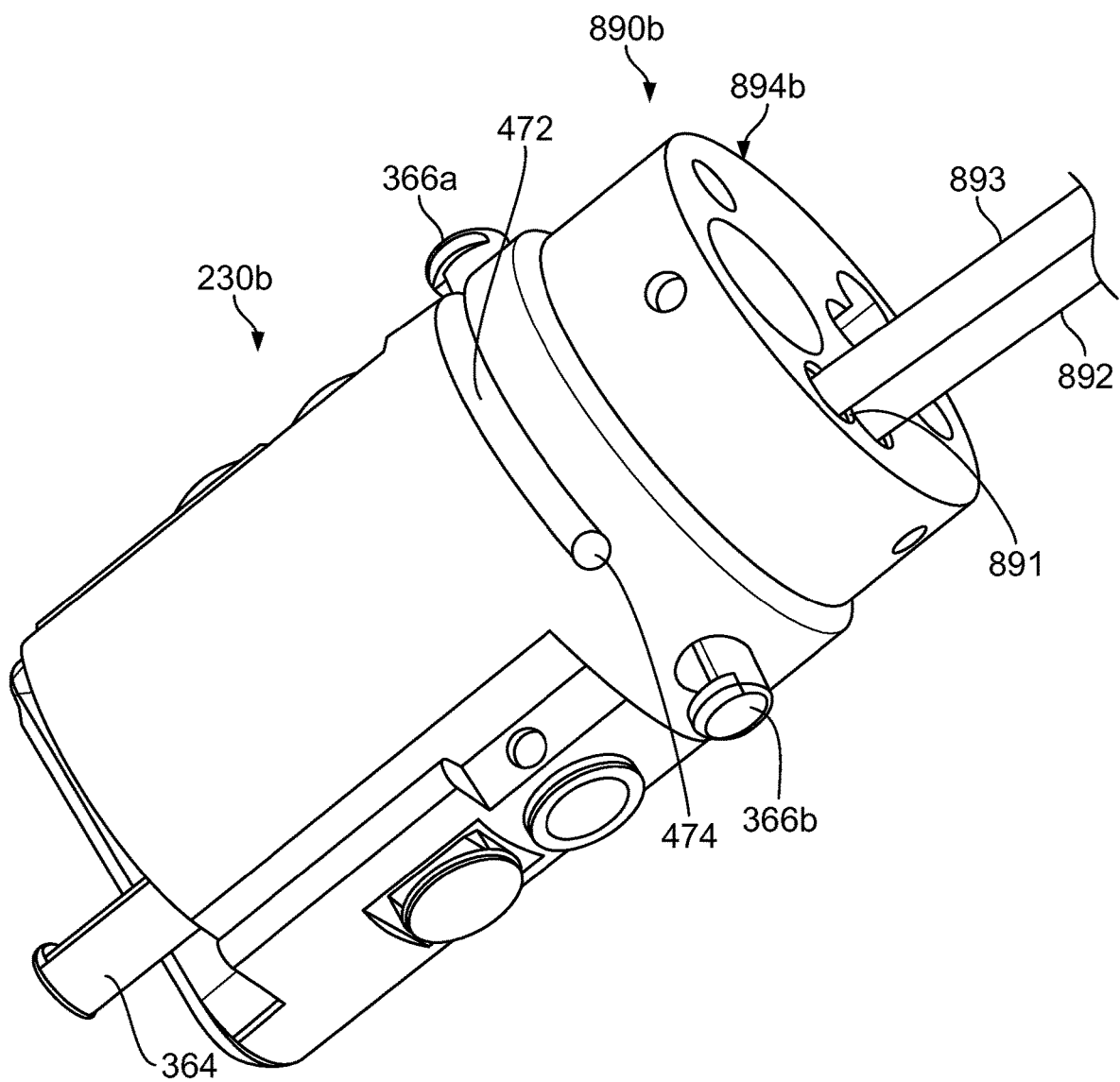
FIG. 10B schematically depicts an isometric view of an inner part of a tip section having a I/I channels manifold partially internal and partially external to the unitary fluid channeling component of the tip section, according to a second embodiment of the current specification.
Figure 10C:
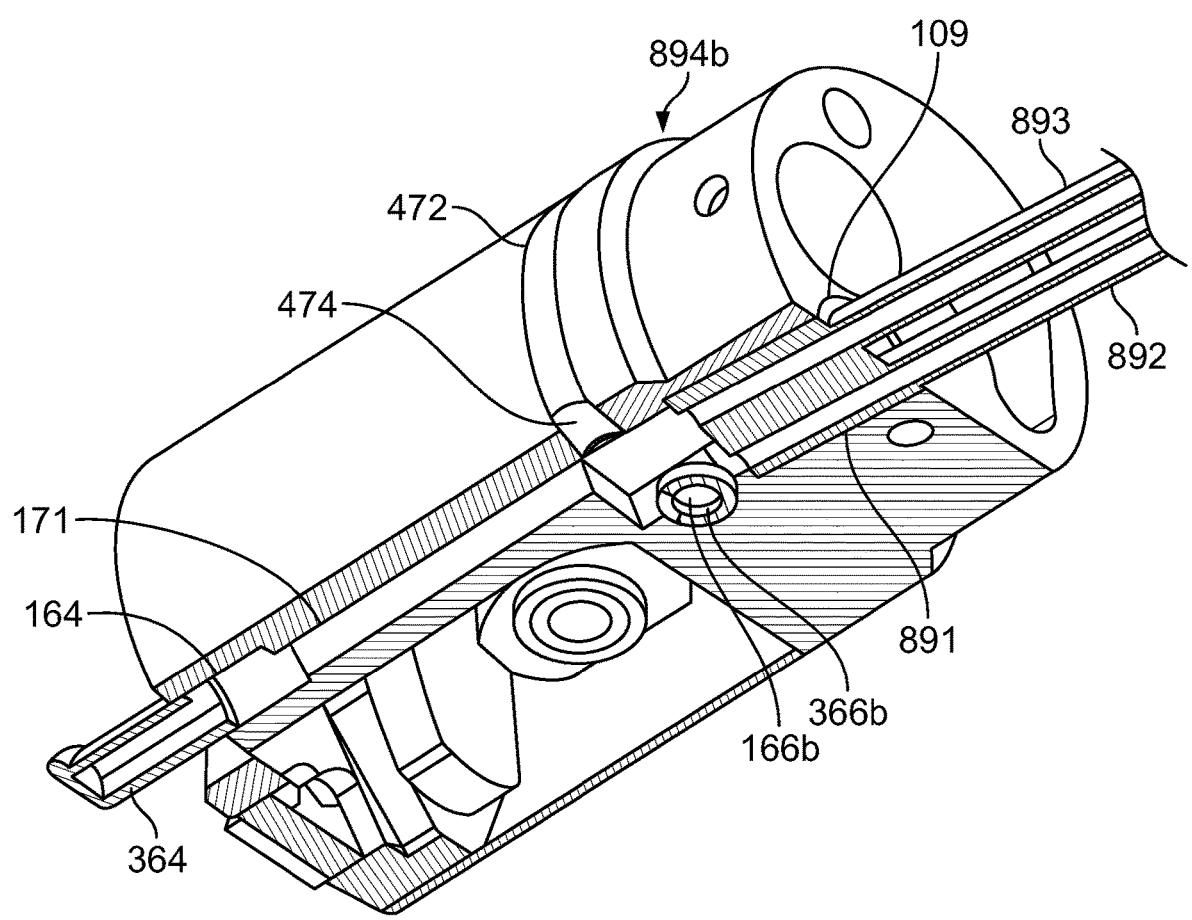
FIG. 10C schematically depicts an isometric cross section of the inner part of a tip section a having I/I channels manifold partially internal and partially external to the unitary fluid channeling component of the tip section, according to a second embodiment of the current specification.

In contrast to the first embodiment depicted in FIGS. 9A through 9D, in the embodiment depicted in FIGS. 10A through 10C, cleaning fluids are supplied to left injector 366a via a groove 472 in unitary fluid channeling component 894b. Groove 472 is connected in one side to proximal opening 891 by hole 474 and is opened to left opening 166a which can hardly be seen in this view.

Cover 196b is designed to fit over inner part 890b, and to provide protection to the internal components of inner part 890b. Additionally, cover 196b is tightly fitted and preferably hermetically seals groove 472 to convert it to a fluid tight conduit.

FIG. 10B schematically depicts an isometric view of inner part 890b of an endoscope tip section having I/I channels manifold partially internal and partially external to unitary fluid channeling component 894b according to a second exemplary embodiment of the current specification.

FIG. 10C schematically depicts an isometric cross section of unitary fluid channeling component 894b according to the second exemplary embodiment of the current specification.

According to the second exemplary embodiment of the current specification, proximal opening 891 for gas tube 892 and liquid tube 893 is seen in this figure opened to I/I channel manifold which comprises:

a) a right opening 166b, connected to proximal opening 891, into which right injector 366b is inserted;
b) a front channel 171 connected to front opening 164 into which front injector 364 is inserted; and
c) hole 474 connected to groove 472 which is opened to left opening 166a (seen in FIG. 10A) into which left injector 366a (seen in FIG. 10A) is inserted.

Figure 11A:
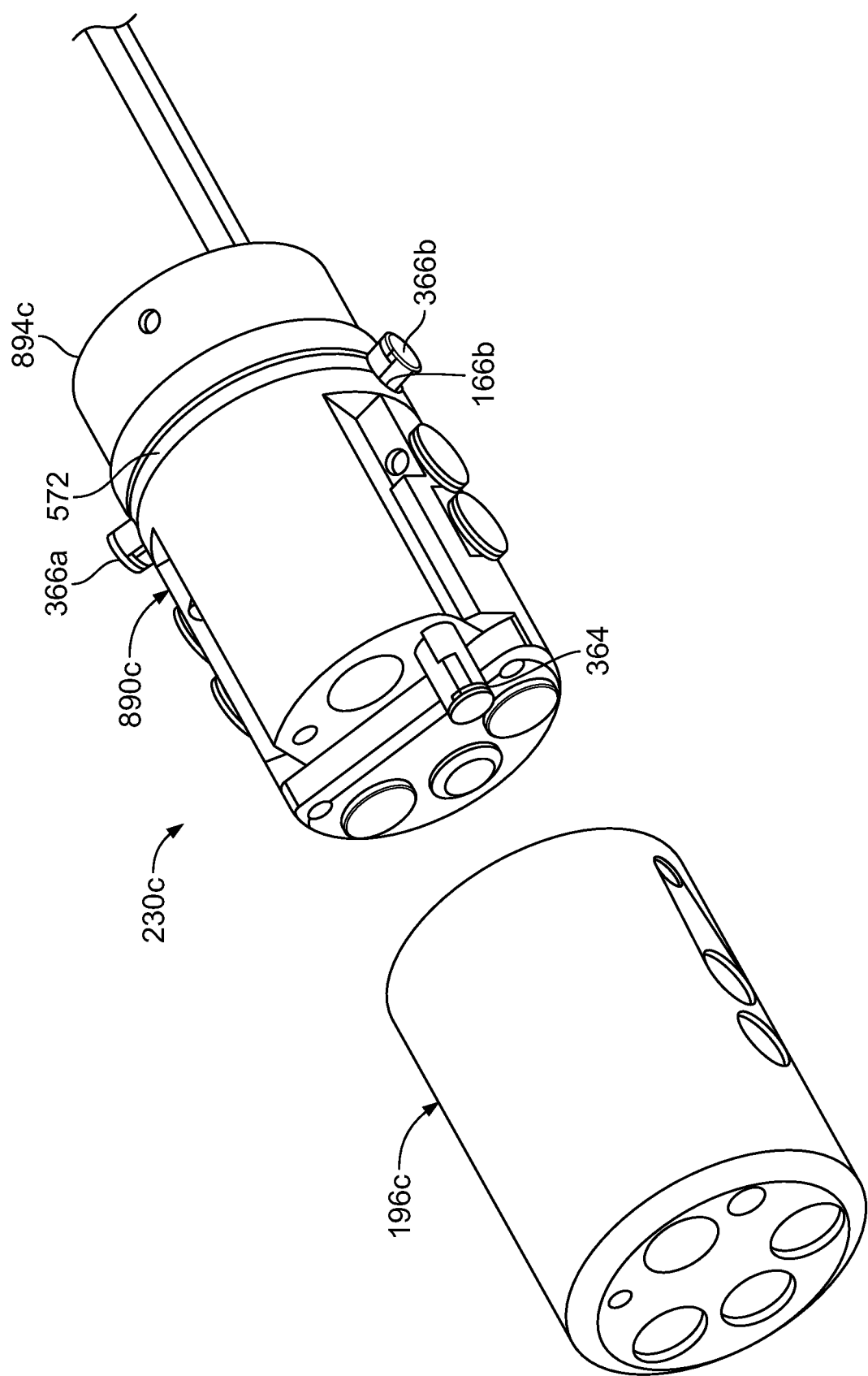
FIG. 11A schematically depicts an isometric view of a partially disassembled tip section of an endoscope having a I/I channels manifold partially internal and partially external to the unitary fluid channeling component of the tip section, according to a third embodiment of the current specification.

FIG. 11A schematically depicts an isometric view of a partially disassembled tip section 230c of an endoscope having I/I channels manifold partially internal and partially external to unitary fluid channeling component 894c according to a third exemplary embodiment of the current specification.

In contrast to the first embodiment depicted in FIGS. 9A through 9D, in the embodiment depicted in FIGS. 11A through 11D, fluids (liquid and/or gas) are supplied to left injector 366b via a groove 572 in unitary fluid channeling component 894c. However, in contrast to the second embodiment, depicted in FIGS. 10A through 10C, groove 572 is connected in the right side to right opening 166b and opened on the left to left opening 166a which can hardly be seen in this view.

Cover 196c is designed to fit over inner part 890c, and to provide protection to the internal components of inner part 890c. Additionally, cover 196c is tightly fitted and preferably hermetically seals groove 572 to convert it to a fluid tight conduit.

Figure 11B:
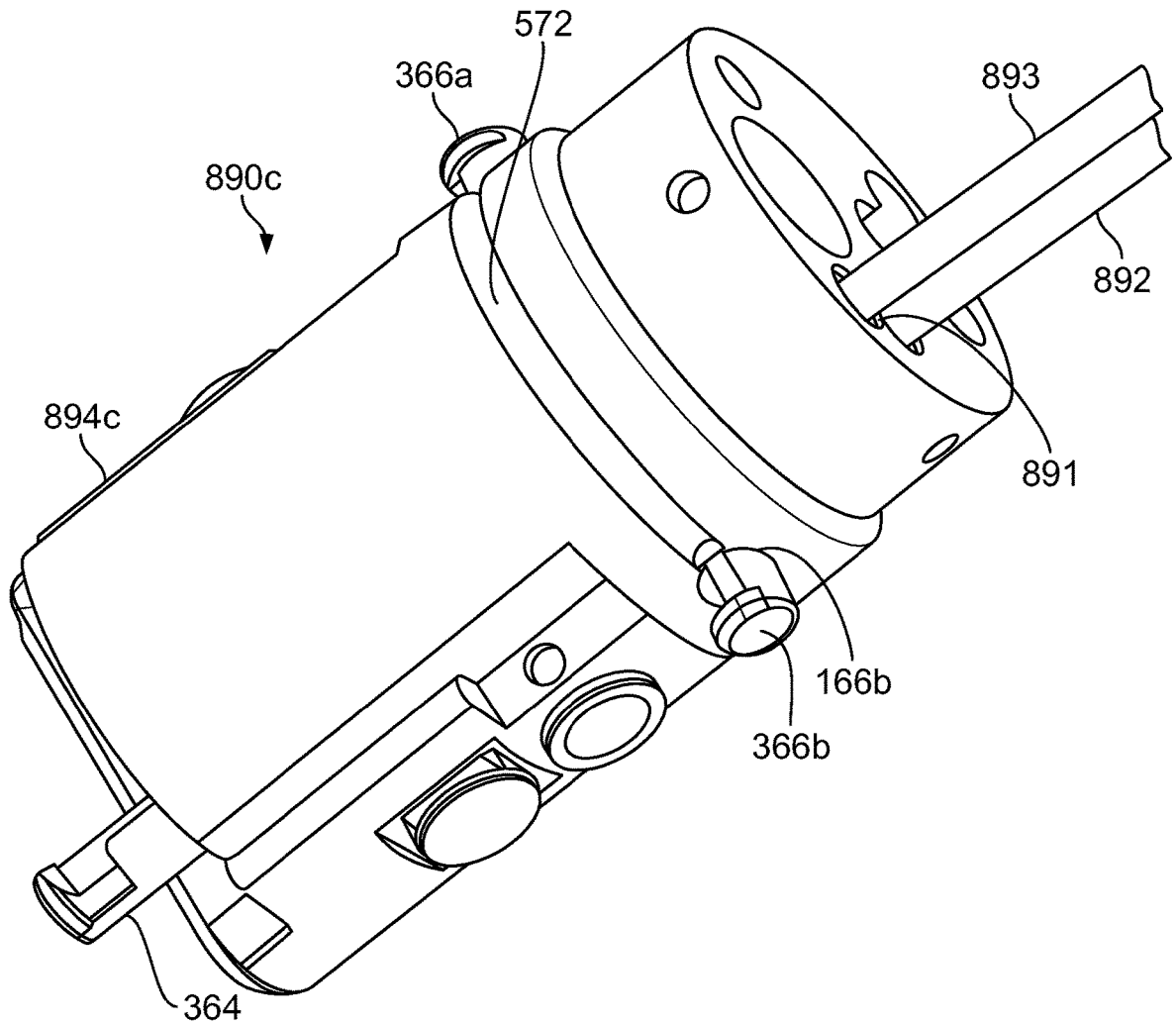
FIG. 11B schematically depicts an isometric view of an inner part of a tip section having a I/I channels manifold partially internal and partially external to a unitary fluid channeling component of the inner part of the tip section, according to a third embodiment of the current specification.

FIG. 11B schematically depicts an isometric view of inner part 890c of an endoscope tip section having I/I channels manifold partially internal and partially external to unitary fluid channeling component 894c according to a third exemplary embodiment of the current specification.

It should be noted that the location of groove 572 on surface of unitary fluid channeling component 894c, and its depth and shape may be different.

Figure 11C:
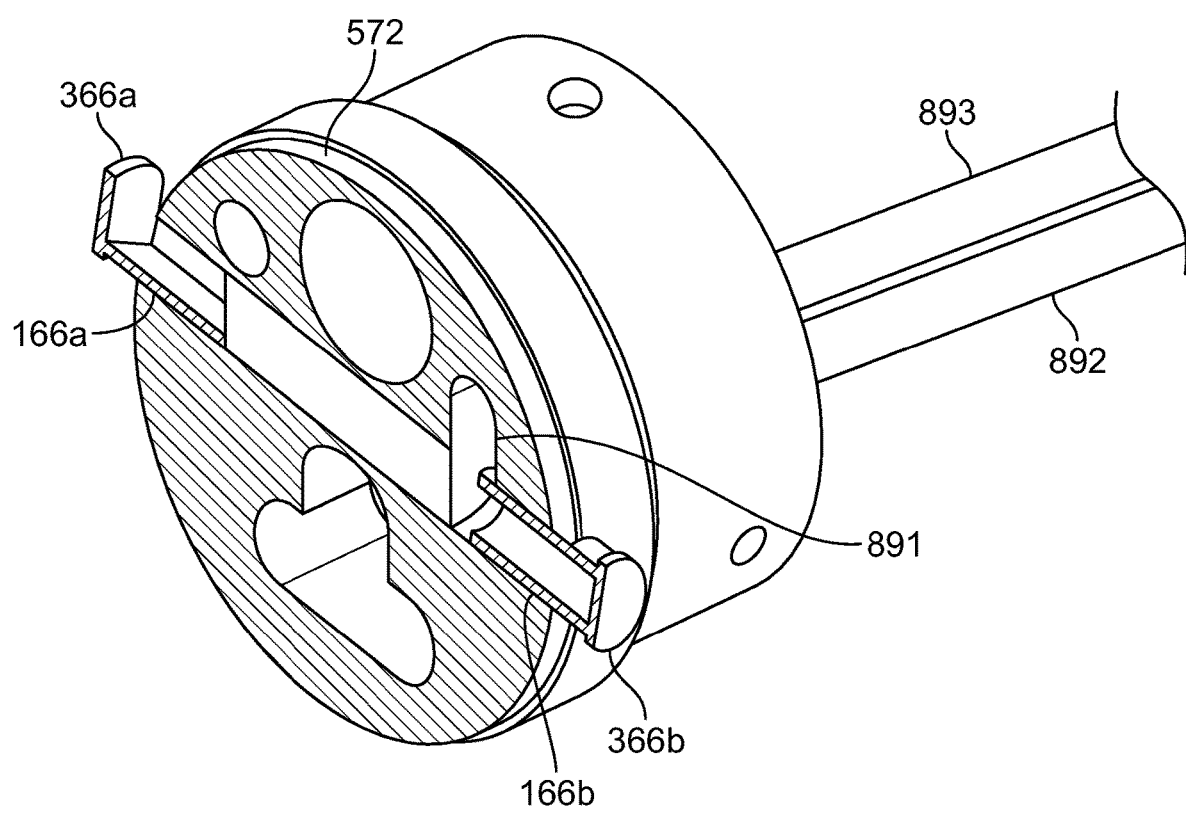
FIG. 11C schematically depicts an isometric cross section of the unitary fluid channeling component, according to a third embodiment of the current specification.

FIG. 11C schematically depicts an isometric cross section of unitary fluid channeling component 894c according to the third exemplary embodiment of the current specification.

Proximal opening 891 for gas tube 892 and liquid tube 893 is seen in this figure opened to right opening 166b and through it to groove 572 leading to left opening 166a.

Figure 11D:
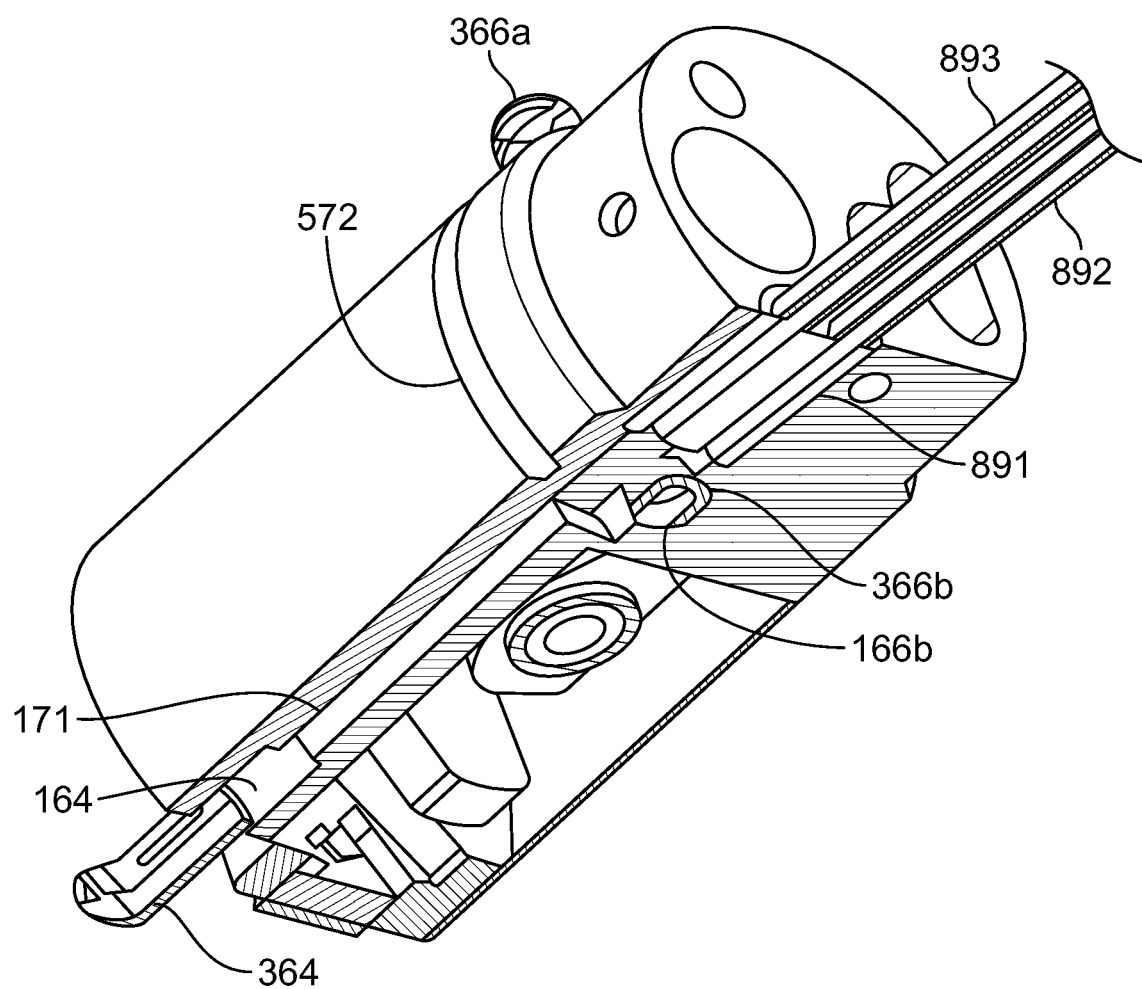
FIG. 11D schematically depicts another isometric cross section of an inner part of a tip section having a I/I channels manifold partially internal and partially external to a unitary fluid channeling component of the inner part of the tip section, according to a third embodiment of the current specification.

FIG. 11D schematically depicts another isometric cross section of unitary fluid channeling component 894c according to the third exemplary embodiment of the current specification.

Proximal opening 891 for gas tube 892 and liquid tube 893 is seen in this figure opened to right opening 166b and through it to I/I manifold which comprises:

a) a right opening 166b, connected to proximal opening 891, into which right injector 366b is inserted;
b) a front channel 171, connected to proximal opening 891, and leading to front opening 164 into which front injector 364 is inserted; and
c) a groove 572 which receives cleaning fluids from right opening 166b, and is opened to left opening 166a (seen in FIG. 11C) into which left injector 366a is inserted.

Figure 12A:
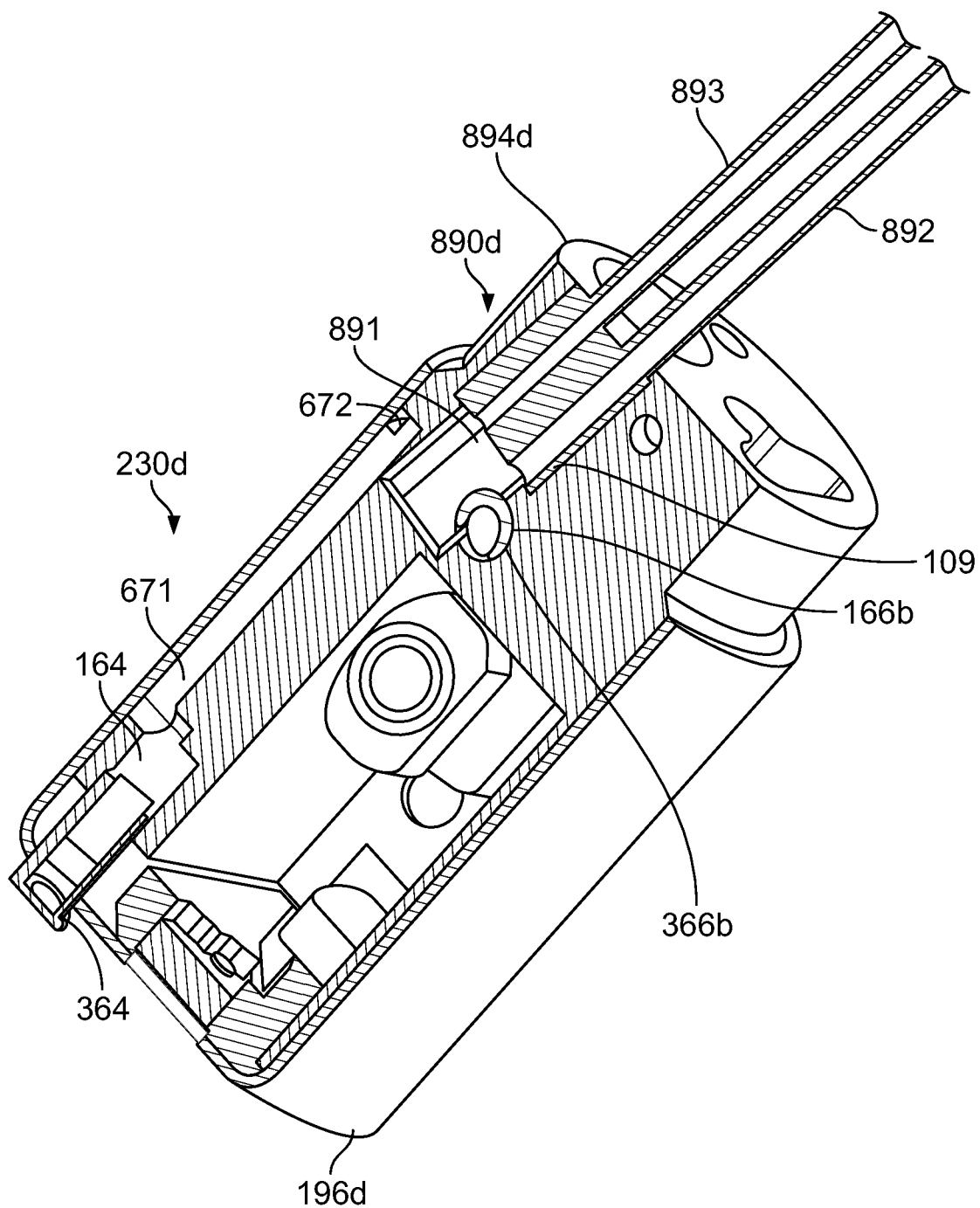
FIG. 12A schematically depicts an isometric cross section view of an assembled tip section of an endoscope a having I/I channels manifold external to a unitary fluid channeling component of the inner part of the tip section, according to a fourth embodiment of the current specification.

FIG. 12A schematically depicts an isometric cross section view of an assembled tip section 230d of an endoscope having I/I channels manifold external to unitary fluid channeling component 894d according to a fourth exemplary embodiment of the current specification.

Figure 12B:
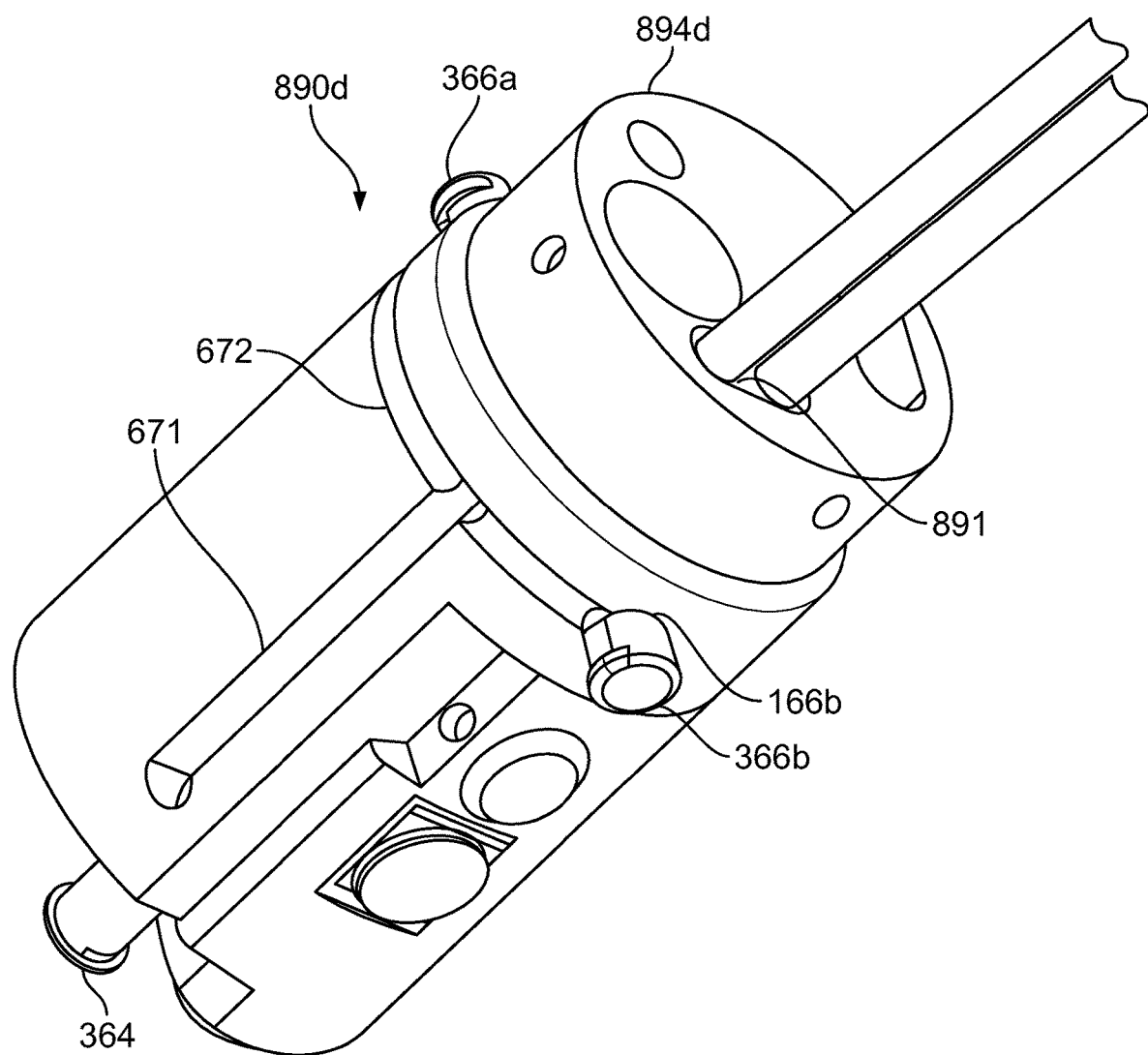
FIG. 12B schematically depicts an isometric view of an inner part of a tip section having a I/I channels manifold external to the unitary fluid channeling component, according to a fourth embodiment of the current specification.
Figure 12C:
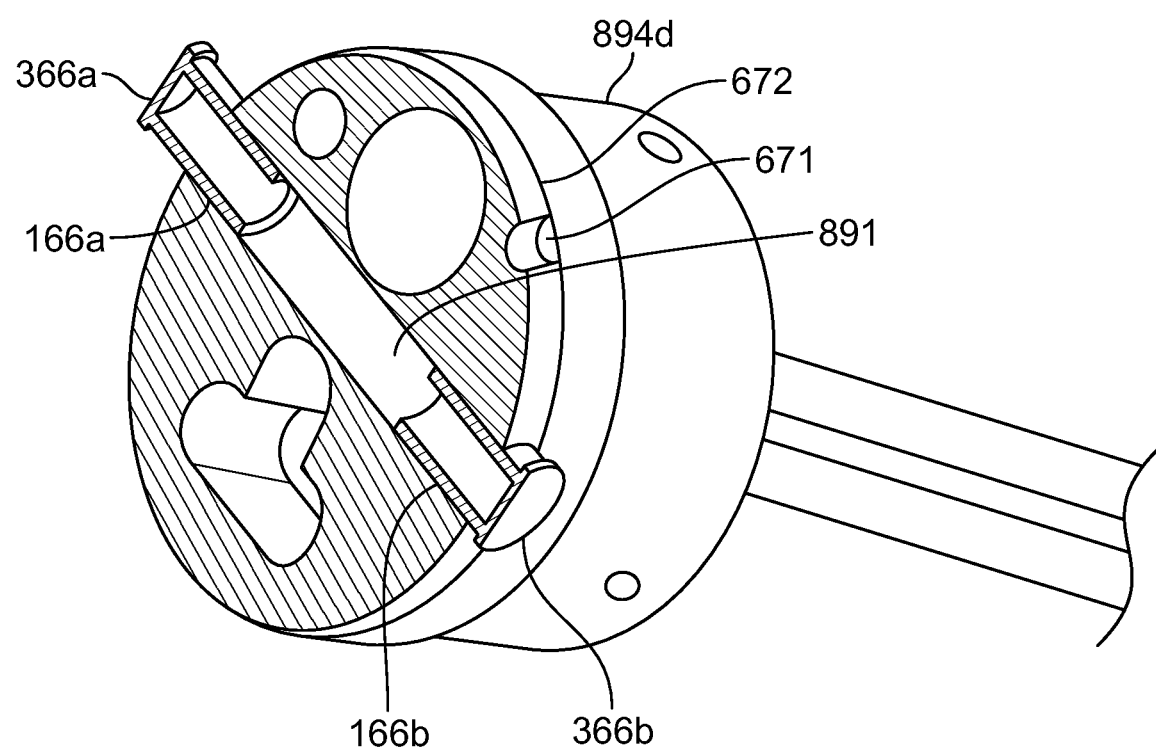
FIG. 12C schematically depicts an isometric cross section of a unitary fluid channeling component, according to a fourth embodiment of the current specification.

Similar to the third embodiment depicted in FIGS. 11A through 11D, groove 672 is connected in the right side to right opening 166b and opened on the left to left opening 166a (seen in FIG. 12C).

However, in contrast to the first, second and third embodiments depicted in FIGS. 9A through 9D, FIGS. 10A through 10C, and FIGS. 11A through 11D respectively, in the embodiment depicted in FIGS. 12A through 12C, fluids are supplied to front injector 364 via a front groove 671 in unitary fluid channeling component 894d. Front groove 671 is opened in its proximal end to groove 672, and at its distal end to front opening 164.

Cover 196d is designed to fit over inner part 890d, and to provide protection to the internal components of inner part 890d. Additionally, cover 196d is tightly fitted and preferably hermetically seals grooves 671 and 672 to convert them to fluid tight conduits.

FIG. 12B schematically depicts an isometric view of inner part 890d of an endoscope tip section having I/I channels manifold external to unitary fluid channeling component 894d according to a fourth exemplary embodiment of the current specification.

It should be noted that the location of grooves 671 and 672 on surface of unitary fluid channeling component 894d, and their depth and shape may be different. For example, the location of any of the grooves may be completely or partially inside the cover, for example, within the walls of the cover.

FIG. 12C schematically depicts an isometric cross section of unitary fluid channeling component 894d according to the fourth exemplary embodiment of the current specification.

Proximal opening 891 for gas tube 892 and liquid tube 893 is seen in this figure opened to right opening 166b and through it to groove 672 leading to left opening 166a. Also seen in this figure is the intersection of groove 672 and front groove 671.

According to the fourth embodiment of the current specification, proximal opening 891 for gas tube 892 and liquid tube 893 is opened to right opening 166b and through it to an I/I manifold which comprises:
a) a right opening 166b, connected to proximal opening 891, into which right injector 366b is inserted;
b) groove 672 which receives I/I fluids from right opening 166b, and is opened to left opening 166a into which left injector 366a is inserted; and
c) front groove 671, receiving I/I fluids from groove 672, and connected to front opening 164 (seen in FIG. 12A) into which front injector 364 (seen in FIGS. 12A and 12B) is inserted.

Figure 13A:
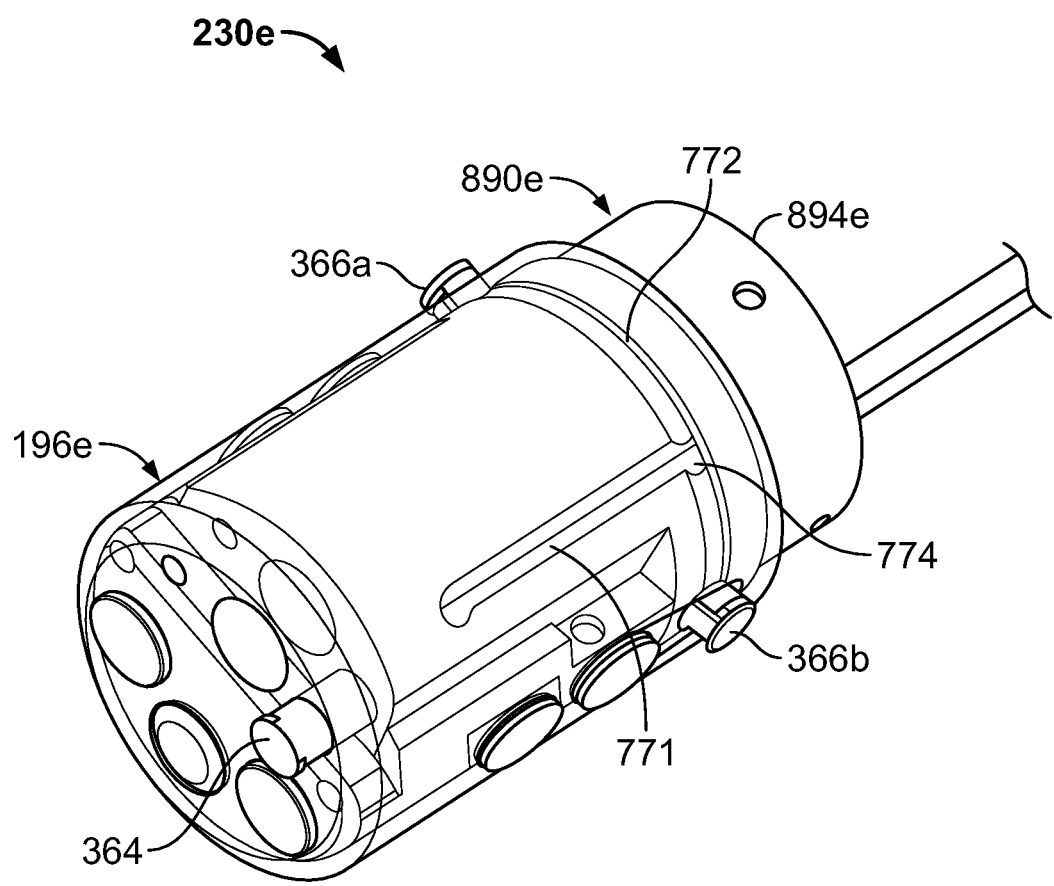
FIG. 13A schematically depicts an isometric view of an assembled tip section of an endoscope having a I/I channels manifold partially external to a unitary fluid channeling component of an inner part of the tip section, according to a fifth embodiment of the current specification.

FIG. 13A schematically depicts an isometric view of an assembled tip section 230e of an endoscope having I/I channels manifold partially external to unitary fluid channeling component 894e according to a fifth exemplary embodiment of the current specification.

For clarity, cover 196d was drawn partially transparent to show inner part 890e.

Figure 13B:
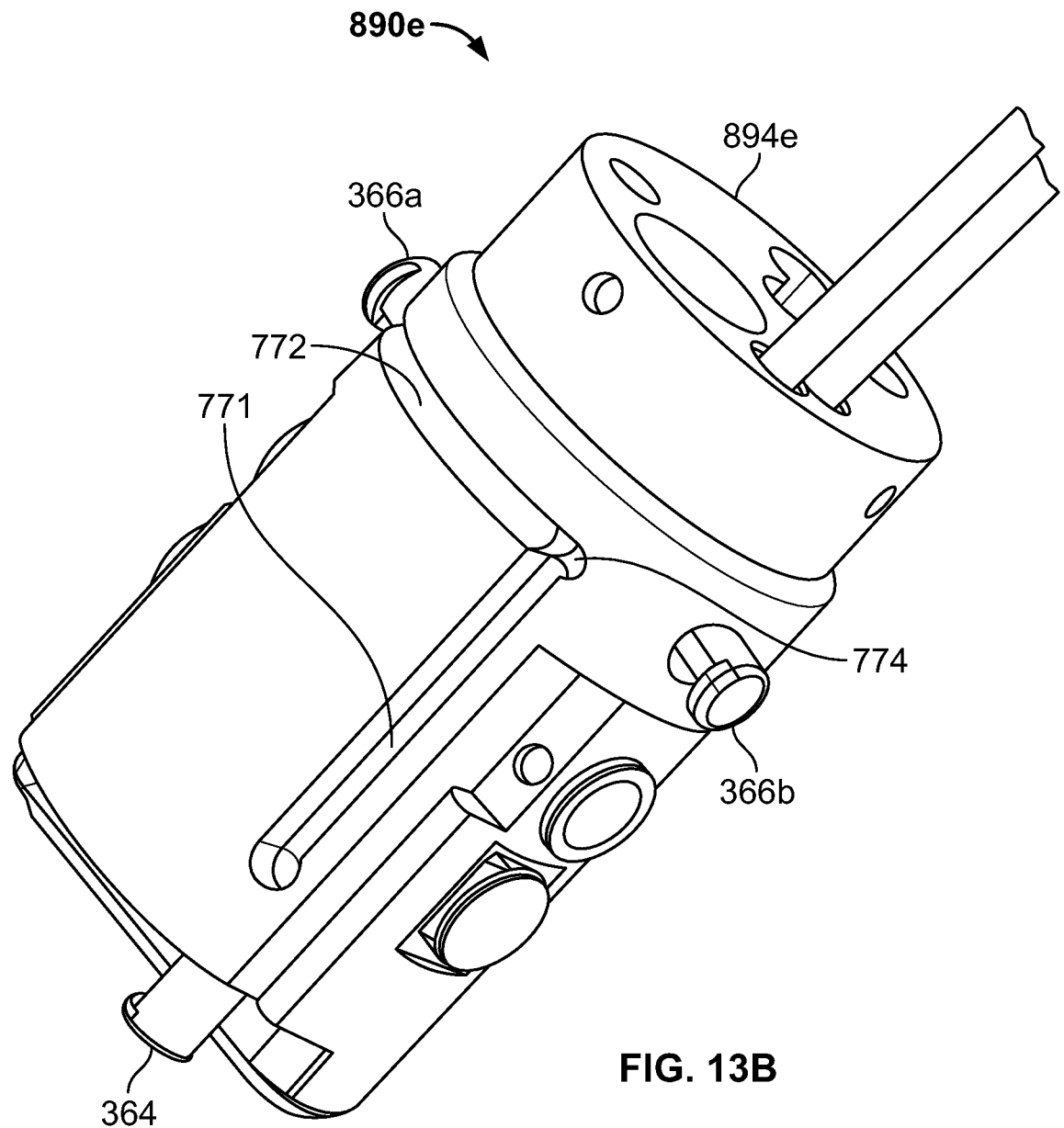
FIG. 13B schematically depicts an isometric view of an inner part of a tip section having a I/I channels manifold partially external to the unitary fluid channeling component, according to a fifth embodiment of the current specification.
Figure 13C:
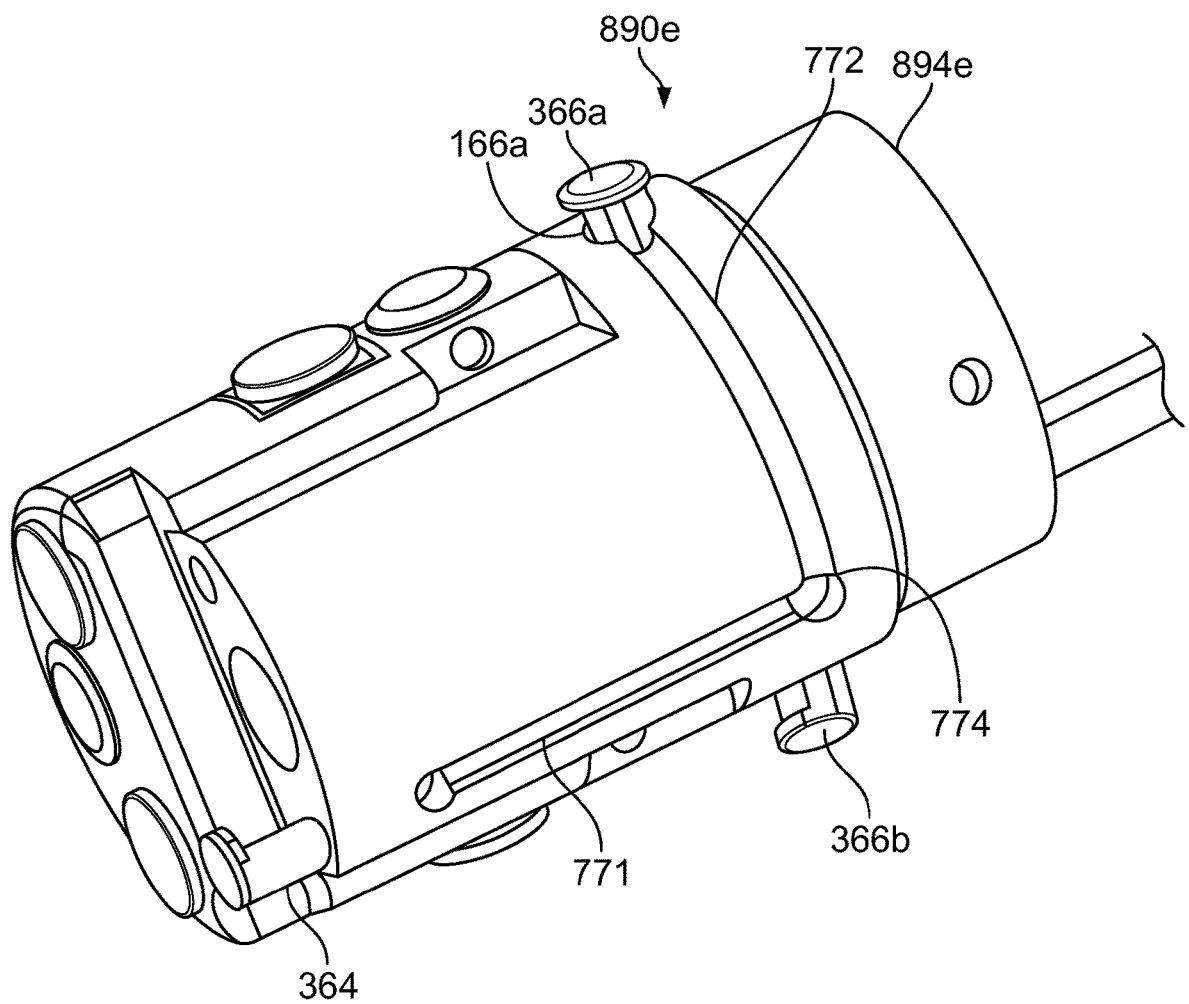
FIG. 13C schematically depicts another isometric view of an inner part of a tip section having a I/I channels manifold partially external to the unitary fluid channeling component, according to a fifth embodiment of the current specification.

Similar to the second embodiment depicted in FIGS. 10A through 10C, groove 772 is connected to proximal opening 891 (seen in FIG. 13D) by hole 774 and opened on the left to left opening 166a (seen in FIG. 13C).

Similar to the fourth embodiment depicted in FIGS. 12A through 12C, cleaning fluids are supplied to front injector 364 via a front groove 771 in unitary fluid channeling component 894e. Front groove 771 is opened in its proximal end to groove 772, and at its distal end to front opening 164 (seen in FIG. 13D).

Cover 196e is designed to fit over inner part 890e, and to provide protection to the internal components of inner part 890e. Additionally, cover 196e is tightly fitted and preferably hermetically seals grooves 771 and 772 to convert them to fluid tight conduits.

FIG. 13B schematically depicts an isometric view of inner part 890e of an endoscope tip section having I/I channels manifold partially external to unitary fluid channeling component 894e according to a fifth exemplary embodiment of the current specification.

It should be noted that the location of grooves 771 and 772 on surface of unitary fluid channeling component 190d, and their depth and shape may be different.

FIG. 13C schematically depicts another isometric view of inner part 890e of an endoscope tip section having I/I channels manifold partially external to unitary fluid channeling component 894e according to a fifth exemplary embodiment of the current specification.

Figure 13D:
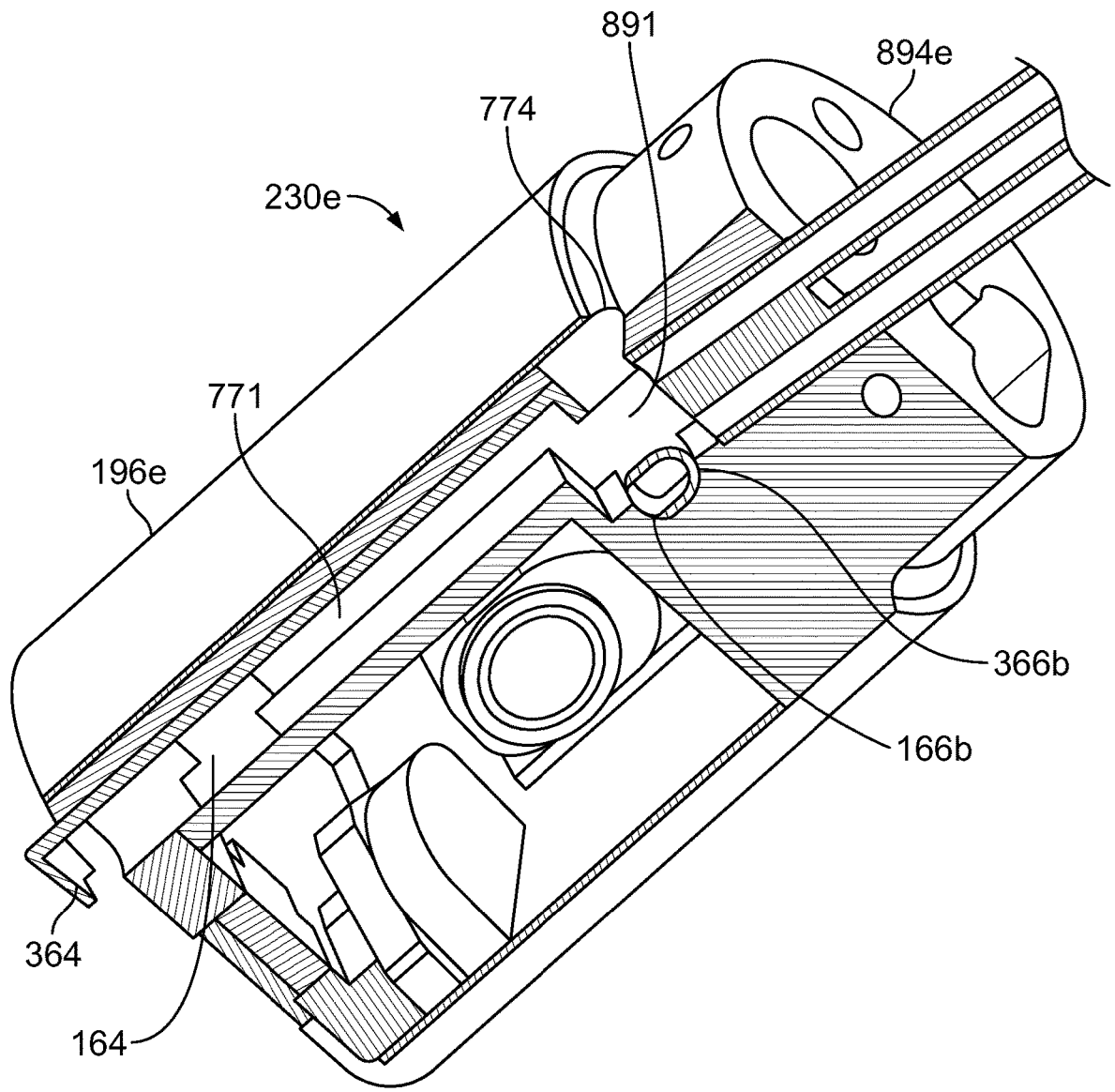
FIG. 13D schematically depicts an isometric cross section of an endoscope tip section according to a fifth embodiment of the current specification.

This embodiment depicts groove 772 connection to left opening 166a (seen in FIG. 13D).

FIG. 13D schematically depicts an isometric cross section of endoscope tip section 230e according to the fifth exemplary embodiment of the current specification.

Proximal opening 891 for gas tube 892 and liquid tube 893 is seen in this figure opened to right opening 166b. Also seen in this figure is hole 774 connecting proximal opening 891 to front groove 771 and the connection of front groove 771 to front opening 164.

According to the fifth embodiment of the current specification, proximal opening 891 for gas tube 892 and liquid tube 893 is opened to right opening 166b and through hole 774 to I/I manifold which comprises:
a) a right opening 166b, connected to proximal opening 891, into which right injector 366b is inserted;
b) groove 772 (seen in FIGS. 13A through 13C) which receives fluids via hole 774 connected to proximal opening 891, and is opened to left opening 166a (seen in FIG. 13C) into which left injector 366a (seen in FIGS. 13A through 13C) is inserted; and
c) front groove 771, receiving I/I fluids from hole 774, and connected to front opening 164 into which front injector 364b is inserted.

Figure 14A:
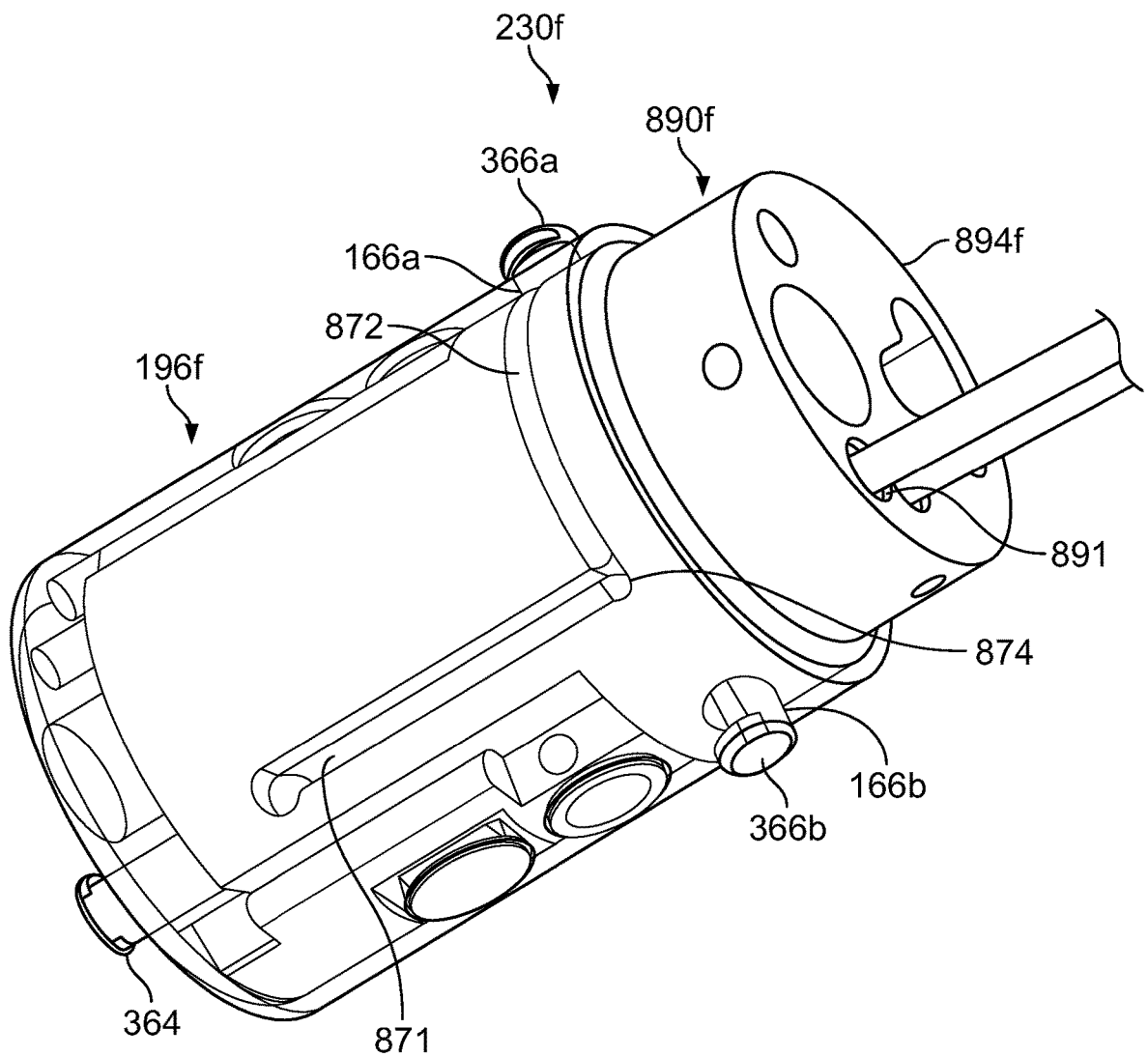
FIG. 14A schematically depicts an isometric view of an assembled tip section of an endoscope having a I/I channels manifold external to a unitary fluid channeling component of an inner part of the tip section, according to a sixth embodiment of the current specification.

FIG. 14A schematically depicts an isometric view of an assembled tip section 230f of an endoscope having I/I channels manifold external to unitary fluid channeling component 894f in inner part 890f according to a sixth exemplary embodiment of the current specification.

Similar to the fourth embodiment depicted in FIGS. 12A through 12C, groove 872 in unitary fluid channeling component 894f is connected in the right side to right opening 166b and opened on the left to left opening 166a.

Similar to the fourth embodiment depicted in FIGS. 12A through 12C, front groove 871 is connected in its proximal end to groove 872.

However, in contrast to the fourth embodiment, cleaning fluids are supplied to grooves 871 and 872 via hole 874, connecting them to proximal opening 891.

Cover 196f is designed to fit over inner part 890f, and to provide protection to the internal components of inner part 890f. Additionally, cover 196f is tightly fitted and preferably hermetically seals grooves 871 and 872 to convert them to fluid tight conduits.

Figure 14B:
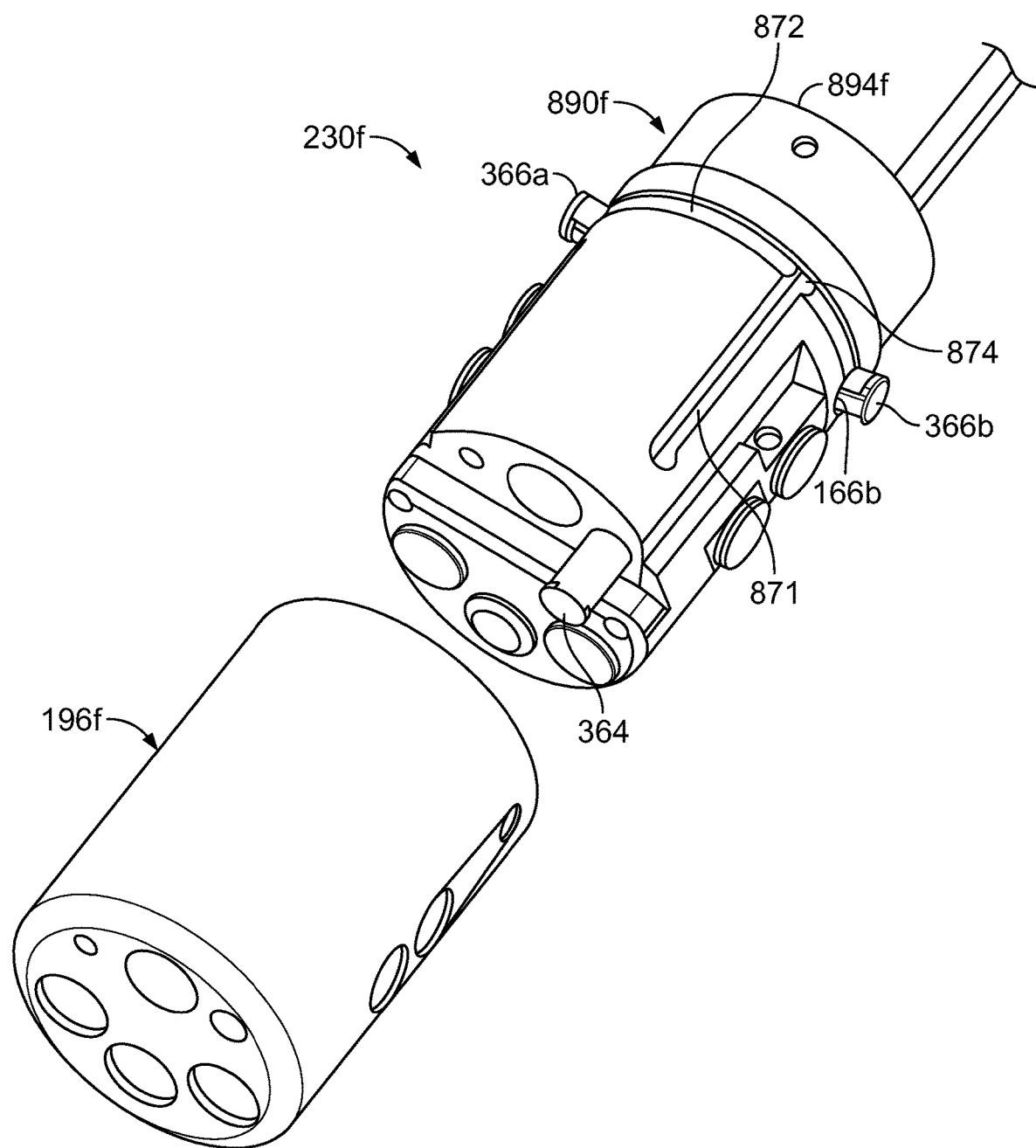
FIG. 14B schematically depicts an isometric view of a partially disassembled tip section of an endoscope having a I/I channels manifold external to the unitary fluid channeling component, according to a sixth embodiment of the current specification.

FIG. 14B schematically depicts an isometric view of a partially disassembled tip section 230f of an endoscope having I/I channels manifold external to unitary fluid channeling component 894f in inner part 890f according to a sixth exemplary embodiment of the current specification.

It should be noted that the location of grooves 871 and 872 on surface of unitary fluid channeling component 894d, and their depth and shape may be different.

According to the sixth embodiment of the current specification, proximal opening 891 (seen in FIG. 14A) for gas tube 892 and liquid tube 893 is connected to hole 874 and through it to an I/I manifold which comprises:
a) groove 872 which receives cleaning fluids from proximal opening 891 via hole 874 and is connected to right opening 166b into which right injector 366b is inserted;
b) same groove 872 connected to left opening, to which left injector 366a is inserted; and
c) front groove 871, receiving I/I fluids from groove 872, and connected to front opening into which front injector 364 is inserted.

It should be noted that optionally I/I injectors 336a and 336b, and optionally also 364 may be constructed as identical interchangeable inserts.

Figure 15A:
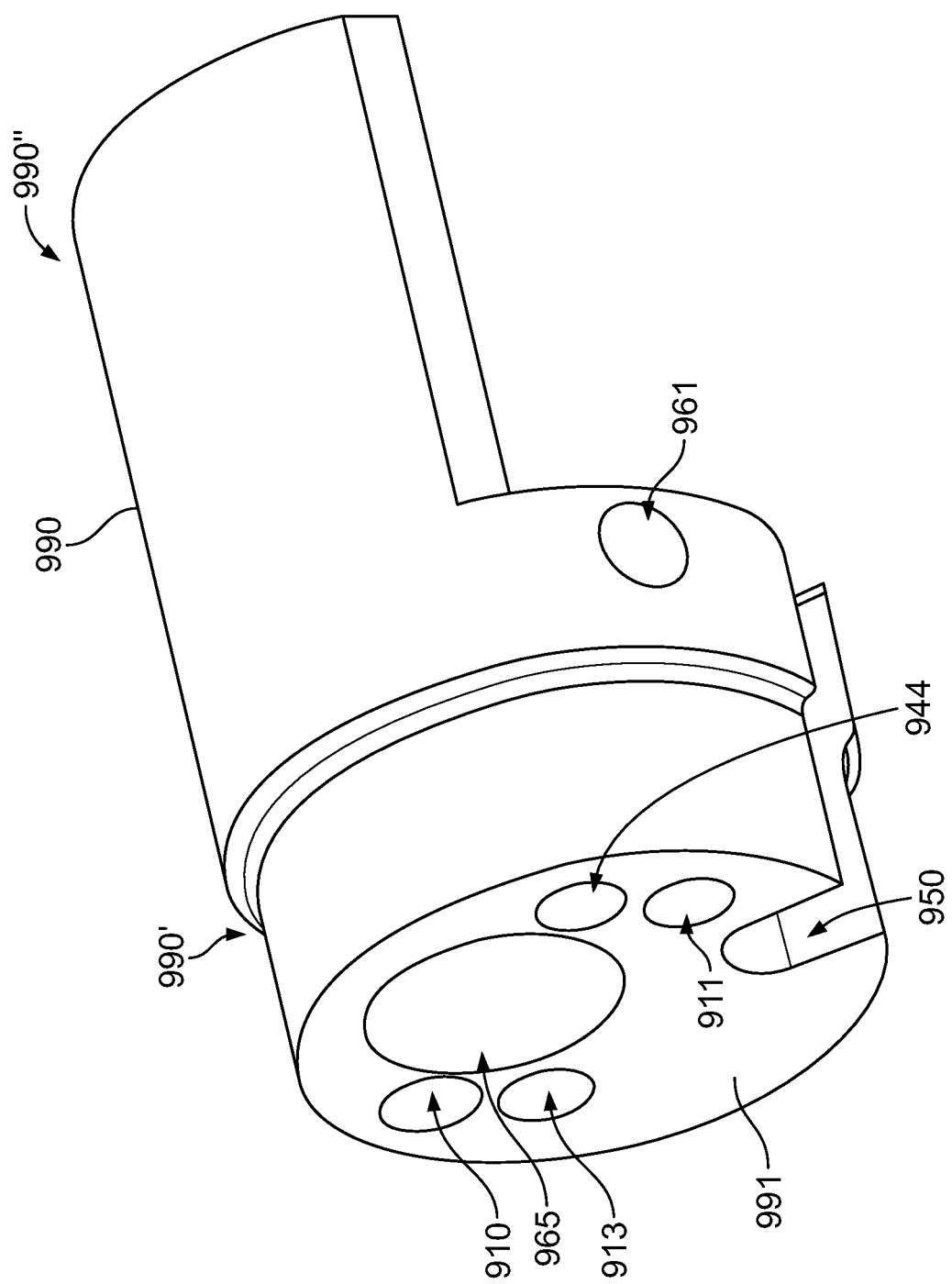
FIG. 15A schematically depicts an isometric proximal view of a main section of an inner part of an endoscope tip section, according to an embodiment of the current specification.
Figure 15B:
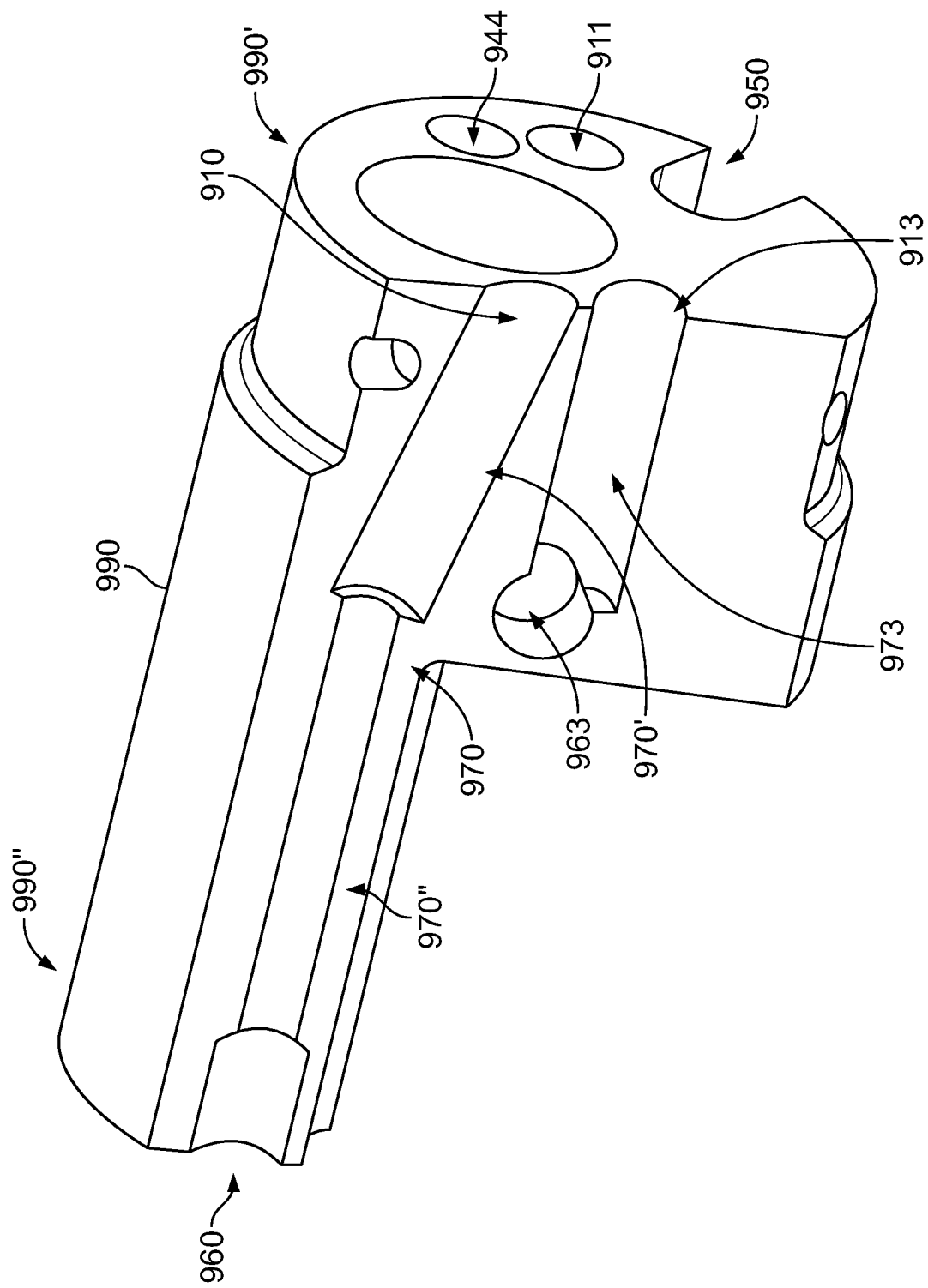
FIG. 15B schematically depicts an isometric cross section of the main section of FIG. 15A, according to an embodiment of the current specification.

Reference is now made to FIG. 15A which schematically depicts an isometric proximal view of a main section of an inner part of an endoscope tip section, according to an exemplary embodiment of the current specification and to FIG. 15B, which schematically depicts an isometric cross section of the main section of FIG. 15A, according to an exemplary embodiment of the current specification.

Unitary fluid channeling component 990 of an inner part of a tip section of an endoscope (such as a colonoscope) is configured to be located within the tip section and may be used for accommodating fluid channels, working channels and optionally cable channel/recess and for holding in place the components, such as tubing/tubes and injectors. Unitary fluid channeling component 990 may be a part of the inner part of the tip section in a similar manner to that described, for example, in FIG. 8.

Unitary fluid channeling component 990, according to some embodiments, may generally include two parts: a proximal fluid channeling component section 990' and a distal fluid channeling component section 990". Proximal fluid channeling component section 990' may have an essentially cylindrical shape. Distal fluid channeling component section 990" may partially continue the cylindrical shape of proximal fluid channeling component section 990' and may have a shape of a partial cylinder (optionally elongated partial cylinder), having only a fraction of the cylinder (along the height axis of the cylinder), wherein another fraction of the cylinder (along the height axis of the cylinder) is missing. Distal fluid channeling component section 990" may be integrally formed as a unitary block with proximal fluid channeling component section 990'. The height of distal fluid channeling component section 990" may be higher than that of proximal fluid channeling component section 990'. In the embodiment comprising distal fluid channeling component section 990", the shape of the partial cylinder (for example, partial cylinder having only a fraction of a cylinder shape along one side of the height axis) may provide a space to accommodate a central section (not shown).

On proximal surface 991 of fluid channeling component 990 is proximal opening 944 of the jet fluid channel leading to distal opening of a jet channel (not shown). A jet fluid tube may be inserted through a flexible shaft and may be used for delivering fluid to, and optionally suction of fluid from the body cavity, for cleaning purposes.

On proximal surface 991 of unitary fluid channeling component 990 is proximal opening 965 of the working channel leading to a distal opening of the working channel (not shown).

Unitary fluid channeling component 990 includes groove 950 extending from proximal surface 991 along the length of proximal fluid channeling component section 990'. Groove 950 is adapted to guide (and optionally hold in place) an electric cable(s) which may be connected at its distal end to the electronic components such as viewing elements (for example, cameras) and/or light sources in the endoscope's tip section and deliver electrical power and/or command signals to the tip section and/or transmit video signal from the cameras to be displayed to the user. According to this embodiment, the electrical cable(s) do not have to be threaded through proximal fluid channeling component section 990' (which may be complicated) but can be simply placed in groove 950 and held by it.

On proximal surface 991 of unitary fluid channeling component 990 are I/I tubes proximal openings: front proximal opening 910; right side proximal opening 911; and left side proximal opening 913. Front proximal opening 910, right side proximal opening 911 and left side proximal opening 913 lead to front channel 970 (seen in FIG. 15B), right side channel, and left side channel 973, respectively. Front channel 970 extends from front proximal opening 910, through proximal fluid channeling component section 990' and distal fluid channeling component section 990" to front opening 960. Left side channel 973 extends from right proximal opening 913, through proximal fluid channeling component section 990' to left opening 963. Right side channel extends from right proximal opening 911, through proximal fluid channeling component section 990' to right opening, similar to the left side arrangement.

Front channel 970 may include two parts: a proximal part 970' (extending through proximal fluid channeling component section 990') and a distal part 970" extending through distal fluid channeling component section 990"). Proximal part 970' of front channel 970 is adapted to receive, through front proximal opening 910, tube 980 (shown in FIG. 15C) which is adapted to transfer fluid (liquid and/or gas) to front channel 970. Tube 980 may be divided at any point along its length (for example at junction 981) into two tubes, one adapted to transfer gas and the other adapted to transfer liquid (such as water).

Left side channel 973 may be adapted to receive, at its proximal part, through left side proximal opening 913, tube 982 (shown in FIG. 15C) which is adapted to transfer fluid (liquid and/or gas) to left side channel 973. Tube 982 may be divided at any point along its length (for example at junction 983) into two tubes, one adapted to transfer gas and the other adapted to transfer liquid (such as water).

Right side channel may be adapted to receive, at its proximal part, through right side proximal opening 911, tube 984 (shown in FIG. 15C) which is adapted to transfer fluid (liquid and/or gas) to right side channel. Tube 984 may be divided at any point along its length (for example at junction 985) into two tubes, one adapted to transfer gas and the other adapted to transfer liquid (such as water).

The endoscopist can thus decide which fluid (gas, liquid or both) he would like to pass through the I/I channel, which fluid, as mentioned herein, may be used for cleaning and/or insufflation purposes.

Figure 15C:
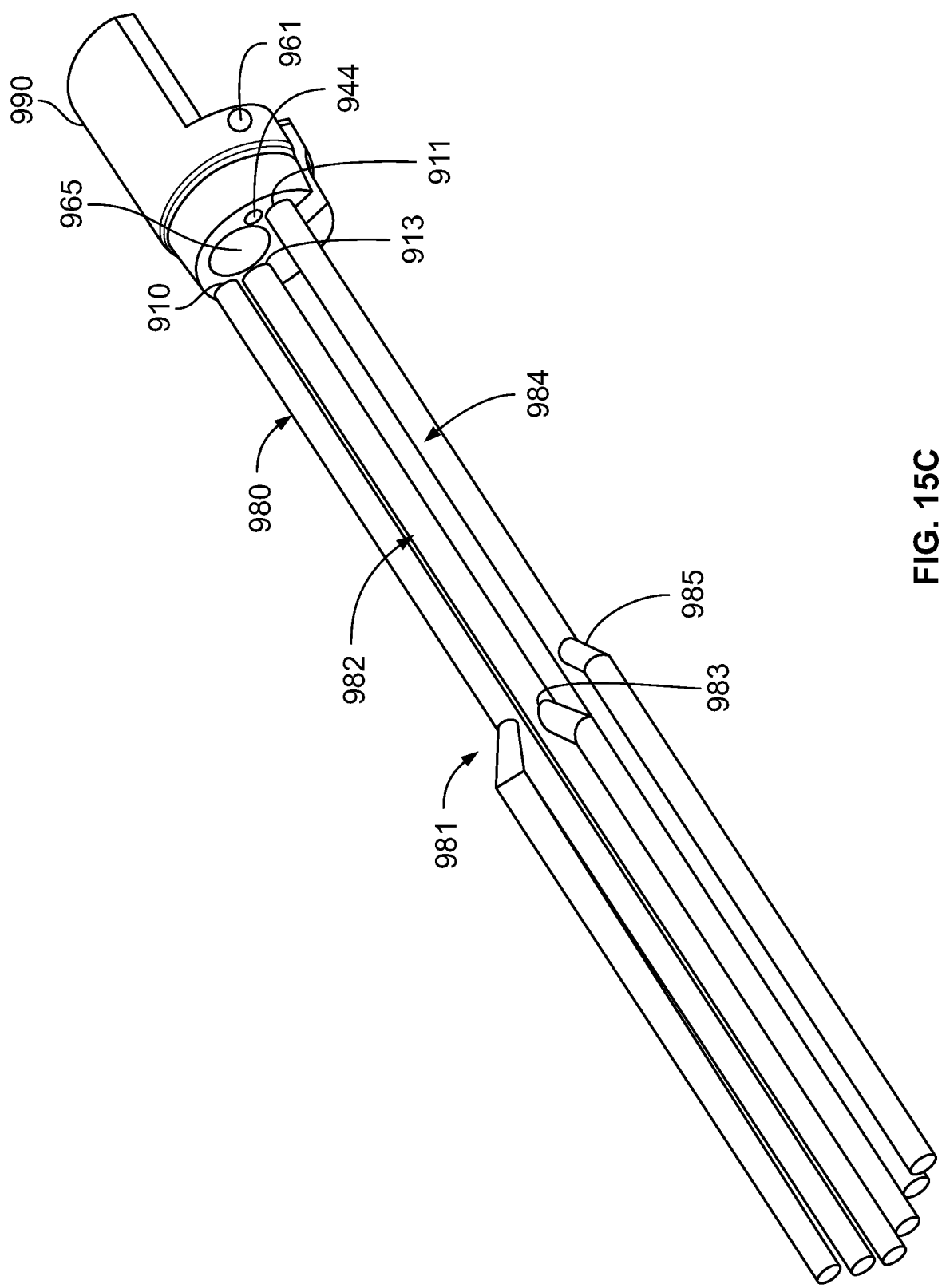
FIG. 15C schematically depicts an isometric proximal view of the main section of FIG. 15A, having liquid and gas tubes connected thereto, according to an embodiment of the current specification.

FIG. 15C schematically depicts an isometric proximal view of the main section of FIG. 15A, having liquid and gas tubes connected thereto, according to an exemplary embodiment of the current specification.

Referring back to FIG. 2A, electronic circuit board assembly 400 may be configured to carry a front looking viewing element 116, a first side looking viewing element and a second side viewing element 116*b* which may be similar to front looking viewing element 116 and may include a Charge Coupled Device (CCD) or a Complementary Metal Oxide Semiconductor (CMOS) image sensor.

Electronic circuit board assembly 400 may be configured to carry front illuminators 240*a*, 240*b*, 240*c*, which may be associated with front looking viewing element 116 and may be positioned to essentially illuminate the field of view of front looking viewing element 116.

In addition, electronic circuit board assembly 400 may be configured to carry side illuminators 250*a* and 250*b*, which may be associated with side looking viewing element 116*b* and may be positioned to essentially illuminate side looking viewing element's 116*b* field of view. Electronic circuit board assembly 400 may also be configured to carry side illuminators, which may be associated with the opposite side looking viewing element, which may be similar to side illuminators 250*a* and 250*b*.

Front illuminators 240*a*, 240*b*, 240*c* and side illuminators 250*a* and 250*b* may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally, in contrast to a non-discrete illuminator, which may be, for example, a fiber optic merely transmitting light generated remotely.

A significant problem exists in the art when attempts are made to pack all necessary components into the small inner volume of the endoscope. This problem dramatically increases when three viewing elements and respective illumination sources (such as LEDs) are packed in the tip of the endoscope. There is thus provided, according to some embodiments of the specification, a flexible electronic circuit for carrying and packing within the limited inner volume of the endoscope's tip, at least a front viewing element and one or more (for example two) side view viewing elements and their respective illumination sources.

According to some embodiments, the flexible circuit board consumes less space and leaves more volume for additional necessary features. The flexibility of the board adds another dimension in space that can be used for components positioning.

The use of the circuit board according to embodiments of the specification can significantly increase reliability of the electric modules connection thereto as no wires are for components connectivity. In addition, according to some embodiments, the components assembly can be machined and automatic.

The use of the circuit board, according to embodiments of the specification, may also allow components (parts) movement and maneuverability during assembly of the viewing element head (tip of the endoscope) while maintaining a high level of reliability. The use of the circuit board, according to embodiments of the specification, may also simplify the (tip) assembling process.

According to some embodiments, the flexible circuit board is connected to the main control unit via multi-wire cable; this cable is welded on the board in a designated location, freeing additional space within the tip assembly and adding flexibility to cable access. Assembling the multi-wire cable directly to the electrical components was a major challenge which is mitigated by the use of the flexible board according to embodiments of the specification.

Figure 16:
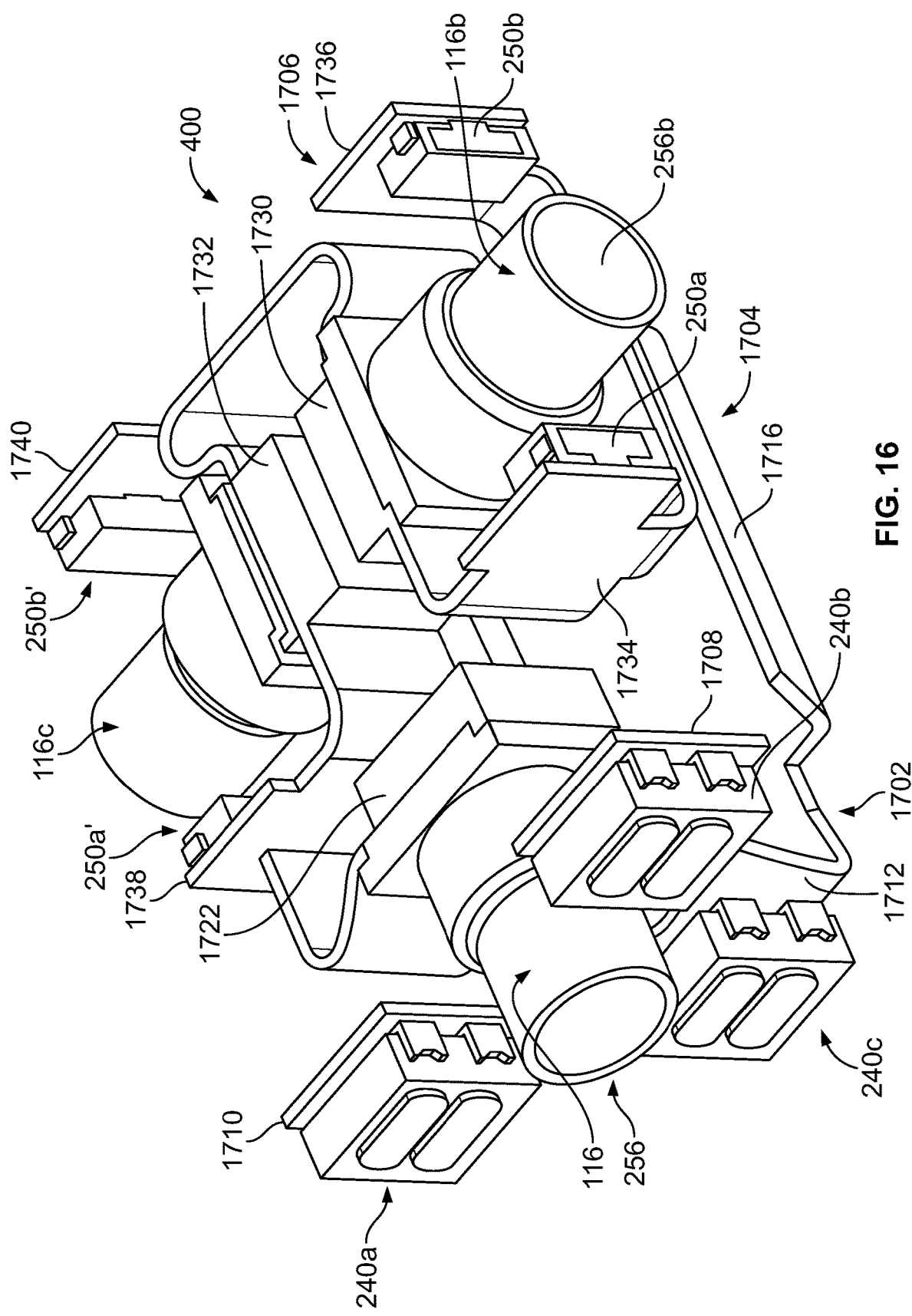
FIG. 16 schematically depicts an isometric view of a folded flexible electronic circuit board carrying a front view camera, two side view cameras, and illumination sources, according to an embodiment of the current specification.

FIG. 16 schematically depicts an isometric view of a folded flexible electronic circuit board carrying a front view camera, two side view cameras, and illumination sources, according to embodiments of the specification.

Flexible electronic circuit board 400, shown here in a folded configuration, is configured to carry: forward looking viewing element 116; LEDs 240a, 240b and 240c positioned to essentially illuminate the field of view (FOV) of forward looking viewing element 116; side looking viewing element 116b; LEDs 250a and 250b positioned to essentially illuminate the FOV of side looking viewing element 116b; side looking viewing element 116c and LEDs 250a' and 250b' positioned to essentially illuminate the FOV of side looking viewing element 116c.

Figure 17:
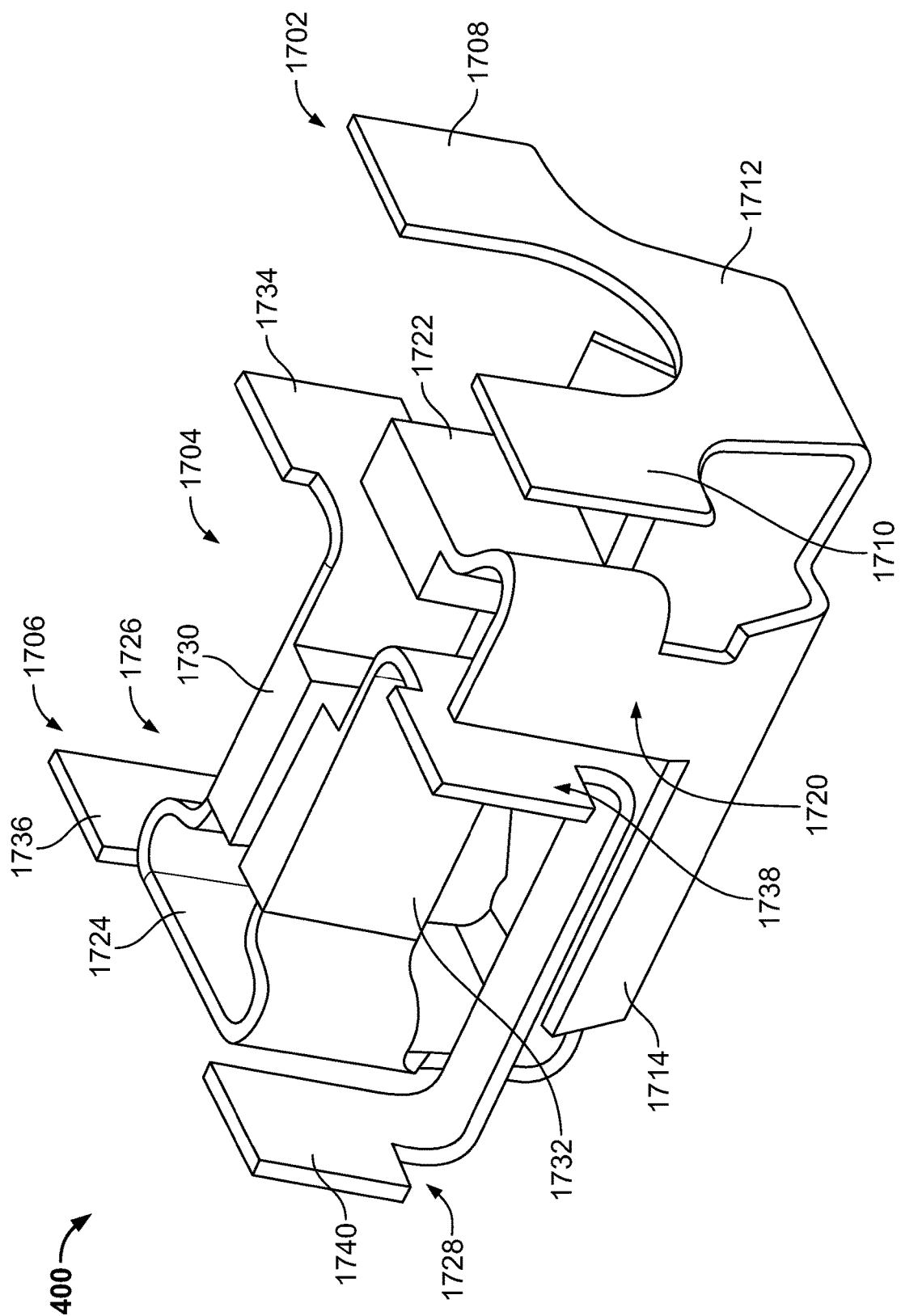
FIG. 17 schematically depicts an isometric view of a folded flexible electronic circuit board, according to an embodiment of the current specification.
Figure 18:
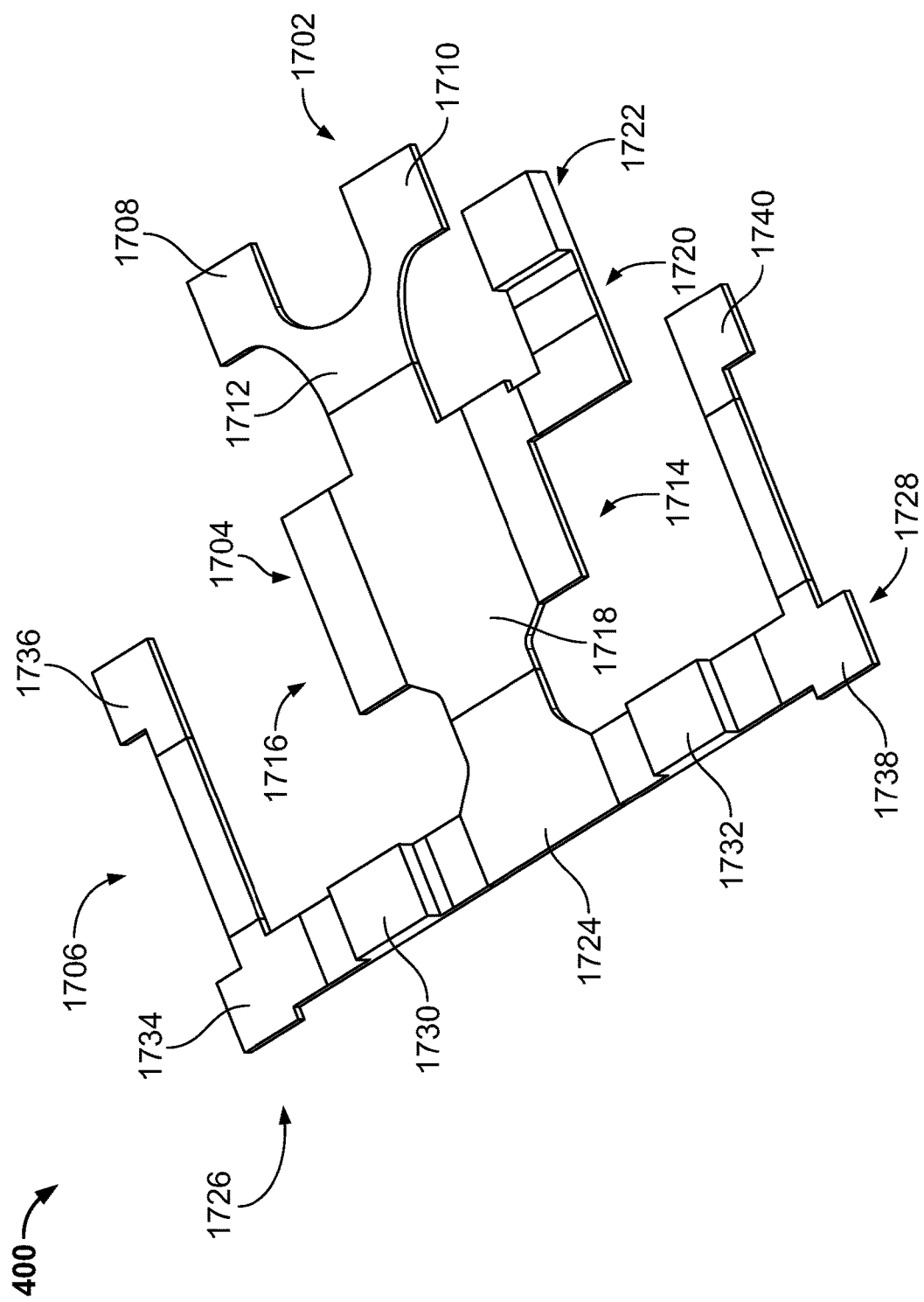
FIG. 18 schematically depicts an isometric view of a flexible electronic circuit board in an unfolded, flat configuration, according to an embodiment of the current specification.

As can also be seen in FIGS. 17 and 18, which schematically depict isometric views of a folded and flat flexible electronic circuit board, respectively, according to embodiments of the specification, flexible electronic circuit board 400 includes three sections: front section 1702, main section 1704 and rear section 1706.

Front section 402 of flexible electronic circuit board 1700 includes first front LED surface 1708, second front LED surface 1710 and a bottom front LED surface 1712. First front LED surface 1708, second front LED surface 1710 and a bottom front LED surface 1712 are flat surfaces formed from a unitary piece of a printed circuit board (PCB) layer. First front LED surface 1708 is adapted to carry front LED 240b, second front LED surface 1710 is adapted to carry front LED 240a and a bottom front LED surface 1712 is adapted to carry front LED 240c. First front LED surface 1708, second front LED surface 1710 and a bottom front LED surface 1712 have an arcuate shape when viewed as a whole, which is configured to support forward looking viewing element 116.

Front section 1702 of flexible electronic circuit board 400 is connected to main section 1704 through bottom section 1712. Main section 1704 of flexible electronic circuit board 1700 includes a center portion 1718, a first foldable side panel 1714 and a second foldable side panel 1716. When flexible electronic circuit board 400 is in a folded configuration, first foldable side panel 1714 and second foldable side panel 1716 are configured to fold upwards (towards the length axis of the endoscope tip), for example, as shown herein, forming an angle of about 45 degrees with center portion 1718 of main section 1704. First foldable side panel 1714 also includes an arm section 1720, extending therefrom, having a front sensor surface 1722 (may also be referred to as a camera surface) adapted to carry forward looking viewing element 116. When flexible electronic circuit board 400 is in a folded position, arm section 1720 is folded to be essentially perpendicular to center portion 1718 of main section 1704, and front sensor surface 1722 is folded to be essentially perpendicular to center portion 1718 and to arm section 1720, such that it faces forwards, essentially at the same direction of first front LED surface 1708, second front LED surface 1710 and a bottom front LED surface 1712. This configuration enables forward looking viewing element 116 and LEDs 240a, 240b, and 240c to face the same direction.

As described hereinabove, main section 1704 is connected to bottom section 1712 of front section 1702. On the opposing end of main section 1704, it is connected to rear section 1706.

Rear section 1706 includes a rear central portion 1724. Rear central portion 1724 is connected to a first rear arm section 1726, extending from one side of rear central portion 1724 and to a second rear arm section 1728, extending from the opposing side of rear central portion 1724.

First rear arm section 1726 includes a first side sensor surface 1730 (adapted to carry side looking viewing element 116b). Second rear arm section 1728 includes a second side sensor surface 1732 (adapted to carry side looking viewing element 116c).

First rear arm section 1726 further includes a first side LED surface 1734 and a second side LED surface 1736, adapted to carry side LEDs 250a and 250b, respectively. Second rear arm section 1728 further includes a third side LED surface 1738 and a fourth side LED surface 1740, adapted to carry side LEDs 250a' and 250b', respectively.

According to some embodiments, front sensor surface 1722 (which is adapted to carry forward looking viewing element 116), first side sensor surface 1730 and second side sensor surface 1732 (which are adapted carry side looking viewing elements 116b and 116c respectively) are thicker than the front and side LED surfaces. For example, the sensor surface thickness is configured for locating the sensor (of the viewing element) such that the welding pins of the sensor wrap the surface and are welded on the opposite side of the sensor in specific welding pads.

The sensor surfaces may be rigid and used as a basis for the viewing element assembly. The height of the sensor surface has significant importance allowing the sensor conductors to bend in a way such that they will directly reach the welding pads on the opposite side of the sensor rigid surface. The rigid basis also serves as electrical ground filtering electromagnetic noise to and from the sensor and thus increasing signal integrity.

When flexible electronic circuit board 400 is in a folded configuration, rear central portion 1724 is folded upwards, perpendicularly to center portion 1718 of main section 1704. First side sensor surface 1730 and second side sensor surface 1732 are positioned perpendicularly to center portion 1718 and also perpendicularly to rear central portion 1724. In addition, first side sensor surface 1730 and second side sensor surface 1732 are positioned essentially parallel and "back to back" to each other such that when they carry side looking viewing element 116b and side looking viewing element 116c, these viewing elements view opposing sides. First side LED surface 1734 and a second side LED surface 1736 are positioned perpendicularly to first side sensor surface 1730 and adapted to carry, on their inner sides, side LEDs 250a and 250b, respectively, such that LEDs 250a and 250b are positioned in proximity to side looking viewing element 116b. Third side LED surface 1738 and a fourth side LED surface 1740 are positioned perpendicularly to second side sensor surface 1732 and adapted to carry, on their inner sides, side LEDs 250a' and 250b', respectively, such that LEDs 250a' and 250b' are positioned in proximity to side looking viewing element 116c.

According to some embodiments of the specification, front section 1702, main section 1704 and rear section 1706 of flexible electronic circuit board 400 are all integrally formed from a unitary piece of circuit board layer.

Figure 19:
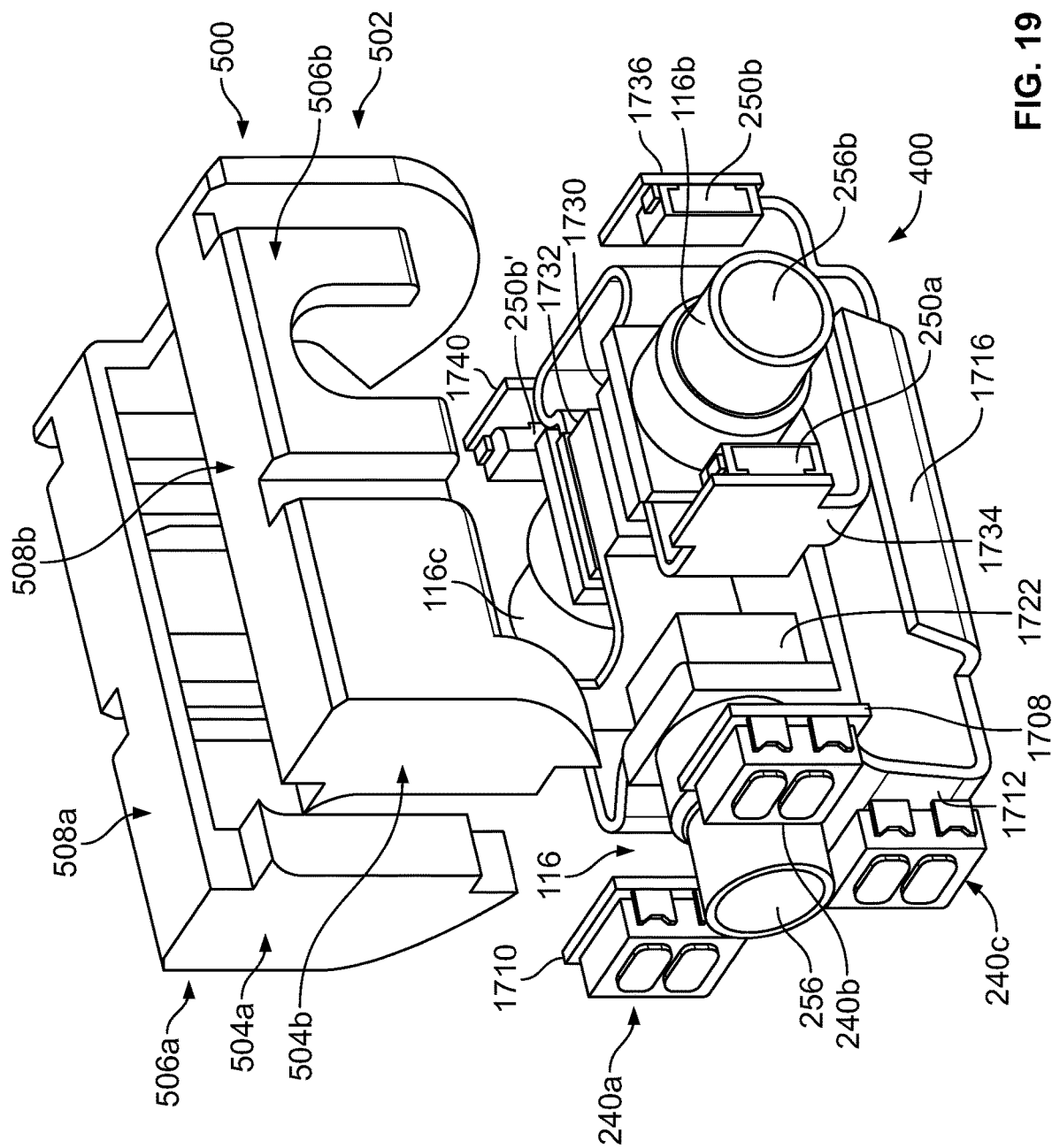
FIG. 19 schematically depicts an isometric exploded view of a folded flexible electronic circuit board, carrying cameras and illumination sources, and a flexible electronic circuit board holder, according to an embodiment of the current specification.
Figure 20:
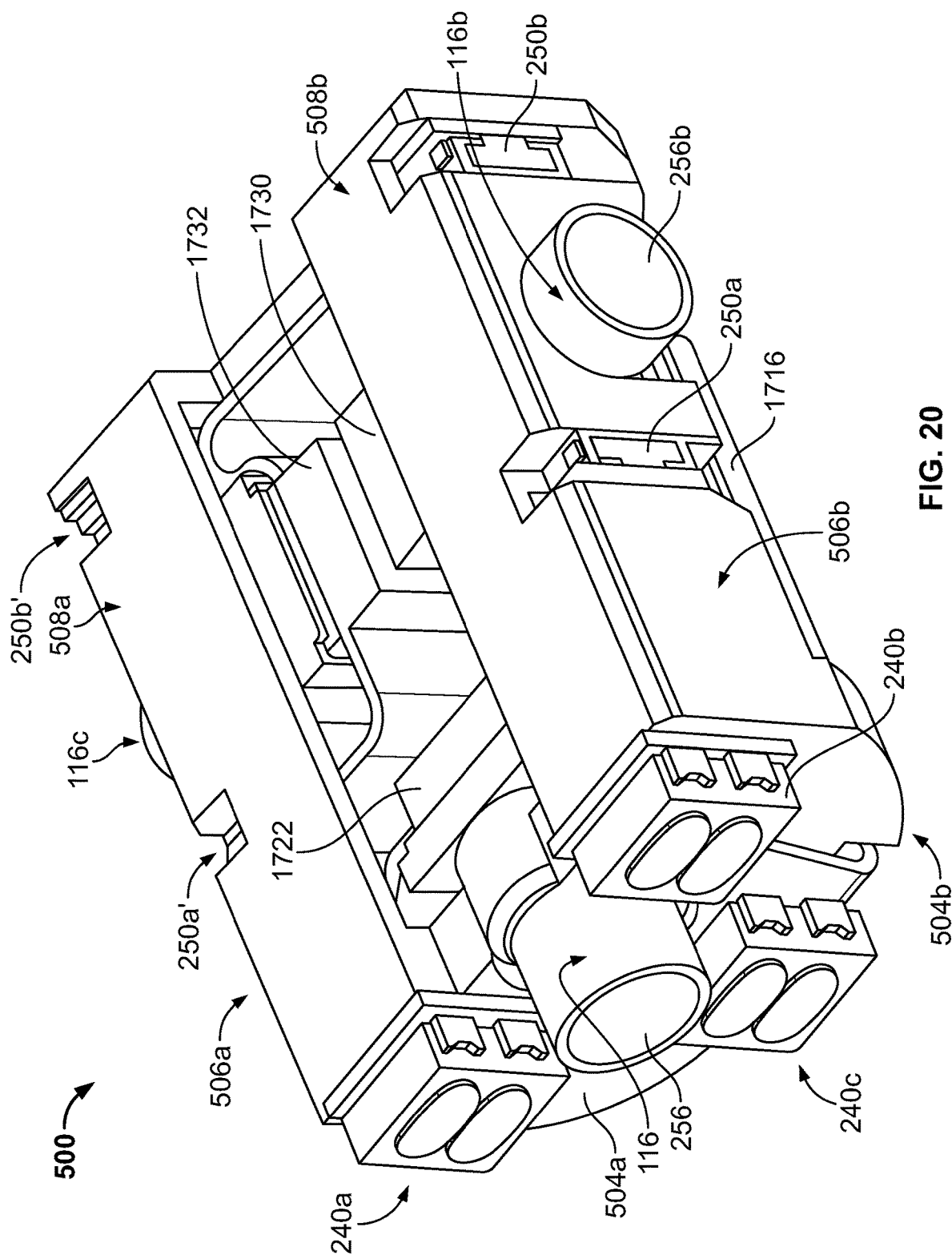
FIG. 20 schematically depicts an isometric assembled view of a folded flexible electronic circuit board, carrying cameras and illumination sources, and a flexible electronic circuit board holder, according to an embodiment of the current specification.

Reference is now made to FIGS. 19 and 20 which schematically depict isometric views (FIG. 19 shows an exploded view) of a folded flexible electronic circuit board carrying viewing elements and illumination sources and a flexible electronic circuit board holder, according to an exemplary embodiment of the current specification.

Similar to FIG. 16, flexible electronic circuit board 400, shown in FIG. 19 in its folded configuration, is configured to carry: forward looking viewing element 116; LEDs 240a, 240b and 240c positioned to illuminate essentially the FOV of forward looking viewing element 116; side looking viewing element 116b; LEDs 250a and 250b positioned to illuminate essentially the FOV of side looking viewing element 116b; side looking viewing element 116c and LEDs 250a' and 250b' positioned to illuminate essentially the FOV of side looking viewing element 116c.

Flexible electronic circuit board holder 500 is adapted to hold flexible electronic circuit board 400 in its desired folded position, and secure the front and side looking viewing elements and their corresponding illuminators in place. As shown in FIG. 19, flexible electronic circuit board holder 500 is a unitary piece of rigid material, such as brass, stainless steel, aluminum or any other material.

According to some embodiments, the use of metal for the construction of the flexible electronic circuit board holder is important for electric conductivity and heat transfer purposes. The flexible electronic circuit board holder, according to embodiments of the specification, (such as flexible electronic circuit board holder 500) can be used as a heat sink for some or all of the electronic components located at the tip section, particularly illuminators (such as side or front LEDs) and reduce overall temperature of the endoscope tip. This may solve or at least mitigate a major problem of raised temperatures of the endoscope tip and/or any of its components, particularly when using LED illuminators.

Flexible electronic circuit board holder 500 includes a back portion 502 adapted to support second side LED surface 1736 and fourth side LED surface 1740.

Flexible electronic circuit board holder 500 further includes front portions 504a and 504b, supporting the back sides (opposing to the sides where the LEDs are attached) of first front LED surface 1708 and second front LED surface 1710, respectively.

Flexible electronic circuit board holder 500 further includes two side portions 506a and 506b on the two opposing sides of flexible electronic circuit board holder 500. Each of side portions 506a and 506b include two small openings for the side LEDs (250a, 250b, 250a', 250b') and one opening for side looking viewing element 116b and 116a. Side portions 506a and 506b of flexible electronic circuit board holder 500 abut first and second side foldable panels 1716 and 1714, respectively, of flexible electronic circuit board 400.

Figure 21:
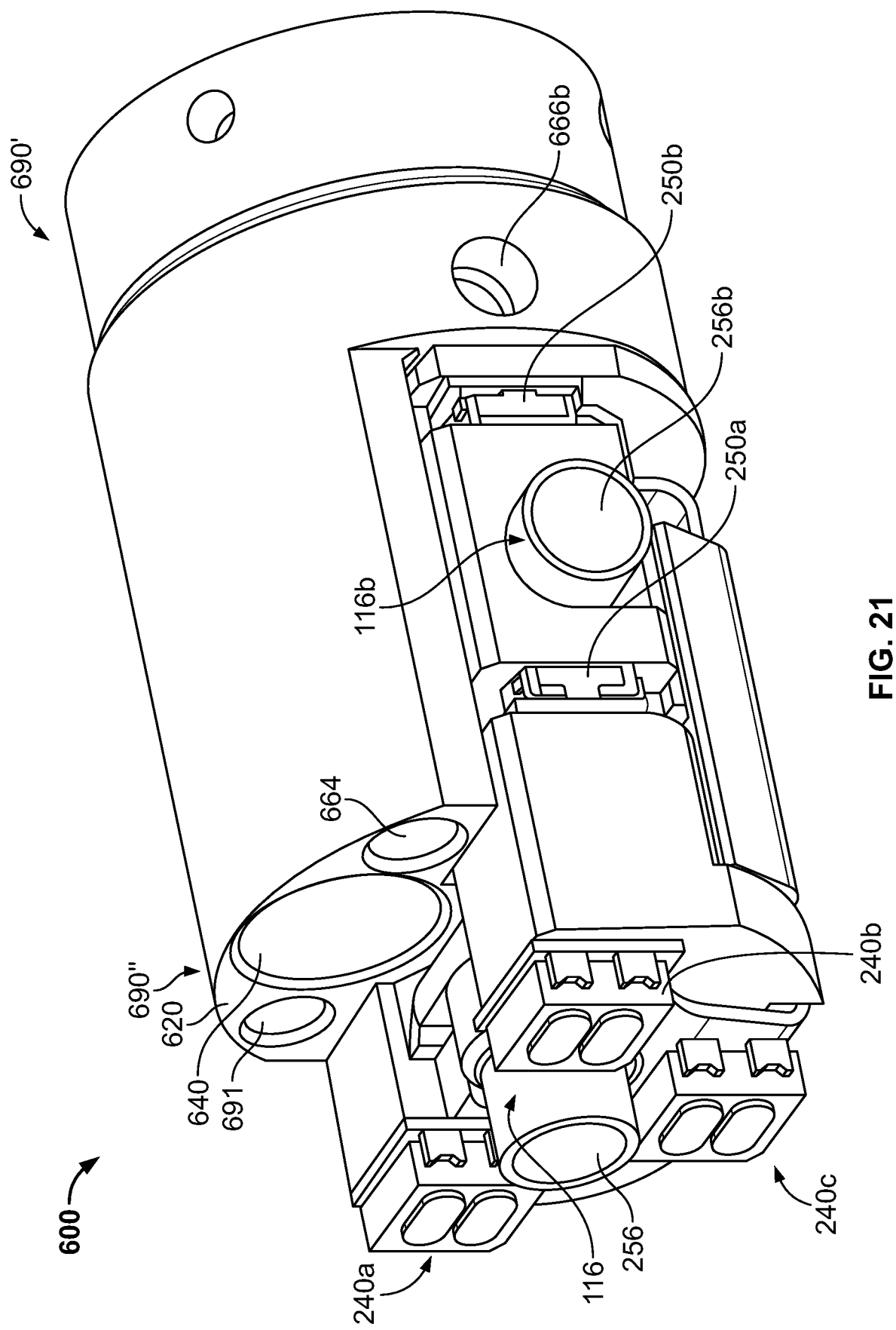
FIG. 21 schematically depicts an isometric assembled view of a folded flexible electronic circuit board carrying cameras and illumination sources, a flexible electronic circuit board holder, and a fluid channeling component, according to an embodiment of the current specification.

Flexible electronic circuit board holder 500 further includes a top part including top portions 508a and 508b (the top part of the flexible electronic circuit board holder may also include one top portion) covering the top part of flexible electronic circuit board 400 and configured to support fluid channeling component 600 (shown in FIG. 21).

Reference is now made to FIG. 21, which schematically depicts an isometric view of a folded flexible electronic circuit board carrying cameras and illumination sources, a flexible electronic circuit board holder, and a fluid channeling component, according to an exemplary embodiment of the current specification. FIG. 20 schematically depicts an isometric view of a folded flexible electronic circuit board carrying cameras and illumination sources and a flexible electronic circuit board holder. FIG. 21 adds to the configuration of FIG. 20, a fluid channeling component 600, which includes irrigation and insufflation (I/I) channels, jet channel and a working channel. Fluid channeling component 600 is a separate component from flexible electronic circuit board 400. This configuration is adapted to separate the fluid channels and working channel, which are located in fluid channeling component 600, from the sensitive electronic and optical parts which are located in the area of flexible electronic circuit board 400.

Fluid channeling component 600 (or according to some embodiments, a unitary fluid channeling component), according to some embodiments, may generally include two parts: a proximal fluid channeling component section 690' and a distal fluid channeling component section 690''. Proximal fluid channeling component section 690' may have an essentially cylindrical shape. Distal unitary channeling component section 690'' may partially continue the cylindrical shape of proximal fluid channeling component section 690' and may have a shape of a partial cylinder (optionally elongated partial cylinder), having only a fraction of the cylinder (along the height axis of the cylinder), wherein another fraction of the cylinder (along the height axis of the cylinder) is missing. Distal fluid channeling component section 690'' may be integrally formed as a unitary block with proximal fluid channeling component section 690'. The height of distal fluid channeling component section 690'' may be higher than that of proximal fluid channeling component section 690'. In the embodiment comprising distal fluid channeling component section 690'', the shape of the partial cylinder (for example, partial cylinder having only a fraction of a cylinder shape along one side of the height axis) may provide a space to accommodate flexible electronic circuit board 400 and flexible electronic circuit board holder 500.

Front face 620 of distal fluid channeling component section 690'' includes a distal opening 640 of a working channel (located inside fluid channeling component 690).

Front face 620 of distal fluid channeling component section 690" further includes distal opening 691 of a jet fluid channel which may be used for providing a high pressure jet of fluid, such as water or saline, for cleaning the walls of the body cavity (such as the colon) and optionally for suction. Front face 620 of distal fluid channeling component section 690" further includes irrigation and insufflation (I/I) opening 664 which may be used for injecting fluid (liquid and/or gas) to wash contaminants such as blood, feces and other debris from front optical assembly 256 of forward looking viewing element 116.

Proximal fluid channeling component section 690' of fluid channeling component 600 includes I/I openings aimed at a first side optical assembly 256b and at a second, opposite side optical assembly, and used for injecting fluid (the term "fluid" may include gas and/or liquid) to wash contaminants such as blood, feces and other debris from the first side optical assemblies 256b and second, opposite side optical assembly of a first side looking viewing element 116b and a second, opposite side looking viewing element. According to some embodiments, the injectors may supply liquid for cleaning any of the tip elements (such as any optical assembly, windows, LEDs, and other elements).

Figure 22:
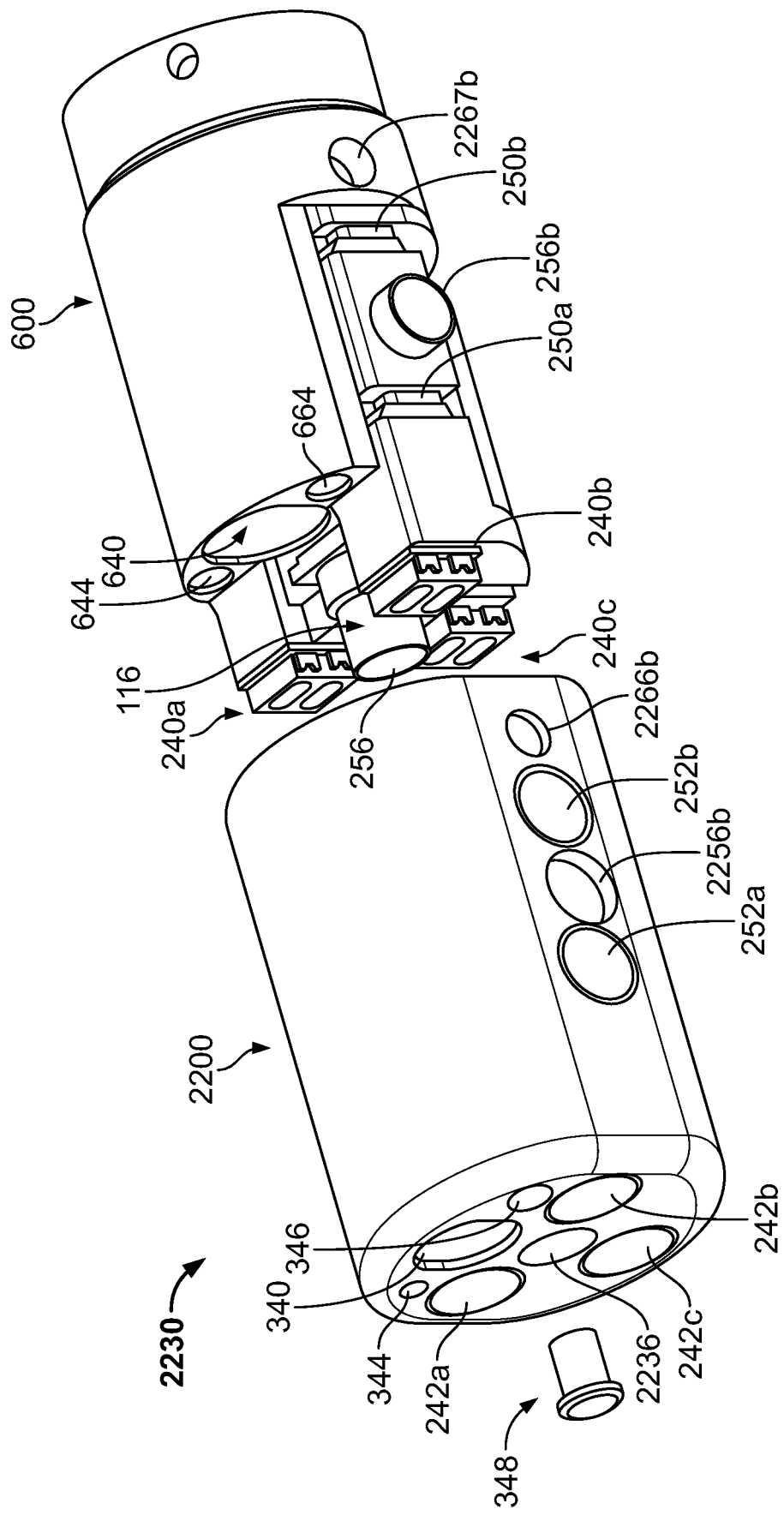
FIG. 22 schematically depicts an isometric view of a folded flexible electronic circuit board carrying cameras and illumination sources, a flexible electronic circuit board holder, a fluid channeling component, and a tip cover (in an exploded view), according to an embodiment of the current specification.
Figure 23A:
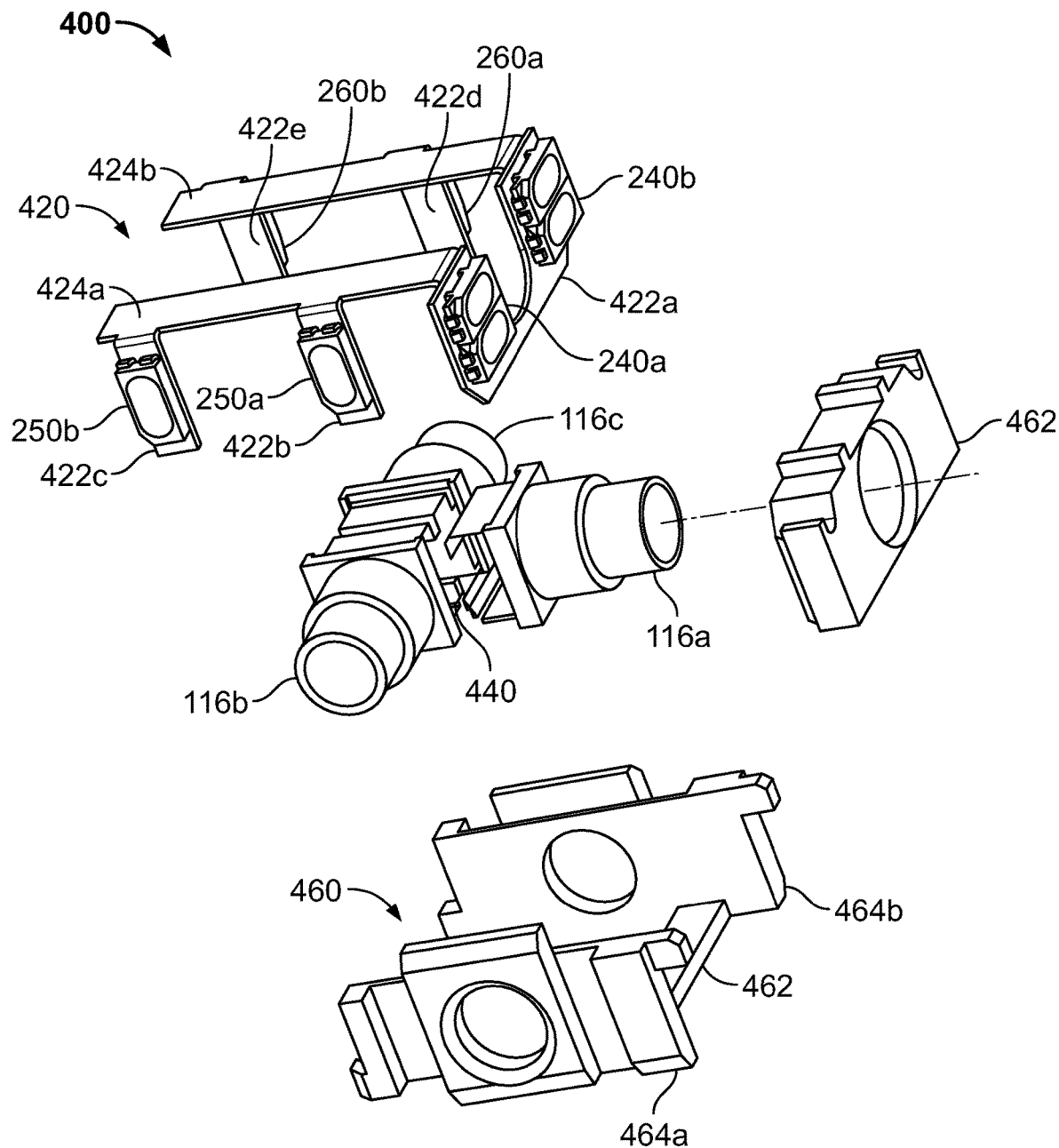
FIG. 23A shows a first exploded view of a tip section of a foldable electronic circuit board according to some embodiments.
Figure 23B:
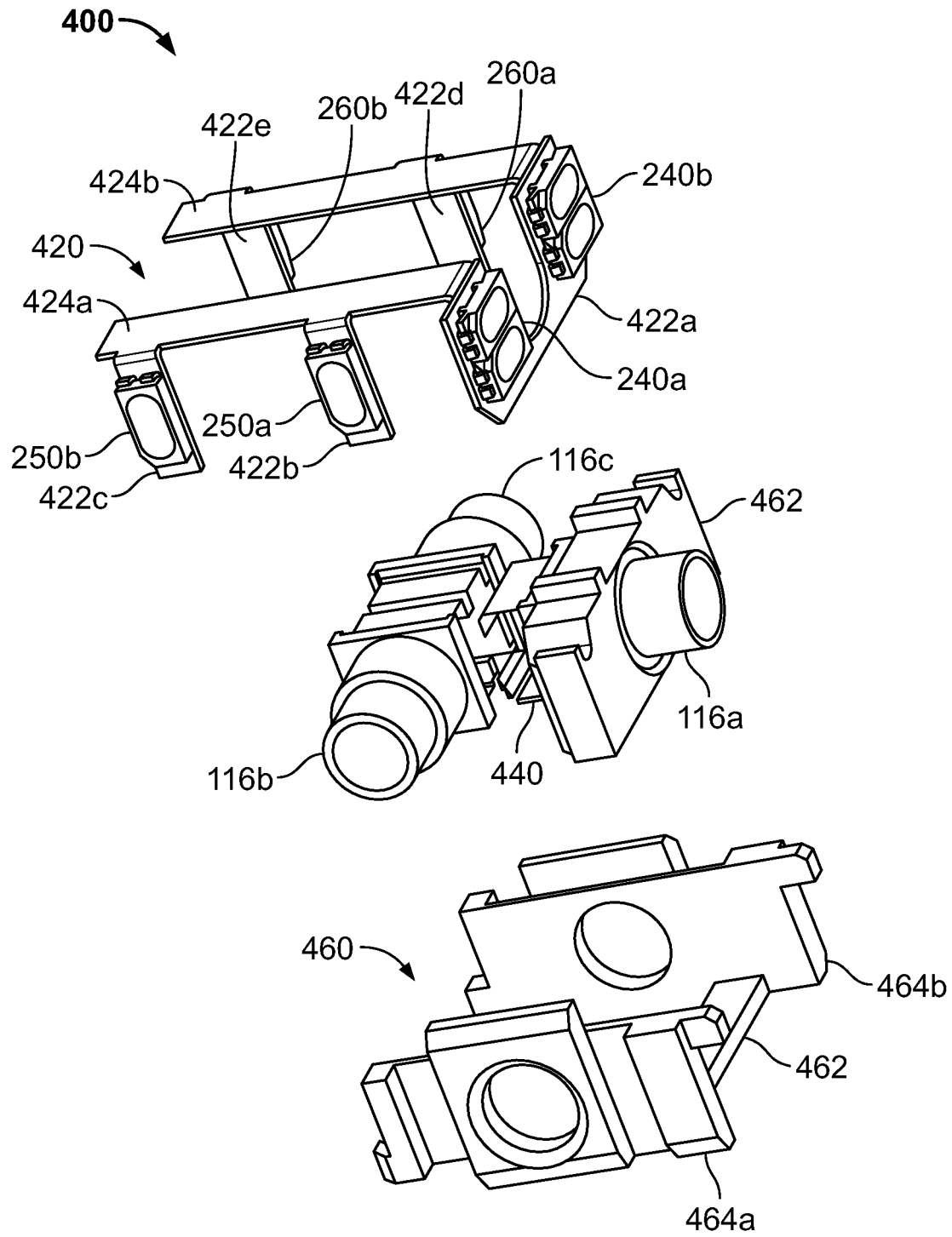
FIG. 23B shows a second exploded view of a tip section of a foldable electronic circuit board according to some embodiments.
Figure 23C:
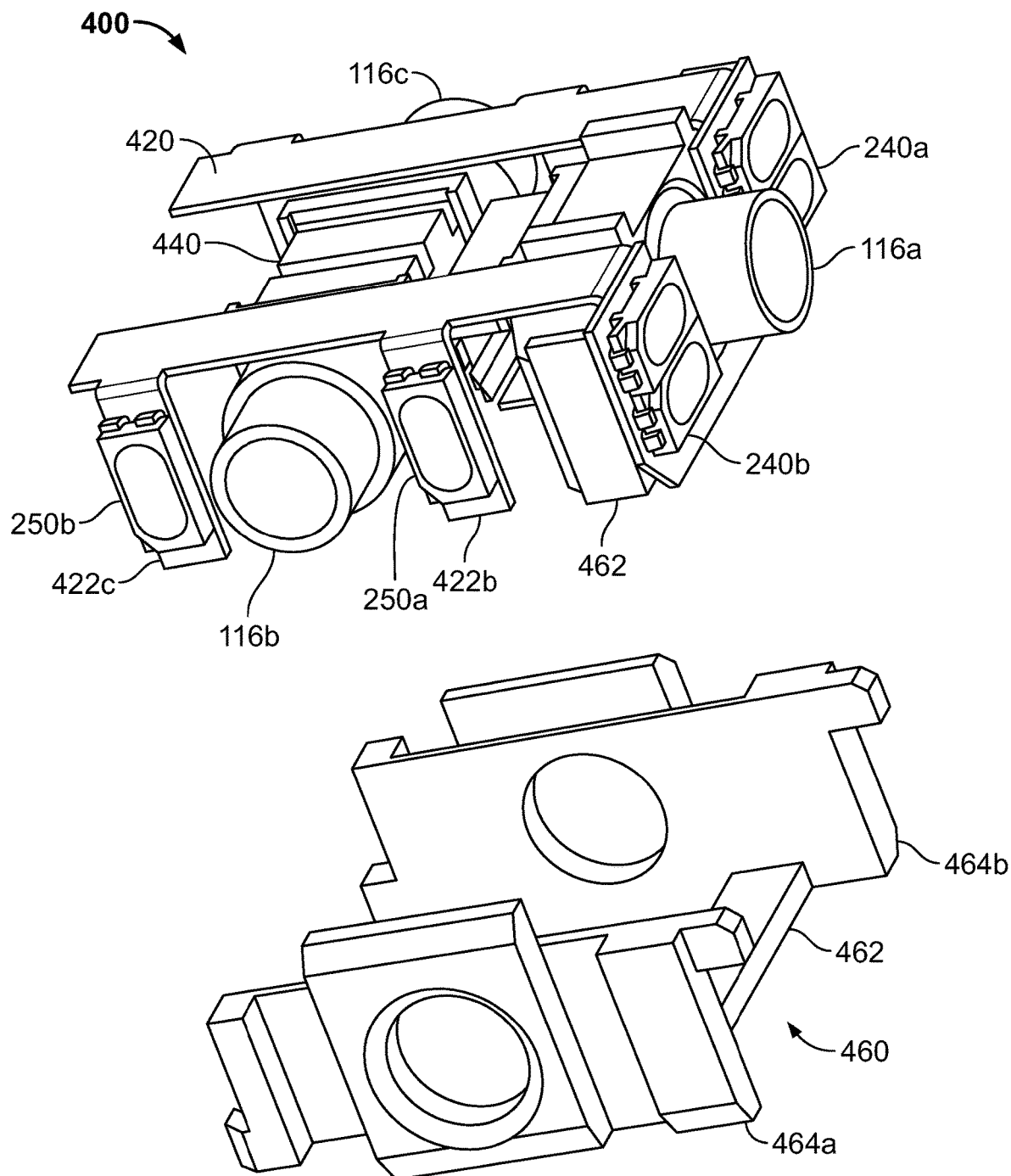
FIG. 23C shows a third exploded view of a tip section of a foldable electronic circuit board according to some embodiments.
Figure 23D:
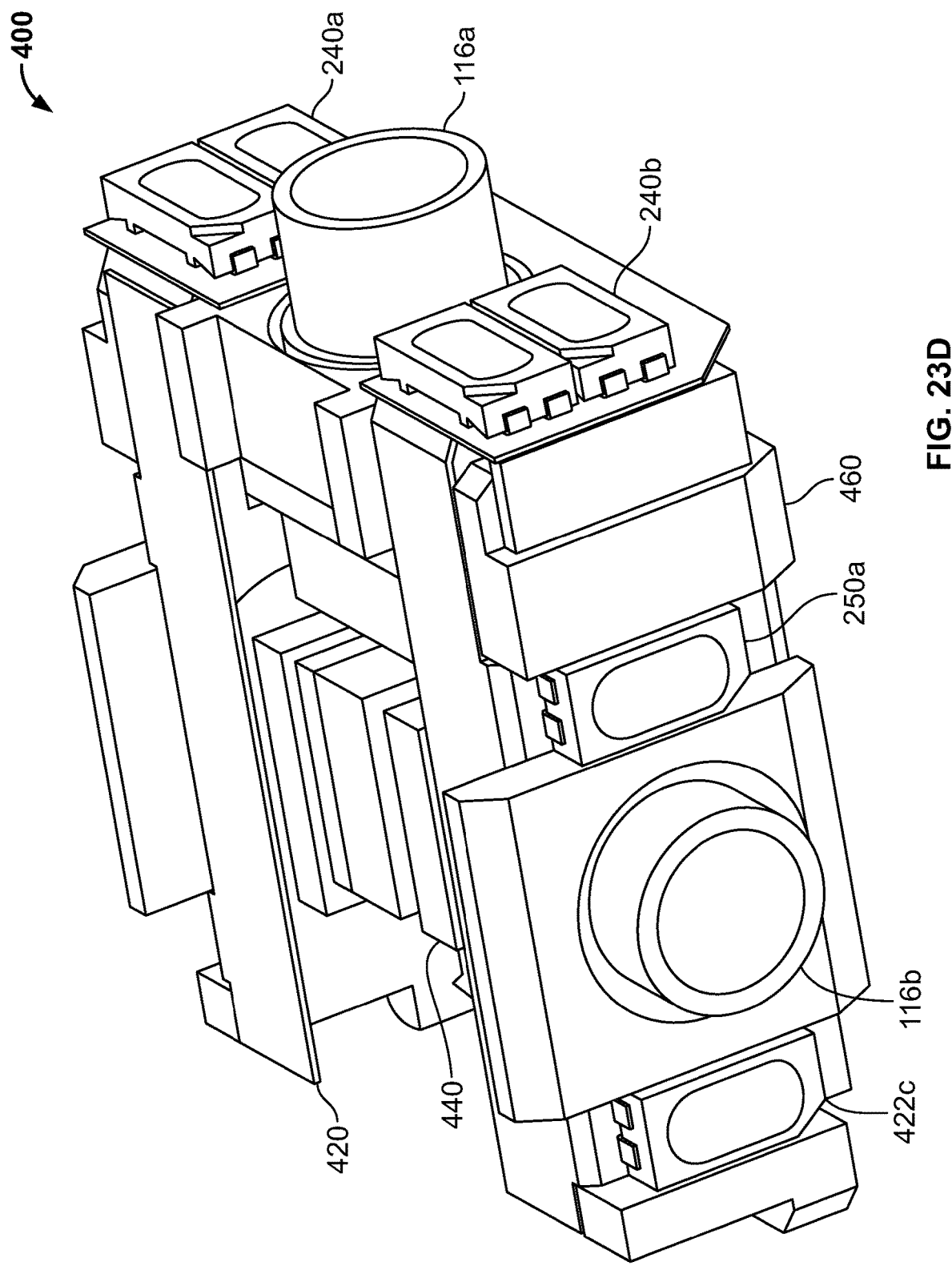
FIG. 23D shows an assembled perspective view of a tip section of a foldable electronic circuit board, such as that shown in FIG. 23C, according to some embodiments.

Reference is now made to FIG. 22, which schematically depicts an isometric view of a folded flexible electronic circuit board carrying cameras and illumination sources, a flexible electronic circuit board holder, a fluid channeling component, and a tip cover (in an exploded view), which together form a tip section of an endoscope, according to an exemplary embodiment of the current specification.

Fluid channeling component 600, flexible electronic circuit board 400 and flexible electronic circuit board holder 500 are described in FIGS. 20 and 21. Tip cover 2200 is designed to fit over the inner parts of the tip section 2230, and to provide protection to the internal components in the inner part.

Tip cover 2200 includes hole 2236 configured to align with front optical assembly 256 of forward looking viewing element 116; optical windows 242a, 242b and 242c of LEDs 240a, 240b and 240c (seen for example in FIGS. 16 and 19-22); distal opening 340 of a working channel; distal opening 344 of a jet fluid channel; I/I injector 346 having a nozzle 348 (aligning with I/I opening 664 of fluid channeling component 600); a first hole 2256b and a second hole on the opposite side configured to align with a first side optical assembly 256b and a second, opposite side optical assembly of side looking viewing elements; optical windows 252a and 252b for LEDs 250a and 250b for a first side viewing element; and optical windows on the opposite side for LEDs for an opposite side viewing element; a first side hole 2266b and a second side hole adapted to align with a first I/I opening 2267b and a second, opposite side I/I opening.

In another embodiment, the electronic circuit board is configured to be foldable. Advantageously, the configuration of a foldable electronic circuit board enables having a slim and compact design and improves the performance of the endoscope (particularly, the colonoscope) by allowing the incorporation of additional elements into the endoscope tip section, for example, having an endoscope tip section with an additional working channel (as that in FIG. 2A), which may be used for threading a second medical tool.

Reference is now made to FIGS. 23A, 23B, 23C and 23D, which show exploded views of a foldable electronic circuit board 400 of an endoscope assembly 100 of FIG. 2A according to an embodiment.

According to some embodiments, foldable electronic circuit board 400 has several internal parts including a flexible optical carrier substrate or camera circuit board 440, a flexible LED carrier substrate or illumination circuit board 420, a partially enclosed housing or bottom circuit board holder 460 and a front circuit board holder 462.

The internal parts of foldable electronic circuit board 400 is configured to be assembled, connected or attached together into a condensed structure having a slim and compact design.

Additionally, it should be noted that the internal parts of foldable electronic circuit board 400 is electrically connected and configured to share resources as electrical power and electrical signals.

The flexible optical carrier substrate or camera circuit board 440 is configured to carry, support or position a front-pointing viewing element 116a and two side-pointing viewing elements 116b, 116c which may be similar to front-pointing viewing element 116a and include a Charge Coupled Device (CCD) or a Complementary Metal Oxide Semiconductor (CMOS) image sensor.

According to some embodiments, side-pointing viewing elements 116b and 116c are installed such that their field of views are substantially opposing. However, different configurations and number of side-pointing viewing elements are possible within the general scope of the current specification.

Flexible LED carrier substrate or illumination circuit board 420, which is formed as a flexible unitary piece of a PCB layer, includes two main sections 424a and 424b, a front foldable panel 422a and four side foldable panels 422b, 422c, 422d, 422e.

When flexible LED carrier substrate 420 is in a folded configuration, front foldable panel 422a and four side foldable panels 422b, 422c, 422d, 422e are configured to fold downwards forming a right angle with two main sections 424a and 424b.

Front foldable panel 422a is configured to carry front illuminators 240a, 240b, which are associated with front-pointing viewing element 116a and positioned to essentially illuminate front-pointing viewing element's 116a field of view.

When front foldable panel 422a is in a folded configuration, it forms a right angle with main sections 424a and 424b such that it faces forward, essentially at the same direction of front-pointing viewing element 116a and therefore enables front illuminators 240a, 240b to face the same direction as front-pointing camera 116a and essentially illuminate front-pointing viewing element's 116a field of view.

Side foldable panels 422b, 422c are configured to carry side illuminators 250a, 250b respectively, which are associated with side-pointing viewing element 116b and positioned to essentially illuminate side-pointing viewing element's 116b field of view.

When side foldable panels 422b, 422c are in a folded configuration, side foldable panels 422b, 422c are configured to form a right angle with main section 424a such that it faces sideways, essentially at the same direction of side-pointing viewing element 116b and therefore enables side illuminators 250a, 250b to face the same direction as side-pointing viewing element 116b and essentially illuminate side-pointing viewing element's 116b field of view.

Side foldable panels 422d, 422e are configured to carry side illuminators 260a, 260b respectively, which are associated with side-pointing viewing element 116c and positioned to essentially illuminate side-pointing viewing element's 116c field of view.

When side foldable panels 422d, 422e are in a folded configuration, side foldable panels 422d, 422e are configured to form a right angle with main section 424b such that it faces sideways, essentially at the same direction of side-pointing viewing element 116c and therefore enables side illuminators 260a, 260b to face the same direction as side-pointing viewing element 116c and essentially illuminate side-pointing viewing element's 116c field of view.

Front illuminators 240a, 240b and side illuminators 250a, 250b, 260a and 260b are optionally be discrete illuminators and may include a light-emitting diode (LED), which may be a white light LED, an infrared light LED, a near infrared light LED, an ultraviolet light LED or any other LED.

The term "discrete", concerning discrete illuminator, refers to an illumination source, which generates light internally, in contrast to a non-discrete illuminator, which may be, for example, a fiber optic merely transmitting light generated remotely.

Partially enclosed housing or bottom circuit board holder 460 is configured to hold and support flexible LED carrier substrate 420 in its desired folded configuration and secure flexible optical carrier substrate 440, including side pointing viewing elements 116b and 116c and their corresponding illuminators, in place.

Partially enclosed housing 460 includes a bottom portion 462 and two side portions 464a and 464b formed as a unitary piece of rigid material, such as brass, stainless steel, aluminum or any other material.

Each of side portions 464a and 464b are perpendicularly connected to bottom portion 462 at each opposite side and have an aperture configured to fit side pointing viewing elements 116b and 116c.

Front circuit board holder 462 is configured to work in conjunction with partially enclosed housing 460 and hold and support flexible LED carrier substrate 420 in its desired folded configuration and secure flexible optical carrier substrate 440 including front pointing camera 116a and its corresponding illuminator in place.

Partially enclosed housing 460 is formed as a unitary piece of rigid material, such as brass, stainless steel, aluminum or any other material.

The use of metal for the construction of partially enclosed housing 460 and front circuit board holder 462 improves electric conductivity and allows efficient heat dissipation. According to some embodiments, partially enclosed housing 460 and front circuit board holder 462 function as a heat sink for some or all of the electronic components located within foldable electronic circuit board 400, particularly illuminators (such as front illuminators 240a, 240b and side illuminators 250a, 250b, 260a and 260b) and reduce overall temperature of the endoscope tip section. This will solve or at least mitigate a major problem of raised temperatures of endoscope tip and/or any of its components, particularly when using LED illuminators.

Figure 24A:
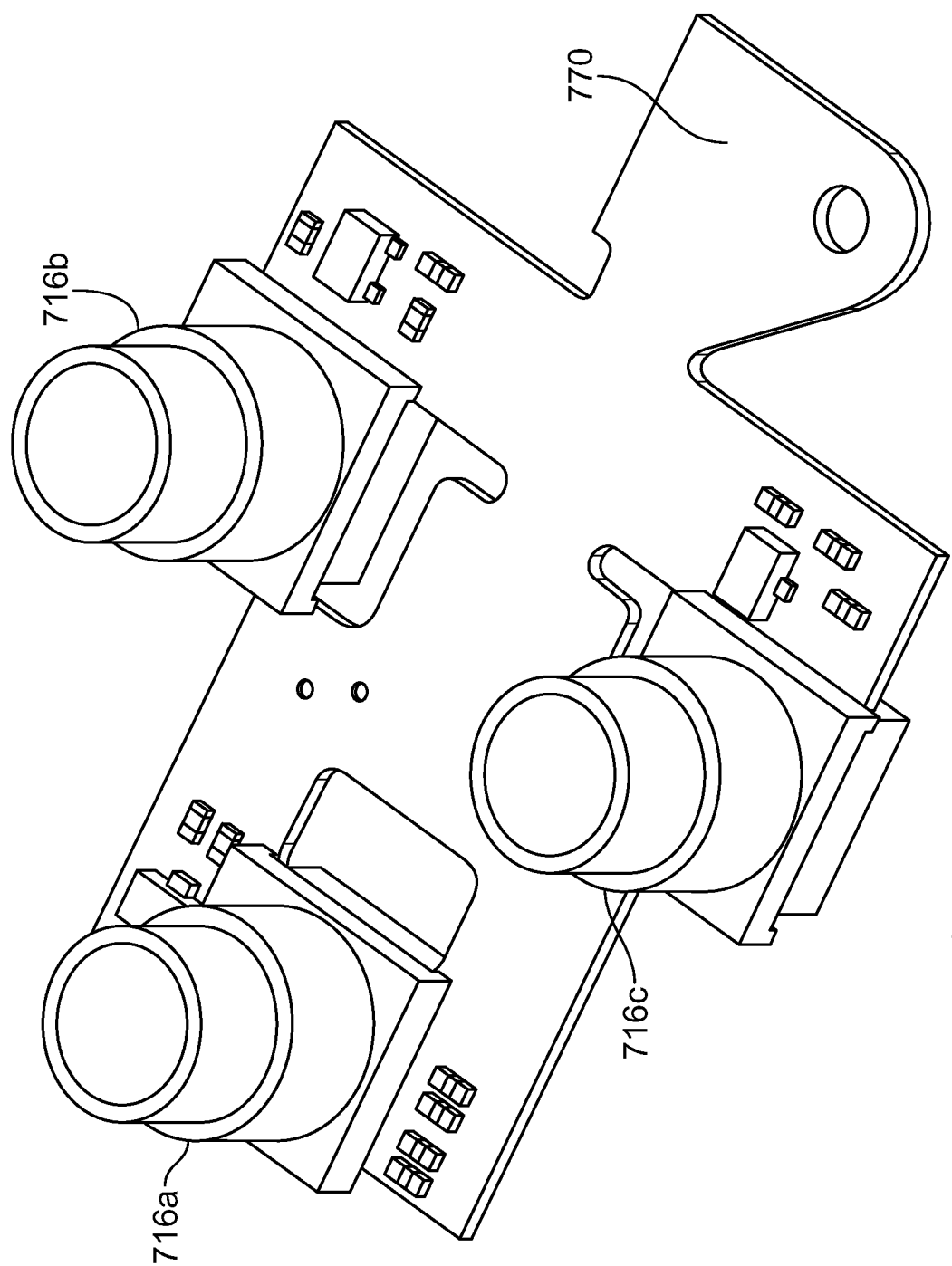
FIG. 24A shows a first perspective view of a camera circuit board according to some embodiments.
Figure 24B:
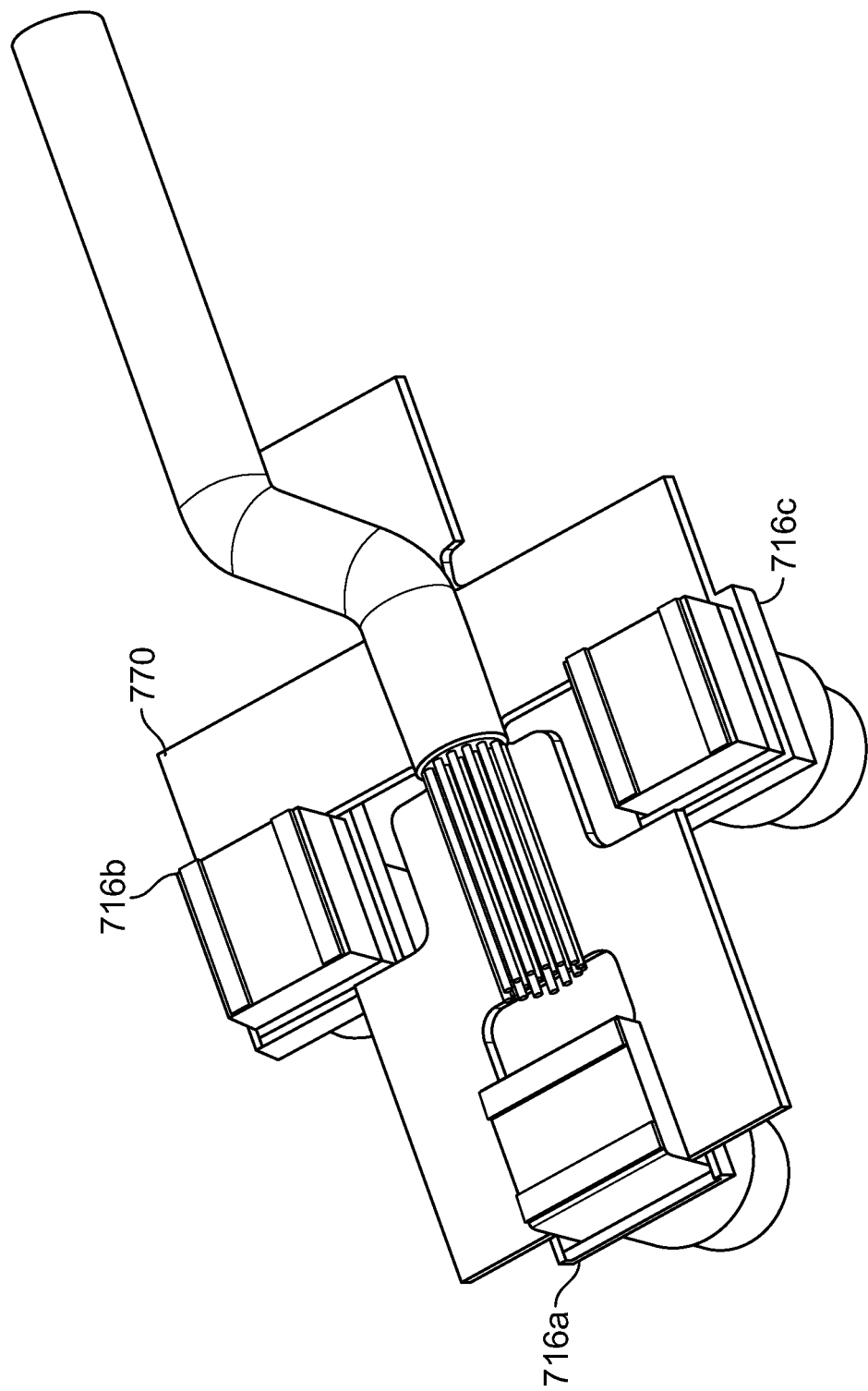
FIG. 24B shows a second perspective view of a camera circuit board according to some embodiments.
Figure 24C:
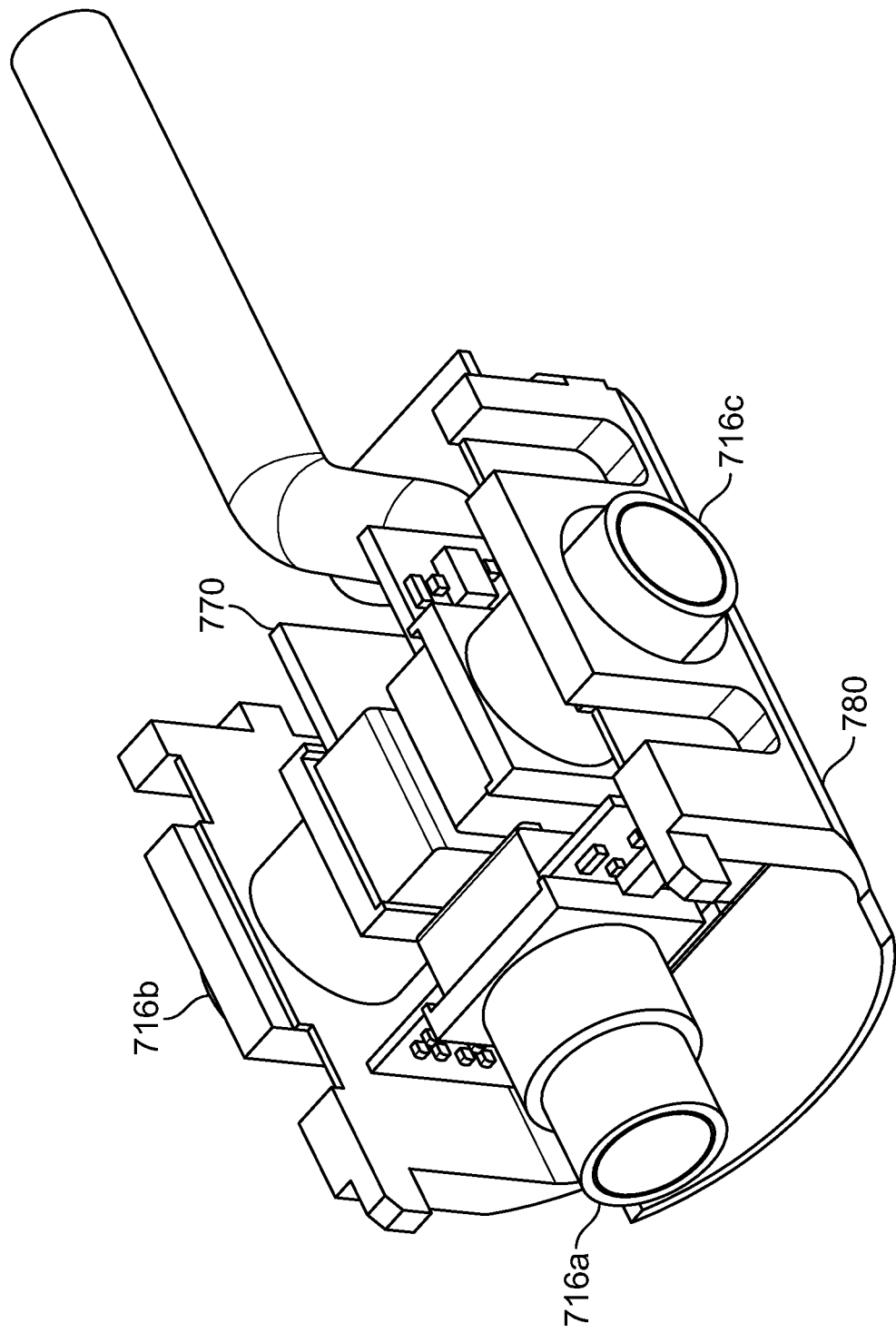
FIG. 24C shows a third perspective view of a camera circuit board according to some embodiments.

Reference is now made to FIGS. 24A, 24B and 24C, which show a perspective view of a flexible optical carrier substrate or camera circuit board 770 of an endoscope assembly according to an embodiment. As an example, the flexible optical carrier substrate 770 is configured for the endoscope assembly 100 of FIG. 2A that comprises a single front working channel.

Flexible optical carrier substrate 770 may be similar to flexible optical carrier substrate 440 (FIGS. 23A through 23D) and is configured to carry, support or position a front-pointing camera 716a and two side-pointing cameras 716b, 716c which may be similar to front-pointing camera 116 (FIG. 2A) and may include a Charge Coupled Device (CCD) or a Complementary Metal Oxide Semiconductor (CMOS) image sensor.

According to some embodiments, side-pointing cameras 716b and 716c are installed such that their field of views are substantially opposing. However, different configurations and number of side-pointing cameras are possible within the general scope of the current specification.

A partially enclosed housing or circuit board holder 780, which is further discussed below, holds and supports flexible optical carrier substrate 770, as shown in FIG. 24C.

Figure 25:
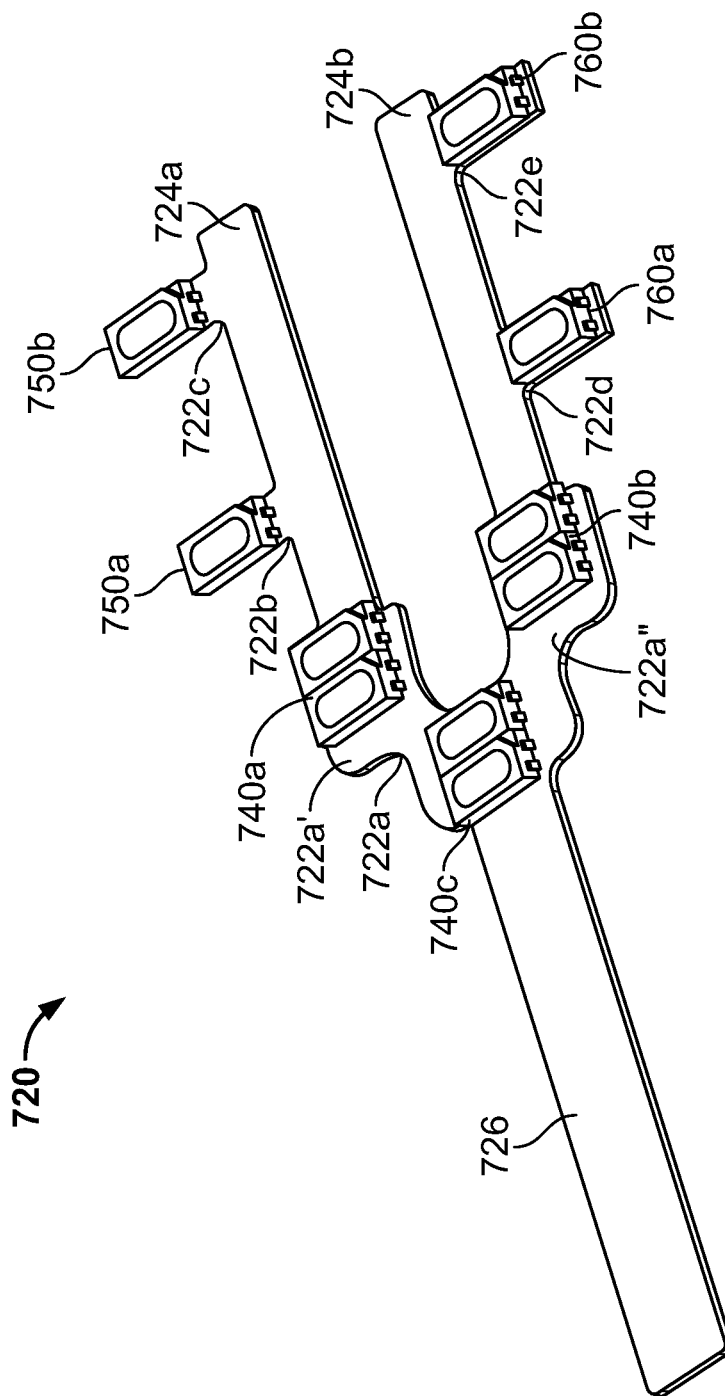
FIG. 25 shows a perspective view of a flexible illumination circuit board according to some embodiments.

Reference is now made to FIG. 25, which shows a perspective view of a flexible LED carrier substrate or illumination circuit board 720 of an endoscope assembly according to an embodiment. As discussed earlier, an endoscopic tip, such as tip section 200 of FIGS. 2A and 2B, has a distal face 320 and side edges 362a, 362b extending proximally from the distal face 320. The distal face 320 and side edges 362a, 362b together define an internal volume of the tip 200.

Referring back to FIG. 25, flexible LED carrier substrate 720, which is formed as a folded unitary piece of a PCB layer, comprises front/central carrier portion or panel 722a, connector 726 which is attached to a first end of central carrier portion or panel 722a, two main sections or parallel strips 724a and 724b, which are connected to a second end of central carrier portion or panel 722a, and four side foldable protrusions or panels 722b, 722c, 722d, 722e that protrude from respective portions of parallel strips 724a and 724b.

When flexible LED carrier substrate 720 is in a folded configuration, foldable central carrier portion or panel 722a and four side foldable protrusions or panels 722b, 722c, 722d, 722e are configured to fold downwards, forming right angles with the two parallel strips or main sections 724a and 724b.

Foldable central carrier portion or panel 722a is configured to carry front illuminators 740a, 740b and 740c, which are associated with front-pointing camera 716a (FIGS. 24A through 24C) and positioned to essentially illuminate front-pointing camera's 716a (FIGS. 24A through 24C) field of view. In the pictured embodiment, the central carrier portion 722a approximates a U-shape, having a first arm 722a' and a second arm 722a". In accordance with an embodiment, the first arm 722a' extends from the central carrier portion 722a to connect the central carrier portion 722a at its second end with the first strip 724a while the second arm 722a" extends from the central carrier portion 722a to connect the central carrier portion 722a at its second end with the second strip 724b. The first and second arms 722a', 722a" are configured to carry first and second illuminators 740a and 740b. The third illuminator 740c is mounted centrally on a base segment of the U-shape of the central carrier portion 722a.

Figure 26A:
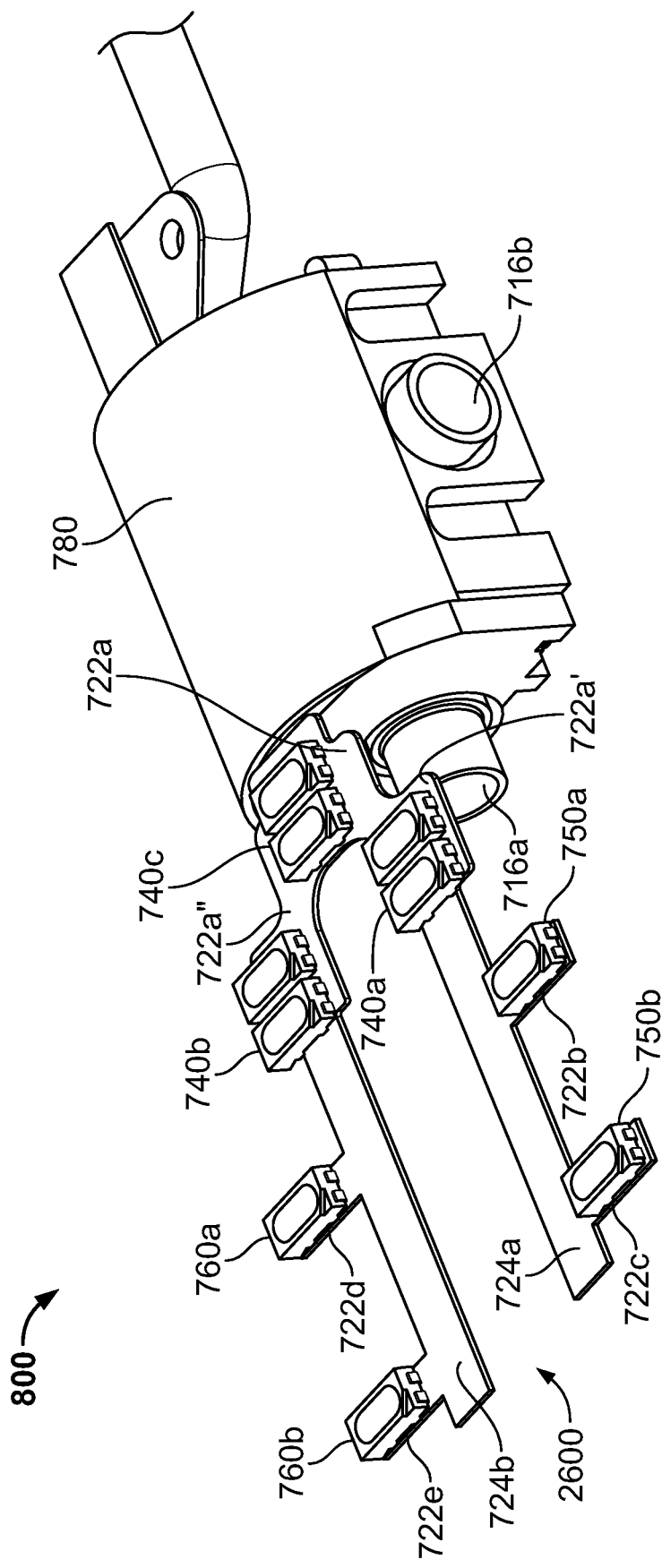
FIG. 26A shows a first perspective view of a foldable electronic circuit board according to some embodiments.
Figure 26B:
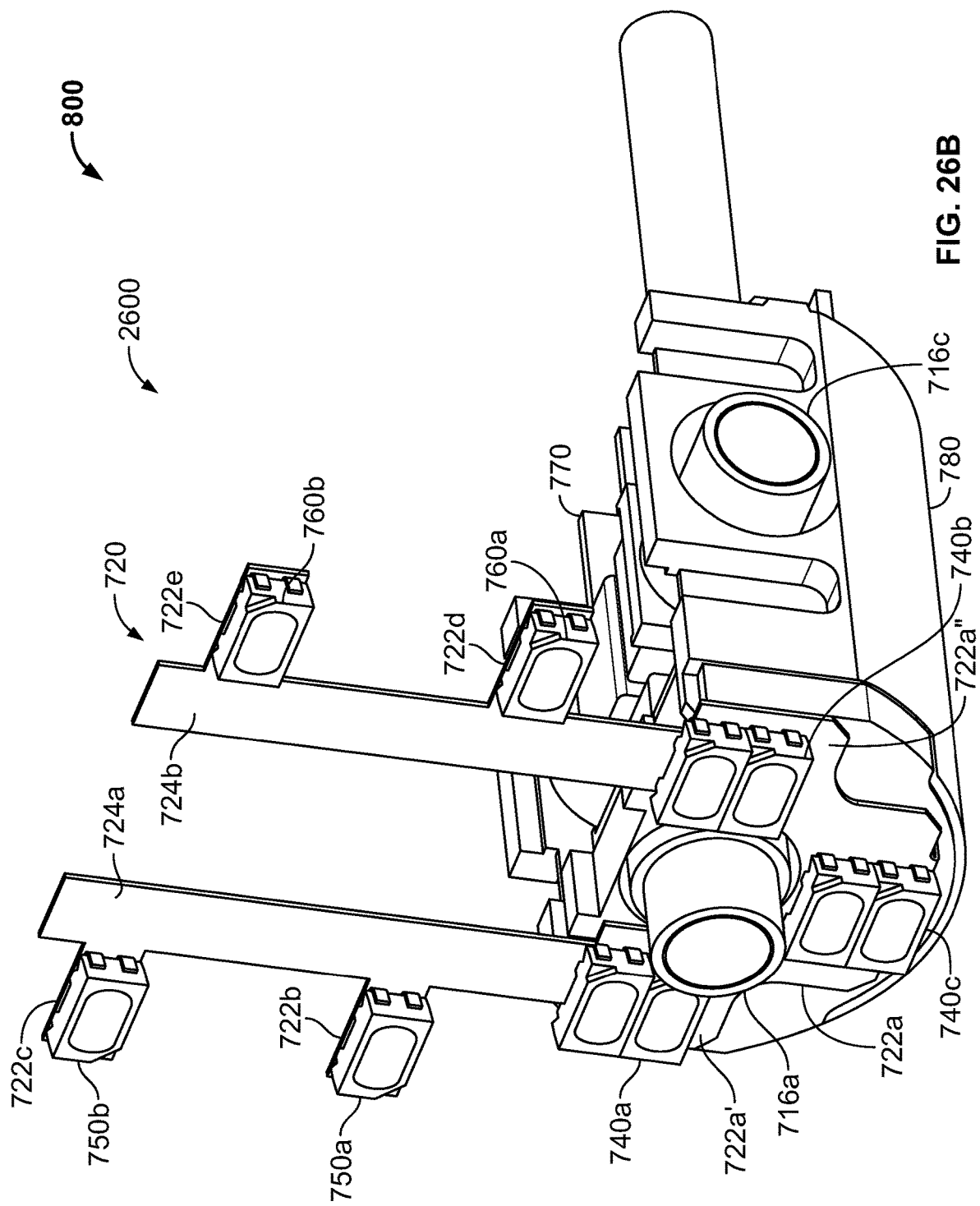
FIG. 26B shows a second perspective view of a foldable electronic circuit board according to some embodiments.
Figure 26C:
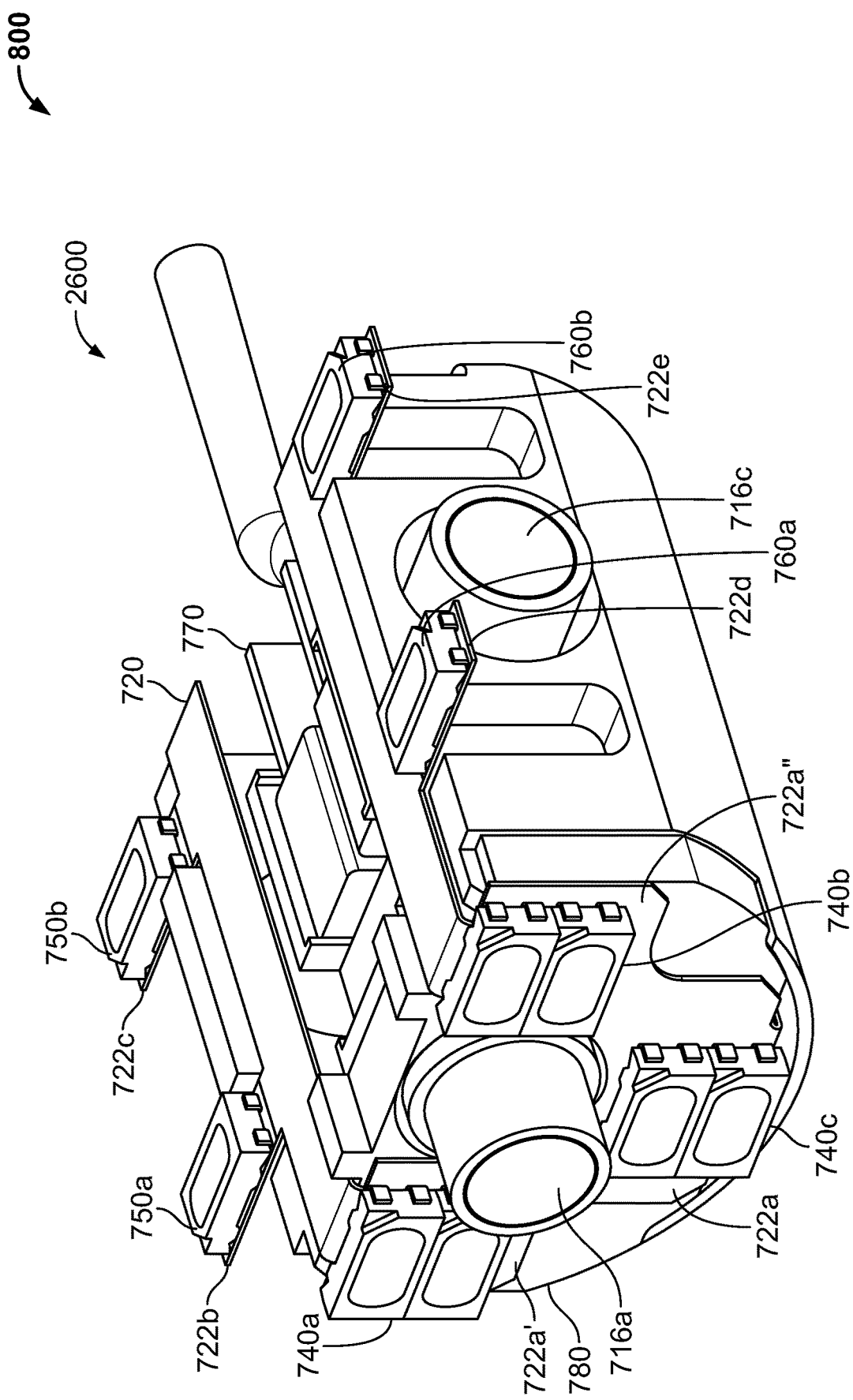
FIG. 26C shows a third perspective view of a foldable electronic circuit board according to some embodiments.
Figure 26D:
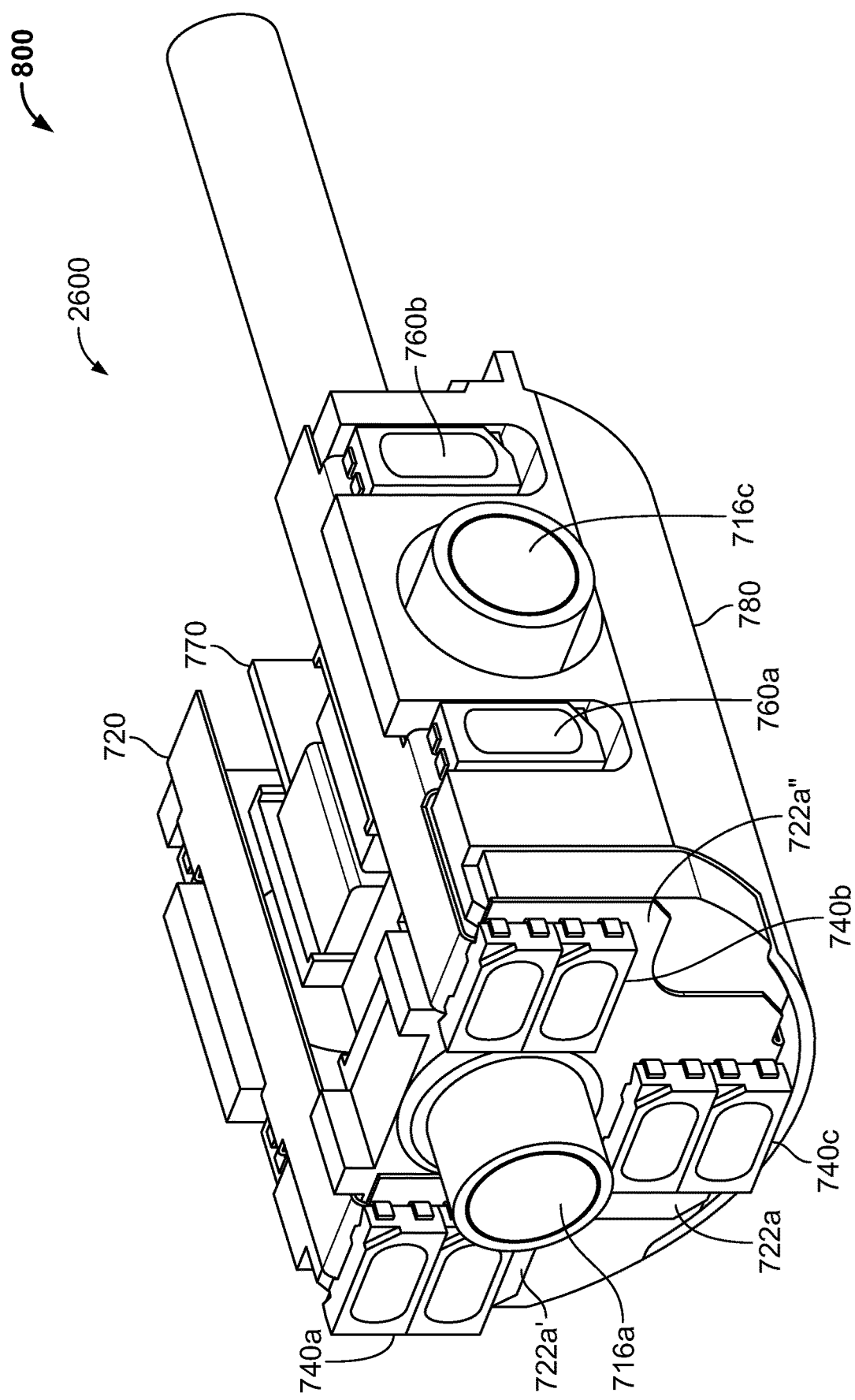
FIG. 26D shows a fourth perspective view of a foldable electronic circuit board according to some embodiments.

Referring to FIGS. 25 through 26D simultaneously, when front foldable central carrier portion or panel 722a, along with first and second arms 722a', 722a", is in a folded configuration, it forms a right angle with the two parallel strips 724a and 724b such that it faces forward, essentially at the same direction of front-pointing camera 716a (FIGS. 24A through 24C) and therefore enables front illuminators 740a, 740b and 740c, to face the same direction as front-pointing camera 716a (FIGS. 24A through 24C) and essentially illuminate front-pointing camera's 716a (FIGS. 24A through 24C) field of view. In one embodiment, the front-pointing camera 716a (FIGS. 24A through 24C) is positioned between the first and second illuminators 740a and 740b when the central carrier portion 722a, along with first and second arms 722a', 722a", is in a folded configuration. In another embodiment, the front-pointing camera 716a (FIGS. 24A through 24C) is surrounded by the first, second and third illuminators 740a, 740b, 740c when the central carrier portion 722a, along with first and second protrusions 722a', 722a", is in a folded configuration. In the folded configuration, the front-pointing camera and the three illuminators 740a, 740, 740c lie within a plane defined by the distal face 320 (of the endoscopic tip 200 of FIGS. 2A, 2B).

Side foldable protrusions or panels 722b, 722c are configured to carry side illuminators 750a, 750b respectively, which are associated with side-pointing camera 716b (FIGS. 24A through 24C) and positioned to essentially illuminate side-pointing camera's 716b (FIGS. 24A through 24C) field of view.

When side foldable protrusions or panels 722b, 722c are in a folded configuration, side foldable protrusions or panels 722b, 722c are configured to form a right angle with first strip 724a such that they face sideways, essentially at the same direction of side-pointing camera 716b (FIGS. 24A through 24C) and therefore enable side illuminators 750a, 750b, to face the same direction as side-pointing camera 716b (FIGS. 24A through 24C) and essentially illuminate the field of view of side-pointing camera 716b (FIGS. 24A through 24C). In one embodiment, the side-pointing camera 716b (FIGS. 24A through 24C) is positioned between the side illuminators 750a, 750b when the side foldable protrusions 722b, 722c are in a folded configuration. In the folded configuration, the side-pointing camera 716b and the side illuminators 750a, 750b lie within a plane defined by a first side edge, such as side edge 362a of the endoscopic tip 200 of FIG. 2B.

Side foldable protrusions or panels 722d, 722e are configured to carry side illuminators 760a, 760b respectively, which are associated with side-pointing camera 716c (FIGS. 24A through 24C) and positioned to essentially illuminate side-pointing camera's 716c field of view.

When side foldable protrusions or panels 722d, 722e are in a folded configuration, side foldable protrusions or panels 722d, 722e form a right angle with second strip 724b such that they face sideways, essentially at the same direction of side-pointing camera 716c (FIGS. 24A through 24C) and therefore enable side illuminators 760a, 760b, to face the same direction as side-pointing camera 716c (FIGS. 24A through 24C) and essentially illuminate side-pointing camera's 716c (FIGS. 24A through 24C) field of view. In one embodiment, the side-pointing camera 716c (FIGS. 24A through 24C) is positioned between the side illuminators 760a, 760b when the side foldable protrusions 722d, 722e are in a folded configuration. In the folded configuration, the side-pointing camera 716c and the side illuminators 760a, 760b lie within a plane defined by a second side edge, such as side edge 362b of the endoscopic tip 200 of FIG. 2B.

It is noted that the number of front/central carrier portion and side foldable protrusions or panels and associated number of front and side illuminators may vary in various embodiments. For example, while in one embodiment, the base of the central carrier portion 722a along with the first and second arms 722a', 722a" together carry three front illuminators, in alternate embodiments first and second arms carry illuminators 740a, 740b while the base of the central carrier portion 722a may not carry any illuminator. Thus, in one embodiment, the central carrier portion 722a along with the first and second arms 722a', 722a" together support at least two illuminators. In yet another embodiment, the central carrier portion 722a along with the first and second arms 722a', 722a" together support at least one illuminator.

Front illuminators 740a, 740b, 740c and side illuminators 750a, 750b, 760a and 760b may optionally be discrete illuminators and may include a light-emitting diode (LED), which may be a white light LED, an infrared light LED, a near infrared light LED, an ultraviolet light LED or any other LED.

Connector 726 is configured to connect flexible LED carrier substrate 720 to a partially enclosed housing 780 (FIGS. 26A through 26D). Once folded, the two parallel strips 724a, 724b extend in a proximal direction from the central carrier portion 722a, as shown in FIGS. 26A through 26D.

Reference is now made to FIG. 25 along with FIGS. 26A, 26B, 26C and 26D, which show a perspective view of a foldable electronic circuit board 2600 of an endoscope assembly 800 according to an embodiment.

Partially enclosed housing or circuit board holder 780 is configured to hold and support flexible LED carrier substrate 720 in its desired folded configuration and secure flexible optical carrier substrate 770 including front pointing camera 716a, side pointing cameras 716b and 716c and their corresponding illuminators in place.

Partially enclosed housing 780 is formed as a unitary piece of rigid material, such as brass, stainless steel, aluminum or any other material.

The use of metal for the construction of partially enclosed housing 780 improves electric conductivity and allows efficient heat dissipation. According to some embodiments, partially enclosed housing 780 is used as a heat sink for some or all of the electronic components located within foldable electronic circuit board 2600, particularly illuminators (such as front illuminators 740a, 740b, 740c and side illuminators 750a, 750b, 760a and 760b) and reduce the overall temperature of the endoscope tip section. This will solve or at least mitigate a major problem of raised temperatures of endoscope tip and/or any of its components, particularly when using LED illuminators.

Figure 27A:
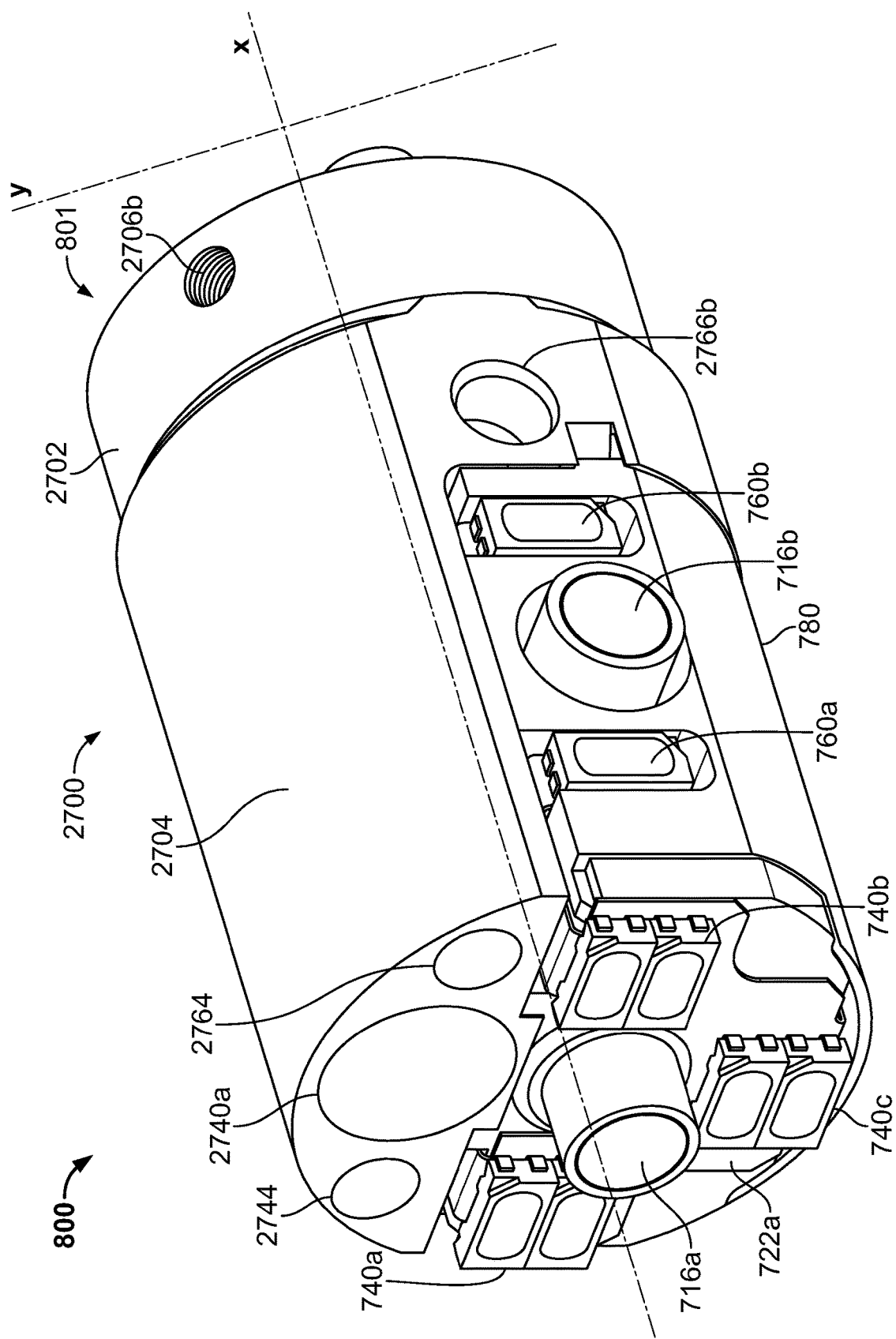
FIG. 27A shows a perspective view of an endoscope's tip section according to some embodiments.

Reference is now made to FIG. 27A, which shows a perspective view of a tip section 801 of an endoscope assembly 800 (which, in one example, is similar to endoscope assembly 100 of FIG. 2A), according to an embodiment.

According to some embodiments, fluid channeling component or manifold 2700 is configured as a separate component from foldable electronic circuit board 2600 (FIGS. 26A through 26D). This configuration is adapted to separate the fluid channels 2744 (jet channel), 2764 (injector channel) and working channel 2740a which are located in fluid channeling component or manifold 2700, from the sensitive electronic and optical parts which are located in the area of the foldable electronic circuit board. FIGS. 38J and 38K, described later in this specification, also show another perspective view of a tip 3801 and manifold 600.

According to some embodiments, fluid channeling component or manifold 2700 includes a proximal fluid channeling section or base 2702, which has a substantially cylindrical shape, and a primary distal channeling section or casing 2704. Primary distal fluid channeling section or casing 2704 partially continues the cylindrical shape of proximal fluid channeling section or base 2702 and has a shape of a partial cylinder (optionally elongated partial cylinder). Primary distal fluid channeling section or casing 2704 forms a fraction of the cylinder (along the height axis of the cylinder), wherein the other fraction of the cylinder (along the height axis of the cylinder) is missing. Primary distal fluid channeling section or casing 2704 is integrally formed as a unitary block with proximal fluid channeling section or base 2702 and extends outward from the base 2702. The height or width, along axis 'y', of primary distal fluid channeling section or casing 2704 is less than that of proximal fluid channeling section or base 2702. The length, along axis 'x', of casing 2704 is greater than the length of base 2702. In the embodiment comprising primary distal fluid channeling section or casing 2704, the casing 2704 has the shape of a partial cylinder (for example, partial cylinder having only a fraction of a cylinder shape along one side of the height axis 'y') and provide a space to accommodate foldable electronic circuit board 2600 (FIGS. 26A through 26D).

Therefore, as shown in FIG. 27A, the manifold 2700 combined with the partially enclosed housing 780 of FIGS. 26A through 26D create a substantially cylindrical housing.

Proximal fluid channeling section or base 2702 includes integrated screw nuts 2706*b*, which are configured for securing tip section 801 to an endoscope shaft. In accordance with an embodiment, the fluid channels 2744, 2764 and working channel 2740*a* extend through the base and the casing.

Primary distal fluid channeling section or casing 2704 includes working channel 2740*a* which is configured for insertion of a medical (such as a surgical) tool, for example, to remove, treat and/or extract a sample of the object of interest found in the colon or its entirety for biopsy.

According to various embodiments, a fluid channeling component or manifold, such as manifold 2700, is used for heat transfer purposes. The manifold, according to embodiments of the specification (such as manifold 2700), can be used as a heat sink for some or all of the illuminators (such as side or front LEDs) and/or other electronic components, and reduce overall temperature of the endoscope tip. This will solve or at least mitigate a major problem of raised temperatures of the endoscope tip and/or any of its components, particularly when using LED illuminators.

Figure 27B:
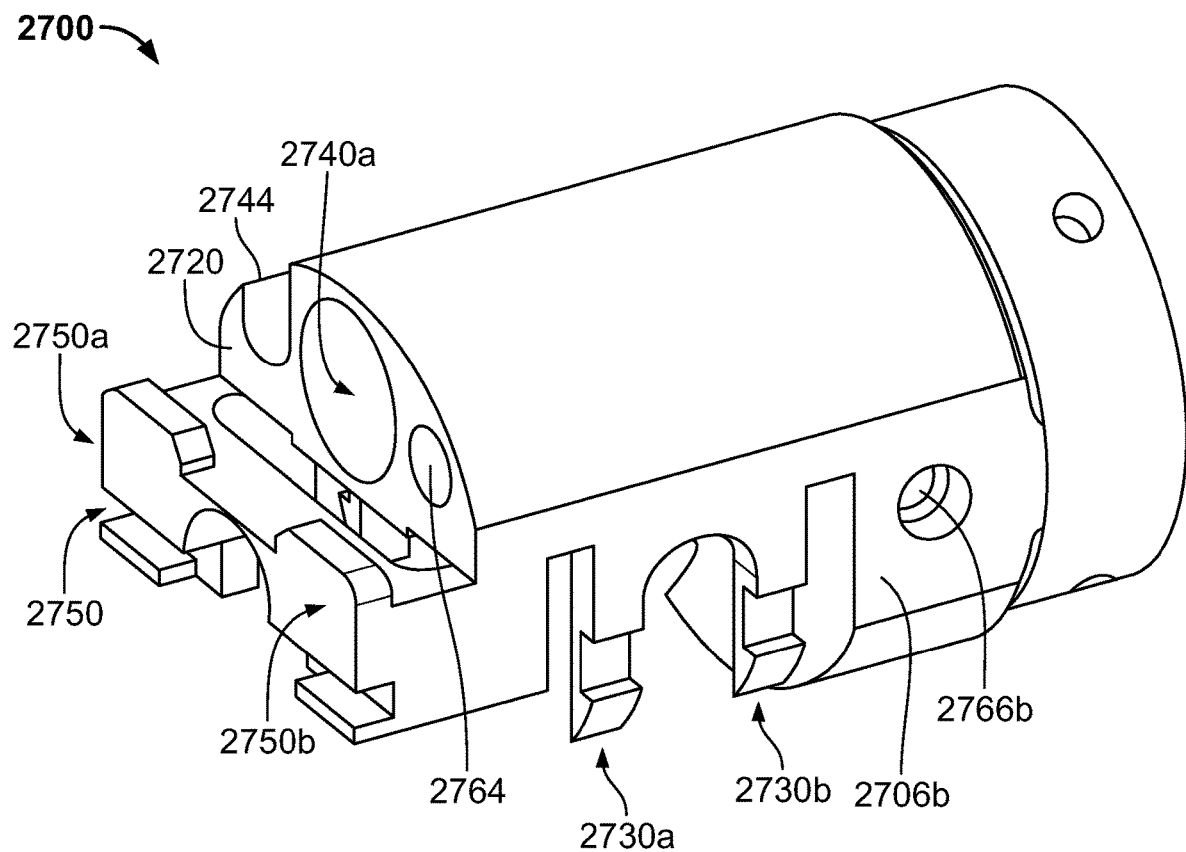
FIG. 27B shows a perspective view of a fluid channeling component of the endoscopic tip section of FIG. 27A.

FIG. 27B shows an embodiment of the fluid channeling component or manifold 2700 which also includes parts enabling this component to function as a flexible electronic circuit board holder. Manifold 2700 includes a front portion 2750 (shown here as formed of two front portions 2750*a* and 2750*b*), supporting the back sides (opposing to the sides where the LEDs are attached) of the first front LED surface (740*a* of FIG. 27A) and second front LED surface (740*b* of FIG. 27B), respectively. Front portions 2750*a* and 2750*b* form an arc shape between them which is configured to accommodate and support forward looking viewing element 716*a* of FIG. 27A. According to some embodiments, front portion 2750 distally protrudes from front face 2720. A jet channel opening 2744 and an injector channel opening 2764 are also seen on the front face 2720.

Fluid channeling component or manifold 2700 further includes a first side portion 2760 and a second, opposite side portion on the two opposing sides thereof. Each of side portions include two small openings for the side LEDs (760*a*, 760*b* of one side in FIG. 27A, the LEDs on the other side are not visible) and one opening for side looking viewing elements.

Each of the side portions further includes an I/I injector opening 2766*b* aimed at side optical assembly 716*b* of FIG. 27A on the first side portion 2760, and a similar I/I injector opening on the second, opposite side portion, used for injecting fluid (the term "fluid" may also include gas and/or liquid) to wash contaminants such as blood, feces and other debris from side optical assemblies of side looking viewing elements. According to some embodiments, the openings may supply liquid for cleaning any of the tip elements (such as any optical assembly, windows, LEDs, and other elements).

Each of the side portions further includes two viewing element holders, for example viewing element holders 2730*a* and 2730*b* of first side portion 2760, adapted to receive a viewing element bridge which is adapted to support assemblies (716*b* of FIG. 27A) of side looking viewing elements.

Figure 28A:
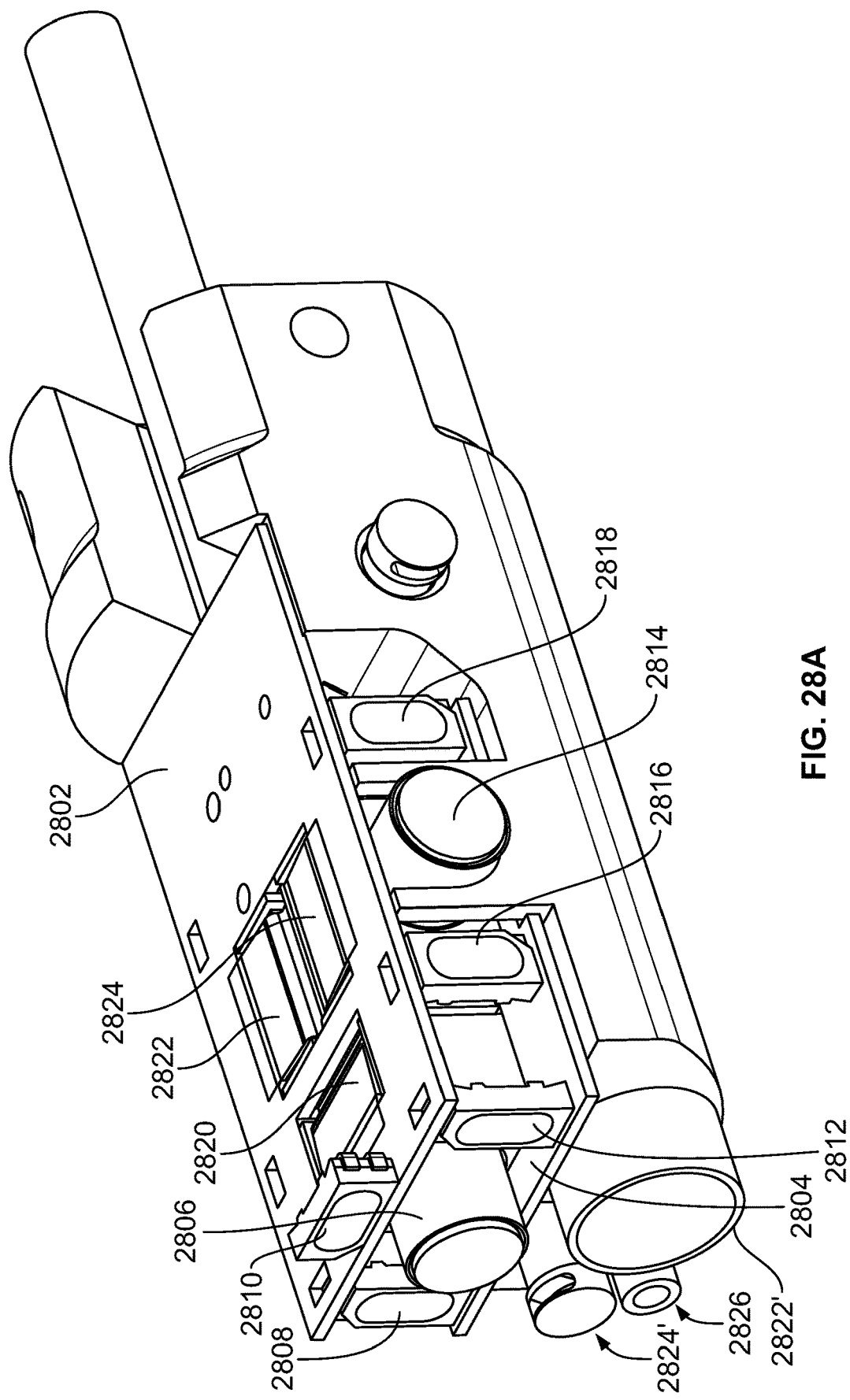
FIG. 28A illustrates an upper base board and a lower base board associated with a fluid channeling component and adapted to support the optical assembly and illuminators of an endoscope, in accordance with an embodiment of the present specification.

FIG. 28A illustrates an upper base board and a lower base board associated with a fluid channeling component wherein jet and nozzle openings may be placed adjacent to each other or on either side of a working/service channel and adapted to support the optical assembly and illuminators of an endoscope, in accordance with an embodiment of the present specification. FIG. 28A illustrates upper base board 2802 and lower base board 2804 supporting the optical assembly and illuminators shown in the endoscope assembly 6400 of FIG. 64. The front optical assembly comprises a front lens assembly 2806 and a front image sensor. The side optical assembly comprises a side lens assembly 2814 and a side image sensor. The front image sensor's pins and rigid area 2820 are bent to be soldered to the upper base board 2802 and lower base board 2804. The side image sensors' pins and rigid areas 2822 and 2824 (for the right and left side image sensors respectively) are bent to be soldered to the upper base board 2802 and lower base board 2804. The upper base board 2802 and the lower base board 2804 have grooves/holes enabling the front and side illuminators to be placed within the grooves/holes. The upper and lower base boards 2802, 2804 hold three sets of front illuminators 2808, 2810, 2812 and on each side panel two sets of illuminators 2816, 2818 (the figure illustrates only one side panel of the endoscope, however it should be understood by those of ordinary skill in the art that the other side panel is equivalent to this side panel). Front illuminators 2808, 2812 are placed between the upper and lower base boards 2802, 2804, while front illuminator 2810 is placed above front lens assembly 2806. The two sets of illuminators 2816, 2818 are placed between the upper and lower base boards 2802, 2804.

As shown in FIG. 28A, jet opening 2826 and nozzle opening 2824' may be positioned adjacent to each other on front panel of the tip in accordance with an embodiment. In another embodiment, the jet opening 2826 and nozzle opening 2824' may be positioned on either side of the working/service channel opening 2822' on the front panel of the tip. A tip cover sheaths the endoscope tip and the components therein.

Figure 28B:
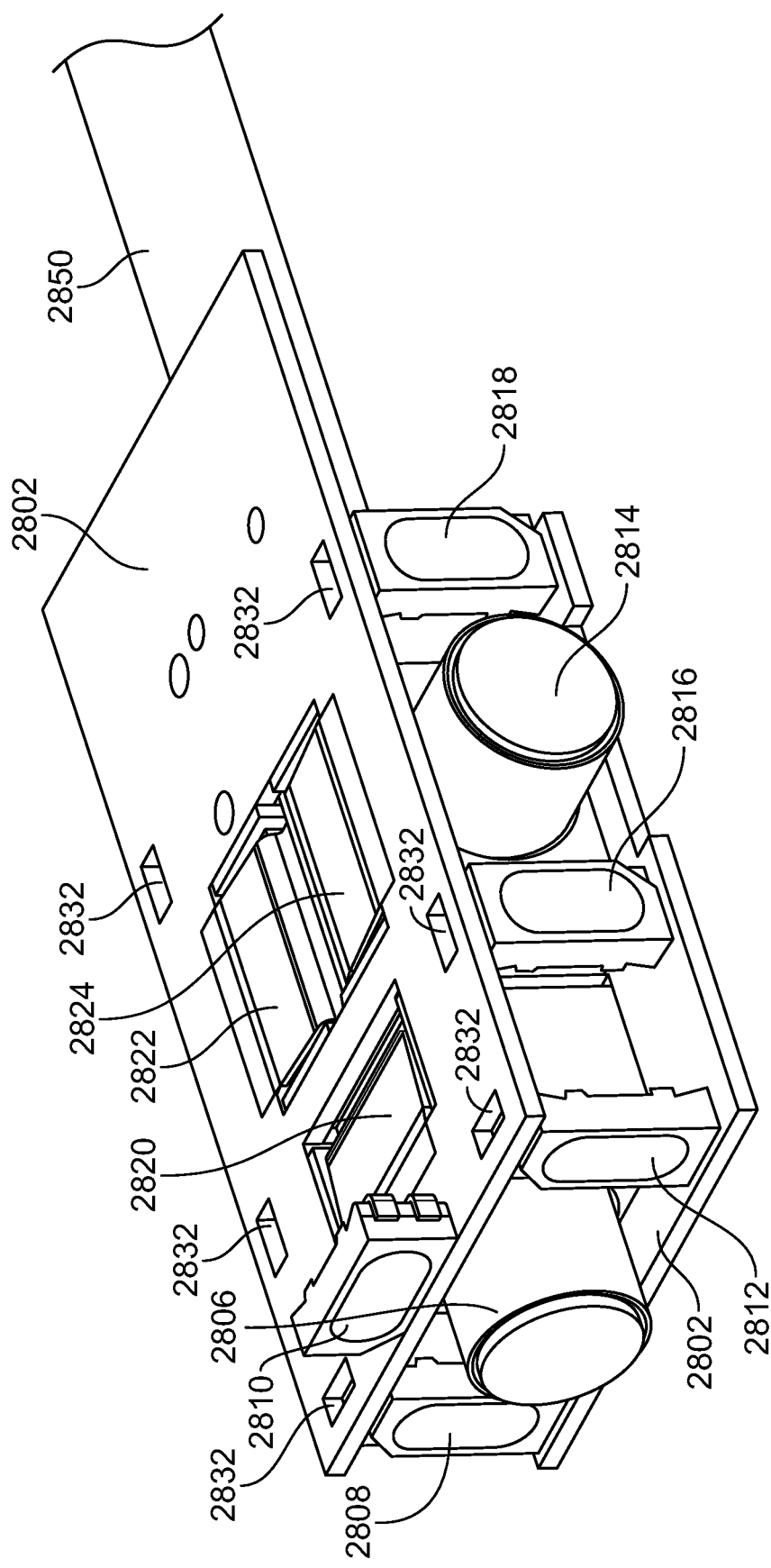
FIG. 28B illustrates a top view of an upper base board adapted to support the optical assembly and illuminators of an endoscope, in accordance with an embodiment of the present specification.

FIG. 28B illustrates a top view of an upper base board 2802 adapted to support the optical assembly and illuminators of an endoscope, in accordance with an embodiment of the present specification. In various embodiments, the upper base board 2802 is provided with grooves/holes 2832 for the front illuminators 2808, 2810, 2812 and for the first set of side illuminators 2816, 2818 and the second set of side illuminators to be placed within. In the illustrated embodiment, one groove is provided on the upper base board 2802 for each illuminator supported by the upper base board 2802. In one embodiment, grooves 2832 are identical for all illuminators, while in another embodiment each groove may be adapted to different sizes of illuminators. For example, different sizes of illuminators may comprise LEDs (Light Emitting Diode) adapted to emit white light, infrared light, ultraviolet light, near-infrared light and other wavelengths of light.

An electrical cable 2850 threaded through the upper base board 2802, in one embodiment, transfers the information from the optical assemblies to the illuminators and to a main control unit.

Figure 28C:
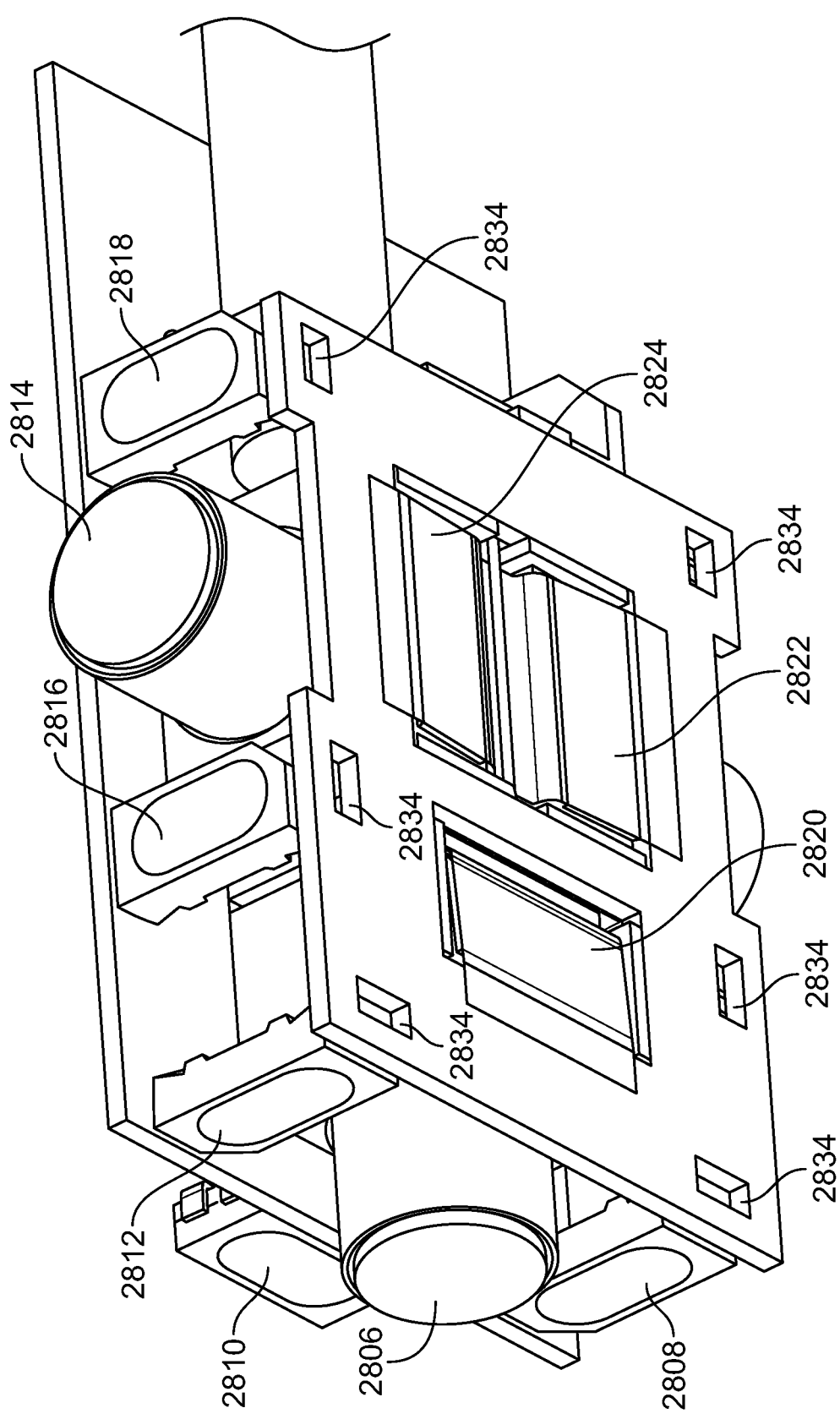
FIG. 28C illustrates a bottom side view of a lower base board adapted to support the optical assembly and illuminators of an endoscope, in accordance with an embodiment of the present specification.

FIG. 28C illustrates a bottom side view of a lower base board 2804 of the electronic circuit board adapted to support the optical assembly and illuminators of an endoscope, in accordance with an embodiment of the present specification. In various embodiments, the lower base board 2804 is provided with grooves/holes 2834 for front illuminators 2808, 2810, 2812 and for the first set of side illuminators 2816, 2818 and the second set of side illuminators to be placed within. In the illustrated embodiment, one groove is provided on the lower base board 2804 for each illuminator supported by the base board 2804. In various embodiments, the pins and the rigid area(s) of the endoscope's image sensors are bent to be soldered to the upper and lower base boards 2802, 2804. In one embodiment, grooves 2834 are identical for all illuminators, while in another embodiment each groove may be adapted to different sizes of illuminators. For example, different sizes of illuminators may comprise LEDs (Light Emitting Diode) adapted to emit white light, infrared light, ultraviolet light, near-infrared light and other wavelengths of light.

Figure 29A:
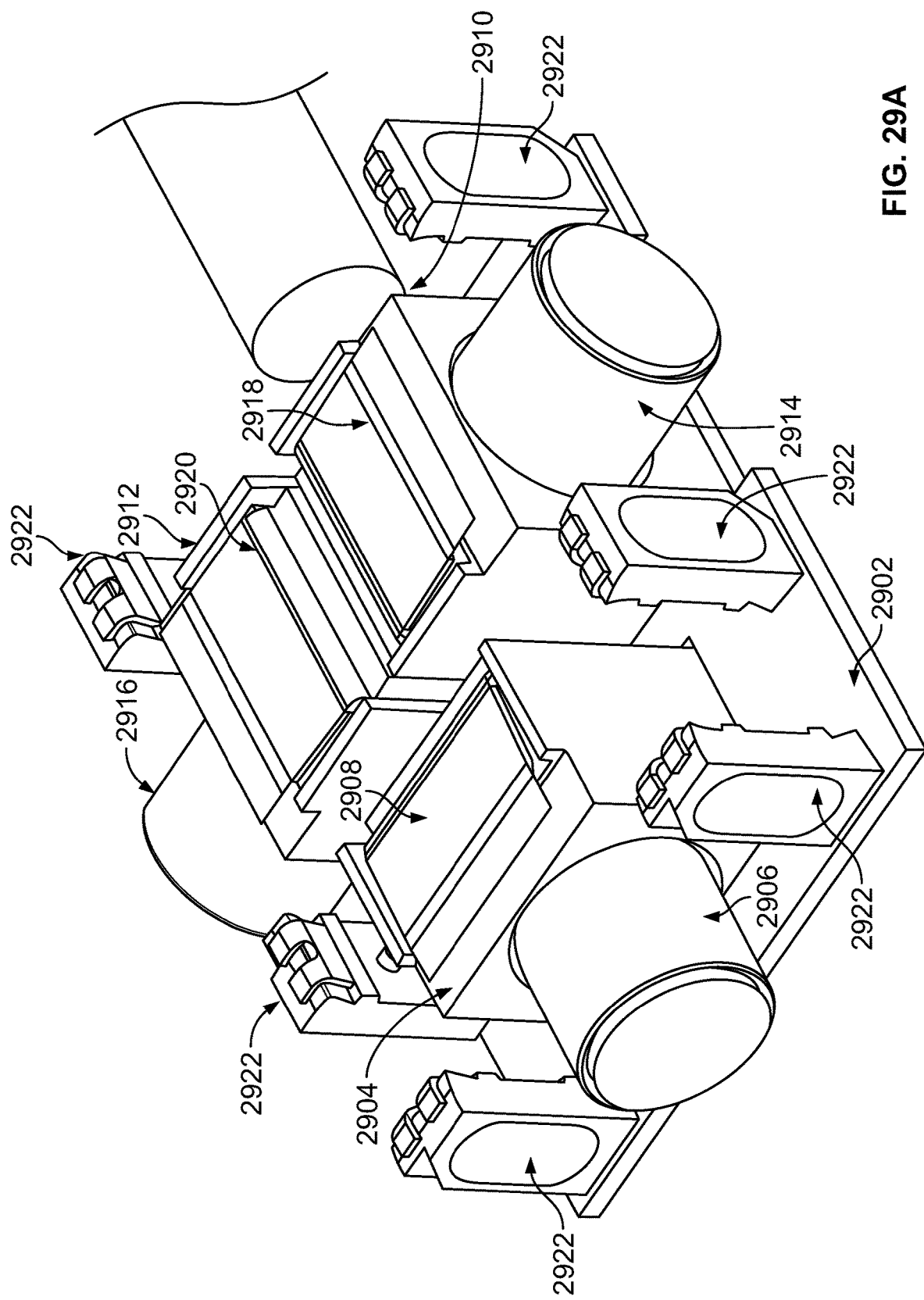
FIG. 29A illustrates the optical assembly and illuminators supported by a lower base board, where the upper base board shown in FIG. 28A is removed.

FIG. 29A illustrates the optical assembly and illuminators supported by a lower base board 2902 with the upper base board shown in FIG. 28A removed. In an embodiment, metal frames are provided to hold the front and side lens assemblies and also to support the associated image sensors. As illustrated, a metal frame 2904 is provided to support front lens assembly 2906 and support the image sensor 308 associated with the front lens assembly 2906. Metal frames 2910 and 2912 are provided to support side lens assemblies 2914, 2916 and support the associated image sensors 2918 and 2920, respectively. In an embodiment, the metal frames 2904, 2910, 2912 may also serve as a heat sink to the light emitting diodes (LEDs) and sensors incorporated in the endoscope. Illuminators 2922 are attached to the lower base board 2902 by means of grooves/holes (shown in FIG. 29B) made in the lower base board 2902.

Figure 29B:
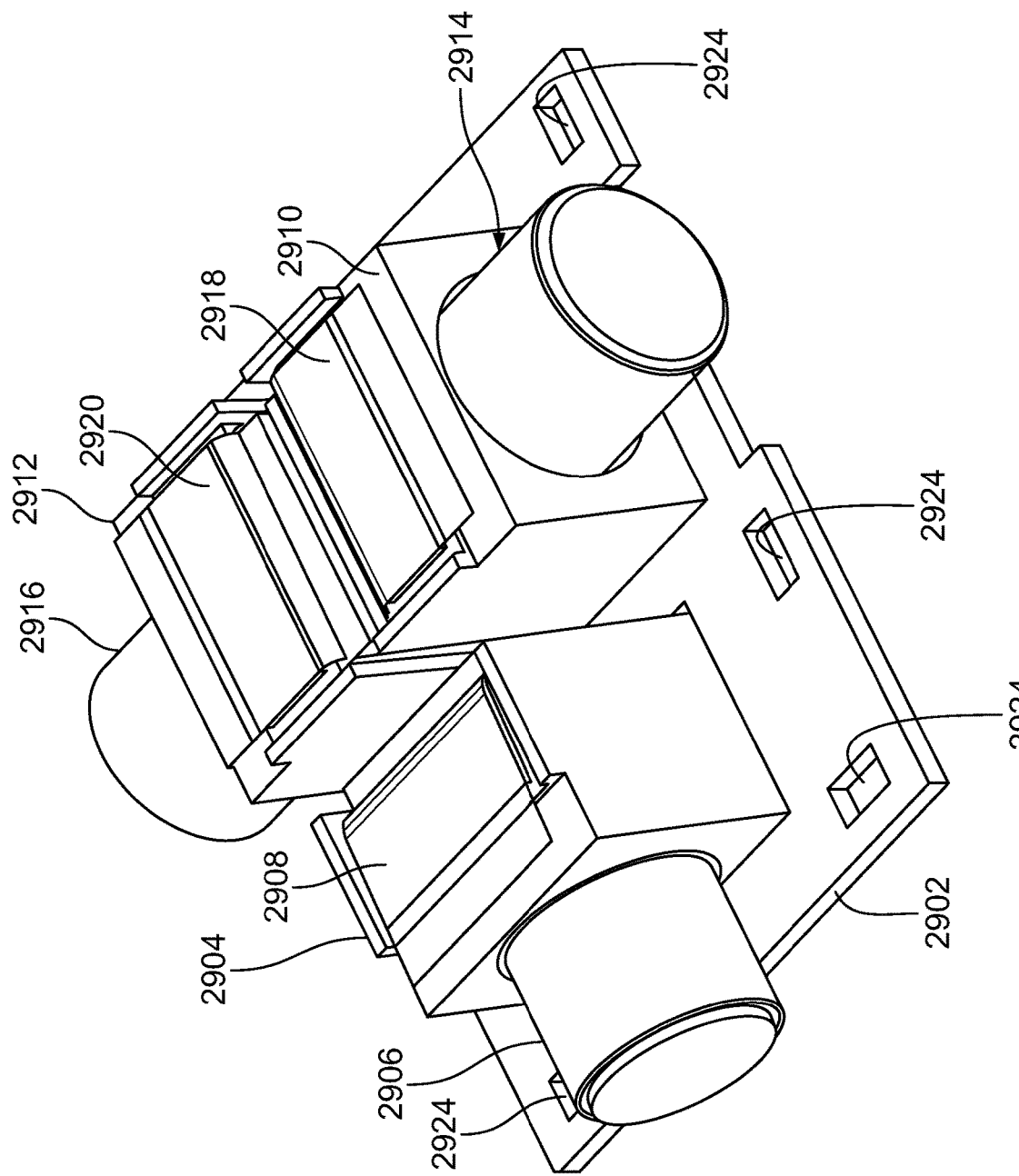
FIG. 29B illustrates another view of the optical assembly supported by a lower base board as shown in FIG. 29A with the illuminators removed.

FIG. 29B illustrates another view of the optical assembly supported by a lower base board 2902 as shown in FIG. 29A with the illuminators 2922 (shown in FIG. 29A) removed. The lower base board 2902 comprises grooves 2924 for enabling the illuminators 2922 (shown in FIG. 29A) to be coupled with the based board 2902.

Figure 29C:
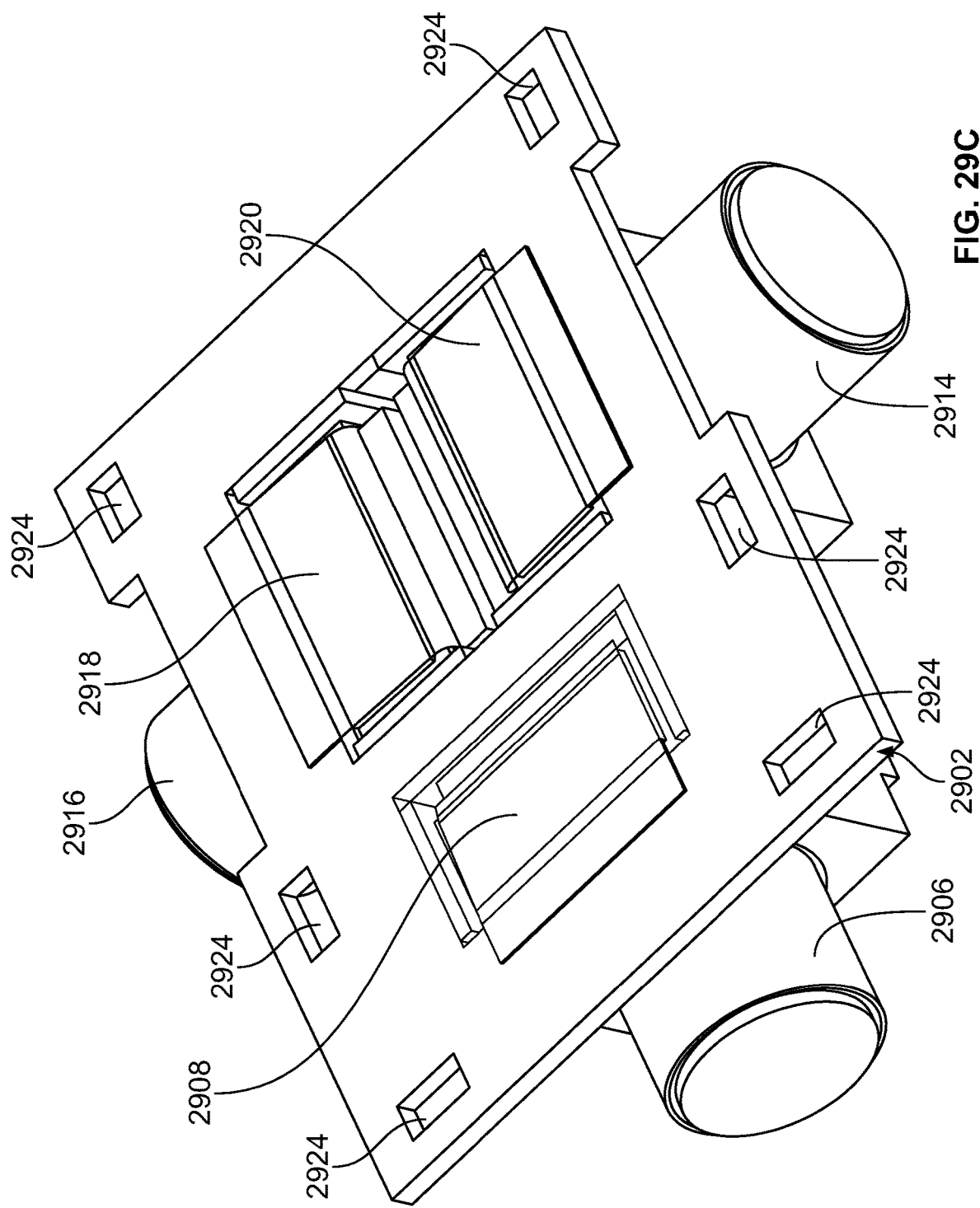
FIG. 29C illustrates a bottom view of the optical assembly supported by a lower base board, as shown in FIG. 29B, where the illuminators are removed.

FIG. 29C illustrates a bottom view of the optical assembly supported by a lower base board 2902 as shown in FIG. 29B with the illuminators 2922 removed. As shown, the lower base board 2902 fits around the image sensors exposing the image contact areas and supports the lens assemblies. The grooves 2924 allow the illuminators 2922 (shown in FIG. 29A) to be secured to the base board 2902.

Figure 30A:
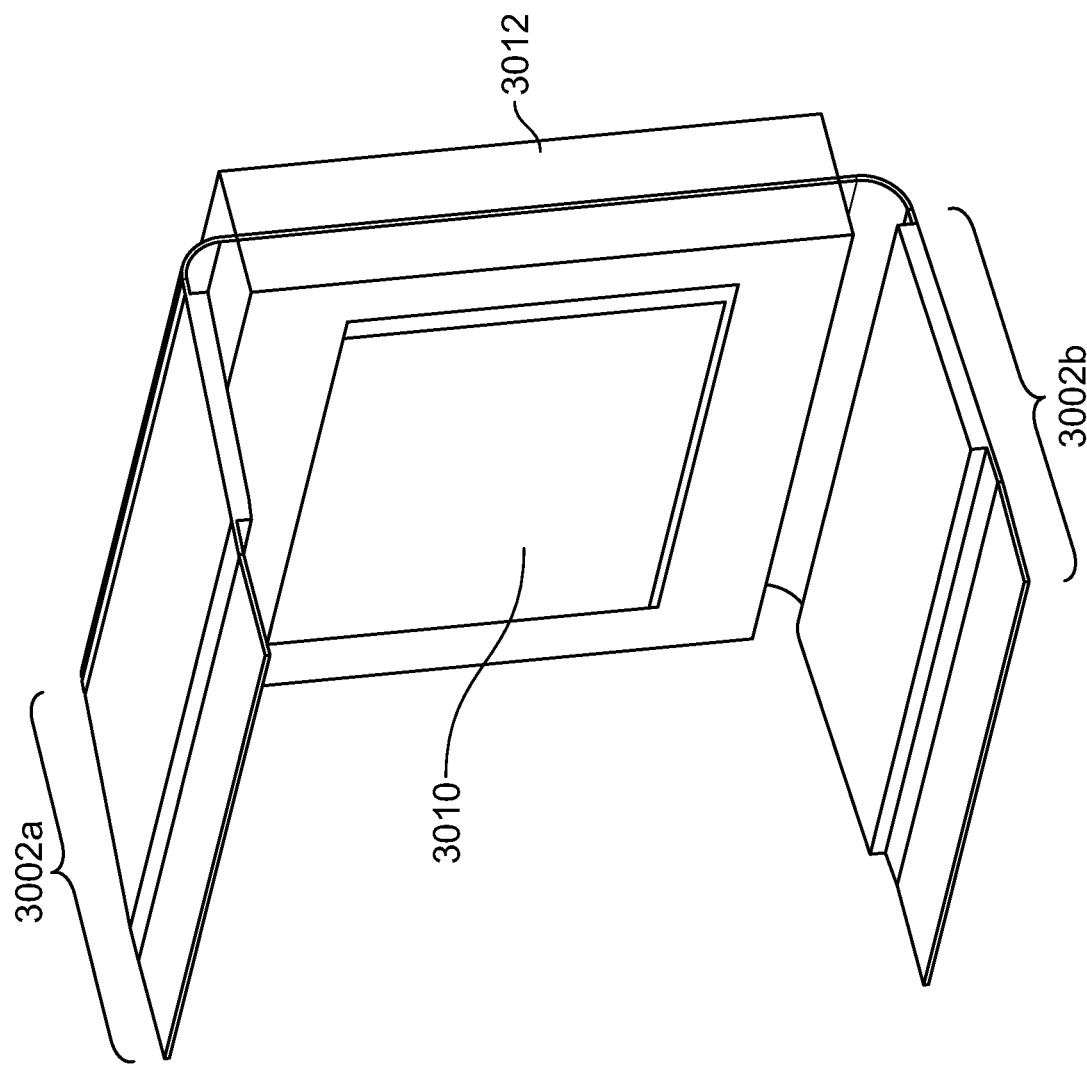
FIG. 30A illustrates an image sensor comprising two image sensor contact areas, in accordance with an embodiment of the present specification.

FIG. 30A illustrates an image sensor 3002 (shown as 2908, 2918 and 2920 in FIGS. 29A, 29B, and 29C, respectively) in a folded position as when placed between upper and lower base boards, in accordance with an embodiment of the present specification. As shown, the image sensor 3002 comprises two horizontal bent image sensor contact areas 3002a and 3002b, positioned parallel to a plane of the upper and lower base boards (not shown in figure). The image sensor contact areas 3002a and 3002b comprise a plurality of connector pins. The image sensor 3002 further comprises a vertical portion positioned between the image sensor contact areas 3002a and 3002b. A top edge of the vertical portion is coupled with an edge of the image sensor contact area 3002a while a bottom edge of the vertical portion is coupled with an edge of the image sensor contact area 3002b, as shown in FIG. 30A. The vertical portion comprises a first surface 3010 which in an embodiment is made of glass and an opposing second surface 3012 which in an embodiment comprises a printed circuit board or a computer chip.

The image sensor 402 captures still images and/or video feeds and in various embodiments comprises a Charge Coupled Device (CCD) or a Complementary Metal Oxide Semiconductor (CMOS) image sensor (not shown in figure). The image sensor 3002 is incorporated in the endoscope and is associated with a lens assembly as illustrated in FIGS. 28A through 28C and 29A through 29C. In an embodiment, three sets of optical assemblies, each comprising a lens assembly associated with an image sensor in a folded position as shown in FIG. 30A, are assembled in a tip portion of the endoscope. The three sets of optical assemblies comprise a front lens assembly associated with a front image sensor, a first side lens assembly associated with a first side image sensor and a second side assembly associated with a second side image sensor. The two side image sensors are assembled back to back as shown in FIGS. 29A through 29C such that the two glass surfaces 3010 are facing in opposite directions.

In the embodiment illustrated in FIG. 30A, the folded position of the image sensor 3002 causes the first glass surface 3010 of the image sensor 3002 associated with a front lens assembly to face in a direction of the tip of the endoscope when the image sensor 3002 is positioned between upper and lower base boards (not shown in FIG. 30A) and assembled in the tip portion of the endoscope. The second opposing surface 3012 faces in an opposite direction towards an electrical connector end of the endoscope when the image sensor 3002 is in the illustrated folded position. Once the image sensor 3002 is assembled within an endoscope, the front glass surface 3010 faces forward and in an outward direction when viewed with respect to the center of the endoscope tip.

Figure 30B:
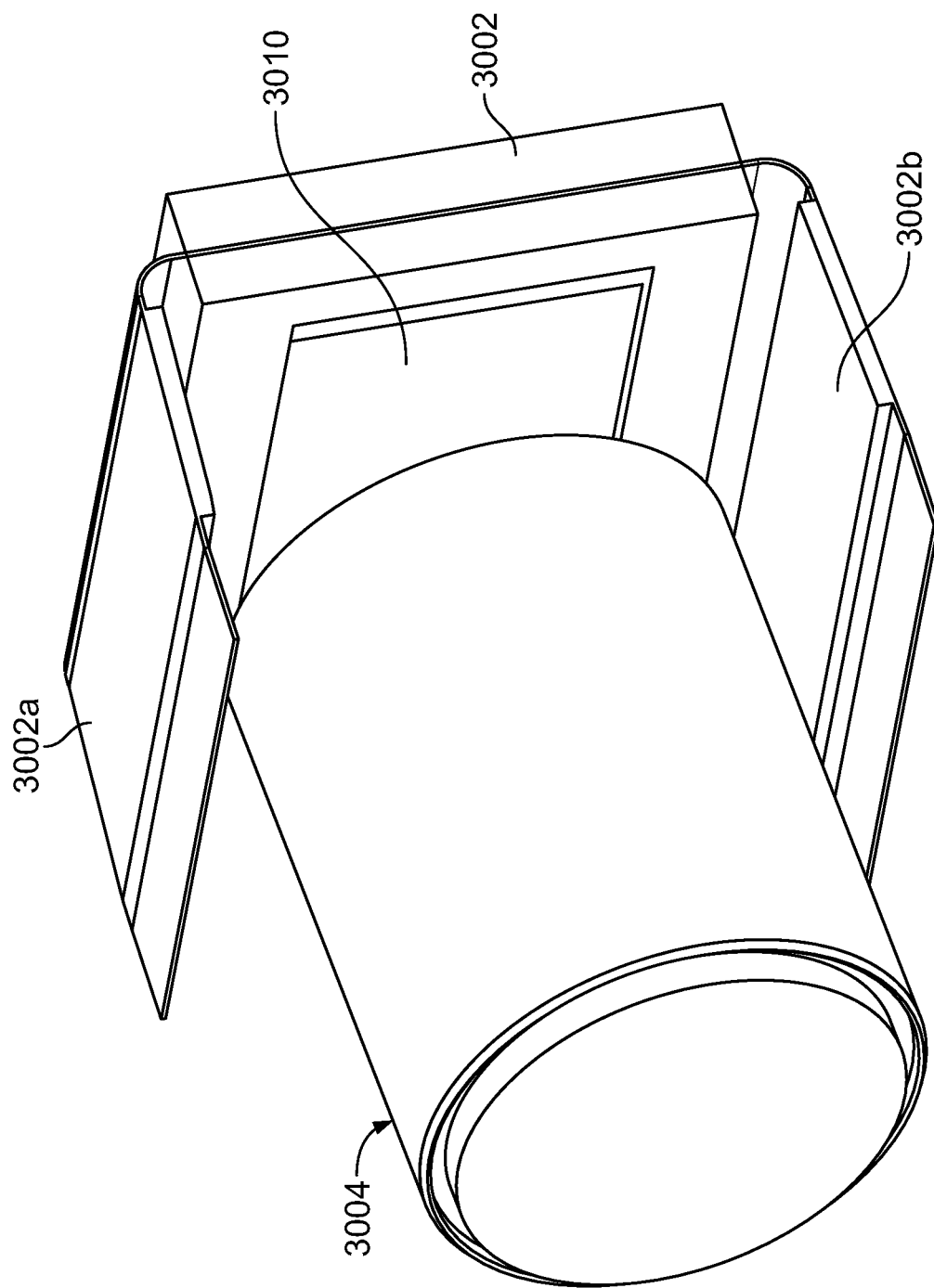
FIG. 30B illustrates a lens assembly being coupled with the image sensor, in accordance with an embodiment of the present specification.

FIG. 30B illustrates a lens assembly 404 being coupled with the image sensor 3002. As illustrated, the lens assembly 3004 is positioned between the image sensor contact areas 3002a and 3002b, such that a rear portion of the lens assembly 3004 is closely associated and/or in contact with the first glass surface 3010 of the image sensor 3002. In the assembled position as shown in FIG. 30B, a front portion of the lens assembly 3004 projects in an outward direction and the lens assembly 3004 extends outwards beyond the area defined by the image sensor contact areas 3002a and 3002b. Hence, the effective area occupied by just the lens assembly 3004 on a circuit board of the endoscope is limited to the portion of the lens assembly 3004 that extends outwards beyond the area occupied by the image sensor contact areas 3002a and 3002b as shown in FIG. 30B.

The folded position of the image sensor 3002 reduces the length of space occupied by the lens assembly 3004 on a circuit board placed in an endoscope tip, thereby enabling the two side optical assemblies to be placed closer to each other than would have been possible with the methods of folding the image sensor used in prior art. This reduces the distance between the first and the second side assemblies 6406, 6408 illustrated in FIG. 64. Hence, due to the folding position of the image sensor as illustrated, each of the side optic assembly occupies approximately 1.3 mm less space on the endoscope circuit board, thereby leading to the diameter of the endoscope tip being reduced by approximately 2.6 mm as compared to prior art.

Figure 30C:
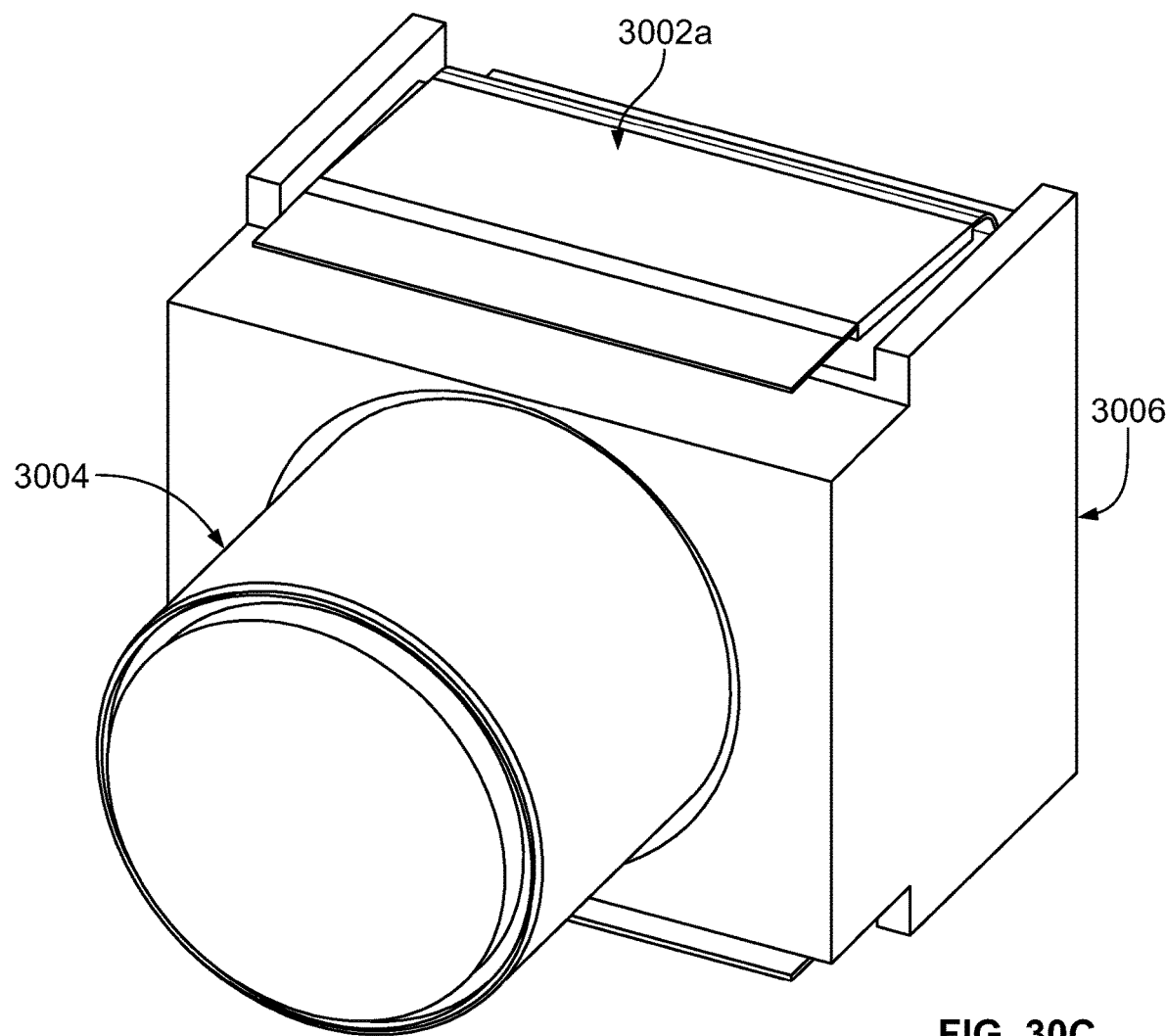
FIG. 30C illustrates a metal frame positioned to support and hold the lens assembly and the associated image sensor, in accordance with an embodiment of the present specification.

FIG. 30C illustrates a metal frame 3006 positioned to support and hold the lens assembly 3004 and the associated image sensor 3002. As shown, the metal frame 3006 is molded to enclose the lens assembly 3002 in a manner that supports the image sensor 3002 and the image sensor contact areas 3002a and 3002b.

Figure 31A:
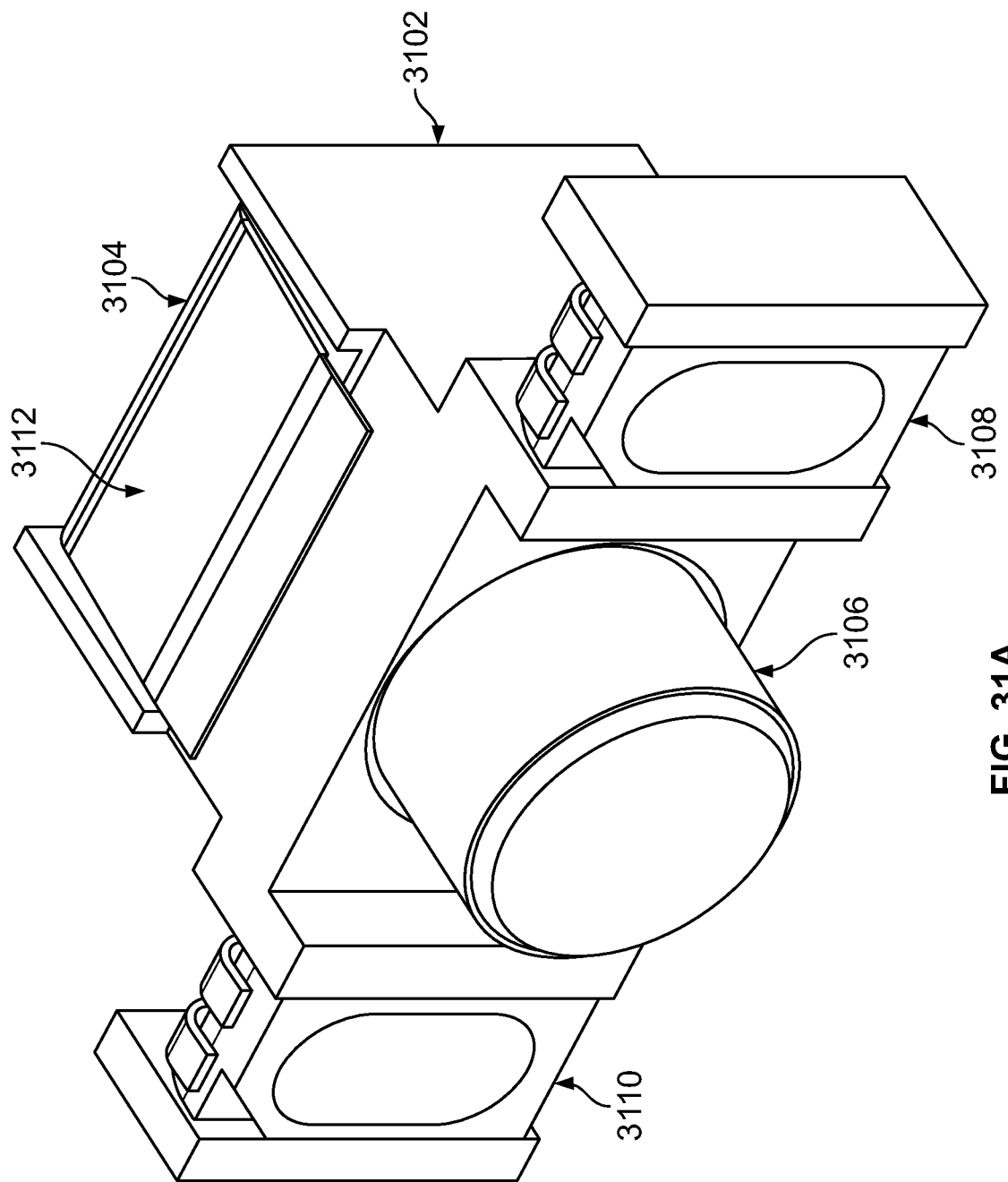
FIG. 31A illustrates a viewing element holder for supporting a lens assembly, image sensor and side illuminators, in accordance with an embodiment of the present specification.

In an embodiment of the present specification, a viewing element holder is employed for supporting the lens assembly and the image sensor as well as the illuminators associated with the lens assembly. FIG. 31A illustrates a viewing element holder for supporting a lens assembly, image sensor and side illuminators, in accordance with an embodiment of the present specification. As illustrated, viewing element holder 3102 which, in one embodiment, is a metal frame, is fitted around image sensor 3104, lens assembly 3106 and illuminators 3108, 3110, such that image sensor contact area 3112 is exposed as shown. The frame 3102 provides support to the image sensor 3104, lens assembly 3106 and illuminators 3108, 3110, enabling the said components to remain in a fixed position. In an embodiment, the image sensor 3104 is coupled with the frame 3102 in a manner identical to that illustrated in FIGS. 30B and 30C. The folding position of the image sensor 3104 inside the viewing element holder 3102 results in a reduction of the endoscope tip diameter. Further, in various embodiments, the image sensor 3104 is soldered to upper and lower base boards such as shown in FIG. 28B.

Figure 31B:
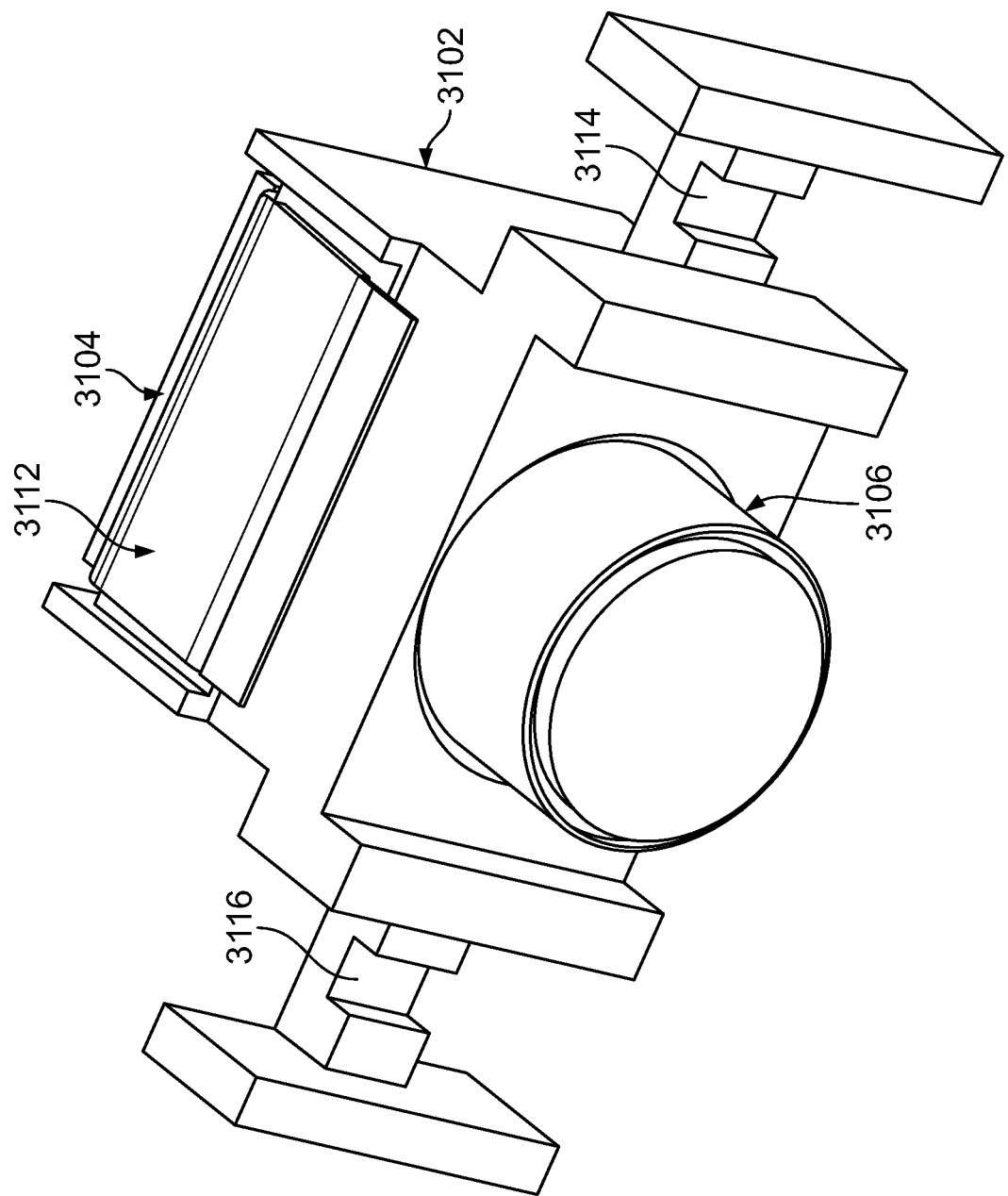
FIG. 31B illustrates grooves built in the viewing element holder for supporting the illuminators, in accordance with an embodiment of the present specification.

FIG. 31B illustrates grooves built in the viewing element holder for supporting the illuminators, in accordance with an embodiment of the present specification. Grooves 3114 and 3116 are provided in the viewing element holder 3102 for supporting illuminators 3108 and 3110 (shown in FIG. 31A) respectively. In one embodiment grooves 3114, 3116 are identical for all illuminators, while in another embodiment each groove may be adapted to different sizes of illuminators. For example, different sizes of illuminators may comprise LEDs (Light Emitting Diode) adapted to emit white light, infrared light, ultraviolet light, near-infrared light and other wavelengths of light. In other embodiments, more number of grooves may be provided in the viewing element holder 3102 in order to support more number of illuminators.

Figure 32A:
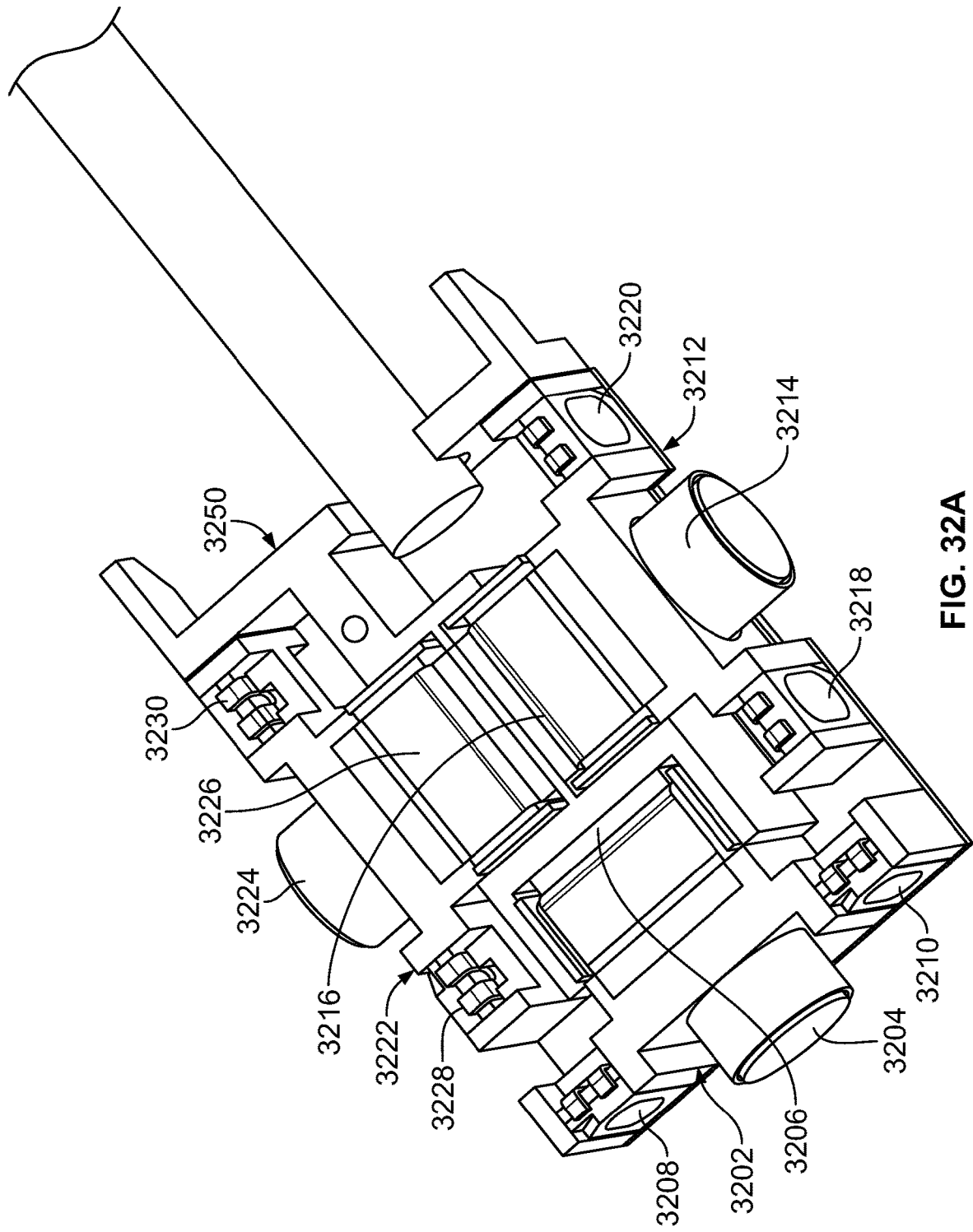
FIG. 32A illustrates a plurality of optical assemblies supported by viewing element holders and assembled to be placed in a tip of an endoscope, in accordance with an embodiment of the present specification.

FIG. 32A illustrates a plurality of viewing element holders that are assembled to be placed in a tip of an endoscope, in accordance with an embodiment of the present specification. As shown in the figure, viewing element holder metal frame 3202 supports a front lens assembly 3204, associated image sensor 3206 and illuminators 3208 and 3210. Viewing element holder metal frame 3212 supports a side lens assembly 3214, associated image sensor 3216 and illuminators 3218 and 3220. Viewing element holder metal frame 3222 supports a side lens assembly 3224, associated image sensor 3226 and illuminators 3228 and 3230. In various embodiments, the viewing element holder metal frames act as a heat sink for the light emitting diodes employed in the illuminators. In one embodiment, a metal component, such as metal supporting frame 3250 is placed between the viewing element holders 3202, 3212 and 3222. Metal supporting frame 3250 acts as a heat sink for the illuminators and also supports the viewing element holders 3202, 3212 and 3222 by fixedly placing them between the upper and lower base boards (not shown in FIG. 32A). The metal supporting frame 3250 may also integrate with the optical assemblies and act as a heat sink for the LEDs while supporting the optical assemblies to be fixedly placed between the upper and lower base boards.

Figure 32B:
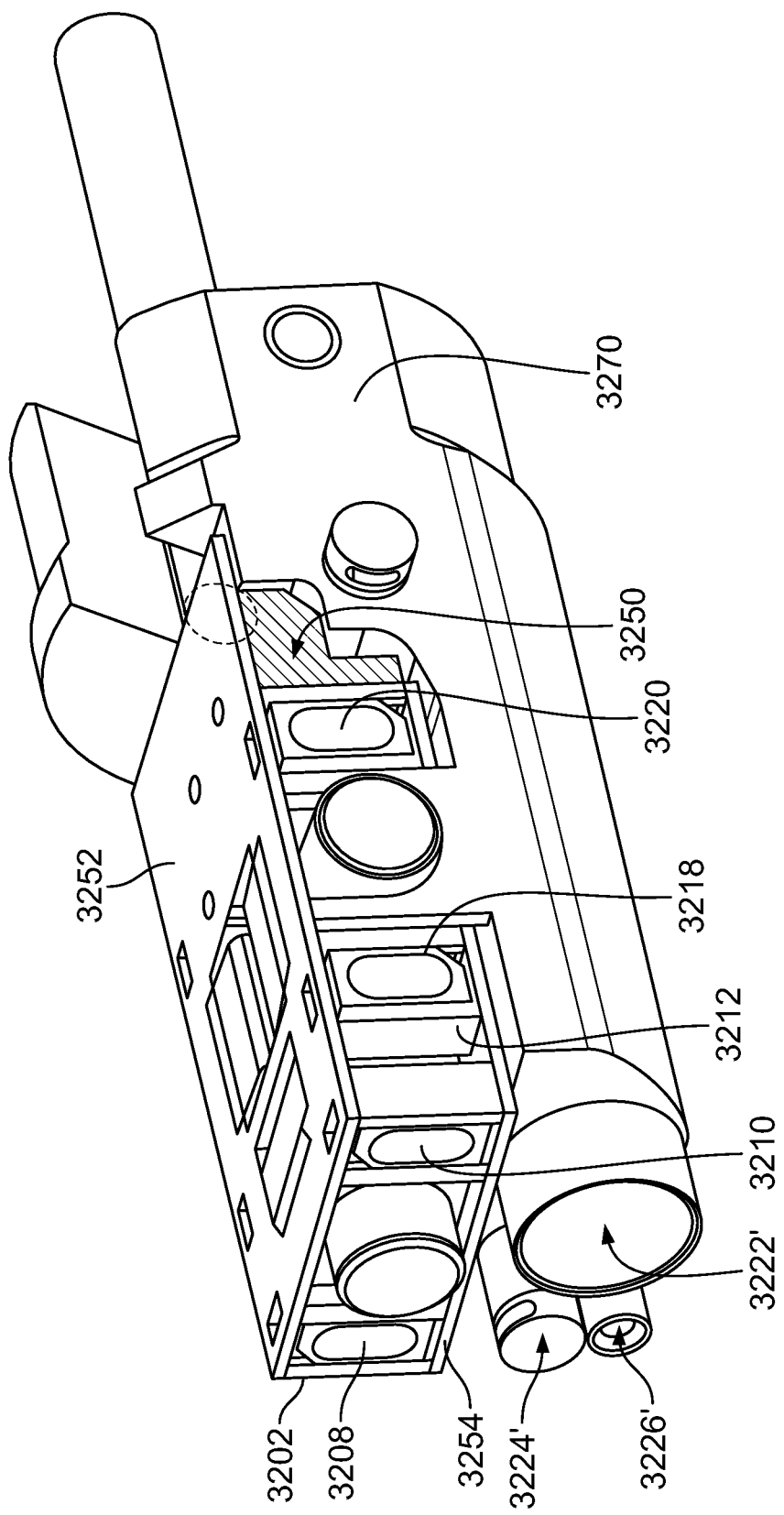
FIG. 32B illustrates the assembly shown in FIG. 32A coupled with an upper circuit board and a lower circuit board and associated with a fluid channeling component in a tip of an endoscope, in accordance with an embodiment of the present specification.

FIG. 32B illustrates the assembly shown in FIG. 32A coupled with an upper circuit board 3252 and a lower circuit board 3254 and associated with a fluid channeling component 3270 in a tip of an endoscope, in accordance with an embodiment of the present specification. The metal supporting frame 3250 of the front viewing element holder 3202, first side viewing element holder 3212 and a second side viewing element holder is adapted to act as a heat sink and is connected to the fluid channeling component 3270 such that the heat generated by the front illuminators 3208, 3210, the first side illuminators 3218, 3220, and second side illuminators and associated sensors may be transferred to the fluid channeling component 3270, causing a lowering of the temperature of the tip of the endoscope.

Also shown in FIG. 32B is jet opening 3226' and nozzle opening 3224' which may be positioned adjacent to each other on front panel of the tip. In another embodiment, the jet opening 3226' and nozzle opening 3224' may be positioned on either side of the working/service channel opening 3222' on the front panel of the tip. A tip cover sheaths the endoscope tip and the components therein.

The present specification discloses circuit boards particularly designed to hold front and side illuminators (associated with front and side optical assemblies of an endoscope respectively) in a desired position within a tip portion of an endoscope. The use of the illuminator circuit boards provided by the present specification eases the assembly of the illuminators within the circuit board placed in an endoscope's tip portion, as the illuminator boards pre-define precise locations for the front and side illuminators.

The present specification provides a convenient way of separating the optical assemblies from their associated illuminators. It is easier to first assemble an optical assembly and then to place the associated illuminators within the confined space of an endoscope tip. As the sizes of the components in an assembled endoscope's tip are very small, the pre-defined illuminator board helps keep all the components in desired, fixed positions.

Figure 33A:
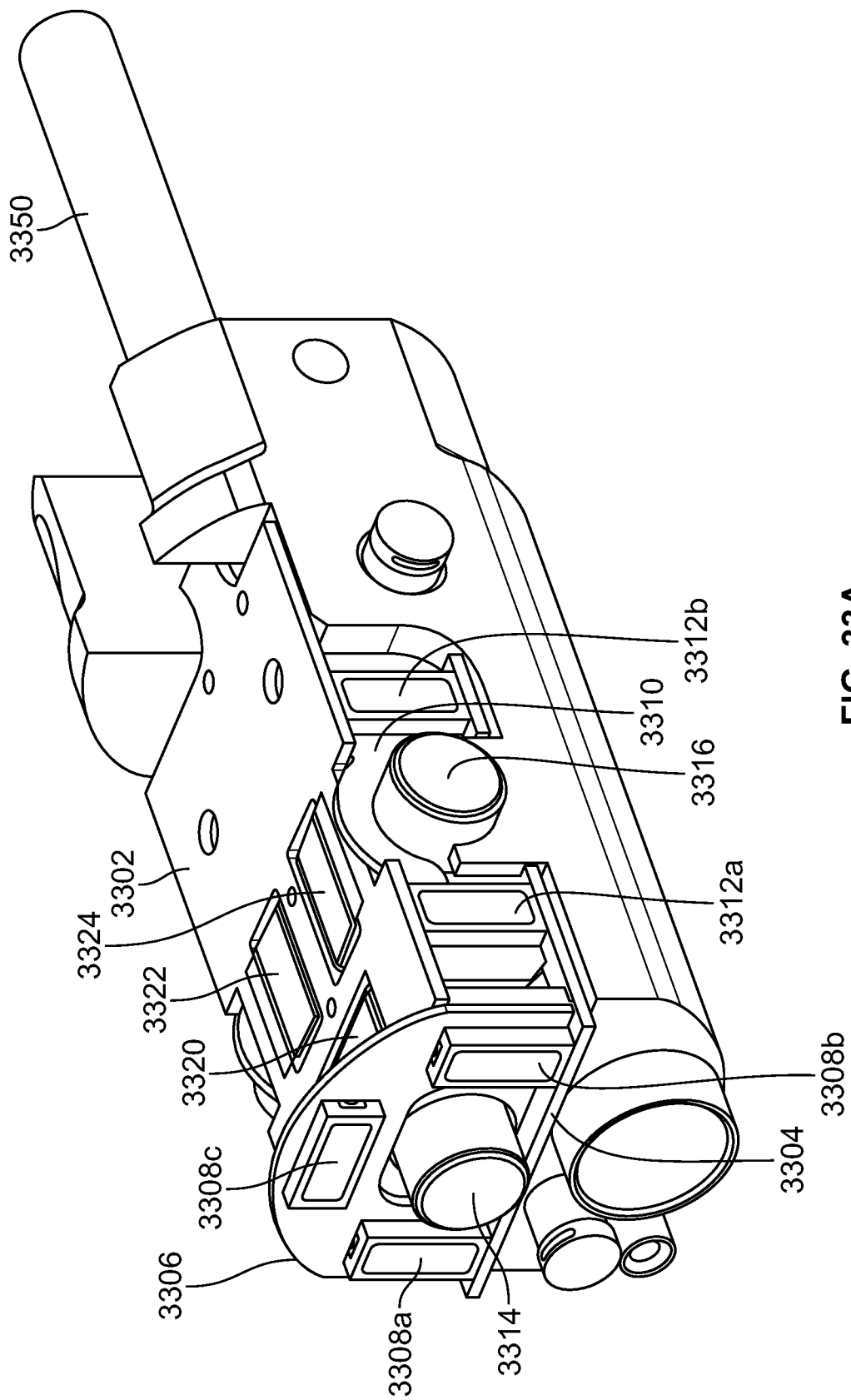
FIG. 33A illustrates a front illuminator electronic circuit board adapted for supporting the front illuminators of an endoscope, in accordance with an embodiment of the present specification.

FIG. 33A illustrates a front illuminator electronic circuit board 3306 adapted for supporting the front illuminators 3308a, 3308b, 3308c of an endoscope, in accordance with an embodiment of the present specification. FIG. 33A illustrates upper base board 3302, lower base board 3304, a front illuminator electronic circuit board 3306 for supporting the front illuminators 3308a, 3308b, 3308c, and a side illuminator electronic circuit board 3310 for supporting the side illuminators 3312a, 3312b. The front illuminators 3308a, 3308b, 3308c are associated with a front optical assembly comprising a front lens assembly 3314 and a front image sensor. The side illuminators 3312a, 3312b are associated with a side optical assembly comprising a side lens assembly 3316 and a side image sensor. The front image sensor's pins and rigid area 3320 are bent to be soldered to the upper base board 3302 and lower base board 3304. The side image sensors' pins and rigid areas 3322 and 3324 (for the right and left side image sensors respectively) are bent to be soldered to the upper base board 3302 and lower base board 3304. An electrical cable 3350 threaded through the upper base board 3302 transfers the information from the optical assemblies to a main control unit.

The front illuminator electronic circuit board 3306 holds a set of three front illuminators 3308a, 3308b, and 3308c. On each side panel, a side illuminator electronic circuit board 3310 holds a set of side illuminators 3312a, 3312b (the figure illustrates only one side panel of the endoscope, however it should be understood by those of ordinary skill in the art that the other side panel is equivalent to the shown side panel). In one embodiment, front illuminators 3308a, 3308b are positioned between the upper 3302 and lower 3304 base boards while front illuminator 3308c is positioned above front lens assembly 3314 and above the upper base board 3302. The two side illuminators 3312a, 3312b on both sides of the endoscope tip are positioned between the upper 3302 and lower 3304 base boards on either side of the side lens assembly 3316.

In various embodiments, any material that is used for constructing a PCB (Printed circuit boards) may be used for constructing the front and side illuminator circuit boards. Typical materials used for making PCB boards are ceramic, polyamides for flexible board, and glass-reinforced epoxy, such as, FR4 (a composite material composed of woven fiberglass cloth with an epoxy resin binder that is flame resistant (self-extinguishing)). Also in various embodiments, the front and side illuminator circuit boards may or may not be made of the same materials as the upper and lower base boards.

Figure 33B:
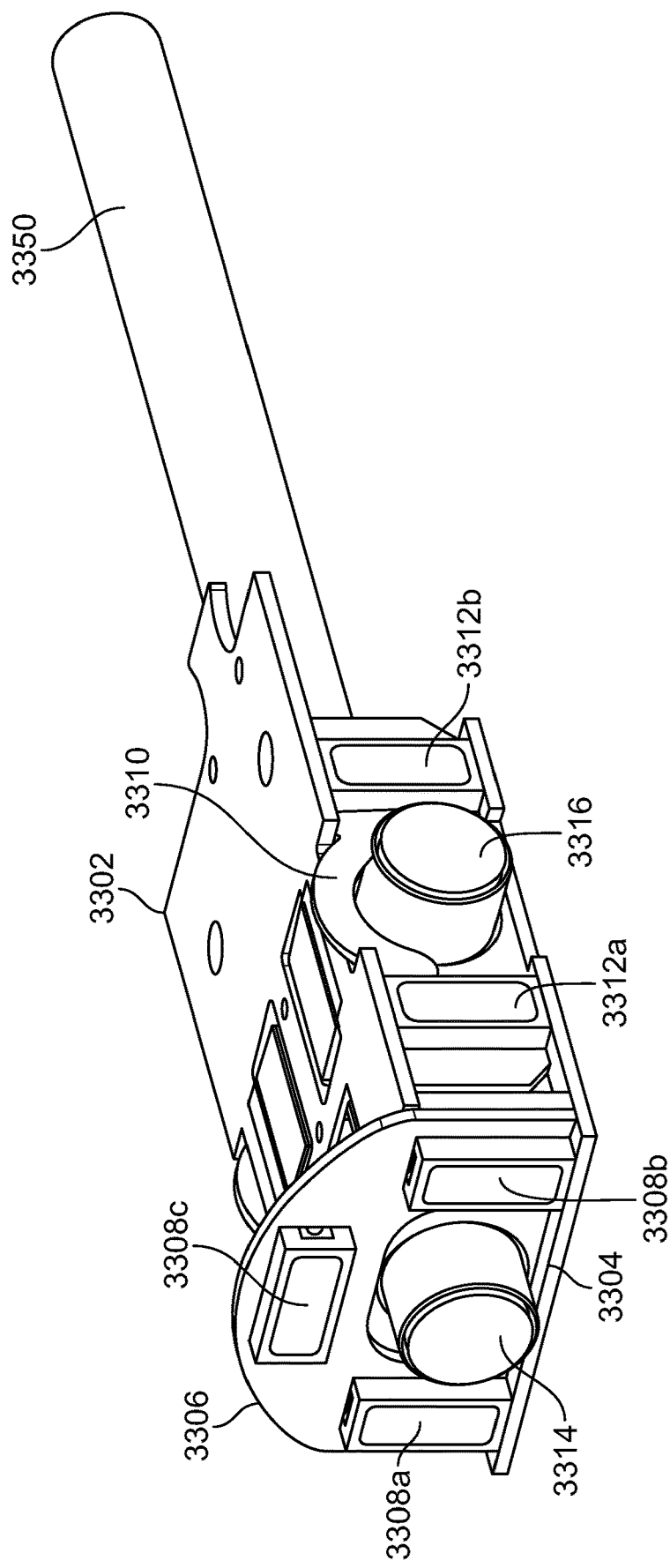
FIG. 33B illustrates upper and lower base boards integrated with the front and side illuminator electronic circuit boards, in accordance with an embodiment of the present specification.

FIG. 33B illustrates upper 3302 and lower 3304 base boards integrated with the front 3306 and side 3310 illuminator electronic circuit boards, in accordance with an embodiment of the present specification. As shown, the front illuminator electronic circuit board 3306 is integrated with the upper base board 3302 and lower base board 3304 and holds the front illuminators 3308a, 3308b, 3308c in place and enables the front lens assembly 3314 to protrude therethrough. The side illuminator circuit board 3310 is positioned in a side panel of the endoscope tip between the upper base board 3302 and lower base board 3304 and the side illuminators 3312a, 3312b in place and enables the side lens assembly 3316 to protrude therethrough. An electrical cable 3350 threaded through the upper base board 3302 transfers the information from the optical assemblies to the illuminators and to a main control unit.

Figure 34:
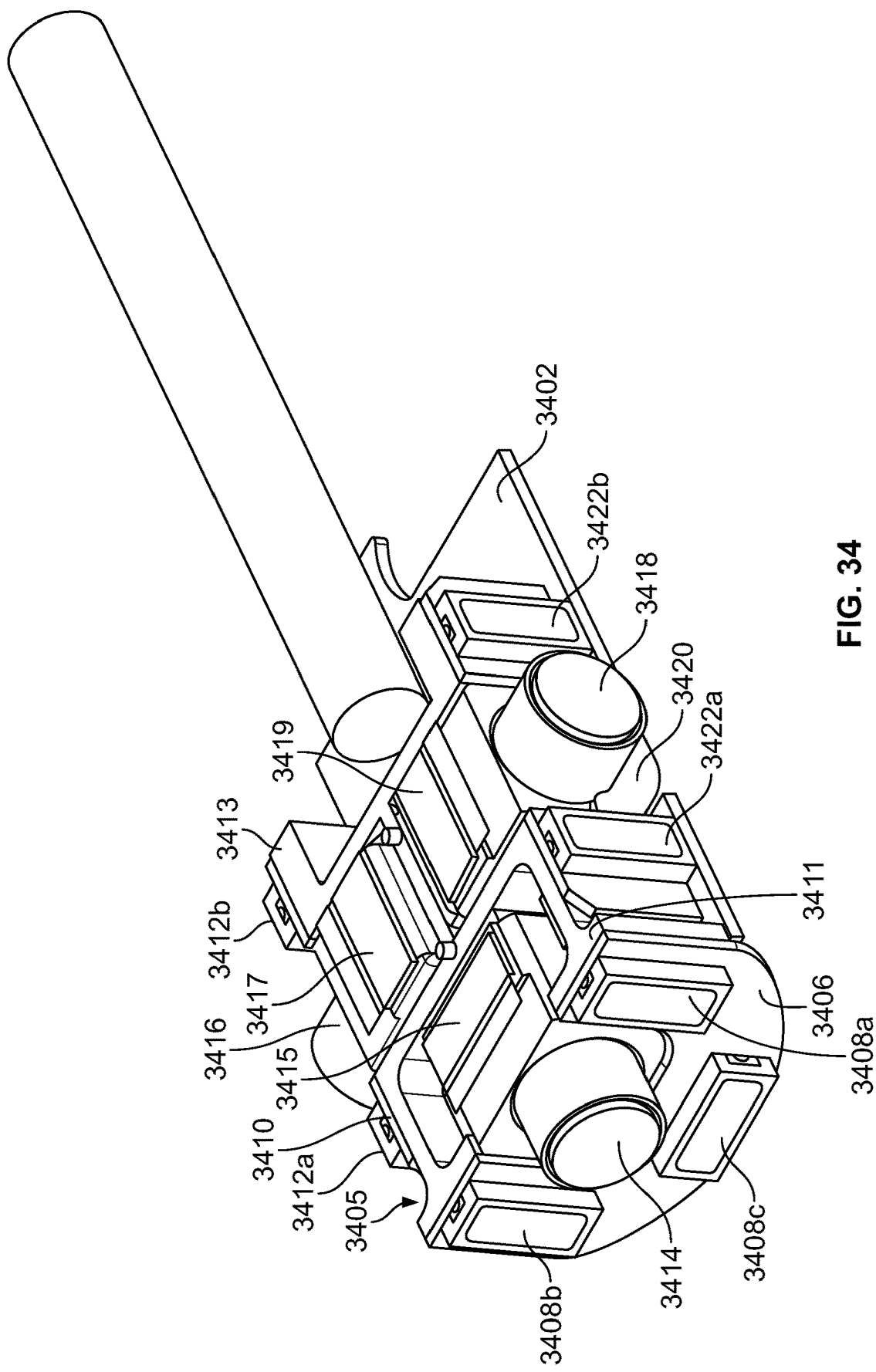
FIG. 34 illustrates optical assemblies and illuminators supported by an upper base board with the lower base board shown in FIG. 33A removed, in accordance with an embodiment of the present specification.

FIG. 34 illustrates optical assemblies and illuminators supported by an upper base board 3402 with the lower base board shown as 3304 in FIG. 33A removed to assist visualization. With regards to FIG. 34, the endoscope tip has been flipped about its horizontal axis such that the tip is being viewed from its underside as compared to the view depicted in FIG. 33. In an embodiment, a metal frame 3405 having front 3411 and rear 3413 portions is provided to support the associated image sensors 3415, 3417, 3419 and also the front 3414 and side 3416, 3418 lens assemblies. In various embodiments, the illuminator circuit boards 3406, 3410 and 3420 are soldered to the lower (removed for visualization) and upper 3402 base boards and are supported by the metal frame 3405. As illustrated, the metal frame 3405 includes a front portion 3411 provided to support the front lens assembly 3414 and support the front image sensor 3415 associated with the front lens assembly 3414. The front 3411 and rear 3413 portions of the metal frame 3405 support the side lens assemblies 3416, 3418 and support their associated image sensors 3417, 3419, respectively. In an embodiment, the metal frame 3405 also serves as a heat sink to the light emitting diodes (LEDs) and sensors incorporated in the endoscope.

A front illuminator circuit board 3406 holds the front illuminators 3408a, 3408b, 3408c in place and two side illuminator circuit boards 3410, 3420 hold the side illuminators 3412a, 3412b and 3422a, 3422b respectively, associated with the side optical lens assemblies 3416 and 3418 respectively, in place. A left side illuminator circuit board 3410 supports the side illuminators 3412a, 3412b. A right side illuminator circuit board 3420 supports the illuminators 3422a, 3422b associated with the right side lens assembly 3418. In an embodiment, the front illuminators circuit board 3406 is soldered to the metal frame 3405 which supports all three optical assemblies and separates the optical assemblies form one another. In one embodiment, the front illuminator circuit board 3406 is supported by a front portion 3411 of the metal frame and the side illuminator circuit boards 3410, 3420 are supported by both the front portion 3411 and a rear portion 3413 of the metal frame 3405.

In one embodiment, front illuminator circuit board 3406 is adapted to hold three sets of illuminators 3408a, 3408b, 3408c in place, wherein each set of illuminators may have 1, 2, 3 or more light sources such as, but not limited to, an LED. In one embodiment, side illuminator circuit boards 3410 and 3420 are adapted to hold two set of illuminators 3412a, 3412b and 3422a, 3422b in place, wherein each set of illuminators may have 1, 2, 3 or more light sources such as, but not limited to, an LED.

Figure 35A:
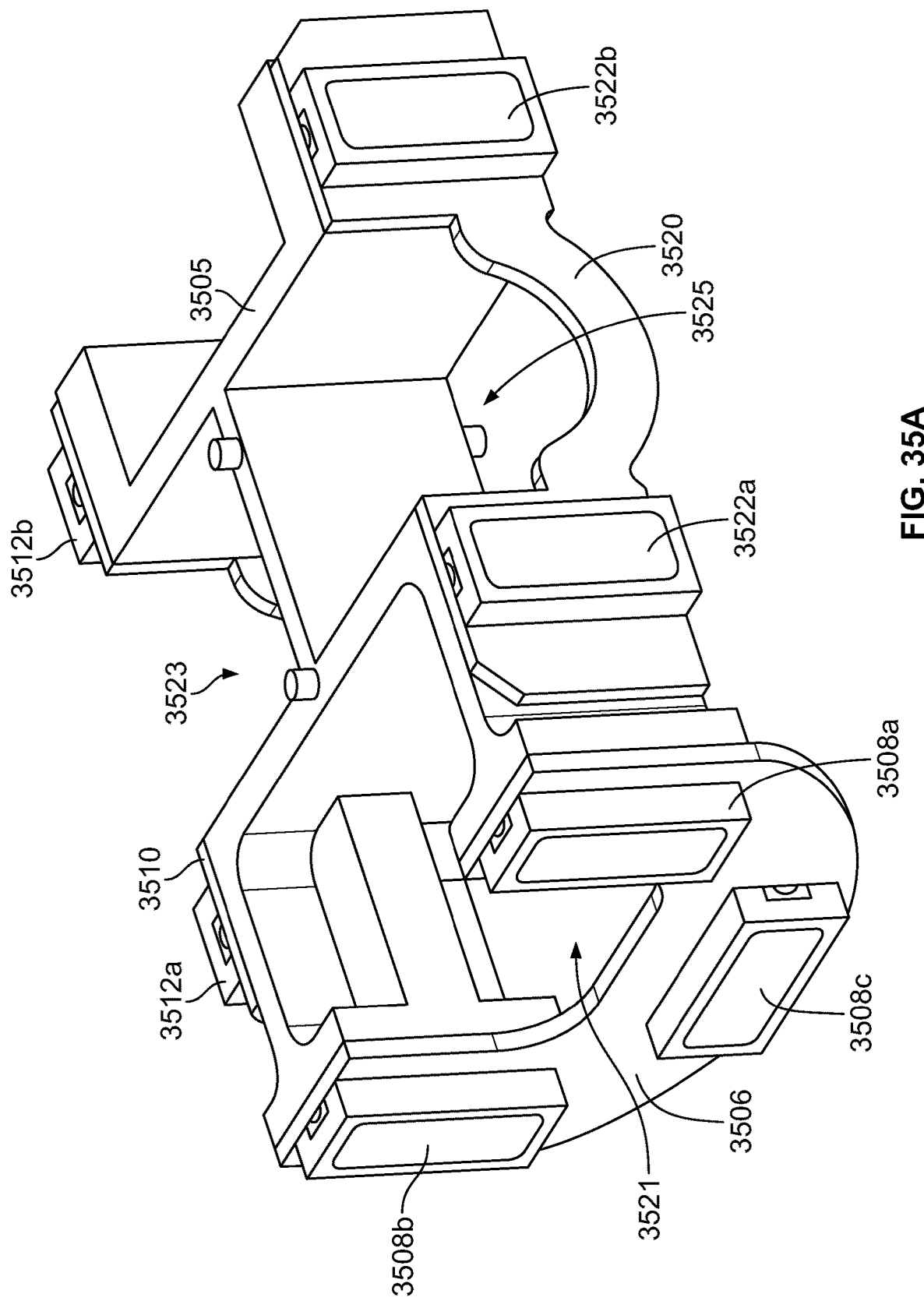
FIG. 35A illustrates the metal frame and illuminator circuit boards as shown in FIG. 34 with the optical assemblies and upper base board removed, in accordance with an embodiment of the present specification.

FIG. 35A illustrates the metal frame 3505 and illuminator circuit boards 3506, 3510, 3520 of FIG. 34 with the optical assemblies and upper base board removed to assist with visualization. Metal frame 3505 comprises a front recess area 3521 for a front lens assembly to protrude therethrough, a first side recess area 3523 for a first side lens assembly to protrude therethrough and a second side recess area 3525 on an opposite side for a second side lens assembly to protrude therethrough. A front illuminator electronic circuit board 3506 holds front illuminators 3508a, 3508b, 3508c. As can be seen in the figure, the front illuminator electronic circuit board 3506 is 'U' shaped and is coupled with the metal frame 3505 in a manner such that the front recess 3521 of the metal frame 3505 aligns with the inner surface of the curved portion of the 'U' shaped circuit board 3506.

Side illuminator electronic circuit boards 3510,3520 hold side illuminators 3512a, 3512b and 3522a, 3522b respectively. As can be seen in the figure, the side illuminator electronic circuit boards 3510, 3520 are 'U' shaped and are coupled with the metal frame 3505 in a manner such that the side recesses 3523, 3525 of the metal frame 3505 align with the inner surface of the curved portions of the 'U' shaped circuit boards 3510, 3520.

Figure 35B:
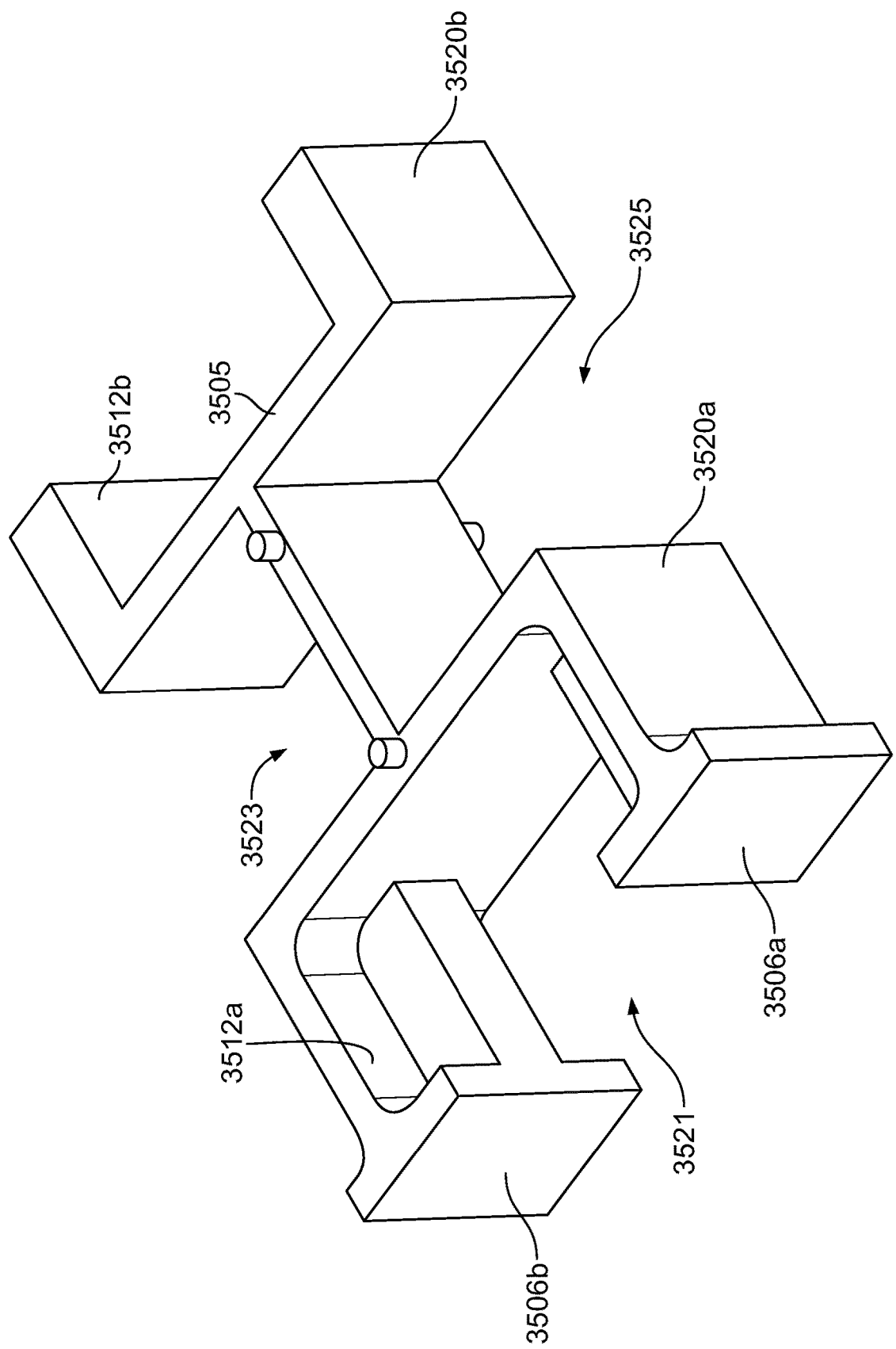
FIG. 35B illustrates a metal frame with the illuminator circuit boards shown in FIG. 35A removed, in accordance with an embodiment of the present specification.

FIG. 35B illustrates the metal frame 3505 with the illuminator circuit boards shown in FIG. 35A removed. In one embodiment, as depicted in FIG. 35B, the metal frame 3505 approximates an 'H' shape with side support walls 3512a, 3512b, 3520a, 3520b extending outwardly at 90 degrees from each leg of the 'H'. Two front support walls 3506a, 3506b are positioned at the end of and perpendicular to side support walls 3520a, 3512a respectively. The metal frame 3505 is designed to comprise recesses 3521, 3523, 3525 to accommodate the front lens assembly and the two side lens assemblies respectively in an endoscope tip. The frame 3505 comprises: front support walls 3506a and 3506b for supporting the front illuminator electronic circuit board shown as 3506 in FIG. 35A; side support walls 3512a, 3512b for supporting the side illuminator electronic circuit board shown as 3510 in FIG. 35A; and support walls 3520a, 3520b for supporting the second side illuminator electronic circuit board shown as 3520 in FIG. 35A.

Figure 36:
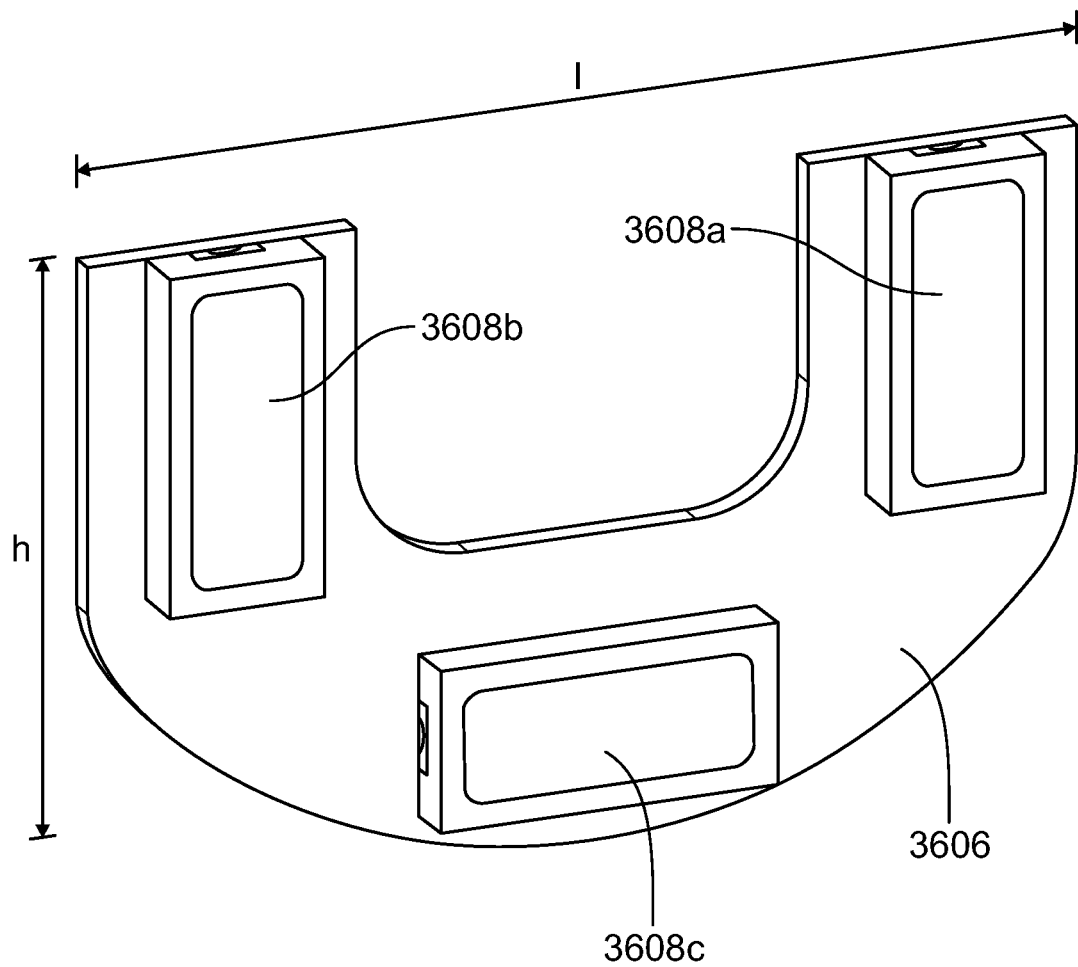
FIG. 36 illustrates a front illuminator electronic circuit board, in accordance with an embodiment of the present specification.

FIG. 36 illustrates a front illuminator electronic circuit board 3606, in accordance with an embodiment of the present specification. In one embodiment, as depicted in FIG. 36, the circuit board 3606 is shaped as a 'U' and holds front illuminators 3608a, 3608b, 3608c in place. In various embodiments, the length l of the front illuminator electronic circuit board 3606 ranges from 7.5 mm to 9.5 mm and in an embodiment the length l is approximately 8.8 mm. In various embodiments, the height h of the front illuminator electronic circuit board 3606 ranges from 5 mm to 6.5 mm and in an embodiment the height h is approximately 5.7 mm.

Figure 37:
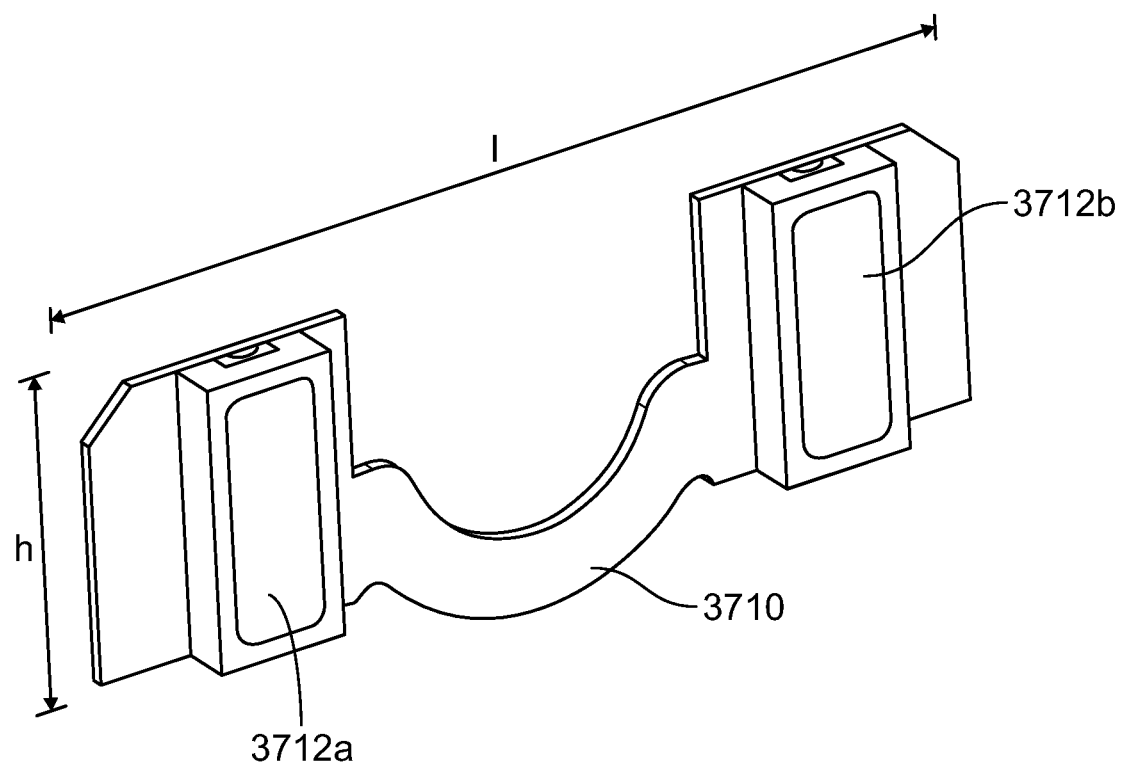
FIG. 37 illustrates a side illuminator electronic circuit board, in accordance with an embodiment of the present specification.

FIG. 37 illustrates a side illuminator electronic circuit board 3710, in accordance with an embodiment of the present specification. In one embodiment, as depicted in FIG. 37, the circuit board 3710 is shaped as a 'U' and holds side illuminators 3712*a*, 3712*b* in place. In various embodiments, the length l of the side illuminator electronic circuit board 3710 ranges from 7.5 mm to 9.5 mm and in an embodiment the length l is approximately 8.8 mm. In various embodiments, the height h of the side illuminator electronic circuit board 3710 ranges from 3 mm to 4.5 mm and in an embodiment the height h is approximately 3.7 mm.

According to another aspect of the present specification, an advantageous configuration of the electronic circuit board assembly enables having a slim and compact design of the endoscope. The configuration of the electronic circuit board assembly, in this embodiment, is described with reference to a tip section that includes a single side looking viewing element. However, in alternate embodiments, tip section may include more than one side looking viewing elements—in which case, the side looking viewing elements may be installed such that their fields of views are substantially opposing. However, different configurations and number of side looking viewing elements are possible within the general scope of the current specification.

Reference is now made to FIGS. 38A through 38F which show exploded views of a plurality of internal parts of an electronic circuit board assembly, which when assembled, connected or attached together, form a condensed tip section of a multi-viewing elements endoscope, according to an aspect of the present specification.

Additionally, it should be noted that the plurality of internal parts of the electronic circuit board assembly may be electrically connected and may be configured to share resources, such as electrical power and electrical signals.

FIG. 38A illustrates a base board 3805 of an electronic circuit board assembly in accordance with one embodiment of the present specification. Referring to FIG. 38A, the base board 3805 is shaped roughly as an "L" with a first member 3805*a* extending in a y direction and in an x direction. The first member 3805*a* is integrally formed with a second member 3805*b*, wherein said first member 3805*a* and said second member 3805*b* lie in the same horizontal plane and said second member 3805*b* extends from said first member 3805*a* at an angle of substantially 90 degrees. The second member 3805*b* extends in a y direction and in an x direction. In one embodiment, the length of the second member 3805*b* is greater than the length of the first member 3805*a*. In other words, the second member 3805*b* extends further in the x direction than the first member 3805*a* extends in the y direction. In one embodiment, the second member 3805*b* is further integrally formed with an offset member 3805*c* at the end of the second member 3805*b* that is opposite the end to which the first member 3805*a* is formed. The offset member 3805*c* lies in the same horizontal plane as the first member 3805*a* and second member 3805*b* and extends in a y direction and in an x direction. In one embodiment, the offset member 3805*c* is offset from the second member 3805*b* in the same y direction in which the first member 3805*a* is formed to the second member 3805*b*. In one embodiment, each member 3805*a*, 3805*b*, 3805*c* has the same thickness and therefore the entire base board 3805 has a single thickness.

In one embodiment, the first member 3805*a* comprises at least two openings 3806 for the insertion of attachment pegs of a first metal frame as described with reference to FIGS. 38B and 38C below. In one embodiment, the second member 3805*b* comprises at least two openings 3807 for the insertion of attachment pegs of a second metal frame as described with reference to FIGS. 38B and 38C below. In one embodiment, the offset member comprises at least one opening 3808 for a multi-wire electrical cable which is welded on the base board 3805 in a designated location, thereby freeing additional space within the tip assembly. The opening 3808 is where the electrical cable is welded to the base board 3805.

Figure 38B:
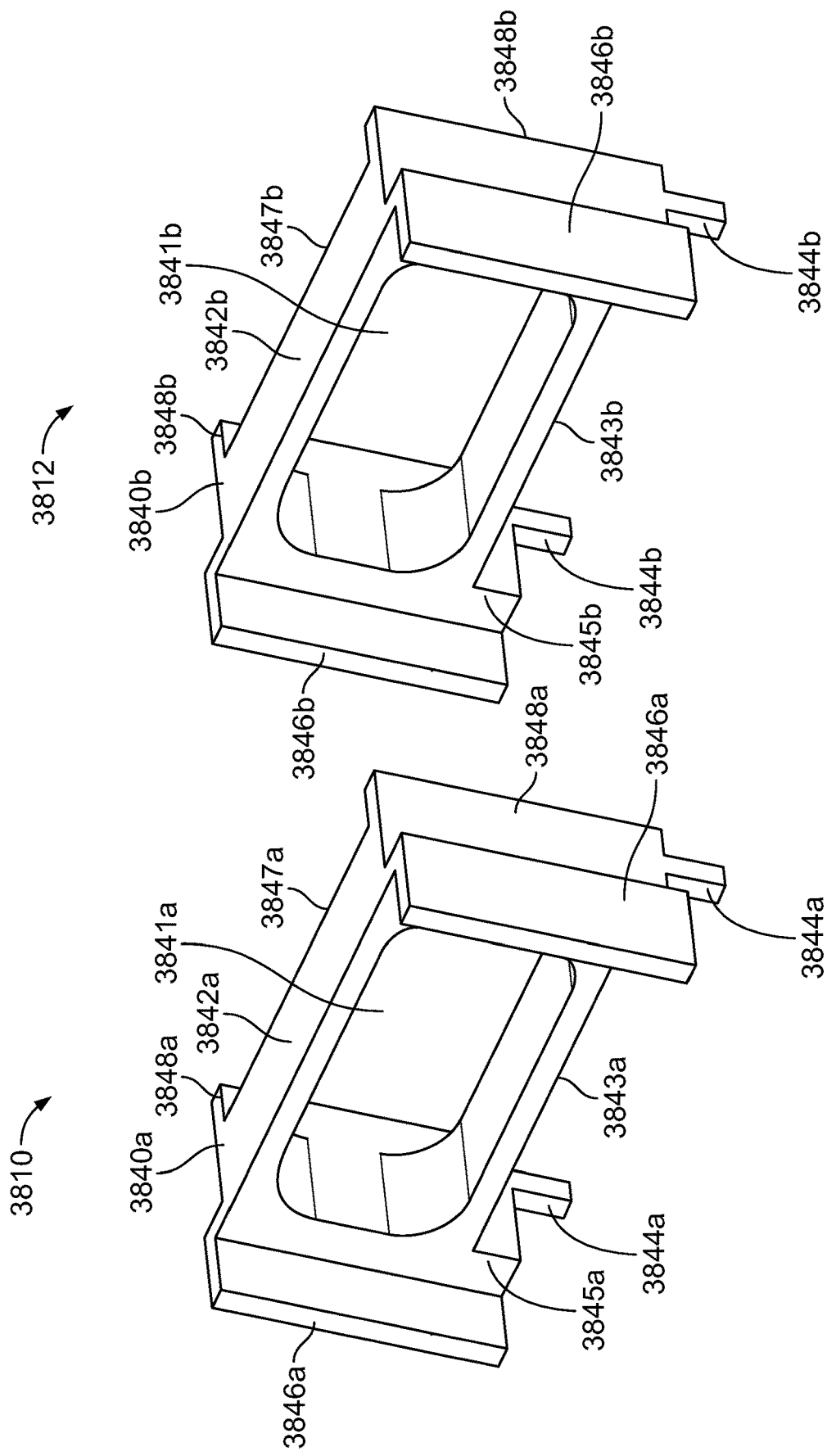
FIG. 38B illustrates first and second metal frames for supporting a front looking and a side looking viewing element of an electronic circuit board assembly, in accordance with an embodiment of the present specification.

FIG. 38B illustrates one embodiment of a first metal frame 3810 and a second metal frame 3812 for supporting a front looking viewing element and a side looking viewing element respectively, of an electronic circuit board assembly. In one embodiment, the first metal frame 3810 and the second metal frame 3812 are identical in shape. The first and second metal frames 3810, 3812 comprise substantially rectangular shaped metal bodies 3840*a*, 3840*b* each having a substantially oval shaped opening 3841*a*, 3841*b* at the center of each metal body 3840*a*, 3840*b*. In addition, each metal body 3840*a*, 3840*b* comprises a top surface 3842*a*, 3842*b* and a bottom surface 3843*a*, 3843*b*. Extending from the bottom surface 3843*a*, 3843*b* of each metal body 3840*a*, 3840*b* are at least two attachment pegs 3844*a*, 3844*b* to be inserted into corresponding openings in the first and second members of the base board as discussed with reference to FIGS. 38A and 38C.

Further, each metal body 3840*a*, 3840*b* includes a front surface 3845*a*, 3845*b* comprising a first pair of side walls 3846*a*, 3846*b* and a rear surface 3847*a*, 3847*b* comprising a second pair of side walls 3848*a*, 3848*b*. The front surfaces 3845*a*, 3845*b* and first pairs of side walls 3846*a*, 3846*b* are configured to receive image sensors as discussed with reference to FIG. 38G below. The rear surfaces 3847*a*, 3847*b* and second pairs of side walls 3848*a*, 3848*b* are configured to receive printed circuit boards as discussed with reference to FIG. 38E below.

Figure 38C:
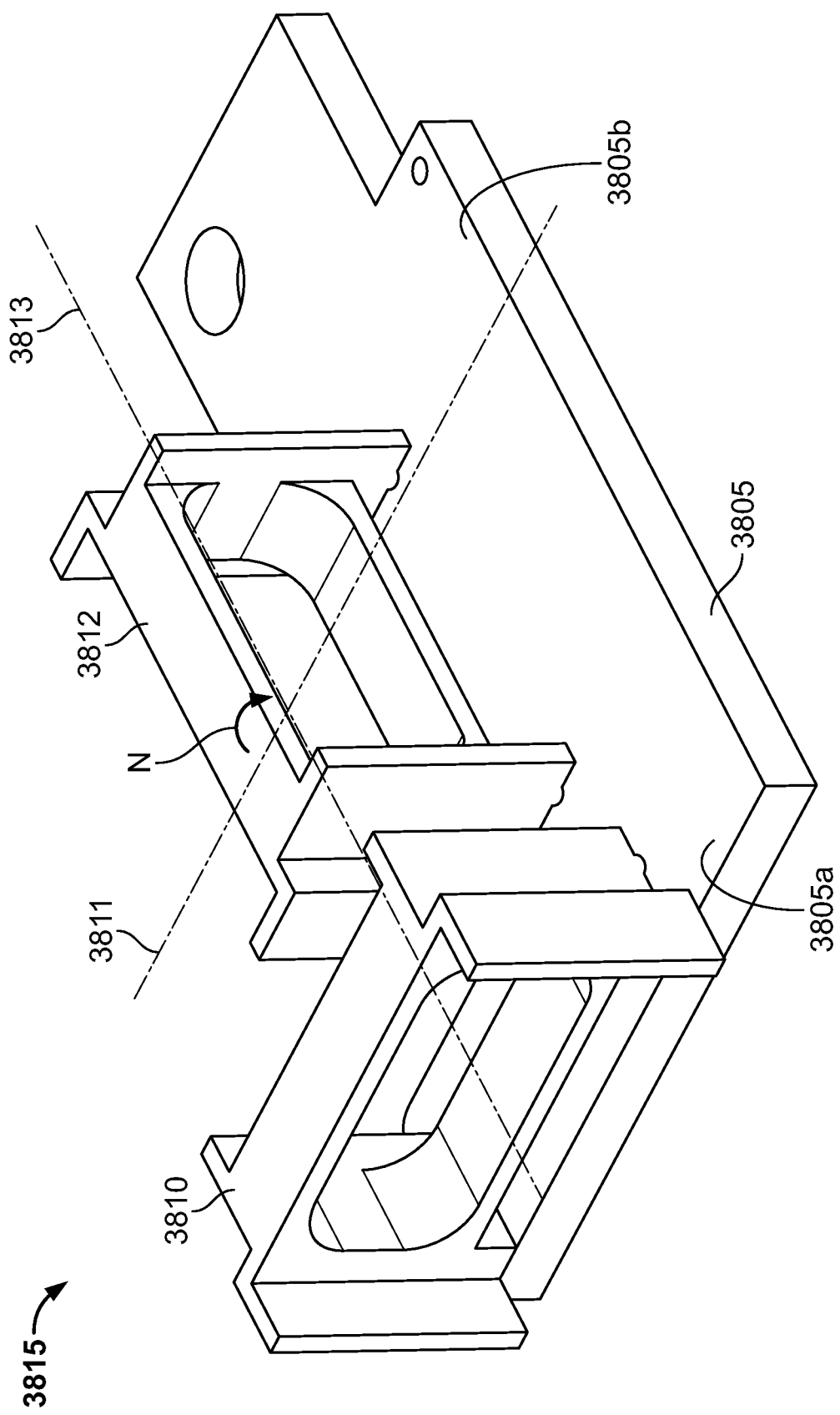
FIG. 38C illustrates a first intermediate assembly with metal frames placed on the base board of an electronic circuit board assembly, in accordance with an embodiment of the present specification.

FIG. 38C illustrates a first intermediate assembly 3815 with first 3810 and second 3812 metal frames placed on the base board 3805 of an electronic circuit board assembly, in accordance with one embodiment of the present specification. The attachment pegs (3844*a* in FIG. 38B) of the first metal frame 3810 have been inserted into the openings (3806 in FIG. 38A) of the first member 3805*a* of the base board 3805. The first metal frame 3810 is attached to the base board 3805 such that the front surface 3845*a* of the first metal frame 3810 faces forward and outward from the center of the endoscope tip and the rear surface 3847*a* of the first metal frame 3810 faces inward toward the center of the endoscope tip, once fully assembled. The attachment pegs (3844*b* in FIG. 38B) of the second metal frame 3812 have been inserted into the openings (3807 in FIG. 38A) of the second member 3805*b* of the base board 3805. The second metal frame 3812 is attached to the base board 3805 such that the front surface 3845*b* of the second metal frame 3812 faces sideward and outward from the center of the endoscope tip and the rear surface 3847*b* of the second metal frame 3812 faces inward toward the center of the endoscope tip, once fully assembled. In one embodiment, the first 3810 and second 3812 metal frames are soldered to the base board 3805.

In one embodiment, the base board 3805 is rigid while in another embodiment it is semi-rigid. The two metal frames 3810, 3812 form base structures for respectively supporting a front and a side looking viewing element of the endoscope. The metal frames 3810, 3812 are placed on the base board 3805 such that the respective central axes 3811, 3813 of the frames form an angle 'N' to each other. In various embodiments, the angle 'N' ranges from 70 to 135 degrees. In one embodiment the angle 'N' is 90 degrees.

Figure 38D:
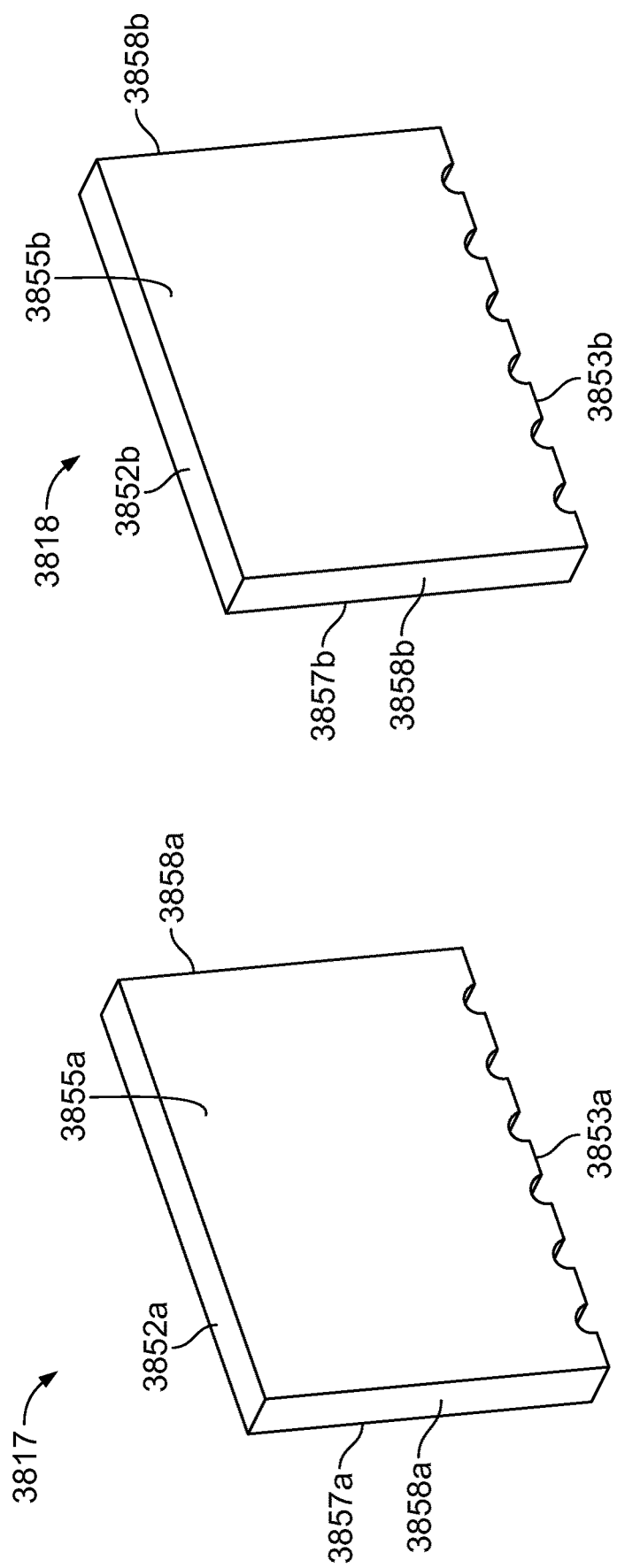
FIG. 38D illustrates one embodiment of first and second printed circuit boards for inclusion with an electronic circuit board assembly.

FIG. 38D illustrates one embodiment of a first printed circuit board 3817 and a second printed circuit board 3818 for inclusion with an electronic circuit board assembly. In one embodiment, the printed circuit boards 3817, 3818 are substantially rectangular shaped and each includes a top surface 3852*a*, 3852*b*, a bottom surface 3853*a*, 3853*b*, a front surface 3855*a*, 3855*b*, a rear surface 3857*a*, 3857*b*, and two side surfaces 3858*a*, 3858*b*.

Figure 38E:
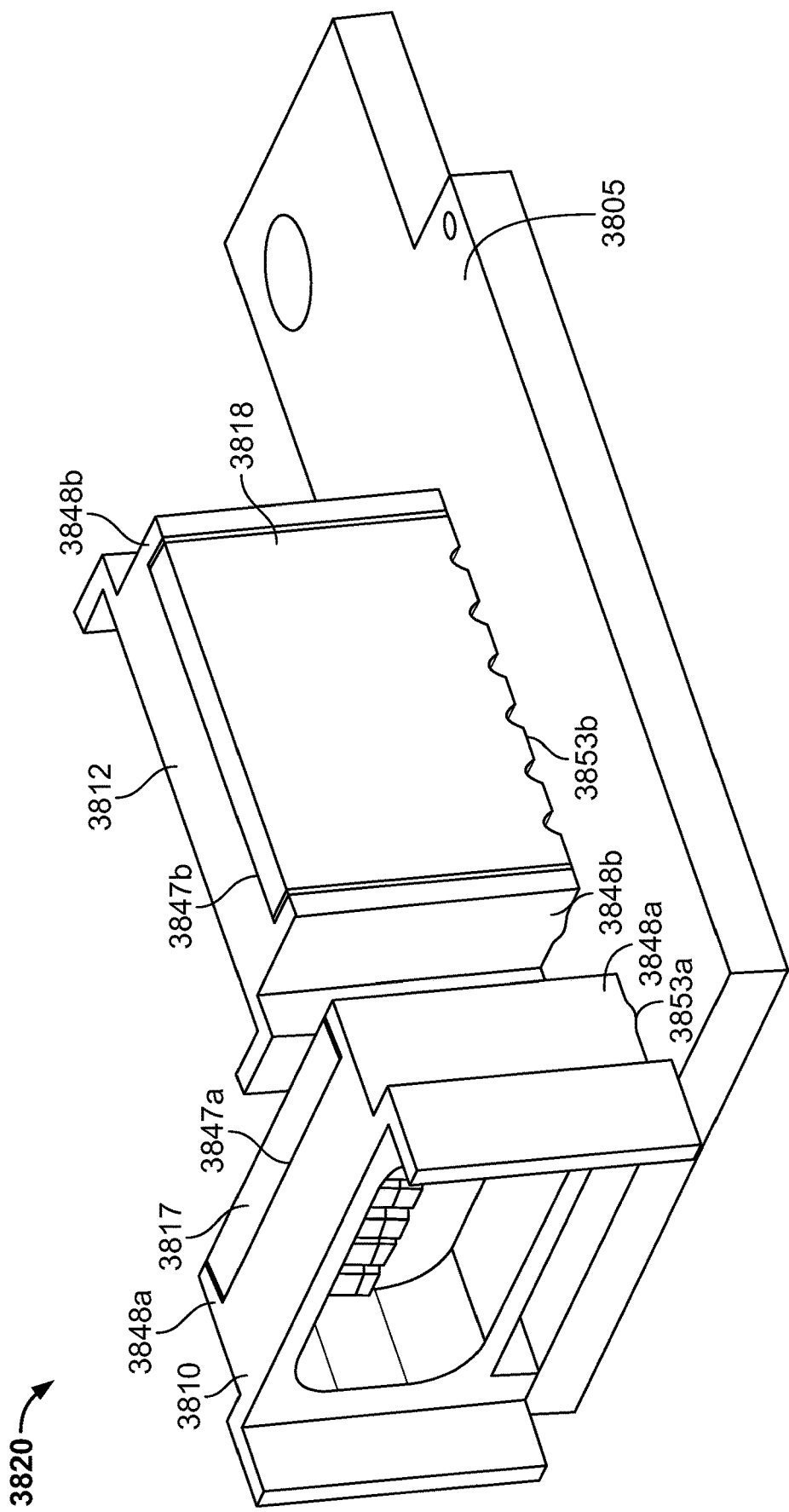
FIG. 38E illustrates a second intermediate assembly formed by attaching printed circuit boards to a first intermediate assembly, in accordance with an embodiment of the present specification.

Referring to FIG. 38E, the two printed circuit boards (PCBs) 3817, 3818 are placed against the rear surfaces 3847*a*, 3847*b* of the respective metal frames 3810, 3812 to form a second intermediate assembly 3820. In one embodiment, the first printed circuit board 3817 is positioned on the base board 3805 such that the front surface (3855*a* in FIG. 38D) of the first printed circuit board 3817 touches the rear surface 3847*a* of the first metal frame 3810 and the side surfaces (3858*a* in FIG. 38D) of the first printed circuit board 3817 touch the second pair of side walls 3848*a* of the first metal frame 3810. In one embodiment, the second printed circuit board 3818 is positioned on the base board 3805 such that the front surface (3855*b* in FIG. 38D) of the second printed circuit board 3818 touches the rear surface 3847*b* of the second metal frame 3812 and the side surfaces (3858*b* in FIG. 38D) of the second printed circuit board 3818 touch the second pair of side walls 3848*b* of the second metal frame 3812. In another embodiment, the printed circuit boards 3817, 3818 are flipped horizontally such that their rear surfaces (3857*a*, 3857*b* in FIG. 38D) touch the rear surfaces 3847*a*, 3847*b* of the metal frames 3810, 3812. In both embodiments, the rear surfaces 3847*a*, 3847*b* and second pairs of side walls 3848*a*, 3848*b* of the metal frames 3810, 3812 act to contain the printed circuit boards 3817, 3818. In one embodiment, the printed circuit boards 3817, 3818 fit snugly within the pairs of side walls 3848*a*, 3848*b* and against the rear surfaces 3847*a*, 3847*b* of the metal frames 3810, 3812. The snug fit helps to maximize the use of available area in the tip, allowing the endoscope tip to have a smaller overall diameter. In one embodiment, the bottom surfaces 3853*a*, 3853*b* of the printed circuit boards 3817, 3818 are soldered to the base board 3805.

Figure 38F:
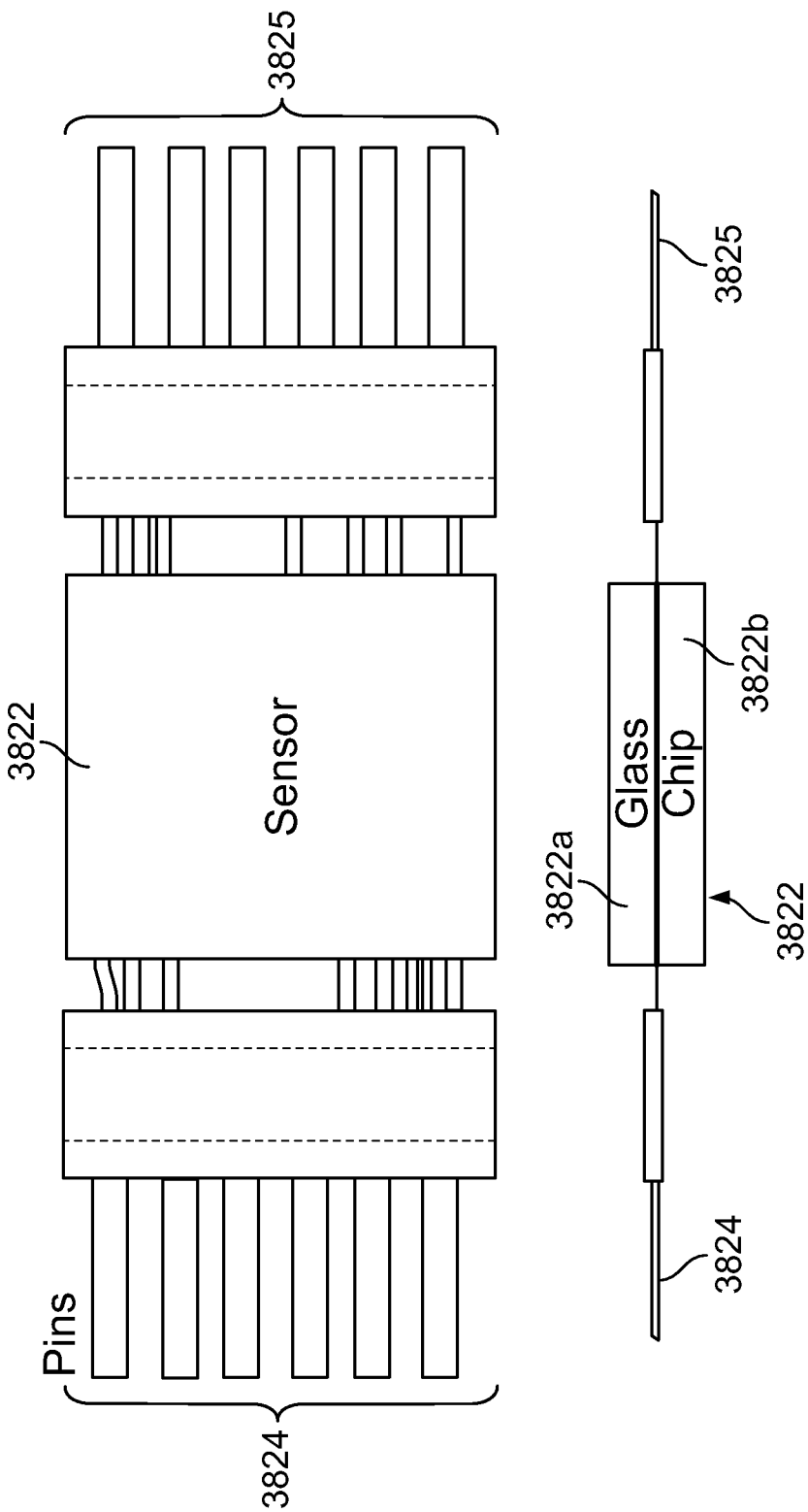
FIG. 38F illustrates an image sensor with a plurality of connector pins in accordance with an embodiment of the present specification.

FIG. 38F illustrates horizontal and side views of an image sensor 3822 with a first plurality of connector pins 3824 on a first end of the sensor 3822 and a second plurality of connector pins 3825 on the opposite side of the sensor, in accordance with one embodiment of the present specification. The image sensor 3822 includes an outer surface comprising a piece of glass 3822*a* and an inner surface comprising a printed circuit board or computer chip 3822*b*. The image sensor 3822 captures still images and/or video feeds and in various embodiments comprises a Charge Coupled Device (CCD) or a Complementary Metal Oxide Semiconductor (CMOS) image sensor.

Figure 38G:
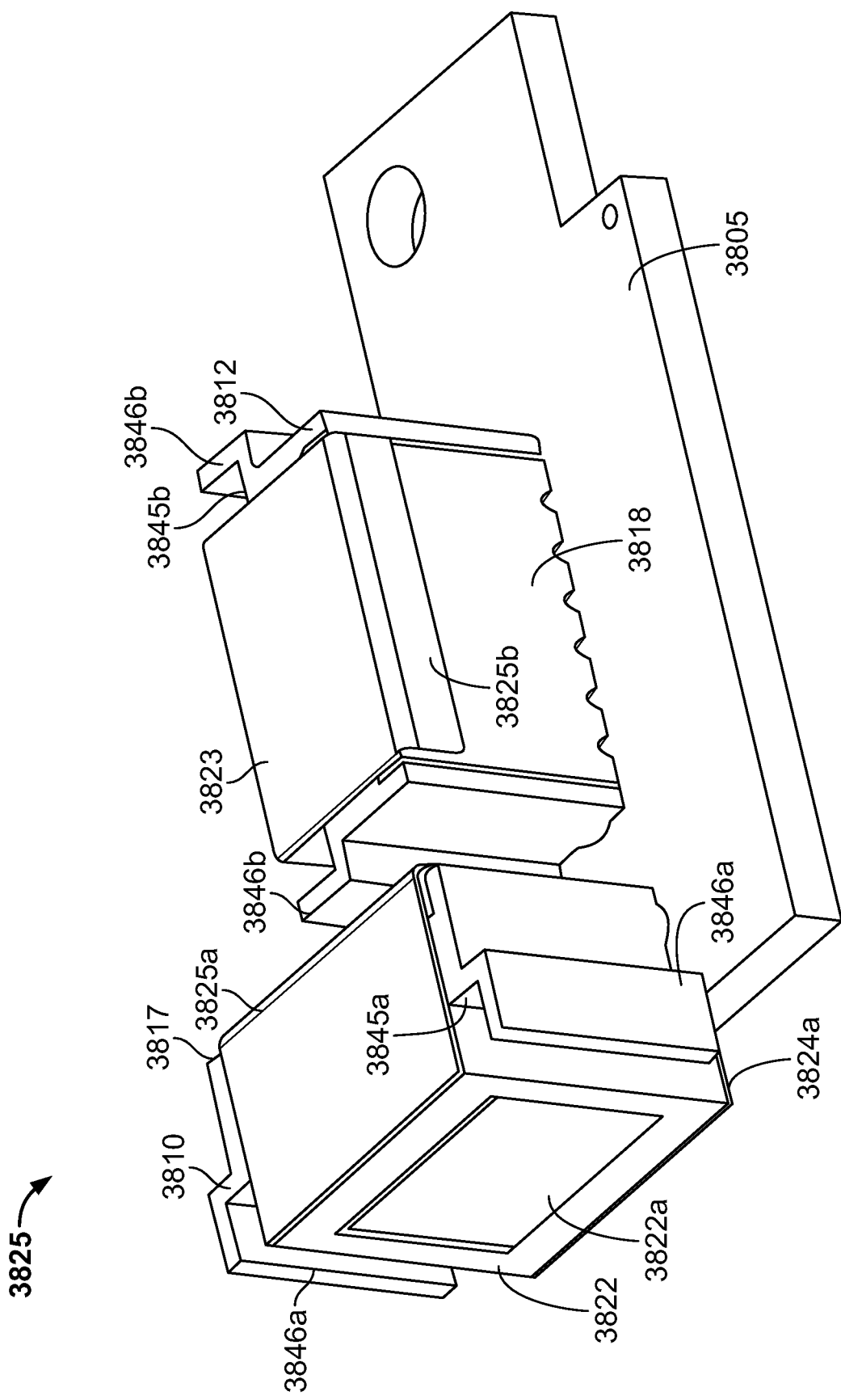
FIG. 38G illustrates one embodiment of a third intermediate assembly formed by attaching image sensors to a second intermediate assembly.

FIG. 38G illustrates one embodiment of a third intermediate assembly 3825 formed by attaching image sensors 3822, 3823 to a second intermediate assembly (3820 from FIG. 38E). In one embodiment, a first image sensor 3822 is positioned such that the inner surface of the first image sensor 3822, comprising a computer chip, comes to rest on the front surface 3845*a* and between the first pair of side walls 3846*a* of the first metal frame 3810. In this manner, the outer surface of the first image sensor 3822, comprising a piece of glass 3822*a*, faces forward and outward from the center of the endoscope tip, once fully assembled. The first plurality of connector pins 3824*a* on a first end of the image sensor 3822 is folded underneath the base board 3805 and soldered to the base board 3805. The second plurality of connector pins 3825*a* on a second end of the first image sensor 3822 is folded over the top surface of the first metal frame 3810 and soldered to the first printed circuit board 3817. In one embodiment, a second image sensor 3823 is positioned such that the inner surface of the second image sensor 3823, comprising a computer chip, comes to rest on the front surface 3845*b* and between the first pair of side walls 3846*b* of the second metal frame 3812. In this manner, the outer surface of the second image sensor 3823, comprising a piece of glass, faces sideward and outward from the center of the endoscope tip, once fully assembled. The first plurality of connector pins on a first end of the image sensor 3823 is folded underneath the base board 3805 and soldered to the base board 3805. The second plurality of connector pins 3825*b* on a second end of the second image sensor 3823 is folded over the top surface of the second metal frame 3812 and soldered to the second printed circuit board 3818. In accordance with an embodiment, the front and side looking image sensors 3822, 3823 are similar or identical in terms of, for example, field of view, resolution, light sensitivity, pixel size, focal length, focal distance and/or the like.

The printed circuit boards 3817, 3818 supply respective front and side looking viewing sensors 3822, 3823 with electrical power and derive still images and/or video feeds captured by the image sensors.

In accordance with an embodiment, each of the front and side looking image sensors 3822, 3823 has a lens assembly mounted on their outer surfaces to provide necessary optics for receiving images. Each lens assembly comprises a plurality of lenses, static or movable, which provide a field of view of at least 90 degrees and up to essentially 180 degrees. Front looking image sensor 3822 and corresponding lens assembly with associated printed circuit board 3817 are together referred to as the 'front looking viewing element'. Similarly, side looking sensor 3823 and corresponding lens assembly with associated printed circuit board 3818 are together referred to as the 'side looking viewing element'.

Persons of ordinary skill in the art should note that the metal frames 3810, 3812 not only serve as mechanical support to the printed circuit boards 3817, 3818 and sensors 3822, 3823, thereby providing structural ruggedness, but also act as heat sinks, allowing efficient heat dissipation from the sensors 3822, 3823.

Figure 38H:
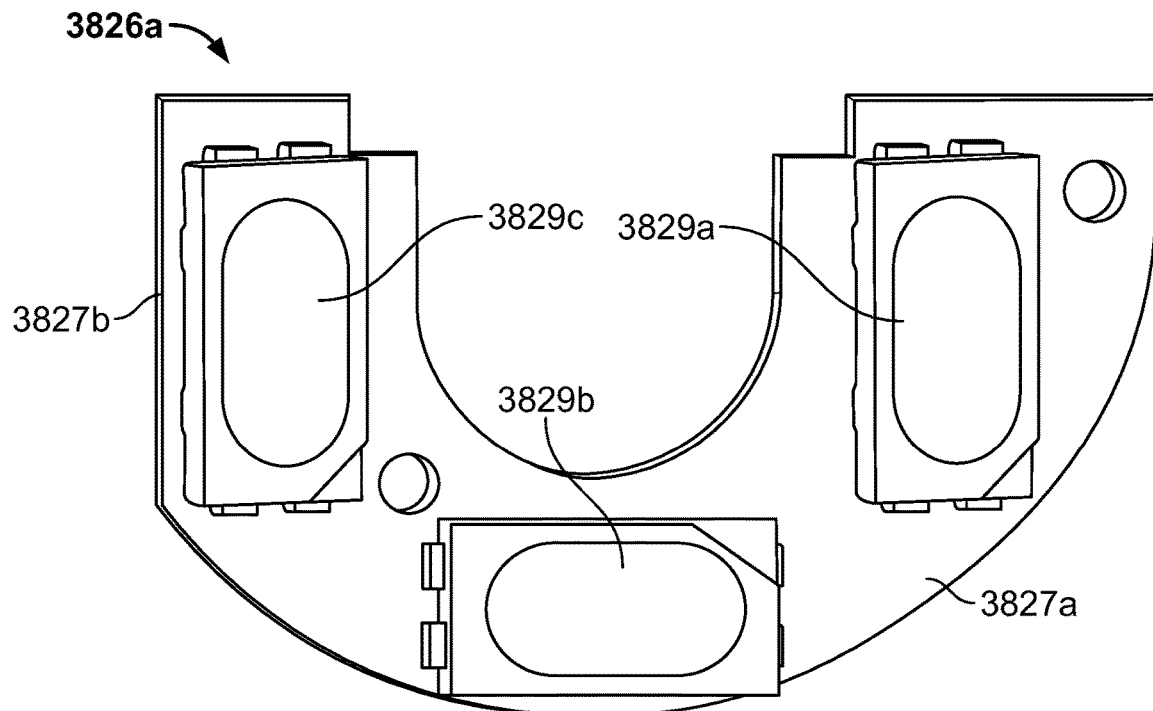
FIG. 38Ha illustrates one embodiment of a front illumination circuit board.
Figure 38H:
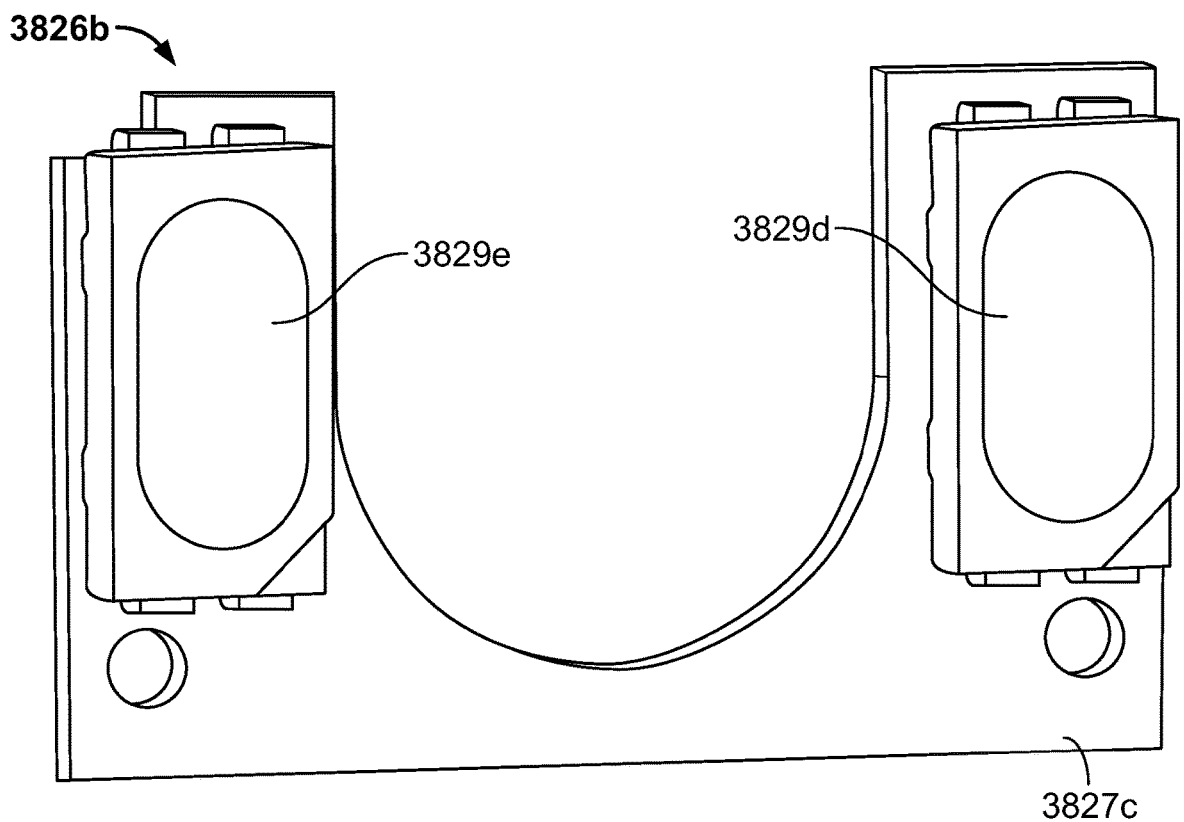

FIG. 38Ha illustrates one embodiment of a front illumination circuit board 3826*a* comprising a front panel 3827*a* approximating a "U" shape. In one embodiment, the front panel 3827*a* is configured to carry three sets of front illuminators 3829*a*, 3829*b*, 3829*c* wherein each set comprises a single illuminator element. In other embodiments, the front foldable panel 3827*a* may be configured to carry three sets of front illuminators 3829*a*, 3829*b*, 3829*c* wherein each set may further comprise 2, 3, or 4 illuminator elements. The three sets of front illuminators 3829*a*, 3829*b*, and 3829*c* are associated with the front looking viewing element of the endoscope and positioned to illuminate the field of view of the front looking viewing element. In one embodiment, sidewall 3827*b* of the circuit board 3827*a* is truncated in order to align with a corresponding sidewall design, wherein the sidewall of a tip cover is adapted to include a depression.

FIG. 38Hb illustrates one embodiment of a side illumination circuit board 3826*b* comprising a side panel 3827*c* approximating a "U" shape. The side panel 3827*c* is configured to carry two sets of side illuminators 3829*d*, 3829*e* wherein each set comprises a single illuminator element in accordance with an embodiment. In other embodiments, the side panel 3827*c* may be configured to carry two sets of side illuminators 3829*d*, 3829*e* wherein each set may further comprise 2, 3, or 4 illuminator elements. The side illuminators 3829*d*, 3829*e* are associated with the side looking viewing element of the endoscope and positioned to essentially illuminate the field of view of the side looking viewing element. In various embodiments, the side illuminators are positioned such that the distance between the center of side illuminator 3829*d* and the center of side illuminator 3829*e* is in a range of 5.5-6.5 mm.

Figure 38I:
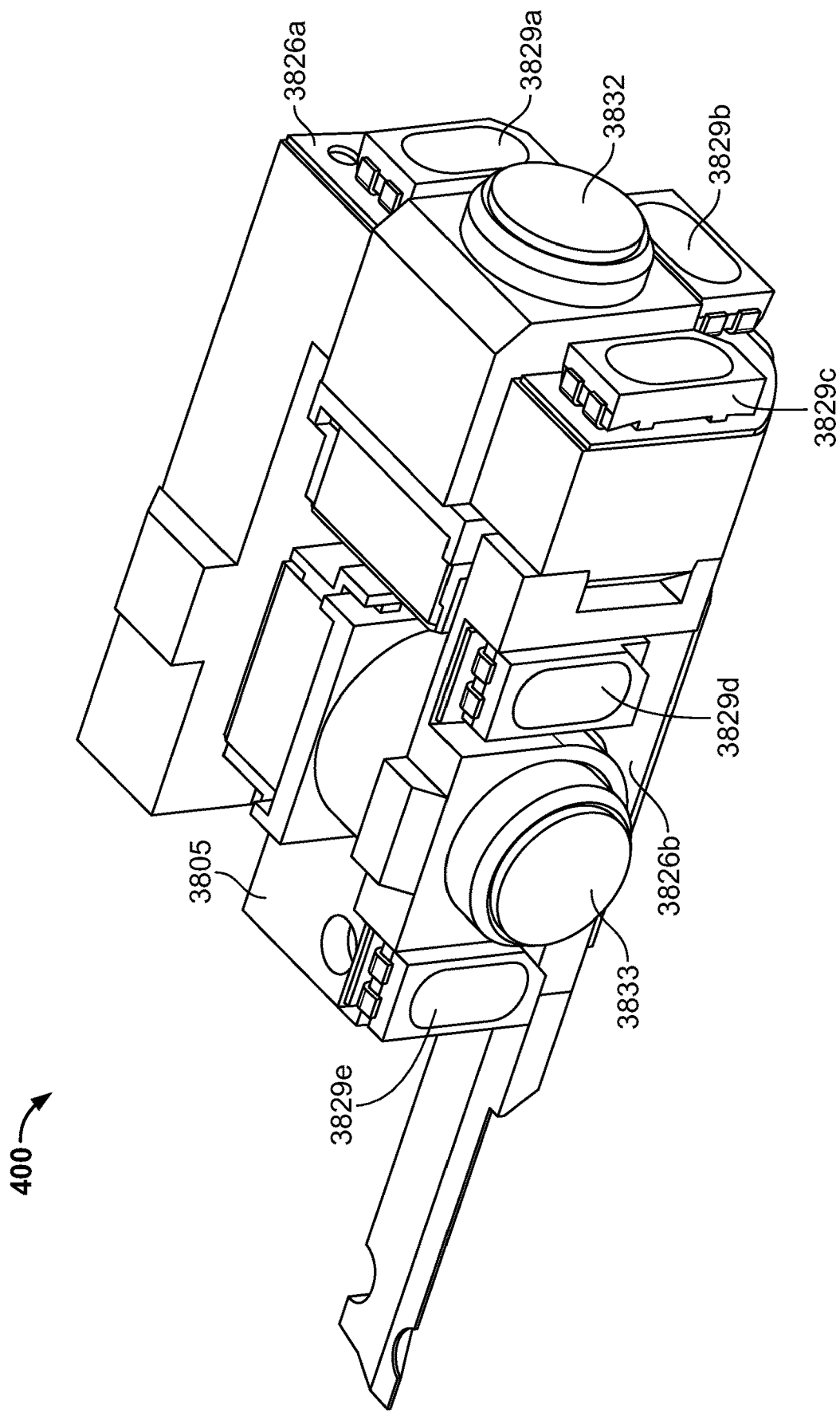
FIG. 38I illustrates one embodiment of an assembled view of an electronic circuit board assembly of the present specification.
Figure 38J:
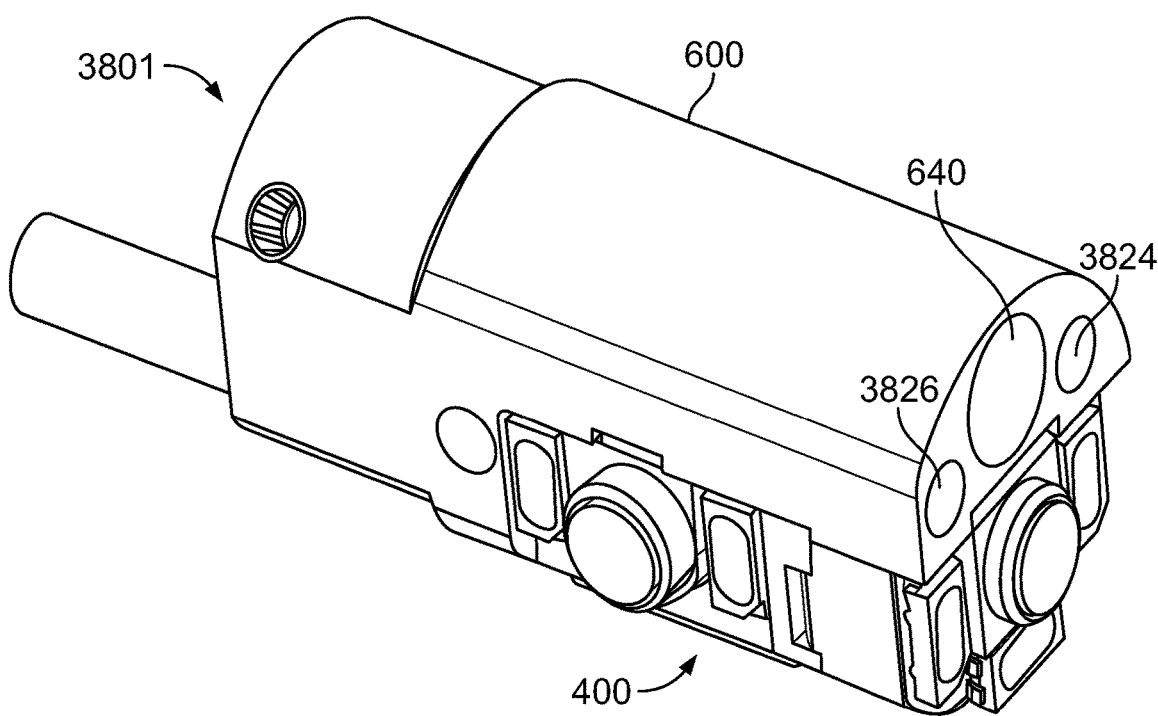
FIG. 38J illustrates one embodiment of a tip section of an endoscope formed by attaching a fluid channeling component to the electronic circuit board assembly of FIG. 38I.
Figure 38K:
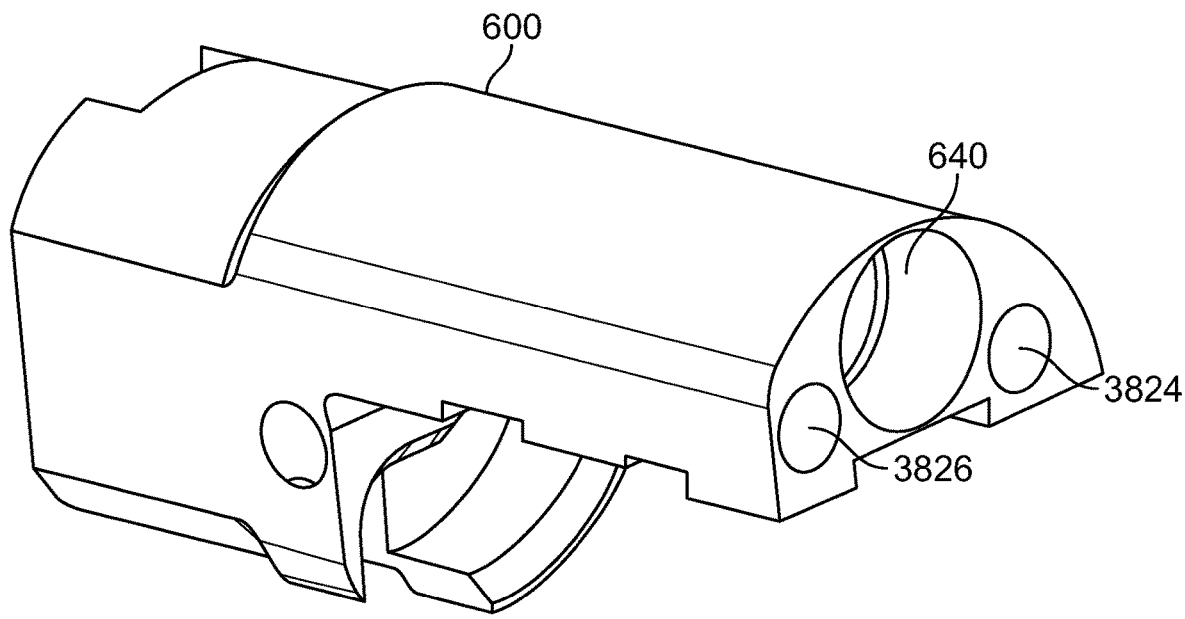
FIG. 38K illustrates one embodiment of a fluid channeling component as shown in FIG. 38J.

As illustrated in FIG. 38I, the base board 3805 is configured to hold and support the illumination circuit boards 3826*a* and 3826*b* and their corresponding illuminators 3829*a* through 3829*e* in the desired configuration. The base board 3805 secures the front and side looking viewing elements 3832, 3833 in place to form an electronic circuit board assembly 400 of the present specification. Finally, FIGS. 38J through 38K illustrate an endoscope tip 3801 and a fluid channeling component or manifold 600 attached to the electronic circuit board assembly 400 of the present specification. Fluid channeling component or manifold 600 includes a front working/service channel 640 that is configured for insertion of a medical (such as a surgical) tool and for applying suction to tissue. According to some embodiments, there is provided herein an endoscope (such as, but not limited to, a gastroscope or colonoscope) that includes (in a tip section thereof), in addition to a front viewing element and one side viewing element, and in addition to a front working/service channel 640, a front nozzle opening 3824 and a front jet opening 3826.

The optical setup for endoscopes typically used in the prior art requires a relatively large overall optical length (total optical track) of the entire optical system, which is disadvantageous for endoscopes, in particular those used as colonoscopes and gastroscopes, particularly if used in endoscopes having side-viewing camera or cameras, such as endoscopes according to embodiments of the present specification.

In addition, in sensors (such as CCD sensors) used in endoscopes of the prior art, the pixels are partially covered by a photo-shielding film, so that the light energy is concentrated in the center of the pixel, where there is a "window" in the photo-shielding film. This improves the signal-to-noise ratio and increases the light utilization efficiency. However, this also causes the sensor to be sensitive to incident angles between the light rays which have passed the micro-lenses of the sensor and the optical axis of the system. Thus, light rays having relatively small incident angles may reach the pixel, while light rays having relatively large incident angles (between the light rays which have passed the micro-lenses of the sensor and the optical axis of the system) may not reach the "window" and thus the pixel, leading to significant energy losses. The losses are maximized at the edges of the field of view, i.e. for light rays having incident angles close to that of the chief ray.

There is thus provided herein, according to some embodiments, a lens system (assembly) configured for use in an endoscope, such as a colonoscope, particularly for use in a multi-sensor endoscope/colonoscope. The lens system, (optionally together with the sensor) according to some embodiments of the specification, has a short total optical length (track), for example, 5 mm or less. The lens system, according to some embodiments of the specification, is configured to provide a large incident angle, for example, a chief incident angle (for example the incident angles forming by rays R6 in FIGS. 41A through 41C) larger than 20°, larger than 25°, larger than 30° or between about 20-40°. The lens system, according to some embodiments of the specification, provides minimal distortion (for example, less than 80%).

According to some embodiments, the sensor which is used together with the lens system, is configured to have a window in the photo-shielding film configured to allow rays having large incident angle (for example, a chief incident angle larger than 20°, larger than 25°, larger than 30° or between about 20-40°) to reach the pixel and thus improve the distortion. According to some embodiments, the width of the window (or any other dimensional parameter) may be about 30-60% of the width of the corresponding pixel. According to some embodiments, the micro-lenses of the sensor may be configured to provide substantially aplanatic conditions. In other words, the sensor may be configured to provide an image substantially free of aberrations.

Figure 39A:
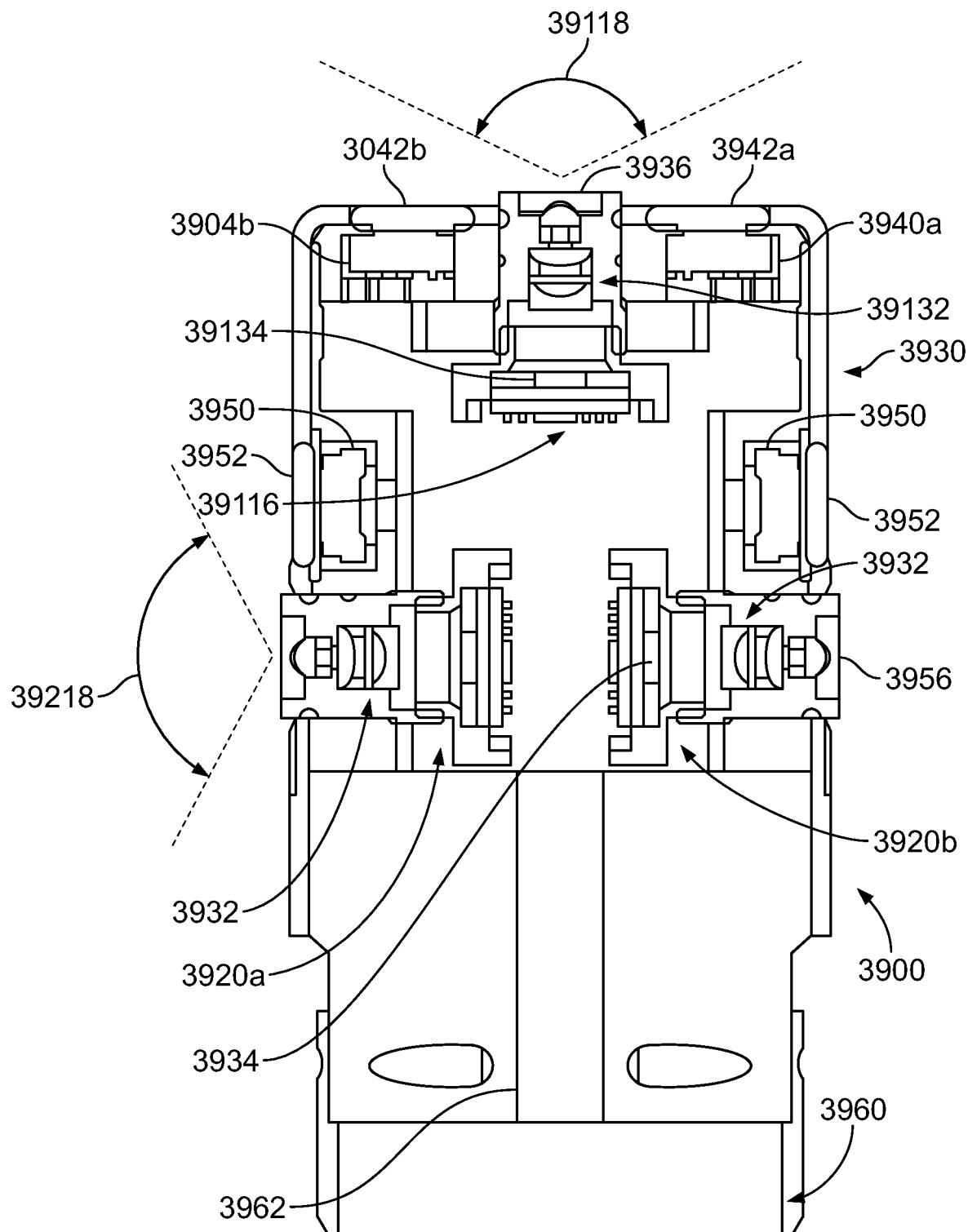
FIG. 39A schematically depicts a cross section of an endoscope front head having multiple fields of view showing some details of the head according to an exemplary embodiment of the current specification.

FIG. 39A schematically depicts a cross section of an endoscope 3900 having multiple fields of view showing some details of the head 3930 according to an exemplary embodiment of the current specification.

According to the current specification, head 3930 of endoscope 3900 comprises at least a forward looking camera 39116 and two side looking cameras 3920*a* and 3920*b*. Each of cameras 39116 and 3920*a*, 3920*b* is provided with an optical imaging system such as lens assemblies (systems) 39132 and 3932 respectively and solid state detector arrays 39134 and 3934 respectively. Front camera elements 3936 and 3956 of cameras 39116 and 3920 respectively may be a flat protective window, but optionally an optical element used as part of the imaging systems such as solid state detector arrays 39134 and 3934 respectively. Optionally, cameras 39116 and 3920 are similar or identical, however different camera designs may be used, for example, field of views 39118 and 3918 may be different. Additionally or alternatively, other camera parameters such as, resolution, light sensitivity, pixel size and pixel number, focal length, focal distance and depth of field may be selected to be the same or different.

Light is provided by light emitting diodes (LED) that illuminates the fields of view. According to some embodiments, white light LEDs may be used. According to other embodiments, other colors of LEDs or any combination of LEDs may be used (for example, red, green, blue, infrared, and ultraviolet).

In the depicted embodiment, field of view 39118 of forward looking camera 39116 is illuminated by two LEDs 3940*a* and 3940*b* located within the endoscope head 3930 and protected by optical windows 3942*a* and 3942*b* respectively.

Similarly, in the depicted embodiment, fields of view of side looking cameras 3920*a* and 3920*b* are each illuminated by a single LED 3950 located within the endoscope head 3930 and each protected by optical window 3952. It should be noted that number of LED light sources and their position in respect to the cameras may vary within the scope of the current specification. For example, few LEDs may be positioned behind the same protective window, a camera and an LED or plurality of LED may be located behind the same protective window, etc.

Head 3930 of endoscope 3900 is located at the distal end of a flexible shaft 3960. Similar to shafts of the art, shaft 3960 comprises a working channel 3962 for insertion of surgical tools. Additionally, shaft 3960 may comprises channels for irrigation, insufflation, suction and supplying liquid for washing the colon wall.

Figure 39B:
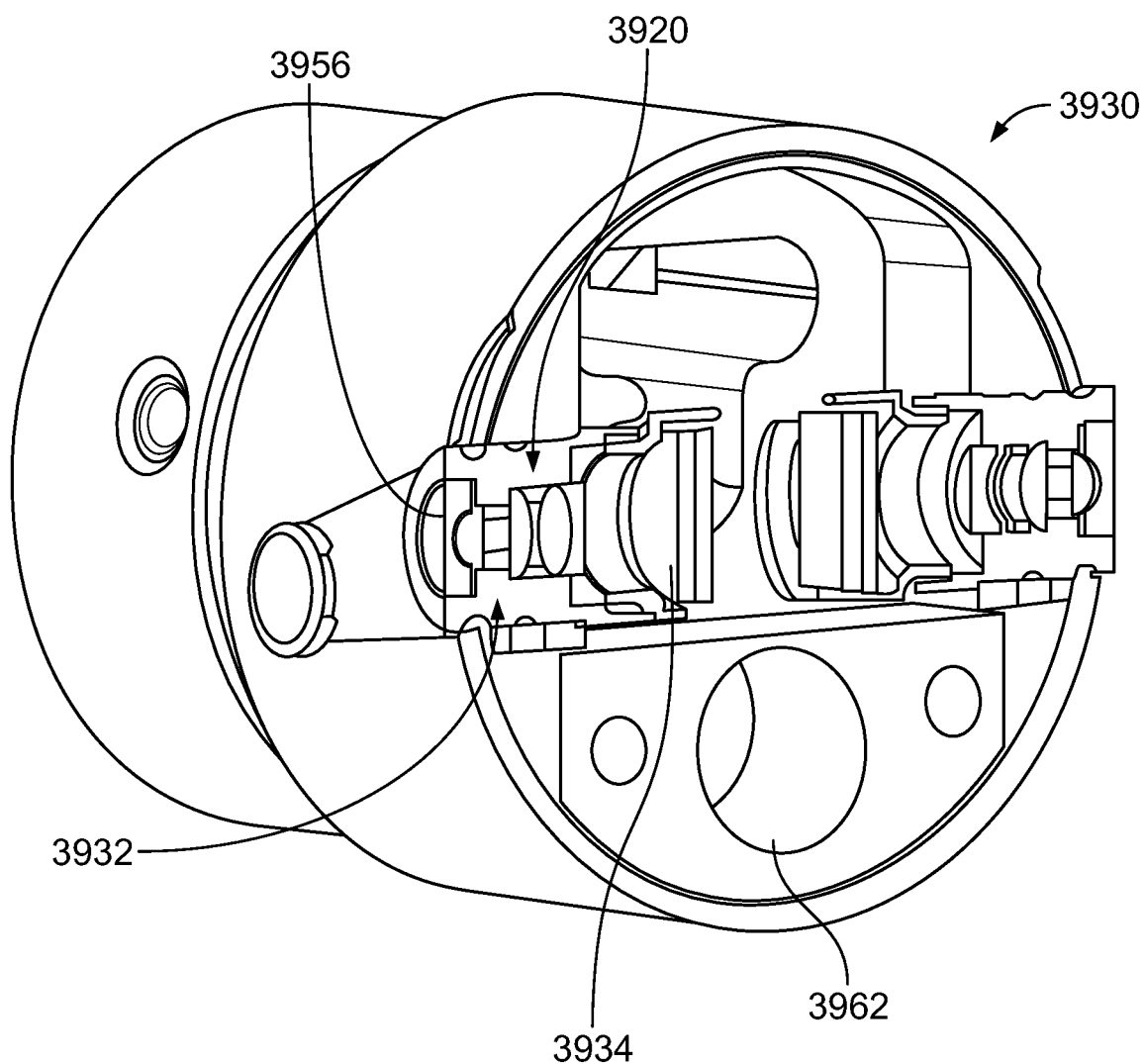
FIG. 39B schematically depicts a cutout isometric view of an endoscope having multiple fields of view according to another exemplary embodiment of the current specification.

FIG. 39B schematically depicts a cross section cutout of an endoscope showing some details of the head 3930 according to an exemplary embodiment of the current specification. For simplicity, details of one of the two side looking cameras are marked in the figure.

According to the current specification, head 3930 of the endoscope comprises at least one side looking camera 3920. Each of cameras 3920 is provided with an optical imaging system such as lens assemblies 3932 and solid state detector arrays 3934. Front camera element 3956 of camera 3920 may be a flat protective window or an optical element used as part of the imaging system 3932.

Figure 39C:
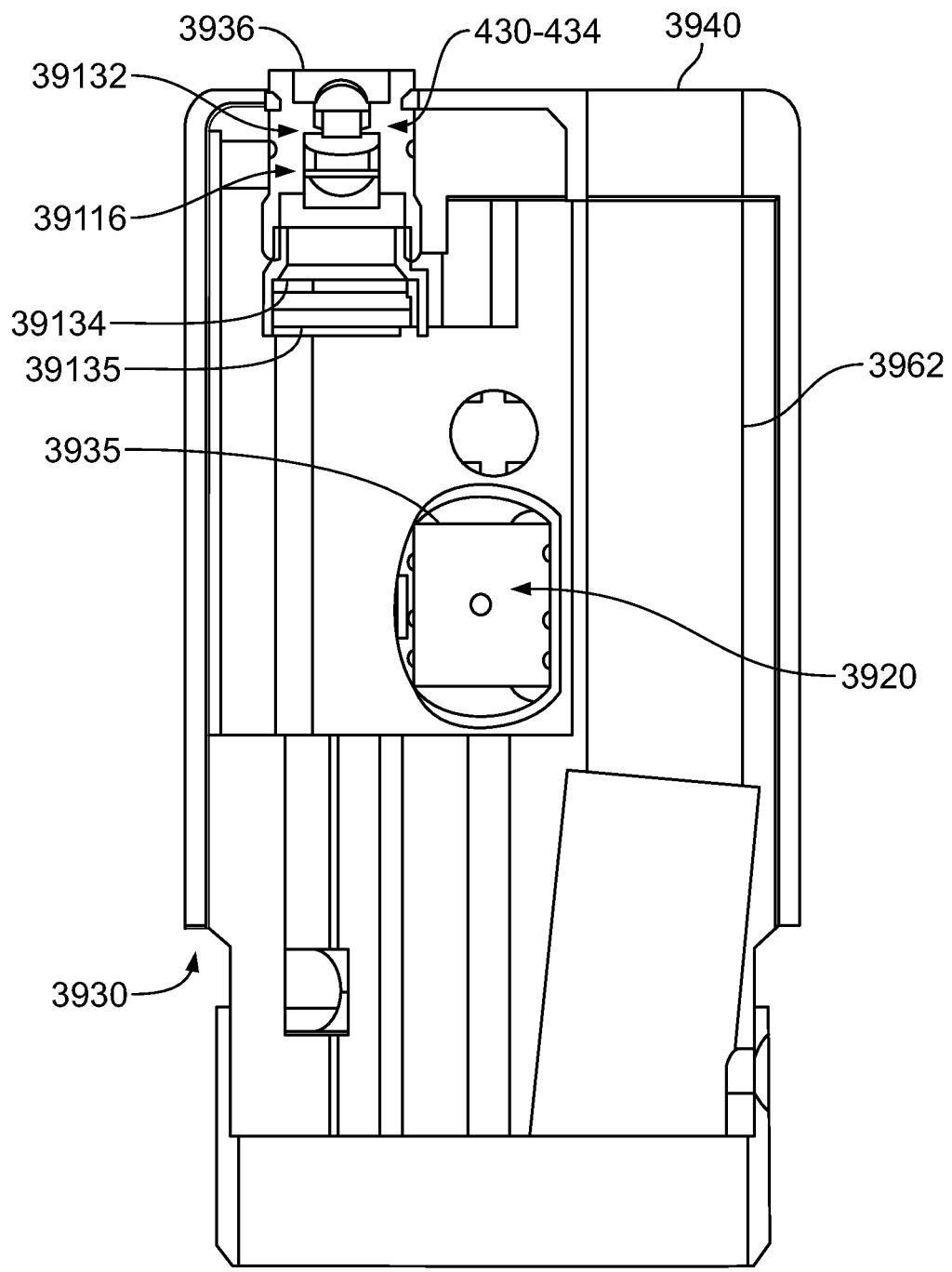
FIG. 39C schematically depicts another cutout isometric view of an endoscope having multiple fields of view according to an exemplary embodiment of the current specification.

FIG. 39C schematically depicts a cross section of an endoscope having multiple fields of view showing some details of the head 3930 according to an exemplary embodiment of the current specification.

According to some embodiments of the current specification, the interior of the head 3930 comprises forward looking and side looking cameras 39116 and 3920, respectively. Cameras 39116 and/or 3920 comprise lens assemblies 39132 having a plurality of lenses 430 to 434 and protective glass 3936 and a solid state detector array 39134 connected to a printed circuit board 39135 and 3935. It is noted that cameras 39116 and 3920 or any element related to them (such as lens assemblies 39132, lenses 430 to 434 and protective glass 3936, solid state detector array 39134 and/or printed circuit board 39135 and 3935) may be the same or different. In other words, the front looking camera and the side looking camera(s) may be the same or different in any one or any combinations of their components or other element related to them (such as optical elements).

Figure 40:
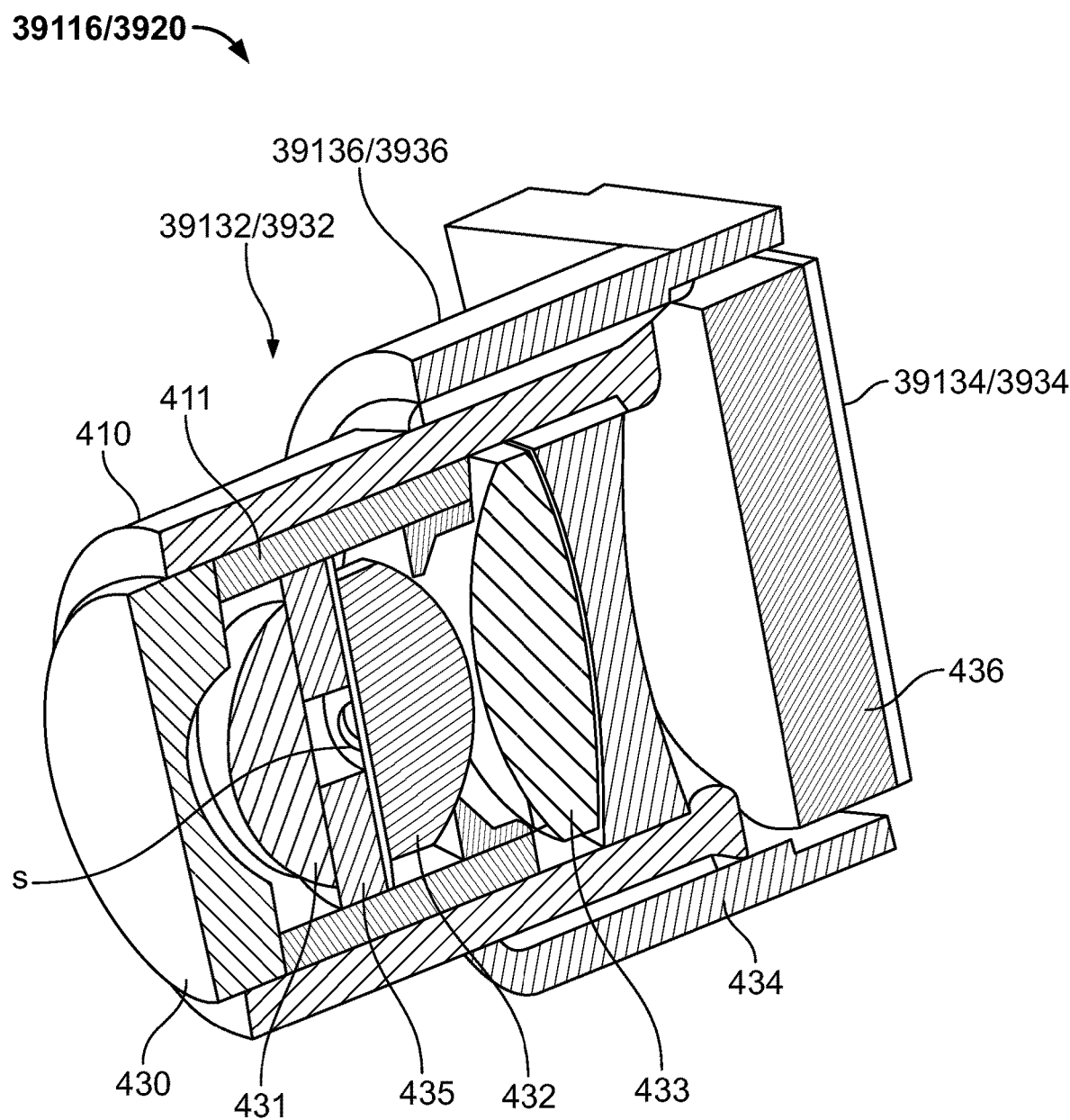
FIG. 40 schematically depicts a cross section of a lens assembly of a camera head, according to an exemplary embodiment of the current specification.

FIG. 40 schematically depicts a cross section of cameras 39116 or 3920, showing some details of lens assemblies 39132 and 3932 according to an exemplary embodiment of the current specification. It should be noted that according to some embodiments of the specification, cameras 39116 and 3920 may be similar or different. Optionally, the focusing distance of camera 39116 is slightly different than that of camera 3920. Differences in focusing distances may be achieved, for example, by (slightly) changing the distance between the lenses that comprise the lens assemblies 39132 and/or 3932, or between the lens assembly and the detector array.

Air gap "S" between lenses 431 and 432 acts as a stop. Air gap S may affect the focal range (the distance between the closest object and farther objects that can be imaged without excessive blurring caused by being out of optimal focusing of the lens system).

According to an exemplary embodiment of the current specification, cameras 39116 and 3920 comprise lens assemblies 39132 and 3932 respectively. The lens assemblies comprise a set of lenses 430 to 434 and protective glass 436.

Lenses 430 to 434 are situated within a (optionally metallic) barrel 410 and connecter thereto (for example, glued in barrel 410). Any one of lens assemblies 39132 and/or 3932 may also include an adapter 411, optionally, as shown in FIG. 40, positioned within barrel 410. Adapter 411 is configured to adjust the location of one or more of the lenses and adjust the distance between lenses. Adapter 411 may also be configured to function as a stop (in this case, between lenses 432 and 433. Protective glass 436 is situated in proximity to the solid state detector arrays 39134 or 3934 and is optionally attached thereto.

Focal distance (the distance to the object to be optimally focused by the lens system) may be changed by changing the distance between lenses 434 and protective glass 436. As lens 434 is fixed to the barrel 410, and protective glass 436 is fixed to lens holder 39136 (3936), this distance may be varied by changing the relative positioning of lens holder 39136 (3936) with respect to barrel 410. The space between the lenses 434 and protective glass 436 may be an empty space or may be filled with glass or other transparent material, or a tubular spacer may be inserted to guarantee the correct distance between these lenses. Optionally, optical filters may be placed within the space. Cameras 39116 and 3920 further comprise solid state detector arrays 39134 and 3934 respectively. Solid state detector arrays 39134 and 3934 may each be connected to printed circuit boards. An electrical cabling may connect the printed boards to a central control system unit of the endoscope.

Solid state detector arrays 39134 and 3934 are attached to lens holders 39136 and 3936 respectively. Lens holder 39136 or 3936 is attached to lens assemblies 39132 or 3932 respectively by attaching detector array cover to barrel 410.

In some applications, protective glass 436 may be a flat-flat optical element, acting primarily as a protection of the detector array (such as detector arrays 39134 and 3934), and may optionally be supplied with the array. However, optical properties of protective glass 436 need to be accounted for in the optical design.

In order to assemble lens assemblies 39132 or 3932, lens 430 may first be inserted from the left, then 431, and 432 from the right. Lenses 433 and 434 which may be glued together (or separated for example by air) are then inserted from right. The complete set is now assembled in a barrel. The assembled detector (such as detector arrays 39134 and 3934), protective glass 436 and cover 39136 (3936) are then added.

Figure 41A:
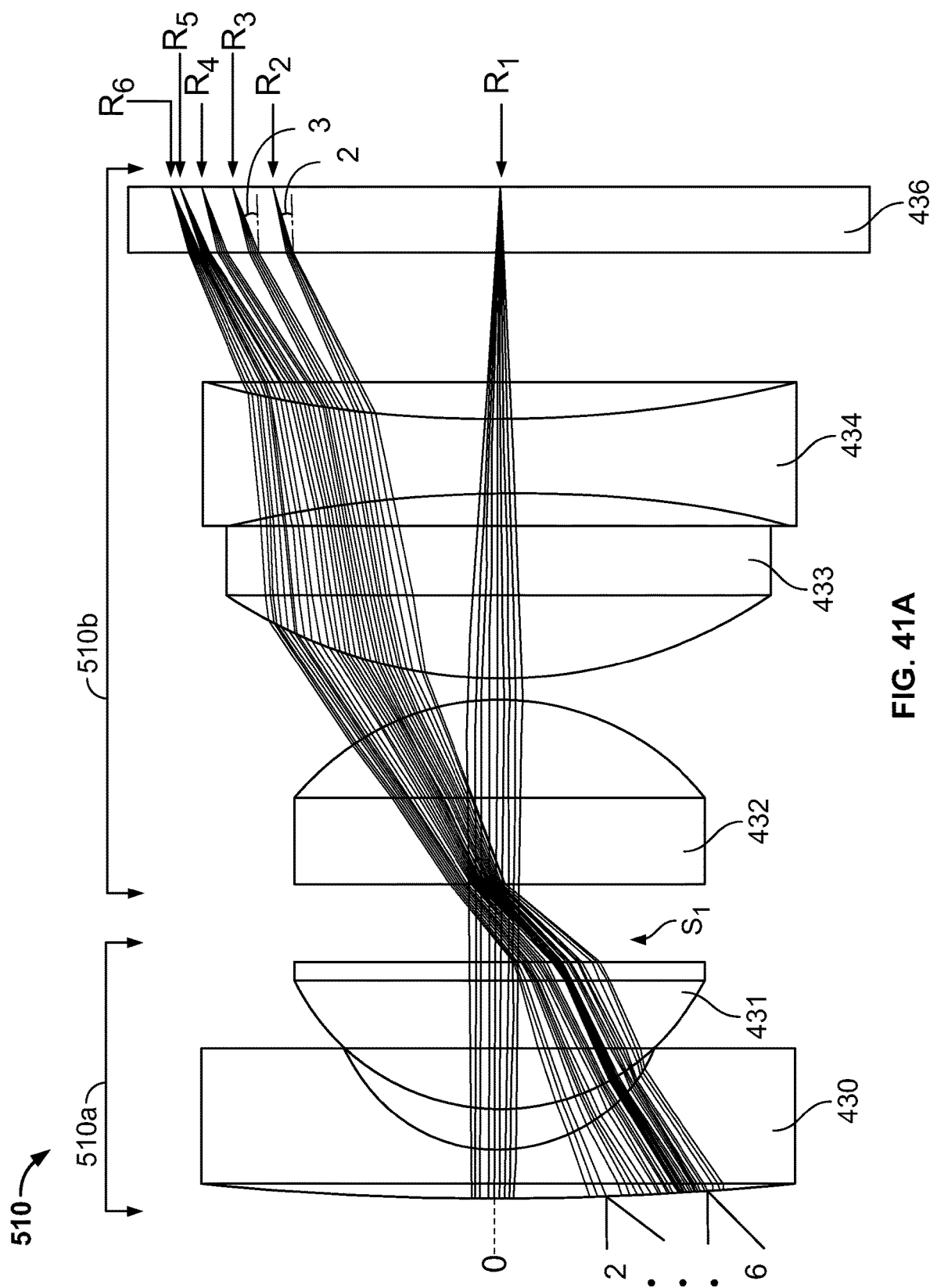
FIG. 41A schematically illustrates example of light propagation within an objective lens system according to an exemplary embodiment of the current specification.
Figure 41B:
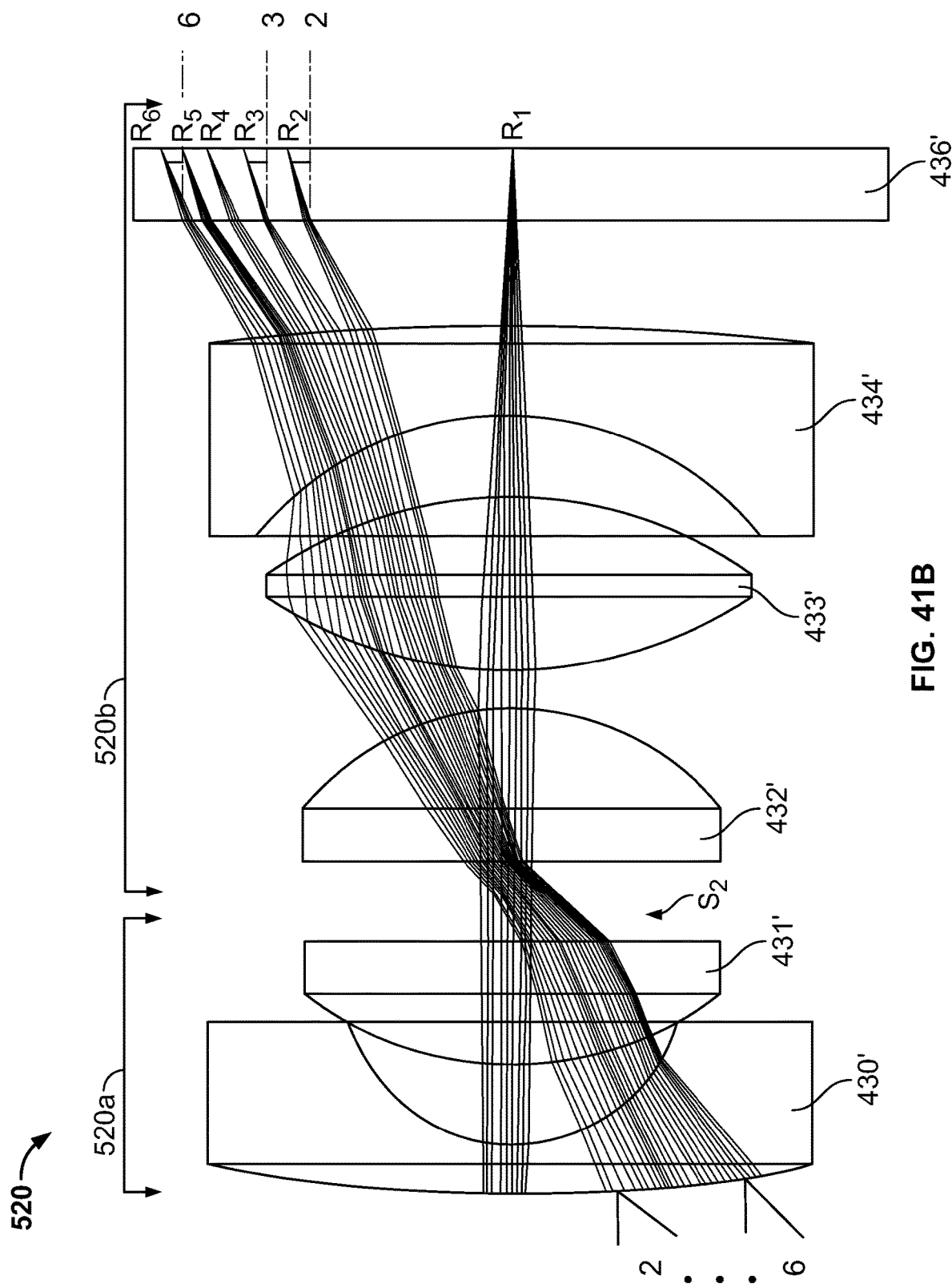
FIG. 41B schematically illustrates another example of light propagation within an objective lens system according to an exemplary embodiment of the current specification.
Figure 41C:
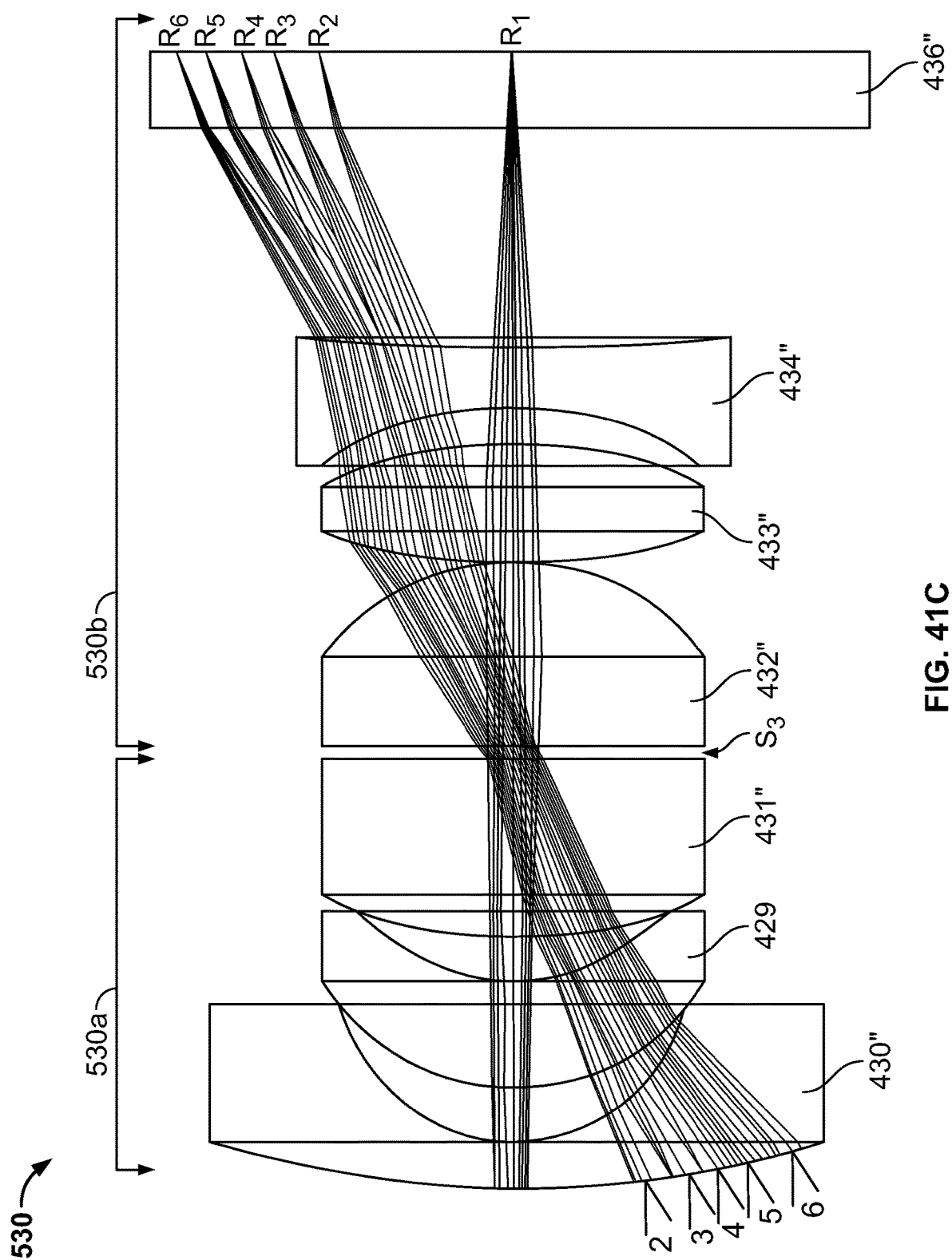
FIG. 41C schematically illustrates another example of light propagation within an objective lens system according to an exemplary embodiment of the current specification.

FIGS. 41a, 41b and 41c illustrate three examples for the lens assemblies such as lens assemblies 39132 and 3932 according to the present specification, having objective lens systems 510, 520 and 530 respectively. The sensor used in the lens assemblies 39132 and 3932, according to this exemplary embodiment, may be a Charge Coupled Device sensor (CCD) having an array of micro-lenses but other sensors, such as CMOS, may also be used.

In an exemplary embodiment of the specification, a color CCD camera having resolution of approximately 800×600 pixels is used with total active area of approximately 3.3× 2.95 mm. The optical resolution of the lens, according to exemplary embodiments of the current specification, is designed to match the resolution of the sensor. The objective lens systems 510 (520/530) are preferably corrected for chromatic, spherical and astigmatism aberrations. In an exemplary embodiment of the specification, objective lens systems 510, 520, 530 are approximately 4.60 mm (4.62) in total length, measured from front face of front lens to the front surface of the sensor. In an exemplary embodiment of the specification, objective lens systems 510 and 520 are wide angle objectives having approximately 170 degrees acceptance angle. In an exemplary embodiment of the specification, objective lens systems 510, 520, 530 have a short focal distance of measured from the front surface of the front lens to the imaged object. In an exemplary embodiment of the specification objective lens systems 510, 520, 530 have depth of focus (DOF) allowing to effectively image objects between 4-110 mm (or between, 3.5-50 mm). In an exemplary embodiment of the specification, objective lens systems 510, 520 and 530 have a maximum diameter of about 2.5 mm, defined by the diameter of the front lens, and are housed in a barrel having a maximum outer diameter of approximately 3.6 mm. It should be noted that other design parameters may be selected within the general scope of the current specification.

The objective lens systems 510, 520, 530 have an optical axis "O" depicted by the dashed line. The lens systems each comprise a front sub-system 510a, 520a, 530a and a rear sub-system 510b, 520b, 530b.

Front sub-systems 510a and 520a of FIGS. 41A and 41B each comprise a front lens 430, 430' located closest to the object to be viewed, having a negative power and lens 431, 431' having a positive power.

Front lens 430, 430' is oriented with its concave surface facing the object to be viewed and optionally has a diameter substantially greater than the largest dimension of the rear sub-system 510b, 520b in the direction perpendicular to the optical axis. Lens 431, 431' has a positive power.

Rear sub-systems 510b, 520b comprise lenses 432, 433, 434 and protective glass 436 and lenses 432', 433', 434', and protective glass 436' respectively, wherein 432 and 432' have a negative power, 433 and 433' have a positive power, 434 and 434' have a negative power, and 436 and 436' have essentially no optic power. It is noted that protective glass 436 and 436' may be a part of the sensor or a part of the rear sub-system 510b, 520b. Lenses 433 and 434, and 433' and 434', of the rear sub-systems 510b and 520b respectively, compose an achromatic sub-assembly (a compound achromatic sub-assembly as seen in FIG. 41A, where lenses 433 and 434 are cemented or non-compound achromatic sub-assembly as seen in FIG. 41B, where lens 433' and lens 434' are separated). Lens 433 and 433' may be biconvex with radius of curvature of its front surface being smaller than radius of curvature of its rear surface, as indicated in Tables T1 and T2 below.

Lens 432 of the objective lens systems 510 may have a focal length f432 satisfying the following condition: f432≤1.8f, where f is the composite focal length of the total system. Particularly, for the data indicated in Table T1, f432=2.05 and f=1.234 mm, the condition: f432≤1.8f is satisfied.

Lens 432' of the objective lens systems 520 may have a focal length f432' satisfying the following condition: f432≤1.8f.

Particularly, for the data indicated in Table T2, f432=2.05 and f=1.15 mm, the condition: f432≤1.8f is satisfied.

The lenses may be coated with an anti-reflection coating (AR coating) for further improving the efficiency of the lens assemblies 39132, 232.

An effective aperture stop S1, S2 is formed between lenses 431 and 432, 431' and 432'. Effective aperture stop S1, S2 may separate between front sub-system 510a, 520a) and rear sub-system 510b, 520b.

Front sub-system 530a, seen in FIG. 41C, comprises a front lens 430" located closest to the object to be viewed, having a negative power and lens 431", having a positive power. Front sub-system 530a further comprises an additional front positive lens (such as the meniscus lens 429) disposed between the first front negative lens 430" and the second front positive lens 431".

Front lens 430" is oriented with its concave surface facing the object to be viewed and optionally having a diameter substantially greater than the largest dimension of the rear sub-system 530b in the direction perpendicular to the optical axis.

Rear sub-system 530b comprises lenses 432", 433", 434", and protective glass 436", wherein 432" has a negative power, 433" has a positive power, 434" has a negative power, and 436" has essentially no optic power. It is noted that protective glass 436" may be a part of the sensor or a part of the rear sub-system 530b. Lenses 433" and 434" compose an achromatic sub-assembly of the rear sub-system 530b and may or may not be cemented to each other. Lens 433" may be biconvex with radius of curvature of its front surface being smaller than radius of curvature of its rear surface, as indicated in Table T3 below.

Lens 432" of the objective lens systems 530 may have a focal length f432 satisfying the following condition: f432"≤1.8f, where f is the composite focal length of the total system. Particularly, for the data indicated in Table T3 f432"=2.26 and f=1.06 mm, the condition: f432"≤1.8f is satisfied.

The lenses may be coated with an anti-reflection coating (AR coating) for further improving the efficiency of the lens assemblies 39132, 3932.

An effective aperture stop S3 is formed between lenses 431" and 432". Effective aperture stop S3 may separate between front sub-system 530a and rear sub-system 530b.

Tables T1, T2 and T3 summarize the parameters of lenses in the objective lens systems 510, 520 and 530, respectively, according to some embodiments of the current specification:

TABLE T1

(FOV = 164o, DOF = 3-110 mm. f = 1.234 mm, total optical track 4.09 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430 | Negative | 15 | 0.7 | 0.2 | 0.18 | N-LASF31 | 1.2 | 0.64 | −0.837 |
| 431 | Plan-convex | 0.9 | Infinity | 0.56 | 0.27 | N-LASF31 | 0.8 | 0.8 | 1.02 |
| $S_1$ | Stop | | | | 0.05 | | 0.104 | | |
| 432 | Plan-convex | Infinity | −1.0 | 0.75 | 0.09 | FK5 | 0.8 | 0.8 | 2.05 |
| 433 | Biconvex | 1.93 | −4.2 | 0.75 | 0.005 | N-LAK22 | 1.1 | 1.1 | 2.13 |
| 434 | Biconcave | −4.2 | 4.44 | 0.3 | 0.65 | N-SF66 | 1.1 | 1.2 | −2.3 |
| 436 | Protection Glass | Infinity | Infinity | 0.3 | 0 | N-BK7 | 1.5 | 1.5 | Infinity |

TABLE T2

(FOV = 164o, DOF = 3-110 mm. f = 1.15 mm, total optical track 4.09 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430 | Negative | 6 | 0.7 | 0.2 | 0.3 | N-LASF31 | 1.2 | 0.66 | −0.913 |
| 431 | Plan-convex | 1.26 | Infinity | 0.50 | 0.27 | N-LASF31 | 0.8 | 0.8 | 1.43 |
| $S_1$ | Stop | | | | 0.05 | | 0.105 | | |
| 432 | Plan-convex | Infinity | −1.0 | 0.60 | 0.15 | FK5 | 0.8 | 0.8 | 2.05 |
| 433 | Biconvex | 1.67 | −1.65 | 0.70 | 0.30 | FK5 | 0.95 | 0.95 | 1.83 |
| 434 | Meniscus | −1.33 | −12.0 | 0.35 | 0.40 | N-SF66 | 1.0 | 1.2 | −1.65 |
| 436 | Protection Glass | Infinity | Infinity | 0.3 | 0 | N-BK7 | 1.5 | 1.5 | Infinity |

Table T3 shows an example of a six-component system also comprising an additional positive lens 429 (for example, as indicated in Table T3, a meniscus lens).

TABLE T3

(FOV = 164o, DOF = 3-110 mm. f = 1.06 mm, total optical track 4.69 mm)

| Lens | Type | $R_1$ | $R_2$ | Th | D | Glass | Semi-Diameter $d_1/2$ | Semi-Diameter $d_2/2$ | $f_{mm}$ |
|---|---|---|---|---|---|---|---|---|---|
| 430" | Negative | 4.3 | 0.75 | 0.2 | 0.22 | N-LASF31 | 1.3 | 0.72 | −1.06 |
| 429 | Meniscus | 0.95 | 0.9 | 0.44 | 0.18 | N-SF66 | 0.8 | 0.65 | 5.75 |
| 431" | Plan-convex | 2.0 | Infinity | 0.75 | 0.02 | N-LASF31 | 0.8 | 0.8 | 2.26 |
| $S_3$ | Stop | | | | 0.02 | | 0.116 | | |
| 432" | Plan-convex | Infinity | −1.0 | 0.78 | 0 | N-PSK57 | 0.8 | 0.8 | 1.69 |
| 433" | Biconvex | 2.52 | −2.0 | 0.50 | 0.154 | YGH52 | 0.8 | 0.8 | 1.49 |
| 434" | Biconcav | −1.44 | 11.0 | 0.25 | 0.91 | PBH56 | 0.8 | 0.9 | −1.50 |
| 436" | Protection Glass | Infinity | Infinity | 0.3 | 0 | N-BK7 | 1.5 | 1.5 | Infinity |

R1—radius of curvature of the lens front surface (front surface is the surface facing the direction of the object);
R2—radius of curvature of the lens rear surface (facing away from the object);
Th—thickness of the lens—from center of front surface to center of rear surface;
Glass—lens glass type;
d1—radius of the front optical surface of the lens;
d2—radius of the rear optical surface of the lens;
D—distance between components such as lenses, measured front center of rear surface of the component, such as lens to the front surface of the next optical element (in the case of a stop, S, the distance is measured front center of rear surface of a component on the front side of the stop, to the front surface of the next component), As commonly used, radius of curvature equal to infinity is interpreted as planar. All lenses are optionally spherical.

FIGS. 41A, 41B and 41C also show the propagation of six incident rays of light R1 to R6 through the objective lens system 510, 520 and 530 respectively, from the front lens 430 (FIG. 41a), 430' (FIG. 41b) or 430" (FIG. 41c) till the creating of an image of the object at an image plane.

Rays R1 to R6 enter the lens assembly at angles α1 (alpha 1) to α6 (alpha 6), respectively, for example, essentially equal to the following angles: α1=0°, α2=45°, α3=60°, α4=75° and α5=84°. The corresponding incident angles (the angles between the light rays which have passed the microlenses of the sensor and the optical axis of the system) are β1 (beta 1)-β6 (beta 6). According to some embodiments, the chief incident angle (for example the incident angles forming by rays R6 in FIGS. 41A through 41C) is larger than 20°, larger than 25°, larger than 30° or between about 20-40°. The lens system, according to some embodiments of the specification provides minimal peripheral distortion (for example, less than 80%).

The optical system assembly 39132, 3932 may be assembled by a method comprising the steps of:
Optionally, cementing the rear doublet of lenses 433-434 (433'-434');
and:
Assembling in the barrel the front lenses 430 (430');
Assembling lens 431 (431') in the barrel;
Assembling lens 432 (432') in the barrel; and
Assembling in the barrel, the rear doublet 433-434 (433'-434'); optionally,
Note that front lens 430 (430') may be assembled last.
In one embodiment, each of the multiple viewing elements of a tip section of an endoscope is embodied as a separate imaging module. The imaging modules are encapsulated together in the endoscopic tip cavity. The modules are individually sealed such that in case of failure in one module, only the failed module is replaced without affecting the other modules.

In a modular design, each of the front and side-pointing image sensors and their respective lens assemblies, together with their circuit boards, comprise individual imaging modules, which are described in greater detail with reference to the figures below. In case of a defect, these modules can be individually replaced or repaired without affecting the other modules. In one embodiment, all the imaging modules are advantageously positioned relatively close to the distal end surface of the tip section. This is enabled by an advantageous miniaturizing of the front and side-pointing viewing elements in modular design, which allows for enough internal space in the tip section for angular positioning of the cameras without colliding.

Further, the modular design makes use of the same space or volume for imaging modules, as used by cameras in existing designs, and does not affect the functionality and design of other components in the tip such as fluid channels, illuminators, etc.

Figure 42:
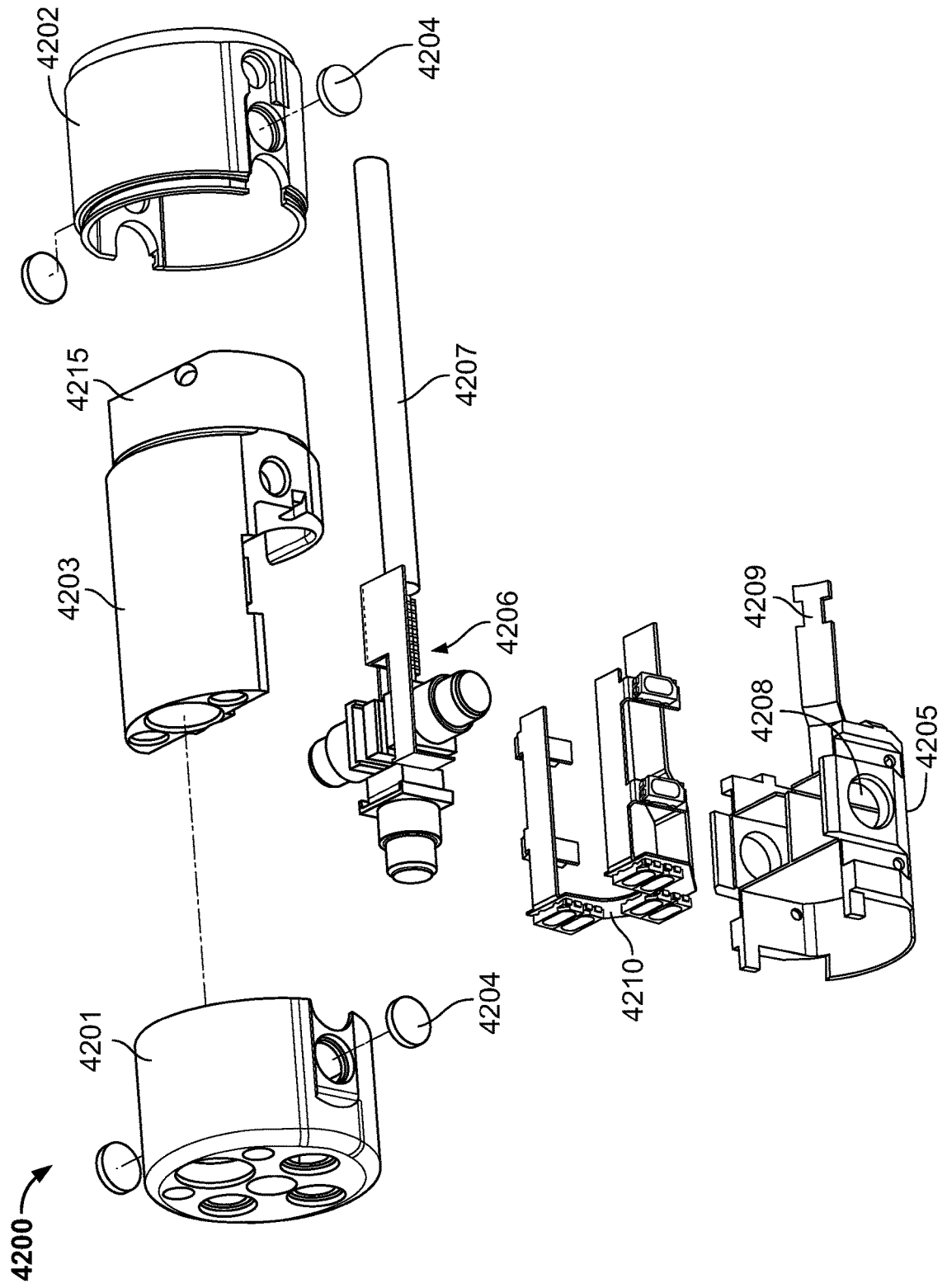
FIG. 42 shows various components of a modular endoscopic tip, according to one embodiment.

Reference is now made to FIG. 42, which shows various components of a modular endoscopic tip 4200, according to one embodiment of the present specification. A modular tip cover or housing comprises a front tip cover 4201 and a rear tip cover 4202. A fluid channeling component or manifold 4203 is designed to fit between the two tip covers. Both front tip cover 4201 and rear tip cover 4202 have a plurality of front and side openings, such as side optical windows 4204, for the purpose of covering, protecting and sealing the viewing elements and the illuminators within the tip.

The modular endoscopic tip 4200 also has a partially enclosed housing or holder 4205 in which an assembly of flexible LED carrier substrate 4210 and imaging module (that in one embodiment is supported or positioned on a flexible optical carrier substrate, such as substrate 770 of FIG. 24A through 24C) 4206 together with their electrical cable 4207 is placed. The partially enclosed housing 4205 has appropriate slots 4208 to fit in the flexible optical carrier substrate or imaging module 4206. It also has a protrusion or portion 4209 for carrying or supporting the associated electrical cable. In accordance with an embodiment, the proximal base 4215 of the manifold 4203 comprises a groove adapted to receive, align or mate with the protrusion 4209 thereby enabling a snug fit between the manifold 4203 and the partially enclosed housing 4205 when assembled. The manifold 4203 and the partially enclosed housing 4205 when assembled form a substantially cylindrical housing defining an internal volume to accommodate the assembly of flexible LED carrier substrate 4210 and imaging module 4206. In accordance with an embodiment, the internal volume (of an endoscopic tip) ranges from 2.75 cm3 to 3.5 cm3.

The flexible LED carrier substrate 4210 is configured to carry the module 4206 which comprises imaging elements as well as optics. The flexible LED carrier substrate and optical carrier substrate—together referred to as flexible electronic circuit board has been described earlier in this specification. Particularly, as described earlier, the flexible circuit board consumes less space and leaves more volume for additional necessary features. In one embodiment, the flexible circuit board can be folded to allow two side imaging modules to be positioned parallel to each other. Thus, the flexibility of the board adds another dimension in space that can be used for components positioning.

The use of the flexible circuit board can significantly increase reliability of the electric modules connected thereto as no wires are used for components connectivity. In addition, according to some embodiments, the components assembly can be machined and automatic.

The use of the flexible circuit board assists in maneuverability of components during assembly of the modular tip 4200 and also simplifies the assembly process. In one embodiment, the flexible circuit board is connected to the control unit of the endoscope via a multi-wire electrical cable which is welded on the board in a designated location, thereby freeing additional space within the tip assembly.

Figure 43:
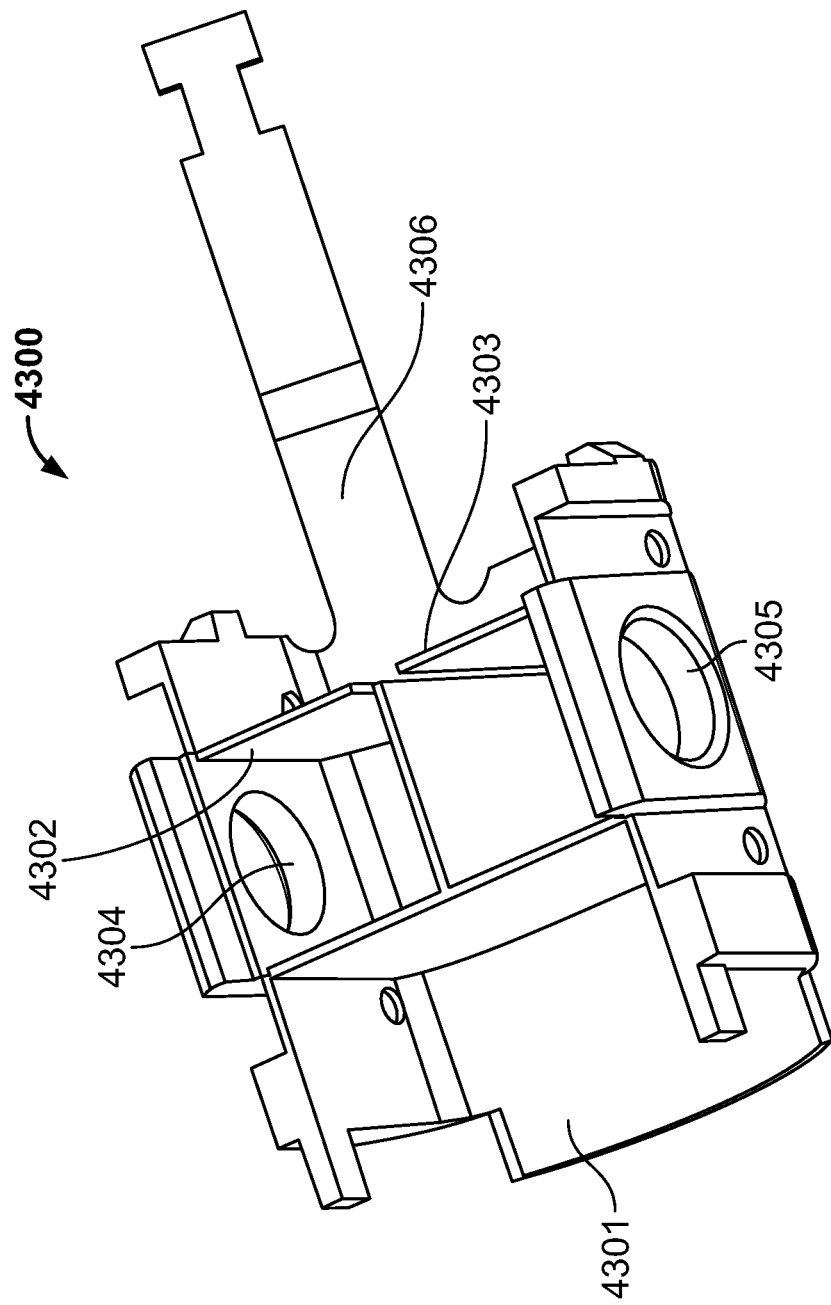
FIG. 43 illustrates one embodiment of a holder for the imaging modules.

FIG. 43 provides a detailed view of the partially enclosed housing or holder 4300 (shown as 4205 in FIG. 42) for housing the imaging module 4206 of FIG. 42, which in one embodiment is positioned or supported on a flexible optical carrier substrate. Referring to FIG. 43, holder 4300 comprises a concave area 4301 in the front, where the front-pointing imaging module can be placed. The holder 4300 further comprises two compartments 4302 and 4303 for carrying the first and the second side-pointing imaging modules, respectively. The compartments are also provided with circular slots or openings 4304 and 4305 to carry the optics of the imaging modules. A rectangular strip or protrusion 4306 in the holder is provided to carry the electrical cable and, as shown in FIG. 42, mate with a groove on the proximal base 4215 of the manifold 4203. It may be appreciated that the holder 4300 is designed such that it corresponds to the shape and size of flexible optical carrier substrate or modular imaging units together with the electrical cable. This can also be seen in elements 4205, 4206 and 4207 of FIG. 42 as described above.

Figure 44:
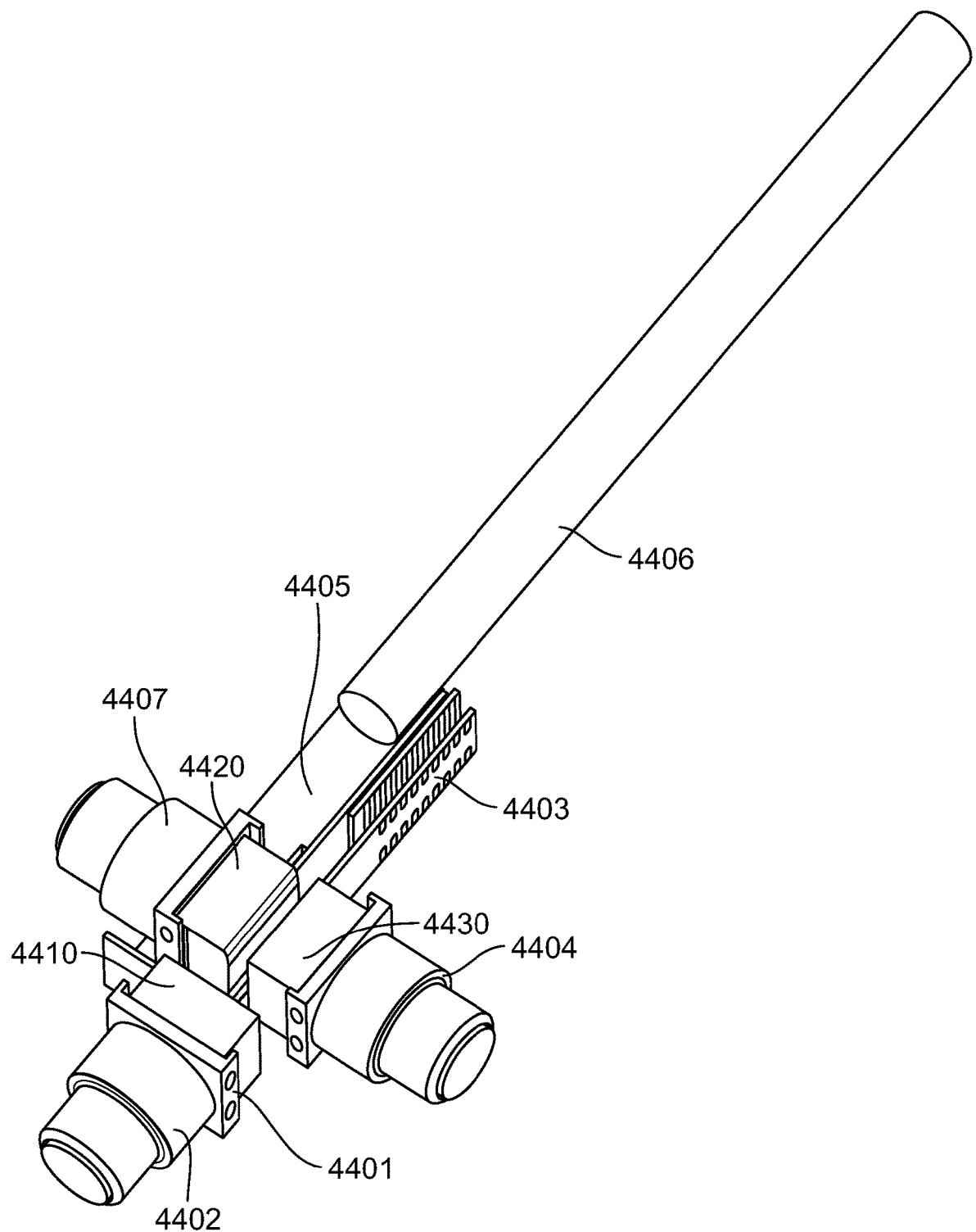
FIG. 44 illustrates a top view of the modular imaging units, according to one embodiment of the present specification.

FIG. 44 illustrates a top view of the modular imaging units when integrated with one another, in accordance with an embodiment. In the present embodiment, three modular imaging units are employed, in a similar configuration as described with reference to FIG. 1J. Referring to FIG. 44, among the three modular imaging units, there is a front-pointing modular unit 4410 and two side-pointing modular imaging units 4420 and 4430. The front-pointing modular unit 4410 comprises a front printed circuit board with integrated sensor 4401. Front-pointing modular unit 4410 further comprises a front lens holder 4402 within which the optics of the imaging unit are placed. The first-side pointing modular unit 4420 comprises a side printed circuit board with integrated sensor 4403. It further comprises a side lens holder 4404 where the optics of the imaging unit are placed. The other side-pointing modular imaging unit 4430 also comprises a side printed circuit board with integrated sensor 4405, together with a side lens holder 4407. All the modular units are supplied power through the electrical cable 4406.

Figure 45:
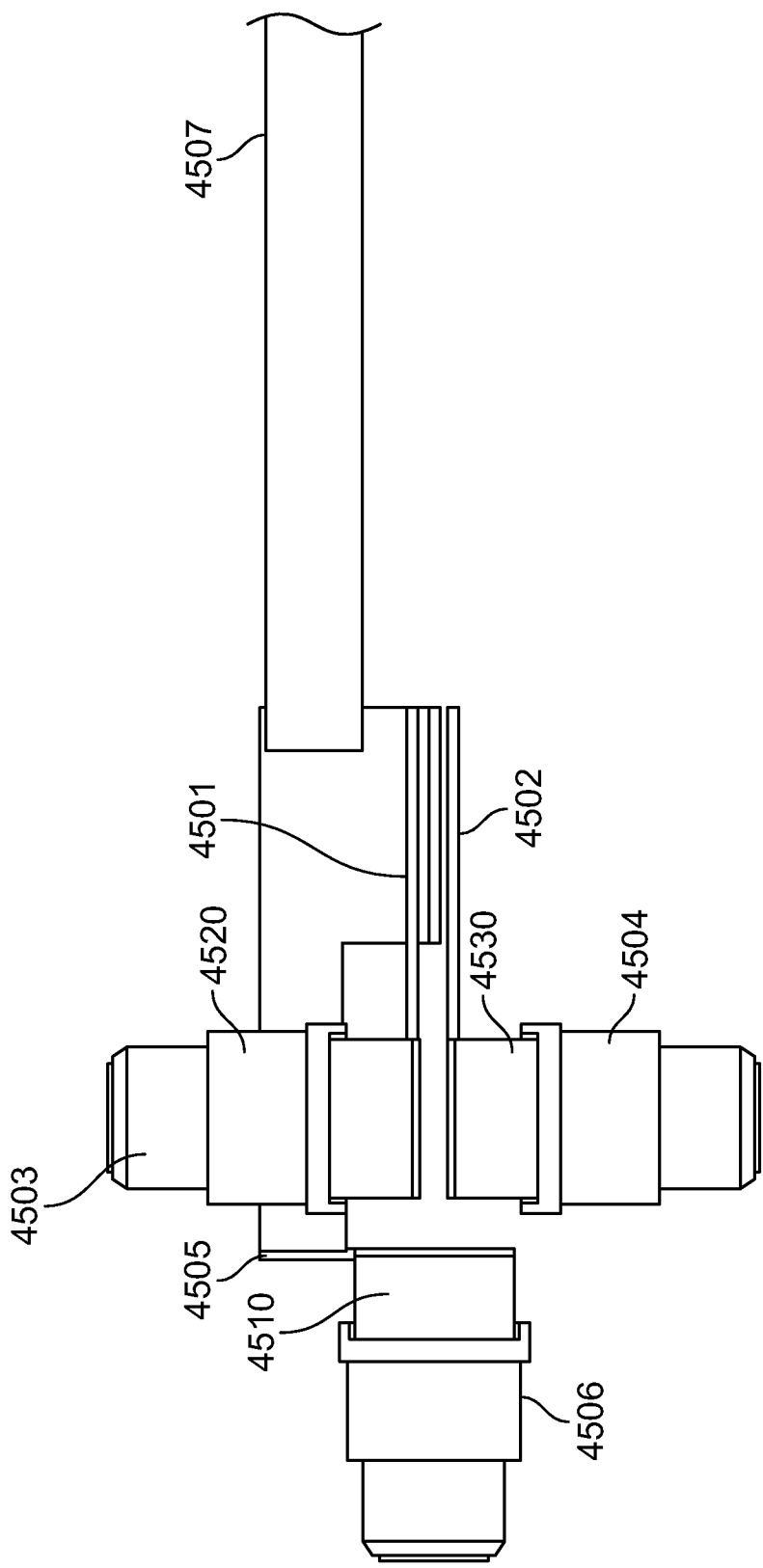
FIG. 45 illustrates a bottom view of the modular imaging units, according to one embodiment of the present specification.

FIG. 45 illustrates a bottom view of the three modular imaging units, including one front-pointing imaging unit 4510 and two side-pointing units 4520 and 4530. Here, the side printed circuit boards with integrated sensors 4501, 4502 are visible for both the side-pointing modular units 4520 and 4530. Also visible are the side lens holders 4503, 4504, and the front printed circuit board with integrated sensor 4505 and the front lens holder 4506 of the front-pointing modular imaging unit 4510. As can be seen from the figure, the electrical cable 4507 is connected to the printed circuit boards 4505, 4501, and 4502 of the front-pointing as well as the side pointing imaging units, respectively.

As described earlier with reference to FIG. 1J, in various embodiments, each imaging module comprises a lens assembly, an image capturing device and an integrated circuit board. Image capturing devices may be Charged Coupled Devices (CCD's) or Complementary Metal Oxide Semiconductor (CMOS) image sensors, or other suitable devices having a light sensitive surface usable for capturing an image. In accordance with an embodiment, the front printed circuit board with integrated sensor 4401 and the side printed circuit boards with integrated sensors 4501, 4502 are supported or positioned over a flexible optical carrier substrate (such as substrate 770 of FIG. 24A through 24C). However, in accordance with another embodiment, the front printed circuit board with integrated sensor 4401 and the side printed circuit boards with integrated sensors 4501, 4502 are all individual units.

In operation, each camera may capture images, substantially independently, and the images may be displayed, substantially simultaneously, using one or more displays e.g. as described in PCT/IL10/000476, which is incorporated herein by reference.

Figure 46:
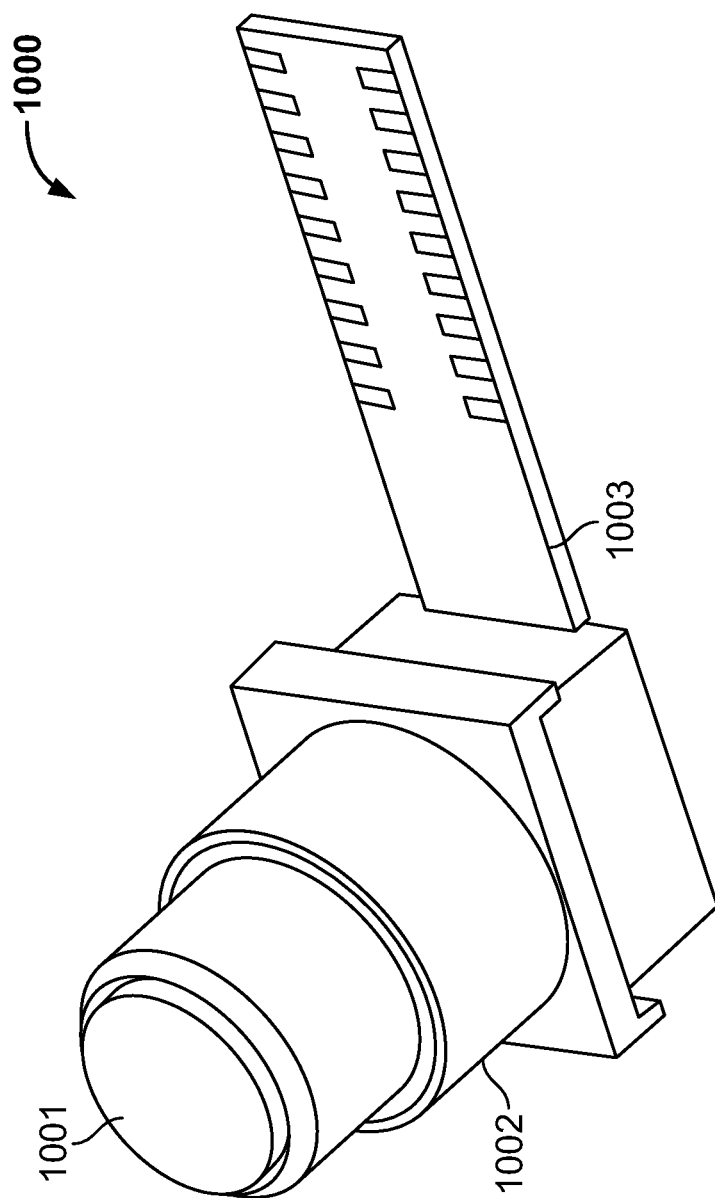
FIG. 46 illustrates a perspective view of a side-pointing modular imaging unit, according to one embodiment of the present specification.

FIG. 46 illustrates a perspective view of a side-pointing modular imaging unit. Referring to FIG. 46, the side-pointing modular imaging unit 1000 comprises a viewing element 1001 in the front. The viewing element may comprise an optic array camera. The imaging module further comprises sensor such as a Charge Coupled Device (CCD) or a Complementary Metal Oxide Semiconductor (CMOS) image sensor and a lens holder 1002 for carrying the optics of the imaging system. The printed circuit board 1003 is used to supply power to and derive images from the image sensor. In one embodiment, the image sensor is integrated with the printed circuit board. The optics of the image system may include a plurality of lenses, static or movable, which may provide a field of view of at least 90 degrees and up to essentially 180 degrees. In one embodiment, the lens assembly provides a focal length of about 2 to 100 millimeters. Side-pointing image sensor 1001 and optics (contained in the lens holder 1002), together with integrated circuit board 1003, may be jointly referred to as a "side-pointing imaging module".

Figure 47:
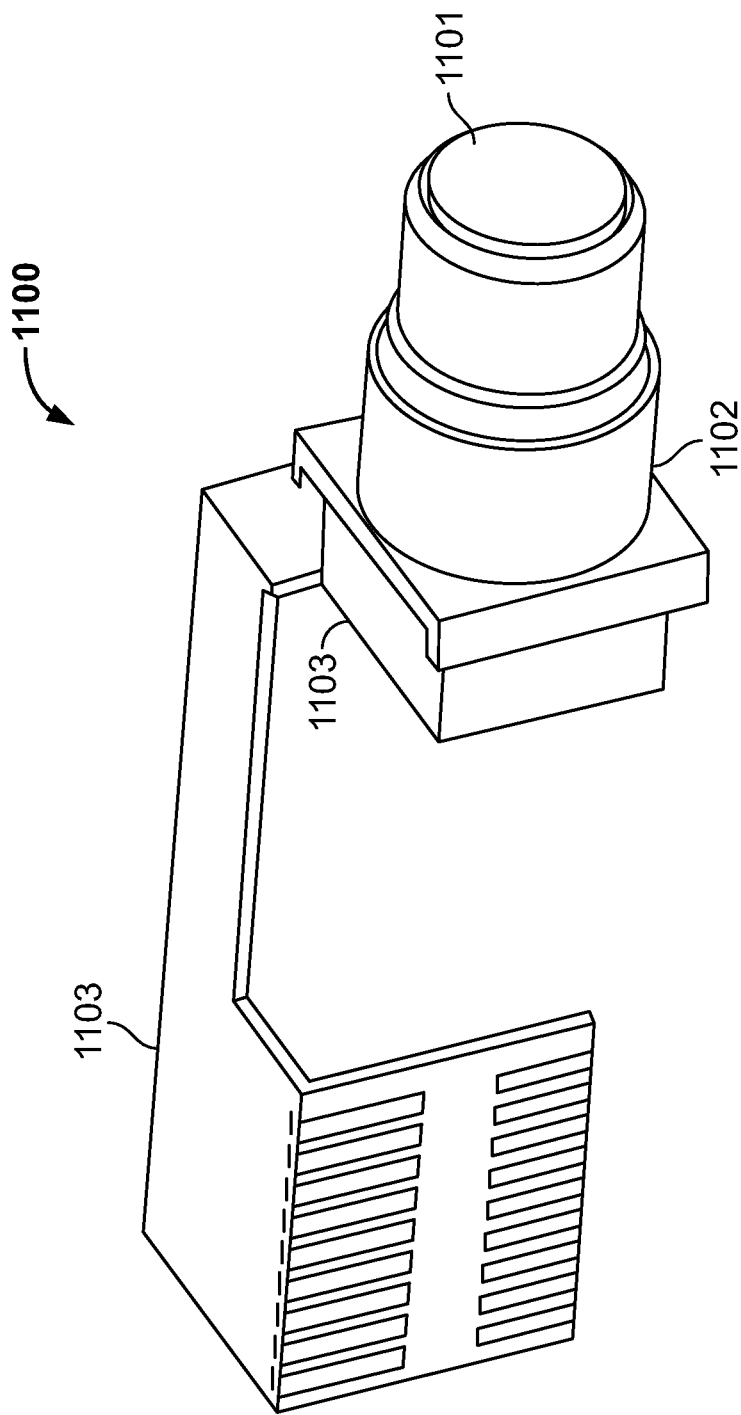
FIG. 47 illustrates a perspective view of a front-pointing modular imaging unit, according to one embodiment of the present specification.

FIG. 47 illustrates a perspective view of a front-pointing modular imaging unit. Referring to FIG. 47, the front-pointing modular imaging unit 1100 comprises a viewing element 1101 in the front. The viewing element may comprise an optic array. The imaging module further comprises sensor such as a Charge Coupled Device (CCD) or a Complementary Metal Oxide Semiconductor (CMOS) image sensor and a lens holder 1102 for optical imaging system. The printed circuit board 1103 is used to supply power to and derive images from the image sensor. The optics of the image system may include a plurality of lenses, static or movable, which may provide a field of view of at least 90 degrees and up to essentially 180 degrees. In one embodiment, the lens assembly provides a focal length of about 3 to 100 millimeters. Front-pointing image sensor 1101 and optics (contained in the lens holder 1102), together with integrated circuit board 1103, may be jointly referred to as a "front-pointing imaging module".

It may be noted that the front and side-pointing image sensors may be similar or identical in terms of, for example, field of view, resolution, light sensitivity, pixel size, focal length, focal distance and/or the like.

Figure 48:
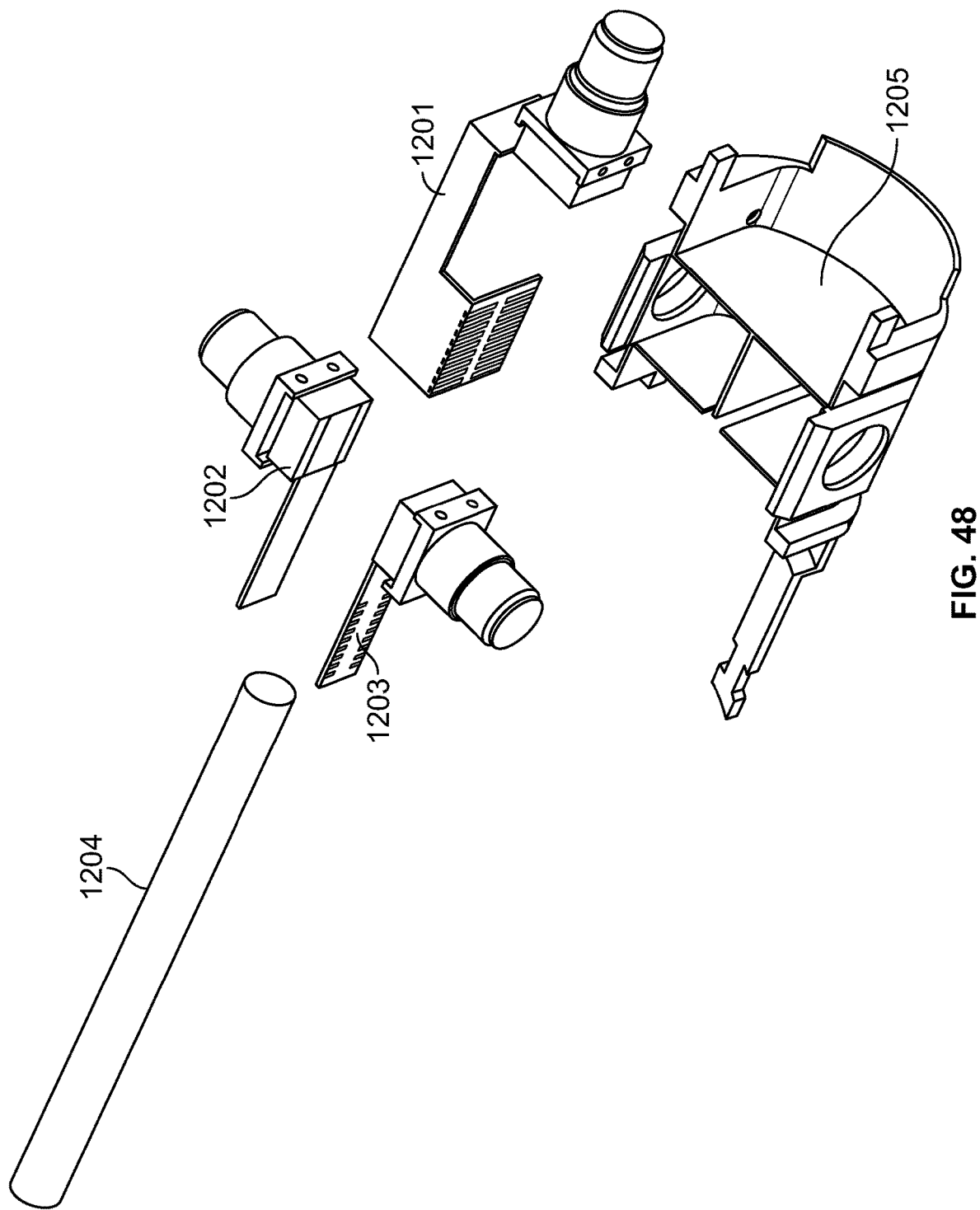
FIG. 48 illustrates the modular nature of the various elements in the endoscopic tip, according to one embodiment of the present specification.

FIG. 48 illustrates the modular nature of the various elements in the endoscopic tip, according to one embodiment of the present specification. Referring to FIG. 48, front-pointing imaging module 1201, side-pointing imaging modules 1202 and 1203, and the electric cable 1204 are all individual units. These units can be housed in the endoscopic tip using the partially enclosed housing or modular holder 1205. The holder allows all the modular units to function together and yet be separate, such that each unit can be individually removed from the assembly. Similarly, modular units can be individually installed into the tip assemble. This allows individual units to be repaired or replaced without affecting the other parts in the endoscopic tip.

Figure 49:
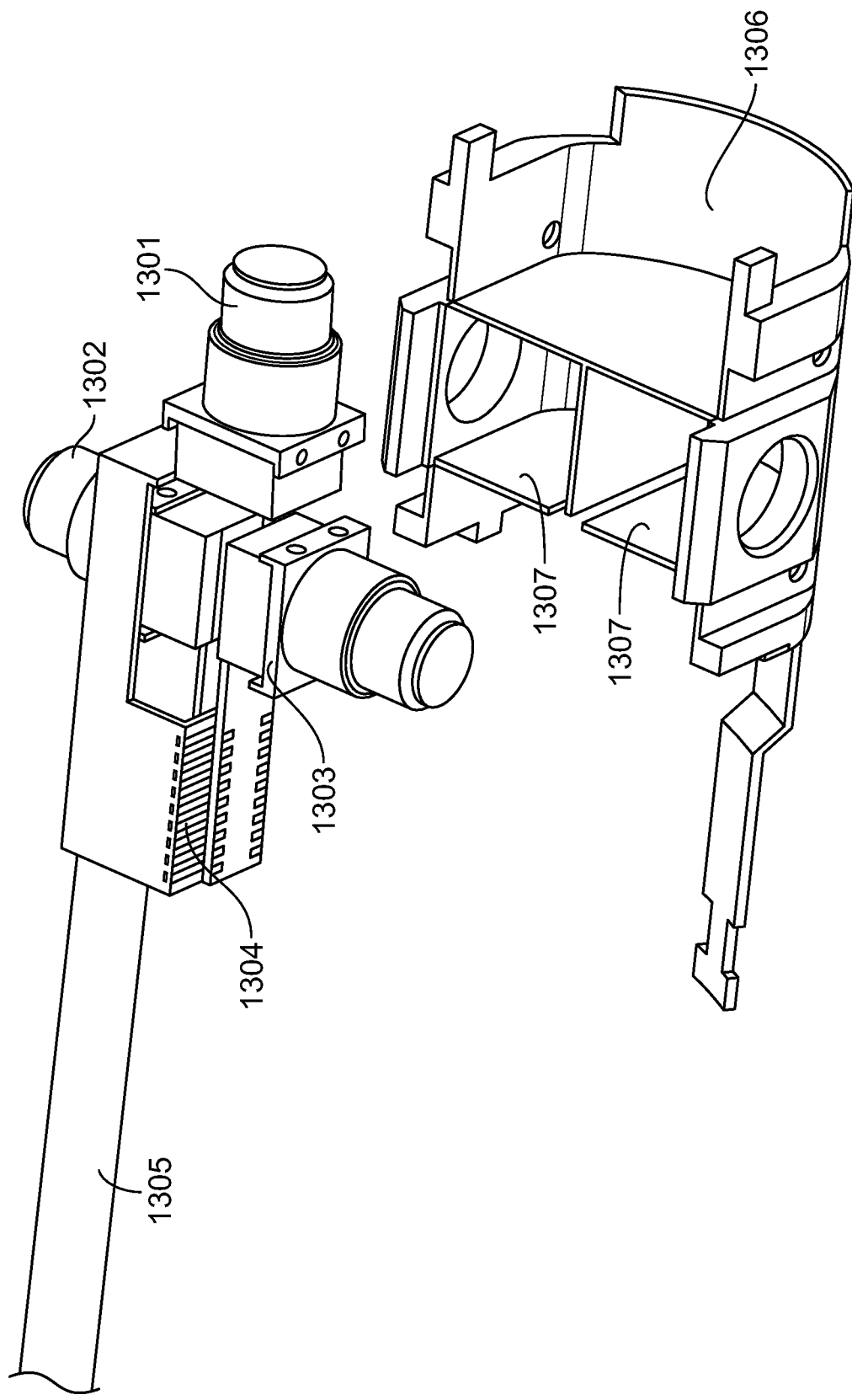
FIG. 49 illustrates a front-pointing imaging module assembled with side-pointing imaging modules, according to one embodiment of the present specification.

FIG. 49 illustrates the front-pointing imaging module 1301 assembled with the side-pointing imaging modules 1302 and 1303. The circuit boards 1304 of all the imaging modules are coupled to each other, in accordance with an embodiment, and connected with the electrical cable 1305. FIG. 49 also shows the partially enclosed housing or holder 1306 which has compartments 1307 for each imaging unit. The compartments enable the imaging modules to be encapsulated from each other, and therefore removal of one imaging module does not damage or affect the other modules.

Figure 50:
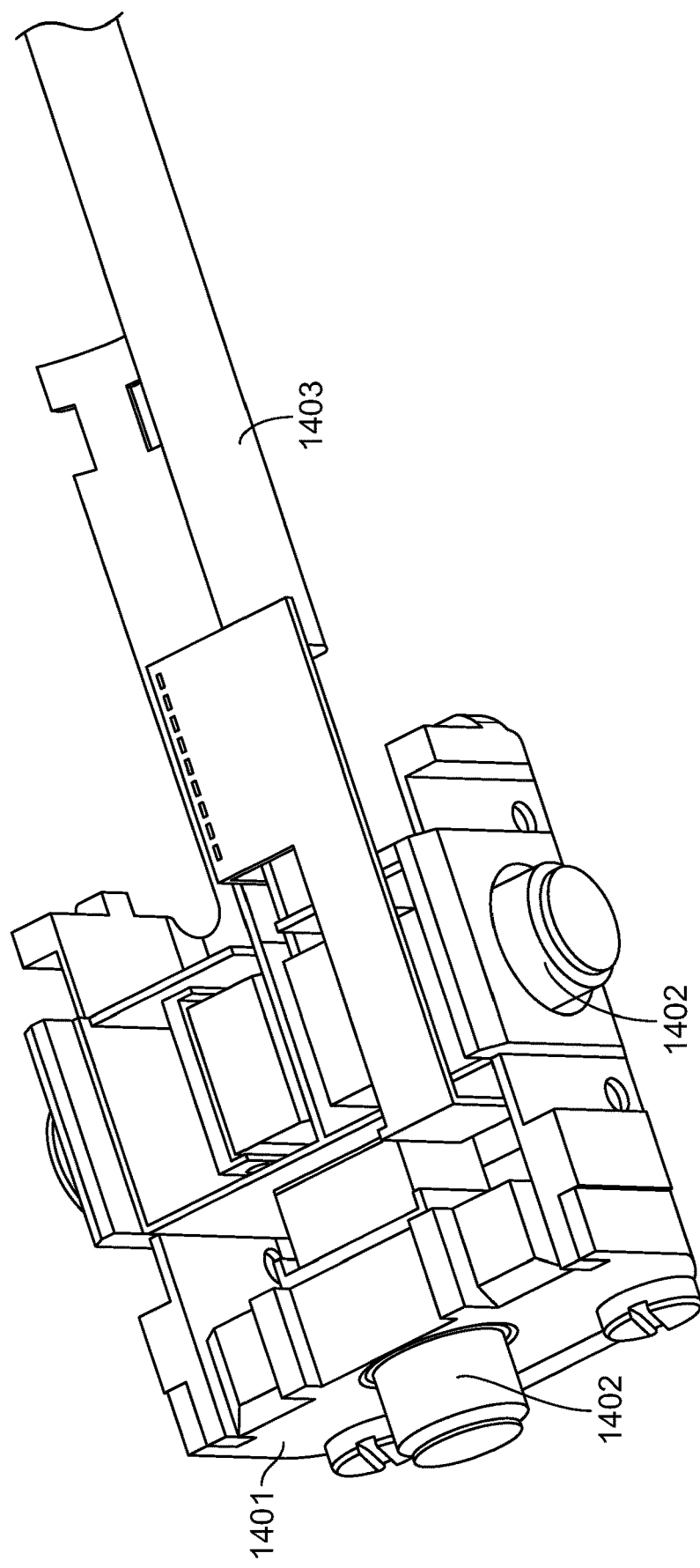
FIG. 50 illustrates a perspective view of assembled components with the modular holder, according to one embodiment of the present specification.

FIG. 50 illustrates a perspective view of the assembled components, wherein the partially enclosed housing, curved member or modular holder 1401 carries the modular imaging units 1402 and the electrical cable 1403.

Figure 51:
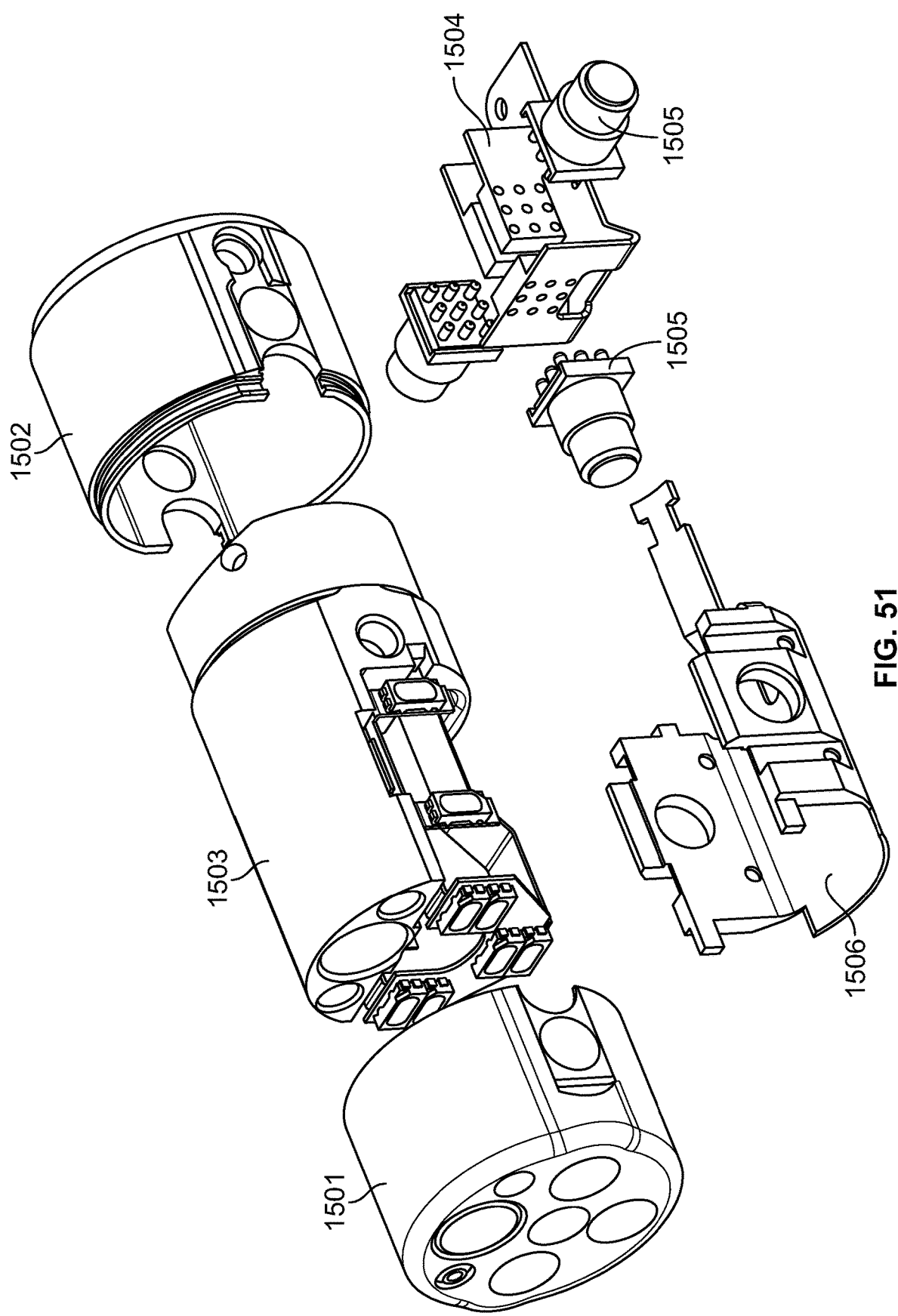
FIG. 51 illustrates another embodiment of the modular endoscopic tip.

FIG. 51 illustrates another embodiment of the modular endoscopic tip. Referring to FIG. 51, the endoscope tip comprises a front tip cover 1501 and a rear tip cover 1502. A fluid channeling component or manifold 1503 is designed to fit between the two tip covers.

In this embodiment, a mechanism for coupling the modular imaging units is integrated with the imaging units themselves. This mechanism, referred to as image modular holder 1504 is used to connect the modular imaging units 1505. The overall structure (comprising all three modular units) is then supported by a partially enclosed housing, curved member or frame 1506, also known as the modular supporter frame.

FIG. 54 illustrates a detailed view of the modular holder 1801. In accordance with an embodiment, the substrate of the modular holder 1801 is flexible so that it can be folded to form the holder 1801 shown in the figure. The modular holder comprises recesses 1802 into which corresponding connectors of imaging units are designed to fit. These connectors are shown and described further with reference to FIGS. 52, 53A and 53B. The recesses 1802 that correspond to the imaging module connectors allow the modules to be physically coupled to each other and to the endoscope tip. Further, the recesses also enable the flow of power and data between the endoscope and the imaging modules. Modular holder comprises recesses 1802 also has a portion 1803 for carrying the associated electrical cable.

Figure 52:
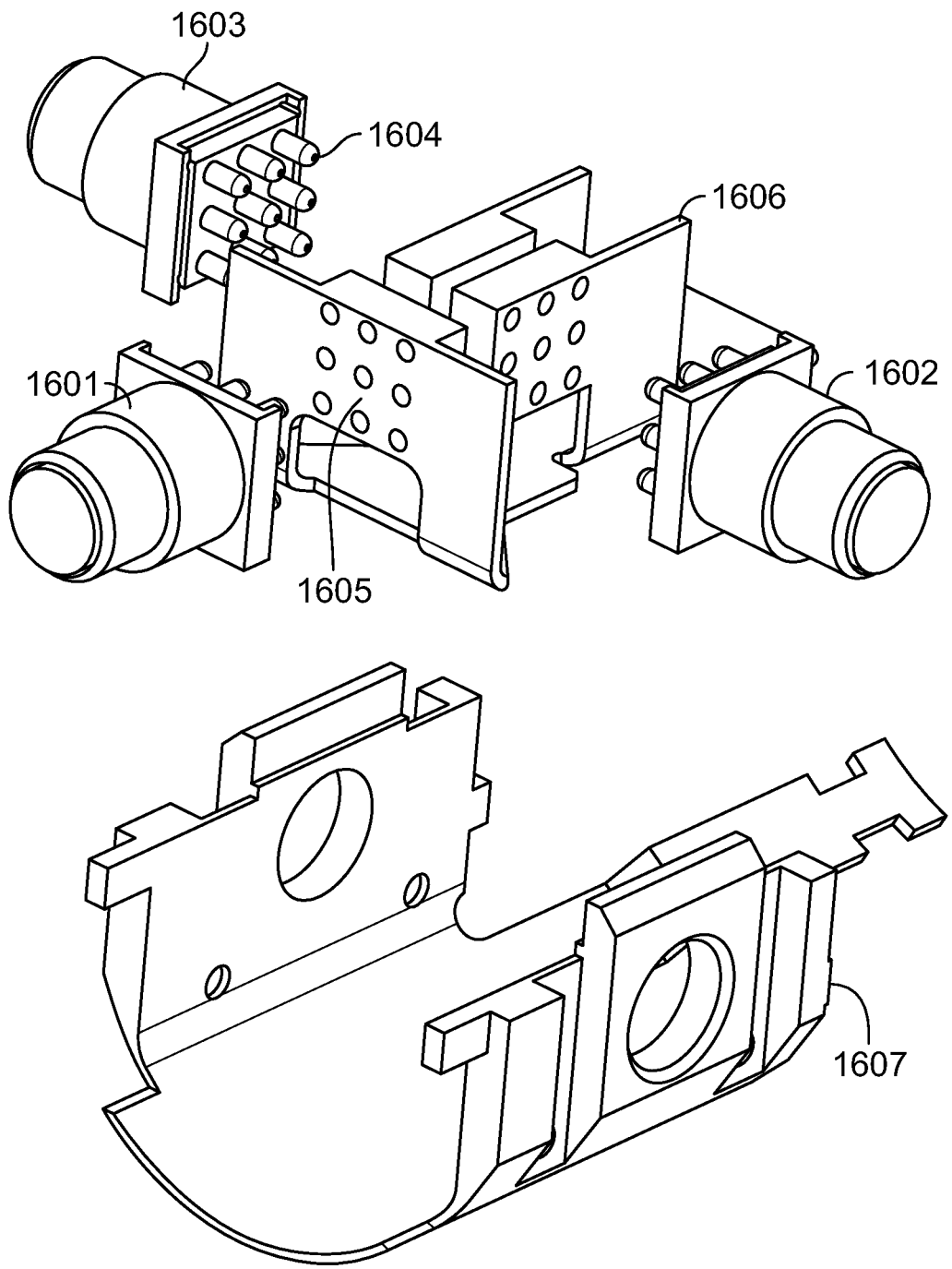
FIG. 52 illustrates a detailed view of the coupling mechanism and the modular holder, according to one embodiment.

FIG. 52 illustrates a detailed view of the coupling mechanism and the modular holder. Referring to FIG. 52, the lens holders 1601, 1602 and 1603 of each imaging unit are provided with protruding connectors 1604 that are designed to fit into corresponding recesses or slots 1605 in the modular holder 1606. Once connected using the connectors, the modular imaging units are held by the partially enclosed housing, curved member or supporter frame 1607. In one embodiment, the electric cable may be connected to modular holder 1606 in the far end relative to lens holder 1601.

FIGS. 53A and 53B provide perspective views of the connecting mechanism between the imaging modules. Referring to both the figures, the modular holder 1701 has slots or recesses 1702 on all three sides 1703, 1704, and 1705 where corresponding connectors 1706 of the three lens holders 1707, 1708 and 1709 can fit in.

A person of ordinary skill in the art would appreciate that the connector mechanism as shown in FIGS. 52 and 53A, 53B further simplifies the process of assembling or removing an individual imaging module from the endoscope tip.

It may be noted that in the embodiment shown in FIGS. 42 through 50, the components can be assembled by soldering the flexible printed circuit boards of imaging modules at the rear part of the tip and connecting them with the electrical cable. Another embodiment is shown in FIGS. 51 through 54, wherein connectors are provided to connect between the flexible PCBs of imaging modules.

In one embodiment (not shown), each imaging module is connected through a different cable to ease the replacement of each imaging module.

In one embodiment, the imaging modules are a part of removable tip. In this case, an endoscope comprises an elongated shaft terminating with a tip section, wherein said tip section comprises a permanent section connected to the elongated shaft and a removable section securely connectable to the permanent section. The removable section comprises imaging modules and at least one light source.

It should be appreciated that the main idea is to use the same space and volume for modular units, as used by the viewing elements in existing tip configurations. The modular design does not affect the design or functioning of other components in the tip, such as fluid channels or illuminators.

Reference is now made to FIG. 55A, which schematically depicts an isometric view of a tip section of an endoscope (including an electronic circuit board carrying cameras and illumination sources, and a fluid channeling component), having a multi component tip cover (shown in an exploded view), according to an exemplary embodiment of the current specification and to FIG. 55B, which schematically depicts an isometric view of the tip section of FIG. 55A, having an assembled multi-component tip cover, according to some exemplary embodiments of the current specification.

Tip section 5500 generally includes an inner part 5510 which includes electronics (such as cameras, a circuit board such as electronic circuit board 400, illumination sources, such as LEDs etc.), fluid channels (such as fluid channeling component 600) and a multi-element tip cover 300. Multi-element tip cover 300 is designed to fit over the inner parts of the tip section 5500, and to provide protection to the internal components in the inner part. Multi-element tip cover 300 includes, according to this embodiment, three parts: a front component 710 configured to cover a front part of the tip section; a right side component 730 configured to cover a right side part of the tip section; and a left side component 5550 configured to cover a left side part of the tip section, wherein the front, right side and left side components are configured to abut each other to cover the tip section, in such way that they cover essentially all inner parts of the tip section.

Front component 710 includes hole 736 configured to align with (and accommodate) front optical assembly 236 of forward looking camera 116; optical windows 242a, 242b and 242c of LEDs 240a, 240b and 240c; distal opening 340 of a working channel; distal opening 344 of a jet fluid channel 644; and irrigation and insufflation (I/I) injector 346 having a nozzle 348 (aligning with opening 664 of fluid channeling component 600).

Left side component 5550 includes hole 756b configured to align with (and accommodate) side optical assembly 256b of side looking cameras 220b; optical windows 252a and 252b of LEDs 250a and 250b on both sides of optical assembly 256b; side I/I injector 266b adapted to align with side I/I opening 666b of fluid component 600. Also seen in FIGS. 55A and 55B are nozzles 267b and a for side I/I injector 266b and a side I/I injector on the opposite side, respectively.

Right side component 730 includes similar elements as left side component 5550.

Left side component 5550 and right side component 730 are each in a shape of essentially half a cylinder (without top and bottom).

Front component 710 has essentially a cup shape having two opposing arms 712 and 714 extending perpendicularly to the cup bottom (which may also be referred to as the cup's front face) and protruding from the cup edges. Upon assembling of the tip cover components, front component 710 may be installed first, and then the side components such that their long edges meet each other on both sides over arms 712 and 714 to assure sealing (FIG. 55B). Adhesives, such as glue, may be added, for example, in cavities 716 (along the external parts of the edges of component 710), 718 (along the internal edges of component 730) and 5520 (along the internal edges of component 5550) to allow complete sealing of tip section 5500.

Multi-element tip covers according to embodiments of the specification, such as multi-element tip cover 300 or any other multi-element tip cover as disclosed herein, solve a significant problem that exists in the art when attempts are made to pack all necessary components into the small inner volume of an endoscope tip and to cover and seal these components. Regular cup shaped tip covers are used for standard tips having just one front camera. However, when standard cup shaped tip covers are used to cover the multi-camera tip, protruding inner tip elements, such as lenses or other parts of the side optical assemblies, are often damaged during the sliding of the cover over them. Using a multi-element tip cover may solve this problem. In addition, a multi-element tip cover assists in aiming its holes/openings/windows exactly at their right place over the corresponding tip inner elements. This is almost impossible using a unitary piece cover. Moreover, separately sealing each one of the elements of the multi-element tip cover improves the overall sealing of the tip due to better access to each element (for example an optical window) compared to the limited access of the same element in a unitary piece cover, such as a cup shaped cover. Separately sealing (and optionally checking for satisfactory sealing) of each one of the elements of the multi-element tip cover may be performed prior to assembling of the cover. This may also improve the sealing of the tip.

Tip section 5500 may include front optical assembly 236 of forward looking camera 116. Optical axis of forward looking camera 116 is substantially directed along the long dimension of the endoscope. However, since forward looking camera 116 is typically a wide angle camera, its FOV may include viewing directions at large angles to its optical axis. It should be noted that number of illumination sources such as LEDs used for illumination of the FOV may vary (for example, 1-5 LEDs may be used on a front face of tip section 5500). Distal opening 340 of a working channel is also located on the front face of tip section 5500, such that a surgical tool inserted through working channel tube, and through the working channel in the endoscope's tip section 5500 and deployed beyond the front face may be viewed by forward looking camera 116.

Distal opening 344 of a jet fluid channel is also located on the front face of tip section 5500. Distal opening 344 of a jet fluid channel may be used for providing a high pressure jet of fluid, such as water or saline, for cleaning the walls of the body cavity.

Also located on the front face of tip section 5500 is an irrigation and insufflation (I/I) injector 346 having a nozzle 348 aimed at front optical assembly 236. I/I injector 346 may be used for injecting fluid (liquid and/or gas) to wash contaminants such as blood, feces and other debris from front optical assembly 236 of forward looking camera. Optionally, the same injector is used for cleaning front optical assembly 236 and one, two or all of optical windows 242a, 242b and 242c. I/I injector 346 may be fed by fluid such as water and/or gas which may be used for cleaning and/or inflating a body cavity.

Visible on a left side of tip section 5500 is the side camera (side looking camera) element 256b of side looking camera 220b and optical windows 252a and 252b of LEDs 250a and 250b for camera 220b. A second side looking camera is positioned on the right side of the tip section 5500 and can be similar to camera 220b. Optical axis of the right side looking camera is substantially directed perpendicular to the long dimension of the endoscope. Optical axis of left side looking camera 220b is substantially directed perpendicular to the long dimension of the endoscope. However, since the right side looking camera and left side looking camera 220b re typically wide angle cameras, their fields of view may include viewing directions at large angles to their optical axes.

Side I/I injector 266b having a nozzle 267b aimed at side optical assembly 256b may be used for injecting fluid to wash contaminants such as blood, feces and other debris from side optical assembly 256b of side looking camera. The fluid may include gas which may be used for inflating a body cavity. Optionally, the same injector is used for cleaning both side optical assembly 256b and optical windows 252a and/or 252b. It is noted that according to some embodiments, the tip may include more than one window and LEDs, on the side and more than one window and LEDs in the front (for example, 1-5 windows and two LEDs on the side). Similar configurations of I/I injector and nozzle exists for cleaning right side optical assembly and optical windows located on the other side of tip 5500. The I/I injectors are configured to clean all or a part of these windows/LEDs. I/I injectors 346 and 266b may be fed from same channel.

It is noted that the side wall 362 has a form of an essentially flat surface which assists in directing the cleaning fluid injected from left side Ill injector 266b towards side optical assembly 256b and optical windows 252a and/or 252b. A right side wall on the other side of the cover is also essentially flat. Lack of such a flat surface may result in dripping of the cleaning fluid along the curved surface of tip section 5500 of the endoscope without performing the desired cleaning action.

It should be noted that while only one side looking camera is seen in FIGS. 55A and 55B, preferably at least two side looking cameras may be located within tip section 5500. When two side looking cameras are used, the side looking cameras are preferably installed such that their field of views are substantially opposing. However, different configurations and numbers of side looking cameras are possible within the general scope of the current specification.

According to some embodiments, the circuit board used for carrying electronic components such as cameras and/or LEDs may be a flexible circuit board that may consume less space and leaves more volume for additional necessary features. The flexibility of the board adds another dimension in space that can be used for components positioning.

The use of a flexible circuit board according to embodiments of the specification can significantly increase reliability of the electric modules connection thereto as no wires are for components connectivity. In addition, according to some embodiments, the components assembly can be machined and automatic.

The use of a flexible circuit board according to embodiments of the specification, may also allow components (parts) movement and maneuverability during assembly of the camera head (tip of the endoscope) while maintaining a high level of reliability. The use of the circuit board according to embodiments of the specification may also simplify the (tip) assembling process.

According to some embodiments, a flexible circuit board may be connected to the main control unit via a multi-wire cable. This cable may be welded on the board in a designated location freeing additional space within the tip assembly and adding flexibility to cable access. Assembling the multi-wire cable directly to the electrical components was a major challenge which is mitigated by the use of the flexible board according to embodiments of the specification.

Reference is now made to FIG. 56, which schematically depicts an isometric view of a tip section of an endoscope (including an electronic circuit board carrying cameras and illumination sources, and a fluid channeling component), having a multi component tip cover (shown in an exploded view), according to an exemplary embodiment of the current specification. Tip section 200 generally includes an inner part 5610 which may be similar to inner part 5510 of tip section 5500 of FIGS. 55A, 55B and a multi-element tip cover 300. Multi-element tip cover 300 is designed to fit over the inner parts of the tip section 200, and to provide protection to the internal components in the inner part. Multi-element tip cover 300 includes, according to this embodiment, a main component 830, configured to cover the majority of the tip section, and a removable window component 850 configured to cover a window opening 860 located on main component 830, such that removable window component 850 is configured to allow access to an inner part 5610 of tip section 200 without removing main component 830. This may allow fixing or replacing one of the components of inner part 5610 (such as a LED, an optical element or any other element) without removing main component 830 and damaging the packing and sealing of tip section 200.

Main component 830 has essentially a cup shape having a front face part configured to cover the front face of tip section 200 and cup edges configured to cover the side surface of tip section 200.

Main component 830 may further include front and side holes, openings, windows and surfaces similar to those of multi-component cover 300 of FIGS. 55A, 55B.

Reference is now made to FIG. 57, which schematically depicts an exploded view of a multi-component tip cover, according to an exemplary embodiment of the current specification. Multi-element tip cover 5700 is designed to fit over the inner part of a tip section and to provide protection to the internal components in the inner part. Multi-element tip cover 5700 includes, according to this embodiment, a front-side component 5730 configured to cover a front part and a side part of the tip section and a side component 5750 configured to cover another side part of the tip section, wherein front-side component 5730 and side component 5750 are configured to abut to cover the tip section.

Reference is now made to FIGS. 58A through 58C. FIG. 58A schematically depicts an isometric view of a tip section of an endoscope (including an electronic circuit board carrying cameras and illumination sources, an electronic circuit board holder, a fluid channeling component), having a multi-component tip cover (shown in an exploded view), according to an exemplary embodiment of the current specification. FIG. 58B schematically depicts an isometric view of the tip section of FIG. 58A, having a multi-component tip cover (partially in an exploded view), according to an exemplary embodiment of the current specification. FIG. 58C schematically depicts an assembled isometric view of the tip section of FIGS. 58A and 58B having a multi-component tip cover, according to an exemplary embodiment of the current specification.

Tip section 5800 generally includes an inner part 5810 which includes electronics (such as cameras, circuit board, LEDs etc.), fluid channels (such as fluid channeling component 1600) and a multi-element tip cover 1010. Multi-element tip cover 1010 is designed to fit over the inner parts of the tip section 5800, and to provide protection to the internal components in the inner part. Multi-element tip cover 1010 includes, according to this embodiment, two parts: a distal component 1050 configured to cover a distal part of the tip section and a proximal component 1030 configured to cover a proximal part of the tip section, wherein the distal component and the proximal component are configured to abut to cover the tip section. Distal component 1050 has a shape of a cylinder having a side wall 1052 and a front face 1054, wherein front face 1054 is configured to cover a front part 5802 of inner part 5810 of tip section 5800 and proximal component 1030 has a shape of a cylinder having a side wall 1032 without a top or a bottom, configured to cover a proximal part 1104 of inner part 5810 of tip section 5800.

Distal component 1050 includes on front face 1054 thereof hole 1056 configured to align with front optical assembly 1236 of forward looking camera 1116; optical windows 1242a, 1242b and 1242c of LEDs 1240a, 1240b and 1240c; distal opening 1340 of a working channel; distal opening 1344 of a jet fluid channel 1644; and I/I injector 1346 (aligning with opening 1664 of fluid channeling component 1600).

Distal component 1050 further includes on side wall 1052 thereof optical windows 1252a of LED 1250a and on an opposing side of side wall 1052 another optical window of another LED.

Distal component 1050 further includes on the edge of side wall 1052 thereof a recess 1756' (essentially in a shape of half a hole) configured to accommodate (along with a recess 1756" on the edge of side wall 1032 of proximal component 1030) optical assembly 1256b of side looking camera 1220b. On an opposing side of side wall 1052 there may be a similar recess to accommodate (along with another recess on the edge of side wall 1032 of proximal component 1030) an optical assembly of a side looking camera located on the other side of inner part 5810.

Proximal component 1030 includes on side wall 1032 thereof optical windows 1252b of LED 1250b and on an opposing side of side wall 1032 another optical window 1252a of another LED.

Proximal component 1030 further includes on the edge of side wall 1032 thereof a recess 1756" (essentially in a shape of half a hole) configured to accommodate (along with recess 1756' on the edge of side wall 1052 of distal component 1050) optical assembly 1256b of side looking cameras 220b. On an opposing side of side wall 1032 there is a similar recess 1756a" to accommodate (along with another recess on the edge of side wall 1032 of proximal component 1050) an optical assembly of a side looking camera located on the other side of inner part 5810.

Proximal component 1030 further includes side I/I injector 1266b adapted to align with side I/I opening 1666b.

Other parts of inner part 5810 of tip section 5800 may generally be similar to inner part 5810 of tip section 100 of FIGS. 55A, 55B.

The method of assembling tip section 5800 over inner part 5810 may include assembling distal component 1050 from the distal part of tip section 5800, assembling proximal component 1030 from the proximal part of tip section 5800 and joining distal component 1050 and proximal component 1030 along their edges (line 1500) such that none of the tip cover components slides over the optical assemblies of the side looking cameras.

Reference is now made to FIG. 2A along with FIGS. 59A and 59B which show a perspective view of a tip section 200 of an endoscope assembly 100 according to an embodiment.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a front optical assembly 256, of front looking camera 116. Front optical assembly 256 may include a plurality of lenses, static or movable, which may provide a field of view of 90 degrees or more, 120 degrees or more or up to essentially 180 degrees. Front optical assembly 256 may provide a focal length in the range of about 3 to 100 millimeters.

Optical axis of front looking camera 116 may be essentially directed along the long dimension of the endoscope. However, since front looking camera 116 is typically a wide angle camera, its field of view may include viewing directions at large angles to its optical axis. Additionally, front panel 320 may include optical windows 242a, 242b and 242c of illuminators 240a, 240b and 240c, respectively. It should be noted that number of illumination sources used for illumination of the field of view may vary.

In addition, front panel 320 may include a working channel opening 340 of a working channel 640, which is further discussed below. In alternate embodiments, the front panel may include more than one working channel opening.

Jet channel opening 344 of jet channel 644 may also be located on front panel 320 of tip cover 300. Jet channel 644 may be configured for providing a high-pressure jet of fluid, such as water or saline, for cleaning the walls of the body cavity.

Also located on front panel 320 of tip cover 300 is injector opening 346 of injector channel 646 having a nozzle 348 aimed at front optical assembly 256. Injector channel 646 may be configured for injecting fluid (liquid and/or gas) to wash contaminants such as blood, feces and other debris from front optical assembly 256 of front looking camera 116. Optionally, injector channel 646 may be configured for cleaning front optical assembly 256 and one, two or all of optical windows 242a, 242b and 242c. Injector channel 646 may be fed by fluid, such as water and/or gas, which may be used for cleaning and/or inflating a body cavity.

Visible on the sidewall 362 of tip cover 300 is side optical assembly 256b for side looking camera 116b, which may be similar to front optical assembly 256 and optical windows 252a and 252b of illuminators 250a and 250b for side looking camera 116b. Also on the sidewall 362 of tip cover 300, on the opposing side to side optical assembly 256b, is an optical assembly for another side looking camera, which may be similar to side optical assembly 256b and optical windows 252a and 252b of illuminators 250a and 250b for side looking camera 116b. The side optical assembly 256b may provide a focal length in the range of about 3 to 100 millimeters.

Optical axis of side looking camera 116b may be essentially directed perpendicular to the long dimension of the endoscope. Optical axis of side looking camera 116b is essentially directed perpendicular to the long dimension of the endoscope. However, since side looking camera 116b is typically a wide angle camera, its field of view may include viewing directions at large angles to its optical axis. In accordance with some embodiments, the side looking camera 116b has a field of view of 90 degrees or more, 120 degrees or more or up to essentially 180 degrees.

In various embodiments, a maximum volume of an endoscopic tip comprising the optical assemblies, such as assemblies 256, 256b, is less than 3.12 cm$^3$. In accordance with one embodiment, the optical assemblies of the present specification do not include any aspherical components, as such components that would lead to an increase in manufacturing cost of the optic assemblies. Also, in various embodiments, each of the optical assemblies has a focal length of approximately 1.2 mm.

In an embodiment, the maximum volume of an endoscopic tip containing an optical assembly within is 3.12 cm$^3$, which may be obtained by using the equation: h*pi*r2; where h and r represent a length and a radius of the endoscope tip respectively. In an embodiment where h is less than 2 cm and the diameter of the endoscope is less than 1.41 cm, the volume of the endoscope tip may be obtained as:

$$2 \text{ cm}*(1.41 \text{ cm}/2)2*\text{pi} = \text{less than } 3.12 \text{ cm}^3$$

In accordance with one embodiment, the maximum volume of an endoscopic tip ranges from 2.75 cm$^3$ to 3.5 cm$^3$.

Also visible is the side service channel opening 350 of side service channel 650.

In addition, side injector opening 266 of side injector channel 666 may be located at distal end of sidewall 362. A nozzle cover 267 may be configured to fit side injector opening 266. Additionally, nozzle cover 267 may include a nozzle 268 which may be aimed at side optical assembly 256b and configured for injecting fluid to wash contaminants such as blood, feces and other debris from side optical assembly 256b of side looking camera 116b. The fluid may include gas which may be used for inflating a body cavity. Optionally, nozzle 268 may be configured for cleaning both side optical assembly 256b and optical windows 252a and/or 252b.

According to some embodiments, side injector channel 666 may be configured to supply fluids for cleaning any of the tip elements (such as any optical assembly, windows, illuminators, and other elements).

Optionally, injector channel 646 and side injector channel 666 may be fed from the same channel.

It is noted that according to some embodiments, although tip section 200 is presented herein showing one side thereof, the opposing side may include elements similar to the side elements described herein (for example, side looking camera, side optical assembly, injector(s), nozzle(s), illuminator(s), window(s), opening(s) and other elements).

In an embodiment, each viewing element provides a field of view (FOV) of 120 degrees or more, and the depth of field ranges from 3 to 100 mm. In an embodiment, a peripheral distortion caused in the optical assemblies of the endoscope is about 80% without reliance on any aspherical components, while the maximum focal length is approximately 1.2 mm or in a range of 1 to 1.4 mm.

Sidewall 362 may have a form of an essentially flat surface which assists in directing the cleaning fluid injected from injector channel 666 towards side optical assembly 256b and optical windows 252a and/or 252b. Lack of such a flat surface may result in dripping of the cleaning fluid along the curved surface of tip section 200 of the endoscope without performing the desired cleaning action.

In accordance with an embodiment, the sidewall 362 is located in a notch/depression in the tip cover 300. This way, side injector opening 266 and corresponding side nozzle 268 may be elevated from the depressed sidewall 362 but still not significantly protrude from the level of cylindrical surface of the tip cover 300. According to an aspect of one embodiment, as shown in FIG. 59C, the sidewall 362 is located in a sufficiently well-defined or deep notch/depression 5963 in the tip cover 300 such that the lens assembly of side optical assembly 256b stays sufficiently embedded in the notch/depression 363 and well below the level 5900 of the cylindrical surface of the tip cover 300. The notch/depression 5963 protects the sidewall 362 and components thereof (side optical assembly 256b, side illuminators 250a, 250b and side nozzle 268) from both longitudinal and latitudinal mechanical shocks.

It is noted that according to some embodiments, tip section 200 may include more than one side looking camera. In this case, the side looking cameras may be installed such that their fields of view are substantially opposing. However, different configurations and number of side looking cameras are possible within the general scope of the current specification.

Reference is now made to FIG. 2A along with FIGS. 60A, 60B, which show a perspective view of a tip section 200 of an endoscope assembly 100 with a medical tool inserted through a side service channel thereof, according to some embodiments.

FIG. 60A shows tip section 200 of endoscope assembly 100, having side service channel 650a through which medical tool 360a is threaded and exits from side service channel opening 350a at essentially a right (90 degree) angle.

FIG. 60B shows tip section 200 of endoscope assembly 100, having side service channel 650b through which medical tool 360b is threaded and exits from side service channel opening 350b at an obtuse angle.

FIG. 61A shows tip section 200 of an endoscope assembly comprising two independent side service channel openings, a first side service channel opening 805a and a second side service channel opening (not visible, as this is on the opposite side of the tip)—one on each side of the tip, in accordance with an embodiment of the present specification. The fluid channeling component comprising the side service channel openings has been described earlier with reference to FIGS. 5A and 5B.

Referring now to FIGS. 2A and 61A simultaneously, tip cover 300 includes a front panel 320 having a front optical assembly 256, of front looking camera 116, along with optical windows 242a, 242b and 242c of illuminators 240a, 240b and 240c, respectively. In one embodiment, the optical axis of the front looking camera 116 is essentially directed along the central longitudinal axis 6103 that runs through the long dimension of the tip of the endoscope. The front panel 320 includes a working channel opening 340 of a working channel 640 and jet channel opening 344 of jet channel 644. Jet channel 644 is configured for providing a high-pressure jet of fluid, such as water or saline, for cleaning the walls of the body cavity. Also located on front panel 320 of tip cover 300 is injector opening 346 of injector channel 646 having a nozzle 348 aimed at front optical assembly 256. Injector channel 646 is configured for injecting fluid (liquid and/or gas) to wash contaminants such as blood, feces and other debris from front optical assembly 256 of front looking camera 116. Optionally, injector channel 646 may be configured for cleaning front optical assembly 256 and one, two or all of optical windows 242a, 242b and 242c. Injector channel 646 is fed by fluid such as water and/or gas which may be used for cleaning and/or inflating a body cavity.

It should be noted that the side service channel opening 805a and the opening on the opposite side of the tip (not visible) are advantageously positioned close to the side injector openings 266 on the opposing sidewalls 362 (at both sides of the tip) and towards the proximal end 6101 of the tip. The sidewall 362 of tip cover 300 comprises side optical assembly 256a for a side looking camera, which may be similar to front optical assembly 256, and optical windows 252a and 252b of illuminators for the side looking camera. Similarly, the sidewall 362 of tip cover 300 on the opposing side to side optical assembly 256a is an optical assembly 256b for side looking camera 116b, which may be similar to side optical assembly 256a, and optical windows 252a and 252b of corresponding illuminators for side looking camera 116b. In one embodiment, the optical axis of one or both of the side looking cameras is essentially perpendicular to the optical axis (which is along the central longitudinal axis 6103 of the endoscope) of the front looking camera 116. In one embodiment, the optical axis of one or both of the side looking cameras forms an obtuse angle with the optical axis of the front camera 116 while in an alternate embodiment the optical axis of one or both of the side cameras forms an acute angle with the optical axis of the front camera 116.

Referring now to FIGS. 2A, 5A, 5B along with FIG. 61A, according to an aspect of the present specification, the position of the side service channel openings close to the side injector openings and towards the proximal end of the tip enables an increased effective functional length of the tip section. In one embodiment, the position of the side service channel openings 805a, 805b relative to the depth of field of 5 millimeters of the side looking cameras allows for a more acute angle of exit 820 of the distal sections 813 of the side service channels with reference to the long dimension of the tip. Acuter angles 820 are desirable so that medical tools inserted through the side service channel openings protrude closer to the sidewalls of the endoscope thereby lowering the possibilities of hurting a body cavity/wall while coming out of the tip while at the same time facilitating smooth passage within the side service channels. In one embodiment, the angle of exit 820 of the side service channels ranges from 5 degrees to 90 degrees and any increment therein, but preferably 45 degrees. Also, the positions of the side service channels allow the side looking cameras to clearly notice the medical tools as the tools protrude from the side service channel openings.

With reference to FIGS. 2A and 61A, in one embodiment, the side optical assembly 256a for the side looking camera is positioned on the circumference of the endoscope at a distance of 8 to 10 millimeters, and preferably at 9 or 9.1 millimeters, from the surface 320 (front panel) of the tip.

In accordance with one embodiment, relative to the side optical assembly 256a, the optical windows 252a and 252b (of the corresponding illuminators) are positioned in close proximity to the optical assembly 256a along a lateral plane that contains the side optical assembly 256a and the optical windows 252a, 252b but does not contain the front optical assembly 256.

In one embodiment, relative to the side optical assembly 256a, the side injector opening 266 is positioned 5.8 to 7.5 millimeters, and preferably 6.7 millimeters, from the optical assembly 256a along the lateral plane that contains the side optical assembly 256a and the optical windows 252a, 252b but does not contain the front optical assembly 256.

In accordance with one embodiment, relative to the side optical assembly 256a, the side service channel opening 805a is positioned 9.5 to 10.5 millimeters, and preferably 10.2 millimeters, from the side optical assembly 256a. The side service channel 812 (as shown in FIG. 5B) has a diameter of about 2.8 to 3.2 millimeters, in one embodiment.

FIG. 61B shows the tip section 200 of the endoscope assembly of FIG. 61A, having side service channel 810a through which medical tool 6120a is threaded and exits from side service channel opening 805a at an acute angle.

FIG. 61C shows the tip section 200 of endoscope assembly of FIG. 61A, having side service channel 810b through which medical tool 6120b is threaded and exits from side service channel opening 805b at essentially a right angle (90 degrees).

Reference is now made to FIG. 2B along with FIG. 62 which together show exploded views of a tip section 200 of an endoscope assembly 100 according to an embodiment having the tip section 200 equipped with two or more front working channels.

Tip section 200 may be turnable by way of flexible shaft which may also be referred to as a bending section, for example a vertebra mechanism.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a front optical assembly 256 of front-pointing camera 116a. Front optical assembly 256 may include a plurality of lenses, static or movable, which may provide a field of view of up to essentially 180 degrees. Front optical assembly 256 may provide a focal length of up to about 100 millimeters.

Optical axis of front-pointing camera 116a may be essentially directed along the long dimension of the endoscope. However, since front-pointing camera 116a is typically a wide angle camera, its field of view may include viewing directions at large angles to its optical axis. Additionally, front panel 320 may include optical windows 242a and 242b of illuminators 240a and 240b, respectively. It should be noted that number of illumination sources used for illumination of the field of view may vary.

In addition, front panel 320 may include a working channel opening 340a of a working channel 640a, and a second working channel opening 340b of a second working channel 640b which are further discussed below.

Jet channel opening 344 of jet channel 644 may also be located on front panel 320 of tip cover 300. Jet channel 644 may be configured for providing a high-pressure jet of fluid, such as water or saline, for cleaning the walls of the body cavity.

Also located on front panel 320 of tip cover 300 is injector opening 346 of injector channel 646 having a nozzle 348 aimed at front optical assembly 256.

Injector channel 646 may be fed by a fluid or fluid blend, such as water and/or gas, and configured for injecting a fluid blend (liquid and/or gas) to wash contaminants such as blood, feces and other debris from front optical assembly 256 of front-pointing camera 116a. In addition, the fluid blend may include gas, which may be used for inflating a body cavity.

Optionally, injector channel 646 may be configured for cleaning front optical assembly 256 and one or both of optical windows 242a and 242b.

A sidewall 362a of tip cover 300 may include an optical assembly 256b for side-pointing camera 116b, which may be similar to front optical assembly 256, and optical windows 252a and 252b of illuminators 250a and 250b for side-pointing camera 116b.

A sidewall 362b of tip cover 300, which may be similar to sidewall 362a and located on the opposite side of tip cover 300, may include an optical assembly 256a for side-pointing camera 116c, which may be similar to front optical assembly 256, and optical windows 262a and 262b of illuminators 260a and 260b for side-pointing camera 116c.

Optical axis of side-pointing cameras 116b and 116c may be essentially directed perpendicular to the long dimension of the endoscope. However, since side-pointing cameras 116b and 116c are typically wide angle cameras, their fields of view may include viewing directions at large angles to their optical axes.

According to some embodiments, side injector channels 666a and 666b may be configured to supply fluids for cleaning any of the tip elements (such as any optical assembly, windows, illuminators, and other elements). Side injectors opening 266a and 266b of side injector channels 666a and 666b may be located at distal end of sidewalls 362a and 362b respectively. Nozzle covers 267a and 267b may be configured to fit side injectors opening 266a and 266b.

Additionally, nozzle covers 267a and 267b may include nozzles 268a and 268b which may be aimed at side optical assembly 256b and 256a and configured for injecting a fluid or fluid blend to wash contaminants such as blood, feces and other debris from side optical assemblies 256b and 256a of side-pointing cameras 116b and 116c. Optionally, nozzles 268a and 268b may be configured for cleaning side optical assemblies 256b and 256a and optical windows 252a, 252b, 262b and/or 262b.

Optionally, injector channel 646 and side injector channels 666a and 666b may be fed from the same channel.

It is noted that according to some embodiments, the endoscope tip may include more than one optical window and illuminator on the side and more than one optical window and illuminator on the front.

Sidewalls 362a and 362b may have a form of an essentially flat surface, which assists in directing the cleaning fluid injected from injector channels 666a and 666b towards side optical assemblies 256b and 256a and optical windows 252a, 252b, 262a and/or 262b. Lack of such a flat surface may result in dripping of the cleaning fluid along the curved surface of tip section 200 of the endoscope without performing the desired cleaning action.

Reference is now made to FIG. 63 which shows a perspective view of a tip section 200 of an endoscope assembly comprising two front working/service channels in close proximity, according to some embodiments. Tip cover 300 may be configured to fit over the inner parts of the tip section 200 including the fluid channeling component, such as the fluid channeling component 645 of FIG. 7, and to provide protection to the internal components in the inner parts.

Tip cover 300 may include a front panel 320 having a front optical assembly 256 of a front looking viewing element. Front optical assembly 256 may include a plurality of lenses, static or movable, which may provide a field of view of up to essentially 180 degrees. Front optical assembly 256 may provide a focal length of up to about 110 millimeters.

Additionally, front panel 320 may include optical windows 242a, 242b and 242c of three separate illuminators. It should be noted that number of illumination sources used for illumination of the field of view may vary.

In an embodiment, the optical windows 242a, 242b and 242c are oval shaped. The oval shape allows the inclusion of a second front service channel 340b on the front panel 320. The oval shape of the optical windows is designed to overcome the problem of crowdedness due to the number of components in the front panel 320 (i.e. two working/service channels 340a, 340b, camera, three illuminators (LEDs), injector and a jet) and also allows the size of the two working/service channels 340a, 340b to be kept at a maximum. In an embodiment, when two working/service channels 340a, 340b of diameters 3.8 mm and 2.8 mm respectively, are included in the front panel 320, the placement of the circuit board assembly as far as possible from the fluid channeling component causes one of the LEDs to be placed almost on the circumference of the front panel 320. Oval shaped optical window 242b covers the LED suitably. If a round shaped optical window is used instead, it would lead to a reduction in the diameters of the front working/service channels 340a, 340b.

The working/service channel 340a may be configured for insertion of a medical (such as a surgical) tool, for example, to remove, treat and/or extract a sample or the entirety of an object of interest found in the colon for biopsy. Once an object of interest has been detected, the endoscope operator may desire to insert one or more medical tools and remove, treat and/or extract a sample or the entirety of the polyp for biopsy. Therefore, it may be beneficial for the endoscope's operator to be able to use more than one medical tool.

In an embodiment, as illustrated, front panel 320 also comprises the secondary working/service channel 340b which may be similar to working/service channel 340a and may be configured for insertion of a medical tool, for example but not necessarily, in addition to the medical tool which may be inserted through working/service channel 340a. The operator may also choose from which working/service channel he or she would like to insert the medical tool, for example, according to the position of the polyp.

The second working/service channel 340b may be configured to improve the performance of the endoscope (such as, but not limited to, gastroscopes and colonoscopes). Current gastroscopes and colonoscopes typically have one service channel which opens at the front distal section of the scope. Such a front service channel is adapted for insertion of a surgical tool. The physician is required to perform all necessary medical procedures, such as biopsy, polyp removal and other procedures, via this one channel. In an embodiment, either one or both of the working/service channels 340a and 340b may be adapted for performing suction during a procedure. In an embodiment, no structural changes are required to be made to the working/service channels 340a and 340b for adapting the same for performing suction.

In an embodiment, the distance between the first and second working/service channels 340a and 340b is approximately in the range of 0.40 mm to 0.45 mm. In one embodiment, the diameter of the first working/service channel 340a is in a range of 3.6 mm to 4.0 mm and the diameter of the second working/service channel 340b is in a range of 2.6 mm to 3.0 mm. In an embodiment, the diameter of the first working/service channel 340a is 3.8 mm while the diameter of the second working/service channel 340b is 2.8 mm. In other embodiments, the diameters of the two working/service channels may be of different dimensions. In an embodiment, the diameters of the two working/service channels are the same. First and second channels may be the same or different in shape and size. The diameter of a working/service channel is limited by the outer diameter of the endoscope tip. In one embodiment, the outer diameter of the endoscope tip is in a range of 7 mm to 12 mm. In one embodiment, the outer diameter of the endoscope tip is 11.9 mm.

A working/second service channel, such as the second working/service channel 340b, allows greater flexibility to the endoscope operator by providing a channel for the insertion of medical tools in addition to, or instead of, the medical tools which may be inserted through working/service channel 340a.

The front panel 320 may further comprise a jet fluid channel 344 which may be configured for providing a high pressure jet of fluid, such as, water or saline, for cleaning the walls of the body cavity (such as the colon) and optionally for suction. The front panel 320 may further comprise an injector channel pathway 346, which may be used for blending two fluids (like air and water) and convey the fluid blend into injector channel 346 which may be configured to inject the fluid blend and wash contaminants such as blood, feces and other debris from front optical assembly 256 of the front-pointing camera.

Visible on the sidewall 362 of tip cover 300 is side optical assembly 256b for a side looking viewing element, which may be similar to front optical assembly 256, and optical windows 252a and 252b of the side illuminators for the side looking viewing element. In an embodiment, the optical windows 252a and 252b are oval in shape. In another embodiment, the optical windows 252a and 252b may be round in shape.

In addition, side injector opening 266 of a side injector channel is located at the proximal end of sidewall 362. It is noted that according to some embodiments, although tip section 200 is presented herein showing one side thereof, the opposing side may include elements similar to the side elements described herein (for example, side looking viewing element, side optical assembly, injector(s), nozzle(s), illuminator(s), window(s), opening(s) and other elements). Sidewall 362 may have a form of an essentially flat surface which assists in directing the cleaning fluid injected from a side injector channel toward side optical assembly 256b and optical windows 252a and/or 252b. Lack of such a flat surface may result in dripping of the cleaning fluid along the curved surface of tip section 200 of the endoscope without performing the desired cleaning action.

It is noted that according to some embodiments, tip section 200 may include more than one side looking viewing element. In this case, the side looking viewing elements may be installed such that their field of views are substantially opposing. However, different configurations and numbers of side looking viewing elements are possible within the general scope of the current specification.

FIG. 64 illustrates a tip of an endoscope, in accordance with an embodiment wherein the jet opening 6426 and nozzle opening 6424 may be positioned adjacent to each other on the front panel 6412. In another embodiment, the jet opening 6426 and nozzle opening 6424 may be positioned on either side of the working/service channel opening 6422 on the front panel 6412. A tip cover sheaths the endoscope tip and the components therein. A diameter of the endoscope tip 6400 ranges from approximately 10 to 15 millimeters. In an embodiment, the diameter is approximately 11.7 millimeters. A side panel 6402 is positioned on a side of the endoscope tip 6400. The side panel 6402 comprises a side optical assembly 6404, optical windows 6406, 6408, and a side nozzle 6410. The side optical assembly 6404 is positioned on the circumference of the endoscope tip at a distance ranging from approximately 6 to 9 millimeters from the surface of the tip 6400, and in an embodiment is positioned at approximately 7.8 or 7.9 millimeters, from the surface of the tip 6400.

A front panel 6412 is positioned on a front end of the endoscope tip 6400. The front panel 6412 comprises a front optical assembly 6414, optical windows 6416, 6418, 6420, a working/service channel opening 6422, a nozzle opening 6424 and a jet opening 6426. The diameter of the front working/service channel ranges from approximately 2.8 to 4.8 millimeters. In one embodiment, the diameter of the front working/service channel ranges from 3.2 mm to 4.8 mm. In another embodiment, the diameter ranges from approximately 4.2 to 4.8 millimeters. In one embodiment, the diameter of the front working/service channel is 3.2 mm. In another embodiment, the diameter of the front working/ service channel is 3.8 mm. In yet another embodiment, the diameter of the front working/service channel is 3.8 mm. In still yet another embodiment, the diameter of the front service channel is 4.8 mm.

Along with FIG. 2A, reference is now made to FIGS. 65A through 65D which show a perspective view of a tip section 200 of a multi jet endoscope assembly 6501 comprising a plurality of side jets, in addition to a front jet, to enable improved flushing according to an embodiment of the present specification.

Tip cover 300 fits over the inner parts of the tip section 200 including electronic circuit board assembly 400 (shown in FIG. 2A) and fluid channeling component 600 (of FIG. 65D) and to provide protection to the internal components in the inner parts. Pins 670 for tip cover 300 are provided on fluid channeling component 600, as shown in FIG. 65D. Further, FIG. 65D shows a groove 6572 for an electrical cable. Tip cover 300 includes a front panel 320 having a front optical assembly 256, of front looking camera 116, along with optical windows 242a, 242b and 242c of illuminators 240a, 240b and 240c, respectively.

The front panel 320 includes a working channel opening 340 of a working channel 640 and jet channel opening 344 of jet channel 644. Jet channel 644 is configured for providing a high-pressure jet of fluid, such as water or saline, for cleaning the walls of the body cavity. Also located on front panel 320 of tip cover 300 is injector opening 346 of injector channel 646 having a nozzle 348 aimed at front optical assembly 256. Injector channel 646 is configured for injecting fluid (liquid and/or gas) to wash contaminants such as blood, feces and other debris from front optical assembly 256 of front looking camera 116. Optionally, injector channel 646 may be configured for cleaning front optical assembly 256 and one two or all of optical windows 242a, 242b and 242c. Injector channel 646 is fed by fluid such as water and/or gas which may be used for cleaning and/or inflating a body cavity. In one embodiment, the optical axis of the front looking camera 116 is essentially directed along the central longitudinal axis 6503 that runs through the long dimension of the tip of the endoscope 6501.

FIG. 65B shows sidewall 362 of tip cover 300 comprising side optical assembly 256a for a side looking camera, which may be similar to front optical assembly 256, and optical windows 252a and 252b of illuminators for the side looking camera. Also, as shown in FIG. 65C, the sidewall 362 of tip cover 300 on the opposing side to side optical assembly 256a is an optical assembly 256b for side looking camera 116b, and optical windows 252a and 252b of corresponding illuminators for side looking camera 116b. In one embodiment, the optical axis of one or both of the side looking cameras are essentially perpendicular to the optical axis (which is along the central longitudinal axis 6503 of the endoscope) of the front looking camera 116. In one embodiment, the optical axis of one or both of the side looking cameras forms an obtuse angle with the optical axis of the front camera 116 while in an alternate embodiment, the optical axis of one or both of the side cameras forms an acute angle with the optical axis of the front camera 116.

In addition, side injector openings 266 of corresponding side injector channels 666 are located at respective distal ends of the opposing sidewalls 362 as shown in FIGS. 65B and 65C. Nozzle covers 267 may be configured to fit the corresponding side injector openings 266. The nozzle covers include nozzles 268 that are aimed at side optical assemblies 256a, 256b and configured for injecting fluid to wash contaminants such as blood, feces and other debris from side optical assemblies 256a, 256b of the side looking cameras. The fluid may include gas which may be used for inflating a body cavity. Optionally, nozzles 268 may be configured for cleaning the side optical assembly and both optical windows on the opposing sides of the tip 200.

According to some embodiments, side injector channels 666 may be configured to supply fluids for cleaning any of the tip elements (such as any optical assembly, windows, illuminators, and other elements). Optionally, injector channel 646 and side injector channels 666 may be fed from the same channel.

As shown in FIGS. 65A through 65D, in accordance with an embodiment, two side jet openings 605a, 610a, fed by a common side jet channel 6506, are provided around the side periphery at the proximal end of the tip 200. Thus, the two side jet openings 605a, 610a which are fed by common side jet channel 6506 form a Y-shaped fluid conduit. The manifold shown in FIG. 65D includes a housing having a partially cylindrical shape with a curved top surface, a partially curved first side and a partially curved second side, wherein manifold housing is formed from a base portion with a first width, a first length, and a proximal surface and an elongated portion, which is attached to the base portion, with a second width, a second length, and a distal surface, wherein the first width is greater than the second width and the first length is less than the second length. A first channel 640 extends from the base portion through the elongated portion, wherein the first channel 640 has an entrance port positioned on said proximal surface of the base portion and an exit port positioned on a distal surface of the elongated portion. A second 644 extends from the base portion through the elongated portion, wherein the second channel 644 has an entrance port positioned on said proximal surface of the base portion and an exit port positioned on a distal surface of the elongated portion.

The manifold further includes a Y-shaped fluid conduit comprising a central stem portion 6506, a first prong portion 605a, and a second prong portion 610a, wherein the central stem portion 6506 extends from an entrance port 607 on the proximal surface of the base portion through the base portion, wherein the first prong portion 605a extends from an end of the central portion through the base portion to an exit port on the partially curved first side; and wherein the second prong portion 610a extends from an end of the central portion through the base portion to an exit port the partially curved second side.

A third channel 646 extends from an entrance port on the proximal surface of the base portion through to an exit port on the partially curved first side. A fourth channel extends from an entrance port on the proximal surface of the base portion through to an exit port on the partially curved second side. Each of the first, second, third, and fourth channels are fluidically isolated and separated from each other.

The common side jet channel 6506 has an entry port 607 at a proximal end of the fluid channeling component 600. Similarly, two side jet openings 605b, 610b, fed by another common side jet channel 6506, are provided on the opposite side. In one embodiment the two side jet openings 605a, 605b, 610a, 610b on either side of the tip are positioned in such a way that the side injector openings 266 (one on both sides of the tip) are situated between them. Additionally, in one embodiment, the two side jet openings 605a, 605b, 610a, 610b on either side of the tip are positioned close to the side optical assemblies 256a, 256b of the side looking cameras (on both sides of the tip) such that when fluid is ejected from the side jet openings it is propelled at an approximately 45 degree angle and past the cameras, so that a physician can see the fluid being expelled. The fluid can be water or saline.

FIG. 65E shows the multi jet endoscope assembly 6501 (of FIGS. 65A through 65C) being moved inside a body cavity 6501 while multiple high-pressure fluid jets are being expelled from the front jet opening 6544 as well as the side jet openings 6505, 6510. As can be seen, the side fluid jets are being expelled at an acute angle relative to a lateral plane containing a first side optical assembly 6556a and a second side optical assembly (not visible) and corresponding side optical windows but not containing front optical assembly 6556 of the front looking camera. The acute angle of exit enables fluid to be expelled along the direction of movement of the endoscope 6501, in accordance with one embodiment.

The side jet openings are fed with high-pressure fluid through side jet channels formed in the fluid channeling component 600 of FIG. 65D. In one embodiment, each side jet opening is fed with a separate corresponding side channel while in other embodiments the side jet openings are fed from a common side channel. The side jet channels may be distinct from or common to the front jet channel 6544.

In accordance with another aspect of the present specification, the side jet channel openings 6505 and 6510 can be operated at a plurality of predefined algorithms such as continuous fluid stream, fluid stream pulsing at different flow rates, fluid stream being expelled at different timings with respect to the different side jet openings, fluid stream at different pressures or any other suitable algorithm as would be evident to persons of ordinary skill in the art. Also, while in one embodiment all side jet openings operate at one selected algorithm, in alternate embodiments each side jet opening can operate independently and at different operating algorithms using a distributer to control the operation of the jets.

In accordance with an aspect of the present specification, a side jet sprinkler comprising a plurality of holes is used over at least one of the side jet openings 605a, 605b, 610a, 610b so as to split the fluid emanating from the underlying side jet opening(s). Referring now to FIG. 66, a side jet sprinkler 6600 is illustrated in accordance with an embodiment of the specification. Side jet sprinkler 6600 may be an attachment or a "patch" that includes a plurality, such as two or more, of holes 6670. As an example, FIG. 66 shows the side jet sprinkler 6600 placed over the side jet opening 610a, such that holes 6670 are aligned directly over side jet opening 610a. Thus, fluid exiting side jet opening 610a may then be split to exit through holes 6670, forming multiple jets of fluid—in a sprinkling manner. Side jet sprinkler 6600 may thus enable a wider coverage of cleaning fluid around periphery of the tip section of the endoscope, allowing an improved cleaning function of a body cavity.

In an embodiment, a front jet sprinkler, with a plurality of holes, may be placed over jet channel opening 344 of front jet channel 644 (FIGS. 65A through 65D). The front jet sprinkler may be configured in a similar manner as side jet sprinkler 6600, such that it may be positioned to fit over jet channel opening 344 on front panel 320.

In an embodiment, the side jet sprinkler 6600 may be removable. It may be placed on tip cover 300 of FIG. 2A, and later removed. In some embodiments, side jet sprinkler 6600 may be pressed against the tip cover 300 such that it sticks to it. Optionally, side jet sprinkler 6600 may be pressed and glued to tip cover 300. In addition to front and side jets, the use of side jet sprinkler 660 may further improve the ability to clean/flush the body cavity.

With reference to FIGS. 65A through 65D and FIG. 66, it should be noted that, in alternate embodiments, the side jet openings (such as 605a, 605b, 610a, 610b) and/or the plurality of holes 6670 of the side jet sprinkler 6600 can be configured around the side periphery in any suitable number, including 2, 4, 6, or 8. Also, the side jet openings 605a, 605b, 610a, 610b and/or holes 6670 can have a plurality of angular configurations causing fluid to exit at different angles relative to a lateral plane that includes the side optical assemblies of side looking cameras and the optical windows of the corresponding illuminators but not the front optical assembly of the front looking camera. In one embodiment, the optical axis of the side looking cameras is perpendicular to the lateral plane as well as the optical axis of the front looking camera which is along the central longitudinal axis 6503 of the endoscope. These angles of fluid exit can range from 45 to 60 degrees or 120 to 135 degrees relative to the lateral plane. Acute angles of exit of 45 to 60 degrees enable fluid to be expelled in the direction of movement of the endoscope while obtuse angles of exit of 120 to 135 degrees enable fluid to be expelled in the direction opposite to the direction of movement of the endoscope, thereby aiding the endoscope movement within a body cavity. This is because, if the jet is directed in an opposite direction of movement of the endoscope, the resistance of the colon walls may push the scope forward like a jet engine.

Referring to FIGS. 67A and 67B, in accordance with one embodiment, side jet openings 6705, 6710 are positioned 8.5 to 9.5 millimeters from the side optical assemblies 1056a, 1056b on the circumference of the endoscope such that the fluid exiting the openings form angles ranging from 50 degrees (as shown in FIG. 67A) to 60 degrees (as shown in FIG. 67B) relative to a lateral plane containing the side optical assemblies 6756a, 6756b and corresponding side optical windows (but not containing front optical assembly of the front looking camera). Also, the side jet openings 6705, 67010 have a diameter of about 1.4 to 1.7 millimeters, in one embodiment.

As shown in FIGS. 68A and 68B, in some embodiments of the specification, side jet openings (such as 605a, 605b, 610a, 610b of FIGS. 65A through 65D) may be covered by peripheral jet openings 130, which comprise, in one embodiment, a plurality of holes drilled through tip cover 300. Peripheral jet openings 130 may further disseminate fluid circulated through side jet openings (such as 605a, 605b, 610a, 610b of FIGS. 65A through 65D) in to multiple smaller exits. Cleaning fluid that is circulated by side jet channels 6506, 6506, may flow through side jet openings and conveyed along an integrated groove connected to side jet channels 6506, 6506 on the periphery of the tip cover 300. The groove is surrounded by the smaller and multiple holes aligned on circumference of tip cover 300 as peripheral jet openings 130. Thus the cleaning fluid emerging from side jet openings (such as 605a, 605b, 610a, 610b of FIGS. 65A through 65D) exits through the multiple holes of peripheral jet openings 130. This enables the cleaning fluid to reach all around (360 degrees) the tip cover 300, into the body cavity, which may allow for a better cleaning procedure that may solve or mitigate the problem of less efficient colonoscopies due to a non-cleaned colon.

Peripheral jet openings 130 may have a plurality of angular configurations causing fluid to exit at different angles relative to a lateral plane that includes the side optical assemblies of side viewing elements and the optical windows of the corresponding illuminators. In an embodiment, peripheral jet openings 130 may be drilled at acute angles relative to the long dimension of the endoscope. In another embodiment, peripheral jet openings 130 may be drilled at 90 degrees relative to the long dimension of the endoscope. In yet another embodiment, peripheral jet openings 130 may be drilled at obtuse angles relative to the long dimension of the endoscope. In an alternative embodiment, each hole of peripheral jet openings 130 may be drilled at angles that are a combination of one or more acute angles, 90 degrees angles, and one or more obtuse angles. Acute angles of exit may enable fluid to be expelled in the direction of movement of the endoscope while obtuse angles of exit may enable fluid to be expelled in a direction opposite to the direction of movement of the endoscope, thereby aiding the endoscope movement within the body cavity.

Reference is now made to FIGS. 2A, 68A and 68B along with FIGS. 69A, 69B, and 70, which respectively show front and rear perspective views, and a side view of a tip section 200 of an endoscope assembly according to an embodiment. The FIGS. 69A, 69B, and 70 illustrate the internal components that are enclosed by tip cover 300 described in FIGS. 68A and 68B above. It should be appreciated that in accordance with this embodiment, the tip cover 300 of FIG. 2A is replaced by the tip cover 300 described in FIGS. 68A and 68B, the fluid channeling component 600 of FIG. 2A is replaced by the fluid channeling component 600 of FIG. 65D, while the circuit board assembly 400 of FIG. 2A remains unchanged.

Tip cover 300 may include a front panel 320 having a front optical assembly 256, of front looking camera 116. Front optical assembly 256 may include a plurality of lenses, static or movable, which may provide a field of view of 90 degrees or more, 120 degrees or more or up to essentially 180 degrees. Front optical assembly 256 may provide a focal length in the range of about 3 to 100 millimeters. Additionally, front panel 320 may include optical windows 242a, 242b and 242c of illuminators 240a, 240b and 240c, respectively. It should be noted that number of illumination sources used for illumination of the field of view may vary. In addition, front panel 320 may include a working channel opening 340 of a working channel 640.

Jet channel opening 344 of jet channel 644 may also be located on front panel 320 of tip cover 300. Jet channel 644 may be configured for providing a high-pressure jet of fluid, such as water or saline, for cleaning the walls of the body cavity.

Also located on front panel 320 of tip cover 300 is injector opening 346 of injector channel 646 having a nozzle aimed at front optical assembly 256. Injector channel 646 may be configured for injecting fluid (liquid and/or gas) to wash contaminants such as blood, feces and other debris from front optical assembly 256 of front looking camera 116. Optionally, injector channel 646 may be configured for cleaning front optical assembly 256 and one, two or all of optical windows 242a, 242b and 242c. Injector channel 646 may be fed by fluid such as water and/or gas which may be used for cleaning and/or inflating a body cavity.

Visible on the sidewall 362 of tip cover 300 is side optical assembly 256b for side looking camera 116b, which may be similar to front optical assembly 256, and optical windows 252a and 252b of illuminators 250a and 250b for side looking camera 116b. Also on the sidewall 362 of tip cover 300 on the opposing side to side optical assembly 256b is an optical assembly for another side looking camera, which may be similar to side optical assembly 256b, and optical windows of illuminators for the other side looking camera. The side optical assembly 256b may provide a focal length in the range of about 3 to 100 millimeters.

In addition, side injector opening 266 may be located on sidewall 362. A nozzle cover may be configured to fit side injector opening 266. Additionally, the nozzle cover may include a nozzle which may be aimed at side optical assembly 256b and configured for injecting fluid to wash contaminants such as blood, feces and other debris from side optical assembly 256b of side looking camera 116b. The fluid may include gas which may be used for inflating a body cavity. Optionally, nozzle may be configured for cleaning both side optical assembly 256b and optical windows 252a and/or 252b.

Side panel 362 also includes at least one side jet opening 610a (which is one of any of the side jet openings such as 605a, 605b, 610a, 610b of FIGS. 65A through 65D) that vents cleaning fluid circulated through side jet channels 6506, 6506. Another, similar, at least one side jet opening (not visible) may provide a second vent on the opposite side panel of the tip section 300. A peripheral groove 330 connected to side jet opening 610a and the other side jet opening on the opposite side panel of the tip section 300 may provide a channel for fluid vent by the two side jet openings. The fluid may circulate through the channel of peripheral groove 330 around the circumference of the tip section 300. In one embodiment, each side jet opening is fed with a separate corresponding side jet channel while in other embodiments the side jet openings are fed from a common side channel. The side jet channels may be distinct from or common to front jet channel 644.

In accordance with another aspect of the specification, side jet openings (such as 605a, 605b, 610a, 610b of FIGS. 65A through 65D) may be operated at a plurality of predefined algorithms, such as continuous fluid stream, fluid stream pulsing at different flow rates, fluid stream being expelled at different timings with respect to the different side jet openings, fluid stream at different pressures or any other suitable algorithm as would be evident to persons skilled in the art. Also, while in one embodiment all side jet openings operate at one selected algorithm, in alternate embodiments each side jet opening may operate independently and at different operating algorithms using a distributer to control the operation of the jets.

It is noted that according to some embodiments, although tip section 300 is presented herein showing one side thereof, the opposing side may include elements similar to the side elements described herein (for example, side viewing element, side optical assembly, injector(s), nozzle(s), illuminator(s), window(s), opening(s) and other elements).

It is noted that according to some embodiments, the tip section may include more than one side viewing elements. In this case, the side viewing elements may be installed such that their field of views are substantially opposing. However, different configurations and numbers of side viewing elements are possible within the general scope of the current specification.

Along with FIGS. 68A, 68B, 69A, 69B and 70, reference is now made to FIG. 71, which shows a cross-section view of tip section 200 enclosed within tip cover 300 of FIGS. 68A, 68B, according to an embodiment. FIG. 71 simultaneously illustrates side viewing elements 116a and 116b. Side illuminators 250a, 250b are positioned to illuminate side viewing element 116a, and side illuminators 250c, 250d are positioned to illuminate side viewing element 116b. Also seen is front viewing element 116 along with front illuminators 240a, 240b.

Additionally, alignment of peripheral jet openings 130 in tip cover 300, with peripheral (jet channel) groove 330, is illustrated. Cross section view of side jet opening 610a may be seen connected to peripheral jet channel groove 330. Fluid may flow through side jet channels 6506, side jet opening 610a, in through peripheral jet channel groove 330, and exit through multiple holes of peripheral jet openings 130 in tip cover 300, thus enabling a 360-degree dispersion of the fluid into the body cavity of a patient.

It should be noted that, in alternate embodiments, the number of peripheral jet openings 130 may vary. In various embodiments, the diameter of each hole in peripheral jet openings 130 may be in the range of 0.40-0.80 millimeters. In some embodiments, the diameter of each hole in peripheral jet openings 130 may be 0.50 millimeters. The minimum distance between two holes may be 0.20 millimeters. These exemplary embodiments may be suitable for endoscopic tip diameters in the range of 9 to 17 millimeters.

Reference is now made to FIG. 72, which illustrates a multi jet ring assembly 7200 in accordance with an alternative embodiment of the specification. Multi jet ring assembly 7200 may be placed over side jet openings, such as 605a, 605b, 610a, 610b of FIGS. 65A through 65D, on a tip cover. The side jet openings may provide an exit for fluid circulated by side jet channels of a tip section of an endoscope assembly. In embodiments, a peripheral groove 7202 may be placed on an internal periphery of multi jet ring assembly 7200, such that the side jet channel openings may be aligned with peripheral groove 7202. Moreover, multiple holes 7204 may be drilled along peripheral groove 7202. Multiple holes 7204 may allow multiple jet exit of the fluid circulated through peripheral groove 7202.

In one embodiment, multi jet ring assembly 7200 is disposable and is adapted for all scopes having a side jet channel (such as 605a, 605b, 610a, 610b of FIGS. 65A through 65D), including scopes having one front working/ service channel, two front working/service channels, and scopes having one or two side working/service channels.

Multiple holes 7204 may have a plurality of angular configurations causing fluid to exit at different angles relative to a long dimension of the endoscope. In an embodiment, multiple holes 7204 may be drilled at acute angles relative to the long dimension of the endoscope. In another embodiment, multiple holes 7204 may be drilled at 90 degrees relative to the long dimension of the endoscope. In yet another embodiment, multiple holes 7204 may be drilled at obtuse angles relative to the long dimension of the endoscope. In an alternative embodiment, each hole of multiple holes 7204 may be drilled at angles that are a combination of one or more acute angles, 90 degrees angles, and one or more obtuse angles. Acute angles of exit may enable fluid to be expelled in the direction of movement of the endoscope while obtuse angles of exit may enable fluid to be expelled in a direction opposite to the direction of movement of the endoscope, thereby aiding the endoscope movement within a body cavity, and vice versa.

A first diameter 7206 of multi jet ring assembly 7200 may be adapted to a diameter of the tip cover, and is of a dimension such that multi jet ring assembly 7200 fits over the tip cover. A second diameter 7208 of multi jet ring assembly 7200 may be larger than first diameter 7206. While first diameter 7206 may define the dimension for the outer edges of multi jet ring assembly 7200, second diameter 7208 may correspond to the inner ring that forms peripheral groove 7202.

Pre-adjustment of the tip cover may be made to pre-define the location of multi jet ring assembly 7200, such that the latter may be slid over tip section and is firmly placed on it. In embodiments, a shallow groove in the tip cover may be made to ensure multi jet ring assembly 7200 may not protrude from outer portion of tip cover and increase the outer diameter of the tip section.

Multiple holes 7202 are thus placed on peripheral groove 7204, which are aligned with one or more side jet openings of the endoscope. In various embodiments, multi jet ring assembly 7200 may be adapted for different types of scopes that have at least one side jet channel, including scopes having one front service channel and scopes having two front service channels. In different embodiments, multi jet ring assembly 7200 may be adapted to scopes with tip sections of different diameters ranging from 5 to 18 millimeters.

The number of multiple holes 7202 may vary in accordance with different embodiments of the specification. Opening angles of multiple holes 7202 may also vary with embodiments. In an embodiment, multiple holes 7202 may be at acute angles relative to the long dimension of the endoscope. In another embodiment, multiple holes 7202 may be at 90 degrees relative to the long dimension of the endoscope. In yet another embodiment, multiple holes 7202 may be at obtuse angles relative to the long dimension of the endoscope. In another embodiment, each hole of multiple holes 7202 may be at angles that are a combination of one or more acute angles, 90 degrees angles, and one or more obtuse angles. Acute angles of exit may enable fluid to be expelled in the direction of movement of the endoscope while obtuse angles of exit may enable fluid to be expelled in a direction opposite to the direction of movement of the endoscope, thereby aiding the endoscope movement within a body cavity, and vice versa.

In embodiments, the diameter of each hole in multiple holes 7204 may range within 0.40 to 0.80 millimeters. In embodiments, the minimum distance between two adjacent holes in multiple holes 7204 may be 0.20 millimeters.

FIGS. 73, 74A, and 74B show side and perspective views of tip section 200 of an endoscope assembly, with multi-jet ring assembly 7200 placed over it. Various components of tip section 200 may be similar to previously described embodiments of components with reference to FIG. 2A or 2B. A tip cover 300 of tip section 200 may comprise one or more side jet openings, such as 605*a*, 605*b*, 610*a*, 610*b* of FIGS. 65A through 65D.

Multi jet ring assembly 7200 may be placed over tip cover 300 such that peripheral groove 7202 is aligned with its side jet openings, such as 605*a*, 605*b*, 610*a*, 610*b* of FIGS. 65A through 65D. Therefore, fluid circulated through side jet openings may be conveyed through peripheral groove 7202 in the internal periphery of multi-jet ring assembly 7200. The fluid may then exit through multiple holes 7204 on peripheral groove 7202, providing 360-degrees vent to the fluid, around tip section 200.

FIGS. 75A and 75B illustrate perspective views of tip section 200 when multi jet ring assembly 7200 is detached from it, in accordance with an embodiment of an endoscope assembly. The figures show a side jet opening 610*a* of tip section 200. In embodiments, peripheral groove 7202 of multi jet ring assembly 7200 may be placed over side jet opening 610*a*.

Referring now to FIGS. 76A and 76B, cross-sectional views of a multi jet ring assembly 7200 placed over tip section 200 are shown, according to embodiments of endoscope assembly of the specification. The figures illustrate a side jet channel 6506 connected to a side jet opening 610*a*. The first diameter 7206 and the second diameter 7208 of multi-jet ring assembly 7200 are also visible along with holes 7204. Although the figure shows one side jet channel and opening, the specification may, in other embodiments, include multiple side jet channels and/or openings in the tip section of the endoscope assembly.

Referring now to FIG. 2A and FIGS. 65A through 65D, in an embodiment, a jet distributer is provided to supply fluids to each of the side jet openings, such as 605*a*, 605*b*, 610*a*, 610*b* in the multi jet endoscope tip 6501 of FIGS. 65A through 65D, and the front jet 344. The jet distributer typically comprises three fluid channels to provide fluid to the front jet 344, right-side-jets 605*a*, 610*a* and left-side-jets 605*b*, 610*b* in the endoscope tip 6501. FIG. 77A illustrates a multi jet distributer pump 4000, in accordance with an embodiment of the present specification. As illustrated, the multi jet distributer 4000 comprises a distributer motor housing 4002 and a distributor motor 4004 coupled with a motor shaft 4006 which in turn is coupled with a distributer disc 4008 adapted to channel fluid out into three exiting fluid pipelines 4010, 4012, and 4014, thereby supplying fluid to three jet openings (front jet 344, right-side-jets 605*a*, 610*a* and left-side-jets 605*b*, 610*b*) in the endoscope tip. The multi jet distributer 4000 further comprises an entering fluid pipeline 4016 that transports fluid from a fluid source, via a conventional jet pump, into the multi-jet distributer 4000. Locking element 4018 enables the distributer disc 4008 to be latched on to the motor shaft 4006.

In one embodiment, jet distributer 4000 comprises two fluid channels to provide fluid to the front jet 344 and sides-jets 605*a*, 605*b*, 610*a*, 610*b* in the endoscope tip. The multi jet distributer 4000 comprises a distributer motor housing 4002 and a distributor motor 4004 coupled with a motor shaft 4006 which, in turn, is coupled with a distributer disc 4008 adapted to channel fluid out into two exiting fluid pipelines, thereby supplying fluid to three jet openings in the endoscope tip. In this embodiment, the two sides-jets are fed by a common jet channel split into two pipelines upon entering the endoscope tip; one provides fluids to the right-side-jets and the other to the left-side-jets.

FIGS. 77B and 77C illustrate additional views of the multi jet distributer pump 4000, in accordance with embodiments of the present specification. As illustrated in FIG. 77C, the distributer disc 4008 is physically detachable from the distributer motor housing 4002 and can be latched in, and out, of the distributor motor housing 4002 by using the locking element 4018 which is fitted in a groove 4020 of the distributor disc 4008.

In one embodiment, the distributer disc 4008 is a substantially cylindrical structure comprising a plurality of circular slots for attaching with fluid pipelines. In an embodiment, the distributor disc 4008 comprises a slot for attaching with an entering fluid pipeline 4016 which has a diameter ranging from approximately 1 to 20 millimeters, and more specifically between 1 to 10 millimeters. In an embodiment, the distributor disc 4008 further comprises at least two slots for attaching with exiting fluid pipelines, each having a diameter ranging from approximately 1 to 20 millimeters, and more specifically between 1 to 10 millimeters. The circular slots on the face of the distributor disc 4008 attaching with the fluid pipelines are separated by a minimum distance. In an embodiment, the length of the entering and exiting pipelines is selected to minimize the overall space requirements of the distributor pump, yet achieve the fluid rate objectives of the present invention as described below. Also, in an embodiment, the fluid pipelines are connected to the distributor disc 4008 by using sealing members such as an O-ring or a gasket. During use, fluid pipelines are threaded and secured via threading onto the distributor disc 4008 and sealed thereto, using the sealing members. In an embodiment, the three exit pipelines connect to, or mate with, complementary fluid channels, which direct fluid through to the jet openings in the endoscope tip, via a main connector. In an embodiment, a universal luer connector is used to connect the fluid pipelines to the main connector. In other embodiments, any suitable connecting element may be used to connect the fluid pipelines to the main connector.

Three of the pipes which are positioned normal to the face of the distributor disc are exiting fluid pipelines 4010, 4012, and 4014 and operate to supply fluid to three jet openings in an endoscope tip. The fourth pipe which is positioned normal to the face of the distributor disc is an entering fluid pipeline 4016.

In various embodiments, a distributor disc rate within the multi jet distributer 4000 can vary from 30 rounds per minute to 100 rounds per minute, and more specifically between 50-65 rounds per minute. The distributor disc rate may also depend upon a fluid flow rate received into the multi-jet distributor.

In an embodiment, a first pipeline supplies fluid to a front panel of the endoscope, a second pipeline supplies fluid to one side of the tip, and a third pipeline supplies fluid to the other side of the tip. In another embodiment, only two pipelines enter the main connector, wherein a first pipeline supplies fluid to the front jet and a second supplies fluid to the side jets of the endoscope.

FIG. 78A illustrates a distributer disc 4008 of a multi jet distributer, in accordance with an embodiment of the present specification. The disc 4008 comprises a distributer rotating plug 5002 for connecting the disc 4008 to the motor shaft 4006. A locking element 4018 may be fitted in a groove 5004 on the disc 4008 to connect the disc to the motor shaft 4006.

FIG. 78B illustrates another view of the distributer disc 4008 of a multi jet distributer, in accordance with an embodiment of the present specification, showing three exiting fluid pipelines 4010, 4012 and 4014 and one entering fluid pipeline 4016.

FIG. 79A is a block diagram illustrating the connection between a multi jet distributor and an endoscope, in accordance with an embodiment of the present specification. A pump, such as jet pump 6002 pumps fluid from a fluid source, via an entering fluid pipeline 6004, into a multi jet distributor 6006. The fluid is supplied by the multi jet distributor 6006 to three jet openings in a tip of an endoscope 6008 via three exiting fluid pipelines 6010, 6012 and 6014 and a main connector 6016. In an embodiment, each of the three exiting fluid pipelines supplies fluid to a fluid channel of the endoscope 6008. In one embodiment, each exiting fluid pipeline is connected to main connector by a luer connector, or by any connecting system of small-scale fluid fittings used for making leak-free connections between a male-taper fitting and its mating female part on medical instruments. The main connector is also coupled with a controller unit (or fuse box) 6018 that acts as a main control unit for the endoscope 6008.

In various embodiments, in order to activate the jet and wash a lumen in a patient's body, a doctor/physician operating the endoscope is required to push a button located either on a handle of the endoscope, on a main control unit, on a fuse box or on a fuse panel of the endoscope. Once the button is pressed, the multi jet distributer starts providing fluid at a pre-determined rate to each of the three fluid channels of the endoscope. In another embodiment, the doctor/physician may be required to push/step on a foot pedal to activate the jet-pump which provides fluid to the multi jet distributer and at the same time activates the multi jet distributer motor. In various embodiments, the operating doctor/physician may change a rate of flow of fluid being supplied by the multi jet distributer dynamically during the operation.

In an embodiment, the multi jet distributor is located outside the endoscope system but is connected to a main control unit or the fuse box of the endoscope as illustrated in FIG. 79A. The multi jet distributer may connect to the fuse box by using a coupling system. In accordance with an embodiment of the present specification, the coupling system comprises a hanger plug and socket pair such that the hanger plug is integrally formed on a distributor disc portion of the multi jet distributor while the hanger socket, to removably yet fixedly receive the hanger plug, is affixed to a side of the fuse box 6018.

In various embodiments, alternate connection systems that are easily connected/disconnected but securely fixed may be used. For example, the connection system may include a magnetic coupling pair where a first magnet is fixed to the multi-distributor jet and a second magnet, having polarity opposite to the first, is affixed to a side of the fuse box. Bringing the first magnet close to the second would result into a strong magnetic coupling to enable the multi jet distributor to be removably, yet securely, attached to the fuse box.

Additional examples may include clips, snaps, clasps, hooks, a female/male attachment pair, and other connection systems that enable removable, yet firm, coupling as would be advantageously evident to persons of ordinary skill in the art In another embodiment, the multi jet distributer is integrated into the control unit, such that the housing of the multi jet distributor is located inside the control unit.

FIG. 79B is a block diagram illustrating another connection between a multi jet distributor and an endoscope, in accordance with an embodiment of the present specification. As illustrated, the multi-jet distributor 6006 supplies fluid to three jet openings in a tip of an endoscope 6008 via a single exiting connector housing within the three pipelines exiting pipeline 6020. Hence, in the embodiment illustrated in FIG. 79B, a single fluid pipeline supplies fluid to the three fluid channels of the endoscope 6008.

FIG. 80A illustrates a sectional view of a distributor disc of a multi jet distributor, in accordance with an embodiment of the present specification. A jet pump 7002 pumps a fluid via an entering fluid pipeline 7004 into a distributor disc 7006, which in turn distributes the fluid into three streams being pumped out via three exiting fluid pipelines 7008, 7010 and 7012 (not shown in FIG. 80A) into a main connector 7014. FIG. 80B illustrates another sectional view of a distributor disc of a multi jet distributor, in accordance with an embodiment of the present specification. The distributor disc 7006 comprises an inlet for an entering fluid pipeline 7004 and three outlets for exiting fluid pipelines 7008, 7010 and 7012. It should be appreciated that the exiting fluid pipelines can number one, two, three, four or more.

In accordance with an aspect of the present specification, a multi jet controller is used to enable the main connector 6016 of FIGS. 79A and 79B to allow selective ejection of fluid from front and/or side jets of the endoscope 6008.

FIG. 81A shows a perspective view of a main connector 8100 employing a multi jet controller 8130 in accordance with an embodiment of the present specification. The controller 8130 comprises a shaft 8105 leading to a valve 8110. The valve 8110, when inserted/placed in a controller housing 8115, operatively connects the valve 8110 to the main connector 8100 via a jet connector 8120. The jet connector 8120 connects a jet pump to the main connector 8100. The main connector 8100 comprises a light guide pin 8125, gas channel 8135 and an electric connector 8140 at one end and a connector 8145 at another end to connect to a main control unit (such as unit 199 of FIG. 1A) through a utility cable/umbilical tube. An endoscopic water bottle connector 8150 is also provided on a side of the main connector 8100.

In accordance with an embodiment, the multi jet controller 8130 has a screw formed on the valve 8110. Once the shaft 8105 is inserted/placed in the controller housing 8115, a rotation of the screw, with the help of the shaft 8105, enables a selective flow of jet fluid into the selected front and/or side jet channels. Thus, the multi jet controller 8130 provides a user with a manual control option to control the operation of the varied jets (front and side jets).

In a first control option only the front jet receives fluid to be ejected through a front jet opening of an endoscope, such as opening 344 of FIGS. 2A, 2B. FIG. 81B shows a first position of the shaft 8105 corresponding to the first control option.

In a second control option the front jet as well as the side jets receive fluid to be ejected through a front jet opening as well as side jet openings of the endoscope, such as openings 605a, 610b of FIG. 65A. FIG. 81C shows a second position of the shaft 8105 corresponding to the second control option.

In accordance with an aspect, the shaft 8105 has indicative signs to indicate to the user the chosen fluid control option. FIGS. 81B and 81C respectively, show signs or indicators 8155 and 8160 corresponding to the first and second fluid control options.

According to some embodiments, one technical problem addressed by the present specification relates to multiple endoscope configurations being required for handling the multiplicity of applications. Different configurations may require different type, number, positioning, directing, focusing or other tuning of the capturing devices, light sources or other components on the endoscope. Therefore, although multiple parts of an endoscope system may be common to many of the configurations, multiple endoscopes may be required. This poses significant requirements on a health institute, including for example financial requirements, storage, maintenance, training or the like.

Some different configurations may also be required for different patients or patient types, such as adults, children, infants, or the like.

Some different configurations may also be required for different procedures, such as colonoscopy, gastroscopy, endoscopic ultrasound (EUS), endoscopic retrograde cholangiopancreatography (ERCP) or the like.

Yet another technical problem addressed by embodiments of the disclosure relates to maintenance costs. When replacing the camera head, for example due to defective objective lens, the entire colonoscope has to be disassembled, which is an expensive process.

According to some embodiments, a technical solution may be the provisioning of an endoscope having a removable tip section. The tip section may also be partially removable, for example, with a permanent section and a removable section. The removable section of the tip may be removably connected or attached to the permanent section of the tip which is connected to a shaft (which may also be referred to as a bending section, for example, a vertebra mechanism), so that endoscopes having different configurations can be used with the same system. According to the endoscopic task to be performed, a removable section having an appropriate configuration is selected and connected to the shaft or to the permanent section. When the endoscopy session is over, the removable section of the tip may be removed and another removable section having the same or a different configuration can be connected to the permanent section or to the shaft.

In some embodiments, the removable section of the tip comprises a substantially full cross section of the tip, for example, the whole distal surface of the tip, possibly excluding some openings or small parts such as rings. In some of these embodiments, all channels and flows going through the tip, such as optic fibers, power supply, water supply, data lines transferring images, working channels for transferring equipment, or the like, are made of at least two parts which may be connected when the removable section is attached to the permanent section. However, in other embodiments of the full cross section removable sections, there may still be some materials or equipment which make their way only through the permanent section, which has one or more protruding parts going into and through the removable section.

In other embodiments, all cross sections of the removable section are substantially partial to the cross sections of the tip, such that at least one of the channels going through the tip is not split and is fully contained within the permanent section.

It will be appreciated that when the removable section is attached to the permanent section, all channels and flows which are split between the permanent section and the removable section are securely connected such that no tool, material or energy may leak between the parts, and that all data may be continuously transferred.

In some embodiments, the removable section may be attached to the permanent section in a secure manner which will ensure that the removable section will not mistakenly disconnect from the permanent section within the body. A verification mechanism may be provided which adds extra security measures.

One technical effect of embodiments of the disclosed subject matter relates to providing an endoscope with a removable tip section. This enables the medical staff to replace the tip section of the endoscope in accordance with the required functionality, so as to use for each type of endoscopic session the most suitable endoscope configuration, equipment, size, or the like. Different removable sections may then be used according to varying needs, thus eliminating the need for purchasing and maintaining multiple endoscopes for different applications. Thus, different removable sections may be of different configurations, for example, having the image capturing components, light sources, or working/service channels located at different locations on the removable section, thus adjusting to the specific body cavity explored or to possible findings within the body cavity. In other embodiments, the relative location between the image capturing components and the light sources may differ. In yet other embodiments, different removable sections may contain different types of cameras, differing for example in their wave length, lens assembly, sensor or other parts, pointing directions, field of view, or other parameters. The light sources may also differ between different configurations, in order to provide the type of light which the used sensor is sensitive to. Different removable sections can be made to adjust to different patients, for example removable sections can be manufactured in different sizes for adults, children or infants. Different removable sections can also be used when different view fields, different viewing angles or different optical characteristics are required, for example, in some situations a viewing angle of 170° may be used, while in situations that require viewing more details of a smaller area, a viewing angle of 140° can be used.

Another technical effect of the disclosed subject matter, according to some embodiments, relates to providing a disposable removable section, thus eliminating the need for sterilization or reprocessing and reducing contamination risks.

Yet another technical effect of the disclosed subject matter, according to some embodiments, relates to providing a removable section which can be made personalized in order to provide good results for a particular patient.

Yet another technical effect of the disclosed subject matter, according to some embodiments, relates to the replaceable top enabling a health care facility to maintain only a small number of endoscope systems, thus reducing cost and maintenance, while using the most appropriate endoscope for each type of endoscopic session, each patient, or the like.

Reference is now made to FIG. 82, which shows a perspective view of a removable tip endoscope.

Endoscope 8200 may include an elongated shaft, a bending section and a tip section 8201 which terminates the endoscope. The bending section may enable the turning of tip section 8201 in different directions. Tip section 8201 may comprise a removable section 8202 and a permanent section 8207 connected along line 8203.

Removable section 8202 may include therein a front-pointing capturing device such as a camera or a video camera 8204 which may capture images through a hole in a distal end surface 8206 of tip section 8201. A discrete front illuminator 8208, which is optionally a light-emitting diode (LED), may be associated with front-pointing camera 8204 and used for illuminating its field of view through another hole in distal end surface 8206. The LED may be a white light LED, an infrared light LED, a near infrared light LED or an ultraviolet light LED. The light may be generated internally within endoscope tip section 8201, or generated remotely and transferred, for example, by a fiber optic. In some embodiments, removable section 8202 may comprise two or more illuminators, wherein at least one may generate the light internally, and at least one may provide remotely generated light.

A front fluid injector 8210 may be used for cleaning at least one of front-pointing camera 8204 and discrete front illuminator 8208. Front fluid injector 8210 may be slightly elevated from distal end surface 8206, to enable it to inject fluid, from its side 8210*a*, onto front-pointing camera 8204 and discrete front illuminator 8208. Front fluid injector 8210 may be configured to inject fluids such as water, air and/or the like.

Distal end surface 8206 may further include a hole defining a working channel 8212. Working channel 8212 may be a hollow tube configured for insertion of a surgical tool to operate on various tissues. For example, miniature forceps may be inserted through working channel 8212 in order to remove a polyp or sample of which for biopsy. In alternative embodiments, working channel 8212 can be used for applying suction for evacuating various liquids and/or solids which exist in the body cavity and interfere with the inspection. In some embodiments, opening 8212 can extend to an internal cylinder which comprises a part of permanent section 8207. It should be appreciated that in various embodiments, the distal end surface 8206 may include more than one working/service channel openings.

A pathway fluid injector 8214, defined by another hole in distal end surface 8206, may be used for inflating and/or cleaning the body cavity into which endoscope 8200 is inserted. Inflation may be performed by flowing air or another gas through pathway fluid injector 8214, and may be beneficial for cases in which the body cavity, such as the colon, is shriveled or otherwise does not allow for efficient inspection. Cleaning may be achieved, for example, by injecting a liquid, such as water or saline, on an unclean area of the body cavity. Furthermore, pathway fluid injector 8214 (or a different tube) may be used for applying suction, in order to evacuate various liquids and/or solids which exist in the body cavity and interfere with the inspection.

Permanent section 8207 of tip section 8201 may include therein a side-pointing camera 8216 which may capture images through a hole in a cylindrical surface 8205 of the permanent section 8207 of tip section 8201. A side illuminator 8222, which is optionally similar to front illuminator 8208, may be associated with side-pointing camera 8216 and used for illuminating its field of view through another hole in cylindrical surface 8205. A side fluid injector 8220 may be used for cleaning at least one of side-pointing camera 8216 and discrete side illuminator 8222. In order to prevent tissue damage when cylindrical surface 8205 of permanent section 8207 contacts a side wall of the body cavity, side fluid injector 8220 and side-pointing camera 8216 may be located in a notch 8218 in the cylindrical surface. This way, side fluid injector 8220 may be elevated from depression 8218 but still not significantly protrude from the level of cylindrical surface 8205. The elevation of side fluid injector 8220 may enable it to inject fluid, from its opening 8220*a*, onto side-pointing camera 8216. In an alternative configuration (not shown), one or more discrete side illuminators may also be included in the depression, so that fluid injected from the side fluid injector may reach them. In yet another configuration (not shown), a side-pointing camera, one or more side illuminators and a side fluid injector may not be located in a depression, but rather be on essentially the same level as the cylindrical surface of the tip section.

It will be appreciated that the division of tip section 8201 into removable section 8202 and permanent section 8207 shown in FIG. 82 is schematic only and is intended as a general demonstration. The cameras, working channels, illumination channels, fluid injectors and other components may be split between removable section 8202 and permanent section 8207 in any other manner as demonstrated in the exemplary embodiments detailed in association with FIG. 83 to FIG. 86 below. For example, in some embodiments, the removable or permanent section may include one or more side working/service channels. In still further embodiments, the removable or permanent section may include a plurality of side jet openings (such as 605*a*, 605*b*, 610*a*, 610*b* of FIGS. 65A through 65D).

It will be appreciated that further flexibility may be provided if any of the capture devices (such as cameras), working/service channels, illumination channels and other components are provided on the removable section rather than on the permanent section. In such arrangements, each removable section is configured and equipped with the camera types and other equipment and arrangement which are most appropriate for the task. However, some equipment, such as cameras of higher quality and price, may be located on the permanent section, so as to better utilize such resources in multiple application types.

Reference is now made to FIG. 83, which shows a perspective view of a substantially full cross section of a removable tip removed from the permanent section, in accordance with one embodiment of the present specification.

Removable section 8302 of a tip of an endoscope is shown removed from permanent section 8307, wherein permanent section 8307 is connected to a shaft.

Removable section 8302 may comprise one or more capture devices, for example, video camera 8304, one or more light sources such as light source 8328, or one or more fluid injectors, such as 8332 or 8336.

One or more cables providing power to camera 8304 and transferring images from camera 8304 to the shaft go through removable section 8302, into and through an elongated section 8308 protruding from removable section 8302. When removable section 8302 is connected to permanent section 8307, elongated section 8308 enters a corresponding recess 8312 in permanent section 8307. In some embodiments, elongated section 8308 may end with a connector, wherein recess 8312 contains a corresponding connector, such that when elongated section 8308 is entered into recess 8312, the two connectors connect such that power or data can flow between the endoscope and camera 8304. For example, a plug located at the end of elongated section 8308 may enter a corresponding socket inside recess 8312. In alternative embodiments, recess 8312 may comprise a plug and elongated section 8308 may comprise a socket.

Thus, electric signals or data may pass through elongated section 8308 and recess 8312 from the shaft to the camera.

In some embodiments, elongated section 8308 may protrude from permanent section 8307 while recess 8312 may be placed on removable section 8302.

It will be appreciated that removable section 8302 or permanent section 8307 may comprise additional one or more pairs of protruding sections and corresponding channels, for transferring water or other fluids or liquids, optic fibers or any other material or equipment. When the protruding sections and corresponding channels are used for transferring fluids or liquids, one or two of them may be constructed with gaskets for sealing the fluids or liquids and avoiding leakage into the body or into other parts of the endoscope tip, from a gap between removable section 8302 and permanent section 8307.

Permanent section 8307 may also comprise a hollow elongated section 8316 protruding therefrom containing channel 8320. When removable section 8302 is connected to permanent section 8307, hollow elongated section 8316 is inserted into a corresponding channel 8324 in removable section 8302, which extends through the entire length of removable section 8302, thus enabling a surgical tool to pass through a working channel extending from the shaft through channel 8320 of hollow elongated section 8316 and through channel 8324 in removable section 8302 to distal surface 8305 of removable section 8302, so that the surgical tool can be used for operating on the body cavity of the patient.

Removable section 8302 may also comprise one or more side-pointing capturing devices such as camera 8338, one or more light sources 8340 or one or more fluid injectors 8344. The utilities to camera 8338, light source 8340 or injector 8344, may be received from the same provisioning as the front facing camera, light sources and injectors, through corresponding pipes within the body of removable section 8302 around channel 8324. The images captured by camera 8338 may also be transferred through the same channels.

It will be appreciated that removable section 8302 or permanent section 8307 may comprise additional side pointing cameras, light sources or injectors.

Removable section 8302 and permanent section 8307 may be connected by any known mechanism, such as a locking mechanism, fastening mechanism, snap mechanism, or the like.

Removable section 8302 or permanent section 8307 may be equipped with a button 8352 for releasing the connection. In order to avoid harming the body cavity of the user, button 8352 may be placed within a recess so as not to protrude from the surface of the tip section. In some embodiments, the connection may only be released if a corresponding command is provided from an external source, such as simultaneously clicking on a control on display 120 of FIG. 1A which may be translated to an electrical or mechanical effect required for releasing the connection, in order to prevent unwanted accidental release.

In some embodiments, permanent section 8307 may comprise a button or another sensitive area such as switch 8348 which may be touched or pressed by removable section 8302, only when removable section 8302 is securely connected to permanent section 8307. Such button may also be electrically connected to the endoscope handle or controller and may provide an indication to the endoscope operator whether the parts are securely connected. The indication may be visual, such as an icon on display 120. In some embodiments, when the connection is released, a vocal indication may also be provided as well to alert the operator.

In some embodiments, there may be two degrees or two mechanisms of connection between removable section 8302 and permanent section 8307. If one degree or one mechanism is released while the endoscope is being used, the operator may receive a first alert so he or she can remove the endoscope or otherwise correct the situation before the removable section is released within the body cavity of the patient.

It will be appreciated by a person skilled in the art that if the endoscope comprises an optic fiber, then each of removable section 8302 and permanent section 8307 may comprise a part of the fiber, wherein the sections may comprise corresponding lenses for providing continuity between the fiber parts by transferring light.

Reference is now made to FIG. 84, which shows a perspective view of a substantially full cross section removable tip section attached to the permanent section, in accordance with one embodiment of the present specification.

In FIG. 84, removable section 8302 is fully connected to permanent section 8307, such that elongated section 8308 and hollow elongated section 8316 of FIG. 83 are inserted into corresponding recess 8312 and channel 8324, respectively. Electric signals or energy as well as water or fluids may pass through permanent section 8307 to removable section 8302, and images captured by the cameras are transferred back and may be displayed to an operator.

Reference is now made to FIG. 85, which shows a perspective view of a partial cross section removable tip section in accordance with one embodiment of the present specification.

In FIG. 85, distal face 8305 of the endoscope tip is comprised of two parts, wherein a first part 8305' of distal face is of permanent section 8507, while the other part 8305" is of removable section 8502. Thus, each cross section of removable section 8502 comprises a partial cross section of the tip section, when assembled, of the two sections. In the exemplary embodiment of FIG. 85, channel 8320' fully contained within permanent section 8507 forms a working channel and reaches through permanent section 8507 to the distal face so that tools or other equipment can be passed.

Removable section 8502 may be equipped with cameras 8304 or 8338, light sources 8328 or 8340, or one or more fluid injector 8332, 8336 or 8344 which may be located at the front face or on the side face of removable section 8502 as required. The cameras, light sources or fluid injectors may be implemented and receive utilities as detailed in association with FIG. 8 above.

Removable section 8502 may also comprise one or more elongated sections such as elongated section 8308' which fits into recess 8312' of permanent section 8507. The one or more elongated sections, such as elongated section 8308', may function as an anchoring mechanism to secure removable section 8502 within permanent section 8507. Alternatively or additionally, the one or more elongated sections, such as elongated section 8308', may be used for transferring electric energy, fluids, liquids, optic fibers or other equipment or materials between removable section 8502 and/or surface 8305" and the endoscope handle and/or console.

In order to provide for full and tight connection between removable section 8502 and permanent section 8507, removable section 8502 may comprise a trapeze shaped bulge which fits into recess 8544 of permanent section 8507. In alternative embodiments, removable section 8502 may comprise a recess and permanent section 8507 may comprise a bulge.

Permanent section 8507 and removable section 8502 may be connected in any required manner as detailed in association with FIG. 83 above.

Reference is now made to FIG. 86, showing a perspective view of a partial cross section removable tip section attached to the permanent section in accordance with one embodiment of the present specification.

When removable section 8502 is securely attached to permanent section 8507, first part 8305' of the tip section distal face, which is part of removable section 8502, and second part 8305" of the tip section distal face, which is part of permanent section 8507, are substantially on the same plane with minimal or no gap therebetween, and complement each other to create the full distal face of the tip section. When removable section 8502 and permanent section 8507 are securely attached, switch 8348 of FIG. 85 may be pressed to provide an indication to an operator of the endoscope. Removable section 8502 and permanent section 8507 may be released by pressing button 8352, with or without providing an external release command.

When removable section 8502 is securely attached to permanent section 8507, utilities and equipment may be passed through a working channel formed by channel 8320' and through elongated section 8308' and corresponding channels in permanent section 8507.

According to an aspect of some embodiments, there is provided an interface unit configured to functionally associate with an endoscope system which comprises at least two simultaneously operating imaging channels associated with at least two displays, respectively.

The multi-camera endoscope of the present specification may typically provide the image data collected by the cameras simultaneously, whereas image data from each camera is delivered by an imaging channel associated exclusively with one camera, respectively. Imaging channels may be physical such as distinct video cables, each video cable being exclusively associated with one camera. Imaging channels may also be virtual, image data from each camera being uniquely coded prior to transfer through a single physical channel common to all cameras—such as a single video cable—and decoded at the output of the physical channel, thus discriminating the image data from each camera. The image data from each imaging channel may be displayed simultaneously to the physician on a display or on several displays. A display, or several such displays, may be associated exclusively with only a single imaging channel.

According to some embodiments, each imaging channel is associated exclusively with a physical display such as a video screen. The endoscope may comprise, e.g. three cameras, a first camera pointing forward substantially along the axis of the unbent probe, and the second and third cameras pointing sidewise from that axis, the second camera across from the third camera. According to some embodiments, each of the three respective imaging channels may be associated with a video screen, wherein the screens are arranged side by side, tilted at an angle relative to each other, substantially along an arc, to form a panoramic view for the physician. Image data from the first camera may thus be displayed on the central screen and image data from the second and third cameras may be displayed, e.g., on the right screen and on the left screen, respectively, thus providing to the physician a more realistic view of the surroundings of the tip of the probe over a wider solid angle.

FIGS. 87A and 87B depict schematically an endoscope system 10 and an interface unit 8700 associated with endoscope system 10, according to an aspect of some embodiments. Endoscope system 10 comprises an endoscope 20, a main controller 30 (which may be similar to the main control unit 199 of FIG. 1A) connected to endoscope 20 by a utility cable 32 (also referred to as an umbilical tube) and at least two screen displays 40a, and 40b, respectively, functionally associated with main controller 30. Endoscope 20 comprises a handle 22 and a distal tip 24 housing at least two cameras 26a and 26b, respectively, as depicted schematically in FIG. 87B.

Cameras 26a and 26b are configured to collect still images and video images according to a mode of operation selected by a user of endoscope system 10. Cameras 26a and 26b are associated with respective imaging channels 50a and 50b, implemented by two video cables included within utility cable 32. Each imaging channel transfers image data from a respective camera in endoscope 20 to main controller 30. Main controller 30 processes independently image data transferred by each of the imaging channels, for displaying images corresponding to the image data, on screen displays 40a and 40b, respectively. Main controller 30 processes the image data for display, e.g. using frame grabbers (such as 60a and 60b in FIG. 88), each frame grabber being associated with one imaging channel, or using any technique known in the art for processing image data received from a camera for displaying a corresponding image. Thus, screen display 40a is associated exclusively with imaging channel 50a and therethrough with camera 26a, and screen display 40b is associated exclusively with imaging channel 50b and therethrough with camera 26b.

According to some embodiments, endoscope system 10 may comprise three imaging channels, carrying image data from three cameras to three screen displays, respectively. Embodiments of endoscope system 10 comprising any number of imaging channels and corresponding cameras and screen displays are contemplated.

Endoscope 20 further comprises fluid injectors 28 for cleaning the optical element of camera 26a and/or for slightly inflating the body conduit in which the tip 24 is advanced. Utility cable 32 correspondingly comprises one or more fluid pathways 34 for passing a fluid to injectors 28.

Interface unit 8700 is functionally associated with endoscope system 10 to process image data received from imaging channels 50a and 50b and to display a corresponding image on an interface unit display 8720. FIG. 88 schematically displays a functional block diagram of interface unit 8700 according to some embodiments. Interface unit 8700 comprises an image processor 8710 functionally associated with imaging channels 50a and 50b. Interface unit 8700 further comprises interface unit display 8720, functionally associated with image processor 8710. Image processor 8710 is configured to process image data received simultaneously from imaging channel 50a and from imaging channel 50b, and to generate images that contain image data from the imaging channels. Images generated by image processor 8710 are displayable on a single display. Thereby, interface unit 8700 is configured to display on interface unit display 8720 images that include image data received substantially simultaneously from imaging channels 50a and 50b.

According to some embodiments, image processor 8710 comprises a synchronization module 8730. Synchronization module 8730 is configured to generate synchronization signals to synchronize image data received through imaging channels 50a and 50b. For example, in some embodiments, cameras 26a and 26b may each comprise a sensor, such as but not limited to a charge-coupled device (CCD) for image capturing. In some embodiments, synchronization module 8730 synchronizes image data received through imaging channels 50a and 50b by generating a common clock signal and driving the CCD in camera 26a and the CCD in camera 26b with the common clock signal. In some embodiments, synchronization module 8730 synchronizes image data received through imaging channels 50a and 50b by generating an initiating synchronization signal initiating the scan in the CCD of camera 26a and in the CCD of camera 26b at the same instant.

According to some embodiments, image processor 8710 is configured to simultaneously receive incoming video streams from imaging channels 50a and 50b and to generate from the two incoming video streams a single video stream displayable on interface unit display 8720. According to some embodiments, reduced-size images corresponding to each video stream incoming from imaging channels 50*a* and 50*b* respectively, are simultaneously displayed on interface unit display 8720. According to some embodiments, the two reduced-size images corresponding to imaging channels 50*a* and 50*b* are displayed on interface unit display 8720 side by side on one level horizontally. According to some embodiments, the two reduced-size images are arranged on interface unit display 8720 vertically, substantially one on top of the other. According to some embodiments, image processor 8710 is configured to generate a single video stream from the two incoming video streams substantially in real time.

According to some embodiments, image processor 8710 and interface unit display 8720 are encased together with main controller 30. According to some embodiments, image processor 8710 is encased together with main controller 30 and interface unit display 8720 is encased in a different case. According to some embodiments, interface unit display 8720 is connected with cables to image processor 8710 and, in embodiments in which image processor 8710 is encased together with main controller 30, interface unit display 8720 is substantially portable within a limit imposed by the cables. According to some embodiments, interface unit display 8720 is functionally associated with image processor 8710 wirelessly. According to some embodiments, image processor 8710 is assembled at a desired location along endoscope 20 between tip 24 and main controller 30, e.g. inside handle 22.

According to some embodiments, interface unit 8700 further comprises an interface unit computer 8750, functionally associated with image processor 8710. According to some embodiments, interface unit computer 8750 is configured to operate a files managing system comprising a files storage module 8760. For example, interface unit computer 8750 may be a personal computer running a commercially available operating system and comprising a primary storage module (e.g. RAM) and a secondary storage module (e.g. HDD). According to some embodiments, interface unit computer 8750 is configured to generate digital files of images generated by image processor 8710 and to store such files in files storage module 8760. Generating a file from an image or from a series of images or from a video stream may be accomplished using a suitable, possibly commercially available, computer application.

According to some embodiments, interface unit computer 8750 comprises a communication channel having a communication interface port 8770 configured to allow communication between interface unit computer 8750 and a computer network. According to some embodiments, a suitable communication channel may employ standard LAN connector and correspondingly suitable cables, and additionally or alternatively a wireless connection using a WiFi protocol, or any other suitable technique for communication between a computer and a computer network known in the art. According to some embodiments, communication interface port 8770 comprises a video output, e.g. S-video or composite. According to some embodiments, communication interface port 8770 comprises a high definition video output, e.g. HDMI.

According to some embodiments, interface unit computer 8750 is configured to transfer files generated and stored within interface unit computer 8750 to a network computer or another suitable network device using the communication channel and communication interface port 8770. According to some embodiments, files from interface unit computer 8750 may be stored in a network computer, and files may be retrieved to interface unit computer 8750 through communication interface port 8770 and associated communication channel. According to some embodiments, communication interface port 8770 may be used to store, in a network computer, a video stream in real time. According to some embodiments, communication interface port 8770 may be used to store, in a network computer, captured still images. According to some embodiments interface unit computer 8750 may employ communication interface port 8770 for communication with a local network, such as a local computer network in a hospital or in a medical care facility, for storing files with the network and retrieving files therefrom. According to some embodiments, interface unit computer may communicate using communication interface port 8770 with an Electronic Medical Records (EHR) application for storing and retrieving files, video streams, capture images and other desired medical records, during an endoscopy procedure. Such an EHR application may be accessed, according to some embodiments, through a local network and, according to some embodiments, through the Internet. According to some embodiments, interface unit 8700 is compatible with an EHR application capable of recording a single video stream using a video interface such as S-video, composite or a High-Definition video interface as described above. According to some embodiments, communication interface port 8770 may additionally comprise a standard communication port (COM port) of interface computer 8750, for interfacing with a respective serial port in a network computer.

In operation during an endoscopy procedure, it is sometimes desired to record a single video frame as a still image. For example, the physician may advance the endoscope in a body conduit while video images are continuously recorded. When the physician identifies a site of particular interest—for example a local tumor in the body conduit—the physician may wish to take a still image of the tumor. Endoscope system 10 comprises an imaging switch 8780, the activation of which commands image processor to freeze the video display on displays 40*a* and 40*b* and on interface unit display 8720. Activation of imaging switch 8780 further commands storing the frozen images on displays 40*a* and 40*b* to an EHR system through communication interface port 8770. When imaging switch 8780 is activated, image processor 8710 generates, for a pre-determined time period T, which may be for any time period but is preferably between 0.25 and 1 second, a video stream comprising substantially a single image that is the image which is frozen on display 40*a*. Subsequently, when the pre-determined time period T ends, a second single image is generated by image processor 8710, which is the frozen image on display 40*b*. Thus, stills images of a particular site of interest selected by the physician during an endoscopy procedure may be stored sequentially, as an integral part of a video stream communicated from endoscope system 10 to an EHR system through communication interface port 8770. Such still images may also contain textual or other identification data inserted thereon by imaging processor 8710, identifying each image as corresponding to camera 26*a* (and display 40*a*) or to camera 26*b* (and display 40*b*).

Thus, according to some embodiments, interface unit 8700 is configured to receive through two (or more) imaging channels 50*a* and 50*b*, two (or more) video streams associated with two (or more) views generated by endoscope 20. In one embodiment, the interface unit integrates with the hospital system using a protocol such as TCP/IP or file transfer. In another embodiment, the interface unit 8700 does not integrate with the hospital system using a protocol such as TCP/IP or file transfer. Rather, in one embodiment, the interface unit 8700 outputs a new video stream that is a combination of the multiple (left, center and right when there are three) video streams and which also contains additional information on the video stream. This includes patient information, if such information has been entered by the user. Interface unit 8700 is configured to generate a single video stream comprising images associated with image data in the two or more incoming video streams, and to display the single video stream on interface unit display 8720. Interface unit 8700 is yet further configured to generate and to store, in file storage module 8760, files associated with a single video stream generated as described above. In one embodiment, the interface unit 8700 is configured to communicate with a computer network through a communication interface port 8770 for storing a single video stream comprising images associated with the at least two views provided by endoscope 20, whereas the single video stream is communicated to the computer network substantially in real time as an endoscopic procedure is carried out.

Embodiments of endoscope system 10 comprising two imaging channels as described above are provided herein as a non-limiting example only. It should be understood that an interface unit, such as interface unit 8700 and compatible, according to the teachings herein, with an endoscope system having more than two imaging channels, e.g. having three or four imaging channels or having any number of imaging channels, is contemplated.

In one embodiment, the interface unit is associated with an endoscope system comprising three imaging channels. The interface unit is able to receive and independently capture three separate video streams from the endoscope. In this embodiment, the interface unit is capable of recording these as separate video files (left, center, right) or capturing three separate still JPEG files (left, center, right). It does this by use of 3 distinct video capture devices, one for each incoming stream. The software included in the interface unit is able to independently control how these images or video files are recorded to hard disk. For purposes of the current embodiment, all three streams are controlled independently but are triggered simultaneously.

The interface unit includes an interface unit display for displaying the incoming video streams. In one embodiment, the interface unit display is a 1080p display. In one embodiment, the display includes a DVI output that can be converted to any number of other video formats using external converter devices. This stream is sent to an image management system. When the user triggers an image capture event (that is, they want to save three still images from the three independent streams), the interface unit captures and saves the images immediately. In one embodiment, the image capture event is triggered by pressing a button on the endoscope. In another embodiment, the image capture event is triggered by pressing a button on the interface unit or on the interface unit display touchscreen. The interface unit then changes its own display to display a first single still image only and sends a "footswitch" trigger pulse to the image management and documentation capture PC. In one embodiment, there is a serial data connection between the interface unit and the capture PC. The interface panel then changes its own display to display a second single still image and sends another trigger pulse to the capture PC. The process is then repeated for the third still image. As a result, full screen left, center and right individual images are put on the video stream sequentially for the image management capture PC to grab using its frame grabber. This preserves the correct aspect ratio. All of this is done transparent to the user and no additional cropping or other image manipulation is needed.

In one embodiment, the interface unit does not generate the image or video files itself. Rather, the image and video files are generated from the video streams by the capture PC. In another embodiment, the interface unit generates the image and video files itself. In one embodiment, the interface unit includes a file storage module. The images are saved to a hard disk drive on the interface unit. The images are organized based on the procedure number (this is automatically generated each time a capture event is triggered) and also the number in sequence that the photos were taken (2nd captured image, 3rd captured image) and also the orientation of the image (left, center, or right). In one embodiment, the video files are organized in the same manner and are also saved to a hard disk drive on the interface panel.

In various embodiments, other document systems, such as, Provation or Olympus EndoBase, receive the incoming video stream into their video capture cards. As mentioned above, this video signal comes from the DVI output of the interface unit and, if necessary, is converted to either a standard definition video signal (down-converted to S-Video or Composite) or to a 1080p signal using an HD-SDI protocol. This is decided by the capabilities of the video capture card that is inside the receiving documentation system computer. In one embodiment, the interface unit includes a "footswitch" type protocol that outputs from a serial communications port (COM port). This protocol involves changing the state of PIN 4 on a standard 9-pin RS-232 connection. A NULL Modem Cable (9-pin RS-232) is connected between the output COM port on the interface unit and an incoming COM port on the receiving documentation system computer. When a capture event is triggered, the interface units sends the capture PC a "footswitch" type trigger pulse (as mentioned earlier) so the capture PC can capture a frame of video from the outgoing video stream.

In one embodiment, the communication between the interface unit and the image management and communication system capture PC is in one direction from the interface unit to the capture PC. The interface unit does not receive information from the documentation system. In one embodiment, the interface unit does not send any data to the documentation system other than the "footswitch" type trigger pulse.

FIG. 89 schematically depicts a layout of an endoscope system 8810 and an associated interface unit 8900 deployed in an operating room, according to an aspect of some embodiments. A patient 8880 is supported on a bed 8882 and a physician 8884 is employing an endoscope 8820 of endoscope system 8810 in an endoscopic procedure. An assistant 8886 assists physician 8884 on the other side of bed 8882 across from physician 8884.

Endoscope 8820 is connected to a main controller 8830 by a utility cable 8832. Endoscope 8820 provides three simultaneous endoscopic views using three cameras housed in the tip of endoscope 8820. Main controller 8830 is connected to three display screens, 8840*a*, 8840*b*, and 8840*c*, respectively, wherein each display screen is configured to display a corresponding view of the three endoscopic views provided by endoscope system 8810, substantially as described above. Display screens 8840 are positioned facing physician 8884 and possibly elevated so that physician 8884 may conduct the endoscopic procedure by looking at the screen displays and having an undisturbed line of site thereto.

Interface unit 8900 comprises an image processor encased with main controller 8830, and an interface unit display 8920 functionally associated with the image processor 8910. The image processor simultaneously receives image data associated with the three views provided by endoscope 8820 from three respective imaging channels and generates images comprising image data from the three views, whereas the images are displayable on interface unit display 8920. For example, the three cameras of endoscope 8820 may provide three incoming video streams, respectively, and the image processor may then generate a single video stream comprising image data from the three incoming video streams, substantially as described above.

According to some embodiments, interface unit display 8920 is functionally associated with the image processor encased with main controller 8830 by a cable. In some embodiments, interface unit display 8920 is wirelessly associated with the image processor. According to some embodiments, interface unit display 8920 is substantially portable and may be deployed in a multitude of positions within the operating room. Moreover, according to some embodiments, interface unit display 8920 may be easily displaced from position to position within the operating room during a procedure. For example, interface unit display 8920*b* or 8920*c* may be positioned so that both physician 8884 and assistant 8886 can watch the screen thereof, or interface unit display 8920*a* may be positioned facing assistant 8886.

In some embodiments, interface unit 8900 comprises an interface unit computer, functionally associated with main controller 8830 and with the image processor encased therewith, and having substantially similar respective functionality to that of interface unit computer 8750 of FIG. 88 above.

In some embodiments, interface unit 8900 comprises a user interface module 8922 associated with interface unit display 8920, and assistant 8886 may employ user interface module 8922 to command interface unit 8900 and/or interface unit computer, and/or endoscope system 8810. For example, assistant 8886 may employ user interface module 8922 to input and store, in the interface unit computer, patient-related textual information, such as relevant biographical data, before or during an endoscopic procedure. According to some embodiments, user interface module 8922 comprises a touch screen 8924.

According to some embodiments, interface unit computer may communicate with a computer network, substantially as described above and using an access point 8890 installed in the operating room and allowing access to such a computer network. Access point 8890 may comprise a LAN connector to which the interface unit computer is connected through a LAN cable. According to some embodiments, access point 8890 may be a WiFi modem with which the interface unit computer may communicate wirelessly.

Thus, according to an aspect of some embodiments and referring simultaneously to FIGS. 87A through 89, there is provided an interface unit (8700, 8900) configured to functionally associate with an endoscope system (10, 8810) which comprises at least two simultaneously operating imaging channels (50*a*, 50*b*) associated with at least two displays (40*a*, 40*b* in FIGS. 87A and 88; 8840*a*, 8840*b*, and 8840*c* in FIG. 89), respectively. The interface unit comprises an image processor (8710) functionally associated with the at least two imaging channels, and configured to generate images comprising image data received simultaneously from the at least two imaging channels. The interface unit further comprises an interface unit display (8720 in FIGS. 87A and 88, 8920 in FIG. 89), functionally associated with the image processor. Images generated by the image processor and comprising image data from the at least two imaging channels are displayable on the interface unit display.

According to some embodiments, each imaging channel is associated with an image capturing device (26*a*, 26*b*), respectively.

According to some embodiments, the interface unit display is substantially portable.

According to some embodiments, the interface unit display is functionally associated with the image processor wirelessly.

According to some embodiments, the image capturing devices may capture video images, and the image data in each of the at least two imaging channels comprise an incoming video stream corresponding to video images. The image processor is configured to generate a single video stream displayable on the interface unit display, so that reduced-size images corresponding to each incoming video stream are simultaneously displayed on the interface unit display. According to some embodiments, the image processor is configured to generate a single video stream from the at least two incoming video streams substantially in real time.

According to some embodiments, the interface unit further comprises an interface unit computer (8750) operating a files managing system and comprising a files storage module (8760), wherein the interface unit computer is configured to generate and store, in the files storage module, files of images generated by the image processor.

According to some embodiments, the interface unit further comprises a user interface module (8922) allowing a user to command the computer. According to some embodiments, the user interface module comprises a touch screen (8924).

According to some embodiments, the interface unit further comprises a communication channel comprising a communication interface port (8770) configured to allow communication between the interface unit computer and a computer network at least for transferring files between the interface unit computer and the computer network. According to some embodiments, the computer network is a local computer network. According to some embodiments, the local computer network is a hospital network. According to some embodiments, the computer network is the Internet.

According to some embodiments, the communication channel comprises a LAN communication interface port, and operates an Internet Protocol. According to some embodiments, the communication channel comprises a WiFi communication interface port. According to some embodiments, the communication channel comprises a video/audio communication interface port, configured for outputting a video stream. According to some embodiments, the communication interface port comprises an S-video or a composite port. According to some embodiments, the communication interface port comprises an HDMI port.

According to some embodiments, the interface unit is configured to communicate through the communication interface port to a network computer, substantially in real time, a video stream generated by the image processor. According to some embodiments, the image processor is configured, when commanded, to capture a substantially single video frame in each of the imaging channels at the moment of the command and to communicate through the communication interface port to a network computer, a video stream comprising sequentially, still images of the single video frames wherein each such still image is included in the video stream for a pre-determined time period.

According to some embodiments, the interface unit further comprises a synchronization module (8730) functionally associated with at least two of the image capturing devices, and configured for generating a synchronization signal for synchronizing incoming video streams in the imaging channels corresponding to the at least two image capturing devices.

FIG. 90 details how the video controller or the controller circuit board 9020 of the main controller 30 of FIG. 87A (which may be similar to the main control unit 199 of FIG. 1A) operatively connects with the endoscope 9010 and the display units 9050. Referring to FIG. 90, video controller/controller circuit board 9020 comprises a camera board 9021 that controls the power supplies to the LEDs 9011, transmits controls for the operation of image sensor(s) 9012 (comprising one or more cameras) in the endoscope, and converts pre-video signals from image sensors to standard video signals. The image sensor 9012 may be a charge coupled device (CCD) or a complementary metal oxide semiconductor (CMOS) imager. The camera board 9021 receives pre-video signal(s) 9013 generated by the CCD imager and also other remote commands 9014 from the endoscope 9010.

Controller circuit board 9020 further comprises elements for processing the video obtained from the image sensors 9012 through the camera board 9021, as well as other elements for system monitoring and control.

All these elements are connected with the Base Board Module 9052, which is a PCB. In one embodiment, elements which are ICs (Integrated Circuits) are connected by soldering, element 9026 (SOM or System on Module) is connected by mounting, while all other elements are connected by means of cables.

Various elements on the Base Board Module 9052 are described as follows:

FPGA (Field Programmable Gate Array) 9023:

FPGA 9023 is a logic device programmed specifically for the system requirements and performs tasks that may be categorized by two types: logic tasks which must be implemented by hardware (as opposed to software), and logic tasks related to video image processing. In one embodiment, the Base Board Module 9052 includes one or more double data rate type three synchronous dynamic random access memory modules (DDR3) 9033 in communication with the FPGA 9023.

Logic tasks which must be implemented by hardware include, but are not limited to:
1. Initializing some Base Board Module's 9052 ICs upon system power-up;
2. Monitoring the buttons 9040 for White Balance, LED on/off, Air Flow, and Power on/off on the front-panel 9035;
3. Monitoring SOM's 9026 proper operation using a watchdog mechanism;
4. Backing-up some of the system's parameters (example: airflow level), even while the system is switched off; and
5. Communicating with the Camera Board 9021.

Logic tasks related to video image processing include, but are not limited to:
1. Multiplexing video inputs—Each of the multiple imaging elements has several video interfaces which are multiplexed via Video Input Interface 9051. Further, several auxiliaries are multiplexed via Auxiliary Video Input Interface 9025.
2. Optional digital signal processor (DSP) 9022 playback output and DSP record input.
3. Internal test pattern to video outputs via Video Output Interface 9024 to multiple displays.
4. Conversion between cameras' video standard to display video standard.
5. OSD (On Screen Display) insertion, also known as graphic overlay.
6. PIP (Picture-in-Picture).
7. Stitching images from several cameras into one image displayed on a single screen.
8. Image adjustments, such as brightness, contrast, etc.

DSP (Digital Signal Processor) 9022:

DSP 9022 is used for recording compressed (coded) video and playing back decompressed (decoded) video. In one embodiment, the standard of compressed video is H264 or equivalent (such as MPEG).

Operationally, FPGA 9023 selects for the DSP 9022 the desired video to be recorded, i.e. any of the inputs, or, more likely, a copy of one or more of the screens. In the latter case, this includes the OSD and format conversion. In the likely case of the screen's format differing from that of DSP's 9022 required video input format, the FPGA 9023 also converts the screen's format to the desired DSP 9022 format while transmitting video to the DSP 9022.

Auxiliary Video Input Interface 9025:

In one embodiment, the video input to the Auxiliary Video Input Interface 9025 may comprise analog video, such as in CVBS (color, video, blanking, sync), S-Video or $YP_BP_R$ format or digital video (DVI), and may be displayed as such.

SOM (System on Module) 9026:

The SOM 9026 provides an interface to input devices such as keyboard, mouse, and touchscreen via Touch I/F 9027. Through these input devices, together with the buttons 9040 in the Front Panel 9035, the user controls the system's functionality and operational parameters. In one embodiment, a peripheral component interconnect express (PCIe) bus connects the SOM 9026 with the FPGA 9023. Most common types of data traffic over the PCIe are:

a. SOM 9026 to FPGA 9023: Commands (for example, when the user changes operational parameters); and
b. FPGA 9023 to SOM 9026: Registers values, which provide an indication of the internal status, and captured images.

Other Functionalities:

The controller circuit board 9020 may further control one or more fluid, liquid and/or suction pump(s) which supply corresponding functionalities to the endoscope through pneumatic I/F 9028, pump 9029 and check valve 9030. The controller circuit board 9020 further comprises an on-board power supply 9045 and a front panel 9035 which provides operational buttons 9040 for the user.

The camera board 9021 receives video signal 9013 which, in one embodiment, comprises three video feeds, corresponding to video pickups by three endoscopic tip viewing elements (one front and two side-looking viewing elements), as generated by the image sensor 9012. In one embodiment, the three video feed pickups, corresponding to the three viewing elements (the front-looking, left-side looking and right-side looking viewing elements) of an endoscopic tip (such as the three viewing elements of the tip section 200 of FIG. 2A or 2B), are displayed on three respective monitors.

FIG. 91A shows a configuration 9100 of three monitors to display three video feeds respectively, from a front and two side-looking viewing elements of an endoscopic tip, in accordance with an embodiment of the present specification. The configuration 9100 comprises a left-side monitor 9105, a center monitor 9110 and right-side monitor 9115 placed side-by-side or contiguously such that the respective horizontal bottom edges 9106, 9111, 9116 are at the substantially same level. In other words, the geometric centers or centroids of the three monitors 9105, 9110 and 9115 are maintained at the substantially same level 'L1'. In accordance with an embodiment, the center monitor 9110 is a square-screen monitor while the left and right-side monitors 9105, 9115 are rectangular or wide-screen monitors. Additionally, in one embodiment, the wide-screen/rectangular monitors 9105, 9115 are oriented such that their longer edges 9106, 9116 are horizontal.

Persons of ordinary skill in the art would appreciate that the embodiments of the present specification are directed to both still images as well as video signals generated by the viewing elements of the endoscopic tip. Therefore, it is an intent of the inventors that the term 'video' should be understood to encompass both still images as well as moving images and videos. In other words, the aforementioned three video feeds comprise both still image as well as video signals. Also, as would be evident to those of ordinary skill in the art, monitors or display panels are measured/sized in several ways, one of which is by aspect ratios. The aspect ratio of an image is the ratio of the width of the image to its height. Examples of 'square format' aspect ratios typically comprise 4:3 and 5:4, while example 'rectangular' or 'wide-screen' aspect ratios typically comprise 16:9 and 16:10.

In one embodiment, the center monitor 9110 displays the video feed pickup by the front-looking viewing element while the left and right-side monitors 9105, 9115 display video feeds from the two side-looking viewing elements of the endoscopic tip. The three video feeds are generated in native or standard square formats having aspect ratios such as 4:3 or 5:4. While the square center monitor 9110 displays the square formatted video feed 9102 of the front-looking viewing element on full screen without distortion, the wide-screen or rectangular left and right-side monitors 9105, 9115 would either display the square formatted video feeds (from the two side-looking viewing elements) only on a part of the wide-screen or would require the 4:3 or 5:4 aspect ratio of the square formatted video feeds to be modified or modulated to fill up the entire wide-screen of the monitors 9105, 9115, causing unacceptable distortion of the videos and therefore adversely affecting their diagnostic value. Therefore, in accordance with an aspect of the present specification, a main control unit (such as the main controller 30 of FIG. 87A) processes the native or square formatted video feeds for appropriate on-screen display.

In one embodiment, the two square formatted video feeds 9101, 9103 corresponding to the two side-looking viewing elements are processed for display such that the video 9101 is displayed right-aligned on the left-side monitor 9105 and the video 9103 is displayed left-aligned on the right-side monitor 9115. In one embodiment, the aspect ratios of the square formatted video feeds 9101, 9103 are not modulated causing portions 641, 643 of the screens 9105, 9115 to be devoid of video. In other embodiments, the aspect ratios of 4:3 or 5:4 of the two square formatted video feeds 9101, 9103 of the two side-looking viewing elements are partially modulated or modified by an optimal percentage 'p' that allows the two video feeds 9101, 9103 to stretch along the length dimension of the wide-screens 9105, 9110 while ensuring minimal distortion. In accordance with an embodiment, the optimal percentage 'p' is not more than 30%. In other embodiments, the optimal percentage 'p' is 5%, 10%, 15%, 20%, 25% or 30% or any increment therein. Since a modulation of 'p' stretches the two video feeds 9101, 9103 along the length of the wide-screens 9105, 9115 the portions 9141, 9143 are progressively reduced in terms of area with an increase in modulation of the video feeds displayed.

Additionally, the three video feeds 9101, 9102, 9103 corresponding to the front-looking and two side-looking viewing elements of the endoscopic tip are processed for on-screen display such that all three videos 9101, 9102, 9103 on the three monitors 9105, 9110 and 9115 are displayed at the same level vertically.

FIG. 91B shows another configuration 9125 of three monitors to display three video feeds 9101, 9102, 9103 respectively from the front and two side-looking viewing elements of the endoscopic tip, in accordance with an embodiment of the present specification. In configuration 9125 all three monitors, that is, the left-side monitor 9105, center monitor 9110 and right-side monitor 9115, are rectangular or wide-screen monitors. In one embodiment, the center monitor 9110 displays the video feed 9102 picked up by the front-looking viewing element while the left and right-side monitors 9105, 9115 display video feeds 9101, 9103 from the two side-looking viewing elements of the endoscopic tip. The three video feeds 9101, 9102, 9103 are in native or standard square formats having aspect ratios such as 4:3 or 5:4.

In accordance with an embodiment, while the left and right-side monitors 9105, 9115 are oriented such that their longer edges 9106, 9116 are horizontal, the center monitor 9110 is oriented vertically such that its shorter edge 9112 remains horizontal and the longer edge 9111 is vertical. In one embodiment, the three monitors 9105, 9110, 9115 are placed side-by-side or contiguously such that the respective bottom edges 9106, 9112, and 9116 are at the substantially same level 'L2'. The configuration 625, therefore, causes the center monitor 9110 to appear raised with respect to the left and right-side monitors 9105, 9115.

In one embodiment, the two square formatted video feeds 9101, 9103 corresponding to the two side-looking viewing elements are processed for display such that the video 9101 is displayed right-aligned on the left-side monitor 9105 and the video 9103 is displayed left-aligned on the right-side monitor 9115. The square formatted video feed 9102 corresponding to the front-looking viewing element is processed to be rotated for proper viewing and also vertically bottom-aligned for display on the center monitor 9110. The respective alignments of the video feeds 9101, 9102, 9103 on the three monitors 9105, 9110 and 9115 ensure that the videos 9101, 9102, 9103 are displayed at substantially the same level.

FIG. 91C shows configuration 9130 in accordance with another embodiment. In configuration 9130 all three monitors, that is, the left-side monitor 9105, center monitor 9110 and right-side monitor 9115, are rectangular or wide-screen monitors. In one embodiment, the center monitor 9110 displays the video feed 9102 picked up by the front-looking viewing element while the left and right-side monitors 9105, 9115 display video feeds 9101, 9103 from the two side-looking viewing elements of the endoscopic tip. The three video feeds 9101, 9102, 9103 are in native or standard square formats having aspect ratios such as 4:3 or 5:4. In accordance with an embodiment, while the left and right-side monitors 9105, 9115 are oriented such that their longer edges 9106, 9116 are horizontal, the center monitor 9110 is oriented vertically such that its shorter edge 9112 remains horizontal and the longer edge 9111 is vertical. The three monitors 9105, 9110, 9115 are placed side-by-side or contiguously such that the respective top edges 9107, 9113 and 9117 are at the substantially same level 'L3'. The configuration 9130, therefore, causes the center monitor 9110 to appear lowered with respect to the left and right-side monitors 9105, 9115.

In one embodiment, the two square formatted video feeds 9101, 9103 corresponding to the two side-looking viewing elements are processed for display such that the video 9101 is displayed right-aligned on the left-side monitor 9105 and the video 9103 is displayed left-aligned on the right-side monitor 9115. The square formatted video feed 9102 corresponding to the front-looking viewing element is processed to be rotated for proper viewing and also vertically top-aligned for display on the center monitor 9110. The respective alignments of the video feeds 9101, 9102, 9103 on the three monitors 9105, 9110 and 9115 ensure that the videos 9101, 9102, 9103 are displayed at substantially the same level.

FIG. 91D shows configuration 9135 in accordance with yet another embodiment. In configuration 9135 all three monitors, that is, the left-side monitor 9105, center monitor 9110 and right-side monitor 9115, are rectangular or wide-screen monitors. In one embodiment, the center monitor 9110 displays the video feed 9102 picked up by the front-looking viewing element while the left and right-side monitors 9105, 9115 display video feeds 9101, 9103 from the two side-looking viewing elements of the endoscopic tip. The three video feeds 9101, 9102, 9103 are in native or standard square formats having aspect ratios such as 4:3 or 5:4. In accordance with an embodiment, while the left and right-side monitors 9105, 9115 are oriented such that their longer edges 9106, 9116 are horizontal, the center monitor 9110 is oriented vertically such that its shorter edge 9112 remains horizontal and the longer edge 9111 is vertical. Additionally, the three monitors 9105, 9110, 9115 are placed side-by-side or contiguously such that their geometric centers or centroids are maintained at the substantially same level 'L4'. The configuration 9135, therefore, causes the center monitor 9110 to appear vertically in a middle position with respect to the left and right-side monitors 9105, 9115.

In one embodiment, the two square formatted video feeds 9101, 9103 corresponding to the two side-looking viewing elements are processed for display such that the video 9101 is displayed right-aligned on the left-side monitor 9105 and the video 9103 is displayed left-aligned on the right-side monitor 9115. The square formatted video feed 9102 corresponding to the front-looking viewing element is processed to be rotated for proper viewing and also vertically center-aligned for display on the center monitor 9110. The respective alignments of the video feeds 9101, 9102, 9103 on the three monitors 9105, 9110 and 9115 ensure that the videos 9101, 9102, and 9103 are displayed at substantially the same level.

FIG. 91E shows configuration 9140 in accordance with yet another embodiment. In configuration 9140 all three monitors, that is, the left-side monitor 9105, center monitor 9110 and right-side monitor 9115, are rectangular or wide-screen monitors. In one embodiment, the center monitor 9110 displays the video feed 9102 picked up by the front-looking viewing element while the left and right-side monitors 9105, 9115 display video feeds 9101, 9103 from the two side-looking viewing elements of the endoscopic tip. The three video feeds 9101, 9102, 9103 are in native or standard square formats having aspect ratios such as 4:3 or 5:4. In accordance with an embodiment, the three monitors 9105, 9110 and 9115 are oriented vertically such that their shorter edges 9109, 9112, 9118 remain horizontal and the longer edges 9106, 9111, 9116 are vertical. Additionally, the three monitors 9105, 9110, 9115 are placed side-by-side or contiguously such that their geometric centers or centroids are maintained at the substantially same level 'L5'.

In one embodiment, the three square formatted video feeds 9101, 9102, 9103 corresponding to the front-looking and the two side-looking viewing elements are processed to be rotated for proper viewing and also bottom-aligned in one embodiment (as shown in FIG. 6E) and top-aligned in an alternate embodiment for display. The respective alignments of the video feeds 9101, 9102, 9103 on the three monitors 9105, 9110 and 9115 ensure that the videos 9101, 9102, 9103 are displayed at substantially the same level.

While configuration 9100 of FIG. 91A causes portions 9141, 9143 of the left and right-side wide-screen monitors 9105, 9115 to be devoid of video, configurations 9125, 9130, 9135 and 9140 of FIGS. 91B through 91E, respectively, additionally cause portions 9150 and 9151 (relating to configuration 9135 of FIG. 91D) of the center monitor 9110 to be also devoid of video since, in configurations 9125, 9130, 9135 and 9140 native or square formatted video feed 9102 corresponding to the front-looking viewing element is displayed on a rectangular or wide-screen center monitor 9110. Referring to FIGS. 91B through 91E, in one embodiment, the aspect ratios of the three square formatted video feeds 9101, 9102, 9103 (corresponding to the front-looking and two side-looking viewing elements of the endoscopic tip) are not modulated, causing portions 9141, 9150, 9151 (relating to configuration 9135 of FIG. 91D) and 9143 of the respective screens 9105, 9110 and 9115 to be devoid of video. In other embodiments, the aspect ratios of 4:3 or 5:4 of the three square formatted video feeds 9101, 9102, 9103 are partially modulated or modified by an optimal percentage 'p' that allows the three video feeds 9101, 9102, 9103 to stretch along the length/longer dimension of the wide-screens 9105, 9110 and 9115 while ensuring minimal distortion. In accordance with an embodiment, the optimal percentage 'p' is not more than 30%. In other embodiments, the optimal percentage 'p' is 5%, 10%, 15%, 20%, 25% or 30% or any increment therein. Since a modulation of 'p' stretches the three video feeds 9101, 9102, 9103 along the length of the wide-screens 9105, 9110 and 9115 the portions 9141, 9142 and 9143 are progressively reduced in terms of area with an increase in modulation of the video feeds displayed.

In accordance with an aspect of the present specification, the portions 9141, 91509151 (relating to configuration 9135 of FIG. 91D) and 9143 are advantageously utilized to display a plurality of patient related information and/or data. In one embodiment, the patient related information and/or data comprises a plurality of real-time physiological parameters such as patient's pulse rate, oxygen levels, blood pressure or any other vital physiological parameters as would be evident to persons of ordinary skill in the art. In one embodiment, the patient related information and/or data comprises archived images/videos of endoscopic procedures and/or related anatomical anomalies (such as polyps, for example) of the patient. In one embodiment, the physiological parameters are combined with or toggled with previously archived images/videos of an endoscopic procedure similar to the one being carried out and displayed on the screens 9105, 9110 and 9115. This provides a physician with an advantage to compare the anatomical views of previous endoscopic procedures with those of the current procedure to diagnose and/or review anomalies and/or improvements thereof. In one embodiment, the plurality of patient related information and/or data is accessed from electronic storage memory of a main control unit and/or from a local and/or remote hospital where the patient's records are being maintained.

In accordance with an aspect of the present specification, the three monitors 9105, 9110 and 9115 of FIGS. 91A through 91E together provide a panoramic view based on an overlap between fields of view of the three viewing elements (front-looking and the two side-looking viewing elements). FIG. 94 shows an example of a panoramic view portrayed by the three monitors 9405, 9410 and 9415 that respectively display video feeds generated by a left-side, front and a right-side viewing element of an endoscopic tip. Portions 9420 and 9425 show images that fall within an overlap between fields of view of the three viewing elements.

In accordance with an embodiment of the present specification, the three monitors 9105, 9110 and 9115 of FIGS. 91A through 91E are placed side-by-side or contiguously in a linear fashion. That is, the three monitors 9105, 9110 and 9115 are not placed at an angle to each other. However, in accordance with alternate embodiments, the left and right-side monitors 9105, 9115 are angled with reference to the center monitor 9110. Such angled configurations are being described hereunder with reference to FIGS. 92A and 92B.

FIG. 92A shows an embodiment according to the present specification where three monitors 9205, 9210 and 9215 are placed side-by-side or contiguously in a non-linear configuration 9200. In one embodiment, the three monitors 9205, 9210 and 9215 display video feeds 9201, 9202, 9203 from corresponding front-looking and two side-looking viewing elements of an endoscopic tip. In one embodiment, the left and right-side monitors 9205, 9215 are oriented at an angle 'N' with reference to the center monitor 9210 and towards a viewer. The non-linear configuration 9200 advantageously simulates and portrays an actual greater than 180 degree field of view offered together by a front-looking and two side-looking viewing elements of an endoscopic tip. Thus, the video feeds 9201, 9203 from the two side-looking viewing elements having been picked up from the two respective sides of, and from slightly behind, the front-looking viewing element, are correspondingly displayed on the left and right-side monitors 9205, 9215 and slightly closer to the viewer due to the angle 'N'. The angled configuration 9200 provides the viewer with a perceived simulation of the way the front-looking and the two side-looking viewing elements capture respective views/videos 9201, 9202, 9203. In various embodiments, the angle 'N' ranges from 10 to 30 degrees. In one embodiment, the angle 'N' is 20 degrees.

In one embodiment, the three monitors 9205, 9210 and 9215 are standalone display units which are physically placed side-by-side or contiguously and at the same level while the left-side and right-side monitors 9205, 9215 are manually adjustable to form angle 'N' with reference to the center monitor 9210. In one embodiment, the three panels are enabled for vertical adjustments using a clamp or hanger attached to back sides of the each of the three panels wherein the clamp or hanger is adjustable on respective vertical shafts. However, in another embodiment, the three display panels or monitors 9205, 9210 and 9215 are integrated within a unitary frame encasement 9220 as shown in FIG. 92B. Referring now to FIG. 92B, the frame encasement 9220 is manufactured to enable the left and right-side panels 9205, 9215 to be pre-configured at angle 'N' with reference to the center panel 710. In one embodiment, the unitary frame encasement is enabled for vertical adjustments using a clamp or hanger attached to back sides of the unitary frame encasement, wherein the clamp or hanger is adjustable on respective vertical shafts.

In one embodiment, black image stripes 9207 and 9212 are superimposed between the three contiguous display panels 9205, 9210, 9215 of FIG. 92B to ensure that a viewer senses each of the correspondingly displayed contiguous videos 9201, 9202, 9203 as different/distinct, thereby avoiding confusion arising out of a visual overlap between the fields of view of the front and two side-looking viewing elements. In accordance with an embodiment, the black image stripes 9207, 9212 are not more than 6 inches wide.

FIGS. 93A and 93B show first contiguous video feed group 9305, 9310, 9315 and second contiguous video feed group 9306, 9311, 9316 displayed on a single monitor 9325 in accordance with an embodiment of the present specification.

Referring now to FIG. 93A, in one embodiment, a front-looking and two side-looking (left-side looking and right-side looking) viewing elements (hereinafter together referred to as 'three viewing elements') of an endoscopic tip are wide angle viewing elements, wherein each viewing element has a field of view of greater than 100 degrees and up to essentially 180 degrees. Therefore, together, the three viewing elements provide a combined field of view greater than 180 degrees covering the front and two side views. In one embodiment, the combined greater than 180 degrees field of view (based on an overlap between fields of view of the three viewing elements) is processed by a main control unit (such as the main controller 30 of FIG. 87A), and displayed on the single monitor 9325 to simulate the real-life panoramic view while ensuring none or minimal/partial modulation of the native/standard aspect ratios of the three video feeds generated by the three viewing elements.

In accordance with an embodiment of the present specification, the three video feeds 9305, 9310, 9315 of the three viewing elements are combined into a resultant single video frame covering an integrated front and two side views based on an overlap between fields of view of the front and two side-looking viewing elements. In other words, the resultant single video frame represents an integrated field of view combining the fields of views of the three viewing elements. Thereafter, the resultant single video frame is sliced or broken-up into a center video frame 9310 that represents a planar front view of the front-looking viewing element. In one embodiment, the center video frame 9310 covers a sum of X degrees of views on either side (that is, the left and the right sides) of a center of the integrated field of view of the resultant single video frame. In one embodiment, X is 15 degrees. In one embodiment, X is up to 30 degrees for the front viewing element. The portion, of the resultant single video frame, remaining beyond X degrees on the left side of the center of the integrated field of view forms a left video frame 9305 representing a planar left side view of the left side-looking viewing element. Similarly, the portion of the resultant single video frame remaining beyond X degrees on the right side of the center of the integrated field of view forms a right video frame 9315 representing a planar right side view of the right side-looking viewing element. Thus, in accordance with an embodiment, the resultant single video frame representing an integrated field of view by combining the fields of view of the three viewing elements is broken-up or sliced to form three video frames 9305, 9310 and 9315. In one embodiment, the three video frames 9305, 9310 and 9315 are displayed contiguously on the single monitor 9325.

Referring now to FIG. 93B, in accordance with another embodiment of the present specification, a unitary video feed from any one of the three viewing elements is separately sliced or broken up into three video frames 9306, 9311 and 9316 (depending upon the video feed of which viewing element is required to be displayed), since each of the three viewing elements offers a field of view of greater than 100 degrees and essentially up to 180 degrees. In this embodiment, the video feeds from the three viewing elements can be toggled or selected, using toggling/selection buttons on the handle 104 of FIG. 1A (or the handle 22 of FIG. 87A), to display a unitary video feed corresponding to any one of the viewing elements (front-looking viewing element or any one of the left or right-looking viewing elements). Therefore, in one embodiment, a unitary video frame representative of a viewing element, that is toggled or selected for display on the monitor 9325, is sliced or broken-up into a center video frame 9311 that represents a planar front view covering a sum of X degrees of views on either side (that is, the left and the right sides) of the center of field of view of the viewing element. In one embodiment, X is 15 degrees. In one embodiment, X is up to 30 degrees. The portion of the unitary video frame remaining beyond X degrees on the left side of the center of field of view forms a left video frame 9306 representing a planar left side view. Similarly, the portion of the unitary video frame remaining beyond X degrees on the right side of the center of field of view forms a right video frame 9316 representing a planar right side view. Thus, in accordance with an embodiment, the unitary video frame representing a field of view of any one of the three viewing elements is broken-up or sliced to form three video frames 9306, 9311 and 9316. In one embodiment, the three video frames 9306, 9311 and 9316 are displayed contiguously on the single monitor 9325.

In one embodiment, black image stripes 9307 and 9312 are superimposed between the three contiguous video frames 9305, 9310, 9315 of FIG. 93A and the three contiguous video frames 9306, 9311, 9316 of FIG. 93B to ensure that a viewer senses each of the three contiguous video frames as different or distinct. In accordance with an embodiment, the black image stripes 9307, 9312 are not more than 6 inches wide.

Persons of ordinary skill in the art would appreciate that the planes of left, center and right side views are not coplanar. Therefore, in one embodiment, the left and right video frames 9305, 9315 as well as the video frames 9306, 9316 are displayed in a slightly skewed or twisted form, as shown in FIGS. 93A and 93B, with reference to the respective center video frames 9310 and 9311 to simulate the real-life non-coplanar views generated by the three viewing elements of the endoscopic tip.

In one embodiment, the first and second contiguous video frame groups 9305, 9310, 9315 and 9306, 9311, 9316 are natively square formatted with aspect ratios 4:3 or 5:4. In one embodiment, the monitor 9325 is a rectangular or wide-screen display monitor. In an alternate embodiment, the monitor 9325 is a square display monitor.

According to an embodiment, the native or standard square aspect ratios of 4:3 or 5:4 of the first and second contiguous video frame groups 9305, 9310, 9315 and 9306, 9311, 9316 are not modified or modulated for display on to the monitor 9325. In accordance with an aspect of the present specification, the square aspect ratios of 4:3 or 5:4 of the first and second contiguous video frame groups 9305, 9310, 9315 and 9306, 9311, 9316 are partially modified or modulated (for display on to the monitor 9325) by an optimal percentage 'p' while ensuring minimal distortion. In accordance with an embodiment, the optimal percentage 'p' is not more than 30%. In other embodiments, the optimal percentage 'p' is 5%, 10%, 15%, 20%, 25% or 30% or any increment therein.

There is provided, according to an aspect of some embodiments, an endoscope configured to provide quasi-simultaneously N views, N being greater than 1. The endoscope comprises N optical systems configured to collect light from directions associated with the N views, and further comprises M image capturing devices, where M is smaller than N. The image capturing devices are configured to capture light collected by the N optical systems, thereby providing N views quasi-simultaneously. According to some embodiments, M equals to one. According to some embodiments, M equals to two. According to some embodiments, N equals to three.

FIG. 95A schematically depicts an embodiment of tip 9510 of an endoscope configured to provide multiple views according to the teachings of this specification. Tip 9510 comprises three optical systems, 9520, 9530 and 9540, respectively, and a single image capturing device 9550 having a light sensitive surface 9552. Center optical system 9520 comprises a center lens assembly 9522. Center optical system 9520 is directed forward, thereby being configured to collect light substantially from a forward direction of tip 9510. Center optical system 9520 is further configured to generate from such collected light an image on a center portion 9552a of light sensitive surface 9552, thereby allowing tip 9510 to provide a forward directed view.

Left optical system 9530 comprises a left side lens assembly 9532 and a left side prism 9534. Left optical system 9530 is directed to a direction substantially perpendicular to the forward direction of tip 9510, referred to as a left direction, thereby being configured to collect light substantially from a left direction of tip 9510. Left side prism 9534 is configured to deflect light generally coming from the left direction of tip 9510 and collected by left side lens assembly 9532 towards image capturing device 9550. Left optical system 9530 is further configured to generate from such light collected by left side lens assembly 9532 an image on a left portion 9552b of light sensitive surface 9552, thereby allowing tip 9510 to provide also a left side directed view. Left portion 9552b is positioned substantially sidewise to center portion 9552a.

Right optical system 9540 comprises a right side lens assembly 9542, and a right side prism 9544. Right optical system 9540 is directed to a direction substantially perpendicular to the forward direction of tip 9510, referred to as a right direction, thereby being configured to collect light substantially from a right direction of tip 110. Right side prism 9544 is configured to deflect light generally coming from the right direction of tip 9510 and collected by right side lens assembly 9542, towards image capturing device 9550. Right optical system 9540 is further configured to generate from such light collected by right side lens assembly 9542 an image on a right portion 9552c of light sensitive surface 9552, thereby allowing tip 9510 to provide also a right side directed view. Right portion 9552c is positioned substantially sidewise to center portion 9552a.

In operation, an image is obtained from image capturing device 9550 using any suitable technique adapted to obtain images from image capturing device 9550. For example, in some embodiments, image capturing device 9550 comprises a CCD, and obtaining an image therefrom comprises applying a scan signal to the CCD as is known in the art. A typical image 9560 obtained from image capturing device 9550 is in a form of a split screen, as is schematically depicted in FIG.

95B. Image 9560 generally comprises three fields 9562*a*, 9562*b* and 9562*c*, associated with the three portions 9552*a*, 9552*b* and 9552*c*, respectively, wherein each field includes an image obtained from a center view, a left view and a right view, respectively, by tip 9510. Images associated with the three fields 9562*a*, 9562*b*, and 9562*c* are consequently separated to form separated still images or separated sequences of video images, associated respectively with each of the three views, using any suitable technique of image processing as is known in the art.

FIG. 96 schematically depicts an embodiment of tip 9610 of an endoscope configured to provide three views, namely a left view, a forward view and a right view, according to the teachings herein. Tip 9610 comprises three optical systems 9620, 9630 and 9640, associated with a forward view, a left view and a right view, respectively. Tip 9610 further comprises a single image capturing device 9650 having a light sensitive surface 9652. Tip 9610 further comprises a stepwise rotating optical element. In one embodiment, the stepwise rotating optical element comprises a semi-transparent mirror 9662. In another embodiment, the stepwise rotating optical element comprises a lens. Semi-transparent mirror 9662 is associated with a controllably rotatable component such as an actuator or a step motor. Upon command, the controllably rotatable component rotates and positions semi-transparent mirror 9662 in one of three pre-defined positions, associated with the three views available by tip 9610.

Left optical system 9630 is directed to a direction substantially perpendicular to the forward direction of tip 9610, referred to as a left direction, thereby being configured to collect light substantially from a left direction of tip 9610. When semi-transparent mirror 9662 is positioned in position 9662*a*, semi-transparent mirror 9662 reflects light collected by left optical system 9630 towards light sensitive surface 9652 of image capturing device 9650. Accordingly, when semi-transparent mirror 9662 is positioned in position 9662*a*, left optical system 9630 and semi-transparent mirror 9662 are configured together to generate an image on light sensitive surface 9652 from light collected from the left direction, thereby allowing tip 9610 to provide a left side directed view.

Center optical system 9620 is directed forward, thereby being configured to collect light substantially from a forward direction of tip 9610. When semi-transparent mirror 9662 is positioned in position 9662*b*, light collected by optical system 9620 penetrates through semi-transparent mirror 9662 towards light sensitive surface 9652. Accordingly, when semi-transparent mirror 9662 is positioned in position 9662*b*, center optical system 9620 and semi-transparent mirror 9662 are configured together to generate an image on light sensitive surface 9652 from light collected from the forward direction, thereby allowing tip 9610 to provide a forward directed view.

Right optical system 9640 is directed to a direction substantially perpendicular to the forward direction of tip 9610, referred to as a right direction, thereby being configured to collect light substantially from a right direction of tip 9610. When semi-transparent mirror 9662 is positioned in position 9662*c*, semi-transparent mirror 9662 reflects light collected by right optical system 9640 towards light sensitive surface 9652. Accordingly, when semi-transparent mirror 9662 is positioned in position 9662*c*, right optical system 9640 and semi-transparent mirror 9662 are configured together to generate an image on light sensitive surface 9652 from light collected from the right direction, thereby allowing tip 9610 to provide a right side directed view.

In operation, an image is obtained from image capturing device 9650 using any suitable technique adapted to obtain images from image capturing device 9650. Typically, obtaining an image from image capturing device 9650 may take a pre-determined time 'Tim'. For example, in some embodiments, image capturing device 9650 comprises a CCD, and obtaining an image therefrom comprises applying a scan signal to the CCD as is known in the art. The time 'Tim' to obtain a single image from a CCD substantially corresponds to the time of a complete scan of the CCD. According to some embodiments of use, rotation of semi-transparent mirror 9662 is synchronized with time periods 'Tim' of obtaining images from image capturing device 9650. For example, sequentially obtaining images corresponding to a left view, a center view and a right view, respectively, comprises iterating the steps of rotating semi-transparent mirror 9662 and positioning it in position 9662*a*; obtaining a left view image; rotating semi-transparent mirror 9662 and positioning it in position 9662*b*; obtaining a forward view image; rotating semitransparent mirror 9662 and positioning it in position 9662*c*; and obtaining a right view image.

According to some embodiments, tip 9610 further comprises a shutter assembly 9670 comprising left shutter 9672*a*, a center shutter 9672*b* and a right shutter 9672*c*, corresponding to left optical system 9630, center optical system 9620 and right optical system 9640, respectively. Shutter assembly 9670 is configured to allow passage of light to image capturing device 9650 from no more than one of the three directions—left, forward and right. In operation, shutter assembly 9670 is substantially synchronized with semi-transparent mirror 9662, so that when semi-transparent mirror 9662 is positioned in position 9662*a*, left shutter 9672*a* is open and center shutter 9672*b* and right shutter 9672*c* are closed, thus allowing light collected by left optical system 9630 to form an image on light sensitive surface 9652, and blocking light coming from the forward direction and from the right direction. Likewise, when semi-transparent mirror 9662 is positioned in position 9662*b*, center shutter 9672*b* is open and right shutter 9672*c* and left shutter 9672*a* are closed, and when semi-transparent mirror 9662 is positioned in position 9662*c*, right shutter 9672*c* is open and left shutter 9672*a* and center shutter 9672*b* are closed.

FIG. 97A schematically depicts an embodiment of tip 9710 of an endoscope configured to provide three views, namely a left view, a forward view and a right view, according to the teachings herein. Tip 9710 comprises three optical systems, 9720, 9730 and 9740, associated with a left view, a forward view and a right view, respectively. Tip 9710 further comprises a single image capturing device 9750 having three light sensitive surfaces 9752*a*, 9752*b* and 9752*c*, facing optical systems, 9720, 9730 and 9740, respectively. Left optical system 9720 is configured to collect light substantially from a left direction of tip 9710 and to generate an image on light sensitive left surface 9752*a*, thereby allowing tip 9710 to provide a left side directed view. Likewise center optical system 9730 is configured to collect light substantially from a forward direction of tip 9710 and to generate an image on light sensitive center surface 9752*b*, and right optical system 9740 is configured to collect light substantially from a right direction of tip 9710 and to generate an image on light sensitive right surface 9752*c*, thereby allowing tip 9710 to provide a center directed view and a right side directed view, respectively.

In operation, images are obtained from image capturing device 9750 from each light sensitive surface independently. According to some exemplary embodiments, image capturing device 9750 comprises three CCD elements assembled together to form three light sensitive surfaces 9752*a*, 9752*b*, and 9752*c*, respectively. A single scan circuitry provides scan signals to scan the three CCD elements. According to some embodiments, a substantially same scan signal is employed to scan light sensitive elements 9752*a*, 9752*b* and 9752*c*. Images corresponding to three views, for example three video streams, are thus obtained substantially simultaneously from image capturing device 9750.

FIG. 97B schematically depicts an embodiment of tip 9715 of an endoscope configured to provide three views, namely a left view, a forward view and a right view, according to the teachings herein. Tip 9715 comprises three optical systems, 9725, 9735 and 9745, associated with a left view, a forward view and a right view, respectively. Tip 9715 further comprises a single image capturing device 9755 having three light sensitive elements 9753*a*, 9753*b* and 9753*c*, facing optical systems, 9725, 9735 and 9745, respectively. Light sensitive elements 9753*a* and 9753*b* are mechanically connected to each other by a flexible member 9754 and light sensitive elements 9753*b* and 9753*c* are mechanically connected to each other by a flexible member 9756. When assembled, light sensitive element 9753*a* are arranged to be tilted at an angle relative to light sensitive element 9753*b*, wherein the angle is selected from within a pre-determined range.

For example, in some embodiments, light sensitive element 9753*a* is assembled to be perpendicular to light sensitive element 9753*b*. According to some embodiments, light sensitive element 9753*a* is arranged to be at a desired angle between zero degrees and ninety degrees relative to light sensitive element 9753*b*. Likewise, light sensitive element 9753*c* is arranged to be tilted at an angle relative to light sensitive element 9753*b*, wherein the angle is selected from within a pre-determined range. In some embodiments, light sensitive element 9753*c* is assembled perpendicular to light sensitive element 9753*b*. According to some embodiments, light sensitive element 9753*c* is arranged to be at a desired angle between zero degrees and ninety degrees relative to light sensitive element 9753*b*. According to some embodiments, left optical system 9725 and right optical system are arranged to be directed to a direction to which light sensitive elements 9753*a* and 9735*b*, respectively, face. According to some embodiments, tip 9715 provides a left view and a right view that are not necessarily perpendicular to a forward view. According to some embodiments, left optical system 9725 and right optical system 9745 are controllably tilted by an alignment module so as to collect light from a selected direction having an angle with the forward direction of tip 9715 between zero and ninety degrees. According to some embodiments, when left optical system 9725 and/or right optical system 9745 are controllably tilted as described above, light sensitive elements 9753*a* and 9753*c*, respectively, are accordingly tilted to be facing optical systems 9725 and 9745 respectively. According to some embodiments, tilting optical systems 9725 and/or 9745 and correspondingly obtaining a left view and/or a right view, which divert from perpendicular to a forward view, are employed in real time, during an endoscopy procedure. According to some embodiments, obtaining images from image capturing device 9755 is substantially similar to obtaining images from image capturing device 9750 as described above.

FIG. 98 schematically depicts an embodiment of a tip 9810 of an endoscope configured to provide multiple views according to the teachings herein. Tip 9810 comprises three optical systems, 9820, 9830 and 9840, respectively, a center image capturing device 9850 and a side image capturing device 9860, having corresponding light sensitive surfaces 9852 and 9862, respectively. Center optical system 9820 comprises a center lens assembly 9822. Center optical system 9820 is directed forward, thereby being configured to collect light substantially from a forward direction of tip 9810. Center optical system 9820 is further configured to generate from such collected light an image on center light sensitive surface 9852, thereby allowing tip 9810 to provide a forward directed view.

Left optical system 9830 comprises a left side lens assembly 9832, and a left side prism 9834. Left optical system 9830 is directed to a left direction, thereby being configured to collect light substantially from a left direction of tip 9810. Left side prism 9834 is configured to deflect light generally coming from the left direction of tip 9810 and collected by left side lens assembly 9832, towards side image capturing device 9860. Left optical system 9830 is further configured to generate from such light collected by left side lens assembly 9832 an image on a left portion 9860*a* of light sensitive side surface 9862, thereby allowing tip 9810 to provide also a left side directed view.

Right optical system 9840 comprises a right side lens assembly 9842, and a right side prism 9844. Right optical system 9840 is directed to a right direction thereby being configured to collect light substantially from a right direction of tip 9810. Right side prism 9844 is configured to deflect light generally coming from the right direction of tip 9810 and collected by right side lens assembly 9842, towards side image capturing device 9860. Right optical system 9840 is further configured to generate from such light collected by right side lens assembly 9842 an image on a right portion 9860*b* of light sensitive side surface 9862, thereby allowing tip 9810 to provide also a right side directed view. Right portion 9860*b* is positioned substantially sidewise to left portion 9860*a*.

In operation, images are obtained independently from center image capturing device 9850 and from side image capturing device 9860. Images obtained from side image capturing device 9860 are generally in split screen format, having a left field and a right field, corresponding to left view and right view received from left optical system 9830 and from right optical system 9840, respectively, substantially as described above regarding image 9560 and fields 9562*a*, 9562*b* and 9562*c* in FIG. 95 above. Images obtained from center image capturing device 9850 correspond exclusively to the forward direction view.

FIG. 99 schematically depicts an embodiment of a tip 9910 of an endoscope configured to provide multiple views according to the teachings herein. Tip 9910 comprises three optical systems, 9920, 9930 and 9940, respectively, and a double sided image capturing device 9950, having two light sensitive surfaces 9952 and 9954 on the two sides of double sided image capturing device 9950, respectively.

Center optical system 9920 comprises a center lens assembly 9922. Center optical system 9920 is directed forward, thereby being configured to collect light substantially from a forward direction of tip 9910. Center optical system 9920 is further configured to generate from such collected light an image on center light sensitive surface 9952, thereby allowing tip 9910 to provide a forward directed view.

Left optical system 9930 comprises a left side lens assembly 9932, and a left side prism 9934. Left optical system 9930 is directed to a left direction, thereby being configured to collect light substantially from a left direction of tip 9910. Left side prism 9934 is configured to deflect light generally coming from the left direction of tip 9910 and collected by left side lens assembly 9932, towards image capturing device 9950. Left optical system 9930 is further configured to generate from such light collected by left side lens assembly 9932 an image on a left portion 9954*a* of light sensitive side surface 9954, thereby allowing tip 9910 to provide also a left side directed view.

Right optical system 9940 comprises a right side lens assembly 9942 and a right side prism 9944. Right optical system 9940 is directed to a right direction, thereby being configured to collect light substantially from a right direction of tip 9910. Right side prism 9944 is configured to deflect light generally coming from the right direction of tip 9910 and collected by right side lens assembly 9942 towards image capturing device 9950. Right optical system 9940 is further configured to generate from such light collected by right side lens assembly 9942 an image on a right portion 9954*b* of light sensitive side surface 9954, thereby allowing tip 9910 to provide also a right side directed view. Right portion 9954*b* is positioned substantially sidewise to left portion 9954*a*.

In some embodiments of operation, images are obtained from image capturing device 9950 substantially similarly to obtaining images from image capturing devices 9750 and 9755 in FIGS. 97A and 97B above. Generally, a single scan signal may be employed in embodiments of image capturing device 9950 comprising a double sided CCD or two CCD's assembled back to back. Images obtained from light sensitive side surface 9954 are generally in split screen format, having a left field and a right field, corresponding to left view and right view received from left optical system 9930 and from right optical system 9940, respectively, substantially as described above regarding side image capturing device 9860 in FIG. 98. Images obtained from center light sensitive surface 9952 correspond exclusively to the forward direction view.

Referring back to FIG. 90 again, it should be appreciated that in order to deliver a synchronized display from multiple cameras rapidly and in real-time to the physician, image data from each of the camera sensors should be processed in real-time and synchronized before display. This should be done in a manner that minimizes latency, yet ensures a high quality output. Thus, the video processing architecture of the present specification enables three major functionalities:

a) signal transmission and control for each camera in a manner that optimally shares resources, thereby decreasing the total number of signals which need to be transmitted over cable, resulting in an ability to use a smaller/thinner cable for signal transport while still allowing for a high signal to noise ratio;

b) processing of camera data, wherein data are separately processed to ensure no latency and then synchronized; and c) transmitting the processed data for display in a manner that optimally shares resources.

These functions of the video processing architecture are further explained with reference to FIGS. 100 and 101. For an embodiment in which one front camera and two side cameras are employed, a conventional video processing system would require a transmission of 36 separate signals, in which each camera would have 12 signals associated with it, including 11 control signals and 1 video return. Similarly, for an embodiment in which two cameras (such as one front and one side camera or just two side cameras) are employed, a conventional video processing system would require a transmission of 24 separate signals. In one embodiment, the following signals are required in order to effectively operate a camera and receive video signals from the camera:

1. V01—Vertical Register Clock
2. V02—Vertical Register Clock
3. V03—Vertical Register Clock
4. V04—Vertical Register Clock
5. H01—Horizontal Register Clock
6. H02—Horizontal Register Clock
7. RG—Reset Gate Clock
8. $V_{DD}$—Supply voltage (15V)
9. $V_L$—Supply voltage (−7.5V)
10. SUB—Substrate Clock
11. LED—Light Emitting Diodes Voltage
12. Vout—Video Out Signal
13. Ground While the Ground signal is common, transmitting the rest of the 36 signals (12 signals for each of the three cameras) to and from the circuit board, such as the electronic circuit board assembly 400 of FIGS. 2A, 2B, would require a cable with a diameter of approximately 3 millimeters in order to achieve an acceptable signal to noise ratio, which, given the constrained space in the endoscope tip, is too bulky. Using cables with a smaller diameter would result in video signals with unacceptably high noise levels.

Referring back to FIG. 90, the present embodiments are able to employ a cable with a smaller diameter, i.e. approximately 2.5 millimeters or less, thereby saving valuable space in the endoscope internal volume. To do so, an embodiment of the disclosed video controller 9020 (as shown in FIG. 90) generates a set of signals, smaller/lesser in number than the 36 signals that are conventionally required, which are transmitted by the controller 9020 to the circuit board (such as the electronic circuit board assembly 400 of FIGS. 2A, 2B) in the endoscope tip and then processed by the circuit board to provide each camera with the specific signal instructions needed. This allows the system to manipulate all the requisite signals without having to use 36 different signals. Also, it should be appreciated by those of ordinary skill in the art that while the signal processing details in the disclosed video controller 9020 are being described for endoscope embodiments that use three viewing elements, these are equally applicable to embodiments that use two viewing elements as well.

In one embodiment, the first nine control signals (V01, V02, V03, V04, H01, H02, RG, VDD, and VL) are shared among cameras by splitting the signal in the circuit board (such as the electronic circuit board assembly 400 of FIGS. 2A, 2B) in the optical tip of the endoscope 9010 and branching in the camera head. The remaining signals are not shared. For example, the SUB signals are specific for each camera, as they are used for "Shutter Control". Therefore, in such an embodiment, the system uses individual SUB1, SUB2 and SUB3 signals for the three cameras. Additionally, the LED circuits, which are used for illumination, receive power separately and individually. Therefore, in such an embodiment, there are three signals—LED1, LED2 and LED3 for LED power voltages. With nine signals being shared, the total number of signals required to operate with three cameras reduces from 36 to 18, including three individual video output signals. Thus, the disclosed video controller 9020 generates a plurality of signals specific to each of the cameras/viewing elements and a plurality of shared signals which are not specific to each of the cameras/viewing elements, thereby reducing the total number of signals required to be transmitted.

FIG. 100 is a table detailing the shared and individual signals for each camera. As can be seen from the figure, the sets of signals 10001 and 10002 are jointly shared or common for all the cameras, whereas the sets of signals

10003, 10006 and 10009 are individual signals for the front, two side cameras and the corresponding LEDs. Amongst other signals, Functional GND 10011 is a common signal for all cameras and additional electronic devices in the scope. Signals "+3.3V Secondary Insulated" 10012, SCL_1 10013, and SDA_1 10014 are signals and power for electronic devices, such as memory, that come with additional manufacturer information, switches and switch interface, etc.

FIG. 101 illustrates the various signals that connect camera board 10015 to the CCD cameras and other components in the video processing unit. As can be seen from the figure, there are 13 CCD control signals (9 common, one Ground and 3 individual—SUB1, SUB2 and SUB3) 10016. Also there are 3 signals for LED power 10017 and 3 pre-video output signals 10018 from the CCD cameras.

The other signals (3×CCIR 656 Digital Video, 3×CVBS and 3×S-Video) provide interface with components such as FPGA processor, video output interface, and Digital Signal Processor (DSP), among other components. These components have been described with reference to FIG. 90.

It may be noted that while sharing signals, critical operational constraints should be kept in mind in order to maintain an acceptable signal to noise ratio (SNR) and to not compromise on the output image quality. Referring back to FIG. 90, in one embodiment, the endoscope video processing system 9020 transmits and/or receives at least the Video output, RG, H1, and H2 signals via a coaxial type cable. In one embodiment, the endoscope video processing system 9020 transmits and/or receives the signals using a cable diameter (thickness) no greater than 2.5 mm. In one embodiment, the endoscope video processing system 9020 transmits and/or receives the signals using conductors no smaller than 46 AWG to avoid creating an unacceptable signal to noise ratio.

In one embodiment, the endoscope video processing system 9020 transmits and/or receives the signals using a cable diameter (thickness) no greater than 2.06 mm in diameter. In one embodiment, the endoscope video processing system 9020 transmits and/or receives the signals using a 42AWG coaxial cable with six channels.

In one embodiment, the endoscope video processing system 9020 transmits and/or receives the signals using a cable that is sized based on the number and/or bandwidth of the signals. For example, if one transmits and receives a total of 18 individual signals and shares 9 of those signals between two or more cameras, then one may use a cable having a diameter in the range of 2-2.5 millimeters, thereby enabling an acceptable signal to noise ratio and an acceptable cable size. Persons of ordinary skill in the art should note that any number of signals can be shared, including less than 9 signals, thereby resulting in an increased number of signals generated specific to each camera. In one embodiment, if, however, less than 6 signals are shared, then the total number of individual signals transmitted and received increases to 24, thereby requiring that the cable diameter exceed 2.5 mm or that the internal conductors be smaller than 46AWG (which means that the internal conductors are 42AWG, 40AWG or decreasing increments therefrom in case the cable diameter is retained at less than 2.5 mm), which would not only result in an unacceptable signal to noise ratio (SNR), but also limit the ability to assemble (solder) the components of the circuit board properly. Thus, the system 9020 of present specification optimally shares the signals without compromising on SNR. According to an aspect of the present specification, in endoscope embodiments having two cameras, an optimal sharing of signals is enabled by having the number of signals specific to each of the two cameras to be at least 2 and the number of signals shared to be at least 6. Again, in endoscope embodiments having three cameras, an optimal sharing of signals is enabled by having the number of signals specific to each of the three cameras to be at least 3 and the number of signals shared to be at least 6.

Signal sharing may occur by having the video controller 9020 send a single shared signal to the circuit board (such as the electronic circuit board assembly 400 of FIGS. 2A, 2B), which then applies one or more pre-programmed functions to the shared signal to transform the shared signal into three separate signals, one for each of the three cameras in an endoscope embodiment that uses three cameras (or into two separate signals, one for each of the two cameras in an endoscope embodiment that uses two cameras). It should be appreciated that a "shared signal" is a signal that is addressed to (or directed toward) a single destination, such as a particular circuit, processor, or sensor, and then split, modulated, modified, or otherwise manipulated to create more than one signal of the same type, each of which is addressed to (or directed toward) different destinations, such as different circuits, processors, or sensors. It should be appreciated that a signal "specific to a camera or sensor" is a signal that is addressed to, directed toward, or sent from a single destination to another destination, and is not adapted to be split, modulated, modified, or otherwise manipulated to create more than one signal of the same type, each of which is addressed to (or directed toward) different destinations, such as different circuits, processors, or sensors. In one embodiment, the pre-programmed function splits the received signal and amplifies it for use. In another embodiment, the pre-programmed function scales, adjusts, divides, or multiplies the received shared signal in a manner that is specific to the particular camera. In one embodiment, to achieve effective signal sharing, high speed common/shared signals such as H1, H2, RG or similar produced in the camera board, are produced such that:

Sources of signals are matched by impedance with coaxial cable impedance;

Signals are pre-formed in sources in a manner that compensates for disturbances arising out of factors such as cable parameters not matching with imagers (CCD sensors) and other factors;

Parameters for pre-forming signals are stored in a camera board on-board memory or in the scope; and In the camera head (tip of the endoscope), signals are distributed between imagers.

As mentioned above, each camera generates its own individual video output signal. This raw video data are then processed for display. The video streams received from the different cameras may be displayed separately on display, either side-by-side or interchangeably, wherein the operator may switch between views from the different cameras manually. Alternatively, these video streams may be processed by a controller to combine them into a single, panoramic video frame based on an overlap between fields of view of the cameras. In one embodiment, the three output video streams may be displayed on three different monitors.

In one embodiment, each video signal is separately processed which enhances the speed of processing. However, this may result in a potential lack of synchronization between the signals. Conventional imaging systems use frame grabbers or memories to synchronize different cameras. These, however, are bulky and not suitable for synchronizing multiple cameras in an endoscopic system. To address this problem, the system of the present specification generates specific synchronization signals to co-ordinate the outputs of CCD sensors. Thus, in accordance with an embodiment, the common/shared signals also include synchronization signals for all the cameras. The shared signals also include clock signals for all the cameras. The shared signals include voltage supply signals for all the cameras.

FIGS. 102A and 102B are block diagrams illustrating exemplary synchronization methods. Referring to FIG. 102, the chipset of the system of the present specification has two main components—DSP 10201 and CDS 10202. CDS 10202 comprises the part of camera board that is responsible for the creation of synchronization signals for each CCD camera sensor 10203. The synchronization signals include H1, H2 and RG (horizontal HF sync), as described with reference to FIG. 100 earlier. DSP 10201 processes the raw video data received from the CCD cameras.

Initially, a same "clock" generates a common signal that is transmitted to all of the three cameras. That is, a signal from the clock is amplified, used to drive the circuitry, and used to concurrently trigger a rest signal for the video processing circuitry.

Referring to FIG. 102B, in order to synchronize the video signals, H1, H2 and RG, signals from the CDS 10204 are neglected. Instead, the synchronization signals (CLK) 10205 are generated digitally by using FPGA. By generating the synchronization signals explicitly, the signal timing (Phase), signal frequency (signal width) and signal amplitude can be controlled. The video data received from the CCDs 10206 is processed by the DSP 10207. The CLK signal phase, frequency and amplitude are so adjusted that the video information is triggered exactly on a valid RG signal. Adjusting the CLK signal parameters allows driving and locking on the video signals from all the camera sensors at the same time.

FIGS. 103A and 103B are block diagrams illustrating a method of compensation for high speed CCD synchronization signals time delay in coaxial cable. Referring to FIG. 103A, DSP 10301 produces a plurality of synchronization signals 10310, including H1, H2, RG for CCD imager 10303 and a plurality of signals for component CDS (Correlated Double Sampling) 10302. One of the functions of CDS 10302 is to sample pre-video signal 10320 produced by CCD imager 10303. In a conventional video camera, the imager is placed near (on one board) with DSP and CDS, so that the sampling occurs in similar time with pre-video signal coming into the CDS. In a system with a long cable, the CDS remains placed near the DSP, however, both the CDS and DSP are placed far from imager. Therefore, the pre-video signal comes into the CDS with a time lag. Additionally, high speed synchronization signals such as H1, H2, RG signals are delayed over a long cable. To compensate for this time lag, in one embodiment, the system has additional components 10304, 10305 and 10306, as shown in FIG. 103B. Referring now to FIG. 103B, these components produce the high speed signals H1*, H2*, RG* 10330 and use the original signals H1, H2, RG 10340 from DSP 10307 as base. In one embodiment, component 10304 is placed in an FPGA and produces code 10350 for high speed signals build. Code 10350 uses parameters from memory 10308 according to the scope type, and includes values of signals in any point of time. In one embodiment, component 10304 is a modulator, adapter or converter that modifies the original signals based upon data/parameters from memory 10308 according to the scope type. Code 10350 comes into Analog-to-Digital Converter 10305 and is converted to pulses 10330 similar to H1, H2, RG, but pre-formed for compensation of cable disturbances. From ADC 10305 signals come to amplifiers and impedance matching element 10306.

Thus, the video processing system of the present specification also incorporates a cable compensation methodology. One of ordinary skill in the art would appreciate that different kinds of endoscopic devices have different cable lengths on the scopes. The variation in the cable length is compensated by manipulating the synchronization signals in such a manner that all three CCDs will experience the signals as expected from their side. This is done by following a process similar to that described above, by which the timing and amplitude of the synchronization signal is adjusted. Thus, for each cable length, different timing and amplitude is set. Further, this mechanism can also be automated by "sensing" the feedback from the CCD and tuning the appropriate parameters accordingly.

In accordance with an aspect of the present specification, systems and methods are provided for managing different views in a cohesive manner. In one embodiment, the functionality of switching between views is seamlessly integrated with the image capture functionality.

In one embodiment, the user (physician) is provided with a simple and user friendly interface that helps him or her to toggle between multiple views and manipulate images. The interface also assists the user in better navigation of the endoscope through difficult areas. In one embodiment, the user interface assists the physician in detecting anomalies and also helps the physician to perform the endoscopic procedure in accordance with best practices guidelines.

FIG. 104 illustrates three displays 10041, 10042 and 10043 being operated with a single endoscope 10044. A person of ordinary skill in the art would appreciate that an endoscope is a heavy and difficult to manipulate instrument. Therefore, managing three different displays along with the endoscope may make the process more difficult and complex for the physician handling the endoscope. In order to simplify managing views on three screens, the present specification provides a user friendly and intuitive interface, such that the user is assisted by having three views and is not inhibited in carrying out the endoscopic procedure.

Therefore, in a preferred embodiment, the controls for manipulation are provided by means of buttons 10045 located on the endoscope handle itself. Using these buttons, the physician can easily manipulate images to the benefit of the procedure. Further, in order that the physician instantly recognizes which of the three displays is active or which view the controls are focused on, in one embodiment, an indication is provided on the relevant display. For example, if the second display 10042 is currently active, "Screen 2" 10046 is displayed on the screen. This implies that the physician is currently focusing on the display 10042, and may further use the buttons 10045 on the endoscope handle to manage or manipulate the view.

FIG. 105A illustrates an exemplary configuration of the endoscope handle 10051. Button 10052, when pressed, can be used to toggle between different views. In one embodiment, each time button 10052 is pressed, the next view is activated. As mentioned above, switching can be done between different views on the same monitor, or between different monitors. Button 10053 can be used to capture a still from the video or image being displayed. Button 10054 can be used to record a video; the same button 10054, when pressed again, can be used to stop the recording. In one embodiment, the record function when activated, enables recording of all the views simultaneously.

FIG. 105B illustrates an exemplary indication of video recording on the display screen that helps the user to keep track of the recording progress. Referring to FIG. 105B, active screen indication 10055 indicates the screen that the user is focusing on. As soon as the user initiates recording by pressing the relevant button in the endoscope handle, an icon, such as green icon 10056 is displayed on the active screen. A progress bar, such as progress bar 10057 with a timer 10058, also starts next to the icon 10056. As soon as the user presses a button to stop recording, the progress bar and the timer stop and a second icon, such as a red icon 10059, appears at the end of progress bar 10057. One of ordinary skill in the art would appreciate that the icons may be located at any place on the screen.

FIG. 106A illustrates another exemplary configuration of the endoscope handle 10061. Here, button 10062 can be used to toggle between displays by pressing left or right. In one embodiment, button 10062 is a scroll wheel and can be simply rotated to switch between views. The center 10063 of button 10062, when pressed, can be used to capture a still image. In one embodiment, the action of "pressing and holding" the center button 10063 initiates video recording. Pressing the button 10063 one more time would end the recording. Another button 10064 is provided on the handle that can be used to zoom in and out on the image being displayed, by pressing in forward and reverse directions, respectively.

FIG. 106B illustrates another example of image management indications on the display, the active display being indicated by the sign 10065. Zooming is indicated by means of a slider 10066 between standard "+" and "−" symbols 10067 and 10068 for zoom. As the user moves the relevant button on the endoscope handle forward and backward for zooming (as explained with reference to FIG. 106A above), the slider 10069 correspondingly moves forward or backward to zoom. Icon 10060 appears when the user captures a still image. Further, when a recorded video is being displayed, a set of buttons 10070 indicating standard signs of play, pause, stop, rewind and forward appear on the screen. In one embodiment, where the display comprises a touch-screen, the set of buttons 10070 may be used to control the display of recorded video. Further, in a touch-screen display, the other buttons or icons 10069, 10067, 10068 and 10060 may also be used to effectuate the functions they represent.

In one embodiment, the present specification allows more than one view to be active at the same time. This enables recording of more than one view at a time, which may be critical for the physician for a given case. FIG. 107 depicts this configuration, wherein color coded visual cues, indicators or icons 10071, 10072 and 10073 are used to indicate which of the three displays 10074, 10075 and 10076, respectively, are active. In the present example, displays 10074 and 10075 are active, as shown by the flashing or highlighted colored icons 10071 and 10072. Icon 10073 is not flashing or highlighted in the figure, thereby indicating that display 10076 is currently not active. One of ordinary skill in the art would appreciate that any other type of indication, such as the "Screen 1", "Screen 2" etc. signs described above with reference to FIGS. 104, 105B and 106B, may be used to highlight an active display. In one embodiment, letters "C", "R" are used for indication—L for left camera, C for center camera, R for right camera.

In one embodiment, to activate or deactivate a screen, corresponding color coded buttons are provided on the endoscope handle 10080. Thus, in continuation of the present example, buttons 10077, 10078 and 10079 are used to activate or switch to the corresponding display(s) 10074, 10075 and 10076, respectively. More than one button may be pressed to activate the corresponding number of displays. In one embodiment, the action of "pressing and holding" a button initiates video recording on the corresponding display. Pressing the button one more time would end the recording. In another embodiment, separate buttons may be provided for video recording and image capture, which may be used after the desired screen(s) has been selected using one or more of the buttons 10077, 10078 and 10079.

In another embodiment, a single button, such as the one shown in 10052 of FIG. 105A, may be used for selecting or activating more than one view at a time. Thus, for example, the button may be pressed once for the left view, again to go to the center view, again to go to the right, again to highlight left and center, again to highlight center and right, and again to highlight all of the three views. In one embodiment, only the "record" function is active when more than one view is selected, while other functions, such as zoom, are disabled. In another embodiment, zoom function is enabled, but allows for equal zoom in all the active views in case more than one view is active. Record and zoom buttons may be provided, similar to those shown in FIGS. 105A and 106A.

It may be noted that button configurations exemplified in FIGS. 105A, 106A and 107 may be combined into a single endoscopic handle to easily manage multiple functionalities of display and image manipulation such as toggling, image capture, video recording, freezing an image and zooming. Further, other image manipulation features not described above may be incorporated through buttons, knobs or switches in the endoscope handle.

FIG. 108 illustrates, through a flowchart, the process involved in implementing an image manipulation feature. Referring to FIG. 108, in the first step 10081 the user selects a feature, such as deciding on which channel or screen they wish to view/display information. This would require switching or toggling to the appropriate view. For this purpose, the user provides an input command in step 10082, such as by pushing a button on the endoscope handle or by using the keyboard, mouse or touch screen. The input command is processed by dedicated hardware and software in step 10083, and the corresponding output in the form of image or video is displayed in step 10084.

The hardware components involved in image/video processing in response to user commands has already been described earlier with reference to FIG. 90. Referring now to FIG. 90, the remote commands 9014 include image and video manipulation commands, such as toggle between views, maximize/minimize, zoom, record, freeze, capture, etc. Thus, any inputs received from the endoscope 9010, such as remote commands for image manipulation issued using the buttons on the endoscope handle, are processed through SOM 9026. As mentioned earlier, the user may also issue image manipulation commands through keyboard, mouse or touch-screen. In this case also, the commands are processed by SOM 9026. For recording a video or image, the FPGA 9023 appropriately processes the video or image and sends it for storage to the DDR memory 9033.

It may, therefore, be noted from the above discussion that the primary software and hardware components for enabling and controlling on-screen display in response to user commands are the system on module (SOM) 9026 and the FPGA 9023, respectively. As mentioned earlier, visual cues are provided on the display to assist a physician in selecting image manipulation features such as toggling between views, zoom, record, freeze, capture, etc. In one embodiment, international signs for recording, freezing and zooming might be positioned on the relevant monitors. Optionally, all the visual cues or only those for selected features may appear on the LCD touch screen 9055 on the main panel 9035 also. For example, confirmation that video is recording may appear on the main panel LCD screen 9055 only.

A common problem faced by the physicians operating an endoscope is that the viewing element in the endoscope tip may get embedded in tissue, thereby obstructing the view. In that case, a physician may not know which way to move in order to find the lumen (body cavity). With three viewing elements of the present specification, the likelihood of the view being obstructed reduces. However, it is still possible for the endoscope tip to get embedded in the tissue or become covered in body fluids in a way that the operating physician has no idea where to move the scope.

Further, during the course of an endoscopic procedure, the endoscope encounters junctures which cause the endoscope to change its direction of navigation substantially, and which would normally be not visible from only a front-pointing viewing element. FIG. 109 illustrates critical navigation junctures (CNJs) that an endoscope is likely to encounter during a standard procedure such as ERCP (endoscopic retrograde cholangiopancreatography). Referring to FIG. 109, CNJ1 10091, CNJ2 10092 and CNJ3 10093 are sharp turns within the body cavity which may, during navigation, obstruct the view of the endoscope. The definition of CNJs can be further expanded to include target areas of interest such as polyps, organ outlets, etc.

In order to assist the physician in navigation when faced with an obstruction and to help him or her to reposition the endoscope, in one embodiment, the present specification visually highlights the lumen (body cavity) on the image being displayed, so that the physician understands which way to proceed. An example of this is illustrated in FIG. 110A, wherein a circular ring 11001 highlights the area of interest when the endoscope 11002 is stuck at an odd angle. One of ordinary skill in the art would appreciate that any form of highlighting, such as a flashing border around the lumen, an arrow, or a different color may be used to point out the area of interest or the desired direction of navigation. Further, the highlighting feature can be further expanded to include target areas of interest such as polyps, organ outlets, etc. One such example is shown in FIG. 110A, where an arrow mark 11003 points towards a lesion 11004.

FIG. 110B is a flowchart illustrating the steps involved in a method of visualizing a navigation pathway of an endoscope comprising a tip section having a front-pointing viewing element and two side-pointing viewing elements by using the highlighting feature described above. At step 11012, the endoscope is inserted into a lumen of a body cavity. At step 11014, the endoscope is navigated through the lumen, wherein the lumen defines a navigation pathway comprising a plurality of junctures in which the pathway changes substantially. Then, at step 11016 the endoscope is operated to display a video output from each of the front and side-pointing viewing elements on to at least one monitor, wherein the video output is representative of the navigation pathway within the body lumen. At step 11018, at least one visual highlight is displayed on the monitor. The endoscope is then maneuvered through the lumen, at step 11020, when obstructed by the plurality of junctures, wherein the maneuvering is guided by the visual highlight on the monitor.

In another embodiment, the system of the present specification further assists a physician in following best practices guidelines during an endoscopic procedure. It is known in the art that during an endoscopic procedure, such as colonoscopy, the physician first proceeds within the colon to the cecum. The physician then gradually pulls the endoscope back, from the cecum through the transverse colon, the rectum and out of the body, to look for anomalies such as polyps, lesions, etc. One of the best practices for GI doctors is to spend at least six minutes going from the cecum out of the body, in order to thoroughly investigate the path.

In order to facilitate the physician to demonstrate that they are following best practices guidelines as described above, in one embodiment, a timer button is provided on the handle. The button may be activated at the moment when the physician initiates withdrawal of the endoscope from the cecum. The activation of the button starts a clock which tracks the time taken in investigating the colon. In one embodiment, the timer appears on the display when counted and can visually show progression through an anatomical region based on time. In one embodiment, the timer starts at six minutes and counts down, which ensures that the minimum time required for investigation as per the best practices guidelines, is followed.

In one embodiment, in order to deliver a synchronized display from multiple viewing elements rapidly and in real-time to the physician, image data from each of the image sensors is processed in real-time and synchronized before display. Further, toggling and other image manipulation features are integrated or synced with image capture functionality. This is done in a manner that minimizes latency, yet ensures a high quality output. Thus, there is no time lag between the time a physician clicks to see a view and corresponding image capture and display. The video processing architecture of the present specification, as discussed earlier with reference to FIG. 90, achieves this purpose by implementing:

a) signal transmission/control for each viewing element in a manner that optimally shares resources;

b) processing of viewing element data, wherein data are separately processed to ensure no latency and then synchronized; and c) transmitting the processed data for display in a manner that optimally shares resources.

In accordance with an aspect of the present specification, there is provided a service channel connector having a smooth internal surface which allows easy cleaning and disinfecting of the connector after use. There is also provided a service channel connector having channel dimensions that enable easy insertion of most medical instruments therethrough.

FIG. 111A illustrates an endoscope handle including a Y-shaped service channel connector, in accordance with an embodiment of the present specification. The handle 11100 comprises an umbilical tube/utility cable 11102 for connecting the endoscope to a main controller (such as main control unit 116 of FIG. 1A), knobs 11104 for maneuvering a bending section of an insertion tube 11106 within a lumen, and a service channel port 11107, among other components as described with respect to FIG. 1A. The service channel port 11107 is positioned within a handle of an endoscope, in the lower, distal portion of the handle, close to the insertion tube of an endoscope. The service channel connector (shown in FIG. 111B) of the present specification is connected to the endoscopic handle via a service channel port 11107 and a suction channel resides within the endoscopic handle.

FIG. 111B illustrates a magnified view of the service channel connector 11108, in accordance with an embodiment of the present specification. As shown, the service channel connector 11108 is approximately Y-shaped and, in one embodiment, comprises at its proximal end 11109 a service channel opening 11110 and a suction channel opening 11112. A distal end 11114 of the connector 11108 is connected to the insertion tube 11106 via a working channel opening. The proximal end 11109 is connected to the service channel port 11107 of the handle 11100 through service channel opening 11110 and through a suction channel which runs along the umbilical tube and is connected to a suction pump. Medical instruments, such as snares needles, biopsy forceps etc., may be inserted through the service channel opening 11110 into the insertion tube 11106, via the working channel opening.

FIG. 112 illustrates a conventional service channel connector. As shown, the service channel connector 11200 is approximately shaped as a 'V'. The service channel connector 11200 comprises a top, proximal end 11202 and a bottom, distal end 11204, where the proximal end 11202 is positioned toward the umbilical tube of the endoscopic device and the distal end is positioned toward the insertion tube of the endoscopic device. The proximal and distal ends 11202, 11204 are connected by a first wall 11206, having a flat surface 11206a and two beveled edges, 11206b and 11206c; a second, flat wall 11208, that assumes the approximate shape of a "V"; a third flat wall opposing the second wall, that also assumes the shape of a "V"; and, a fourth wall 11210 that opposes the first wall 11206 and has a flat surface 11210a and two beveled edges 11210b and 11210c, on either side of flat surface 11210a.

The top, proximate end 11202 comprises a circular service channel opening 11212, which in one embodiment, has an internal diameter measuring approximately 2.5-5.5 millimeters, for insertion of medical instruments, such as snares, needles, biopsy forceps etc., into an insertion tube, and a circular suction channel opening 11214. The second, distal end 11204 comprises a circular working channel opening having an internal diameter of approximately 2.5-5.5 millimeters where the working channel begins and exits in the scope tip. A length of the service channel connector 11200 measured from the proximate end 11202 to the distal end 11204 along first wall 11206 is approximately 10-16 millimeters.

FIG. 113A illustrates a service channel connector having an approximate Y-shape, in accordance with an embodiment of the present specification. In an embodiment, the service channel connector is manufactured in two separate portions which are then joined together. FIGS. 113B and 113C respectively illustrate the external and internal/cross sectional views of a first portion of the service channel connector shown in FIG. 113A, while FIGS. 113D and 113E respectively illustrate the external and internal/cross sectional views of a second portion of the service channel connector shown in FIG. 113A. FIGS. 113F and 113G respectively illustrate another internal/cross sectional view of the first and the second portions of the service channel connector, highlighting the regions that are joined together to obtain the complete service channel connector shown in FIG. 113A.

The service channel connector having an approximate Y-shape disclosed in the present specification is now described in detail with reference to FIGS. 113A, 113B, 113C, 113D, 113E, 113F and 113G.

As shown in FIG. 113A, the service channel connector 11300 has an approximate Y-shape. The service channel connector 11300 has a top, proximal end 11301 which houses a service channel opening 11302 and a suction channel opening 11304. The service channel connector 11300 is positioned within a handle of an endoscope, in the lower, distal portion of the handle, close to the insertion tube of an endoscope, as shown in FIG. 111A. Referring now to FIGS. 113A and 113C simultaneously, a service channel 11302a and a suction channel 11304a are in fluid communication with each other and join to form a combined channel 11313, ending in a working channel opening/exit 11306 having an internal diameter of approximately 2.5-8 millimeters. In one embodiment, a working channel opening/exit 11306 is positioned on a bottom, distal end 11303 of service channel connector 11300 and is circular. In one embodiment, working channel opening 11306 is connected to an insertion tube used for endoscopic examination.

U.S. Provisional Patent No. 61/917,530, entitled "Suction Control Unit for An Endoscope Having Two Working Channels" and filed on Dec. 18, 2013, is herein incorporated by reference in its entirety.

Referring to FIG. 113A, in one embodiment, the length of the service channel connecter 11300, measured from the top, proximal end 11301 to the bottom, distal end 11303 along a wall 11310 is approximately 15-21 millimeters, which is longer than the length of the conventional connector 11200 shown in FIG. 112. In one embodiment, circular working channel opening/exit 11306 has an internal diameter of approximately 2.5-8 millimeters, which is larger than the diameter of the working channel of the conventional connector shown in FIG. 112. The increased length and diameter of the connector 11300 disclosed in the present specification enables smoother/easier insertion of larger medical instruments into the insertion tube of the endoscope, as compared to the conventional connector 11200.

In some embodiments where a suction channel is not required, the service channel connector 11300 may be constructed without the suction channel 11304. In some embodiments where two service channel ports are placed in the handle, to provide the user an endoscope with more than one service channel, the service channel connector 11300 may be constructed with two service channel openings 11302. In one embodiment, the two service channel openings may have the same internal diameter. In another embodiment, the two service channel openings may have different internal diameters.

Referring simultaneously to FIGS. 113A, 113B and 113D, service channel connector 11300 comprises a front wall 11308 comprising a first portion 11308a, a second portion 11308b and a third portion 11308c. The first portion 11308a and the third portion 11308c are identical in shape, structure and size and are positioned on either side of the portion 11308a as shown in the figures, forming beveled edges for front wall 11308. The front wall portions 11308a and 11308c are positioned at an angle with respect to the front wall portion 11308b. Further referring to FIGS. 113A, 113B and 113D, service channel connector 11300 comprise a back wall 11310, opposing the front wall 11308, having a first portion with a flat surface 11310a, a second portion with a flat surface 11310b and a third portion with a flat surface 11310c. The first portion 11310a and the third portion 11310c are identical in shape, structure and size and are positioned on either side of the portion 111310b as shown in the figures, forming beveled edges for portion 11310. Referring to FIGS. 113A, 113B and 113D simultaneously, the service channel connector 11300 further comprises a first side wall 11312 and a second opposing side wall 11314.

Referring to FIG. 113B, first portion 11308a of the front wall 11308 comprises four portions connected at an angle to one another: 11308a1, 11308a2, 11308a3, and 11308a4. The portion 11308a1 is connected with portion 11308a2, portion 11308a2 is connected with portion 11308a3, and the portion 408a3 is connected with portion 408a4.

Referring to FIG. 113D, in an embodiment, the third portion 11308c of the front wall 11308 is identical in shape, structure and dimensions to the first portion 11308a, comprising four indented portions 11308c1, 11308c2, 11308c3 and 11308c4, identical to and connected to one another in the same fashion as portions 11308a1, 11308a2, 11308a3 and 11308a4 of first portion 11308a.

Referring to FIG. 113B, the portion 11308b of the front wall 11308 comprises four portions connected at an angle to one another: 11308b1, 11308b2, 11308b3, and 11308b4. In an embodiment, the width of the front wall portion 11308 is approximately 4-8 millimeters. The portion 11308b1 is connected with portion 11308b2; portion 11308b2 is connected with portion 11308b3; and the portion 11308b3 is connected with portion 11308b4.

Referring to FIGS. 113A and 113D simultaneously, in an embodiment, the opposing back wall 11310 comprises a first portion 11310a, a second portion 11310b, and a third portion 11310c. In an embodiment, each of the three portions 11310a, 11310b and 11310c are substantially straight and rectangular in shape without any surface indentations. In an embodiment, the length of each of the three portions 11310a, 11310b and 11310c of the back wall 11310 is approximately in the range of 15-21 millimeters while the width of the portion 11310 is approximately in the range of 4-8 millimeters.

Referring to FIGS. 113A and 113B simultaneously, the first side wall 11312 comprises a first portion 11312a, a second portion 11312b and a third portion 11312c. In an embodiment, as shown, the first portion 11312a is wider at the proximal end 11301 and tapers towards the distal end 11303. In an embodiment, a maximum width 'ee' of the first portion 11312a is approximately in the range of 10-16 millimeters. The second portion 11312b is substantially rectangular and is joined with the first portion 11312a and the third portion 11312c at an angle. As shown in the figures, the third portion 11312c is also substantially rectangular and ends in the working channel opening at the distal end 11303 of the connector 11300. In an embodiment, the total overall length of the portions 11312a (shown as 'ff'), 11312b (shown as 'gg') and 11312c (shown as 'hh'), is approximately in the range of 15-21 millimeters. In the embodiment illustrated in FIG. 113A, portion 11312a, when connected with the substantially rectangular portions 11312b and 11312c, lends an approximate Y-shape to the connector 11300.

Referring now to FIGS. 113A and 113D simultaneously, the second side wall 11314 is identical in shape, structure and design to the first side wall 11312. The second side wall 11314 comprises a first portion 11314a, a second portion 11314b and a third portion 11314c. In an embodiment, as shown in FIG. 113D, the first portion 11314a is wider at a proximal end 11301b and tapering towards the distal end 11303b. In an embodiment, a maximum width ee of the first portion 11314a is approximately in the range of 10-16 millimeters. The second portion 11314b is substantially rectangular and is joined with the first portion 11314a and the third portion 11314c at an angle. As shown in FIG. 113D, the third portion 11314c is also substantially rectangular and ends in the working channel opening at the distal end 11303b of the connector 400. In an embodiment, the total lengths of the portions 11314a, 11314b and 11314c is approximately in the range of 15-21 millimeters. In the embodiment illustrated in FIG. 113D, the portion 11314a connected with the portions 11314b and 11314c lend an approximate Y-shape to the connector 11300.

FIG. 113B illustrates an external cut-away view of a first section 11307 of the service channel connector 11300, in accordance with an embodiment of the present specification. In an embodiment, the service channel connector 11300 of the present specification comprises two individually machined sections, a first section 11307 shown in FIGS. 113B and 113C, and a second section 11309, shown in FIGS. 113D and 113E, that are joined together by a machining process to form the complete service channel connector 11300 illustrated in FIG. 113A.

Thus, as described below, the present specification provides a service channel connector, which, in one embodiment, is based on a two piece construction. The connector comprises two sections, both of which are constructed separately using a machining process such as a milling process. Separate construction of the two parts ensures that the internal walls of the parts are smooth and do not contain any edges or grooves that may retain residue. This enables the connector to be cleaned and disinfected thoroughly. The two sections, which are mirror images of each other, are placed on each other and are precisely aligned before being welded together. The joining of the two sections is performed precisely in a manner that eliminates any visible edges or gaps along the joint line. Hence, the risk of accumulation of residue along the joined edge is eliminated, thereby eliminating risk of contamination of the connector.

In an embodiment, each of the first section 11307 and the second section 11309 is constructed out of stainless steel material by using a machining process, and in one embodiment, a milling process. The milling process is a material removal process, which can create a variety of features on a part by cutting away the unwanted material. Milling is typically used to produce parts that are not axially symmetric and that have many features, such as holes, slots, pockets, etc. Further, in an embodiment, the two sections 11307, 11309 are joined by using a laser welding process in order to obtain the complete Y-shaped service channel connector 11300 illustrated in FIG. 113A.

In various embodiments, the two sections 11307, 11309 are mirror images of each other, and are placed together in precise alignment before joining.

In one embodiment, the first section 11307 illustrated in FIG. 113B comprises a top proximate end 11301a comprising at least a portion of service channel opening 11302/service channel 11302a and at least a portion of suction channel opening 11304/suction channel 11304a; a bottom distal end 11303a comprising at least a portion of the working channel opening 11306; the first side wall 11312; the portion 11308a of the front wall 11308 comprising the four indented portions 11308a1, 11308a2, 11308a3 and 11308a4; at least a segment of front wall portion 11308b, comprising segments of the four indented portions 11308b1, 11308b2, 11308b3 and 11308b4; and at least a segment of the opposing back wall 11310 comprising the portion 11310a and a segment of the portion 11310b.

FIG. 113C illustrates an internal/cross-sectional view of the first section 11307 of the service channel connector 11300, in accordance with an embodiment of the present specification. Referring to FIG. 113C, first section 11307 comprises a portion of the service channel 11302a and a portion of the suction channel 11304a. The first section 11307 further comprises a combined channel 11313 where the service channel 11302a and the suction channel 11304a join resulting in the working channel opening/exit 11306. In various embodiments, the working channel opening 11306 connects with an insertion tube of the endoscope. Medical instruments inserted into the service channel opening 11302, and thus service channel 11302a, enter the insertion tube via the working channel opening 11306. The service channel 11302a has a broad first segment 11324 and a narrower second segment 11326 merging into the combined channel 11313. In an embodiment, a diameter of the broad first segment 11324 is approximately in the range of 2.5-8 millimeters In an embodiment, the length of the combined channel 11313 enables large medical tools to be easily and smoothly inserted into an insertion tube of an endoscope through the service channel opening 11302 via the working channel opening 11306 due to the wider angle of portion 11316 compared to the angle found between portions 11204 and 11212 of 11200, as described above with respect to FIG. 112. The length of the combined channel 11313 is adapted to allow a medical tool to be inserted into the insertion tube without harming the functionality of the device and allows for a wider angle therein so that the physician does not need to exert force when pushing the medical tool into the scope.

As seen in the cross-sectional internal view of the connector 11300 shown in FIG. 113C, the suction channel 11304 tapers and is thus reduced in diameter along the longitudinal axis of the connector 11300. Referring to FIG. 113A, in an embodiment, a diameter of the opening of the suction channel 11304 located at the top/proximal end 11301 of the connector 11300 is adapted to clear blood clots, mucus, waste, etc. and manage high suction load when substances with high viscosity, large size, or a large amount of fluid such as coagulated blood, tissue pieces, mucus, waste, etc. in the lumen are suctioned. In an embodiment, the suction channel 11304a is narrower than the service channel 11302a and merges with the combined channel 11313 at the distal end 11303. Referring to FIG. 113C, in an embodiment, the service channel 11302a and the suction channel 11304a are partially separated by a wall 11327 that defines the bordering outlines of service channel 11302a and suction channel 11304a. Note that wall 11327 does not create a closed channel inside the connector 11300. The combined channel 11313 ends in the working channel opening 11306 at the distal end 11303a of the connector 11300. Since, the first section 11307 of the service channel connector 11300 is fabricated using a milling process, all the internal walls of the connector are smooth and do not contain any rough portions/niches where residue might accumulate leading to contamination.

FIG. 113D illustrates an external view of a second section 11309 of the service channel connector 11300, in accordance with an embodiment of the present specification. In one embodiment, the second section 11309 comprises a top proximate end 11301b comprising at least a portion of service channel opening 11302/service channel 11302a and at least a portion of suction channel opening 11304/suction channel 11304a; a bottom distal end 11303b comprising at least a portion of the working channel opening 11306; the second side wall 11314; the portion 11308c of the front wall 11308 comprising the four indented portions 11308c1, 11308c2, 11308c3 and 11308c4; at least a segment of front wall portion 11308b, comprising segments of the four indented portions 11308b1, 11308b2, 11308b3 and 11308b4; and at least a segment of the opposing back wall 11310 comprising the portion 11310c and a segment of the portion 11310b.

FIG. 113E illustrates an internal/cross sectional view of the second section 11309 of the service channel connector 11300, in accordance with an embodiment of the present specification. Referring to FIG. 113E, second section 11309 comprises a portion of the service channel 11302a and a portion of the suction channel 11304a. The second section 11309 further comprises a combined channel 11313 where the service channel 11302a and the suction channel 11304a join resulting in the working channel opening/exit 11306. The service channel 11302a has a broad first segment 11324 and a narrower second segment 11326 merging into the combined channel 11313. In an embodiment, a diameter of the broad first segment 11324 is approximately in the range of 2.5-8 millimeters. In an embodiment, the length of the combined channel 11313 enables large medical tools to be inserted easily and smoothly into an insertion tube of an endoscope through the service channel opening 11302 through the combined channel 11313 and subsequently via the working channel opening 11306 due to the wider angle of portion 11316 compared to the angle found between portions 11204 and 11212 of 11200, as described in detail above with respect to FIG. 112. The length of the combined channel 11313 is adapted to allow a medical tool to be inserted into the insertion tube without harming the functionality of the device and allows for a wider angle therein so that the physician does not need to exert force when pushing the medical tool into the scope.

As seen in the cross-sectional internal view of the connector 11300 shown in FIG. 113E, the suction channel 11304 tapers and is thus reduced in diameter, along the longitudinal axis of the connector 11300. Referring to FIG. 113E, in an embodiment, the service channel 11302a and the suction channel 11304a are partially separated by a wall 11327 that defines the bordering outlines of service channel 11302a and suction channel 11304a. Note that wall 11327 does not create a closed channel inside the connector 11300. The combined channel 11313 ends in the working channel opening 11306 at the distal end 11303b of the connector 11300. Since the second section 11309 of the service channel connector 11300 is fabricated using a milling process, all the internal walls of the connector are smooth and do not contain any rough portions/niches where residue might accumulate leading to contamination.

In an embodiment, the two sections 11307, 11309 of the service channel connector 11300 may be fabricated using an injection molding process, using materials suitable for the process such as metals, polymers, etc.

In an embodiment, the circular service channel opening 11302 has an internal diameter measuring approximately in the range of 2.5-8 millimeters, for insertion of medical instruments, such as snares, needles, biopsy forceps etc., into an insertion tube. Hence, the internal diameter of the working channel 11306 in the Y-shaped connector 11300 is greater than the internal diameter of the working channel of the conventional connector 11200 shown in FIG. 112. Due to the combination of a larger diameter of working channel 11306 and the Y-shape resulting from the long combined channel 11313 provided in the connector 11300, large medical instruments, measuring approximately 2.8 millimeters, may also be smoothly inserted into the insertion tube of an endoscope.

FIG. 113F illustrates a cross-sectional view of the first section 11307 of the service channel connector showing edges that are welded, in accordance with an embodiment of the present specification. As shown, the first section 11307 comprises a region 11330 running along an edge adjacent to portion 11308b of front wall 11308; a region 11332 running along an edge adjacent to portion 11310b of back wall 11310; and a region 11334 which is a top/proximal portion of wall 11327. In an embodiment, the length and width of regions 11330, 11332 and 11334 are adapted to provide a larger diameter service channel 11302a, suction channel 11304a and working channel 11306.

FIG. 113G illustrates another cross-sectional view of the second section 11309 of the service channel connector 11300 showing edges that are welded, in accordance with an embodiment of the present specification. As shown the second section 11309 comprises a region 11336 running along an edge adjacent to a portion of portion 11308b of front wall 11308; a region 11338 running along an edge adjacent to a portion of 11310*b* of back wall 11310; and a region 11340 which is a top/proximal portion of the wall 11327. In an embodiment, the length and width of regions 11336, 11338 and 11340 are adapted to provide a larger diameter service channel 11302*a*, suction channel 11304*a* and working channel 11306.

After being precisely aligned, where region 11332 is aligned with region 11338, region 11330 with region 11336, and region 11334 with region 11340, said regions are joined together by using a process such as laser welding.

Hence, the present specification provides a service channel connector, which, in one embodiment, is based on a two piece construction. The connector comprises two sections, both of which are constructed separately using a machining process such as a milling process. Separate construction of the two parts ensures that the internal walls of the parts are smooth and do not contain any edges or grooves that may retain residue. This enables the connector to be cleaned and disinfected thoroughly. The two sections, which are mirror images of each other, are placed on each other and are precisely aligned before being welded together. The joining of the two sections is performed precisely in a manner that eliminates any visible edges or gaps along the joint line. Hence, the risk of accumulation of residue along the joined edge is eliminated, thereby eliminating risk of contamination of the connector. Further, since the service channel connector of the present specification is constructed using a milling process, a Y-shape having a longer length and/or larger diameter of service channel, as compared to prior art connectors, is obtained. This enables larger medical instruments to be smoothly inserted via the service channel without having to increase the size of the connector substantially as compared to prior art connectors.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An image capturing assembly adapted to be used in an endoscope, the assembly comprising:
   a manifold having a proximal base with a first length and a first width and a casing extending outward from said proximal base, wherein said casing has a second length and second width and wherein said first length is less than the second length and the first width is greater than the second width;
   a partially enclosed housing wherein said partially enclosed housing is adapted to physically attach to the manifold;
   a LED carrier substrate, wherein said LED carrier substrate is adapted to be foldable and to carry a plurality of LEDs;
   a flexible optical carrier substrate, wherein said flexible optical carrier substrate is adapted to be foldable and to carry a first camera sensor and a second camera sensor, wherein the first camera sensor faces a direction transverse to the second camera sensor when positioned within the partially enclosed housing, and wherein the second camera sensor is aligned with a first opening in the partially enclosed housing and faces a direction transverse to a longitudinal axis of the image capturing assembly; and
   a tip cover adapted to cover said manifold, said partially enclosed housing, said LED carrier substrate, and said flexible optical carrier substrate.

2. The image capturing assembly of claim 1, wherein the manifold is a unitary part.

3. The image capturing assembly of claim 1, wherein the proximal base is substantially cylindrical.

4. The image capturing assembly of claim 1, wherein the casing comprises at least one continuous channel that extends from the proximal base throughout the second length.

5. The image capturing assembly of claim 4, wherein the proximal base comprises a plurality of channels extending through the entire first length and wherein at least one of said channels together with said continuous channel in the casing, creates a fluidically isolated channel extending through the proximal base and casing.

6. The image capturing assembly of claim 1, wherein the manifold combined with the partially enclosed housing create a substantially cylindrical housing.

7. The image capturing assembly of claim 1, wherein the manifold combined with the partially enclosed housing create a substantially cylindrical housing having openings and an internal volume, wherein the flexible optical carrier substrate is adapted to be folded to fit within said internal volume, and wherein said openings are positioned to receive said camera sensors.

8. The image capturing assembly of claim 7, wherein the substantially cylindrical housing is adapted to receive a folded LED carrier substrate.

9. The image capturing assembly of claim 8, wherein the substantially cylindrical housing in combination with the folded LED carrier substrate and the folded flexible optical carrier substrate creates an assembled image capture assembly having a front facing camera together with at least one LED and a side facing camera together with at least one LED.

10. The image capturing assembly of claim 1, wherein the tip cover comprises a first portion that covers a first half of said assembled image capturing assembly and a second portion that covers a second half of said assembled image capturing assembly.

11. An image capturing assembly adapted to be used in an endoscope, the assembly comprising:
   a manifold having a proximal base with a first length and a first width and a casing extending outward from said proximal base, wherein said casing has a second length and second width and wherein said first length is less than the second length and the first width is greater than the second width;
   a partially enclosed housing wherein said partially enclosed housing is adapted to physically attach to the manifold, and includes a first groove on a first side of the partially enclosed housing and a second groove on a second side of the partially enclosed housing, wherein the first side opposes the second side;
   a LED carrier substrate, wherein said LED carrier substrate is adapted to be foldable and to carry a first LED and a second LED, wherein the first groove receives the first LED, and the second groove receives the second LED;
   a flexible optical carrier substrate, wherein said flexible optical carrier substrate is adapted to be foldable and to carry a plurality of camera sensors; and a tip cover adapted to cover said manifold, said partially enclosed housing, said LED carrier substrate, and said flexible optical carrier substrate.

12. The image capturing assembly of claim 11, wherein the partially enclosed housing further includes a third groove on the first side of the partially enclosed housing, wherein the third groove receives a third LED of the LED carrier substrate, and wherein the a first camera sensor of the plurality of camera sensors is positioned between the first LED and the third LED.

13. The image capturing assembly of claim 11, wherein the proximal base is substantially cylindrical.

14. The image capturing assembly of claim 11, wherein the casing comprises at least one continuous channel that extends from the proximal base throughout the second length.

15. The image capturing assembly of claim 14, wherein the proximal base comprises a plurality of channels extending through the entire first length and wherein at least one of said channels together with said continuous channel in the casing, creates a fluidically isolated channel extending through the proximal base and casing.

16. The image capturing assembly of claim 11, wherein the manifold combined with the partially enclosed housing create a substantially cylindrical housing.

17. The image capturing assembly of claim 11, wherein the manifold combined with the partially enclosed housing create a substantially cylindrical housing having openings and an internal volume, wherein the flexible optical carrier substrate is adapted to be folded to fit within said internal volume, and wherein said openings are positioned to receive said camera sensors.

18. The image capturing assembly of claim 17, wherein the substantially cylindrical housing is adapted to receive a folded LED carrier substrate.

19. The image capturing assembly of claim 18, wherein the substantially cylindrical housing in combination with the folded LED carrier substrate and the flexible optical carrier substrate creates an assembled image capture assembly having a front facing camera together with at least one LED and a side facing camera together with at least one LED.

20. An image capturing assembly adapted to be used in an endoscope, the assembly comprising:

a manifold having a proximal base with a first length and a first width and a casing extending outward from said proximal base, wherein said casing has a second length and second width and wherein said first length is less than the second length and the first width is greater than the second width;

a partially enclosed housing wherein said partially enclosed housing is adapted to physically attach to the manifold, wherein the partially enclosed housing extends along a longitudinal axis of the image capturing assembly a distance of approximately the second length and adjacent to the casing;

a LED carrier substrate, wherein said LED carrier substrate is adapted to be foldable and to carry a plurality of LEDs;

a flexible optical carrier substrate, wherein said flexible optical carrier substrate is adapted to be foldable and to carry a plurality of camera sensors; and a tip cover adapted to cover said manifold, said partially enclosed housing, said LED carrier substrate, and said flexible optical carrier substrate.

\* \* \* \* \*